(12) United States Patent
Bannen et al.

(10) Patent No.: US 11,708,367 B2
(45) Date of Patent: Jul. 25, 2023

(54) COMPOUNDS FOR THE TREATMENT OF KINASE-DEPENDENT DISORDERS

(71) Applicant: Exelixis, Inc., Alameda, CA (US)

(72) Inventors: Lynne Canne Bannen, Novato, CA (US); Minna Bui, Oakland, CA (US); Faming Jiang, Castro Valley, CA (US); Yong Wang, South San Francisco, CA (US); Wei Xu, Danville, CA (US)

(73) Assignee: EXELIXIS, INC., Alameda, CA (US)

(*) Notice: Subject to any disclaimer, the term of this patent is extended or adjusted under 35 U.S.C. 154(b) by 0 days.

(21) Appl. No.: 16/964,228

(22) PCT Filed: Jan. 25, 2019

(86) PCT No.: PCT/US2019/015289
§ 371 (c)(1),
(2) Date: Jul. 23, 2020

(87) PCT Pub. No.: WO2019/148036
PCT Pub. Date: Aug. 1, 2019

(65) Prior Publication Data
US 2021/0040099 A1 Feb. 11, 2021

Related U.S. Application Data

(60) Provisional application No. 62/622,626, filed on Jan. 26, 2018, provisional application No. 62/622,629, filed on Jan. 26, 2018.

(51) Int. Cl.
| C07D 487/04 | (2006.01) |
| C07D 239/88 | (2006.01) |
| C07D 403/04 | (2006.01) |
| C07D 403/12 | (2006.01) |
| C07D 405/12 | (2006.01) |

(52) U.S. Cl.
CPC ......... *C07D 487/04* (2013.01); *C07D 239/88* (2013.01); *C07D 403/04* (2013.01); *C07D 403/12* (2013.01); *C07D 405/12* (2013.01)

(58) Field of Classification Search
CPC .. C07D 487/04; C07D 239/88; C07D 403/04; C07D 403/12; C07D 405/12; A61K 31/517
See application file for complete search history.

(56) References Cited

U.S. PATENT DOCUMENTS

| 2007/0015746 A1 | 1/2007 | Martin et al. |
| 2007/0238726 A1 | 10/2007 | Blake et al. |
| 2013/0331359 A1 | 12/2013 | Yun et al. |
| 2014/0221425 A1 | 8/2014 | Yun et al. |
| 2017/0042880 A1 | 2/2017 | Aftab et al. |
| 2018/0009758 A1 | 1/2018 | Horn |
| 2018/0244667 A1* | 8/2018 | Long .................. A61K 31/4985 |
| 2019/0248772 A1 | 8/2019 | Sun et al. |

FOREIGN PATENT DOCUMENTS

| CN | 104817497 A | 8/2015 |
| CN | 105797123 A | 7/2016 |
| CN | 106400155 A | 2/2017 |
| EP | 2769976 A1 | 8/2014 |
| WO | 2005/030140 A1 | 4/2005 |
| WO | 2005030140 A2 | 4/2005 |
| WO | 2010045095 A1 | 4/2010 |
| WO | 2011/017639 A1 | 2/2011 |
| WO | 2012006960 A1 | 1/2012 |
| WO | 2012034055 A2 | 3/2012 |
| WO | 2016184434 A1 | 11/2016 |
| WO | 2019/125798 A1 | 6/2019 |

OTHER PUBLICATIONS

Acute Leukemia, Merck Manual (Online Edition) 6 pages, pp. 1-6 (2013).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*

* cited by examiner

*Primary Examiner* — Deepak R Rao
(74) *Attorney, Agent, or Firm* — Honigman LLP; Heidi Berven; Li Gao

(57) ABSTRACT

Disclosed herein are compounds of Formula (I'). Compounds of Formula (I') inhibit, regulate and/or modulate kinase receptor, particularly Axl and Mer signal transduction pathways related to the changes in cellular activities as mentioned above, compositions which contain these compounds, and methods of using them to treat kinase-dependent diseases and conditions. The present invention also provides methods for making compounds as mentioned above, and compositions which contain these compounds.

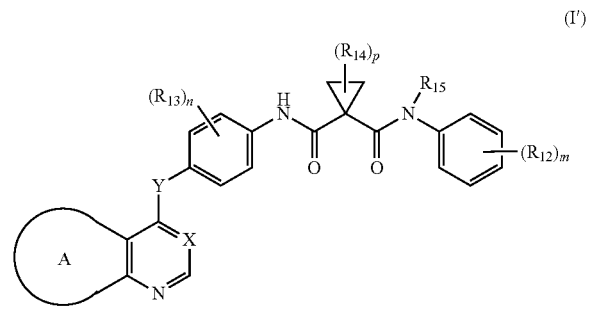

20 Claims, No Drawings
Specification includes a Sequence Listing.

COMPOUNDS FOR THE TREATMENT OF KINASE-DEPENDENT DISORDERS

This application is a United States National Phase filing of PCT/US2019/015289, filed Jan. 25, 2019, which claims the benefit of priority to U.S. Provisional Application No. 62/622,626, filed Jan. 26, 2018 and U.S. Provisional Application No. 62/622,629, filed Jan. 26, 2018, the entire contents of which are incorporated herein by reference.

FIELD OF THE INVENTION

The invention relates to compounds for modulating protein kinase enzymatic activity for modulating cellular activities such as proliferation, differentiation, programmed cell death, migration, and chemoinvasion. Even more specifically, the invention relates to compounds which inhibit, regulate, and/or modulate Axl and Mer receptor tyrosine kinases, compositions which contain these compounds, methods of using them to treat kinase-dependent diseases and conditions, synthesis of the compounds, and processes for formulating the compounds for pharmaceutical purposes.

CROSS-REFERENCE TO RELATED APPLICATIONS

This application claims the benefit of priority to U.S. Provisional Application No. 62/622,626, filed Jan. 26, 2018, and to U.S. Provisional Application No. 62/622,629, filed Jan. 26, 2018, the entire contents of which are incorporated herein by reference.

BACKGROUND OF THE INVENTION

Human Axl belongs to the TAM subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers such as lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis most likely by generation of soluble Mer extracellular domain protein as a decoy receptor. Tumor cells secrete a soluble form of the extracellular Mer receptor which reduces the ability of soluble Gas-6 ligand to activate Mer on endothelial cells leading to cancer progression.

Therefore a need exists for compounds that inhibit TAM receptor tyrosine kinases such as Axl and Mer for the treatment of selected cancers.

SUMMARY OF THE INVENTION

In one aspect, the present invention comprises a compound for modulating kinase activity according to Formula I', Formula I, or Formula II.

In one aspect, the invention includes a compound of Formula I':

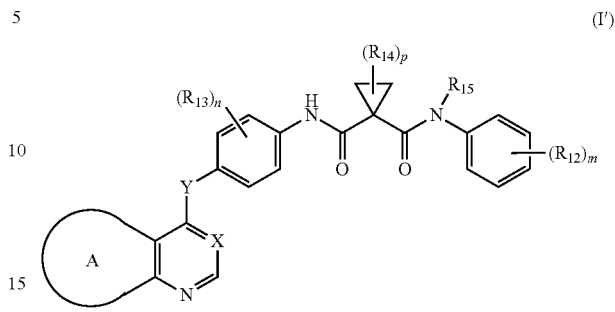

(I')

or a pharmaceutically acceptable salt thereof, wherein:
X is N or CH;
Y is selected from O, S, SO, $SO_2$, NH, and —N($C_{1-6}$ alkyl)-;
(i) ring A is

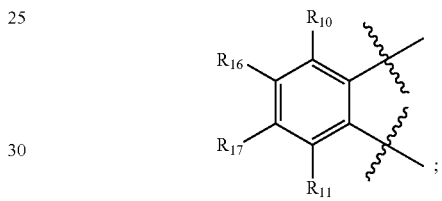

$R_{16}$ is selected from the group consisting of ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; —CN; —NHOH, —C(O)$R^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and $R_{17}$ is selected from —H; halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; (4-14 membered heterocycloalkyl)-($C_1$-$C_4$) alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$ NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the ($C_1$-$C_6$) alkyl; ($C_2$-$C_6$) alkenyl; ($C_2$-$C_6$) alkynyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R_{16}$ or $R_{17}$ are each optionally substituted with 1, 2, 3, 4, or 5 independently selected $R^b$ substituents, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$ haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{16}$ is each optionally substituted with 1, 2, 3, 4, or 5 independently selected R$^b$ substituents; and $R_{17}$ is selected from the group consisting of $(C_2-C_6)$ alkenyl; $(C_2-C_6)$ alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ and $R_{17}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected R$^b$ substituents; or (ii) ring A is

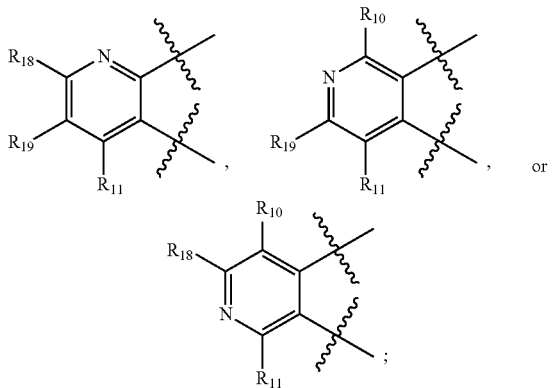

$R_{18}$ and $R_{19}$ are each independently selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$haloalkoxy; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{18}$ or $R_{19}$ are each optionally substituted with 1, 2, 3, 4, or 5 independently selected R$^b$ substituents; or $R_{18}$ and $R_{19}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected R$^b$ substituents;

$R_{10}$ and $R_{11}$ are each independently selected from the group consisting of —H; halo; $(C_1-C_6)$ alkyl; $(C_1-C_6)$ haloalkyl; $(C_1-C_6)$haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^3$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the $(C_1-C_6)$ alkyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkyl ene-; (5-14 membered heteroaryl)-$(C_1-C_4)$ alkyl ene-; and (4-14 membered heterocycloalkyl)-$(C_1-C_4)$ alkylene- of $R_1$ or $R_2$ are each optionally substituted with 1, 2, 3, 4, or 5 independently selected R$^b$ substituents;

each $R_{13}$ is independently selected from the group consisting of —H; halo; —OH; —CN; optionally substituted $(C_1-C_6)$ alkyl; $(C_1-C_6)$ alkoxy; $(C_1-C_6)$ haloalkoxy; —NH$_2$; —NH$(C_1-C_6)$alkyl; —N$(C_1-C_6$ alkyl)$_2$; and $(C_3-C_6)$ cycloalkyl; wherein the $(C_1-C_6)$ alkoxy; —NH$(C_1-C_6)$alkyl; —N$(C_1-C_6$ alkyl)$_2$; and $(C_3-C_6)$ cycloalkyl of $R_3$ are each optionally substituted with 1, 2, or 3 independently selected R$^g$ substituents;

each $R_{14}$ is independently selected from the group consisting of halo; —OH; —NH$_2$; —CN; $(C_1-C_6)$ alkyl; $(C_1-C_6)$ alkoxy; $(C_1-C_6)$ haloalkyl; $(C_1-C_6)$ haloalkoxy; —COOH; —NH$(C_1-C_6)$alkyl; —N$(C_1-C_6$ alkyl)$_2$; phenyl; phenyl-$(C_1-C_2)$ alkylene; $(C_3-C_6)$ cycloalkyl; $(C_3-C_6)$ cycloalkyl-$(C_1-C_4)$ alkylene-; 4- to 6-membered heterocycloalkyl; (4- to 6-membered heterocycloalkyl)-$(C_1-C_4)$ alkylene-; 5- to 6-membered heteroaryl; (5- to 6-membered heteroaryl)-($C_1$-$C_4$) alkylene-; and —$OR^e$; wherein the ($C_1$-$C_6$) alkyl; phenyl; phenyl-($C_1$-$C_2$) alkylene; ($C_3$-$C_6$) cycloalkyl; ($C_3$-$C_6$) cycloalkyl-($C_1$-$C_4$) alkylene-; 4- to 6-membered heterocycloalkyl; (4- to 6-membered heterocycloalkyl)-($C_1$-$C_4$) alkylene-; 5- to 6-membered heteroaryl; and (5- to 6-membered heteroaryl)-($C_1$-$C_4$) alkylene- of $R_{14}$ are each optionally substituted with 1, 2, or 3 independently selected $R^g$ substituents;

$R_{15}$ is H;

each $R_{12}$ is independently selected from the group consisting of —H; halo; —OH; —$COOR^e$; —$CONR^eR^e$; —CN; —$NH_2$; —NH(($C_1$-$C_6$) alkyl); —N(($C_1$-$C_6$) alkyl)$_2$; ($C_1$-$C_6$) alkyl; ($C_1$-$C_6$) alkoxy; ($C_1$-$C_6$) haloalkyl; ($C_1$-$C_6$) haloalkoxy; —$CONR^aR^a$; —$NR^aCOR^a$; —$NR^aCONR^aR^a$; —$SO_2R^a$; —$NR^aS(O)_2R^a$; —$NR^aS(O)_2NR^aR^a$; ($C_3$-$C_6$) cycloalkyl; 4- to 6-membered heterocycloalkyl; phenyl; 5- or 6-membered heteroaryl; ($C_3$-$C_6$) cycloalkyl-($C_1$-$C_4$) alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene-; wherein the ($C_1$-$C_6$) alkyl; ($C_3$-$C_6$) cycloalkyl; 4- to 6-membered heterocycloalkyl; phenyl; 5- or 6-membered heteroaryl; ($C_3$-$C_6$) cycloalkyl-($C_1$-$C_4$) alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene- of $R_{12}$ are each optionally substituted with 1, 2, or 3 independently selected $R^f$ substituents;

each $R^a$ is independently selected from the group consisting of —H; —CN; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl-($C_1$-$C_4$) alkylene-; and (4-14 membered heterocycloalkyl)-($C_1$-$C_4$) alkylene-; wherein the ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R^a$ are each optionally substituted with 1, 2, 3, 4, or 5 independently selected $R^d$ substituents;

each $R^b$ is independently selected from the group consisting of halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl-($C_1$-$C_4$) alkylene-; —CN; —OH; —$NH_2$; —$NO_2$; —$NHOR^c$; —$OR^c$; —$SR^c$; —$C(O)R^c$; —$C(O)NR^cR^c$; —$C(O)OR^c$; —$C(O)NR^cS(O)_2R^c$; —$OC(O)R^c$; —$OC(O)NR^cR^c$; —$C(=NOH)R^c$; —$C(=NOH)NR^c$; —$C(=NCN)NR^cR^c$; —$NR^cC(=NCN)NR^cR^c$; —$C(=NR^c)NR^cR^c$; —$NR^cC(=NR^c)NR^cR^c$; —$NHR^c$; —$NR^cR^c$; —$NR^cC(O)R^c$; —$NR^cC(=NR^c)R^c$; —$NR^cC(O)OR^c$; —$NR^cC(O)NR^cR^c$; —$NR^cS(O)R^c$; —$NR^cS(O)_2R^c$; —$NR^cS(O)_2NR^cR^c$; —$S(O)R^c$; —$S(O)NR^cR^c$; —$S(O)_2R^c$; —$S(O)_2NR^cC(O)R^c$; —$Si(R^c)_3$; —$P(O)R^cR^c$; —$P(O)(OR^c)(OR^c)$; —$B(OH)_2$; —$B(OR^c)_2$; and —$S(O)_2NR^cR^c$; wherein the ($C_1$-$C_6$) alkyl; ($C_1$-$C_6$) haloalkyl; ($C_1$-$C_6$) haloalkoxy; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalky-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^b$ are each further optionally substituted with 1, 2, or 3 independently selected $R^d$ substituents;

each $R^c$ is independently selected from the group consisting of —H; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene-; wherein the ($C_1$-$C_6$) alkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^c$ are each optionally substituted with 1, 2, 3, 4, or 5 independently selected $R^f$ substituents;

each $R^d$ is independently selected from the group consisting of ($C_1$-$C_6$) alkyl; ($C_1$-$C_6$) haloalkyl; halo; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkylene-; —CN; —$NH_2$; —$NHOR^6$; —$OR^e$; —$SR^e$; —$C(O)R^e$; —$C(O)NR^eR^e$; —$C(O)OR^e$; —$OC(O)R^e$; —$OC(O)NR^eR^e$; —$NHR^e$; —$NR^eR^e$; —$NR^eC(O)R^e$; —$NR^eC(O)NR^eR^e$; —$NR^eC(O)OR^e$; —$C(=NR^e)NR^eR^e$; —$NR^eC(=NR^e)NR^eR^e$; —$NR^eC(=NOH)NR^eR^e$; —$NR^eC(=NCN)NR^eR^e$; —$S(O)R^e$; —$S(O)NR^eR^e$; —$S(O)_2R^e$; —$NR^eS(O)_2R^e$; —$NR^eS(O)_2NR^eR^e$; and —$S(O)_2NR^eR^e$; wherein the ($C_1$-$C_6$) alkyl; ($C_1$-$C_6$) haloalkyl; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^d$ are each optionally substituted with 1, 2, or 3 independently selected $R^f$ substituents;

each $R^e$ is independently selected from the group consisting of —H; ($C_1$-$C_6$) alkyl; ($C_3$-$C_6$) cycloalkyl; ($C_3$-$C_6$) cycloalkyl-($C_1$-$C_4$) alkylene-; ($C_6$-$C_{10}$) aryl; ($C_6$-$C_{10}$) aryl-($C_1$-$C_4$) alkylene-; 5- or 6-membered heteroaryl; (5- or 6-membered heteroaryl)-($C_1$-$C_4$) alkylene-; 4-7-membered heterocycloalkyl; (4-7-membered heterocycloalkyl)-($C_1$-$C_4$) alkylene-; ($C_1$-$C_6$) haloalkyl; ($C_1$-$C_6$) haloalkoxy; ($C_2$-$C_4$) alkenyl; and ($C_2$-$C_4$) alkynyl; wherein the ($C_1$-$C_4$) alkyl; ($C_3$-$C_6$) cycloalkyl; ($C_6$-$C_{10}$)aryl; 5 or 6-membered heteroaryl; 4-7-membered heterocycloalkyl; ($C_6$-$C_{10}$) aryl-($C_1$-$C_4$) alkylene-; (5- or 6-membered heteroaryl)-($C_1$-$C_4$) alkylene-; (4-7-membered heterocycloalkyl)-($C_1$-$C_4$) alkylene-; ($C_2$-$C_4$) alkenyl; and ($C_2$-$C_4$) alkynyl of $R^e$ are each optionally substituted with 1, 2, or 3 $R^f$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo; —OH; —CN; —COOH; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$) haloalkoxy; phenyl; 5-6 membered heteroaryl; 4-6 membered heterocycloalkyl; and (C$_3$-C$_6$) cycloalkyl; wherein the (C$_1$-C$_6$) alkyl; phenyl; (C$_3$-C$_6$) cycloalkyl; 4-6 membered heterocycloalkyl; and 5-6 membered heteroaryl of $R^f$ are each optionally substituted with 1, 2, or 3 substituents selected from halo; —OH; —CN; —COOH; —NH$_2$; (C$_1$-C$_4$) alkyl; (C$_1$-C$_4$) alkoxy; (C$_1$-C$_4$) haloalkyl; (C$_1$-C$_4$) haloalkoxy; phenyl; (C$_3$-C$_{10}$) cycloalkyl; 5-6 membered heteroaryl; and 4-6 membered heterocycloalkyl;

each $R^g$ is independently selected from the group consisting of halo; —OH; —CN; —COOH; —COO—(C$_1$-C$_4$) alkyl; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$) haloalkyl; (C$_1$-C$_6$) haloalkoxy; phenyl; 5-6 membered heteroaryl; 4-6 membered heterocycloalkyl; and (C$_3$-C$_6$) cycloalkyl;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4;

provided that when X is C—H, Ring A is

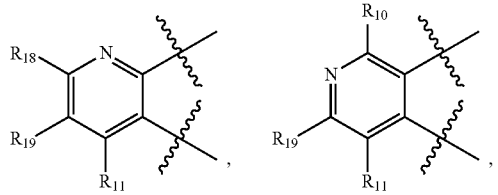

In one embodiment, the compound of Formula I' is a compound of Formula I:

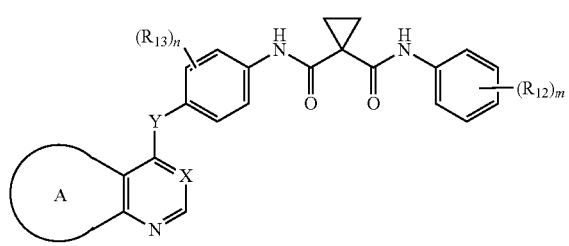

wherein:

X is selected from N and C—H;

Y is O, S, SO, SO$_2$, NH, or N—(C$_1$-C$_6$ alkyl);

$R_{13}$ is selected from —H, halo, —CN, and optionally substituted C$_{1-6}$ alkyl;

$R_{12}$ is —H or halo;

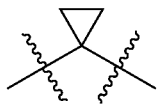 [SMILES: *C1(*)CC1]

is optionally substituted with one, two, three, or four groups independently selected from the group consisting of halo, and C$_1$-C$_6$ alkyl, wherein "〜〜" indicate points of attachment;

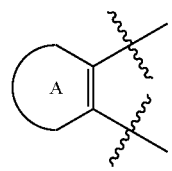

is selected from the group consisting of

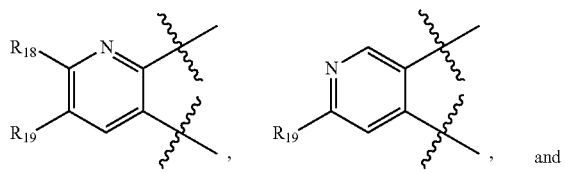

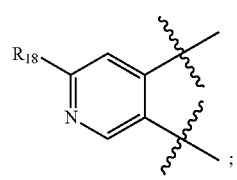

wherein $R_{18}$ and $R_{19}$ are selected from the group consisting of H, halo, —CN, optionally substituted C$_1$-C$_6$ alkyl, C(O)NR$_5$R$_6$, optionally substituted 5 or 6-membered heteroaryl, and optionally substituted C$_1$-C$_6$ alkoxy; or when

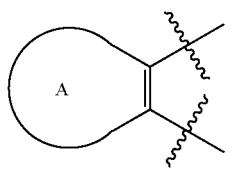 is 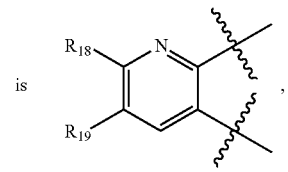, $R_{18}$ and $R_{19}$ can be joined together to form a 5 or 6-membered optionally substituted cycloalkyl or heterocycloalkyl;

$R_5$ and $R_6$ are selected from the group consisting of H, optionally substituted C$_{1-6}$ alkyl, or $R_5$ and $R_6$ taken together with the nitrogen to which they are attached to form a 5- or 6-membered optionally substituted heterocycle; and m and n are each independently 1 or 2;
provided that when

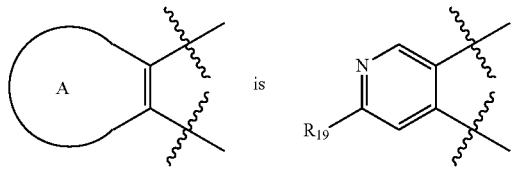

and X is C—H, $R_{19}$ is not optionally substituted $C_1$-$C_6$ alkyl, halo, or optionally substituted $C_1$-$C_6$ alkoxy.

In one embodiment, the compound of Formula I' is a compound of Formula II:

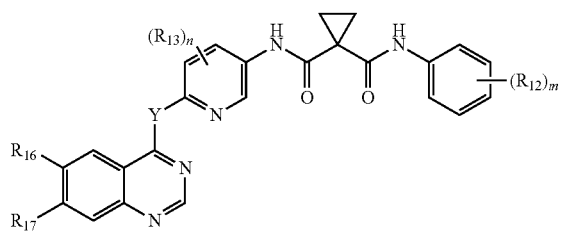

II or a pharmaceutically acceptable salt thereof, wherein:

$R_{16}$ is selected from the group consisting of —CN and —CO—$NR_5R_6$;

$R_{17}$ is selected from H and optionally substituted $C_1$-$C_6$ alkoxy;

$R_{13}$ is selected from the group consisting of —H, halo, —CN, or optionally substituted $C_{1-6}$ alkyl;

$R_{12}$ is —H or halo;

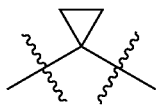

is optionally substituted with one, two, three, or four groups independently selected from the group consisting of halo, and $C_1$-$C_6$ alkyl, wherein "〜〜〜" indicate points of attachment;

$R_5$ and $R_6$ are each independently selected from the group consisting of H, optionally substituted $C_1$-$C_6$ alkyl, optionally substituted $C_3$-$C_6$ heterocycloalkyl, and optionally substituted $C_1$-$C_6$ cycloalkyl;

Y is O, S, SO, $SO_2$, NH, or N—($C_1$-$C_6$ alkyl); and m and n are each independently 1 or 2.

In one aspect, the invention includes a pharmaceutical composition comprising a compound described herein, and a pharmaceutically acceptable carrier or excipient.

In another aspect, the invention includes a method of treating a disease, disorder, or syndrome mediated at least in part by modulating in vivo activity of a protein kinase, comprising administering to a subject in need thereof a therapeutically effective amount of a compound described herein, or a pharmaceutical composition thereof.

DETAILED DESCRIPTION OF THE INVENTION

Abbreviations and Definitions

The following abbreviations and terms have the indicated meanings throughout:

| Abbreviation | Meaning |
|---|---|
| Ac | Acetyl |
| anhyd | Anhydrous |
| Aq | Aqueous |
| Ar | Argon |
| Boc | Tert-butoxycarbonyl |
| Br | Broad |
| ° C. | Degrees Celsius |
| c- | Cyclo |
| calcd | Calculated |
| CBZ | CarboBenZoxy = benzyloxycarbonyl |
| d | Doublet |
| dd | Doublet of doublets |
| ddd | Doublet of doublets of doublets |
| dt | Doublet of triplets |
| DCM | Dichloromethane |
| DMF | N,N-Dimethylformamide |
| DMSO | Dimethyl sulfoxide |
| Dppf | 1,1'-bis(diphenylphosphano)ferrocene |
| EA | Elemental Analysis |
| EI | Electron Impact ionization |
| eq or equiv | Equivalent |
| Fmoc | Fluorenylmethyloxycarbonyl |
| g | Gram(s) |
| h or hr | Hour(s) |
| HPLC | High pressure liquid chromatography |
| $H_2$ | Hydrogen |
| L | Liter(s) |
| LiHMDS | Lithium bis(trimethylsilyl)azide |
| M | Molar or molarity |
| m | Multiplet |
| MHz | Megahertz (frequency) |
| Min | Minute(s) |
| mL | Milliliter(s) |
| Mp | Melting point |
| m/z | Mass to charge ratio |
| μL | Microliter(s) |
| Mol | Mole(s) |
| MS | Mass spectral analysis |
| $N_2$ | Nitrogen |
| N | Normal or normality |
| nM | Nanomolar |
| NMR | Nuclear magnetic resonance spectroscopy |
| Pd/C | Palladium on carbon |
| Q | Quartet |
| RT | Room temperature |
| s | Singlet |
| soln | Solution |
| S/C | Substrate/catalyst ratio |
| t or tr | Triplet |
| THF | Tetrahydrofuran |
| TLC | Thin layer chromatography |
| v/v | Volume to volume |

The symbol means a single bond, and "=" means a double bond.

As used herein, the singular forms "a," "an," and "the" include plural reference unless the context clearly dictates otherwise.

When a variable is defined genetically, with a number of possible substituents, each individual radical can be defined with or without the bond. For example, if $R^z$ can be hydrogen, this can be indicated as "—H" or "H" in the definition of $R^z$.

When chemical structures are depicted or described, unless explicitly stated otherwise, all carbons are assumed to have hydrogen substitution to conform to a valence of four.

For example, in the structure on the left-hand side of the schematic below, there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

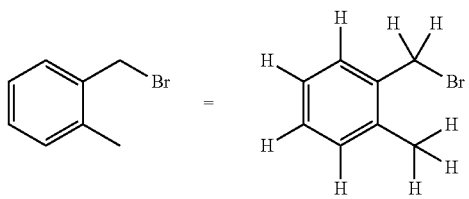

If a group "R" is depicted as "floating" on a ring system, as for example in the formula:

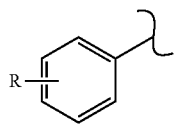

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

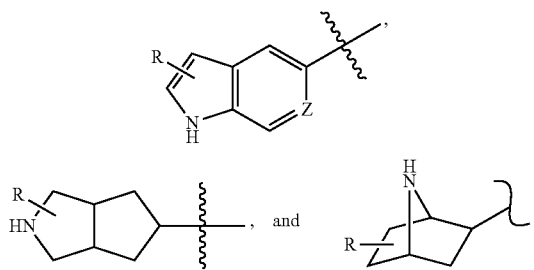

then, unless otherwise defined, a substituent "R" may reside on any atom of the fused ring system, assuming replacement of a depicted hydrogen (for example the —NH— in the formula above), implied hydrogen (for example, in the formula above, where the hydrogens are not shown but understood to be present), or expressly defined hydrogen (for example, where in the formula above, "Z" equals =CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, for example in the formula:

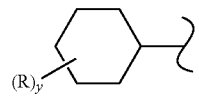

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group, there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

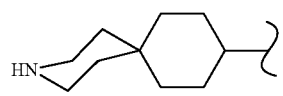

"Halogen" or "halo" refers to fluorine, chlorine, bromine, or iodine.

The term "$C_{n-m}$" or "$C_n$-$C_m$" indicates a range which includes the endpoints, wherein n and m are integers and indicate the number of carbons. Examples include $C_{1-4}$, $C_1$-$C_4$, $C_{1-6}$, $C_1$-$C_6$, and the like.

"Alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl, and heptyl. ($C_1$-$C_6$)alkyl is preferred. The term "$C_{n-m}$ alkyl" or ($C_n$-$C_m$) alkyl, refers to an alkyl group having n to m carbon atoms. When optionally substituted, one or more hydrogen atoms of the alkyl group (e.g., from 1 to 4, from 1 to 2, or 1) may be replaced with a moiety as described below under "Optional Substitution." In some aspects, the alkyl group is unsubstituted or not optionally substituted.

"Alkylene" refers to an optionally substituted bivalent saturated aliphatic radical having from 1 to 10 carbon atoms, 1 to 8 carbon atoms, 1 to 6 carbon atoms, 1 to 4 carbon atoms, or 1 to 2 carbon atoms. When optionally substituted, one or more hydrogen atoms of the alkylene group (e.g., from 1 to 4, from 1 to 2, or 1) may be replaced with a moiety as described below under "Optional Substitution." In some aspects, the alkylene group is unsubstituted or not optionally substituted. The term "$C_{n-m}$ alkylene" refers to an alkylene group having n to m carbon atoms. Examples of alkylene groups include, but are not limited to, methylene, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

The term "alkenyl" refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" or ($C_n$-$C_m$) alkenyl refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

The term "alkynyl" refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" or ($C_n$-$C_m$) alkynyl refers to an alkynyl group having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

"Alkoxy" refers to a moiety of the formula —OR', wherein R' is an ($C_1$-$C_6$)alkyl moiety as defined herein. The term "$C_{n-m}$ alkoxy" or ($C_n$-$C_m$) alkoxy refers to an alkoxy group, the alkyl group of which has n to m carbons. Examples of alkoxy moieties include, but are not limited to, methoxy, ethoxy, isopropoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety as described below under "Optional Substitution," with the proviso that no hydrogen atom alpha to the ether oxygen is replaced by a hydroxy, amino, or thio group. In some aspects, the alkoxy group is unsubstituted or not optionally substituted.

"Alkoxycarbonyl" refers to a group —C(O)—R' wherein R' is ($C_1$-$C_6$)alkoxy as defined herein.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN or CN.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfide" refers to a sulfur atom as a divalent substituent, forming a thiocarbonyl group (C=S) when attached to carbon.

The term "heteroatom" used herein is meant to include boron, phosphorus, sulfur, oxygen, and nitrogen.

The term "haloalkyl" as used herein refers to an alkyl group in which one or more of the hydrogen atoms has been replaced by a halogen atom. The term "$C_{n-m}$ haloalkyl" or ($C_n$-$C_m$) haloalkyl refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" or ($C_n$-$C_m$) haloalkoxy refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

"Aryl" means a monovalent six- to fourteen-membered, mono- or bi-carbocyclic ring (e.g., having two fused rings), wherein the monocyclic ring is aromatic and at least one of the rings in the bicyclic ring is aromatic. The term "$C_{n-m}$ aryl" or "($C_n$-$C_m$) aryl" refers to an aryl group having from n to m ring carbon atoms. In some embodiments, aryl groups have from 6 to about 10 carbon atoms. In some embodiments aryl groups have 6 carbon atoms. In some embodiments aryl groups have 10 carbon atoms. Unless stated otherwise, the valency of the group may be located on any atom of any ring within the radical, valency rules permitting. Representative examples include phenyl, naphthyl, and indanyl, and the like.

An aryl group can be unsubstituted or optionally substituted. When optionally substituted, one or more hydrogen atoms of the aryl group (e.g., from 1 to 5, from 1 to 2, or 1) may be replaced with a moiety as described below under "Optional Substitution." In some aspects, the alkoxy group is unsubstituted or not optionally substituted.

"Arylene" means a divalent six- to fourteen-membered, mono- or bi-carbocyclic ring, wherein the monocyclic ring is aromatic and at least one of the rings in the bicyclic ring is aromatic. Representative examples include phenylene, naphthylene, and indanylene, and the like.

"Cycloalkyl" refers to a non-aromatic hydrocarbon ring system (monocyclic, bicyclic, or polycyclic), including cyclized alkyl and alkenyl groups. The term "$C_{n-m}$ cycloalkyl" or "($C_n$-$C_m$) cycloalkyl" refers to a cycloalkyl that has n to m ring member carbon atoms. Cycloalkyl groups can include mono- or polycyclic (e.g., having 2, 3, or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl, or cyclohexyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl. In some embodiments, cycloalkyl includes a single saturated carbocyclic ring of three to eight ring carbons, such as cyclopropyl, cyclobutyl, cyclopentyl, and cyclohexyl. Cycloalkyl may optionally be substituted with one or more substituents, such as one, two, or three substituents. In some embodiments, the cycloalkyl substituent is selected from the group consisting of ($C_1$-$C_6$)alkyl, hydroxy, ($C_1$-$C_6$)alkoxy, halo($C_1$-$C_6$)alkyl, halo($C_1$-$C_6$)alkoxy, halo, amino, mono- and di($C_1$-$C_6$)alkylamino, hetero($C_1$-$C_6$)alkyl, acyl, aryl, and heteroaryl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety as described below under "Optional Substitution." In some aspects, a substituted cycloalkyl group can incorporate an exo- or endocyclic alkene (e.g., cyclohex-2-en-1-yl). In some aspects, a cycloalkyl group is unsubstituted or not optionally substituted.

"Cycloalkyloxycarbonyl" means a group —C(O)—OR' wherein R' is ($C_3$-$C_6$)cycloalkyl as defined herein.

"Phenyloxycarbonyl" refers to a group —C(O)—Ophenyl.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, and —N(R')—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R' is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, an additional nitrogen substituent is not present. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, and N-oxide or a protected derivative thereof.

A five-membered heteroaryl ring is a heteroaryl group having five ring atoms wherein one or more (e.g., 1, 2, 3, or 4) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl group having six ring atoms wherein one or more (e.g., 1, 2, 3, or 4) ring atoms are independently selected from N, O, and S. Exemplary six-membered ring heteroaryls are pyridyl, pyrazinyl, pyrimidinyl, triazinyl, and pyridazinyl.

"Heteroarylene" means a monocyclic, fused bicyclic, or fused tricyclic, divalent radical of 5 to 14 ring atoms containing one or more, preferably one, two, three, or four ring heteroatoms independently selected from —O—, —S(O)$_n$— (n is 0, 1, or 2), —N—, and —N(R$^{19}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{19}$ is hydrogen, alkyl, or alkenyl. Unless stated otherwise, the valencies may be located on any atom of any ring of the heteroarylene group, valency rules permitting. In particular, when the point of valency is located on the nitrogen, an additional nitrogen substituent is not present. More specifically, the term heteroaryl includes, but is not limited to, thien-diyl, benzo[d]isoxazol-diyl, benzo[d]isothiazol-diyl, 1H-indazol-diyl (optionally substituted at the N1 position with R$^{19}$), benzo[d]oxazol-diyl, benzo[d]thiazol-diyl, 1H-benzo[d]imidazol-diyl (optionally substituted at the N1 position with R$^{19}$), 1H-benzo[d][1,2,3]triazol-diyl (optionally substituted at the N1 position with R$^{19}$), imidazo[1,2-a]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl, and the like.

As used herein, "heterocycloalkyl" or "heterocyclo" refer to a non-aromatic ring or ring system, which may optionally contain one or more alkenylene groups as part of the ring structure, which has at least one heteroatom ring member independently selected from boron, nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6-, and 7-membered heterocycloalkyl groups. Heterocycloalkyl groups can include mono- or bicyclic or polycyclic (e.g., having two or three fused or bridged rings) ring systems or spirorcycles. In some embodiments, the heterocycloalkyl group is a monocyclic group having 1, 2, or 3 heteroatoms independently selected from nitrogen, sulfur, and oxygen. Ring-forming carbon atoms and heteroatoms of a heterocycloalkyl group can be optionally oxidized to form an oxo or sulfido group or other oxidized linkage (e.g., C(O), S(O), C(S), S(O)$_2$, N-oxide, and the like.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, and the like. A heterocycloalkyl group containing a fused aromatic ring can be attached through any ring-forming atom, including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

"Heterocycloalkyl" or "heterocyclo," can be unsubstituted or optionally substituted. When optionally substituted, one or more hydrogen atoms of the group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycyl group is unsubstituted or not optionally substituted.

Optional Substitution

A group is optionally substituted herein unless expressly provided otherwise. The term "optionally substituted" refers to being substituted or unsubstituted. In certain embodiments, alkyl, alkenyl, alkynyl, carbocycloalkyl, heterocyclyoalkyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted"

or "unsubstituted" "substituted" or "unsubstituted" cycloalkyl, "substituted" or "unsubstituted" heterocycloalkyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen (halo), —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —OP(R$^{cc}$)$_2$, —OP(R$^{cc}$)$_3$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, (C$_3$-C$_{10}$) carbocycloalkyl, 3-14 membered heterocycloalkyl, (C$_6$-C$_{14}$) aryl, and 5-14 membered heteroaryl, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{aa}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{bb}$ is, independently, selected from hydrogen, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, C$_{6-14}$ aryl, and 5-14 membered heteroaryl, or two R$^{bb}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{cc}$ is, independently, selected from hydrogen, (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{cc}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O) N(R$^{ff}$)$_2$, —NR$^{ff}$C(=O)R$^{ee}$, —NR$^{ff}$CO$_2$R$^{ee}$, —NR$^{ff}$C(=O)N (R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C (=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi (R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP (=O)(R$^{ee}$)$_2$, —OP(=O)(OR$^{ee}$)$_2$, (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-10 membered heterocycloalkyl, (C$_6$-C$_{10}$) aryl, 5-10 membered heteroaryl, wherein each alkyl, alkenyl, alkynyl, cycloalkyl, heterocycloalkyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from (C$_1$-C$_6$) alkyl, (C$_1$-C$_6$) perhaloalkyl, (C$_2$-C$_6$) alkenyl, (C$_2$-C$_6$) alkynyl, (C$_3$-C$_{10}$) cycloalkyl, (C$_6$-C$_{10}$) aryl, 3-10 membered heterocycloalkyl, and 3-10 membered heteroaryl, wherein each alkyl, alkenyl, alkynyl, heteroalkyl, heteroalkenyl, heteroalkynyl, cycloalkyl, heterocycloalkyl, aryl, and heteroaryl is independently substituted with 0, 1, 2, 3, 4, or 5 R$^{gg}$ groups;

each instance of R$^{ff}$ is, independently, selected from hydrogen, (C$_1$-C$_6$) alkyl, (C$_1$-C$_6$) perhaloalkyl, (C$_2$-C$_6$) alkenyl, (C$_2$-C$_6$) alkynyl, (C$_3$-C$_{10}$) cycloalkyl, (C$_6$-C$_{10}$) aryl, and 5-10 membered heteroaryl, or two R$^{ff}$ groups are joined to form a 3-10 membered heterocycloalkyl or 5-10 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{gg}$ groups; and each instance of R$^{gg}$ is, independently, halogen, —CN, —NO$_2$, —SO$_2$H, —SO$_3$H, —OH, —OC$_{1-6}$ alkyl, —ON (C$_{1-6}$ alkyl)$_2$, —N(C$_{1-6}$ alkyl)$_2$, —N(C$_{1-6}$ alkyl)$_3$$^+$X$^-$, —NH (C$_{1-6}$ alkyl)$_2$$^+$X$^-$, —NH$_2$(C$_{1-6}$ alkyl)$^+$X$^-$, —NH$_3$$^+$X$^-$, —N (OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, (C$_1$-C$_6$) alkyl, (C$_1$-C$_6$) perhaloalkyl, (C$_2$-C$_6$) alkenyl, (C$_2$-C$_6$) alkynyl, (C$_3$-C$_{10}$) cycloalkyl, (C$_6$-C$_{10}$) aryl, 3-10 membered heterocycloalkyl, 5-10 membered heteroaryl; or two geminal R$^{gg}$ substituents can be joined to form =O or =S; wherein X$^-$ is a counterion.

As noted previously, nitrogen atoms can be substituted or unsubstituted as valency permits and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, (C$_1$-C$_{10}$) alkyl, (C$_1$-C$_{10}$) perhaloalkyl, (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl, or two R$^{cc}$ groups attached to an N atom are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{33}$, —N(R$^{cc}$)$_2$, —C(=O)R$^{33}$, —C(=O)N(R$^{cc}$)$_2$, —CO$_2$R$^{33}$, —SO$_2$R$^{33}$, —C(=NR$^{cc}$)R$^{33}$, —C(=NR$^{cc}$)OR$^{33}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{33}$, —C(=S)N(R$^{cc}$)$_2$, —C(=O)SR$^{cc}$, —C(=S)SR$^{cc}$, (C$_1$-C$_{10}$) alkyl (e.g., aralkyl, heteroaralkyl), (C$_2$-C$_{10}$) alkenyl, (C$_2$-C$_{10}$) alkynyl, (C$_3$-C$_{10}$) cycloalkyl, 3-14 membered heterocycloalkyl, (C$_6$-C$_{14}$) aryl, and 5-14 membered heteroaryl groups, wherein each alkyl, alkenyl, alkynyl, cycloalkyl, heterocycloalkyl, aralkyl, aryl, and heteroaryl is independently substituted with 0, 1, 2, 3, 4, or 5 R$^{dd}$ groups, and wherein R$^{33}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{33}$) include, but are not limited to, formamide, acetamide, chloroacetamide, trichloroacetamide, trifluoroacetamide, phenyl acetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, in-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyl oxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, (phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6- sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonyl aminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, TV-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methyl amine, N-allyl amine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-tri phenyl methyl amine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, NN isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, n-copper chelate, N-zinc chelate, N-nitroamine, N-nitrosoamine, amine n-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyl oxym ethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxy ethyl, 1-(2-chloroethoxy)ethyl, 1-methyl-1-methoxy ethyl, 1-methyl-1-benzyl oxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenyl methyl, di(p-methoxyphenyl)phenylmethyl, tri(p-methoxyphenyl) methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropyl silyl (TIPS), dimethylisopropylsilyl (IPDMS), diethylisopropylsilyl (DEIPS), dimethyl thexyl silyl, t-butyldimethylsilyl (TBDMS), t-butyldiphenylsilyl (TBDPS), tribenzylsilyl, tri-p-xylylsilyl, triphenylsilyl, diphenylmethyl silyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, N-benzyl thiocarbonate, 4-ethoxy-1-napththyl carbonate, methyl dithiocarbonate, 2-iodobenzoate, 4-azidobutyrate, 4-nitro-4-methylpentanoate, o(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —OR$^{aa}$ (when the O atom is attached to a carbonyl group, wherein R$^{aa}$ is as defined herein), —O(C=O)R$^{LG}$, or —O(SO)$_2$R$^{LG}$ (e.g., tosyl, mesyl, besyl), wherein R$^{LG}$ is optionally substituted alkyl, optionally substituted aryl, or optionally substituted heteroaryl. In certain embodiments, the leaving group is a halogen.

The terms for which definitions are given above are specifically exemplified in the Examples.

"Yield" for each of the reactions described herein is expressed as a percentage of the theoretical yield.

"Patient" for the purposes of the present invention includes humans and any other animals, particularly mammals, and other organisms. Thus the methods are applicable to both human therapy and veterinary applications. In a preferred embodiment the patient is a mammal, and in a most preferred embodiment the patient is human. Examples of the preferred mammals include mice, rats, other rodents, rabbits, dogs, cats, swine, cattle, sheep, horses, and primates.

"Kinase-dependent diseases or conditions" refer to pathologic conditions that depend on the activity of one or more kinases. Kinases either directly or indirectly participate in the signal transduction pathways of a variety of cellular activities including proliferation, adhesion, migration, differentiation, and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

"Therapeutically effective amount" is an amount of a compound of the invention that, when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and orppharyngeal cancer; Lung: bronchogenic carcinoma (squamous cell, undifferentiated small cell, undifferentiated large cell, adenocarcinoma, non-small cell lung cancer), alveolar (bronchiolar) carcinoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" includes "pharmaceutically acceptable acid addition salts" and "pharmaceutically acceptable base addition salts." "Pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salts" include those derived from inorganic bases such as sodium, potassium, lithium, ammonium, calcium, magnesium, iron, zinc, copper, manganese, aluminum salts, and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

The term compound as used herein is meant to include all stereoisomers, geometric isomers, tautomers, and isotopes of the structures depicted. The term is also meant to refer to compounds of the inventions, regardless of how they are prepared, e.g., synthetically, through biological process (e.g., metabolism or enzyme conversion), or a combination thereof.

Compounds of the invention can also include all isotopes of atoms occurring in the intermediates or final compounds. Isotopes include those atoms having the same atomic number but different mass numbers. For example, isotopes of hydrogen include tritium and deuterium.

Any one of the process steps or sequences disclosed and/or claimed herein can be performed under an inert gas atmosphere, more particularly under argon or nitrogen. In addition, the methods of the present invention may be carried out as semi-continuous or continuous processes, more preferably as continuous processes.

Moreover, many of the process steps and sequences that are described herein can be telescoped.

In general, the nomenclature used in this Application is based on naming conventions adopted by the International Union of Pure and Applied Chemistry (IUPAC). Chemical structures shown herein were prepared using CHEMDRAW®. Any open valency appearing on a carbon, oxygen, or nitrogen atom in the structures herein indicates the presence of a hydrogen atom.

Embodiments of the Invention

In one aspect, the present invention comprises a compound for modulating kinase activity according to Formula I', Formula I, or Formula II.

In one aspect, the invention includes a compound of Formula I':

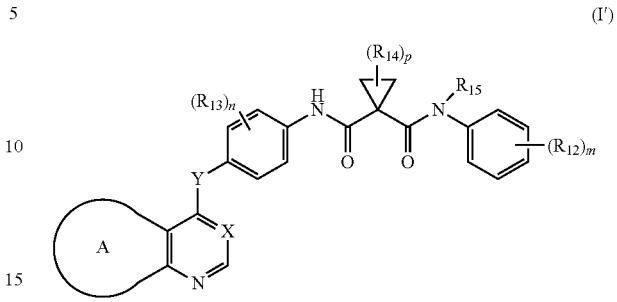

(I')

or a pharmaceutically acceptable salt thereof, wherein:
Y is selected from O, S, SO, SO$_2$, NH, and —N(C$_{1-6}$ alkyl)-;
(i) ring A is

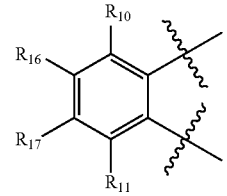

and X is N;
R$_{16}$ is selected from the group consisting of (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and R$_{17}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{16}$ or R$_{17}$ are each optionally substituted with 1, 2, 3, 4, or 5 independently selected R$^b$ substituents, provided when R$_{16}$ or R$_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$ haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{16}$ is each optionally substituted with 1, 2, 3, 4, or 5 independently selected $R^b$ substituents; and $R_{17}$ is selected from the group consisting of $(C_2-C_6)$ alkenyl; $(C_2-C_6)$ alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ and $R_{17}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected $R^b$ substituents; or (ii) ring A is

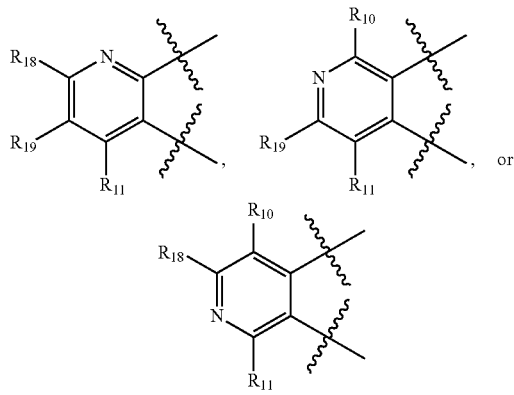

and X is N or CH, wherein $R_{18}$ and $R_{19}$ are each independently selected from —H; halo; $(C_1-C_6)$ alkyl; $(C_2-C_6)$ alkenyl; $(C_2-C_6)$ alkynyl; $(C_1-C_6)$ haloalkyl; $(C_1-C_6)$haloalkoxy; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; (4-14 membered heterocycloalkyl)-$(C_1-C_4)$ alkylene-; —CN; —NO$_2$; —OR$^a$; —SR$^a$; —NHOR$^3$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$ NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the $(C_1-C_6)$ alkyl; $(C_2-C_6)$ alkenyl; $(C_2-C_6)$ alkynyl; $(C_6-C_{10})$ aryl; $(C_3-C_{10})$ cycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl)-$(C_1-C_4)$ alkylene-; and (4-14 membered heterocycloalkyl)-$(C_1-C_4)$ alkylene- of $R_{18}$ or $R_{19}$ are each optionally substituted with 1, 2, 3, 4, or 5 independently selected $R^b$ substituents; or $R_{18}$ and $R_{19}$ taken together with the atoms to which they are attached form a fused $C_{3-7}$ cycloalkyl ring or a fused 4- to 10-membered heterocycloalkyl ring; wherein the fused $C_{3-7}$ cycloalkyl ring and fused 4- to 10-membered heterocycloalkyl ring are each optionally substituted with 1, 2, or 3 independently selected $R^b$ substituents;

$R_{10}$ and $R_{11}$ are each independently selected from the group consisting of —H; halo; $(C_1-C_6)$ alkyl; $(C_1-C_6)$ haloalkyl; $(C_1-C_6)$haloalkoxy; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkylene-; (5-14 membered heteroaryl-$(C_1-C_4)$ alkylene-; (4-14 membered heterocycloalkyl)-$(C_1-C_4)$alkylene-; —CN; —NO$_2$; —OR$^a$; —SR$^a$; —NHOR$^3$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the $(C_1-C_6)$ alkyl; $(C_6-C_{10})$ aryl; $(C_3-C_{10})$ cycloalkyl; 5-14 membered heteroaryl; 4-14 membered heterocycloalkyl; $(C_6-C_{10})$ aryl-$(C_1-C_4)$ alkylene-; $(C_3-C_{10})$ cycloalkyl-$(C_1-C_4)$ alkyl ene-; (5-14 membered heteroaryl)-$(C_1-C_4)$ alkyl ene-; and (4-14 membered heterocycloalkyl)-$(C_1-C_4)$ alkylene- of $R_1$ or $R_2$ are each optionally substituted with 1, 2, 3, 4, or 5 independently selected $R^b$ substituents;

each $R_{13}$ is independently selected from the group consisting of —H; halo; —OH; —CN; optionally substituted $(C_1-C_6)$ alkyl; $(C_1-C_6)$ alkoxy; $(C_1-C_6)$ haloalkoxy; —NH$_2$; —NH(C$_1$-C$_6$)alkyl; —N(C$_1$-C$_6$ alkyl)$_2$; and $(C_3-C_6)$ cycloalkyl; wherein the $(C_1-C_6)$ alkoxy; —NH(C$_1$-C$_6$)alkyl; —N(C$_1$-C$_6$ alkyl)$_2$; and $(C_3-C_6)$ cycloalkyl of $R_3$ are each optionally substituted with 1, 2, or 3 independently selected $R^g$ substituents;

each $R_{14}$ is independently selected from the group consisting of halo; —OH; —NH$_2$; —CN; $(C_1-C_6)$ alkyl; $(C_1-C_6)$ alkoxy; $(C_1-C_6)$ haloalkyl; $(C_1-C_6)$ haloalkoxy; —COOH; —NH(C$_1$-C$_6$)alkyl; —N(C$_1$-C$_6$ alkyl)$_2$; phenyl;

phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; (5- to 6-membered heteroaryl)-(C$_1$-C$_4$) alkylene-; and —OR$^e$; wherein the (C$_1$-C$_6$) alkyl; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; and (5- to 6-membered heteroaryl)-(C$_1$-C$_4$) alkylene- of R$_{14}$ are each optionally substituted with 1, 2, or 3 independently selected R$^g$ substituents;

R$_{15}$ is H;

each R$_{12}$ is independently selected from the group consisting of —H; halo; —OH; —COOR$^e$; —CONR$^e$R$^e$; —CN; —NH$_2$; —NH((C$_1$-C$_6$) alkyl); —N((C$_1$-C$_6$) alkyl)$_2$; (C$_1$-C$_6$) alkyl; (C$_1$-C$_6$) alkoxy; (C$_1$-C$_6$) haloalkyl; (C$_1$-C$_6$) haloalkoxy; —CONR$^a$R$^a$; —NR$^a$COR$^a$; —NR$^a$CONR$^a$R$^a$; —SO$_2$R$^a$; —NR$^a$S(O)$_2$R$^a$; —NR$^a$S(O)$_2$NR$^a$R$^a$; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene-; wherein the (C$_1$-C$_6$) alkyl; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$) alkylene-; (4- to 6-membered heterocycloalkyl)-(C$_1$-C$_4$) alkylene-; phenyl-(C$_1$-C$_2$) alkylene; and (5- or 6-membered heteroaryl)-(C$_1$-C$_4$) alkylene- of R$_{12}$ are each optionally substituted with 1, 2, or 3 independently selected R$^f$ substituents;

each R$^a$ is independently selected from the group consisting of —H; —CN; (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl-(C$_1$-C$_4$) alkylene-; and (4-14 membered heterocycloalkyl)-(C$_1$-C$_4$) alkylene-; wherein the (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$^a$ are each optionally substituted with 1, 2, 3, 4, or 5 independently selected R$^d$ substituents;

each R$^b$ is independently selected from the group consisting of halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; (4-10 membered heterocycloalkyl-(C$_1$-C$_4$) alkylene-; —CN; —OH; —NH$_2$; —NO$_2$; —NHOR$^c$; —OR$^c$; —SR$^c$; —C(O)R$^c$; —C(O)NR$^c$R$^c$; —C(O)OR$^c$; —C(O)NR$^c$S(O)$_2$R$^c$; —OC(O)R$^c$; —OC(O)NR$^c$R$^c$; —C(=NOH)R$^c$; —C(=NOH)NR$^c$; —C(=NCN)NR$^c$R$^c$; —NR$^c$C(=NCN)NR$^c$R$^c$; —C(=NR$^c$)NR$^c$R$^c$; —NR$^c$C(=NR$^c$)NR$^c$R$^c$; —NHR$^c$; —NR$^c$R$^c$; —NR$^c$C(O)R$^c$; —NR$^c$C(=NR$^c$)R$^c$; —NR$^c$C(O)OR$^c$; —NR$^c$C(O)NR$^c$R$^c$; —NR$^c$S(O)R$^c$; —NR$^c$S(O)$_2$R$^c$; —NR$^c$S(O)$_2$NR$^c$R$^c$; —S(O) R$^c$; —S(O)NR$^c$R$^c$; —S(O)$_2$R$^c$; —S(O)$_2$NR$^c$C(O)R$^c$; —Si (R$^c$)$_3$; —P(O)R$^c$R$^c$; —P(O)(OR$^c$)(OR$^c$); —B(OH)$_2$; —B(OR$^c$)$_2$; and —S(O)$_2$NR$^c$R$^c$; wherein the (C$_1$-C$_6$) alkyl; (C$_1$-C$_6$) haloalkyl; (C$_1$-C$_6$) haloalkoxy; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalky-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R$^b$ are each further optionally substituted with 1, 2, or 3 independently selected R$^d$ substituents;

each R$^c$ is independently selected from the group consisting of —H; (C$_1$-C$_6$) alkyl; (C$_1$-C$_6$) haloalkyl; (C$_2$-C$_6$) alkenyl; (C$_2$-C$_6$) alkynyl; (C$_6$-C$_{10}$) aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl-(C$_1$-C$_4$) alkylene-; and (4-10 membered heterocycloalkyl)-(C$_1$-C$_4$) alkylene-; wherein the (C$_1$-C$_6$) alkyl; (C$_2$-C$_6$) alkenyl; (C$_2$-C$_6$) alkynyl; (C$_6$-C$_{10}$)aryl; (C$_3$-C$_{10}$) cycloalkyl; 5-10 membered heteroaryl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R$^c$ are each optionally substituted with 1, 2, 3, 4, or 5 independently selected R$^f$ substituents;

each R$^d$ is independently selected from the group consisting of (C$_1$-C$_6$) alkyl; (C$_1$-C$_6$) haloalkyl; halo; (C$_6$-C$_{10}$) aryl; 5-10 membered heteroaryl; (C$_3$-C$_{10}$) cycloalkyl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; (4-10 membered heterocycloalkyl)-(C$_1$-C$_4$) alkylene-; —CN; —NH$_2$; —NHOR$^6$; —OR$^e$; —SR$^e$; —C(O)R$^e$; —C(O)NR$^e$R$^e$; —C(O)OR$^e$; —OC(O)R$^e$; —OC(O)NR$^e$R$^e$; —NHR$^e$; —NR$^e$R$^e$; —NR$^e$C (O)R$^e$; —NR$^e$C(O)NR$^e$R$^e$; —NR$^e$C(O)OR$^e$; —C(=NR$^e$) NR$^e$R$^e$; —NR$^e$C(=NR$^e$)NR$^e$R$^e$; —NR$^e$C(=NOH)NR$^e$R$^e$; —NR$^e$C(=NCN)NR$^e$R$^e$; —S(O)R$^e$; —S(O)NR$^e$R$^e$; —S(O)$_2$ R$^e$; —NR$^e$S(O)$_2$R$^e$; —NR$^e$S(O)$_2$NR$^e$R$^e$; and —S(O)$_2$NR$^e$R$^e$; wherein the (C$_1$-C$_6$) alkyl; (C$_1$-C$_6$) haloalkyl; (C$_6$-C$_{10}$) aryl; 5-10 membered heteroaryl; (C$_3$-C$_{10}$) cycloalkyl; 4-10 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-10 membered heteroaryl)-(C$_1$-C$_4$) alkylene-; and (4-10 membered heterocycloalkyl)-(C$_1$-C$_4$) alkylene- of R$^d$ are each optionally substituted with 1, 2, or 3 independently selected R$^f$ substituents;

each R$^e$ is independently selected from the group consisting of —H; (C$_1$-C$_6$) alkyl; (C$_3$-C$_6$) cycloalkyl; (C$_3$-C$_6$) cycloalkyl-(C$_1$-C$_4$) alkylene-; (C$_6$-C$_{10}$) aryl; (C$_6$-C$_{10}$) aryl-(C$_1$-C$_4$) alkylene-; 5- or 6-membered heteroaryl; (5- or 6-membered heteroaryl)-(C$_1$-C$_4$) alkylene-; 4-7-membered heterocycloalkyl; (4-7-membered heterocycloalkyl)-(C$_1$-C$_4$) alkylene-; (C$_1$-C$_6$) haloalkyl; (C$_1$-C$_6$) haloalkoxy; (C$_2$-C$_4$) alkenyl; and (C$_2$-C$_4$) alkynyl; wherein the (C$_1$-C$_4$) alkyl; (C$_3$-C$_6$) cycloalkyl; (C$_6$-C$_{10}$) aryl; 5 or 6-membered heteroaryl; 4-7-membered heterocycloalkyl; (C$_6$-C$_{10}$) aryl-(C$_1$-C$_4$) alkylene-; (5- or 6-membered heteroaryl)-(C$_1$-C$_4$) alkylene-; (4-7-membered heterocycloalkyl)-(C$_1$-C$_4$) alkylene-; (C$_2$-C$_4$) alkenyl; and (C$_2$-C$_4$) alkynyl of R$^e$ are each optionally substituted with 1, 2, or 3 R$^f$ substituents;

or any two R$^a$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^c$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

or any two R$^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo; —OH; —CN; —COOH; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$)haloalkyl; (C$_1$-C$_6$) haloalkoxy; phenyl; 5-6 membered heteroaryl; 4-6 membered heterocycloalkyl; and (C$_3$-C$_6$) cycloalkyl; wherein the (C$_1$-C$_6$) alkyl; phenyl; (C$_3$. C$_6$) cycloalkyl; 4-6 membered heterocycloalkyl; and 5-6 membered heteroaryl of $R^f$ are each optionally substituted with 1, 2, or 3 substituents selected from halo; —OH; —CN; —COOH; —NH$_2$; (C$_1$-C$_4$) alkyl; (C$_1$-C$_4$) alkoxy; (C$_1$-C$_4$) haloalkyl; (C$_1$-C$_4$) haloalkoxy; phenyl; (C$_3$-C$_{10}$) cycloalkyl; 5-6 membered heteroaryl; and 4-6 membered heterocycloalkyl;

each $R^g$ is independently selected from the group consisting of halo; —OH; —CN; —COOH; —COO—(C$_1$-C$_4$) alkyl; —NH$_2$; —NH—(C$_1$-C$_6$) alkyl; —N((C$_1$-C$_6$) alky)$_2$; (C$_1$-C$_6$) alkyl; (C$_1$-C$_6$) alkoxy; (C$_1$-C$_6$) alkylthio; (C$_1$-C$_6$) haloalkyl; (C$_1$-C$_6$) haloalkoxy; phenyl; 5-6 membered heteroaryl; 4-6 membered heterocycloalkyl; and (C$_3$-C$_6$) cycloalkyl;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4;

provided that when X is C—H, Ring A is

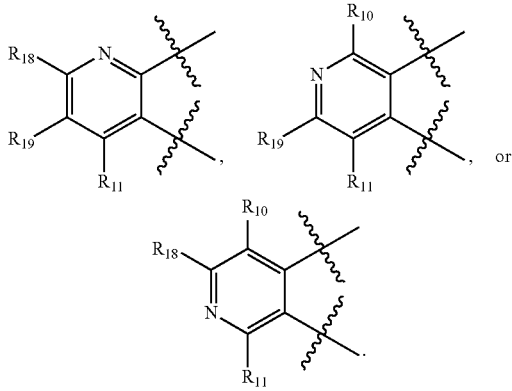

In one aspect, the invention includes a compound of Formula I':

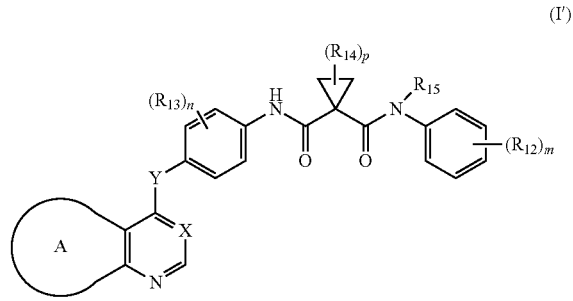

or a pharmaceutically acceptable salt thereof, wherein:

X is N or CH;

Y is selected from O, S, SO, SO$_2$, NH, and —N(C$_{1-6}$ alkyl)-;

(i) ring A is

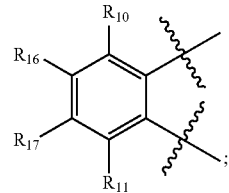

$R_{16}$ is selected from the group consisting of (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; and $R_{17}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$ NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of $R_{16}$ or $R_{17}$ are each optionally substituted with 1, 2, 3, 4, or 5 independently selected $R^b$ substituents, provided when $R_{16}$ or $R_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or $R_{16}$ is selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$) haloalkoxy; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN) NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O) R$^a$; —P(O)R$^a$R$^a$; —P(O)(OR$^a$)(OR$^a$); —B(OH)$_2$;

—B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{16}$ is each optionally substituted with 1, 2, 3, 4, or 5 independently selected R$^b$ substituents; and R$_{17}$ is selected from the group consisting of (C$_2$-C$_6$) alkenyl; (C$_2$-C$_6$) alkynyl; —CN; —NHOH, —C(O)R$^a$; —C(O)NR$^a$R$^a$; —C(O)NHOR$^a$; —C(O)OR$^a$; —C(O)NR$^a$S(O)$_2$R$^a$; —OC(O)NR$^a$R$^a$; C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —S(O)NR$^a$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$, provided when R$_{16}$ or R$_{17}$ is 5-membered heteroaryl or 5-7 membered heterocycloalkyl, then the 5-membered heteroaryl or 5-7 membered heterocycloalkyl does not connect to the fused phenyl ring moiety through a ring nitrogen atom; or R$_{16}$ and R$_{17}$ taken together with the atoms to which they are attached form a fused C$_{3-7}$ cycloalkyl ring or a fused 4- to 10-membered heterocycloalkyl ring; wherein the fused C$_{3-7}$ cycloalkyl ring and fused 4- to 10-membered heterocycloalkyl ring are each optionally substituted with 1, 2, or 3 independently selected R$^b$ substituents; or (ii) ring A is

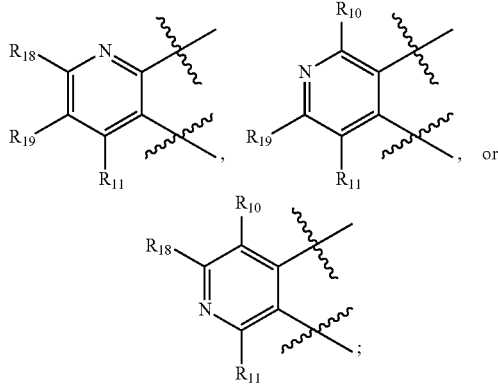

R$_{18}$ and R$_{19}$ are each independently selected from —H; halo; (C$_1$-C$_6$) alkyl; (C$_2$-C$_6$) alkenyl; (C$_2$-C$_6$) alkynyl; (C$_1$-C$_6$) haloalkyl; (C$_1$-C$_6$)haloalkoxy; (C$_6$-C$_{10}$) aryl; (C$_3$-C$_{10}$) cycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^3$; —C(O)R$^a$; —C(O)NR$^a$R$^a$; —C(O)NHOR$^a$; —C(O)OR$^a$; —C(O)NR$^a$S(O)$_2$R$^a$; —OC(O)R$^a$; —OC(O)NR$^a$R$^a$; —NHR$^3$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$ NR$^a$C(O)R$^a$; —P(O)R$^a$R$^a$; —P(O)(OR$^a$)(OR$^a$); —B(OH)$_2$; —B(OR$^a$)$_2$; and —S(O)$_2$NR$^a$R$^a$; wherein the (C$_1$-C$_6$) alkyl; (C$_2$-C$_6$) alkenyl; (C$_2$-C$_6$) alkynyl; (C$_6$-C$_{10}$) aryl; (C$_3$-C$_{10}$) cycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_{18}$ or R$_{19}$ are each optionally substituted with 1, 2, 3, 4, or 5 independently selected R$^b$ substituents; or R$_{18}$ and R$_{19}$ taken together with the atoms to which they are attached form a fused C$_{3-7}$ cycloalkyl ring or a fused 4- to 10-membered heterocycloalkyl ring; wherein the fused C$_{3-7}$ cycloalkyl ring and fused 4- to 10-membered heterocycloalkyl ring are each optionally substituted with 1, 2, or 3 independently selected R$^b$ substituents;

R$_{10}$ and R$_{11}$ are each independently selected from the group consisting of —H; halo; (C$_1$-C$_6$) alkyl; (C$_1$-C$_6$) haloalkyl; (C$_1$-C$_6$)haloalkoxy; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl-(C$_1$-C$_4$) alkylene-; (4-14 membered heterocycloalkyl)-(C$_1$-C$_4$) alkylene-; —CN; —NO$_2$; —OR$^a$; —SR$^a$; —NHOR$^3$; —C(O)R$^a$; —C(O)NR$^a$R$^a$; —C(O)OR$^a$; —C(O)NR$^a$S(O)$_2$R$^a$; —OC(O)R$^a$; —OC(O)NR$^a$R$^a$; —NHR$^a$; —NR$^a$R$^a$; —NR$^a$C(O)R$^a$; —NR$^a$C(=NR$^a$)R$^a$; —NR$^a$C(O)OR$^a$; —NR$^a$C(O)NR$^a$R$^a$; —C(=NR$^a$)R$^a$; —C(=NOH)R$^a$; —C(=NOH)NR$^a$; —C(=NCN)NR$^a$R$^a$; —NR$^a$C(=NCN)NR$^a$R$^a$; —C(=NR$^a$)NR$^a$R$^a$; —NR$^a$C(=NR$^a$)NR$^a$R$^a$; —NR$^a$S(O)R$^a$; —NR$^a$S(O)$_2$R$^a$; —NR$^a$S(O)$_2$NR$^a$R$^a$; —S(O)R$^a$; —S(O)NR$^a$R$^a$; —S(O)$_2$R$^a$; —S(O)$_2$NR$^a$C(O)R$^a$; —P(O)R$^a$R$^a$; —P(O)(OR$^a$)(OR$^a$); —B(OH)$_2$; —B(OR$^a$)$_2$; and S(O)$_2$NR$^a$R$^a$; wherein the (C$_1$-C$_6$) alkyl; (C$_6$-C$_{10}$) aryl; (C$_3$-C$_{10}$) cycloalkyl; 5-14 membered heteroaryl; 4-14 membered heterocycloalkyl; (C$_6$-C$_{10}$) aryl-(C$_1$-C$_4$) alkylene-; (C$_3$-C$_{10}$) cycloalkyl-(C$_1$-C$_4$) alkylene-; (5-14 membered heteroaryl)-(C$_1$-C$_4$) alkylene-; and (4-14 membered heterocycloalkyl)-(C$_1$-C$_4$) alkylene- of R$_1$ or R$_2$ are each optionally substituted with 1, 2, 3, 4, or 5 independently selected R$^b$ substituents;

each R$_{13}$ is independently selected from the group consisting of —H; halo; —OH; —CN; optionally substituted (C$_1$-C$_6$) alkyl; (C$_1$-C$_6$) alkoxy; (C$_1$-C$_6$) haloalkoxy; —NH$_2$; —NH(C$_1$-C$_6$)alkyl; —N(C$_1$-C$_6$ alkyl)$_2$; and (C$_3$-C$_6$) cycloalkyl; wherein the (C$_1$-C$_6$) alkoxy; —NH(C$_1$-C$_6$)alkyl; —N(C$_1$-C$_6$ alkyl)$_2$; and (C$_3$-C$_6$) cycloalkyl of R$_3$ are each optionally substituted with 1, 2, or 3 independently selected R$^g$ substituents;

each R$_{14}$ is independently selected from the group consisting of halo; —OH; —NH$_2$; —CN; (C$_1$-C$_6$) alkyl; (C$_1$-C$_6$) alkoxy; (C$_1$-C$_6$) haloalkyl; (C$_1$-C$_6$) haloalkoxy; —COOH; —NH(C$_1$-C$_6$)alkyl; —N(C$_1$-C$_6$ alkyl)$_2$; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; (5- to 6-membered heteroaryl)-(C$_1$-C$_4$) alkylene-; and —OR$^e$; wherein the (C$_1$-C$_6$) alkyl; phenyl; phenyl-(C$_1$-C$_2$) alkylene; (C$_3$-C$_6$) cycloalkyl; (C$_3$-C$_6$) cycloalkyl-(C$_1$-C$_4$) alkylene-; 4- to 6-membered heterocycloalkyl; (4- to 6-membered heterocycloalkyl)-(C$_1$-C$_4$) alkylene-; 5- to 6-membered heteroaryl; and (5- to 6-membered heteroaryl)-(C$_1$-C$_4$) alkylene- of R$_{14}$ are each optionally substituted with 1, 2, or 3 independently selected R$^g$ substituents;

R$_{15}$ is H;

each R$_{12}$ is independently selected from the group consisting of —H; halo; —OH; —COOR$^e$; —CONR$^e$R$^e$; —CN; —NH$_2$; —NH((C$_1$-C$_6$) alkyl); —N((C$_1$-C$_6$) alkyl)$_2$; (C$_1$-C$_6$) alkyl; (C$_1$-C$_6$) alkoxy; (C$_1$-C$_6$) haloalkyl; (C$_1$-C$_6$) haloalkoxy; —CONR$^a$R$^a$; —NR$^a$COR$^a$; —NR$^a$CONR$^a$R$^a$; —SO$_2$R$^a$; —NR$^a$S(O)$_2$R$^a$; —NR$^a$S(O)$_2$NR$^a$R$^a$; (C$_3$-C$_6$) cycloalkyl; 4- to 6-membered heterocycloalkyl; phenyl; 5- or 6-membered heteroaryl; (C$_3$-C$_6$) cycloalkyl-(C$_1$-C$_4$)

alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene-; wherein the ($C_1$-$C_6$) alkyl; ($C_3$-$C_6$) cycloalkyl; 4- to 6-membered heterocycloalkyl; phenyl; 5- or 6-membered heteroaryl; ($C_3$-$C_6$) cycloalkyl-($C_1$-$C_4$) alkylene-; (4- to 6-membered heterocycloalkyl)-($C_1$-$C_4$) alkylene-; phenyl-($C_1$-$C_2$) alkylene; and (5- or 6-membered heteroaryl)-($C_1$-$C_4$) alkylene- of $R_{12}$ are each optionally substituted with 1, 2, or 3 independently selected $R^f$ substituents;

each $R^a$ is independently selected from the group consisting of —H; —CN; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl-($C_1$-$C_4$) alkylene-; and (4-14 membered heterocycloalkyl)-($C_1$-$C_4$) alkylene-; wherein the ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-14 membered heteroaryl; 4-14 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-14 membered heteroaryl)-($C_1$-$C_4$) alkylene-; and (4-14 membered heterocycloalkyl)-($C_1$-$C_4$) alkylene- of $R^a$ are each optionally substituted with 1, 2, 3, 4, or 5 independently selected $R^d$ substituents;

each $R^b$ is independently selected from the group consisting of halo; ($C_1$-$C_6$) alkyl; ($C_2$-$C_6$) alkenyl; ($C_2$-$C_6$) alkynyl; ($C_1$-$C_6$) haloalkyl; ($C_1$-$C_6$) haloalkoxy; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkyl ene-; —CN; —OH; —$NH_2$; —$NO_2$; —$NHOR^c$; —$OR^c$; —$SR^c$; —$C(O)R^c$; —$C(O)NR^cR^c$; —$C(O)OR^c$; —$C(O)NR^cS(O)_2R^c$; —$OC(O)R^c$; —$OC(O)NR^cR^c$; —$C(=NOH)R^c$; —$C(=NOH)NR^cR^c$; —$C(=NCN)NR^cR^c$; —$NR^cC(=NCN)NR^cR^c$; —$C(=NR^c)NR^cR^c$; —$NR^cC(=NR^c)NR^cR^c$; —$NHR^c$; —$NR^cR^c$; —$NR^cC(O)R^c$; —$NR^cC(=NR^c)R^c$; —$NR^cC(O)OR^c$; —$NR^cC(O)NR^cR^c$; —$NR^cS(O)R^c$; —$NR^cS(O)_2R^c$; —$NR^cS(O)_2NR^cR^c$; —$S(O)R^c$; —$S(O)NR^cR^c$; —$S(O)_2R^c$; —$S(O)_2NR^cC(O)R^c$; —$Si(R^c)_3$; —$P(O)R^cR^c$; —$P(O)(OR^c)(OR^c)$; —$B(OH)_2$; —$B(OR^c)_2$; and —$S(O)_2NR^cR^c$; wherein the ($C_1$-$C_6$) alkyl; ($C_1$-$C_6$) haloalkyl; ($C_1$-$C_6$) haloalkoxy; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalky-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^b$ are each further optionally substituted with 1, 2, or 3 independently selected $R^d$ substituents;

each $R^c$ is independently selected from the group consisting of —H; ($C_1$-$C_6$) alkyl; ($C_1$-$C_6$) haloalkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene-; wherein the ($C_1$-$C_6$) alkyl; ($C_2$-$C_6$) alkenyl; ($C_2$-$C_6$) alkynyl; ($C_6$-$C_{10}$) aryl; ($C_3$-$C_{10}$) cycloalkyl; 5-10 membered heteroaryl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^c$ are each optionally substituted with 1, 2, 3, 4, or 5 independently selected $R^f$ substituents;

each $R^d$ is independently selected from the group consisting of ($C_1$-$C_6$) alkyl; ($C_1$-$C_6$) haloalkyl; halo; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; (4-10 membered heterocycloalkyl)-($C_1$-$C_4$) alkylene-; —CN; —$NH_2$; —$NHOR^6$; —$OR^e$; —$SR^e$; —$C(O)R^e$; —$C(O)NR^eR^e$; —$C(O)OR^e$; —$OC(O)R^e$; —$OC(O)NR^eR^e$; —$NHR^e$; —$NR^eR^e$; —$NR^eC(O)R^e$; —$NR^eC(O)NR^eR^e$; —$NR^eC(O)OR^e$; —$C(=NR^e)NR^eR^e$; —$NR^eC(=NR^e)NR^eR^e$; —$NR^eC(=NOH)NR^eR^e$; —$NR^eC(=NCN)NR^eR^e$; —$S(O)R^e$; —$S(O)NR^eR^e$; —$S(O)_2 R^e$; —$NR^eS(O)_2R^e$; —$NR^eS(O)_2NR^eR^e$; and —$S(O)_2NR^eR^e$; wherein the ($C_1$-$C_6$) alkyl; ($C_1$-$C_6$) haloalkyl; ($C_6$-$C_{10}$) aryl; 5-10 membered heteroaryl; ($C_3$-$C_{10}$) cycloalkyl; 4-10 membered heterocycloalkyl; ($C_6$-$C_{10}$) aryl-($C_1$-$C_4$) alkylene-; ($C_3$-$C_{10}$) cycloalkyl-($C_1$-$C_4$) alkylene-; (5-10 membered heteroaryl)-($C_1$-$C_4$) alkylene-; and (4-10 membered heterocycloalkyl)-($C_1$-$C_4$) alkylene- of $R^d$ are each optionally substituted with 1, 2, or 3 independently selected $R^f$ substituents;

each $R^e$ is independently selected from the group consisting of —H; ($C_1$-$C_6$) alkyl; ($C_3$-$C_6$) cycloalkyl; ($C_3$-$C_6$) cycloalkyl-($C_1$-$C_4$) alkylene-; ($C_6$-$C_{10}$) aryl; ($C_6$-$C_{10}$) aryl-($C_1$-$C_4$) alkylene-; 5- or 6-membered heteroaryl; (5- or 6-membered heteroaryl)-($C_1$-$C_4$) alkylene-; 4-7-membered heterocycloalkyl; (4-7-membered heterocycloalkyl)-($C_1$-$C_4$) alkylene-; ($C_1$-$C_6$) haloalkyl; ($C_1$-$C_6$) haloalkoxy; ($C_2$-$C_4$) alkenyl; and ($C_2$-$C_4$) alkynyl; wherein the ($C_1$-$C_4$) alkyl; ($C_3$-$C_6$) cycloalkyl; ($C_6$-$C_{10}$)aryl; 5 or 6-membered heteroaryl; 4-7-membered heterocycloalkyl; ($C_6$-$C_{10}$) aryl-($C_1$-$C_4$) alkylene-; (5- or 6-membered heteroaryl)-($C_1$-$C_4$) alkylene-; (4-7-membered heterocycloalkyl)-($C_1$-$C_4$) alkylene-; ($C_2$-$C_4$) alkenyl; and ($C_2$-$C_4$) alkynyl of $R^e$ are each optionally substituted with 1, 2, or 3 $R^f$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo; —OH; —CN; —COOH; —$NH_2$; —NH—($C_1$-$C_6$) alkyl; —N(($C_1$-$C_6$) alky)$_2$; ($C_1$-$C_6$) alkyl; ($C_1$-$C_6$) alkoxy; ($C_1$-$C_6$) alkylthio; ($C_1$-$C_6$) haloalkyl; ($C_1$-$C_6$) haloalkoxy; phenyl; 5-6 membered heteroaryl; 4-6 membered heterocycloalkyl; and ($C_3$-$C_6$) cycloalkyl; wherein the ($C_1$-$C_6$) alkyl; phenyl; ($C_3$-$C_6$) cycloalkyl; 4-6 membered heterocycloalkyl; and 5-6 membered heteroaryl of $R^f$ are each optionally substituted with 1, 2, or 3 substituents selected from halo; —OH; —CN; —COOH; —$NH_2$; ($C_1$-$C_4$) alkyl; ($C_1$-$C_4$) alkoxy; ($C_1$-$C_4$) haloalkyl; ($C_1$-$C_4$) haloalkoxy; phenyl; ($C_3$-$C_{10}$) cycloalkyl; 5-6 membered heteroaryl; and 4-6 membered heterocycloalkyl;

each $R^g$ is independently selected from the group consisting of halo; —OH; —CN; —COOH; —COO—($C_1$-$C_4$) alkyl; —$NH_2$; —NH—($C_1$-$C_6$) alkyl; —N(($C_1$-$C_6$) alky)$_2$; ($C_1$-$C_6$) alkyl; ($C_1$-$C_6$) alkoxy; ($C_1$-$C_6$) alkylthio; ($C_1$-$C_6$)

haloalkyl; (C₁-C₆) haloalkoxy; phenyl; 5-6 membered heteroaryl; 4-6 membered heterocycloalkyl; and (C₃-C₆) cycloalkyl;

the ring nitrogen atom on the quinoline moiety in Formula A is optionally oxidized;

the subscript n is an integer of 1, 2, 3, or 4;
the subscript m is an integer of 1, 2, 3, 4, or 5; and
the subscript p is an integer of 0, 1, 2, 3, or 4;
provided that when X is C—H, Ring A is

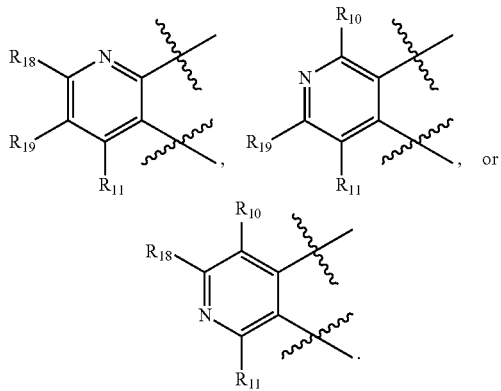

In one embodiment of this aspect, X is N. In another embodiment, X is CH;

In one embodiment of this aspect, Y is selected from O, NH, and —N(C₁₋₆ alkyl)-. In a further aspect, Y is O.

In one embodiment of this aspect, R₁₆ is selected from —H, halo, —CN, (C₁-C₆) alkyl, (C₆-C₁₀)aryl, (C₃-C₁₀) cycloalkyl, 5-14 membered heteroaryl, 4-14 membered heterocycloalkyl, —CN, —NO₂, —ORᵃ, —SRᵃ, —NHOR³, —C(O)Rᵃ, —C(O)NRᵃRᵃ, —C(O)NHORᵃ, —C(O)ORᵃ, —C(O)NRᵃS(O)₂Rᵃ, —OC(O)Rᵃ, —OC(O)NRᵃRᵃ, —NHRᵃ, —NRᵃRᵃ, and —NRᵃC(O)Rᵃ.

In a further embodiment, R₁₆ is selected from —H, halo, —CN, (C₁-C₆) alkyl, 5-14 membered heteroaryl, —O(C₁-C₆), —C(O)(C₁-C₆ alkyl), —C(O)N(C₁-C₆ alkyl)₂, —C(O)NH(C₁-C₆ alkyl), —C(O)NH₂, —C(O)NH(4-6 membered heterocycloalkyl), —C(O)NH(C₃-C₁₀ cycloalkyl), —C(O)NH(C₁-C₄ alkylene-(4-6 membered heterocycloalkyl)), —C(O)NH(C₁-C₄ alkylene-(C₃-C₁₀ cycloalkyl)), —C(O)O(C₁-C₆ alkyl), —NH(C₁-C₆ alkyl), —N(C₁-C₆ alkyl)₂, and —NHC(O)(C₁-C₆ alkyl). In still a further embodiment, R₁₆ is selected from —H, —CN, 5-14 membered heteroaryl, —C(O)NH₂, —C(O)NH(4-6 membered heterocycloalkyl), —C(O)NH(C₃-C₁₀ cycloalkyl), —C(O)NH(C₁-C₄ alkylene-(4-6 membered heterocycloalkyl)), —C(O)O(C₁-C₆ alkyl), —NH(C₁-C₆ alkyl), —N(C₁-C₆ alkyl)₂, and —NHC(O)(C₁-C₆ alkyl).

In some embodiments, each (C₁-C₆) alkyl, (C₆-C₁₀) aryl, (C₃-C₁₀) cycloalkyl, 5-14 membered heteroaryl, or 4-14 membered heterocycloalkyl of R₁₆ is optionally substituted with 1, 2, 3, 4, or 5 substituents independently selected from halo, (C₁-C₆) alkyl, —CN, —NO₂, phenyl, (C₁-C₆) alkoxy, and oxo. In a further embodiment, each (C₁-C₆) alkyl, (C₆-C₁₀) aryl, (C₃-C₁₀) cycloalkyl, 5-14 membered heteroaryl, or 4-14 membered heterocycloalkyl of R₁₆ is optionally substituted with 1, 2, 3, 4, or 5 (C₁-C₆) alkyl substituents.

In one embodiment, R₁₆ is selected from H, —CN, (oxetan-3-yl)carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, pyrazol-4-yl, 1-methyl-pyrazol-4-yl.

In some embodiments, R₁₇ is selected from the group consisting of —H, halo, (C₁-C₆) alkyl, (C₂-C₆) alkenyl, (C₂-C₆) alkynyl, —CN, —NO₂, —ORᵃ, —SRᵃ, —NHOH, —C(O)Rᵃ, —C(O)NRᵃRᵃ, —C(O)NHORᵃ, —C(O)ORᵃ, —C(O)NRᵃS(O)₂Rᵃ, —OC(O)NRᵃRᵃ, C(=NRᵃ)Rᵃ, —C(=NOH)Rᵃ, —C(=NOH)NRᵃ, —C(=NCN)NRᵃRᵃ, —NRᵃC(=NCN)NRᵃRᵃ, —C(=NRᵃ)NRᵃRᵃ, —S(O)NRᵃRᵃ, —S(O)₂NRᵃC(O)Rᵃ, —P(O)RᵃRᵃ, —P(O)(ORᵃ)(ORᵃ), —B(OH)₂, —B(ORᵃ)₂, and S(O)₂NRᵃRᵃ. In a further embodiment, R₁₇ is selected from the group consisting of —H, halo, (C₁-C₆) alkyl, —CN, —NO₂, —O(C₁-C₆) alkyl, —C(O)(C₁-C₆) alkyl, —C(O)NH(C₁-C₆) alkyl, —C(O)N((C₁-C₆) alkyl)₂, and —C(O)O(C₁-C₆) alkyl. In still a further embodiment, R₁₇ is selected from the group consisting of —H, halo, (C₁-C₆) alkyl, —CN, —NO₂, and —O(C₁-C₆) alkyl. In yet a further embodiment, R₁₇ is selected from the group consisting of —H, halo, (C₁-C₆) alkyl, and —O(C₁-C₆) alkyl. In yet a further embodiment, R₁₇ is selected from the group consisting of —H, and methoxy.

In one embodiment of this aspect, ring A is

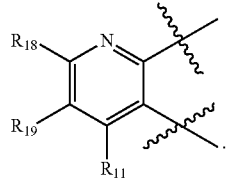

In another embodiment of this aspect, ring A is

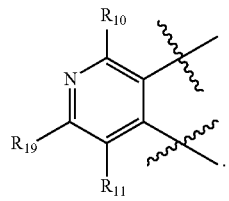

In yet another embodiment of this aspect, ring A is

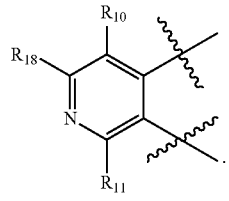

In one embodiment of this aspect, R₁₈ and R₁₉ are each independently selected from —H, halo, (C₁-C₆) alkyl, (C₁-C₆) haloalkyl, (C₁-C₆) haloalkoxy, (C₆-C₁₀) aryl, (C₃-C₁₀) cycloalkyl, 4-14 membered heterocycloalkyl, phenyl, 5-14 membered heteroaryl, (C₆-C₁₀) aryl-(C₁-C₄) alkylene-, (C₃-C₁₀) cycloalkyl-(C₁-C₄) alkylene-, (5-14 membered heteroaryl)-(C₁-C₄) alkylene-, (4-14 membered heterocycloalkyl)-(C₁-C₄) alkylene-, —CN, —NO₂, —ORᵃ, —SRᵃ, —NHORᵃ, —C(O)Rᵃ, —C(O)NRᵃRᵃ, —C(O)NHORᵃ, —C(O)ORᵃ, —C(O)NRᵃS(O)₂Rᵃ, —OC(O)Rᵃ, —OC(O)

$NR^aR^a$, —$NHR^a$, —$NR^aR^a$, —$NR^aC(O)R^a$, —$NR^aC(=NR^a)R^a$, —$NR^aC(O)OR^a$, and —$NR^aC(O)NR^aR^a$. In another embodiment, $R_{18}$ and $R_{19}$ are each independently selected from —H, halo, ($C_1$-$C_6$) alkyl, ($C_1$-$C_6$) haloalkyl, ($C_1$-$C_6$)haloalkoxy, ($C_6$-$C_{10}$) aryl, ($C_3$-$C_{10}$) cycloalkyl, 4-14 membered heterocycloalkyl, phenyl, 5-14 membered heteroaryl, —CN, —$NO_2$, —$OR^a$, —$SR^a$, —$C(O)R^a$, —$C(O)NR^aR^a$, —$C(O)OR^a$, —$NHR^a$, —$NR^aR^a$, and —$NR^aC(O)R^a$. In a further embodiment, $R_{18}$ and $R_{19}$ are each independently selected from —H, halo, ($C_1$-$C_6$) alkyl, phenyl, ($C_3$-$C_{10}$) cycloalkyl, 4-14 membered heterocycloalkyl, 5-14 membered heteroaryl, —CN, —O($C_1$-$C_6$) alkyl, —C(O)($C_1$-$C_6$) alkyl, —$C(O)NH_2$, —C(O)NH($C_1$-$C_6$) alkyl, —C(O)N(($C_1$-$C_6$) alkyl)$_2$, —C(O)O($C_1$-$C_6$) alkyl, —NH($C_1$-$C_6$) alkyl, —N(($C_1$-$C_6$) alkyl)$_2$, and —NHC(O)($C_1$-$C_6$) alkyl. In a further embodiment, $R_{18}$ and $R_{19}$ are each independently selected from —H, halo, ($C_1$-$C_6$) alkyl, 5-14 membered heteroaryl, —CN, —O($C_1$-$C_4$ alkylene-(4-14 membered heterocycloalkyl)), O($C_1$-$C_6$ alkoxy-$C_1$-$C_6$ alkyl)), —$C(O)NH_2$, —C(O)NH($C_1$-$C_6$) alkyl, —C(O)N(($C_1$-$C_6$) alkyl)$_2$, and —$NH_2$.

In one embodiment, the ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, 5-14 membered heteroaryl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, or (4-14 membered heterocycloalkyl)-($C_1$-$C_4$) alkylene-, of $R_{18}$ or $R_{19}$ are each optionally substituted with 1, 2, 3, 4, or 5 substituents independently selected from halo, ($C_1$-$C_6$) alkyl, —CN, —OH, and —C(O)$OR_x$, wherein $R_x$ is ($C_1$-$C_6$) alkyl, phenyl, or benzyl. In a further embodiment, the ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, 5-14 membered heteroaryl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, or (4-14 membered heterocycloalkyl)-($C_1$-$C_4$) alkylene-, of $R_{18}$ or $R_{19}$ are each optionally substituted with —C(O)$OR_x$, wherein $R_x$ is ($C_1$-$C_6$) alkyl, phenyl, or benzyl.

In another embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 independently selected $R^b$ substituents. In a further embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 substituents independently selected from halo, —CN, —$NO_2$, —OH, OXO, ($C_1$-$C_6$) alkyl, —O($C_1$-$C_6$) alkyl, —C(O)($C_1$-$C_6$) alkyl, —$C(O)NH_2$, —C(O)NH($C_1$-$C_6$) alkyl, —C(O)N(($C_1$-$C_6$) alkyl)$_2$, —C(O)O($C_1$-$C_6$) alkyl, —NH($C_1$-$C_6$) alkyl, —N(($C_1$-$C_6$) alkyl)$_2$, and —NHC(O)($C_1$-$C_6$) alkyl. In still a further embodiment, $R_{18}$ and $R_{19}$ taken together with the atoms to which they are attached form a fused $C_3$-$C_7$ cycloalkyl ring or a fused 4- to 10-membered heterocycloalkyl ring, wherein the fused $C_3$-$C_7$ cycloalkyl ring and fused 4- to 10-membered heterocycloalkyl ring are each optionally substituted with 1, 2, or 3 substituents independently selected from halo, ($C_1$-$C_6$) alkyl, and —O($C_1$-$C_6$) alkyl. In yet a further embodiment, $R_{18}$ and $R_{19}$ taken together with the atoms to which they are attached form a fused ring selected from

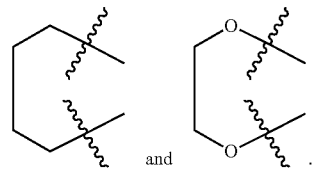 [SMILES: *CCCC* ; *OCCO*]

In one embodiment, $R_{18}$ is selected from H, halo, $NH_2$, methoxy, methyl, —CN, carbamoyl, dimethylcarbamoyl, methylcarbamoyl, pyrazol-4-yl, 1-methyl-pyrazol-4-yl, and 2-methyl-pyrazol-3-yl.

In one embodiment, $R_{19}$ is selected from H, halo, methoxy, methyl, 3-morphlinopropoxy, 2-methoxyethoxy, 1-methyl-pyrazol-4-yl.

In one embodiment of this aspect, each $R_{13}$ is independently selected from the group consisting of —H, halo, —OH, —CN, optionally substituted ($C_1$-$C_6$) alkyl, ($C_1$-$C_6$) alkoxy, ($C_1$-$C_6$) haloalkoxy, —$NH_2$, —NH($C_1$-$C_6$)alkyl, —N($C_1$-$C_6$ alkyl)$_2$, and ($C_3$-$C_6$) cycloalkyl, wherein the ($C_1$-$C_6$) alkyl, ($C_1$-$C_6$) alkoxy, —NH($C_1$-$C_6$)alkyl, —N($C_1$-$C_6$ alkyl)$_2$, and ($C_3$-$C_6$) cycloalkyl of $R_3$ are each optionally substituted with 1, 2, or 3 independently selected $R^g$ substituents. In a further embodiment of this aspect, each $R_{13}$ is independently selected from the group consisting of —H, halo, —OH, —CN, ($C_1$-$C_6$) alkyl, ($C_1$-$C_6$) alkoxy, —$NH_2$, —NH($C_1$-$C_6$)alkyl, and —N($C_1$-$C_6$ alkyl)$_2$, wherein the ($C_1$-$C_6$) alkyl, ($C_1$-$C_6$) alkoxy, —NH($C_1$-$C_6$)alkyl, and —N($C_1$-$C_6$ alkyl)$_2$ of $R_3$ are each optionally substituted with 1, 2, or 3 substituents independently selected from halo, —OH, —CN, ($C_1$-$C_6$) alkyl, and —$NH_2$. In still further embodiment of this aspect, each $R_{13}$ is independently selected from the group consisting of —H, halo, ($C_1$-$C_6$) alkyl, and ($C_1$-$C_6$) alkoxy.

In one embodiment of this aspect, each $R_{14}$ is independently selected from the group consisting of H, halo, —OH, —$NH_2$, —CN, ($C_1$-$C_6$) alkyl, ($C_1$-$C_6$) alkoxy, ($C_1$-$C_6$) haloalkyl, ($C_1$-$C_6$) haloalkoxy, —COOH, —NH($C_1$-$C_6$)alkyl, —N($C_1$-$C_6$ alkyl)$_2$, phenyl, phenyl-($C_1$-$C_2$) alkylene, ($C_3$-$C_6$) cycloalkyl, ($C_3$-$C_6$) cycloalkyl-($C_1$-$C_4$) alkylene-, and 4- to 6-membered heterocycloalkyl. In a further embodiment, each $R_{14}$ is independently selected from the group consisting of H, halo, —OH, —$NH_2$, —CN, ($C_1$-$C_6$) alkyl, ($C_1$-$C_6$) alkoxy, —COOH, —NH($C_1$-$C_6$)alkyl, —N($C_1$-$C_6$ alkyl)$_2$, and phenyl. In still further embodiment, each $R_{14}$ is independently selected from the group consisting of H, halo, and ($C_1$-$C_6$) alkyl. In yet a further embodiment, $R_{14}$ is H.

In one embodiment of this aspect, each $R_{12}$ is independently selected from the group consisting of —H, halo, —OH, —COO($C_1$-$C_6$) alkyl, —CN, —$NH_2$, —NH(($C_1$-$C_6$) alkyl), —N(($C_1$-$C_6$) alkyl)$_2$, —$C(O)NH_2$, —C(O)NH(($C_1$-$C_6$) alkyl), —C(O)N(($C_1$-$C_6$) alkyl)$_2$, ($C_1$-$C_6$) alkyl, ($C_1$-$C_6$) alkoxy, ($C_3$-$C_6$) cycloalkyl, 4- to 6-membered heterocycloalkyl, phenyl, 5- or 6-membered heteroaryl. In a further embodiment, each $R_{12}$ is independently selected from the group consisting of —H, halo, —OH, —CN, —$NH_2$, —NH(($C_1$-$C_6$) alkyl), —N(($C_1$-$C_6$) alkyl)$_2$, ($C_1$-$C_6$) alkyl, and ($C_1$-$C_6$) alkoxy. In still a further embodiment, each $R_{12}$ is independently selected from the group consisting of —H and halo. In yet a further embodiment, m is one and $R_{12}$ is F. In still a further embodiment, m is one and $R_{12}$ is F, which is para to the amine substituent on the phenyl ring.

In one embodiment of this aspect, each $R^a$ is independently selected from the group consisting of —H, —CN, ($C_1$-$C_6$) alkyl, ($C_3$-$C_{10}$) cycloalkyl, 5-14 membered heteroaryl, 4-14 membered heterocycloalkyl, ($C_3$-$C_{10}$) cycloalkyl-($C_1$-$C_4$) alkylene-, and (4-14 membered heterocycloalkyl)-($C_1$-$C_4$) alkylene-, wherein the ($C_1$-$C_6$) alkyl, ($C_3$-$C_{10}$) cycloalkyl, 5-14 membered heteroaryl, 4-14 membered heterocycloalkyl, ($C_3$-$C_{10}$) cycloalkyl-($C_1$-$C_4$) alkylene-, and (4-14 membered heterocycloalkyl)-($C_1$-$C_4$) alkylene- of $R^a$ are each optionally substituted with 1, 2, 3, 4, or 5 independently selected $R^d$ substituents. In one embodiment of this aspect, each $R^a$ is independently selected from the group consisting of —H, ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene-, wherein the ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene- of $R^a$ are each optionally substituted with 1, 2, 3, 4, or 5 substituents independently selected from ($C_1$-$C_6$) alkyl, ($C_1$-$C_6$) alkoxy, and —C(O)O($C_1$-$C_4$) alkyl.

In one embodiment of this aspect, each $R^b$ is independently selected from the group consisting of halo, ($C_1$-$C_6$) alkyl, —CN, —OH, —$NH_2$, —$NO_2$, and —C(O)O($C_1$-$C_4$) alkyl. In a further embodiment, each $R^b$ is independently selected from the group consisting of ($C_1$-$C_6$) alkyl and —C(O)O($C_1$-$C_4$) alkyl.

In one embodiment of this aspect, each $R^c$ is —H or ($C_1$-$C_6$) alkyl.

In one embodiment of this aspect, each $R^d$ is independently selected from the group consisting of ($C_1$-$C_6$) alkyl, halo, phenyl, 5-10 membered heteroaryl, ($C_3$-$C_{10}$) cycloalkyl, 4-10 membered heterocycloalkyl, (4-10 membered heterocycloalkyl)-($C_1$-$C_4$) alkylene-, —CN, and —C(O)O($C_1$-a) alkyl.

In one embodiment of this aspect, each $R^e$ is —H or ($C_1$-$C_6$) alkyl.

In another embodiment, any two $R^a$ substituents together with the nitrogen atom to which they are attached form a 5 or 6-membered heterocycloalkyl.

In another embodiment, any two $R^c$ substituents together with the nitrogen atom to which they are attached form a 5 or 6-membered heterocycloalkyl.

In another embodiment, any two $R^e$ substituents together with the nitrogen atom to which they are attached form a 5 or 6-membered heterocycloalkyl.

In one embodiment, each $R^f$ is independently selected from the group consisting of halo, —OH, —CN, —COOH, —$NH_2$, ($C_1$-$C_6$) alkyl, and ($C_1$-$C_6$) alkoxy.

In one embodiment, each $R^g$ is independently selected from the group consisting of halo, —OH, —CN, —COOH, ($C_1$-$C_6$) alkyl, ($C_1$-$C_6$) alkoxy, and —C(O)O($C_1$-$C_4$) alkyl.

In one embodiment, n is 1 or 2;

In one embodiment, m is 1 or 2. In further embodiment, m is 1.

In one embodiment, p is 1 or 2.

In one embodiment of this aspect, the compound of Formula I' is a compound of Formula I'a, wherein the variables $R_{10}$-$R_{17}$ are defined herein:

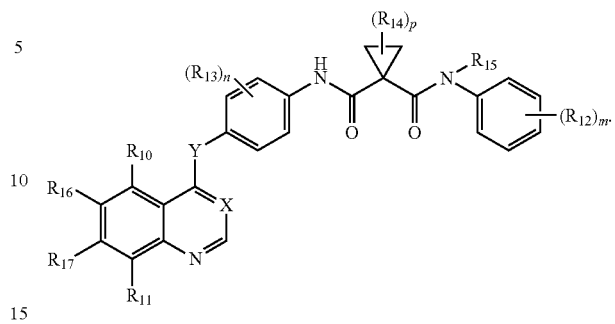

(I'a)

In another embodiment of this aspect, the compound of Formula I' is a compound of Formula I'b, I'c or I'd, wherein the variables $R_{10}$-$R_{19}$ are defined herein:

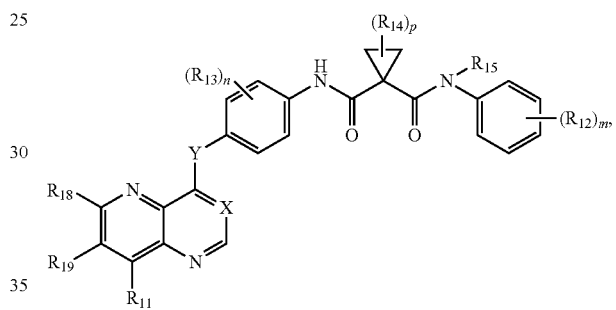

(I'b)

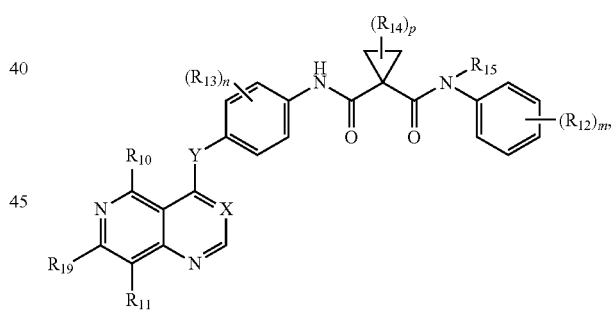

(I'c)

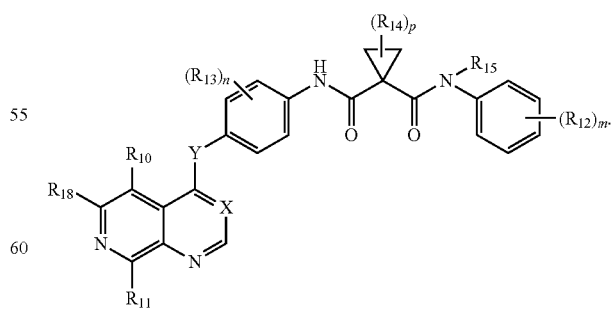

(I'd)

In another embodiment of this aspect, the compound of Formula I' is a compound of Formula (I'a-1), wherein the variables $R_{10}$-$R_{17}$ are defined herein:

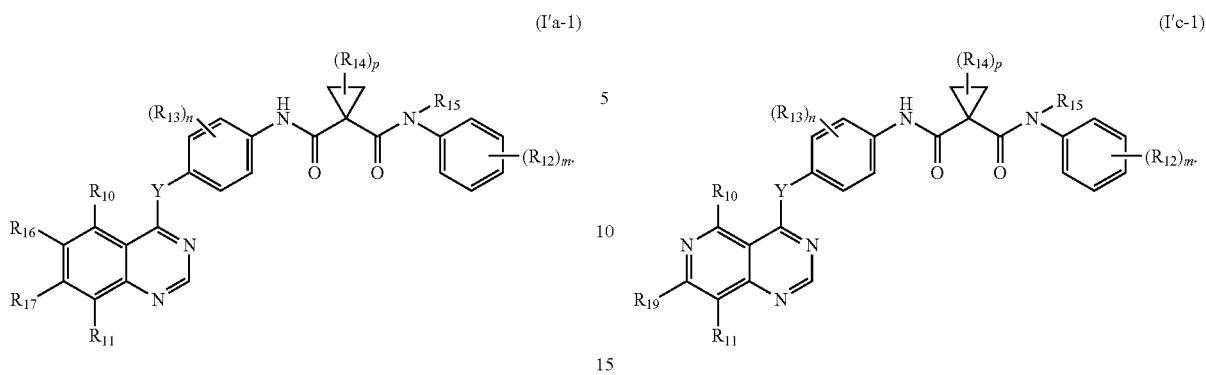

(I'a-1)

In another embodiment of this aspect, the compound of Formula I' is a compound of Formula (I'b-1), wherein the variables $R_{10}$-$R_{19}$ are defined herein:

(I'c-1)

In another embodiment of this aspect, the compound of Formula I' is a compound of Formula (I'c-2), wherein the variables $R_{10}$-$R_{19}$ are defined herein:

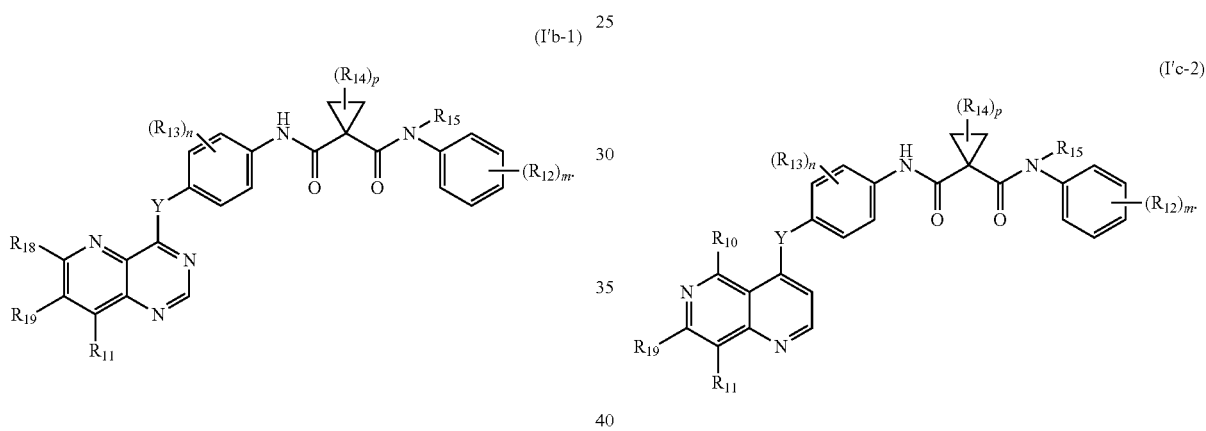

(I'b-1)

(I'c-2)

In another embodiment of this aspect, the compound of Formula I' is a compound of Formula (I'b-2), wherein the variables $R_{10}$-$R_{19}$ are defined herein:

In another embodiment of this aspect, the compound of Formula I' is a compound of Formula (I'd-1), wherein the variables $R_{10}$-$R_{18}$ are defined herein:

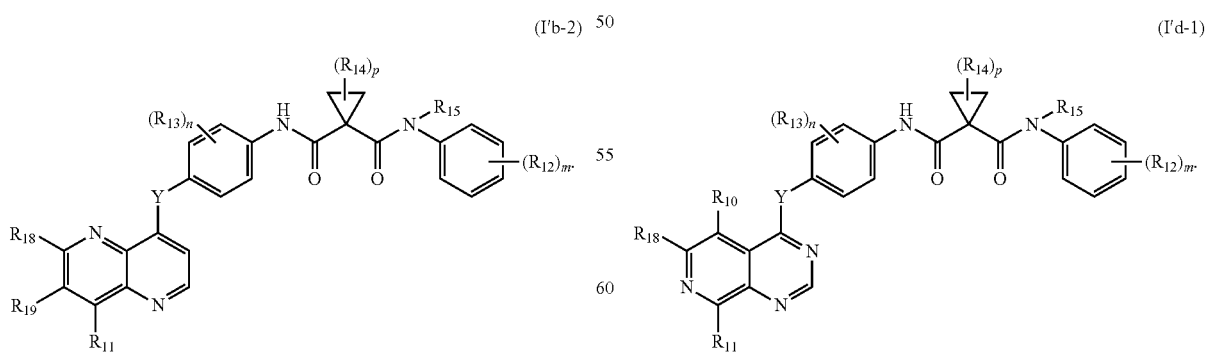

(I'b-2)

(I'd-1)

In another embodiment of this aspect, the compound of Formula I' is a compound of Formula (I'c-1) wherein the variables $R_{10}$-$R_{19}$ are defined herein:

In another embodiment of this aspect, the compound of Formula I' is a compound of Formula (I'd-2), wherein the variables $R_{10}$-$R_{18}$ are defined herein:

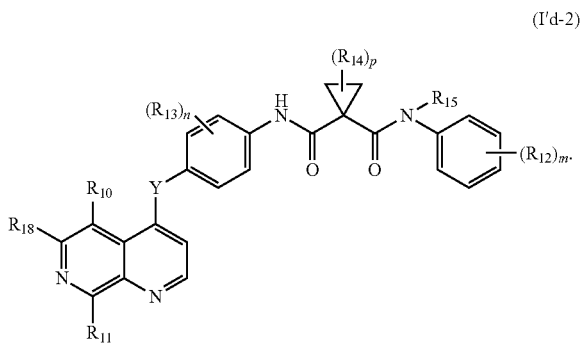

(I'd-2)

In one embodiment, $R_{16}$ is selected from —H, $(C_1-C_6)$ alkyl, $(C_2-C_6)$ alkenyl, $(C_2-C_6)$ alkynyl, —C(=NO—$(C_1-C_6)$ alkyl)$R^a$; halo, —CN, $OR^a$, —C(O)$OR^a$; —C(O)NR$^a$R$^a$, —C(O)NHOR$^a$, —S(O)$_2$NR$^a$R$^a$, phenyl, 5- to 6-membered heteroaryl, $(C_3-C_6)$ cycloalkyl, and 4- to 6-membered heterocycloalkyl, wherein the $(C_1-C_6)$ alkyl; $(C_2-C_6)$ alkenyl, $(C_2-C_6)$ alkynyl, phenyl, 5- to 6-membered heteroaryl, $(C_3-C_6)$ cycloalkyl, and 4- to 6-membered heterocycloalkyl of $R_{16}$ are each optionally substituted with 1, 2, or 3 $R^g$ substituents.

In one embodiment, $R_{17}$ is selected from —H, $(C_1-C_6)$ alkyl, $(C_2-C_6)$ alkenyl, $(C_2-C_6)$ alkynyl, —C(=NO—$(C_1-C_6)$ alkyl)$R^a$, halo, —CN, $OR^a$, —C(O)$OR^a$, —C(O)NR$^a$R$^a$, —C(O)NHOR$^a$, —S(O)$_2$NR$^a$R$^a$, phenyl, 5- to 6-membered heteroaryl, $(C_3-C_6)$ cycloalkyl, and 4- to 6-membered heterocycloalkyl, wherein the$(C_1-C_6)$ alkyl, $(C_2-C_6)$ alkenyl, $(C_2-C_6)$ alkynyl, phenyl, 5- to 6-membered heteroaryl, $(C_3-C_6)$ cycloalkyl, and 4- to 6-membered heterocycloalkyl of $R_{17}$ are each optionally substituted with 1, 2, or 3 $R^g$ substituents.

In one embodiment, $R_{18}$ and $R_{19}$ are each independently selected from —H, $(C_1-C_6)$ alkyl, $(C_2-C_6)$ alkenyl, $(C_2-C_6)$ alkynyl, —C(=NO—$(C_1-C_6)$alkyl)$R^a$, halo, —CN, $OR^a$, —C(O)$OR^a$, —C(O)NR$^a$R$^a$, —C(O)NHOR$^a$, —S(O)$_2$NR$^a$R$^a$, phenyl, 5- to 6-membered heteroaryl, $(C_3-C_6)$ cycloalkyl, and 4- to 6-membered heterocycloalkyl, wherein the $(C_1-C_6)$ alkyl, $(C_2-C_6)$ alkenyl, $(C_2-C_6)$ alkynyl, phenyl, 5- to 6-membered heteroaryl, $(C_3-C_6)$ cycloalkyl, and 4- to 6-membered heterocycloalkyl of $R_{18}$ or $R_{19}$ are each optionally substituted with 1, 2, or 3 $R^b$ substituents.

In one embodiment, $R_{16}$ is selected from H, halo, $NH_2$, $NH(C_{1-6}$ alkyl), $N(C_{1-6}$ alkyl), methoxy, methyl, CN, 3-morphlinopropoxy, 2-methoxyethoxy, (oxetan-3-yloxy)carbamoyl, cyclopropylcarbamoyl, carbamoyl, 2-(pyrrolidin-1-yl)ethylcarbamoyl, 1-(t-butoxycarbonylpyrrolidin-2-yl)methylcarbamoyl, 1-(pyrrolidin-2-yl)methylcarbamoyl, 2-methoxyethylamino, azetidin-1-yl, dimethylcarbamoyl, methylamino, 3-morpholinopropoxy, 2-methoxyethoxy, 2-hydroxyethoxy, propoxy, 2-hydroxypropoxy, methoxycarbonyl, carboxy, methylcarbamoyl, 2-oxazolyl, pyrazol-3-yl, pyrazol-4-yl, 4-isoxazolyl, 3,5-dimethylisoxazol-4-yl, 1-methyl-pyrazol-4-yl, 2-methyl-pyrazol-3-yl, 2-ethyl-pyrazol-3-yl, 2-(2-hydroxyethyl)-pyrazol-3-yl, 2-(2,2,2-trifluoroethyl)-pyrazol-3-yl, 2-(2-fluoroethyl)-pyrazol-3-yl, 2-(2,2-difluoroethyl)-pyrazol-3-yl, 2-trifluoromethyl-pyrazol-3-yl, 2-difluoromethyl-pyrazol-3-yl, 1-methyl-imidazol-4-yl, 1-methyl-imidazol-2-yl, 1H-imidazol-2-yl, (2-hydroxyethoxy)carbamoyl, (2,2-dihydroxyethoxy)carbamoyl, (oxetan-3-yl)carbamoyl, methoxycarbamoyl, 2-trimethylsilylethynyl, ethynyl, 1,3,4-oxadiazol-3-yl, 1H-1,2,3-triazol-5-yl, sulfamoyl, acetyl, and —C(=NOCH$_3$)CH$_3$.

In one embodiment, $R_{16}$ is $R^a$NHC(O)— and $R_{17}$ is H or —OR$^a$.

In another embodiment, $R_{16}$ is 5- or 6-membered heteroaryl optionally substituted with 1, 2, or 3 independently selected $R^b$ substituents and $R_{17}$ is H.

In another embodiment, $R_{16}$ is H and $R_{17}$ is 5- or 6-membered heteroaryl optionally substituted with 1, 2, or 3 independently selected $R^b$ substituents.

In one embodiment, $R_{18}$ and $R_{19}$ are each independently H, halo, CN, $R^a$NHC(O)—, —OR$^a$ or 5- or 6-membered heteroaryl optionally substituted with 1-3 independently selected $R^b$ substituents.

In another embodiment, $R_{18}$ is H and $R_{19}$ is —OR$^a$.

In another embodiment, $R_{19}$ is and $R_{18}$ is —OR$^a$.

In another embodiment, $R_{18}$ and $R_{19}$ are each independently —OR$^a$.

In another embodiment, $R_{18}$ is 5- or 6-membered heteroaryl optionally substituted with 1-3 independently selected $R^b$ substituents and $R_{19}$ is H or —OR$^a$.

In another embodiment, $R_{18}$ is H or —OR$^a$ and $R_{19}$ is 5- or 6-membered heteroaryl optionally substituted with 1-3 independently selected $R^b$ substituents.

In another embodiment, $R_{18}$ is $R^a$NHC(O)— and $R_{19}$ is H or —OR$^a$.

In another embodiment, $R_{19}$ is $R^a$NHC(O)— and $R_{18}$ is H or —OR$^a$.

In one embodiment, $R_{10}$ and $R_{11}$ are each H.

In one embodiment, the subscript m is 1.

In another embodiment, the subscript n is 1.

In another embodiment, the subscript p is 1.

In some embodiments,

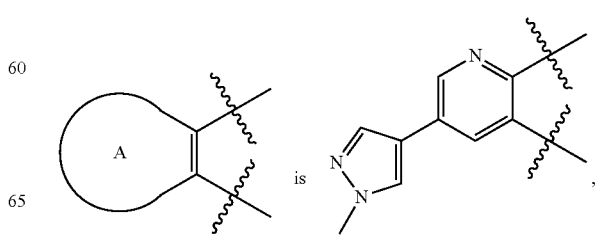

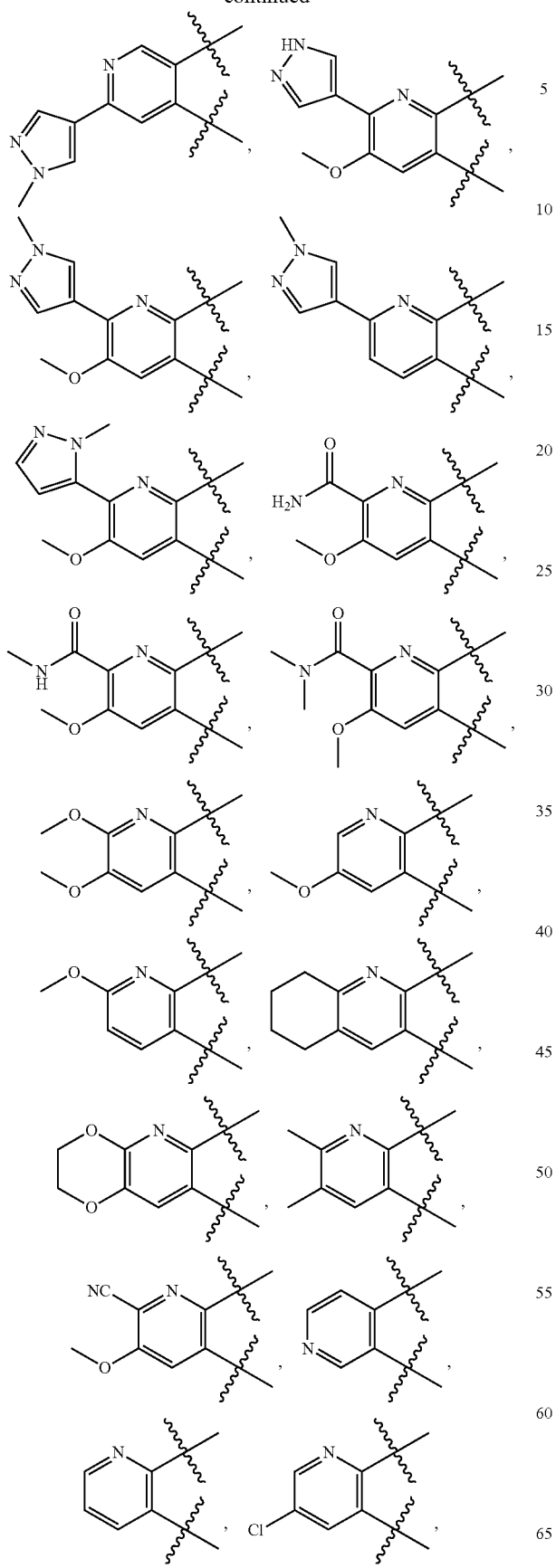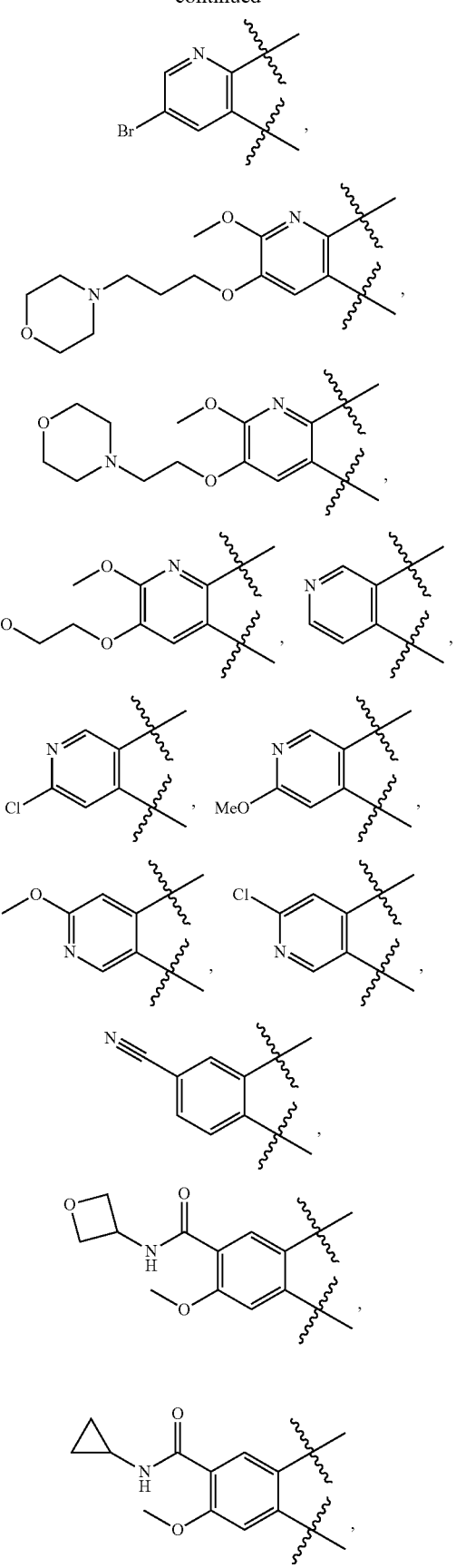

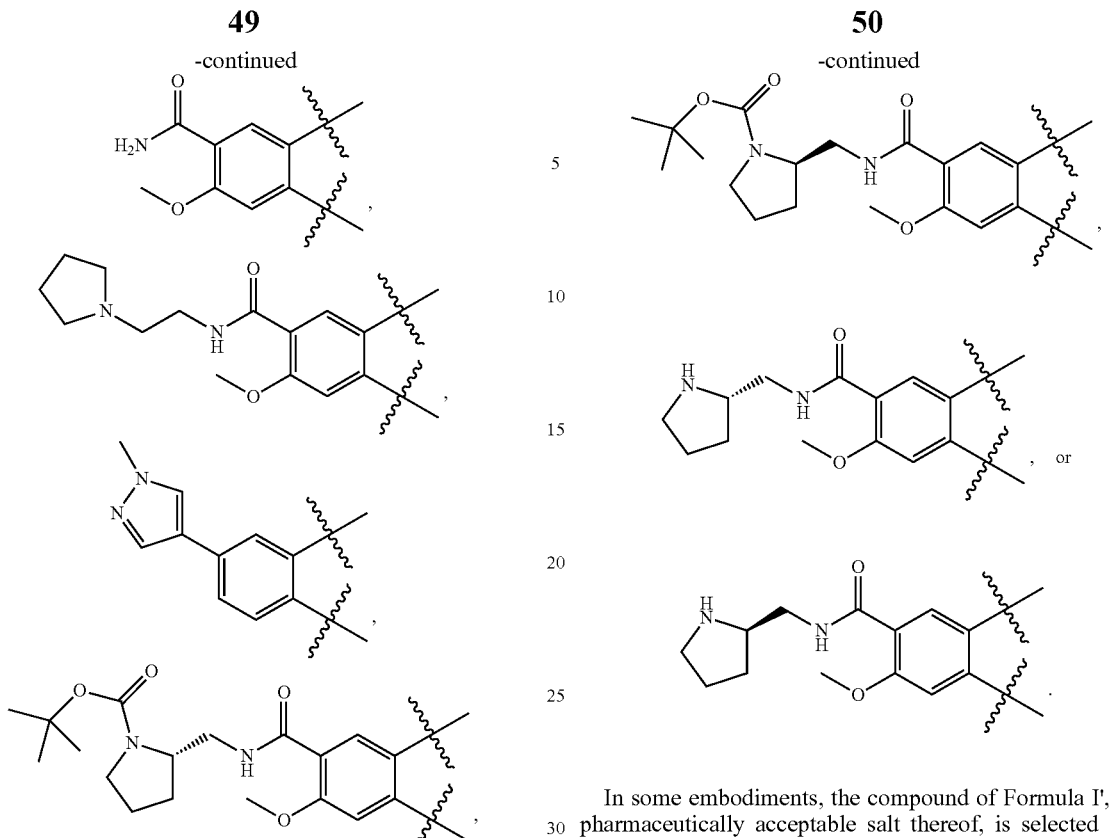

In some embodiments, the compound of Formula I', or a pharmaceutically acceptable salt thereof, is selected from the compounds listed in Table 1, or a pharmaceutically acceptable salt thereof.

TABLE 1

Compounds of Formula I'

| Comp. | Structure | IUPAC Name |
|---|---|---|
| 7 | 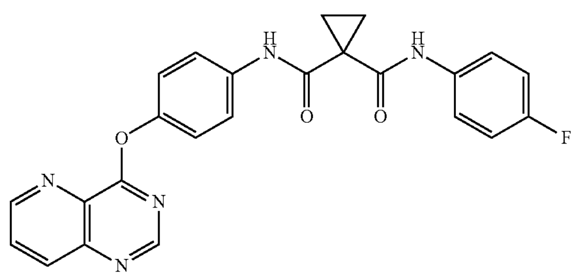 [SMILES: O=C(Nc1ccc(F)cc1)C1(C(=O)Nc2ccc(Oc3ncnc4cccnc34)cc2)CC1] | 1-N'-(4-fluorophenyl)-1-N-(4-pyrido[3,2-d]pyrimidin-4-yloxyphenyl)cyclopropane-1,1-dicarboxamide |
| 12 | 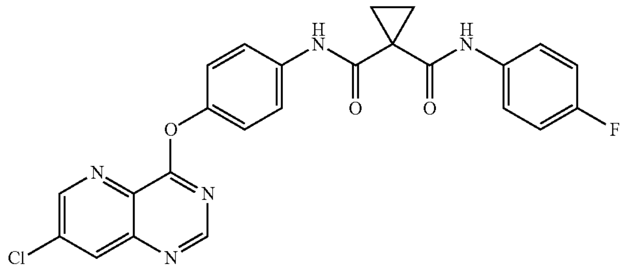 [SMILES: O=C(Nc1ccc(F)cc1)C1(C(=O)Nc2ccc(Oc3ncnc4cc(Cl)cnc34)cc2)CC1] | 1-N-[4-(7-chloropyrido[3,2-d]pyrimidin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 13 | 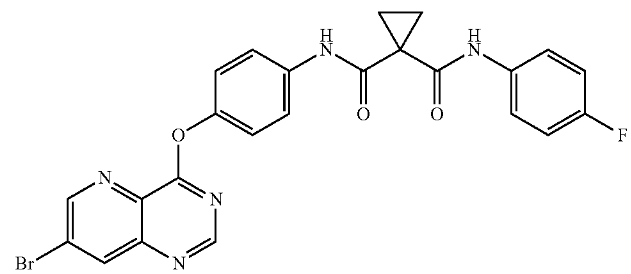 | 1-N-[4-(7-bromopyrido[3,2-d]pyrimidin-4-yl)oxyphenyl]-1-N'-(4-fluorophenyl)cyclopropane-1,1-dicarboxamide |
| 16 | 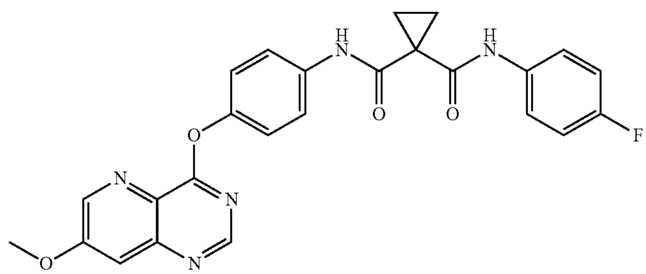 [SMILES: COc1cnc2c(Oc3ccc(NC(=O)C4(C(=O)Nc5ccc(F)cc5)CC4)cc3)ncnc2c1] | 1-N'-(4-fluorophenyl)-1-N-[4-(7-methoxypyrido[3,2-d]pyrimidin-4-yl)oxyphenyl]cyclopropane-1,1-dicarboxamide |
| 19 | 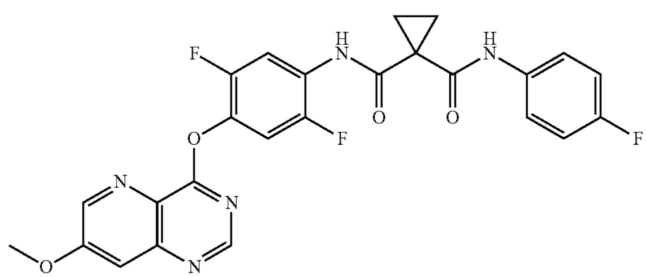 [SMILES: COc1cnc2c(Oc3cc(F)c(NC(=O)C4(C(=O)Nc5ccc(F)cc5)CC4)cc3F)ncnc2c1] | 1-N'-[2,5-difluoro-4-(7-methoxypyrido[3,2-d]pyrimidin-4-yl)oxyphenyl]-1-N-(4-fluorophenyl)cyclopropane-1,1-dicarboxamide |
| 28 | 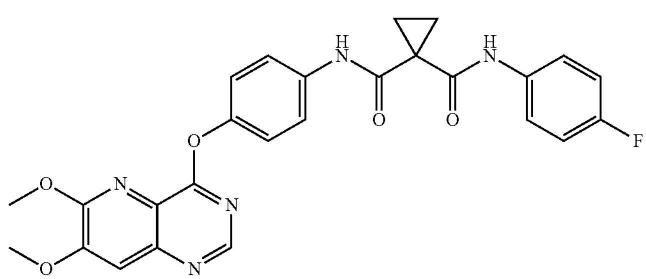 [SMILES: COc1cc2ncnc(Oc3ccc(NC(=O)C4(C(=O)Nc5ccc(F)cc5)CC4)cc3)c2nc1OC] | 1-N-[4-(6,7-dimethoxypyrido[3,2-d]pyrimidin-4-yl)oxyphenyl]-1-N'-(4-fluorophenyl)cyclopropane-1,1-dicarboxamide |
| 29 | 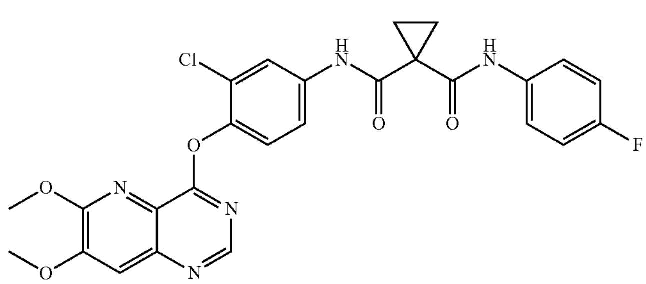 | 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 30 | 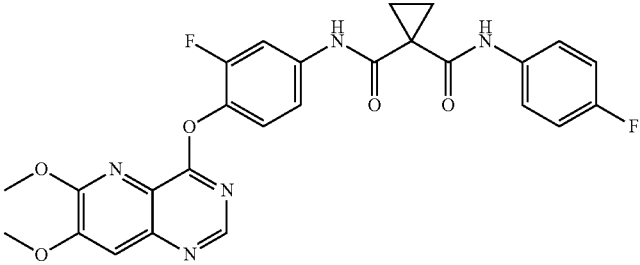 | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide |
| 31 | 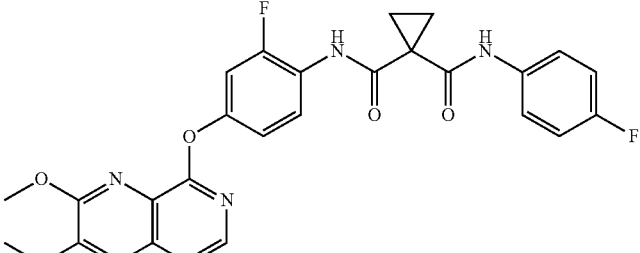 | 1-N'-[4-(6,7-dimethoxypyrido[3,2-d]pyrimidin-4-yl)oxy-2-fluorophenyl]-1-N-(4-fluorophenyl)cyclopropane-1,1-dicarboxamide |
| 32 | 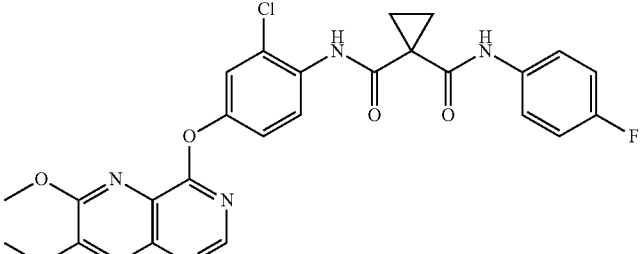 | 1-N'-[2-chloro-4-(6,7-dimethoxypyrido[3,2-d]pyrimidin-4-yl)oxyphenyl]-1-N-(4-fluorophenyl)cyclopropane-1,1-dicarboxamide |
| 33 | 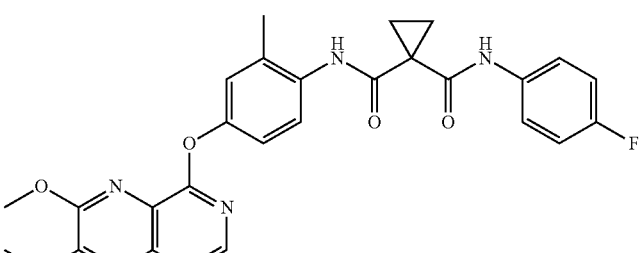 | 1-N'-[4-(6,7-dimethoxypyrido[3,2-d]pyrimidin-4-yl)oxy-2-methylphenyl]-1-N-(4-fluorophenyl)cyclopropane-1,1-dicarboxamide |
| 34 | 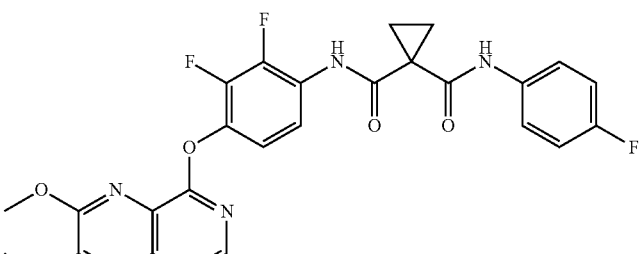 | 1-N'-[4-(6,7-dimethoxypyrido[3,2-d]pyrimidin-4-yl)oxy-2,3-difluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 35 | 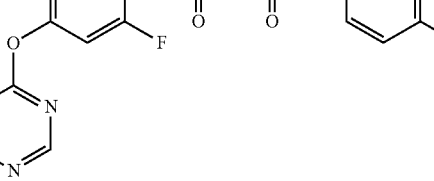 | 1-N'-[4-(6,7-dimethoxypyrido[3,2-d]pyrimidin-4-yl)oxy-2,5-difluorophenyl]-1-N-(4-fluorophenyl)cyclopropane-1,1-dicarboxamide |
| 43 | 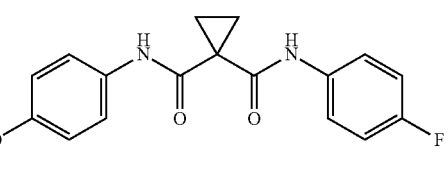 | 1-N-[4-(6,7-dimethyl-pyrido[3,2-d]pyrimidin-4-yl)oxyphenyl]-1-N'-(4-fluorophenyl)cyclopropane-1,1-dicarboxamide |
| 52 | 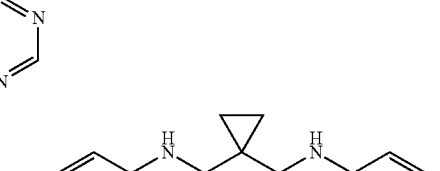 | 1-N'-(4-fluorophenyl)-1-N-[4-(6,7,8,9-tetrahydropyrimido[5,4-b]quinolin-4-yloxy)phenyl]cyclopropane-1,1-dicarboxamide |
| 57 | 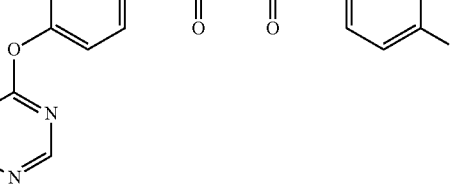 | 1-N-[4-(6-cyano-7-methoxypyrido[3,2-d]pyrimidin-4-yl)oxyphenyl]-1-N'-(4-fluorophenyl)cyclopropane-1,1-dicarboxamide |
| 65 | 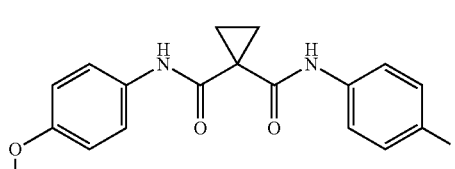 | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide |

TABLE 1-continued

Compounds of Formula I'

| Comp. | Structure | IUPAC Name |
|---|---|---|
| 66 | 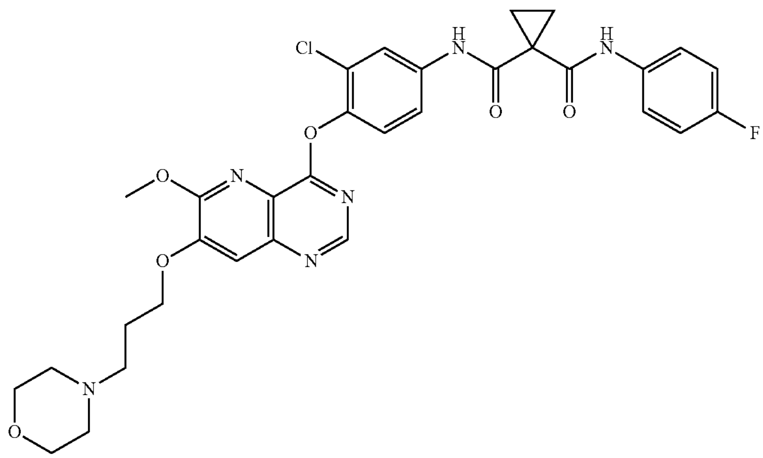 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 67 | 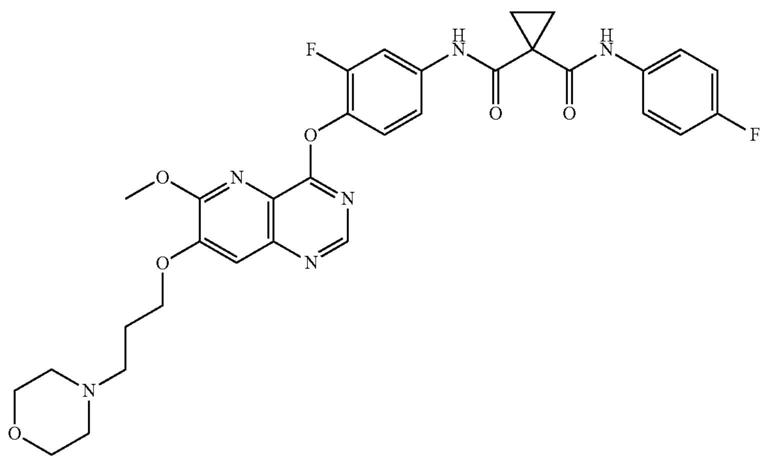 [SMILES: COc1nc2c(Oc3ccc(NC(=O)C4(C(=O)Nc5ccc(F)cc5)CC4)cc3F)ncnc2cc1OCCCN1CCOCC1] | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 68 | 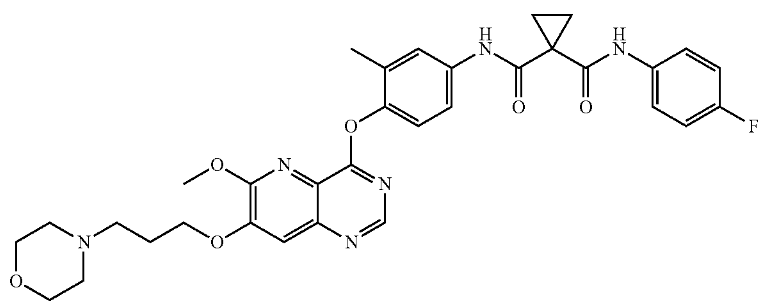 [SMILES: COc1nc2c(Oc3ccc(NC(=O)C4(C(=O)Nc5ccc(F)cc5)CC4)cc3C)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide |
| 69 | 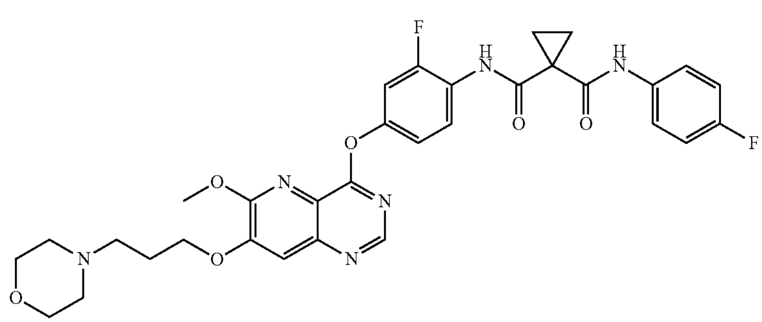 [SMILES: COc1nc2c(Oc3ccc(NC(=O)C4(C(=O)Nc5ccc(F)cc5)CC4)c(F)c3)ncnc2cc1OCCCN1CCOCC1] | 1-N'-[2-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 70 | 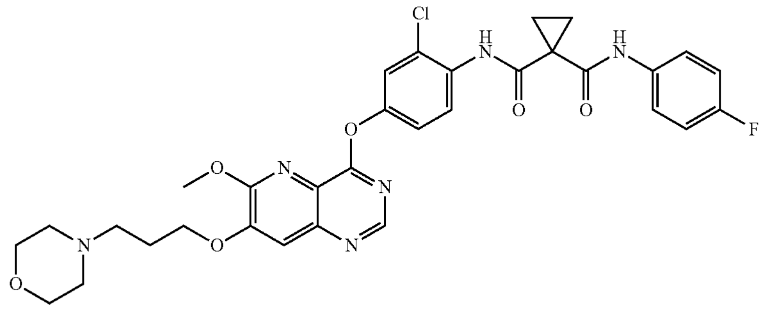 | 1-N'-[2-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 71 | 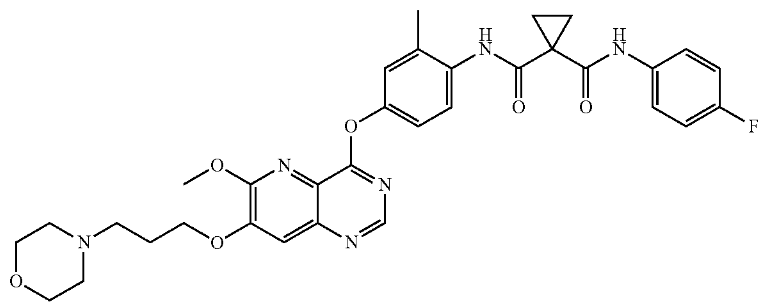 [SMILES: COc1nc2c(Oc3ccc(NC(=O)C4(C(=O)Nc5ccc(F)cc5)CC4)c(C)c3)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide |
| 72 | 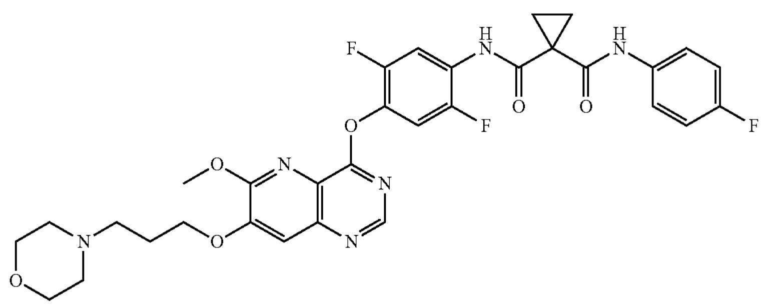 [SMILES: COc1nc2c(Oc3cc(F)c(NC(=O)C4(C(=O)Nc5ccc(F)cc5)CC4)cc3F)ncnc2cc1OCCCN1CCOCC1] | 1-N'-[2,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 73 | 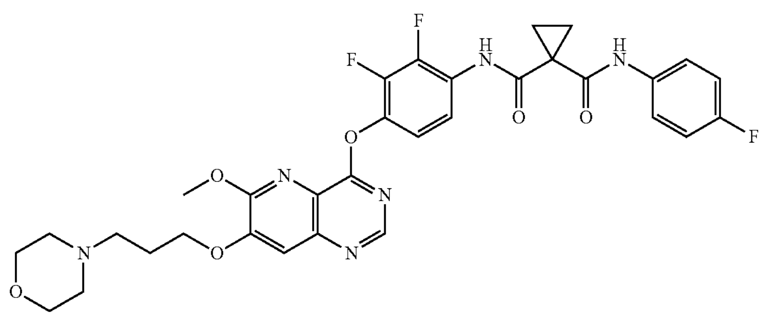 [SMILES: COc1nc2c(Oc3ccc(NC(=O)C4(C(=O)Nc5ccc(F)cc5)CC4)c(F)c3F)ncnc2cc1OCCCN1CCOCC1] | 1-N'-[2,3-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 74 | 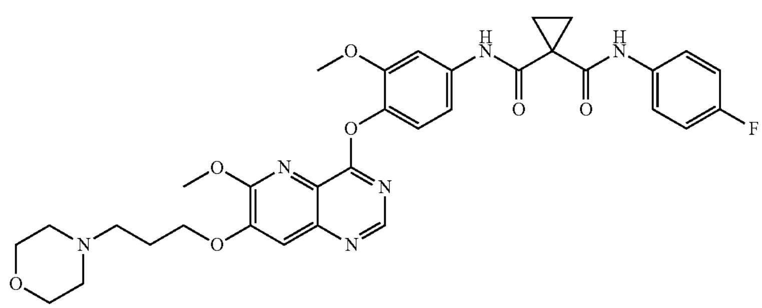 [SMILES: COc1cc(NC(=O)C2(C(=O)Nc3ccc(F)cc3)CC2)ccc1Oc1ncnc2cc(OCCCN3CCOCC3)c(OC)nc12] | 1-N-(4-fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide |

TABLE 1-continued

Compounds of Formula I'

| Comp. | Structure | IUPAC Name |
|---|---|---|
| 75 | 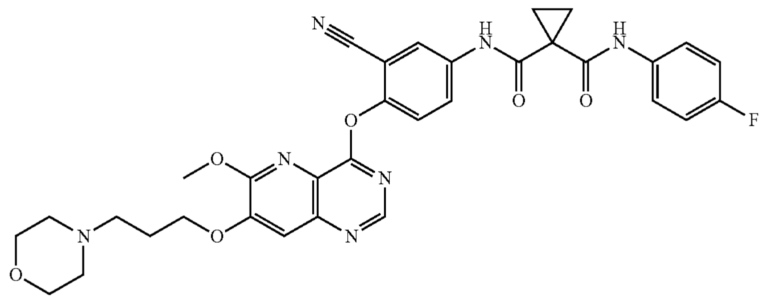 [SMILES: COc1nc2c(Oc3ccc(NC(=O)C4(C(=O)Nc5ccc(F)cc5)CC4)cc3C#N)ncnc2cc1OCCCN1CCOCC1] | 1-N'-[3-cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 76 | 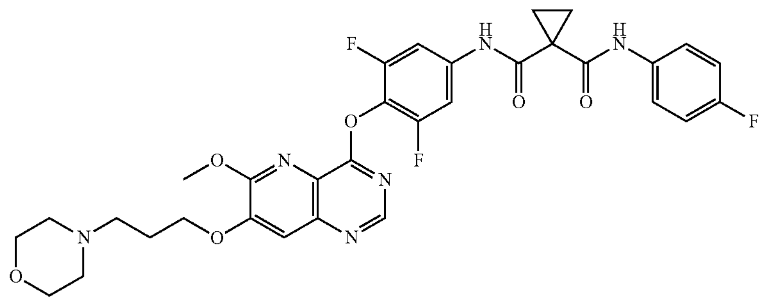 [SMILES: COc1nc2c(Oc3c(F)cc(NC(=O)C4(C(=O)Nc5ccc(F)cc5)CC4)cc3F)ncnc2cc1OCCCN1CCOCC1] | 1-N'-[3,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 78 | 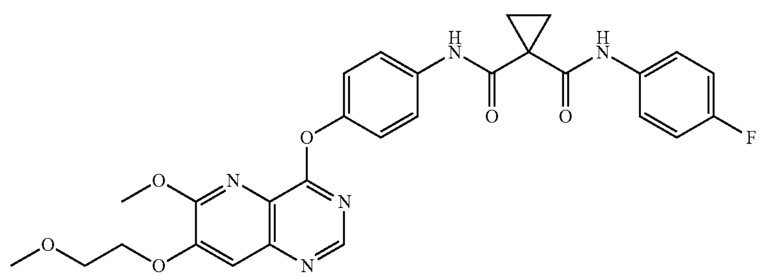 [SMILES: COCCOc1cc2ncnc(Oc3ccc(NC(=O)C4(C(=O)Nc5ccc(F)cc5)CC4)cc3)c2nc1OC] | 1-N'-(4-fluorophenyl)-1-N-[4-[6-methoxy-7-(2-methoxyethoxy)pyrido[3,2-d]pyrimidin-4-yl]oxyphenyl]cyclopropane-1,1-dicarboxamide |
| 79 | 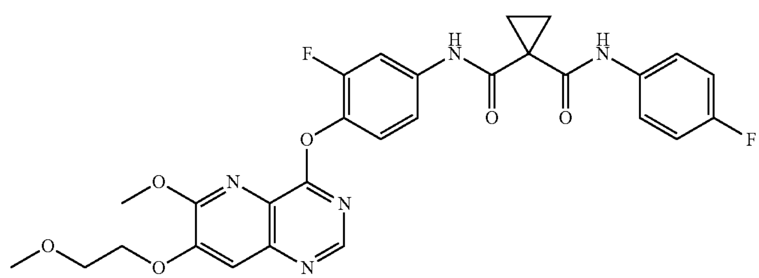 | 1-N'-[3-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 80 | 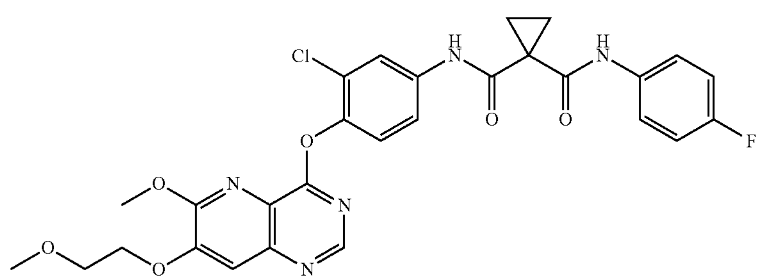 [SMILES: COCCOc1cc2ncnc(Oc3ccc(NC(=O)C4(C(=O)Nc5ccc(F)cc5)CC4)cc3Cl)c2nc1OC] | 1-N'-[3-chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 81 | 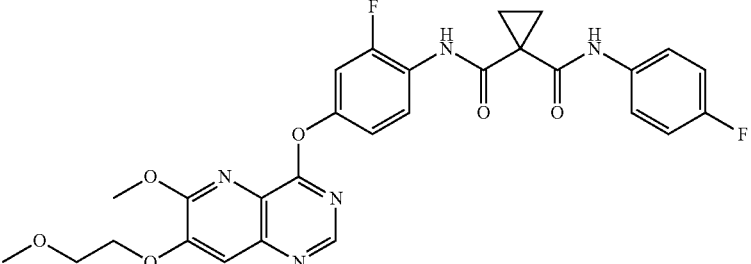 | 1-N'-[2-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 82 | 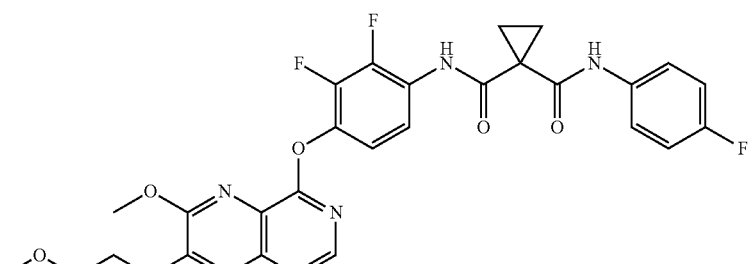 | 1-N'-[2,3-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 83 | 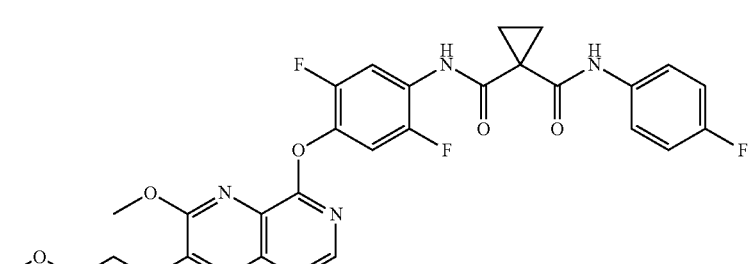 | 1-N'-[2,5-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 85 | 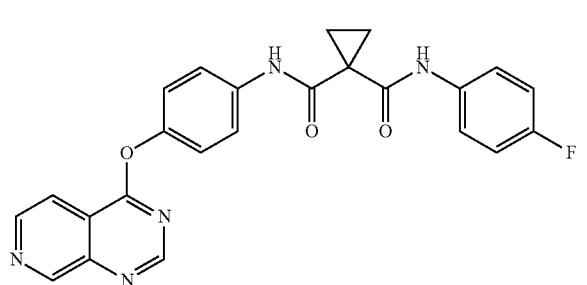 | 1-N'-(4-fluorophenyl)-1-N-(4-pyrido[3,4-d]pyrimidin-4-yloxyphenyl)cyclopropane-1,1-dicarboxamide |
| 88 | 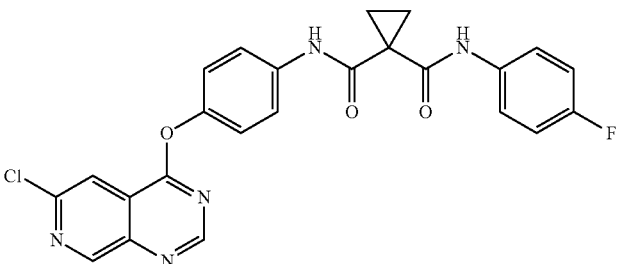 | 1-N-[4-(6-chloropyrido[3,4-d]pyrimidin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 91 | 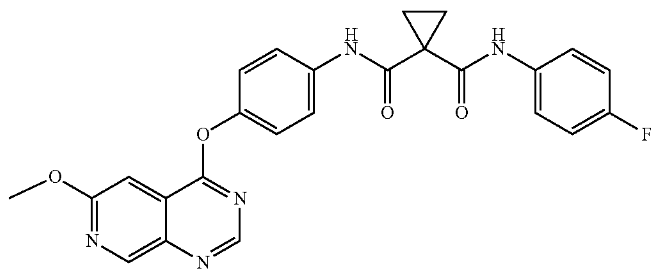 [SMILES: COc1cc2c(Oc3ccc(NC(=O)C4(C(=O)Nc5ccc(F)cc5)CC4)cc3)ncnc2cn1] | 1-N'-(4-fluorophenyl)-1-N-[4-(6-methoxypyrido[3,4-d]pyrimidin-4-yl)oxyphenyl]cyclopropane-1,1-dicarboxamide |
| 95 | 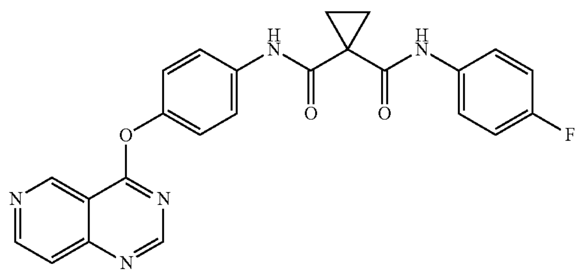 [SMILES: O=C(Nc1ccc(F)cc1)C1(C(=O)Nc2ccc(Oc3ncnc4ccncc34)cc2)CC1] | 1-N'-(4-fluorophenyl)-1-N-(4-pyrido[4,3-d]pyrimidin-4-yloxyphenyl)cyclopropane-1,1-dicarboxamide |
| 101 | 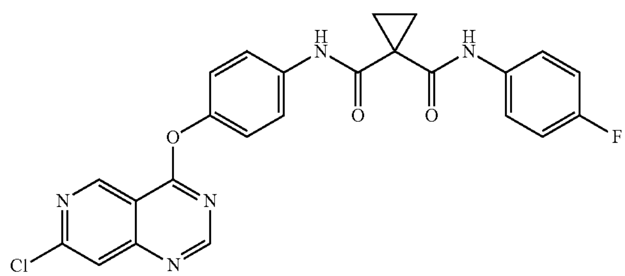 [SMILES: O=C(Nc1ccc(F)cc1)C1(C(=O)Nc2ccc(Oc3ncnc4cc(Cl)ncc34)cc2)CC1] | 1-N-[4-(7-chloropyrido[4,3-d]pyrimidin-4-yl)oxyphenyl]-1-N'-(4-fluorophenyl)cyclopropane-1,1-dicarboxamide |
| 104 | 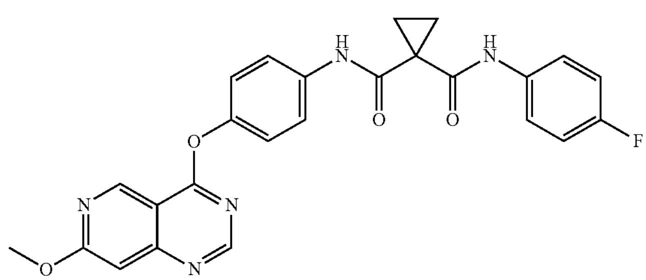 [SMILES: COc1cc2ncnc(Oc3ccc(NC(=O)C4(C(=O)Nc5ccc(F)cc5)CC4)cc3)c2cn1] | 1-N'-(4-fluorophenyl)-1-N-[4-(7-methoxypyrido[4,3-d]pyrimidin-4-yl)oxyphenyl]cyclopropane-1,1-dicarboxamide |
| 106 | 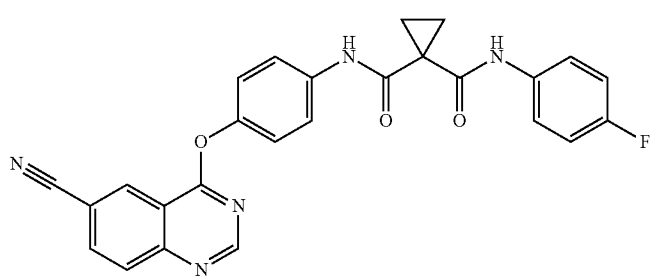 [SMILES: N#Cc1ccc2ncnc(Oc3ccc(NC(=O)C4(C(=O)Nc5ccc(F)cc5)CC4)cc3)c2c1] | 1-N-[4-(6-cyanoquinazolin-4-yl)oxyphenyl]-1-N'-(4-fluorophenyl)cyclopropane-1,1-dicarboxamide |

TABLE 1-continued

Compounds of Formula I'

| Comp. | Structure | IUPAC Name |
|---|---|---|
| 115 | 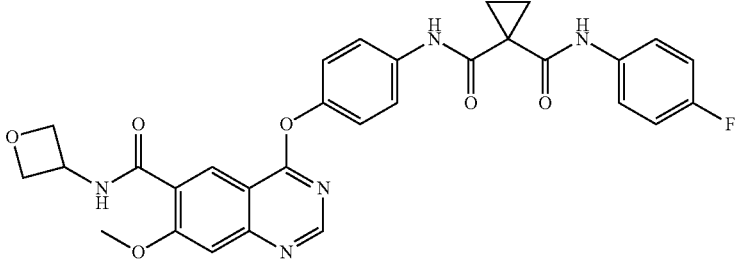 [SMILES: COc1cc2ncnc(Oc3ccc(NC(=O)C4(C(=O)Nc5ccc(F)cc5)CC4)cc3)c2cc1C(=O)NC1COC1] | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide |
| 116 | 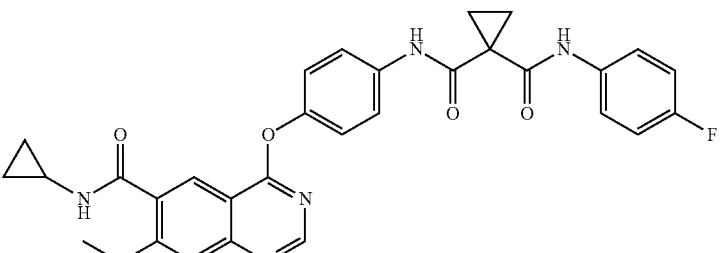 | 1-N-[4-[6-(cyclopropylcarbamoyl)-7-methoxyquinazolin-4-yl]oxyphenyl]-1-N'-(4-fluorophenyl)cyclopropane-1,1-dicarboxamide |
| 117 | 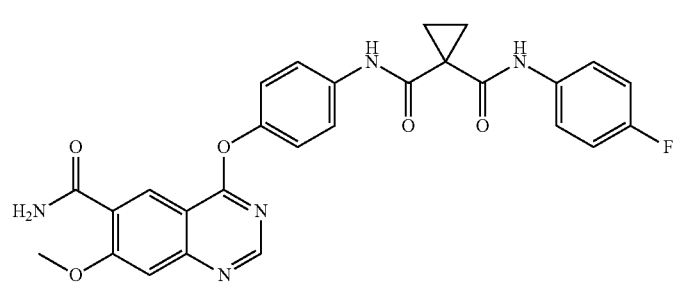 | 1-N-[4-(6-carbamoyl-7-methoxyquinazolin-4-yl)oxyphenyl]-1-N'-(4-fluorophenyl)cyclopropane-1,1-dicarboxamide |
| 118 | 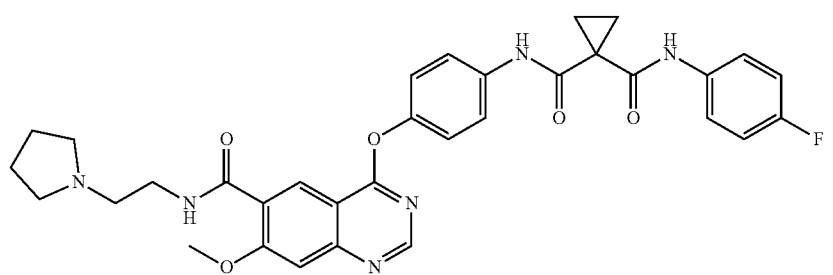 [SMILES: COc1cc2ncnc(Oc3ccc(NC(=O)C4(C(=O)Nc5ccc(F)cc5)CC4)cc3)c2cc1C(=O)NCCN1CCCC1] | 1-N'-(4-fluorophenyl)-1-N-[4-[7-methoxy-6-(2-pyrrolidin-1-ylethyl-carbamoyl)quinazolin-4-yl]oxyphenyl]cyclopropane-1,1-dicarboxamide |
| 119 | 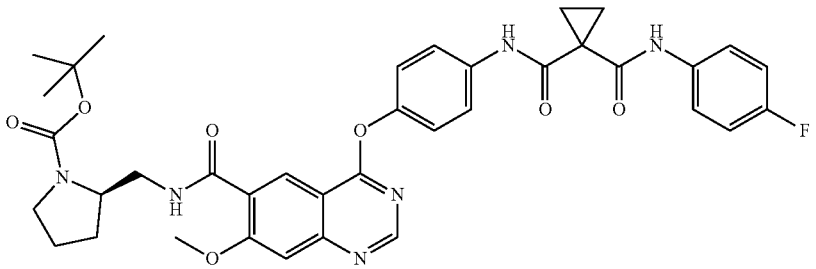 [SMILES: COc1cc2ncnc(Oc3ccc(NC(=O)C4(C(=O)Nc5ccc(F)cc5)CC4)cc3)c2cc1C(=O)NC[C@H]1CCCN1C(=O)OC(C)(C)C] | tert-butyl (2R)-2-[[[4-[4-[[1-[(4-fluoro-phenyl)carbamoyl]cyclo-propane-carbonyl]amino]phenoxy]-7-methoxyquinazoline-6-carbonyl]amino]methyl]pyr-rolidine-1-carboxylate |

TABLE 1-continued

Compounds of Formula I'

| Comp. | Structure | IUPAC Name |
|---|---|---|
| 120 | 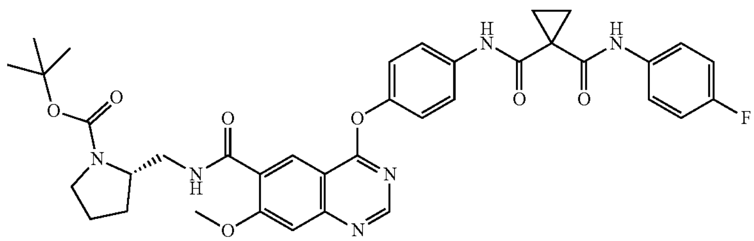 [SMILES: COc1cc2ncnc(Oc3ccc(NC(=O)C4(C(=O)Nc5ccc(F)cc5)CC4)cc3)c2cc1C(=O)NC[C@@H]1CCCN1C(=O)OC(C)(C)C] | tert-butyl (2S)-2-[[[4-[4-[[1-[(4-fluoro-phenyl)carbamoyl]cyclo-propane-carbonyl]amino]phenoxy]-7-methoxyquinazoline-6-carbonyl]amino]methyl]pyr-rolidine-1-carboxylate |
| 121 | 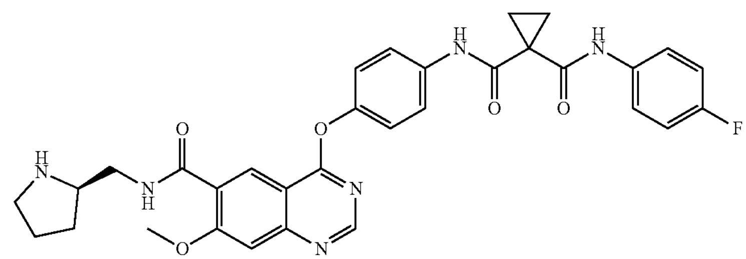 [SMILES: COc1cc2ncnc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methyl-carbamoyl]quinazolin-4-yl]oxyphenyl]cyclopropane-1,1-dicarboxamide |
| 122 | 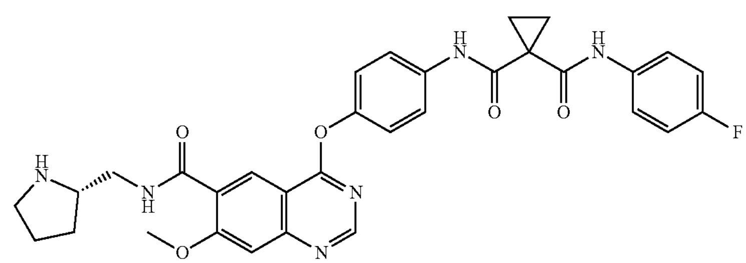 [SMILES: COc1cc2ncnc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methyl-carbamoyl]quinazolin-4-yl]oxyphenyl]cyclopropane-1,1-dicarboxamide |
| 126 | 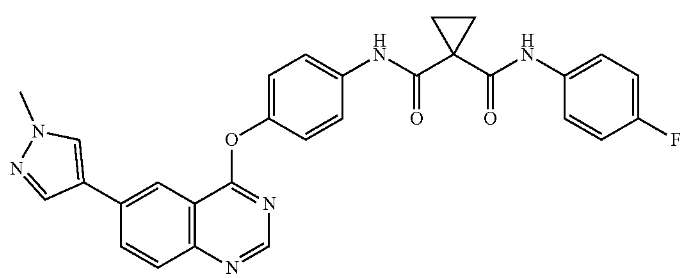 [SMILES: Cn1cc(-c2ccc3ncnc(Oc4ccc(NC(=O)C5(C(=O)Nc6ccc(F)cc6)CC5)cc4)c3c2)cn1] | 1-N'-(4-fluorophenyl)-1-N-[4-[6-(1-methylpyrazol-4-yl)quinazolin-4-yl]oxyphenyl]cyclo-propane-1,1-dicarboxamide |
| 129 | 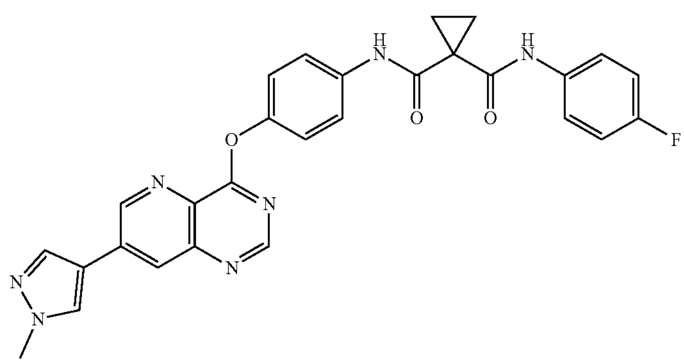 [SMILES: Cn1cc(-c2cnc3c(Oc4ccc(NC(=O)C5(C(=O)Nc6ccc(F)cc6)CC5)cc4)ncnc3c2)cn1] | 1-N'-(4-fluorophenyl)-1-N-[4-[7-(1-methylpyrazol-4-yl)pyrido[3,2-d]pyrimidin-4-yl]oxyphenyl]cyclo-propane-1,1-dicarboxamide |

TABLE 1-continued

Compounds of Formula I'

| Comp. | Structure | IUPAC Name |
|---|---|---|
| 130 | 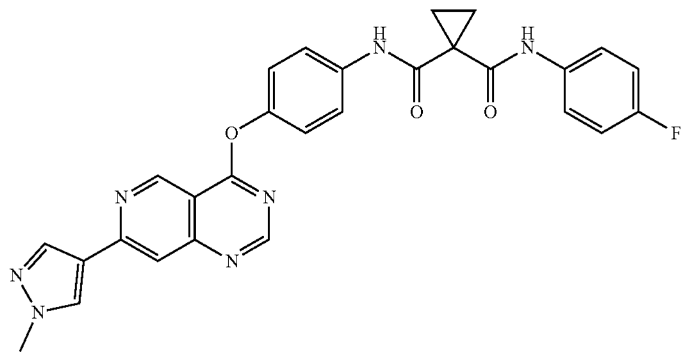 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[4,3-d]pyrimidin-4-yl]oxyphenyl]cyclopropane-1,1-dicarboxamide |
| 139 | 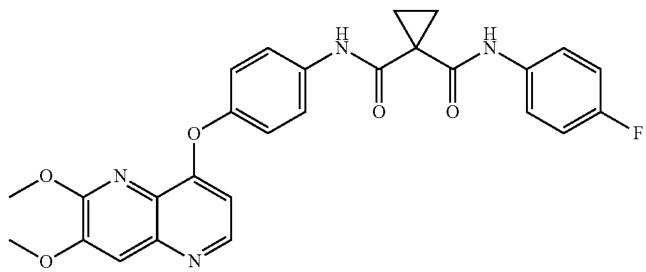 | 1-N-[4-[(6,7-dimethoxy-1,5-naphthyridin-4-yl)oxy]phenyl]-1-N'-(4-fluorophenyl)cyclopropane-1,1-dicarboxamide |
| 140 | 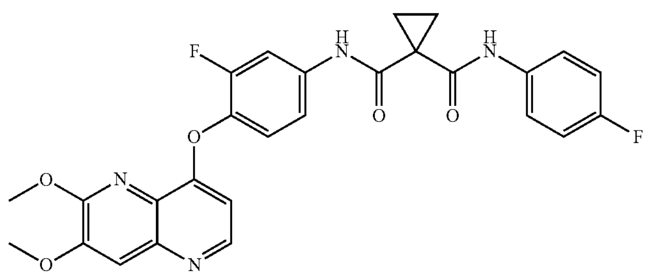 | 1-N'-[4-[(6,7-dimethoxy-1,5-naphthyridin-4-yl)oxy]-3-fluorophenyl]-1-N-(4-fluorophenyl)cyclopropane-1,1-dicarboxamide |
| 141 | 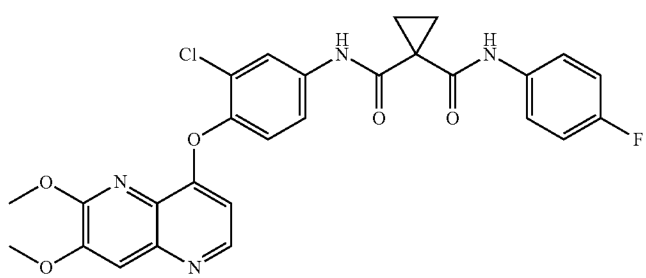 [SMILES: COc1cc2nccc(Oc3ccc(NC(=O)C4(C(=O)Nc5ccc(F)cc5)CC4)cc3F)c2nc1OC] | 1-N'-[3-chloro-4-[(6,7-dimethoxy-1,5-naphthyridin-4-yl)oxy]phenyl]-1-N-(4-fluorophenyl)cyclopropane-1,1-dicarboxamide |
| 142 | 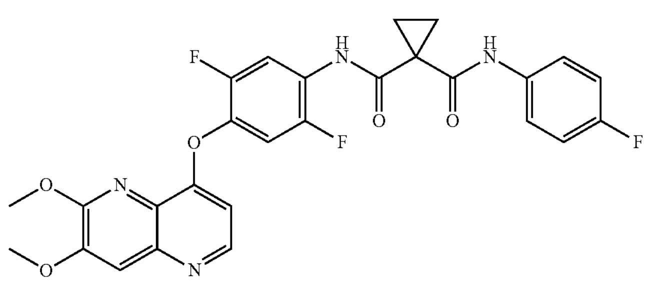 [SMILES: COc1cc2nccc(Oc3cc(F)c(NC(=O)C4(C(=O)Nc5ccc(F)cc5)CC4)cc3F)c2nc1OC] | 1-N'-[4-[(6,7-dimethoxy-1,5-naphthyridin-4-yl)oxy]-2,5-difluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 149 | 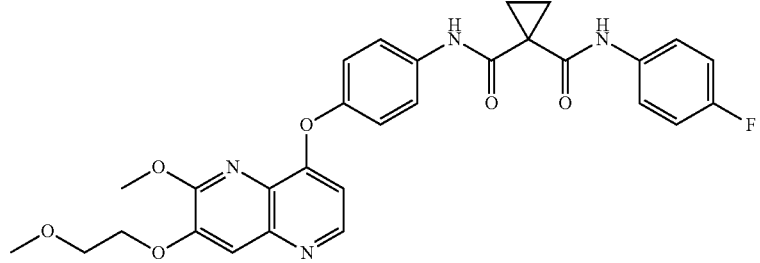 [SMILES: COCCOc1cc2nccc(Oc3ccc(NC(=O)C4(C(=O)Nc5ccc(F)cc5)CC4)cc3)c2nc1OC] | 1-N'-(4-fluorophenyl)-1-N-[4-[[6-methoxy-7-(2-methoxyethoxy)-1,5-naphthyridin-4-yl]oxy]phenyl]cyclopropane-1,1-dicarboxamide |
| 150 | 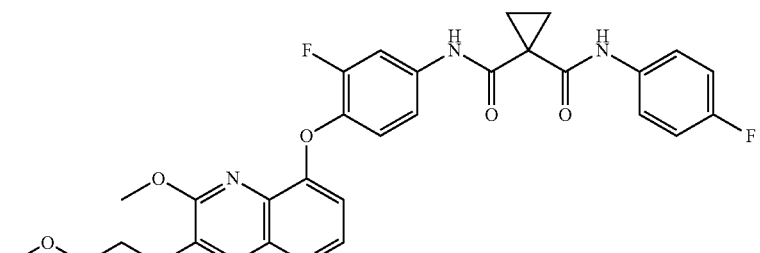 | 1-N'-[3-fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 151 | 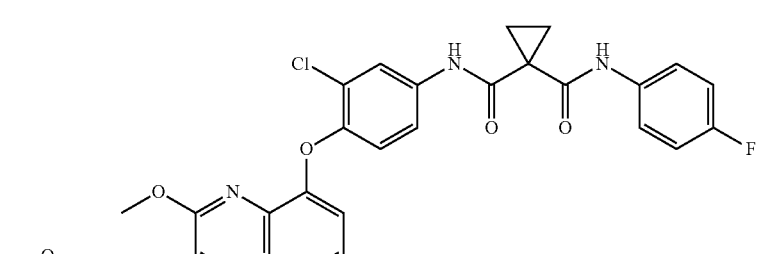 | 1-N'-[3-chloro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 152 | 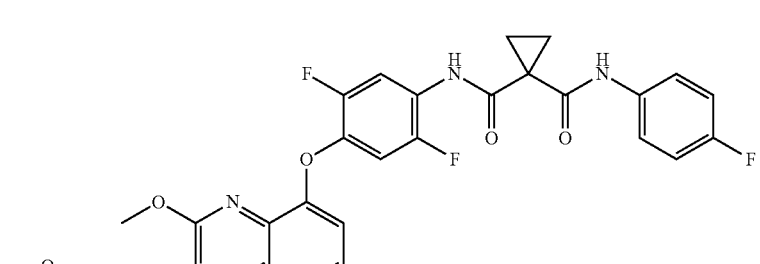 | 1-N'-[2,5-difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 153 | 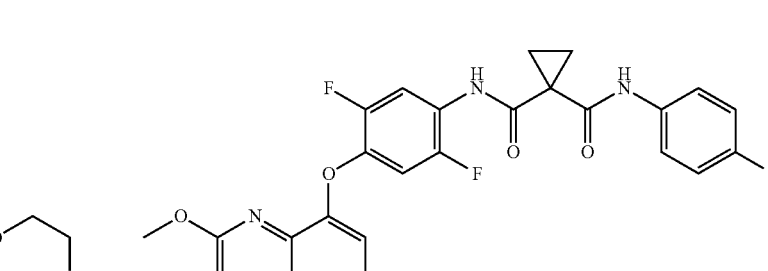 | 1-N'-[2,5-difluoro-4-[[6-methoxy-7-(2-morpholin-4-ylethoxy)-1,5-naphthyridin-4-yl]oxy]phenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 157 | 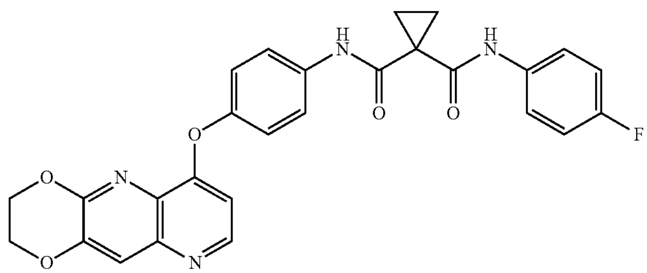 [SMILES: O=C(Nc1ccc(F)cc1)C1(C(=O)Nc2ccc(Oc3ccnc4cc5c(nc34)OCCO5)cc2)CC1] | 1-N-[4-(2,3-dihydro-[1,4]dioxino[2,3-b][1,5]naphthyridin-6-yloxy)phenyl]-1-N'-(4-fluorophenyl)cyclopropane-1,1-dicarboxamide |
| 158 | 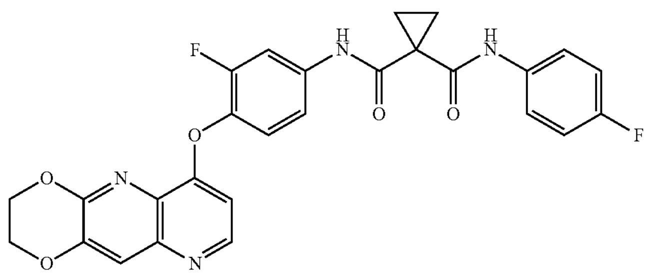 [SMILES: O=C(Nc1ccc(F)cc1)C1(C(=O)Nc2ccc(Oc3ccnc4cc5c(nc34)OCCO5)c(F)c2)CC1] | 1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide |
| 159 | 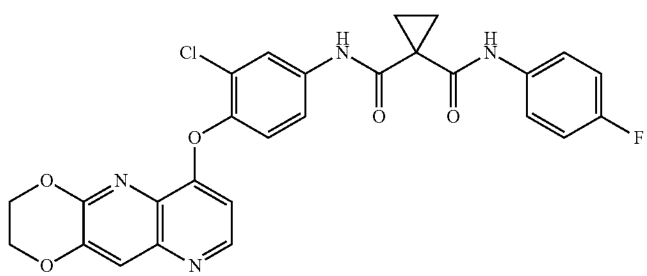 [SMILES: O=C(Nc1ccc(F)cc1)C1(C(=O)Nc2ccc(Oc3ccnc4cc5c(nc34)OCCO5)c(Cl)c2)CC1] | 1-N'-[3-chloro-4-(2,3-dihydro-[1,4]dioxino[2,3-b][1,5]naphthyridin-6-yloxy)phenyl]-1-N-(4-fluorophenyl)cyclopropane-1,1-dicarboxamide |
| 164 | 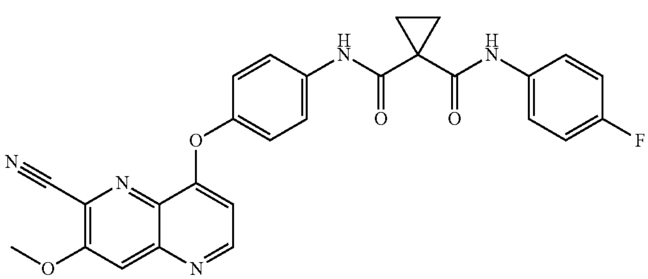 | 1-N-[4-[(6-cyano-7-methoxy-1,5-naphthyridin-4-yl)oxy]phenyl]-1-N'-(4-fluorophenyl)cyclopropane-1,1-dicarboxamide |
| 165 | 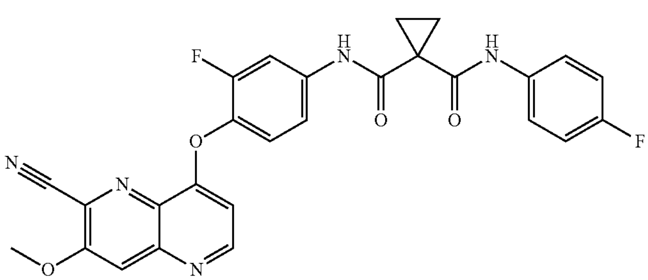 [SMILES: COc1cc2nccc(Oc3ccc(NC(=O)C4(C(=O)Nc5ccc(F)cc5)CC4)cc3F)c2nc1C#N] | 1-N'-[4-[(6-cyano-7-methoxy-1,5-naphthyridin-4-yl)oxy]-3-fluorophenyl]-1-N-(4-fluorophenyl)cyclopropane-1,1-dicarboxamide |

TABLE 1-continued

Compounds of Formula I'

| Comp. | Structure | IUPAC Name |
|---|---|---|
| 166 | 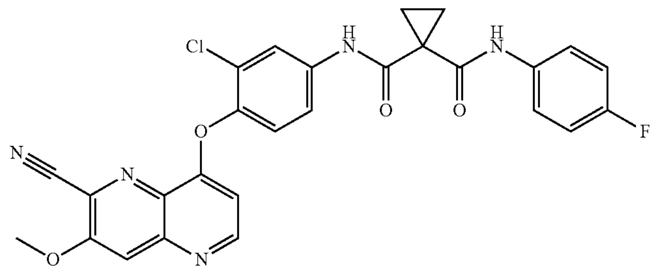 [SMILES: COc1cc2nccc(Oc3ccc(NC(=O)C4(C(=O)Nc5ccc(F)cc5)CC4)cc3Cl)c2nc1C#N] | 1-N'-[3-chloro-4-[(6-cyano-7-methoxy-1,5-naphthyridin-4-yl)oxy]phenyl]-1-N-(4-fluorophenyl)cyclopropane-1,1-dicarboxamide |
| 167 | 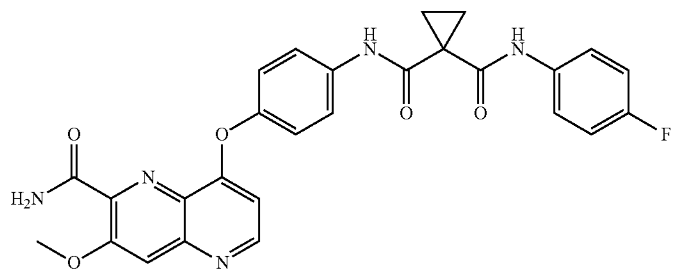 [SMILES: COc1cc2nccc(Oc3ccc(NC(=O)C4(C(=O)Nc5ccc(F)cc5)CC4)cc3)c2nc1C(N)=O] | 1-N-[4-[(6-carbamoyl-7-methoxy-1,5-naphthyridin-4-yl)oxy]phenyl]-1-N'-(4-fluorophenyl)cyclopropane-1,1-dicarboxamide |
| 168 | 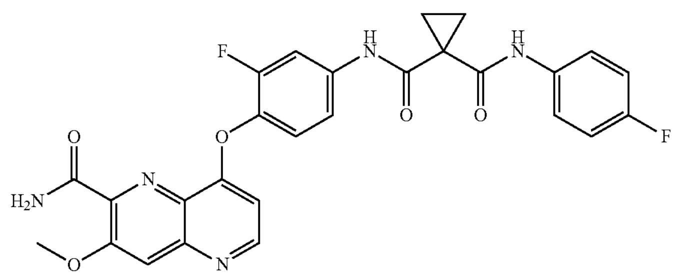 [SMILES: COc1cc2nccc(Oc3ccc(NC(=O)C4(C(=O)Nc5ccc(F)cc5)CC4)cc3F)c2nc1C(N)=O] | 1-N'-[4-[(6-carbamoyl-7-methoxy-1,5-naphthyridin-4-yl)oxy]-3-fluoro-phenyl]-1-N-(4-fluorophenyl)cyclopropane-1,1-dicarboxamide |
| 169 | 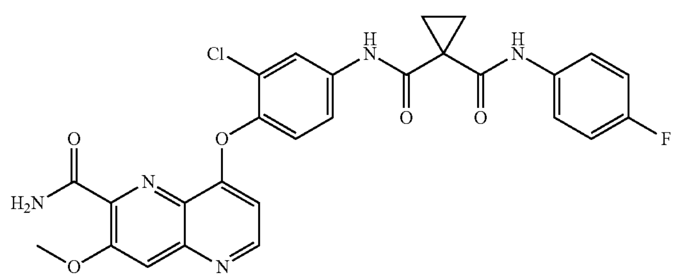 [SMILES: COc1cc2nccc(Oc3ccc(NC(=O)C4(C(=O)Nc5ccc(F)cc5)CC4)cc3Cl)c2nc1C(N)=O] | 1-N'-[4-[(6-carbamoyl-7-methoxy-1,5-naphthyridin-4-yl)oxy]-3-chlorophenyl]-1-N-(4-fluorophenyl)cyclopropane-1,1-dicarboxamide |
| 172 | 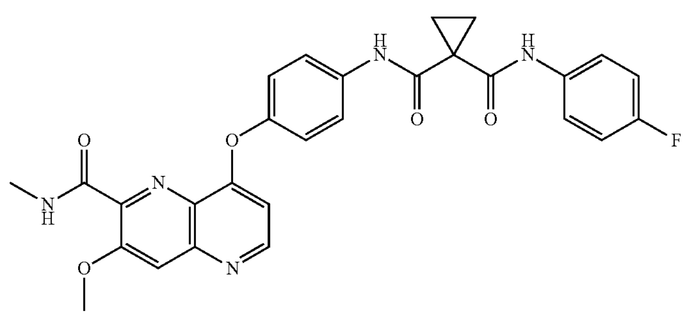 [SMILES: CNC(=O)c1nc2c(Oc3ccc(NC(=O)C4(C(=O)Nc5ccc(F)cc5)CC4)cc3)ccnc2cc1OC] | 1-N'-(4-fluorophenyl)-1-N-[4-[[7-methoxy-6-(methyl-carbamoyl)-1,5-naphthyridin-4-yl]oxy]phenyl]cyclopropane-1,1-dicarboxamide |

TABLE 1-continued

Compounds of Formula I'

| Comp. | Structure | IUPAC Name |
|---|---|---|
| 173 | 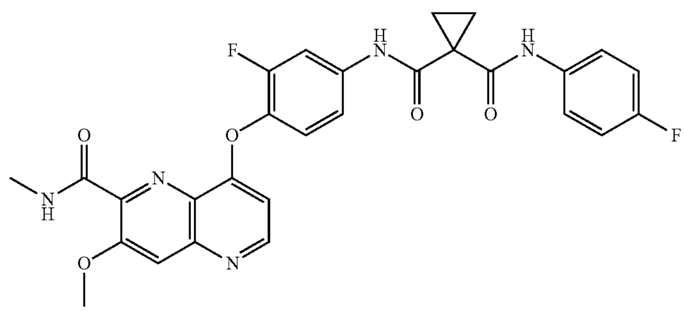 [SMILES: CNC(=O)c1nc2c(Oc3ccc(NC(=O)C4(C(=O)Nc5ccc(F)cc5)CC4)cc3F)ccnc2cc1OC] | 1-N'-[3-fluoro-4-[[7-methoxy-6-(methylcarbamoyl)-1,5-naphthyridin-4-yl]oxy]phenyl]-1-N-(4-fluorophenyl)cyclopropane-1,1-dicarboxamide |
| 174 | 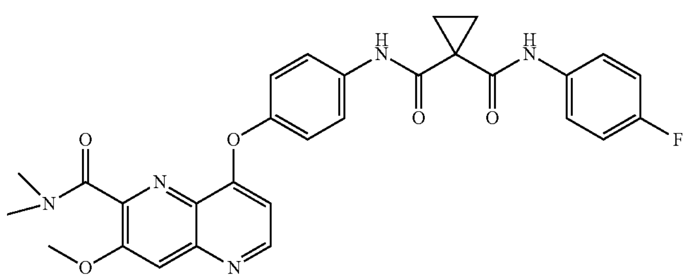 [SMILES: COc1cc2nccc(Oc3ccc(NC(=O)C4(C(=O)Nc5ccc(F)cc5)CC4)cc3)c2nc1C(=O)N(C)C] | 1-N-[4-[[6-(dimethylcarbamoyl)-7-methoxy-1,5-naphthyridin-4-yl]oxy]phenyl]-1-N'-(4-fluorophenyl)cyclopropane-1,1-dicarboxamide |
| 176 | 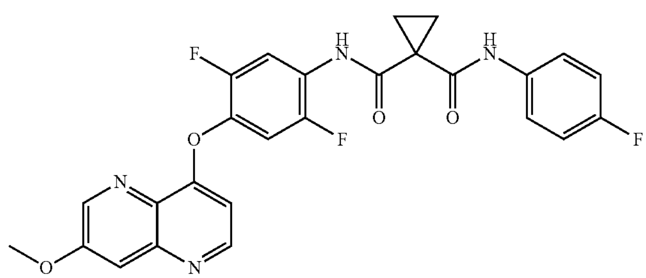 [SMILES: COc1cnc2c(Oc3cc(F)c(NC(=O)C4(C(=O)Nc5ccc(F)cc5)CC4)cc3F)ccnc2c1] | 1-N'-[2,5-difluoro-4-[(7-methoxy-1,5-naphthyridin-4-yl)oxy]phenyl]-1-N-(4-fluorophenyl)cyclopropane-1,1-dicarboxamide |
| 181 | 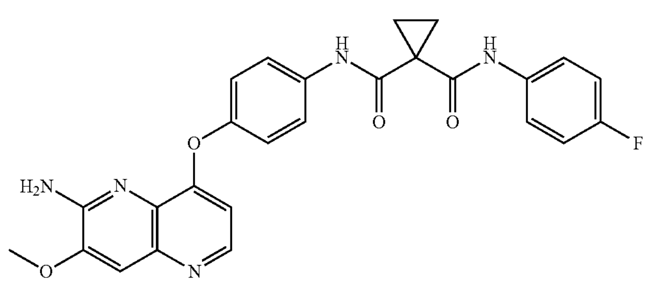 [SMILES: COc1cc2nccc(Oc3ccc(NC(=O)C4(C(=O)Nc5ccc(F)cc5)CC4)cc3)c2nc1N] | 1-N-[4-[(6-amino-7-methoxy-1,5-naphthyridin-4-yl)oxy]phenyl]-1-N'-(4-fluorophenyl)cyclopropane-1,1-dicarboxamide |
| 182 | 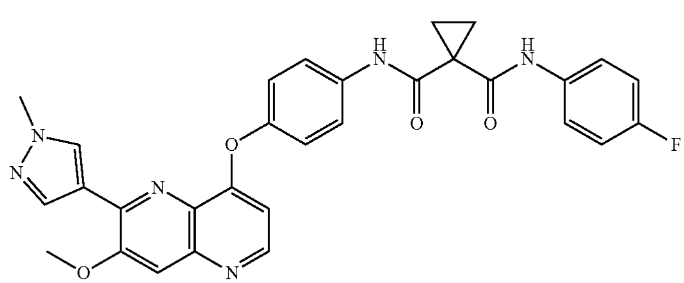 [SMILES: COc1cc2nccc(Oc3ccc(NC(=O)C4(C(=O)Nc5ccc(F)cc5)CC4)cc3)c2nc1-c1cnn(C)c1] | 1-N'-(4-fluorophenyl)-1-N-[4-[[7-methoxy-6-(1-methylpyrazol-4-yl)-1,5-naphthyridin-4-yl]oxy]phenyl]cyclopropane-1,1-dicarboxamide |

TABLE 1-continued

Compounds of Formula I'

| Comp. | Structure | IUPAC Name |
|---|---|---|
| 183 | 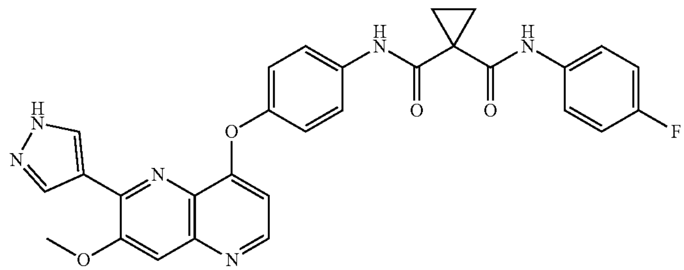 [SMILES: COc1cc2nccc(Oc3ccc(NC(=O)C4(C(=O)Nc5ccc(F)cc5)CC4)cc3)c2nc1-c1cn[nH]c1] | 1-N'-(4-fluorophenyl)-1-N-[4-[[7-methoxy-6-(1H-pyrazol-4-yl)-1,5-naphthyridin-4-yl]oxy]phenyl]cyclopropane-1,1-dicarboxamide |
| 184 | 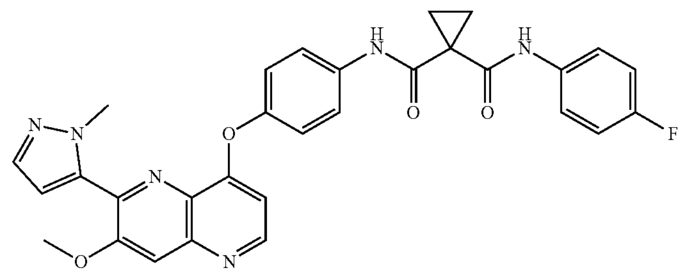 [SMILES: COc1cc2nccc(Oc3ccc(NC(=O)C4(C(=O)Nc5ccc(F)cc5)CC4)cc3)c2nc1-c1ccnn1C] | 1-N'-(4-fluorophenyl)-1-N-[4-[[7-methoxy-6-(2-methyl-pyrazol-3-yl)-1,5-naphthyridin-4-yl]oxy]phenyl]cyclopropane-1,1-dicarboxamide |
| 189 | 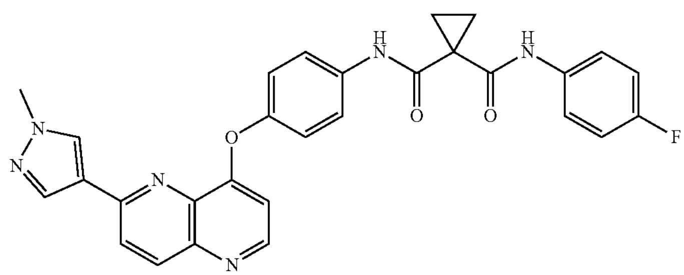 [SMILES: Cn1cc(-c2ccc3nccc(Oc4ccc(NC(=O)C5(C(=O)Nc6ccc(F)cc6)CC5)cc4)c3n2)cn1] | 1-N'-(4-fluorophenyl)-1-N-[4-[[6-(1-methylpyrazol-4-yl)-1,5-naphthyridin-4-yl]oxy]phenyl]cyclopropane-1,1-dicarboxamide |

In one embodiment, the compound of Formula I' is a compound of Formula I:

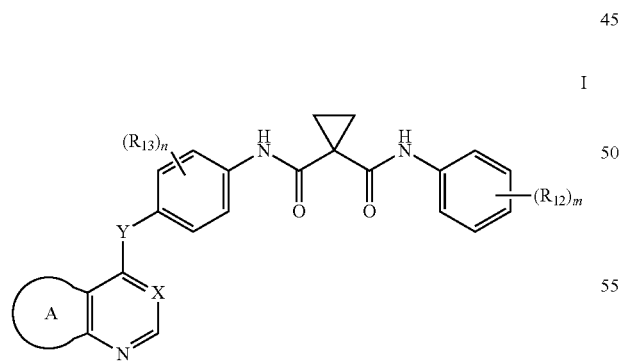

I wherein:
X is selected from N and C—H;
Y is O, S, SO, SO$_2$, NH, or N—(C$_1$-C$_6$ alkyl);
R$_{13}$ is selected from —H, halo, —CN, and optionally substituted C$_{1-6}$ alkyl;

R$_{12}$ is —H or halo;

is optionally substituted with one, two, three, or four groups independently selected from the group consisting of halo, and C$_1$-C$_6$ alkyl, wherein "~~~" indicate points of attachment;

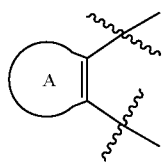

is selected from the group consisting of

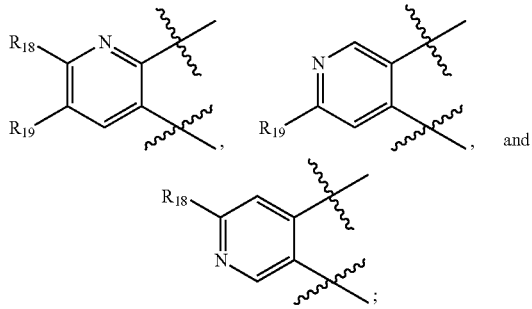

wherein $R_{18}$ and $R_{19}$ are selected from the group consisting of H, halo, —CN, optionally substituted $C_1$-$C_6$ alkyl, $C(O)NR_5R_6$, optionally substituted 5 or 6-membered heteroaryl, and optionally substituted $C_1$-$C_6$ alkoxy; or when

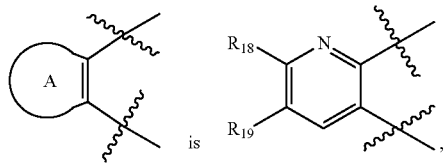

$R_{18}$ and $R_{19}$ can be joined together to form a 5 or 6-membered optionally substituted cycloalkyl or heterocycloalkyl;
$R_5$ and $R_6$ are selected from the group consisting of H, optionally substituted $C_{1-6}$ alkyl, or $R_5$ and $R_6$ taken together with the nitrogen to which they are attached to form a 5- or 6-membered optionally substituted heterocycle; and
m and n are each independently 1 or 2;
provided that when

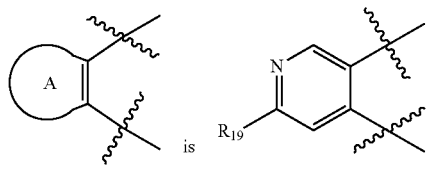

and X is C—H, $R_{19}$ is not optionally substituted $C_1$-$C_6$ alkyl, halo, or optionally substituted $C_1$-$C_6$ alkoxy.

In one embodiment, $R_{19}$ is selected from the group consisting of optionally substituted $C_1$-$C_6$ alkoxy and —CN. In a further embodiment, the $C_1$-$C_6$ alkoxy is optionally substituted with alkoxy or heterocycloalkyl.

In some embodiments,

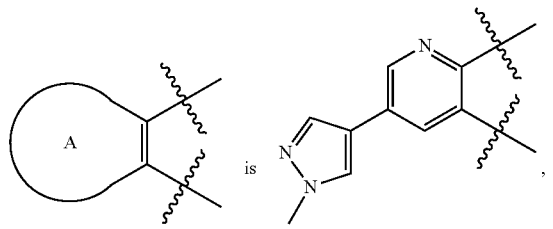

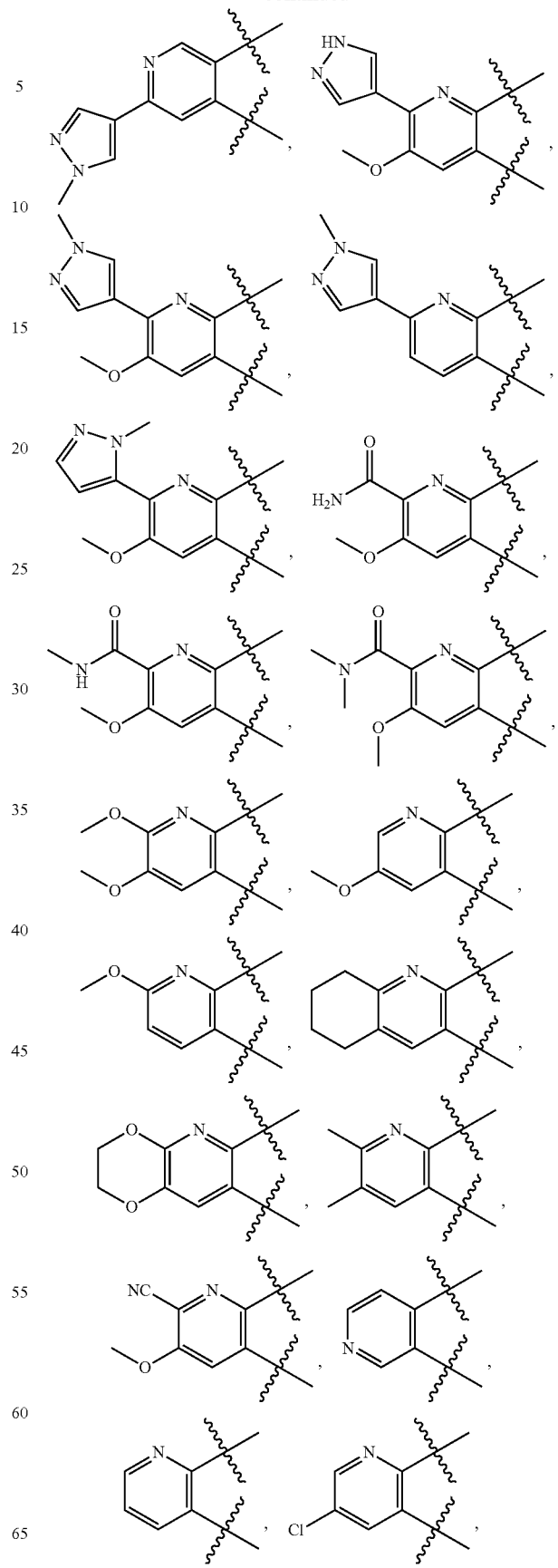

-continued

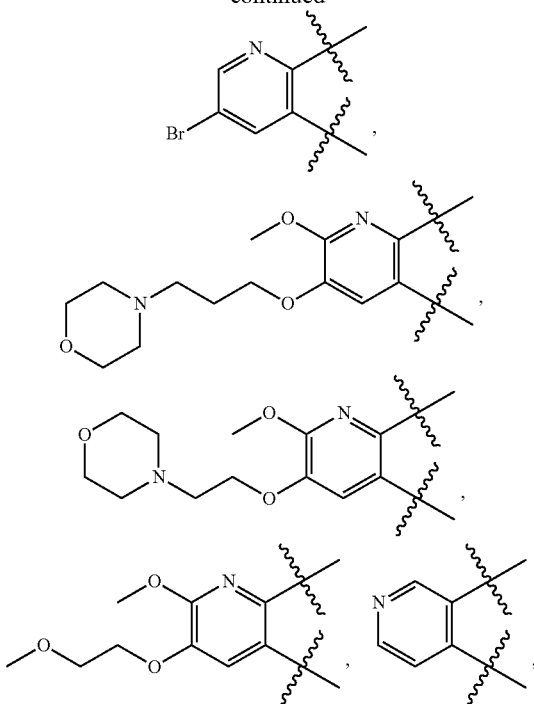

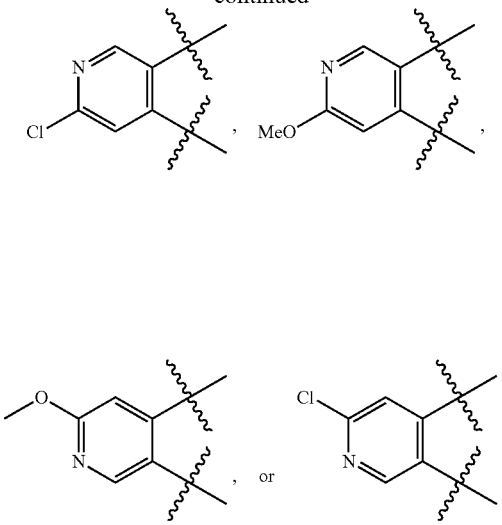

In one embodiment, X is N.

In another embodiment, $R_{13}$ is H.

In one embodiment, the compound of Formula I, or a pharmaceutically acceptable salt thereof, is selected from the compounds listed in Table 2, or a pharmaceutically acceptable salt thereof.

TABLE 2

Compounds of Formula I

| Comp. | Structure | IUPAC Name |
|---|---|---|
| 7 | 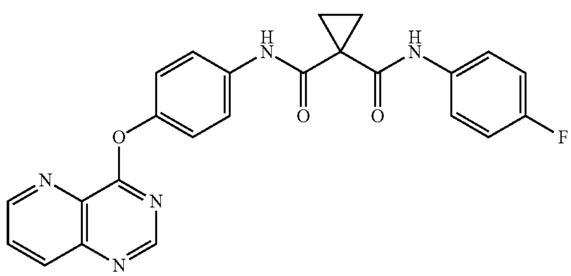 [SMILES: O=C(Nc1ccc(F)cc1)C1(C(=O)Nc2ccc(Oc3ncnc4cccnc34)cc2)CC1] | 1-N'-(4-fluorophenyl)-1-N-(4-pyrido[3,2-d]pyrimidin-4-yloxyphenyl)cyclopropane-1,1-dicarboxamide |
| 12 | 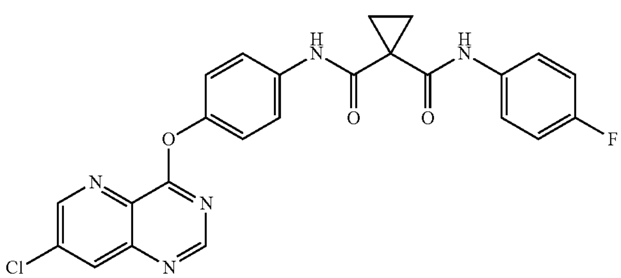 | 1-N-[4-(7-chloropyrido[3,2-d]pyrimidin-4-yl)oxyphenyl]-1-N'-(4-fluorophenyl)cyclopropane-1,1-dicarboxamide |
| 13 | 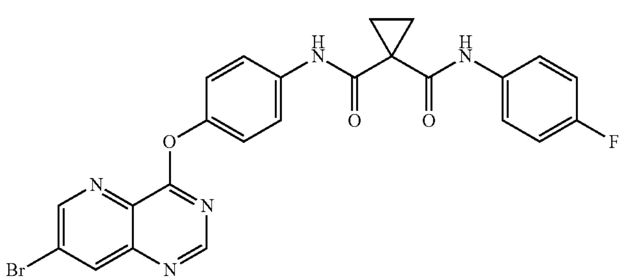 [SMILES: O=C(Nc1ccc(F)cc1)C1(C(=O)Nc2ccc(Oc3ncnc4cc(Cl)cnc34)cc2)CC1] | 1-N-[4-(7-bromopyrido[3,2-d]pyrimidin-4-yl)oxyphenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 16 | 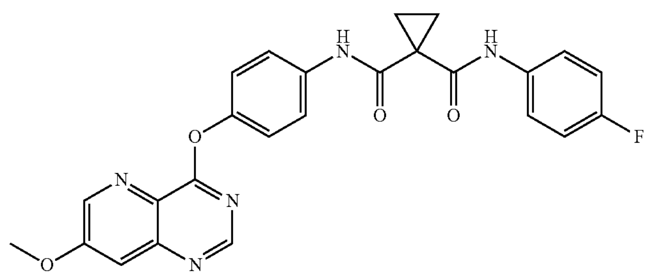 [SMILES: COc1cnc2c(Oc3ccc(NC(=O)C4(C(=O)Nc5ccc(F)cc5)CC4)cc3)ncnc2c1] | 1-N'-(4-fluorophenyl)-1-N-[4-(7-methoxypyrido[3,2-d]pyrimidin-4-yl)oxyphenyl]cyclopropane-1,1-dicarboxamide |
| 19 | 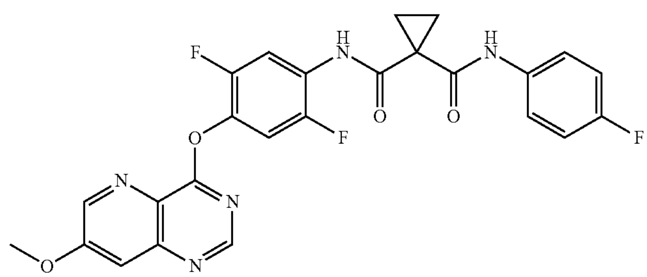 [SMILES: COc1cnc2c(Oc3cc(F)c(NC(=O)C4(C(=O)Nc5ccc(F)cc5)CC4)cc3F)ncnc2c1] | 1-N'-[2,5-difluoro-4-(7-methoxypyrido[3,2-d]pyrimidin-4-yl)oxyphenyl]-1-N-(4-fluorophenyl)cyclopropane-1,1-dicarboxamide |
| 28 | 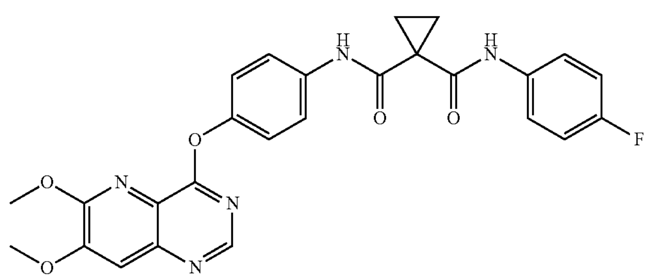 [SMILES: COc1cc2ncnc(Oc3ccc(NC(=O)C4(C(=O)Nc5ccc(F)cc5)CC4)cc3)c2nc1OC] | 1-N-[4-(6,7-dimethoxypyrido[3,2-d]pyrimidin-4-yl)oxyphenyl]-1-N'-(4-fluorophenyl)cyclopropane-1,1-dicarboxamide |
| 29 | 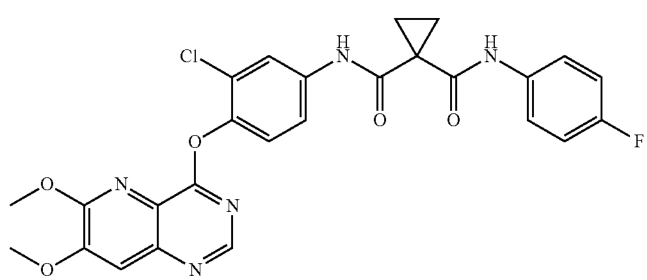 [SMILES: COc1cc2ncnc(Oc3ccc(NC(=O)C4(C(=O)Nc5ccc(F)cc5)CC4)cc3Cl)c2nc1OC] | 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide |
| 30 | 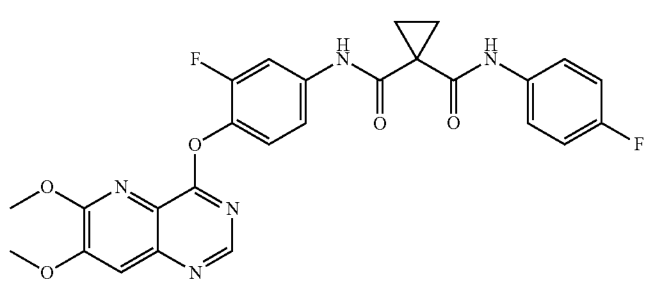 [SMILES: COc1cc2ncnc(Oc3ccc(NC(=O)C4(C(=O)Nc5ccc(F)cc5)CC4)cc3F)c2nc1OC] | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 31 | 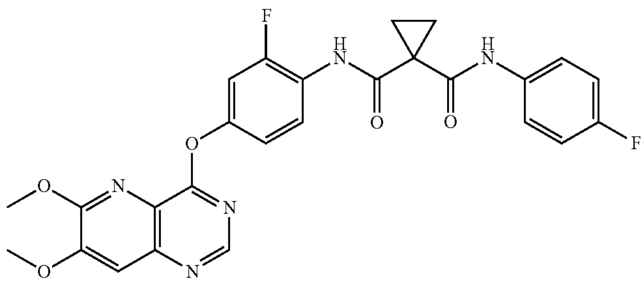 | 1-N'-[4-(6,7-dimethoxypyrido[3,2-d]pyrimidin-4-yl)oxy-2-fluorophenyl]-1-N-(4-fluorophenyl)cyclopropane-1,1-dicarboxamide |
| 32 | 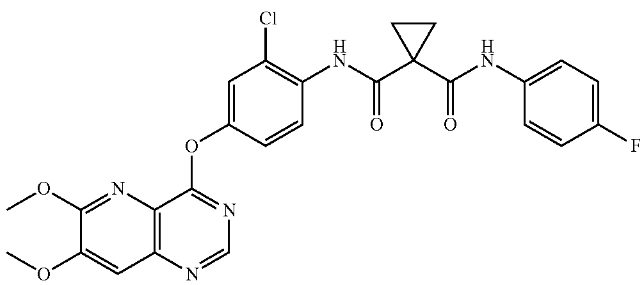 [SMILES: COc1cc2ncnc(Oc3ccc(NC(=O)C4(C(=O)Nc5ccc(F)cc5)CC4)c(F)c3)c2nc1OC] | 1-N'-[2-chloro-4-(6,7-dimethoxypyrido[3,2-d]pyrimidin-4-yl)oxyphenyl]-1-N-(4-fluorophenyl)cyclopropane-1,1-dicarboxamide |
| 33 | 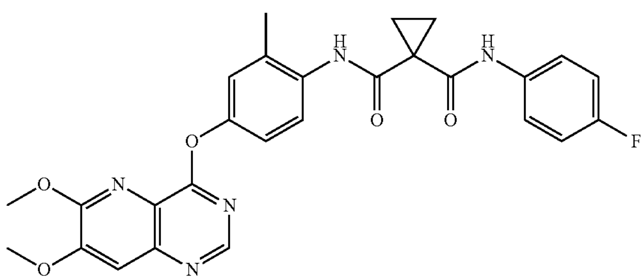 [SMILES: COc1cc2ncnc(Oc3ccc(NC(=O)C4(C(=O)Nc5ccc(F)cc5)CC4)c(C)c3)c2nc1OC] | 1-N'-[4-(6,7-dimethoxypyrido[3,2-d]pyrimidin-4-yl)oxy-2-methylphenyl]-1-N-(4-fluorophenyl)cyclopropane-1,1-dicarboxamide |
| 34 | 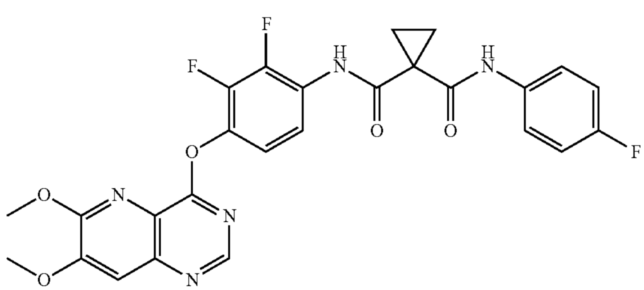 [SMILES: COc1cc2ncnc(Oc3ccc(NC(=O)C4(C(=O)Nc5ccc(F)cc5)CC4)c(F)c3F)c2nc1OC] | 1-N'-[4-(6,7-dimethoxypyrido[3,2-d]pyrimidin-4-yl)oxy-2,3-difluorophenyl]-1-N-(4-fluorophenyl)cyclopropane-1,1-dicarboxamide |
| 35 | 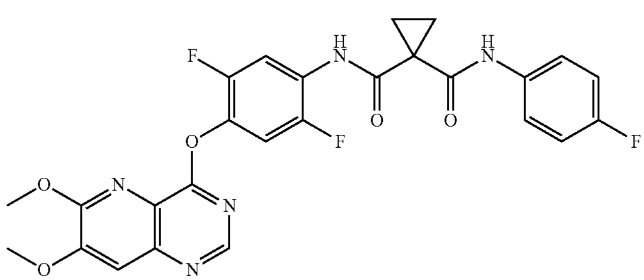 [SMILES: COc1cc2ncnc(Oc3cc(F)c(NC(=O)C4(C(=O)Nc5ccc(F)cc5)CC4)cc3F)c2nc1OC] | 1-N'-[4-(6,7-dimethoxypyrido[3,2-d]pyrimidin-4-yl)oxy-2,5-difluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 43 | 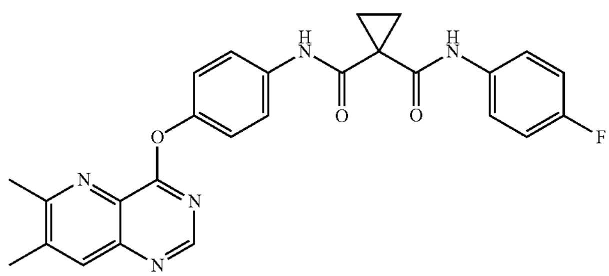 [SMILES: Cc1cc2ncnc(Oc3ccc(NC(=O)C4(C(=O)Nc5ccc(F)cc5)CC4)cc3)c2nc1C] | 1-N-[4-(6,7-dimethylpyrido[3,2-d]pyrimidin-4-yl)oxyphenyl]-1-N'-(4-fluorophenyl)cyclopropane-1,1-dicarboxamide |
| 52 | 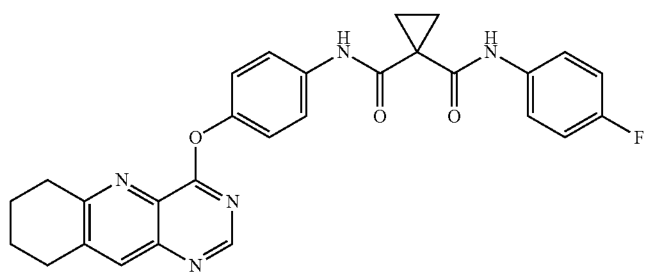 [SMILES: O=C(Nc1ccc(F)cc1)C1(C(=O)Nc2ccc(Oc3ncnc4cc5c(nc34)CCCC5)cc2)CC1] | 1-N'-(4-fluorophenyl)-1-N-[4-(6,7,8,9-tetrahydropyrimido[5,4-b]quinolin-4-yloxy)phenyl]cyclopropane-1,1-dicarboxamide |
| 57 | 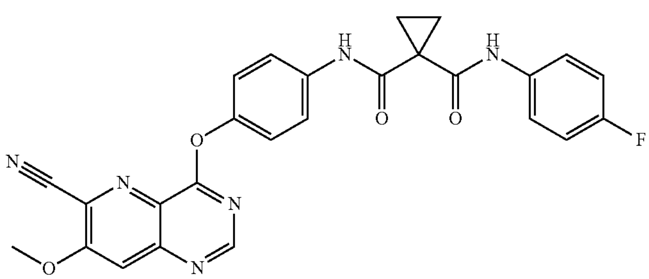 [SMILES: COc1cc2ncnc(Oc3ccc(NC(=O)C4(C(=O)Nc5ccc(F)cc5)CC4)cc3)c2nc1C#N] | 1-N-[4-(6-cyano-7-methoxypyrido[3,2-d]pyrimidin-4-yl)oxyphenyl]-1-N'-(4-fluorophenyl)cyclopropane-1,1-dicarboxamide |
| 65 | 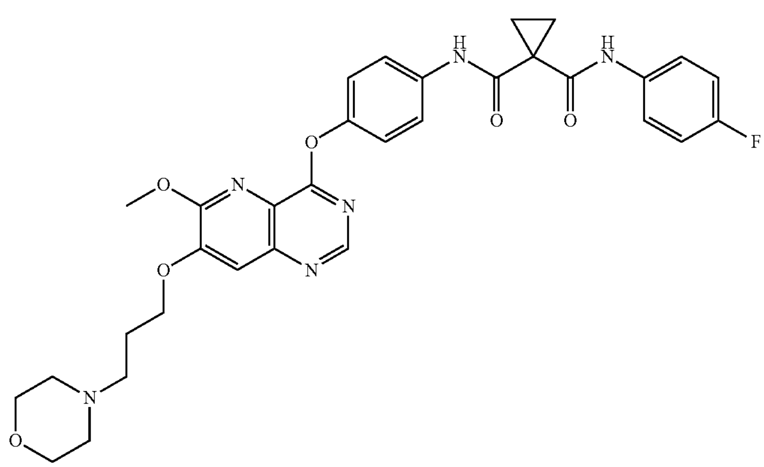 [SMILES: COc1nc2c(Oc3ccc(NC(=O)C4(C(=O)Nc5ccc(F)cc5)CC4)cc3)ncnc2cc1OCCCN1CCOCC1] | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide |

TABLE 2-continued

Compounds of Formula I

| Comp. | Structure | IUPAC Name |
|---|---|---|
| 66 | 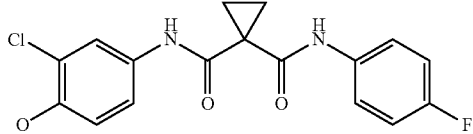 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 67 | 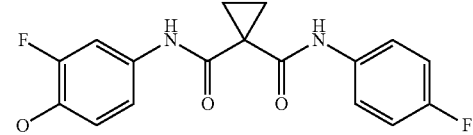 | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 68 | 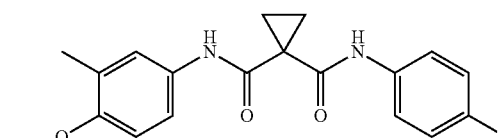 | 1-N-(4-fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide |

TABLE 2-continued

Compounds of Formula I

| Comp. | Structure | IUPAC Name |
|---|---|---|
| 69 | 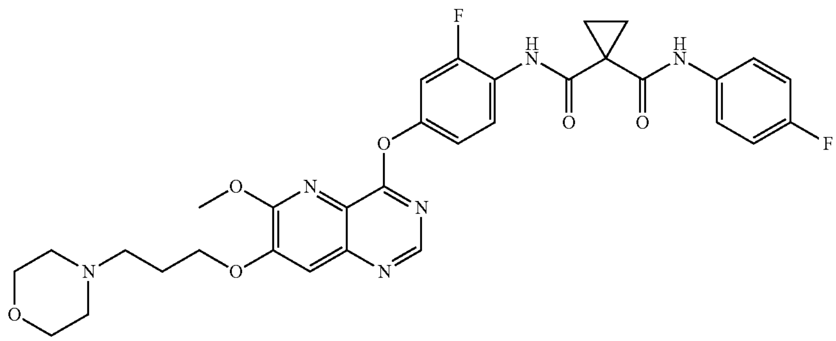 [SMILES: COc1nc2c(Oc3ccc(NC(=O)C4(C(=O)Nc5ccc(F)cc5)CC4)c(F)c3)ncnc2cc1OCCCN1CCOCC1] | 1-N'-[2-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 70 | 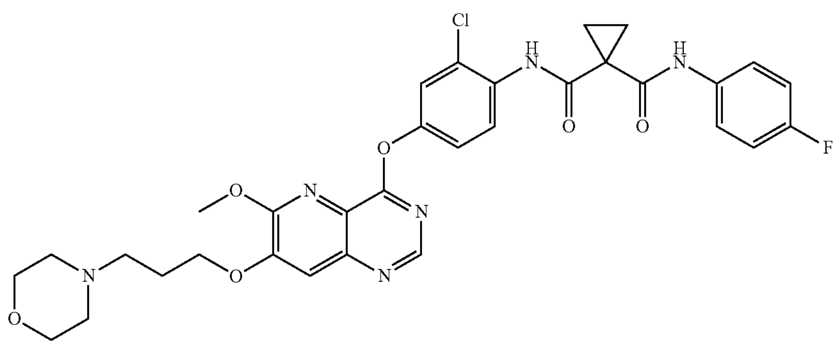 | 1-N'-[2-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 71 | 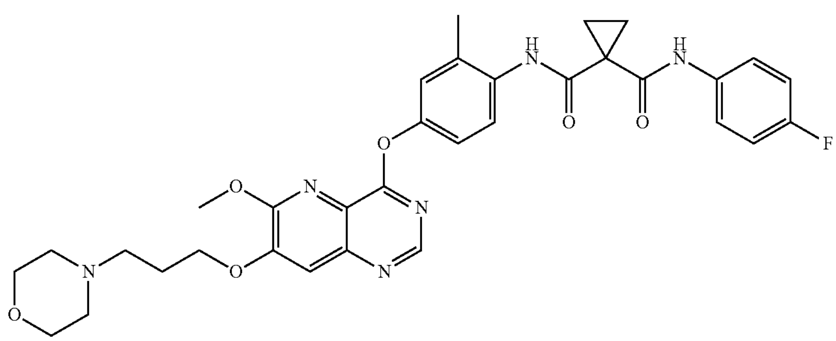 [SMILES: COc1nc2c(Oc3ccc(NC(=O)C4(C(=O)Nc5ccc(F)cc5)CC4)c(C)c3)ncnc2cc1OCCCN1CCOCC1] | 1-N-(4-fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide |
| 72 | 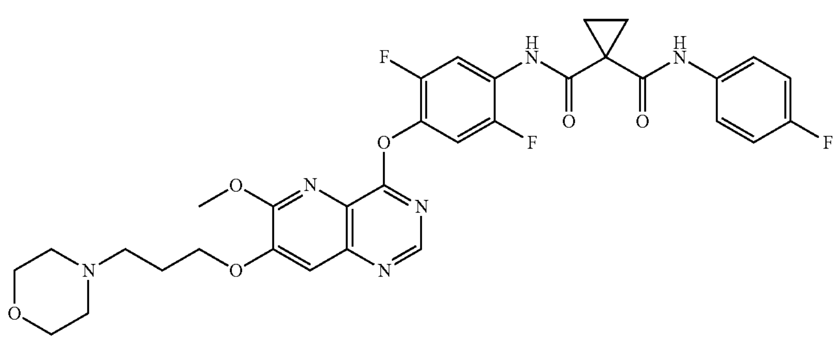 [SMILES: COc1nc2c(Oc3cc(F)c(NC(=O)C4(C(=O)Nc5ccc(F)cc5)CC4)cc3F)ncnc2cc1OCCCN1CCOCC1] | 1-N'-[2,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 73 | 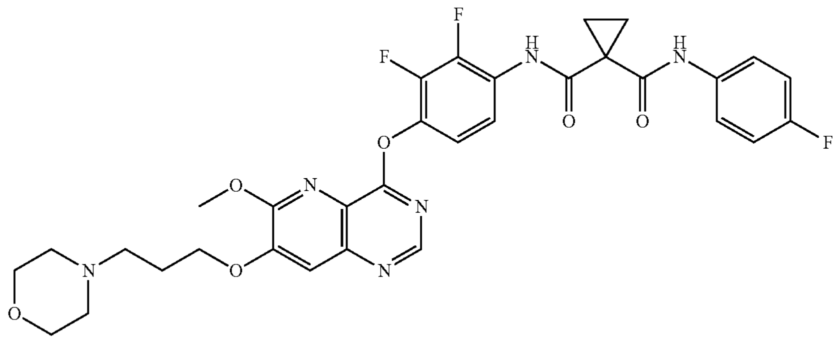 [SMILES: COc1nc2c(Oc3ccc(NC(=O)C4(C(=O)Nc5ccc(F)cc5)CC4)c(F)c3F)ncnc2cc1OCCCN1CCOCC1] | 1-N'-[2,3-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 74 | 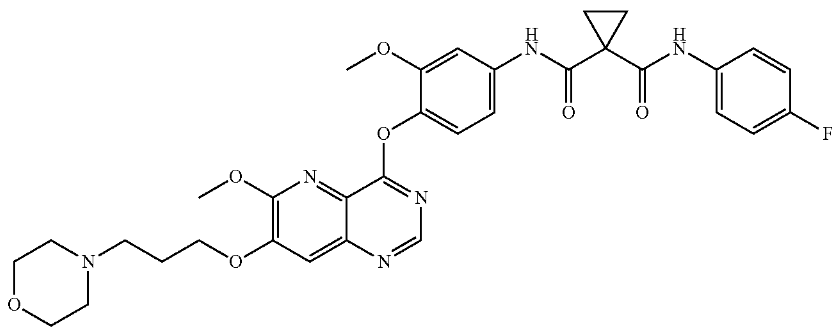 [SMILES: COc1cc(NC(=O)C2(C(=O)Nc3ccc(F)cc3)CC2)ccc1Oc1ncnc2cc(OCCCN3CCOCC3)c(OC)nc12] | 1-N-(4-fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide |
| 75 | 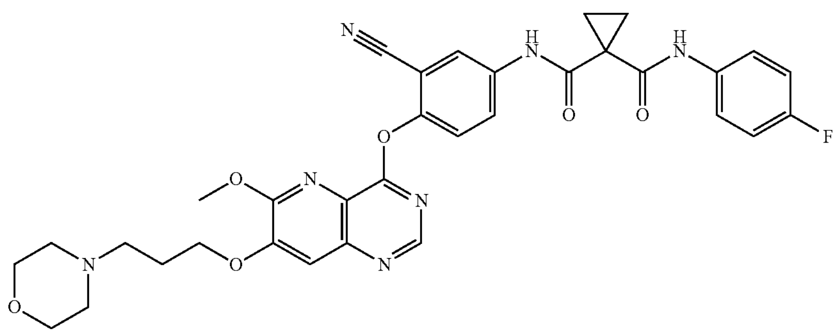 [SMILES: COc1nc2c(Oc3ccc(NC(=O)C4(C(=O)Nc5ccc(F)cc5)CC4)cc3C#N)ncnc2cc1OCCCN1CCOCC1] | 1-N'-[3-cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |
| 76 | 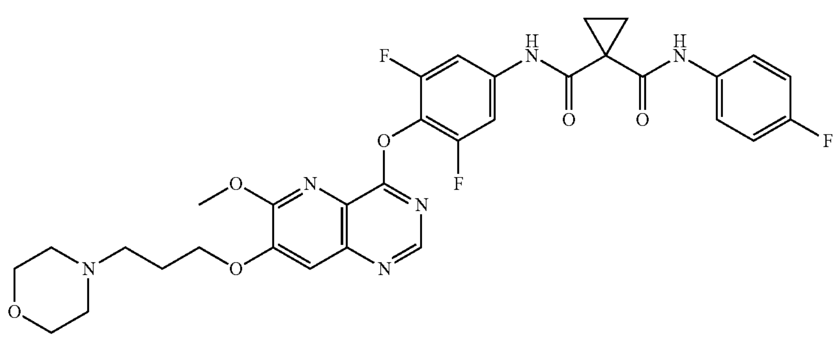 [SMILES: COc1nc2c(Oc3c(F)cc(NC(=O)C4(C(=O)Nc5ccc(F)cc5)CC4)cc3F)ncnc2cc1OCCCN1CCOCC1] | 1-N'-[3,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 78 | 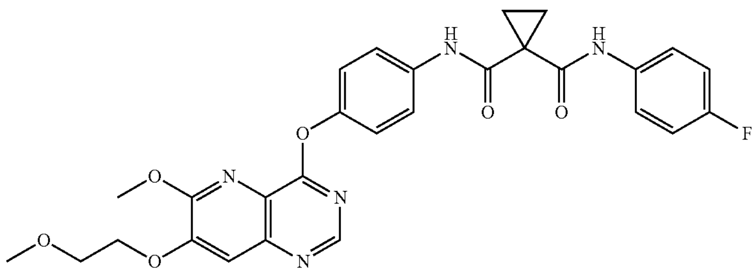 | 1-N'-(4-fluorophenyl)-1-N-[4-[6-methoxy-7-(2-methoxyethoxy)pyrido[3,2-d]pyrimidin-4-yl]oxyphenyl]cyclopropane-1,1-dicarboxamide |
| 79 | 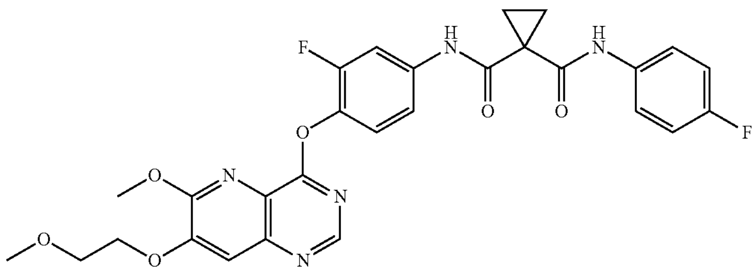 [SMILES: COCCOc1cc2ncnc(Oc3ccc(NC(=O)C4(C(=O)Nc5ccc(F)cc5)CC4)cc3F)c2nc1OC] | 1-N'-[3-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 80 | 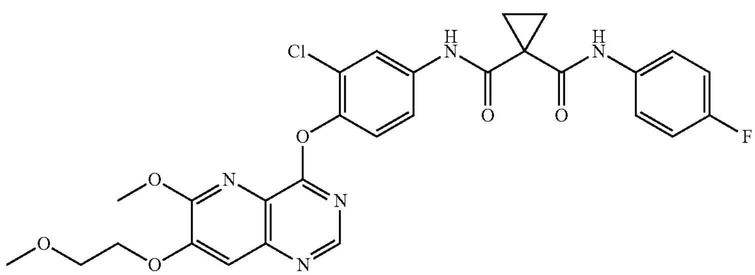 [SMILES: COCCOc1cc2ncnc(Oc3ccc(NC(=O)C4(C(=O)Nc5ccc(F)cc5)CC4)cc3Cl)c2nc1OC] | 1-N'-[3-chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 81 | 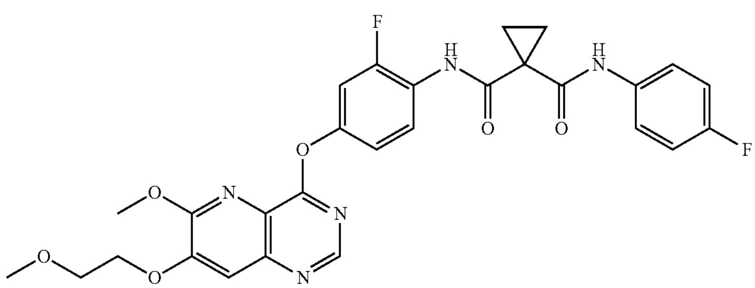 [SMILES: COCCOc1cc2ncnc(Oc3ccc(NC(=O)C4(C(=O)Nc5ccc(F)cc5)CC4)c(F)c3)c2nc1OC] | 1-N'-[2-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 82 | 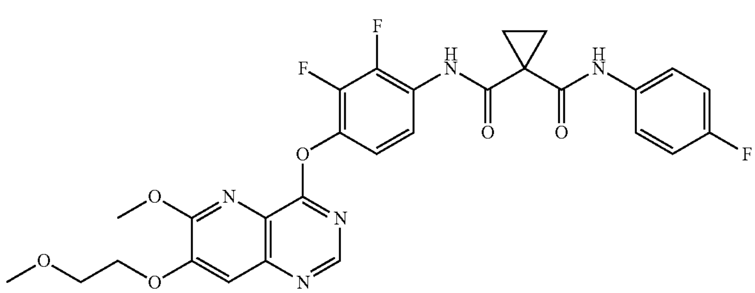 [SMILES: COCCOc1cc2ncnc(Oc3ccc(NC(=O)C4(C(=O)Nc5ccc(F)cc5)CC4)c(F)c3F)c2nc1OC] | 1-N'-[2,3-difluoro-4-[6-methoxy-7-(2-methoxyethoxy)pyrido[3,2-d]pyridmidin-4-yl]oxyphenyl]-1-N-(4-fluorophenyl)cyclopropane-1,1-dicarboxamide |

TABLE 2-continued

Compounds of Formula I

| Comp. | Structure | IUPAC Name |
|---|---|---|
| 83 | 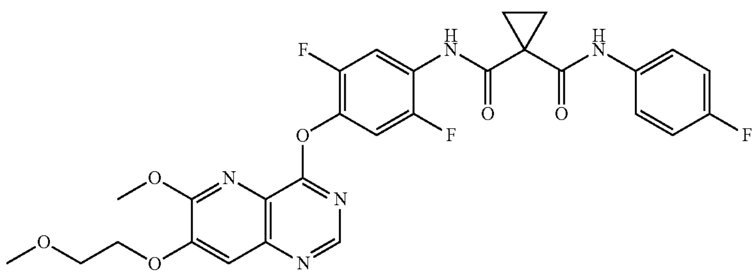 [SMILES: COCCOc1cc2ncnc(Oc3cc(F)c(NC(=O)C4(C(=O)Nc5ccc(F)cc5)CC4)cc3F)c2nc1OC] | 1-N'-[2,5-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide |
| 85 | 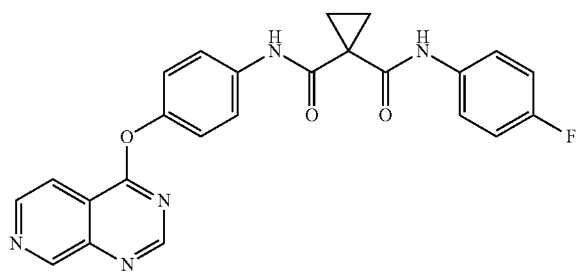 [SMILES: O=C(Nc1ccc(F)cc1)C1(C(=O)Nc2ccc(Oc3ncnc4cnccc34)cc2)CC1] | 1-N'-(4-fluorophenyl)-1-N-(4-pyrido[3,4-d]pyrimidin-4-yloxyphenyl)cyclopropane-1,1-dicarboxamide |
| 88 | 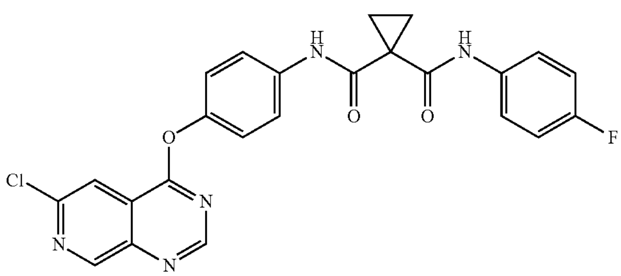 [SMILES: O=C(Nc1ccc(F)cc1)C1(C(=O)Nc2ccc(Oc3ncnc4cnc(Cl)cc34)cc2)CC1] | 1-N-[4-(6-chloropyrido[3,4-d]pyrimidin-4-yl)oxyphenyl]-1-N'-(4-fluorophenyl)cyclopropane-1,1-dicarboxamide |
| 91 | 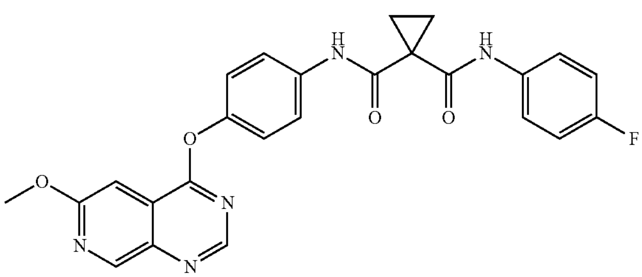 [SMILES: COc1cc2c(Oc3ccc(NC(=O)C4(C(=O)Nc5ccc(F)cc5)CC4)cc3)ncnc2cn1] | 1-N'-(4-fluorophenyl)-1-N-[4-(6-methoxypyrido[3,4-d]pyrimidin-4-yl)oxyphenyl]cyclopropane-1,1-dicarboxamide |
| 95 | 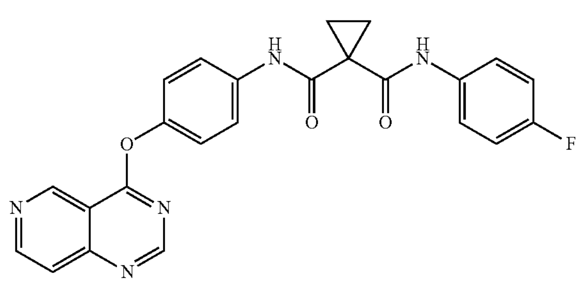 [SMILES: O=C(Nc1ccc(F)cc1)C1(C(=O)Nc2ccc(Oc3ncnc4ccncc34)cc2)CC1] | 1-N'-(4-fluorophenyl)-1-N-(4-pyrido[4,3-d]pyrimidin-4-yloxyphenyl)cyclopropane-1,1-dicarboxamide |

TABLE 2-continued

Compounds of Formula I

| Comp. | Structure | IUPAC Name |
|---|---|---|
| 101 | 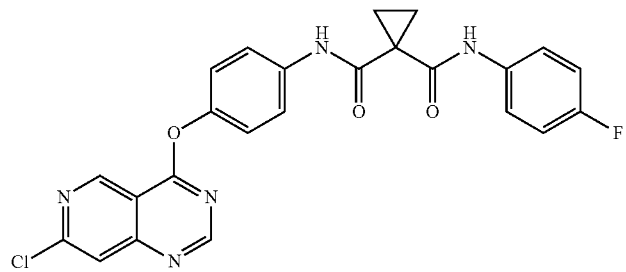 [SMILES: O=C(Nc1ccc(F)cc1)C1(C(=O)Nc2ccc(Oc3ncnc4cc(Cl)ncc34)cc2)CC1] | 1-N-[4-(7-chloropyrido[4,3-d]pyrimidin-4-yl)oxyphenyl]-1-N'-(4-fluorophenyl)cyclopropane-1,1-dicarboxamide |
| 104 | 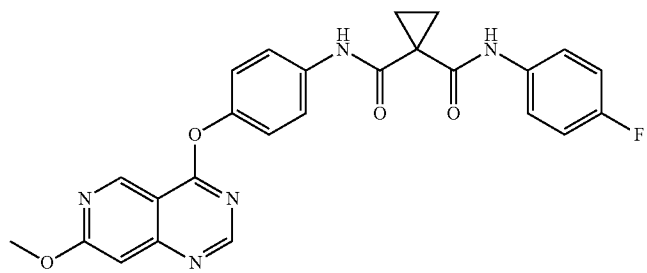 [SMILES: COc1cc2ncnc(Oc3ccc(NC(=O)C4(C(=O)Nc5ccc(F)cc5)CC4)cc3)c2cn1] | 1-N'-(4-fluorophenyl)-1-N-[4-(7-methoxypyrido[4,3-d]pyrimidin-4-yl)oxyphenyl]cyclopropane-1,1-dicarboxamide |
| 129 | 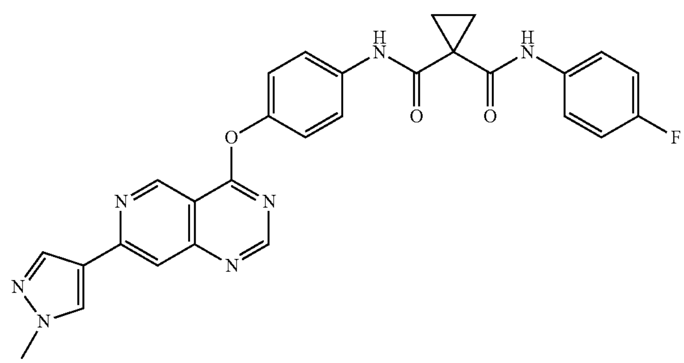 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[3,2-d]pyrimidin-4-yl]oxyphenyl]cyclopropane-1,1-dicarboxamide |
| 130 | 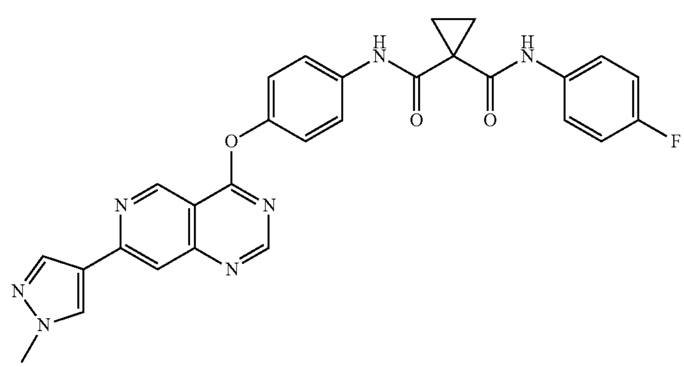 [SMILES: Cn1cc(-c2cc3ncnc(Oc4ccc(NC(=O)C5(C(=O)Nc6ccc(F)cc6)CC5)cc4)c3cn2)cn1] | 1-N'-(4-fluorophenyl)-1-N-[4-[7-(1-methylpyrazol-4-yl)pyrido[4,3-d]pyrimidin-4-yl]oxyphenyl]cyclopropane-1,1-dicarboxamide |
| 139 | 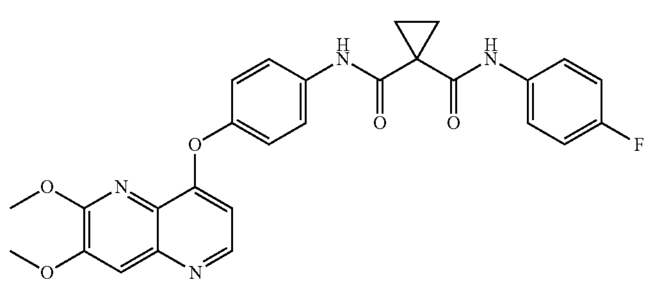 [SMILES: COc1cc2nccc(Oc3ccc(NC(=O)C4(C(=O)Nc5ccc(F)cc5)CC4)cc3)c2nc1OC] | 1-N-[4-[(6,7-dimethoxy-1,5-naphthyridin-4-yl)oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 140 | 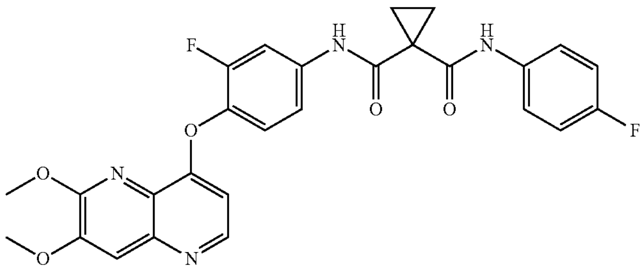 [SMILES: COc1cc2nccc(Oc3ccc(NC(=O)C4(C(=O)Nc5ccc(F)cc5)CC4)cc3F)c2nc1OC] | 1-N'-[4-[(6,7-dimethoxy-1,5-naphthyridin-4-yl)oxy]-3-fluorophenyl]-1-N-(4-fluorophenyl)cyclopropane-1,1-dicarboxamide |
| 141 | 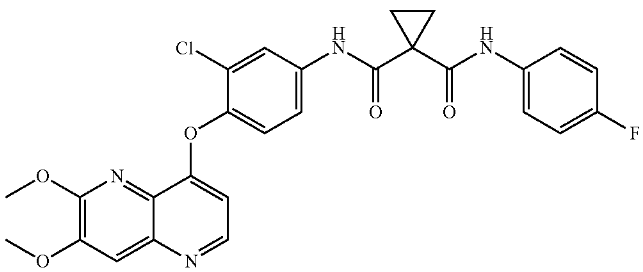 [SMILES: COc1cc2nccc(Oc3ccc(NC(=O)C4(C(=O)Nc5ccc(F)cc5)CC4)cc3Cl)c2nc1OC] | 1-N'-[3-chloro-4-[(6,7-dimethoxy-1,5-naphthyridin-4-yl)oxy]phenyl]-1-N-(4-fluorophenyl)cyclopropane-1,1-dicarboxamide |
| 142 | 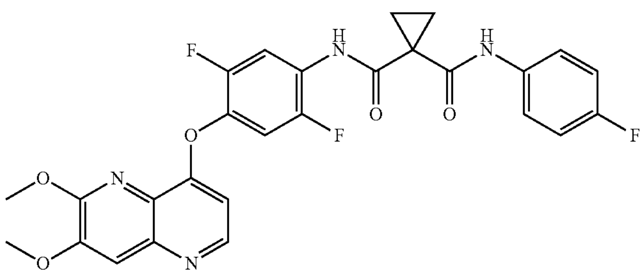 [SMILES: COc1cc2nccc(Oc3cc(F)c(NC(=O)C4(C(=O)Nc5ccc(F)cc5)CC4)cc3F)c2nc1OC] | 1-N'-[4-[(6,7-dimethoxy-1,5-naphthyridin-4-yl)oxy]-2,5-difluorophenyl]-1-N-(4-fluorophenyl)cyclopropane-1,1-dicarboxamide |
| 149 | 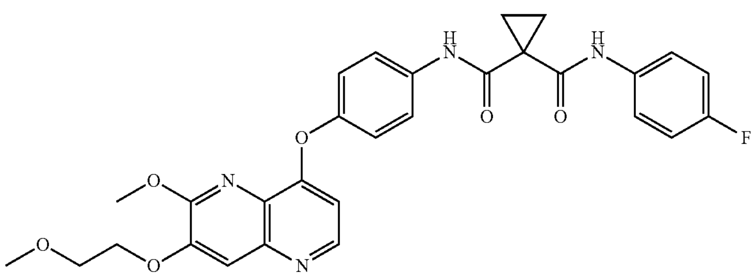 [SMILES: COCCOc1cc2nccc(Oc3ccc(NC(=O)C4(C(=O)Nc5ccc(F)cc5)CC4)cc3)c2nc1OC] | 1-N'-(4-fluorophenyl)-1-N-[4-[[6-methoxy-7-(2-methoxyethoxy)-1,5-naphthyridin-4-yl]oxy]phenyl]cyclopropane-1,1-dicarboxamide |
| 150 | 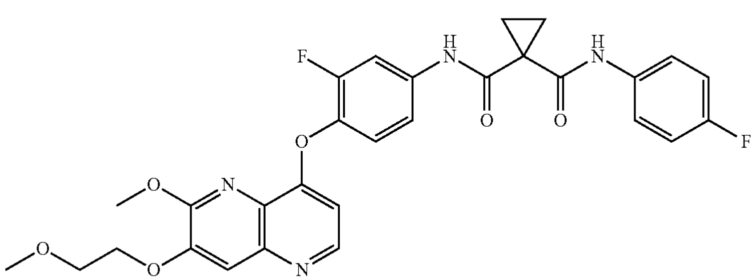 | 1-N'-[3-fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |

TABLE 2-continued

Compounds of Formula I

| Comp. | Structure | IUPAC Name |
|---|---|---|
| 151 | 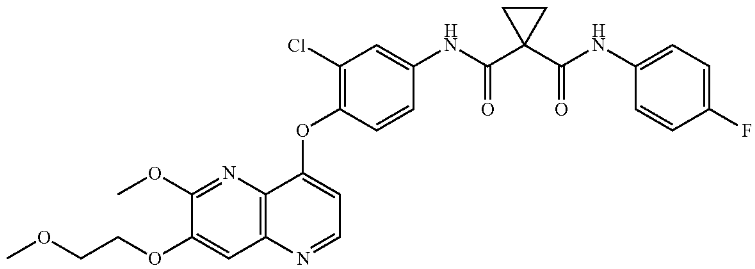 | 1-N'-[3-chloro-4-[[6-methoxy-7-(2-methoxyethoxy)-1,5-naphthyridin-4-yl]oxy]phneyl]-1-N-(4-fluorophenyl)cyclopropane-1,1-dicarboxamide |
| 152 | 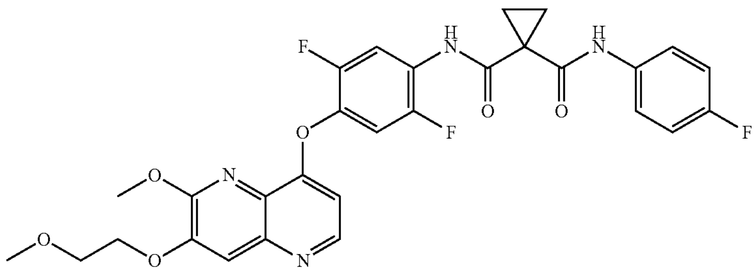 [SMILES: COCCOc1cc2nccc(Oc3cc(F)c(NC(=O)C4(C(=O)Nc5ccc(F)cc5)CC4)cc3F)c2nc1OC] | 1-N'-[2,5-difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide |
| 153 | 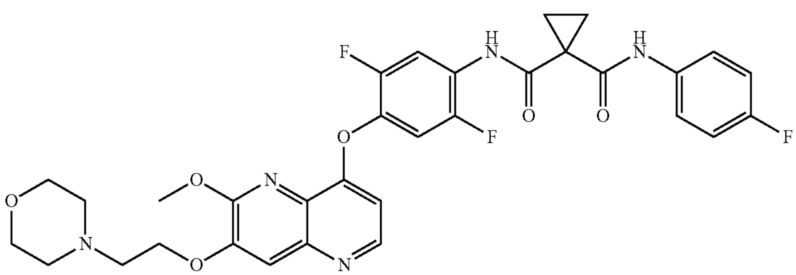 [SMILES: COc1nc2c(Oc3cc(F)c(NC(=O)C4(C(=O)Nc5ccc(F)cc5)CC4)cc3F)ccnc2cc1OCCN1CCOCC1] | 1-N'-[2,5-difluoro-4-[[6-7-(2-morpholin-4-ylethoxy)-1,5-naphthyridin-4-yl]oxy]phenyl]-1-N-(4-fluorophenyl)cyclopropane-1,1-dicarboxamide |
| 157 | 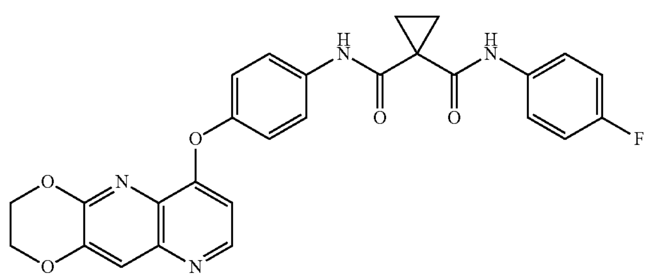 [SMILES: O=C(Nc1ccc(F)cc1)C1(C(=O)Nc2ccc(Oc3ccnc4cc5c(nc34)OCCO5)cc2)CC1] | 1-N-[4-(2,3-dihydro-[1,4]dioxino[2,3-b][1,5]naphthyridin-6-yloxy)phenyl]-1-N'-(4-fluorophenyl)cyclopropane-1,1-dicarboxamide |
| 158 | 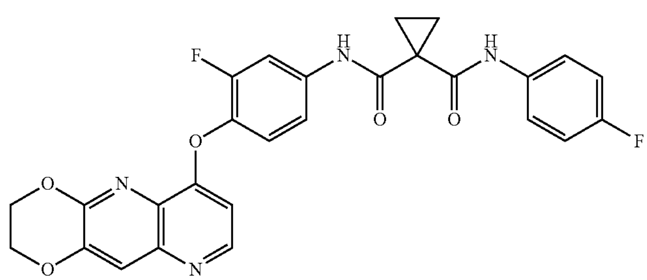 [SMILES: O=C(Nc1ccc(F)cc1)C1(C(=O)Nc2ccc(Oc3ccnc4cc5c(nc34)OCCO5)c(F)c2)CC1] | 1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide |

TABLE 2-continued

Compounds of Formula I

| Comp. | Structure | IUPAC Name |
|---|---|---|
| 159 | 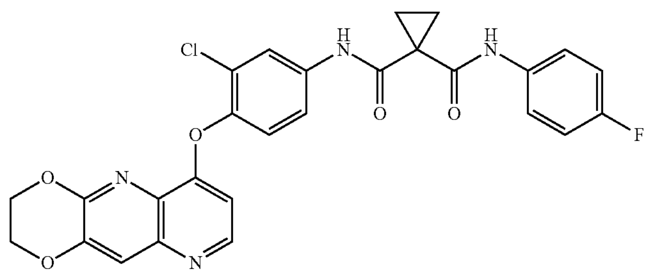 [SMILES: O=C(Nc1ccc(F)cc1)C1(C(=O)Nc2ccc(Oc3ccnc4cc5c(nc34)OCCO5)c(Cl)c2)CC1] | 1-N'-[3-chloro-4-(2,3-dihydro-[1,4]dioxino[2,3-b][1,5]naphthyridin-6-yloxy)phenyl]-1-N-(4-fluorophenyl)cyclopropane-1,1-dicarboxamide |
| 164 | 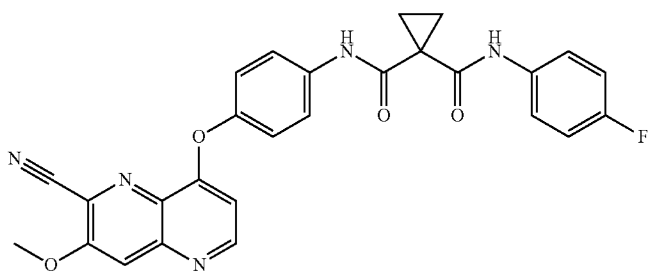 | 1-N-[4-[(6-cyano-7-methoxy-1,5-naphthyridin-4-yl)oxy]phenyl]-1-N'-(4-fluorophenyl)cyclopropane-1,1-dicarboxamide |
| 165 | 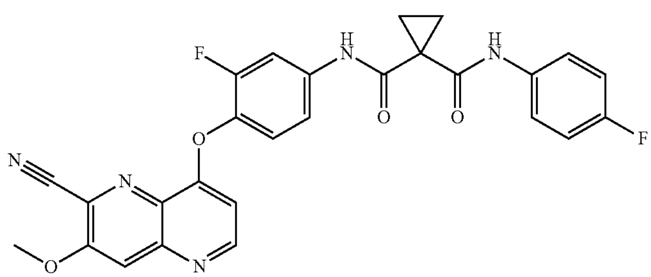 [SMILES: COc1cc2nccc(Oc3ccc(NC(=O)C4(C(=O)Nc5ccc(F)cc5)CC4)cc3F)c2nc1C#N] | 1-N'-[4-[(6-cyano-7-methoxy-1,5-naphthyridin-4-yl)oxy]-3-fluorophenyl]-1-N-(4-fluorophenyl)cyclopropane-1,1-dicarboxamide |
| 166 | 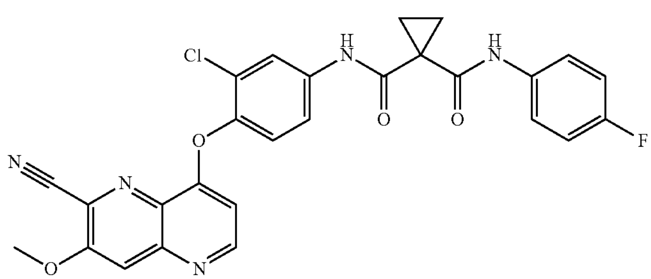 [SMILES: COc1cc2nccc(Oc3ccc(NC(=O)C4(C(=O)Nc5ccc(F)cc5)CC4)cc3Cl)c2nc1C#N] | 1-N'-[3-chloro-4-[(6-cyano-7-methoxy-1,5-naphthyridin-4-yl)oxy]phenyl]-1-N-(4-fluorophenyl)cyclopropane-1,1-dicarboxamide |
| 167 | 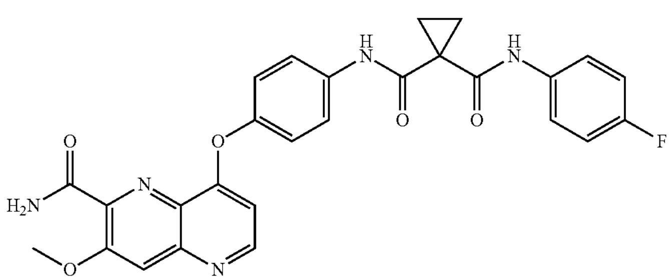 [SMILES: COc1cc2nccc(Oc3ccc(NC(=O)C4(C(=O)Nc5ccc(F)cc5)CC4)cc3)c2nc1C(N)=O] | 1-N-[4-[(6-carbamoyl-7-methoxy-1,5-naphthyridin-4-yl)oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 168 | 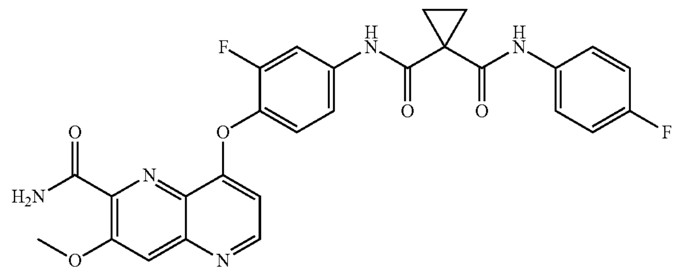 [SMILES: COc1cc2nccc(Oc3ccc(NC(=O)C4(C(=O)Nc5ccc(F)cc5)CC4)cc3F)c2nc1C(N)=O] | 1-N'-[4-[(6-carbamoyl-7-methoxy-1,5-naphthyridin-4-yl)oxy]-3-fluorophenyl]-1-N-(4-fluorophenyl)cyclopropane-1,1-dicarboxamide |
| 169 | 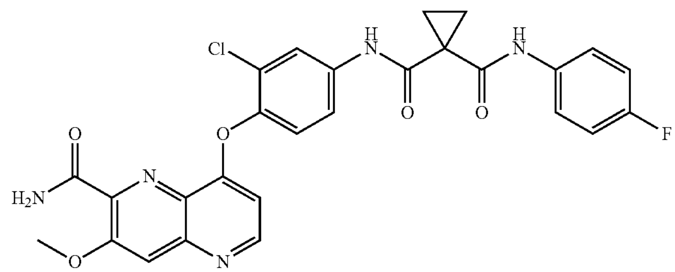 [SMILES: COc1cc2nccc(Oc3ccc(NC(=O)C4(C(=O)Nc5ccc(F)cc5)CC4)cc3Cl)c2nc1C(N)=O] | 1-N'-[4-[(6-carbamoyl-7-methoxy-1,5-naphthyridin-4-yl)oxy]-3-chlorophenyl]-1-N-(4-fluorophenyl)cyclopropane-1,1-dicarboxamide |
| 172 | 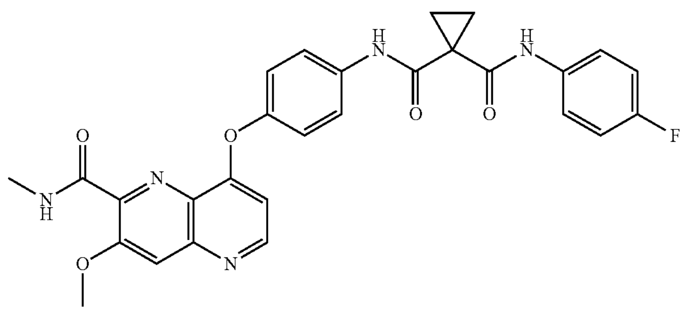 [SMILES: CNC(=O)c1nc2c(Oc3ccc(NC(=O)C4(C(=O)Nc5ccc(F)cc5)CC4)cc3)ccnc2cc1OC] | 1-N'-(4-fluorophenyl)-1-N-[4-[[7-methoxy-6-(methylcarbamoyl)-1,5-naphthyridin-4-yl]oxy]phenyl]cyclopropane-1,1-dicarboxamide |
| 173 | 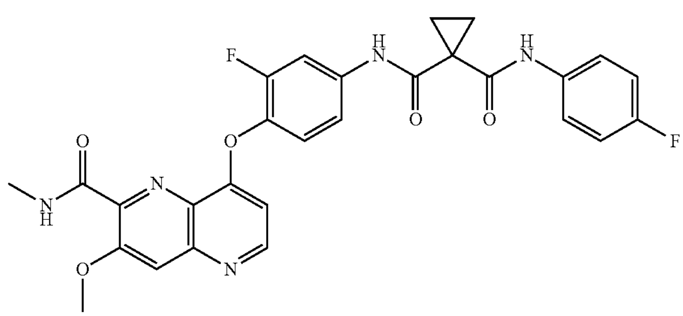 [SMILES: CNC(=O)c1nc2c(Oc3ccc(NC(=O)C4(C(=O)Nc5ccc(F)cc5)CC4)cc3F)ccnc2cc1OC] | 1-N'-[3-fluoro-4-[[7-methoxy-6-(methylcarbamoyl)-1,5-naphthyridin-4-yl]oxy]phenyl]-1-N-(4-fluorophenyl)cyclopropane-1,1-dicarboxamide |
| 174 | 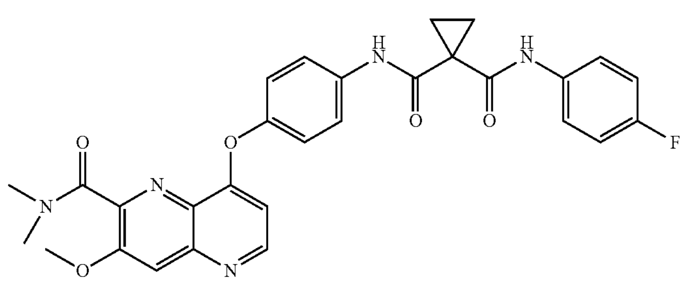 [SMILES: COc1cc2nccc(Oc3ccc(NC(=O)C4(C(=O)Nc5ccc(F)cc5)CC4)cc3)c2nc1C(=O)N(C)C] | 1-N-[4-[[6-(dimethylcarbamoyl)-7-methoxy-1,5-naphthyridin-4-yl]oxy]phenyl]-1-N'-(4-fluorophenyl)cyclopropane-1,1-dicarboxamide |

TABLE 2-continued

Compounds of Formula I

| Comp. | Structure | IUPAC Name |
|---|---|---|
| 176 | 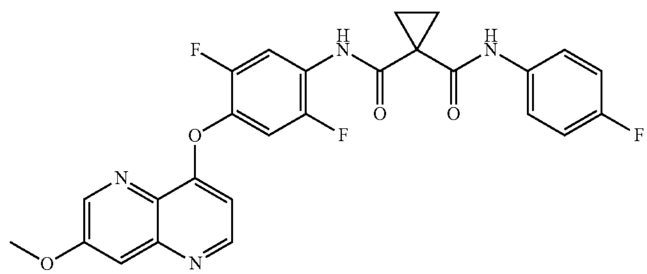 [SMILES: COc1cnc2c(Oc3cc(F)c(NC(=O)C4(C(=O)Nc5ccc(F)cc5)CC4)cc3F)ccnc2c1] | 1-N'-[2,5-difluoro-4-[(7-methoxy-1,5-naphthyridin-4-yl)oxy]phenyl]-1-N-(4-fluorophenyl)cyclopropane-1,1-dicarboxamide |
| 181 | 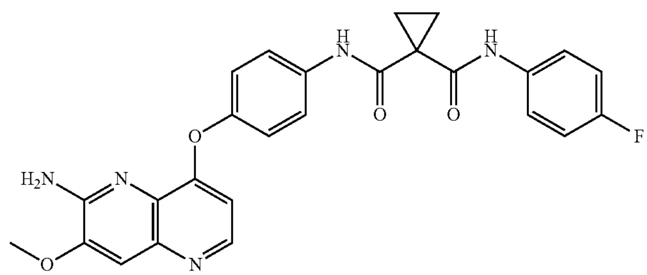 [SMILES: COc1cc2nccc(Oc3ccc(NC(=O)C4(C(=O)Nc5ccc(F)cc5)CC4)cc3)c2nc1N] | 1-N-[4-[(6-amino-7-methoxy-1,5-naphthyridin-4-yl)oxy]phenyl]-1-N'-(4-fluorophenyl)cyclopropane-1,1-dicarboxamide |
| 182 | 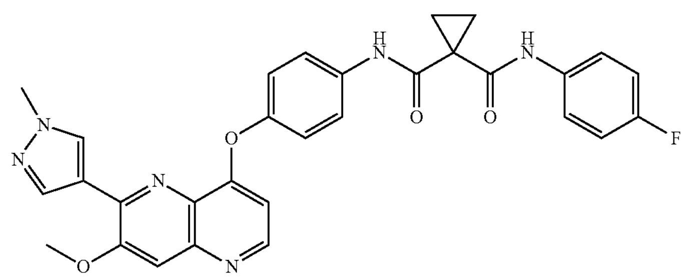 [SMILES: COc1cc2nccc(Oc3ccc(NC(=O)C4(C(=O)Nc5ccc(F)cc5)CC4)cc3)c2nc1-c1cnn(C)c1] | 1-N'-(4-fluorophenyl)-1-N-[4-[[7-methoxy-6-(1-methylpyrazol-4-yl)-1,5-naphthyridin-4-yl]oxy]phenyl]cyclopropane-1,1-dicarboxamide |
| 183 | 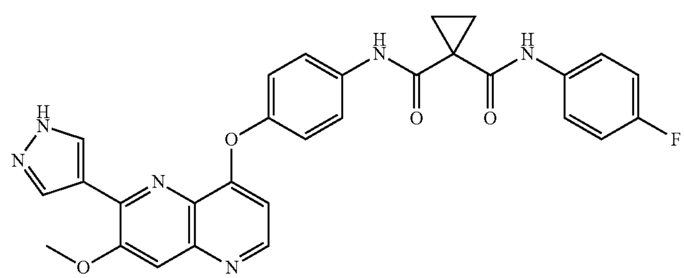 [SMILES: COc1cc2nccc(Oc3ccc(NC(=O)C4(C(=O)Nc5ccc(F)cc5)CC4)cc3)c2nc1-c1cn[nH]c1] | 1-N'-(4-fluorophenyl)-1-N-[4-[[7-methoxy-6-(1H-pyrazol-4-yl)-1,5-naphthyridin-4-yl]oxy]phenyl]cyclopropane-1,1-dicarboxamide |
| 184 | 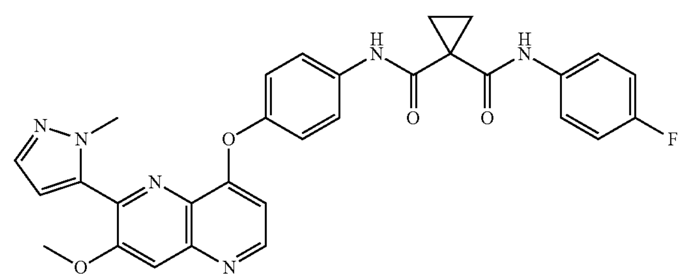 [SMILES: COc1cc2nccc(Oc3ccc(NC(=O)C4(C(=O)Nc5ccc(F)cc5)CC4)cc3)c2nc1-c1ccnn1C] | 1-N'-(4-fluorophenyl)-1-N-[4-[[7-methoxy-6-(2-methylpyrazol-3-yl)-1,5-naphthyridin-4-yl]oxy]phenyl]cyclopropane-1,1-dicarboxamide |

TABLE 2-continued

Compounds of Formula I

| Comp. | Structure | IUPAC Name |
|---|---|---|
| 189 | 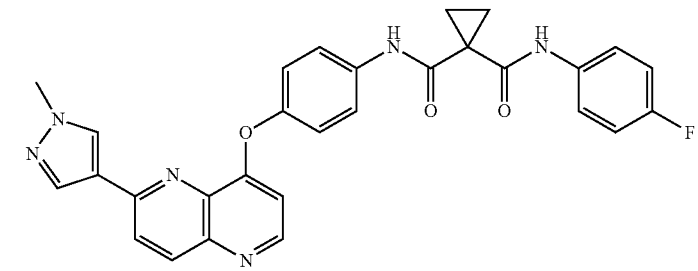 [SMILES: Cn1cc(-c2ccc3nccc(Oc4ccc(NC(=O)C5(C(=O)Nc6ccc(F)cc6)CC5)cc4)c3n2)cn1] | 1-N'-(4-fluorophenyl)-1-N-[4-[[6-(1-methylpyrazol-4-yl)-1,5-naphthyridin-4-yl]oxy]phenyl]cyclopropane-1,1-dicarboxamide |

In one embodiment, the compound of Formula I' is a compound of Formula II:

II or a pharmaceutically acceptable salt thereof, wherein:
$R_{16}$ is selected from the group consisting of —CN and —CO—NR$_5$R$_6$;
$R_{17}$ is selected from H and optionally substituted $C_1$-$C_6$ alkoxy;
$R_{13}$ is selected from the group consisting of —H, halo, —CN, or optionally substituted $C_{1-6}$ alkyl;
$R_{12}$ is —H or halo;

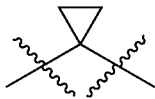 [SMILES: *C1(*)CC1]

is optionally substituted with one, two, three, or four groups independently selected from the group consisting of halo, and $C_1$-$C_6$ alkyl, wherein "〜〜〜" indicate points of attachment;
$R_5$ and $R_6$ are each independently selected from the group consisting of H, optionally substituted $C_1$-$C_6$ alkyl, optionally substituted $C_3$-$C_6$ heterocycloalkyl, and optionally substituted $C_1$-$C_6$ cycloalkyl;
Y is O, S, SO, SO$_2$, NH, or N—($C_1$-$C_6$ alkyl); and
m and n are each independently 1 or 2.
In one embodiment, $R_{17}$ is H.
In another embodiment,

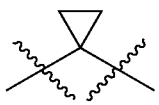 [SMILES: *C1(*)CC1]

is not substituted.

In another embodiment, $R_{12}$ is halo.
In a further embodiment, $R_{12}$ is para fluoro.
In one embodiment, $R_{16}$ is —CN or —CO—NR$_5$R$_6$.
In a further embodiment, $R_{16}$ is —CO—NH$_2$.
In one embodiment, $R_{16}$ and $R_{17}$ are joined together, with the atoms to which they are attached, to form a 5- or 6-membered optionally substituted heterocycloalkyl.
In one embodiment, Y is O.
In some embodiments,

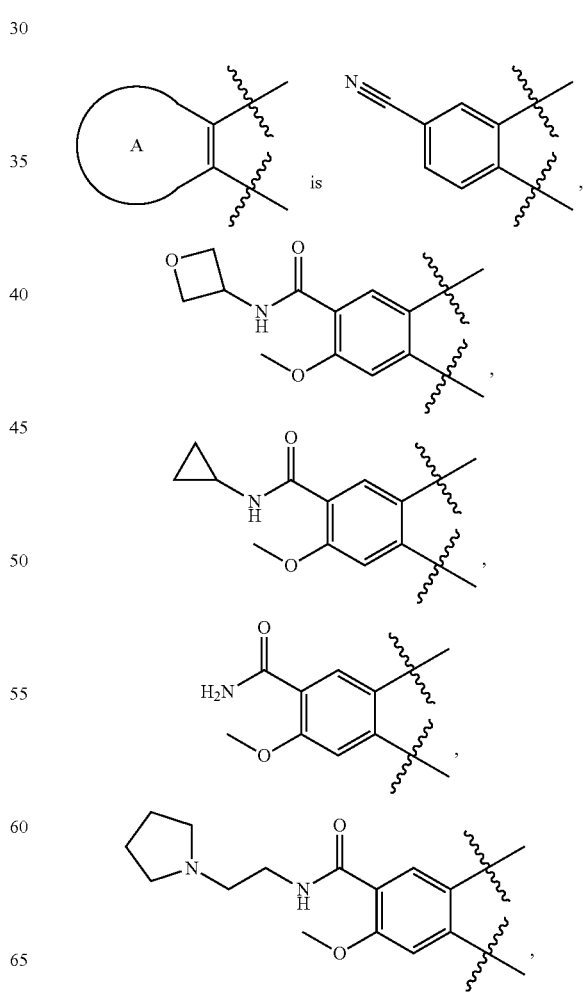

117

-continued

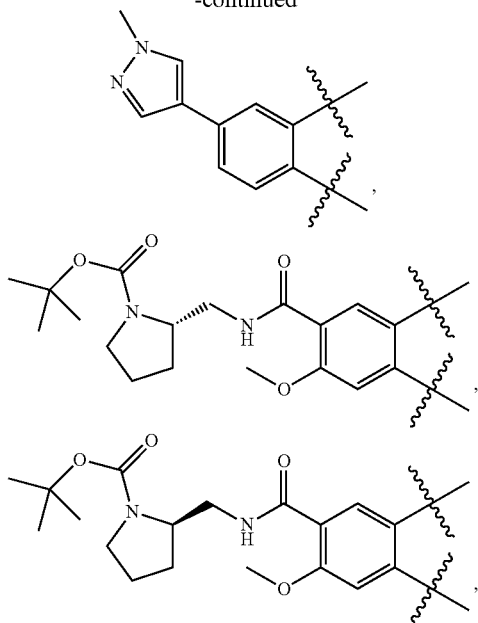

118

-continued

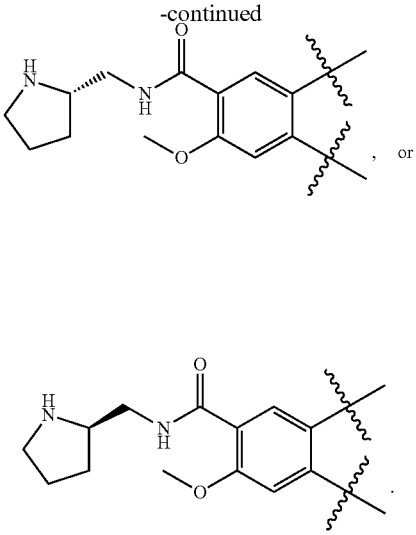

In one embodiment, the compound of Formula II, or a pharmaceutically acceptable salt thereof, is selected from the compounds listed in Table 3, or a pharmaceutically acceptable salt thereof.

TABLE 3

| Compounds of Formula II | | |
|---|---|---|
| Comp. | Structure | IUPAC Name |
| 106 | | 1-N-[4-(6-cyanoquinazolin-4-yl)oxyphenyl]-1-N'-(4-fluorophenyl)cyclopropane-1,1-dicarboxamide |
| 115 | | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide |
| 116 | | 1-N-[4-[6-(cyclopropylcarbamoyl)-7-methoxyquinazolin-4-yl]oxyphenyl]-1-N'-(4-fluorophenyl)cyclopropane-1,1-dicarboxamide |

TABLE 3-continued

Compounds of Formula II

| Comp. | Structure | IUPAC Name |
|---|---|---|
| 117 | 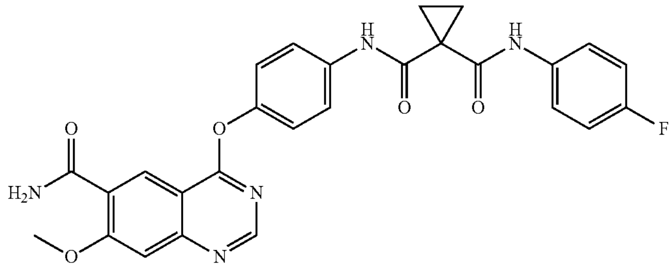 [SMILES: COc1cc2ncnc(Oc3ccc(NC(=O)C4(C(=O)Nc5ccc(F)cc5)CC4)cc3)c2cc1C(N)=O] | 1-N-[4-(6-carbamoyl-7-methoxyquinazolin-4-yl)oxyphenyl]-1-N'-(4-fluorophenyl)cyclopropane-1,1-dicarboxamide |
| 118 | 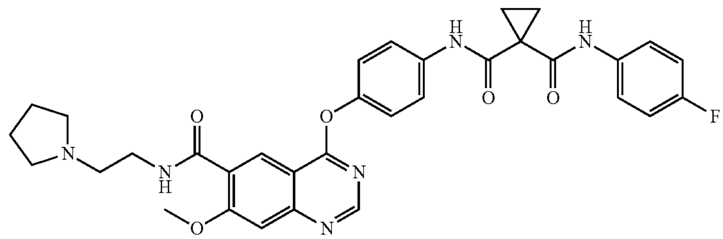 [SMILES: COc1cc2ncnc(Oc3ccc(NC(=O)C4(C(=O)Nc5ccc(F)cc5)CC4)cc3)c2cc1C(=O)NCCN1CCCC1] | 1-N'-(4-fluorophenyl)-1-N-[4-[7-methoxy-6-(2-pyrrolidin-1-ylethylcarbamoyl)quinazolin-4-yl]oxyphenyl]cyclopropane-1,1-dicarboxamide |
| 119 | 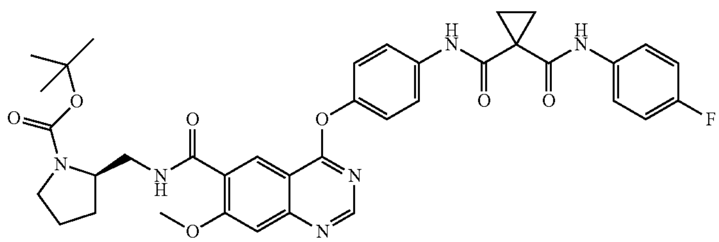 [SMILES: COc1cc2ncnc(Oc3ccc(NC(=O)C4(C(=O)Nc5ccc(F)cc5)CC4)cc3)c2cc1C(=O)NC[C@H]1CCCN1C(=O)OC(C)(C)C] | tert-butyl (2R)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate |
| 120 | 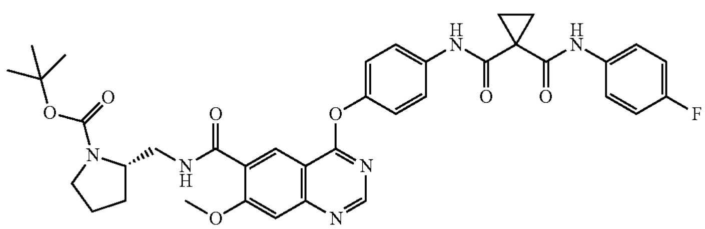 [SMILES: COc1cc2ncnc(Oc3ccc(NC(=O)C4(C(=O)Nc5ccc(F)cc5)CC4)cc3)c2cc1C(=O)NC[C@@H]1CCCN1C(=O)OC(C)(C)C] | tert-butyl (2S)-2-[[[4-[4-[[1-[(4-fluorophenyl)carbamoyl]cyclopropanecarbonyl]amino]phenoxy]-7-methoxyquinazoline-6-carbonyl]amino]methyl]pyrrolidine-1-carboxylate |
| 121 | 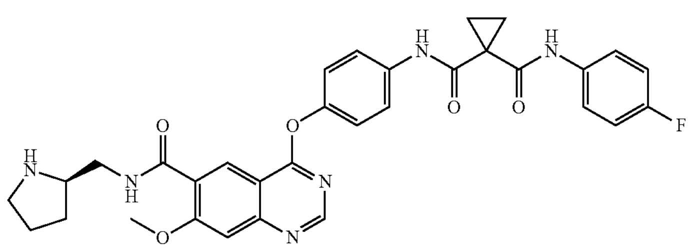 [SMILES: COc1cc2ncnc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide |
| 122 | 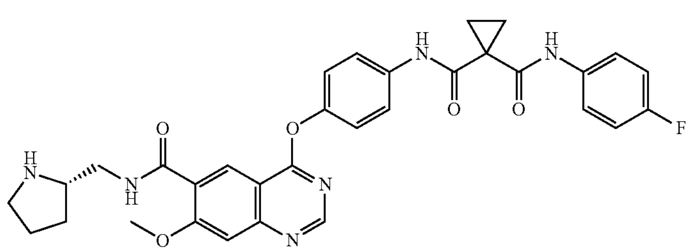 [SMILES: COc1cc2ncnc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide |

TABLE 3-continued

Compounds of Formula II

| Comp. | Structure | IUPAC Name |
|---|---|---|
| 126 | 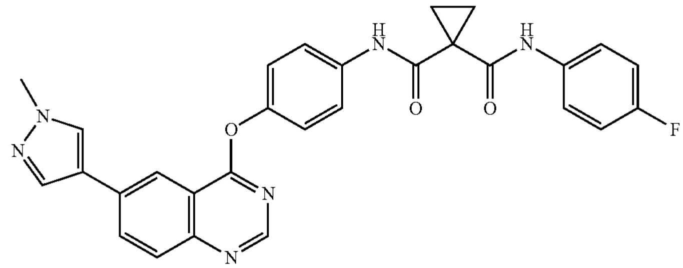 [SMILES: Cn1cc(-c2ccc3ncnc(Oc4ccc(NC(=O)C5(C(=O)Nc6ccc(F)cc6)CC5)cc4)c3c2)cn1] | 1-N'-(4-fluorophenyl)-1-N-[4-[6-(1-methylpyrazol-4-yl)quinazolin-4-yl]oxyphenyl]cyclopropane-1,1-dicarboxamide |

In one aspect, the invention includes a pharmaceutical composition comprising a compound described herein, and a pharmaceutically acceptable carrier or excipient.

In another aspect, the invention includes a method of treating a disease, disorder, or syndrome mediated at least in part by modulating in vivo activity of a protein kinase, comprising administering to a subject in need thereof a therapeutically effective amount of a compound described herein, or a pharmaceutical composition thereof.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as, for example, tablets, suppositories, pills, soft elastic and hard gelatin capsules, powders, solutions, suspensions, aerosols, and the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, and the like. Compositions of the invention may be used in combination with anti cancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate, and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, and the like.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, and the like, a compound(s) of the invention, or a pharmaceutically acceptable salt thereof, and optional pharmaceutical adjuvants in a carrier, such as, for example, water, saline, aqueous dextrose, glycerol, ethanol, and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, and dimethylformamide; oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability, and length of action of the compound, the age, body weight, general health, sex, diet, mode, and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Combination Therapy

A compound as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of a compound of Formula I' or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs (last visited Jan. 22, 2019) and in publically available sources such as Cancer Principles and Practice of Oncology by V. T. Devita and S. Heilman (editors), $11^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as disclosed herein or a pharmaceutically acceptable salt thereof and at least one immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGER protein used, for example, in combination with irinotecan to treat, for example, advanced colorectal cancer and head and neck cancers; and Bevacizumab (Avastin) which is an anti angiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN™™ (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-beta$_2$ antibody (Cambridge Ab Tech). Others are provided in later paragraphs.

Immunotherapies that can be used in combination with a compound as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IE-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

In various embodiments, an immunological therapy or an immunological therapeutic agent can include, one or more of the following: an adoptive cell transfer, an angiogenesis inhibitor, Bacillus Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The function or at least one of the functions of the immunological therapy or immunological therapeutic agent, collectively referred to herein as an "immunotherapeutic agent".

The present disclosure provides a method for preventing, treating, reducing, inhibiting or controlling a neoplasia, a tumor or a cancer in a subject in need thereof, involving administering a therapeutically effective amount of a combination comprising a compound of Formula I' and an immunotherapeutic agent. In one non-limiting embodiment, the method comprises administering a therapeutically effective amount of a combination comprising a compound of Formula I' in combination with an immunotherapeutic agent. In various embodiments, the combination provides a cooperative effect, an additive effect, or a synergistic effect in reducing the number of cancer cells when treated with the combination as compared to each treatment alone. In some embodiments, administration of a therapeutically effective amount of a combination comprising a compound of Formula I' and an immunotherapeutic agent, results in synergistic anti-tumor activity and/or antitumor activity that is more potent than the additive effect of administration of a compound of Formula I' or immunotherapeutic agent alone.

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

The present disclosure provides a combination of a compound of Formula I' and an immunotherapeutic agent. These exemplified combinations can be used to treat a subject with a cancer. In various embodiments, immunotherapeutic agents that find utility in the present compositions, formulations, and methods can include one or more agents or therapies, including: an adoptive cell transfer, an angiogenesis inhibitor, Bacillus Calmette-Guerin therapy, biochemotherapy, a cancer vaccine, a chimeric antigen receptor (CAR) T-cell therapy, a cytokine therapy, gene therapy, an immune checkpoint modulator, for example an immune checkpoint inhibitor, an immunoconjugate, a radioconjugate, an oncolytic virus therapy, or a targeted drug therapy.

In certain embodiments of the present disclosure, a therapeutically effective combination comprises a compound of Formula I' and an immunotherapeutic agent. In various related embodiments, the compound of Formula I' enhances the activity of the immunotherapeutic agent.

In certain embodiments of each of the aforementioned aspects, as well as other aspects and embodiments described elsewhere herein, the immunotherapeutic agent enhances the activity of the compound of Formula I'.

In certain embodiments of each of the aforementioned aspects, as well as other aspects and embodiments described elsewhere herein, the compound of Formula I' and the immunotherapeutic agent act synergistically. In various embodiments described herein, an exemplary immunotherapeutic agent is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art). In some embodiments, the immunotherapeutic agent can be an antibody that modulates a costimulatory molecule, bind to an antigen on the surface of an immune cell, or a cancer cell. In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Barnase-barstar, a scFv-Fc, a sc(Fab)2, a Trimeric antibody construct, a Triabody antibody construct, a Trimerbody antibody construct, a Tribody antibody constuct, a Collabody antibody construct, a (scFv-TNFa)3, or a F(ab)3/DNL antibody construct.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity. In some embodiments, the immunotherapeutic agent is an antibody modulator that targets PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, OX40, 4IBB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors. In some embodiments, the combination of the present disclosure comprises a compound of Formula I' and an immunotherapeutic agent, wherein the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g, SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, a modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide. In some embodiments, the immunotherapeutic agent is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). In one embodiment, the immunomodulator is an inhibitor of PD-1, PD-L1, PD-L2, CTLA-4, TIM-3, LAG-3, CEACAM (e.g, CEACAM-1, -3 and/or -5), VISTA, BTLA, TIGIT, LAIR1, CD160, 2B4 and/or TGF beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CEACAM (e.g, CEACAM-1, -3 and/or -5), CTLA-4, TIM-3, LAG-3, VISTA, BTLA, TIGIT, LAIR1, CD160, 2B4, TGF beta, or a combination thereof.

In some embodiments, where the combination comprises a compound of Formula I' and an immunotherapeutic agent, wherein the immunotherapeutic agent is a monoclonal antibody or a bispecific antibody. For example, the monoclonal or bispecific antibody may specifically bind a member of the c-Met pathway and/or an immune checkpoint modulator (e.g., the bispecific antibody binds to both a hepatocyte growth factor receptor (HGFR) and an immune checkpoint modulator described herein, such as an antibody that binds PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2 or CD27). In particular embodiments, the bispecific antibody specifically binds a human HGFR protein and one of PD-1, PD-L1, and CTLA-4.

In some embodiments, the immunotherapeutic agent is a cytokine, for example, a chemokine, an interferon, an interleukin, lymphokine, or a member of the tumor necrosis factor family. In some embodiments, the cytokine is IL-2, IL15, or interferon-gamma.

In some embodiments of any of the above aspects or those described elsewhere herein, the cancer is selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, glioblastoma multiforme, cervical cancer, stomach cancer, bladder cancer, head and neck cancer, and hepatoma.

In some embodiments of any of the above aspects or those described elsewhere herein, the subject's cancer or tumor does not respond to immune checkpoint inhibition (e.g., to any immune checkpoint inhibitor described herein, such as a PD-1 antagonist or PD-L1 antagonist) or the subject's cancer or tumor has progressed following an initial response to immune checkpoint inhibition (e.g., to any immune checkpoint inhibitor described herein, such as a PD-1 antagonist or PD-L1 antagonist).

In some embodiments of any of the above aspects or those described elsewhere herein, the subject is a human.

A checkpoint inhibitor can be any molecule, agent, treatment and/or method of inhibiting an immune checkpoint, and/or promoting an inhibitor of an immune checkpoint, e.g., by promoting an intrinsic immune checkpoint inhibitor; inhibiting a transcription factor involved in the expression of an immune checkpoint; and/or by acting in concert with some additional extrinsic factor. For example, a checkpoint inhibitor could include a treatment that inhibits transcription factors involved the expression of immune checkpoint genes, or promotes the expression of transcription factors for tumor-suppressor genes, e.g., BACH2 (Luan et al., (2016). Transcription Factors and Checkpoint Inhibitor Expression with Age: Markers of Immunosenescence. Blood, 128(22), 5983). Moreover, a checkpoint inhibitor can inhibit the transcription of immune checkpoint genes; the modification and/or processing of immune checkpoint mRNA; the translation of immune checkpoint proteins; and/or molecules involved in immunity or the immune checkpoint pathway, e.g., PD-1 transcription factors such as HIF-1, STAT3, NF-κB, and AP-1, or the activation of common oncogenic pathways such as JAK/STAT, RAS/ERK, or PI3K/AKT/mTOR (Zerdes et al., Genetic, transcriptional and post-translational regulation of the programmed death protein ligand 1 in cancer: biology and clinical correlations, Oncogenevolume 37, pages 4639-4661 (2018), the disclosure of which is incorporated herein by reference in its entirety).

Checkpoint inhibitors can include treatments, molecules, agents, and/or methods that regulate immune checkpoints at the transcriptional level, e.g., using the RNA-interference pathway co-suppression, and/or post-transcriptional gene silencing (PTGS) (e.g., microRNAs, miRNA; silencing-RNA, small-interfering-RNA, or short-interfering-RNA (siRNA). Transcriptional regulation of checkpoint molecules has been shown to involve mir-16, which has been shown to target the 3'UTR of the checkpoint mRNAs CD80, CD274 (PD-L1) and CD40 (Leibowitz et al., Post-transcriptional regulation of immune checkpoint genes by mir-16 in melanoma, Annals of Oncology (2017) 28; v428-v448). Mir-33a has also been shown to be involved in regulating the expression of PD-1 in cases of lung adenocarcinoma (Boldini et al., Role of microRNA-33a in regulating the expression of PD-1 in lung adenocarcinoma, Cancer Cell Int. 2017; 17: 105, the disclosure of which is incorporated herein by reference in its entirety).

T-cell-specific aptamer-siRNA chimeras have been suggested as a highly specific method of inhibiting molecules in the immune checkpoint pathway (Hossain et al., The aptamer-siRNA conjugates: reprogramming T cells for cancer therapy, Ther. Deliv. 2015 January; 6(1): 1-4, the disclosure of which is incorporated herein by reference in its entirety).

Alternatively, members of the immune checkpoint pathway can be inhibited using treatments that affect associated pathways, e.g., metabolism. For example, oversupplying the glycolytic intermediate pyruvate in mitochondria from CAD macrophages promoted expression of PD-L1 via induction of the bone morphogenetic protein 4/phosphorylated SMAD1/5/IFN regulatory factor 1 (BMP4/p-SMAD1/5/IRF1) signaling pathway. Accordingly, implementing treatments that modulate the metabolic pathway can result in subsequent modulation of the immunoinhibitory PD-1/PD-L1 checkpoint pathway (Watanabe et al., Pyruvate controls the checkpoint inhibitor PD-L1 and suppresses T cell immunity, J Clin Invest. 2017 Jun. 30; 127(7): 2725-2738).

Checkpoint immunity can be regulated via oncolytic viruses that selectively replicate within tumor cells and induce acute immune responses in the tumor-microenvironment, i.e., by acting as genetic vectors that carry specific agents (e.g., antibodies, miRNA, siRNA, and the like) to cancer cells and effecting their oncolysis and secretion of cytokines and chemokines to synergize with immune checkpoint inhibition (Shi et al., Cancer Immunotherapy: A Focus on the Regulation of Immune Checkpoints, Int J Mol Sci. 2018 May; 19(5): 1389). Currently, there are clinical trials underway that utilize the following viruses as checkpoint inhibitors: poliovirus, measles virus, adenoviruses, poxviruses, herpes simplex virus (HSV), coxsackieviruses, reovirus, Newcastle disease virus (NDV), T-VEC (a herpes virus encoded with GM-CSF (granulocyte-macrophage colony stimulating factor)), and H101 (Shi et al., supra).

Checkpoint inhibitors can operate at the translational level of checkpoint immunity. The translation of mRNA into protein represents a key event in the regulation of gene expression, thus inhibition of immune checkpoint translation is a method in which the immune checkpoint pathway can be inhibited.

Inhibition of the immune checkpoint pathway can occur at any stage of the immune checkpoint translational process. For example, drugs, molecules, agents, treatments, and/or methods can inhibit the initiation process (whereby the 40S ribosomal subunit is recruited to the 5' end of the mRNA and scans the 5'UTR of the mRNA toward its 3' end. Inhibition can occur by targeting the anticodon of the initiator methionyl-transfer RNA (tRNA) (Met-tRNAi), its base-pairing with the start codon, or the recruitment of the 60S subunit to begin elongation and sequential addition of amino acids in the translation of immune-checkpoint-specific genes. Alternatively, a checkpoint inhibitor can inhibit checkpoints at the translational level by preventing the formation of the ternary complex (TC), i.e., eukaryotic initiation factor (eIF)2 (or one or more of its α, β, and γ subunits); GTP; and Met-tRNAi.

Checkpoint inhibition can occur via destabilization of eIF2α by precluding its phosphorylation via protein kinase R (PKR), PERK, GCN2, or HRI, or by precluding TCs from associating with the 40S ribosome and/or other initiation factors, thus preventing the preinitiation complex (PIC) from forming; inhibiting the eIF4F complex and/or its cap-binding protein eIF4E, the scaffolding protein eIF4G, or eIF4A helicase. Methods discussing the translational control of cancer are discussed in Truitt et al., New frontiers in translational control of the cancer genome, Nat Rev Cancer. 2016 Apr. 26; 16(5): 288-304, the disclosure of which is incorporated herein by reference in its entirety.

Checkpoint inhibitors can also include treatments, molecules, agents, and/or methods that regulate immune checkpoints at the cellular and/or protein level, e.g., by inhibiting an immune checkpoint receptor. Inhibition of checkpoints can occur via the use of antibodies, antibody fragments, antigen-binding fragments, small-molecules, and/or other drugs, agents, treatments, and/or methods.

Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response ('block' the immune response) against tumor tissues. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264).

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of antibody (Ab), ipilimumab (YERVOY®), that binds to and inhibits CTLA-4 for the treatment of patients with advanced melanoma (Hodi et al. (2010) N Engl J Med 363:711-23) and the development of antibodies such as nivolumab and pembrolizumab (formerly lambrolizumab; USAN Council Statement (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway (Topalian et al. (2012a) N Engl J Med 366:2443-54; Topalian et al. (2012b) Curr Opin Immunol 24:207-12; Topalian et al. (2014) J Clin Oncol 32(10): 1020-30; Hamid et al. (2013) N Engl J Med 369:134-144; Hamid and Carvajal (2013) Expert Opin Biol Ther 13(6):847-61; McDermott and Atkins (2013) Cancer Med 2(5):662-73).

PD-1 is a key immune checkpoint receptor expressed by activated T and B cells and mediates immunosuppression. Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) In vitro characterization of the anti-PD-1 antibody nivolumab, BMS-936558, and in vivo toxicology in non-human primates. Nivolumab has been approved for the treatment of patients with unresectable or metastatic melanoma and disease progression following ipilimumab and, if BRAF V600 mutation positive, a BRAF inhibitor and for the treatment of squamous non-small cell lung cancer.

Recent data suggest a secondary mechanism of anti-CTLA-4 antibodies, which could occur within the tumor itself. CTLA-4 has been found to be expressed in tumors at higher levels on regulatory T-cells (also referred to herein as "Treg cells") as compared with intra-tumoral effector T-cells (also referred to herein as "Teff cells"), resulting in the hypothesis of anti-CTLA-4 preferentially impacting the Treg cell. "Therapeutic use of anti-CTLA-4 antibodies", Christian U. Blank and Alexander Enk, International Immunology, Vol. 27, No. 1, pp. 3-10. A recent study of a PD-1 and CTLA-4 combination show that the combination blockade of the CTLA-4 and PD-1 pathways also cooperates to increase the ratio of Teff cells to both regulatory T-cells and MDSCs, thereby reducing suppression and promoting inflammation in the tumor microenvironment. "Combination of CTLA-4 and PD-1 blockade expands infiltrating T-cells and reduces regulatory T and myeloid cells within B16 melanoma tumors", Curran et al., PNAS|Mar. 2, 2010; vol. 107 (no. 9); pp. 4275-4280, the disclosure of which is incorporated herein by reference in its entirety. The combination of a checkpoint inhibitor and another therapeutic agent(s) may enhance or prolong anti-tumor response of the checkpoint inhibitor and/or effects of the therapeutic agent. In this regard, WO 2015/069770 discloses a combination treatment based on activating the adaptive immune response, in particular the combination of CTLA-4 and PD-1 inhibitors, for the treatment of cancer. The disclosure of WO 2015/069770 is incorporated by reference in its entirety in the disclosure of this application.

One mechanism by which the checkpoint blockade anti-CTLA-4 antibodies mediate anti-tumor effect is by decreasing regulatory T-cells. Due to the distinct mechanism of action of anti-CTLA-4 antibodies, they can successfully combine with the anti-PD1 checkpoint blockade antibodies which work to release the suppressive signaling conferred to effector T-cells. Dual blockade with these antibodies combine to improve anti-tumor response both preclinically (Proc Natl Acad Sci USA 2010, 107, 4275-4280) and in the clinic (N Engl J Med 2013, 369, 122-133; N Engl J Med 2015, 372, 2006-2017).

CTLA-4 attenuates the early activation of naïve and memory T cells through interactions with its ligands B7-1 (CD80) and B7-2 (CD86) (FIG. 1A). PD-1 is an receptor expressed on the surface of activated mature T cells, activated NK cells, B cells, monocytes and multiple normal tissues and plays a crucial role in the maintenance of peripheral tolerance [20-21] (FIG. 1A). In contrast to CTLA-4, PD-1 acts via interactions with its ligands PD-L1 (also known as B7-H1 or CD274) and is involved mainly in T cell activity modulation in peripheral tissues as well as providing a major immune resistance mechanism within the tumor microenvironment.

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-IBB activity, an modulator of OX40 activity, a modulator of KIR activity, a modulator of Tim-3 activity, a modulator of LAGS activity, a modulator of CD27 activity, a modulator of CD40 activity, a modulator of GITR activity, a modulator of LICIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, or an immunostimulatory oligonucleotide. In some embodiments, the immune checkpoint modulator, i.e. is an inhibitor or antagonist, or is an activator or agonist, for example, a CD28 modulator, a 4-IBB modulator, an OX40 modulator, a CD27 modulator, a CD80 modulator, a CD86 modulator, a CD40 modulator, or a GITR modulator, a Lag-3 modulator, a 4IBB modulator, a LIGHT modulator, a CD40 modulator, a GITR modulator, a TGF-beta modulator, a TIM-3 modulator, a SIRP-alpha modulator, a LICIT modulator, a VSIG8 modulator, a BTLA modulator, a SIGLEC7 modulator, a SIGLEC9 modulator, a ICOS modulator, a B7H3 modulator, a B7H4 modulator, a FAS modulator, and/or a BTNL2 modulator. In some embodiments, the immunotherapeutic agent is an immune checkpoint modulator as described above (e.g., an immune checkpoint modulator antibody, which can be in the form of a monoclonal antibody, a bispecific antibody comprising one or more immune checkpoint antigen binding moieties, a trispecific antibody, or an immune cell-engaging multivalent antibody/fusion protein/construct known in the art).

Combination treatments with immune checkpoint inhibitor immunotherapeutic agent may include antibodies that specifically target immune system checkpoints such as CTLA4, PD1 and PD-L1 are one of the most promising new avenues of immunotherapy for cancer and other diseases. Additional checkpoint targets, such as TIM-3, LAG-3, various B-7 ligands, CHK 1 and CHK2 kinases, BTLA, A2aR, and others, are also under investigation. Currently, three checkpoint inhibitors have received rapid approval from the U S. Food and Drug Administration for cancer treatment, including ipilimumab (Yervoy®), a CTLA-4 inhibitor, and pembrolizumab (Keytruda®) and nivolumab (Opdivo®), both PD-1 inhibitors. In addition, several checkpoint inhibitor agents are in clinical trials.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., bit Immunol., 2007; 19: 813-824). The interaction of PD-1 with its ligands, PD-L1 and PD-L2, which are expressed on antigen-presenting cells (APCs) and dendritic cells (DCs), transmits negative regulatory stimuli to down-modulate the activated T cell immune response. Blockade of PD-1 suppresses this negative signal and amplifies T cell responses.

Numerous studies indicate that the cancer microenvironment manipulates the PD-L1-/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumor infiltrating T cells, thus possibly potentiating a vicious cycle of inhibition. Third, this pathway is intricately involved in both innate and adaptive immune regulation through bi-directional signaling. These factors make the PD-1/PD-L1 complex a central point through which cancer can manipulate immune responses and promote its own progression.

CTLA-4 (also known as Cytotoxic T-lymphocyte-associated protein 4, CTLA4, CTLA-4, CD152, cluster of differentiation 152; ALPS5, CD, CELIAC3, GRD4, GSE, and IDDM12). CTLA-4 is a ~24.6-kDa single-pass type I membrane protein that plays an inhibitory role in T-cell function. CTLA-4 was originally identified by differential screening of a murine cytolytic T cell cDNA library, See Brunet et al., A new member of the immunoglobulin superfamily-CTLA-4, Nature. 1987 Jul. 16-22; 328(6127):267-70. CTLA—has been shown to interact with the b7 family ligands CD80 (also known as Cluster of differentiation 80, and B7-1); and CD86 (also known as Cluster of Differentiation 86 or B7-2). See Linsley et al., CTLA-4 is a second receptor for the B cell activation antigen B7, J Exp Med. 1991 Sep. 1; 174(3):561-9. Sequence comparison between the human CTLA-4 DNA encoding region, and that of CD28, reveals significant homology between both sequences, with the greatest similarity between juxtamembrane and cytoplasmic regions; accordingly, CTLA-4 is implicated in abrogating/reducing T-cell activity, and opposes the activity of CD28. CTLA-4 deficient mice have been shown to exhibit massive lymphoproliferation. Chambers et al., Lymphoproliferation in CTLA-4-deficient mice is mediated by costimulation-dependent activation of CD4+ T cells, Immunity. 1997 December; 7(6):885-95. It has been reported that CTLA-4 blockade augments T-cell responses both in vitro and in vivo, enhances an induced autoimmune disease, and exacerbates antitumor immunity. (See Luhder, J. Exp. Med. 1998; 187: 427-432; Walunas et al., Immunity. 1994; 1: 405-413; Kearney, J. Immunol. 1995; 155:1032-1036); Leach, Science 1996; 271:1734-1736). CTLA-4 has also been reported as having alternative and/or additional impact on the initial character of the T-cell immune response (Chambers, Curr.

Opin. Immunol. 1997; 9:396-404; Bluestone, J. Immunol. 1997; 158:1989-1993; Thompson, Immunity 1997; 7:445-450).

The first immune-checkpoint inhibitor to be tested in a clinical trial was ipilimumab (Yervoy, Bristol-Myers Squibb), an CTLA-4 mAh. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAh is a powerful checkpoint inhibitor which removes "the break" from both naïve and antigen-experienced cells. Therapy enhances the antitumor function of CD8+ T cells, increases the ratio of CD8+ T cells to Foxp3+T regulatory cells, and inhibits the suppressive function of T regulatory cells. The major drawback to anti-CTLA-4 mAh therapy is the generation of autoimmune toxicities due to on-target effects of an over-exuberant immune system which has lost the ability to turn itself down. It has been reported that up to 25% of patients treated with ipilimumab developed serious grade 3-4 adverse events/autoimmune-type side effects including dermatitis, enterocolitis, hepatitis, endocrinopathies (including hypophysitis, thyroiditis, and adrenalitis), arthritis, uveitis, nephritis, and aseptic meningitis. In contrast to the anti-CTLA-4 experience, anti-PD-1 therapy appears to be better-tolerated and induces a relatively lower rate of autoimmune-type side effects.

In some embodiments, the immunotherapeutic agent is an agent that inhibits the activity of PD-1. In some embodiments, the immunotherapeutic agent is an agent that inhibits the activity of PD-L1 and/or PD-L2. In some embodiments, the immunotherapeutic agent is an agent that inhibits the activity of CTLA-4. In some embodiments, the immunotherapeutic agent is an agent that inhibits the activity of CD80 and/or CD86. In some embodiments, the immunotherapeutic agent is an agent that inhibits the activity of TIGIT. In some embodiments, the immunotherapeutic agent is an agent that inhibits the activity of KIR. In some embodiments, the immunotherapeutic agent is an agent that enhances or stimulates the activity of activating immune checkpoint receptors.

In some of the embodiments of the methods described herein, the immunotherapeutic agent is a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAGS antagonist, a TIGIT antagonist, a CD20 antagonist, a CD96 antagonist, or an IDO1 antagonist.

In some embodiments, the PD-1 antagonist is an antibody that specifically binds PD-1. In some embodiments, the antibody that binds PD-1 is pembrolizumab (KEYTRUDA®, MK-3475; Merck), pidilizumab (CT-011; Curetech Ltd.), nivolumab (OPDIVO®, BMS-936558, MDX-1106; Bristol Myer Squibb), MEDI0680 (AMP-514; AstraZenenca/MedImmune), REGN2810 (Regeneron Pharmaceuticals), BGB-A317 (BeiGene Ltd.), PDR-001 (Novartis), or STI-A1110 (Sorrento Therapeutics). In some embodiments, the antibody that binds PD-1 is described in PCT Publication WO 2014/179664, for example, an antibody identified as APE2058, APE1922, APE 1923, APE1924, APE 1950, or APE1963 (Anaptysbio), or an antibody containing the CDR regions of any of these antibodies. In other embodiments, the PD-1 antagonist is a fusion protein that includes the extracellular domain of PD-L1 or PD-L2, for example, AMP-224 (AstraZeneca/MedImmune). In other embodiments, the PD-1 antagonist is a peptide inhibitor, for example, AUNP-12 (Aurigene).

In some embodiments, the PD-L1 antagonist is an antibody that specifically binds PD-L1. In some embodiments, the antibody that binds PD-L1 is atezolizumab (RG7446, MPDL3280A; Genentech), MEDI4736 (AstraZeneca/MedImmune), BMS-936559 (MDX-1105; Bristol Myers Squibb), avelumab (MSB0010718C; Merck KGaA), KD033 (Kadmon), the antibody portion of KD033, or STI-A1014 (Sorrento Therapeutics). In some embodiments, the antibody that binds PD-L1 is described in PCT Publication WO 2014/055897, for example, Ah-14, Ah-16, Ab-30, Ab-31, Ab-42, Ab-50, Ab-52, or Ab-55, or an antibody that contains the CDR regions of any of these antibodies, the disclosure of which is incorporated herein by reference in its entirety.

In some embodiments, the CTLA-4 antagonist is an antibody that specifically binds CTLA-4. In some embodiments, the antibody that binds CTLA-4 is ipilimumab (YERVOY®; Bristol Myer Squibb) or tremelimumab (CP-675, 206; Pfizer). In some embodiments, the CTLA-4 antagonist a CTLA-4 fusion protein or soluble CTLA-4 receptor, for example, KARR-102 (Kahr Medical Ltd.).

In some embodiments, the LAGS antagonist is an antibody that specifically binds LAGS. In some embodiments, the antibody that binds LAGS is IMP701 (Prima BioMed), IMP731 (Prima BioMed/GlaxoSmithKline), BMS-986016 (Bristol Myer Squibb), LAGS25 (Novartis), and GSK2831781 (GlaxoSmithKline). In some embodiments, the LAGS antagonist includes a soluble LAGS receptor, for example, IMPS21 (Prima BioMed).

In some embodiments, the KIR antagonist is an antibody that specifically binds KIR. In some embodiments, the antibody that binds KIR is lirilumab (Bristol Myer Squibb/Innate Pharma).

In some embodiments, the immunotherapeutic agent used in the combinations disclosed herein (e.g., in combination with a compound of Formula I') is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In some embodiments, the OX40 agonist includes OX40 ligand, or an OX40-binding portion thereof. For example, the OX40 agonist may be MEDI6383 (AstraZeneca). In some embodiments, the OX40 agonist is an antibody that specifically binds OX40. In some embodiments, the antibody that binds OX40 is MEDI6469 (AstraZeneca/MedImmune), MEDI0562 (AstraZeneca/MedImmune), or MOXR0916 (RG7888; Genentech). In some embodiments, the OX40 agonist is a vector (e.g., an expression vector or virus, such as an adenovirus) capable of expressing OX40 ligand. In some embodiments the OX40-expressing vector is Delta-24-RGDOX (DNAtrix) or DNX2401 (DNAtrix).

In some embodiments, the 4-1BB (CD137) agonist is a binding molecule, such as an anticalin. In some embodiments, the anticalin is PRS-343 (Pieris AG). In some embodiments, the 4-1BB agonist is an antibody that specifically binds 4-1BB. In some embodiments, antibody that binds 4-1BB is PF-2566 (PF-05082566; Pfizer) or urelumab (BMS-663513; Bristol Myer Squibb).

In some embodiments, the CD27 agonist is an antibody that specifically binds CD27. In some embodiments, the antibody that binds CD27 is varlilumab (CDX-1127; Celldex).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518 (GITR, Inc.), MK-4166 (Merck), or INBRX-110 (Five Prime Therapeutics/Inhibrx).

TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and TIM-3.

LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

PD-1 pathway blockade can be combined with vaccines or other a compound of Formula I' antibodies for improved therapeutic efficacy (Hirano, F. et al, Cancer Res., 65(3) 1089-1096 (2005); Li, B. et al, Clin. Cancer Res., 15: 1507-1509 (2009); and Curran, M. A. et al, Proc. Natl. Acad. Set, 107(9):4275-4280 (2010)).

In some embodiments, immunotherapeutic agents useful in the compositions and methods described herein may include a monoclonal antibody, a bispecific antibody comprising one or more immune checkpoint antigen binding moieties, a trispecific antibody, or an immune cell-engaging multivalent antibody/fusion protein/construct known in the art that target specifically both PD-1 and ligand PD-L1.

PD-1 (also known as Programmed Death 1, CD279, PDCD1) is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). PD-1 is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 is a receptor for the ligands CD80, CD86, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2 261). Upon ligand engagement, PD-1 recruits phosphatases such as SHP-1 and SHP-2 to its intracellular tyrosine motifs which subsequently dephosphorylate effector molecules activated by TCR or BCR signalling (Chemnitz, J et al. 2004 J Immunol 173 945-954; Riley, James L 2009 Immunological Reviews 229 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-XL (Kier, Mary E et al. 2008 Annu Rev Immunol 26 677-704). In addition to these direct effects, recent publications have implicated PD-1 as being involved in the suppression of effector cells by promoting the induction and maintenance of regulatory T cells (TREG). For example, PD-L1 expressed on dendritic cells was shown to act in synergy with TGF-β to promote the induction of CD4+ FoxP3+TREG with enhanced suppressor function (Francisco, Loise M et al. 2009 J Exp Med 206 3015-3029).

TIM-3 (also known as T-cell immunoglobulin and mucin-domain containing-3, TIM-3, Hepatitis A virus cellular receptor 2, HAVCR2, HAVcr-2, KIM-3, TIMD-3, TIMD3, Tim-3, and CD366) is a ~33.4-kDa single-pass type I membrane protein involved in immune responses (Sanchez-Fueyo et al., Tim-3 inhibits T helper type 1-mediated auto- and alloimmune responses and promotes immunological tolerance, Nat. Immunol. 4:1093-1101(2003)).

TIM-3 is selectively expressed on Th1-cells, and phagocytic cells (e.g., macrophages and dendritic cells). The use of siRNA or a blocking antibody to reduce the expression of human resulted in increased secretion of interferon γ (IFN-γ) from CD4 positive T-cells, implicating the inhibitory role of TIM-3 in human T cells. Analysis of clinical samples from autoimmune disease patients showed no expression of TIM-3 in CD4 positive cells. In particular, expression level of TIM-3 is lower and secretion of IFN-γ is higher in T cell clones derived from the cerebrospinal fluid of patients with multiple sclerosis than those in clones derived from normal healthy persons (Koguchi K et al., J Exp Med. 203:1413-8. (2006)).

TIM-3 is the receptor for the ligands Galectin-9, which is a member of galectin family, molecules ubiquitously expressed on a variety of cell types and which binds β-galactoside; Phospatidyl serine (PtdSer) (DeKryff et al., T cell/transmembrane, Ig, and mucin-3 allelic variants differentially recognize phosphatidylserine and mediate phagocytosis of apoptotic cells, J Immunol. 2010 Feb. 15; 184(4): 1918-30); High Mobility Group Protein 1 (also known as HMGB1, HMG1, HMG3, SBP-1, HMG-1, and high mobility group box 1) Chiba et al., Tumor-infiltrating DCs suppress nucleic acid-mediated innate immune responses through interactions between the receptor TIM-3 and the alarmin HMGB1, Nat Immunol. 2012 September; 13(9): 832-42); and Carcinoembryonic Antigen Related Cell Adhesion Molecule 1 (also known as CEACAM1, BGP, BGP1, BGP1, carcinoembryonic antigen related cell adhesion molecule 1) (Huang et al., CEACAM1 regulates TIM-3-mediated tolerance and exhaustion, Nature. 2015 Jan. 15; 517 (7534):386-90).

BTLA (also known as B- and T-lymphocyte attenuator, BTLA1, CD272, and B and T lymphocyte associated) is a ~27.3-kDa single-pass type I membrane protein involved in lymphocyte inhibition during immune response. BTLA is constitutively expressed in both B and T cells. BTLA interacts with HVEM (herpes virus-entry mediator), a member of the tumor-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is unique in that it defines a cross talk between these two families of receptors. BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation. The BTLA cytoplasmic tail also contains a third conserved tyrosine-containing motif within the cytoplasmic domain, similar in sequence to a Grb-2 recruitment site (YXN). Also, a phosphorylated peptide containing this BTLA N-terminal tyrosine motif can interact with GRB2 and the p85 subunit of PI3K in vitro, although the functional effects of this interaction remain unexplored in vivo (Gavrieli et al., Bioochem. Biophysi Res Commun, 2003, 312, 1236-43). BTLA is the receptor for the ligands PTPN6/SHP-1; PTPN11/SHP-2; TNFRSF14/HVEM; and B7H4.

VISTA (also known as V-domain Ig suppressor of T cell activation VSIR, B7-H5, B7H5, GI24, PP2135, SISP1, DD1 alpha, VISTA, C10orf54, chromosome 10 open reading frame 54, PD-1H, and V-set immunoregulatory receptor) is a ~33.9-kDa single-pass type I membrane protein involved in T-cell inhibitory response, embryonic stem cells differentiation via BMP4 signaling inhibition, and MMP14-mediated MMP2 activation (Yoon et al., Control of signaling-mediated clearance of apoptotic cells by the tumor suppressor p53, Science. 2015 Jul. 31; 349(6247): 1261669). VISTA interacts with the ligand VSIG-3 (Wang et al., VSIG-3 as a ligand of VISTA inhibits human T-cell function, Immunology. 2019 January; 156(1):74-85)

LAG-3 (also known as Lymphocyte-activation gene 3, LAG3, CD223, and lymphocyte activating 3) is a ~57.4-kDa single-pass type I membrane protein involved in lymphocyte activation that also binds to HLA class-II antigens. LAG-3 is a member of the immunoglobulin supergene family, and is expressed on activated T cells (Huard et al., 1994, Immunogenetics 39:213), NK cells (Triebel et al., 1990, J. Exp. Med. 171:1393-1405), regulatory T cells (Huang et al., 2004, Immunity 21:503-513; Camisaschi et al., 2010, J Immunol. 184:6545-6551; Gagliani et al., 2013, Nat Med 19:739-746), and plasmacytoid dendritic cells (DCs) (Workman et al., 2009, J Immunol 182:1885-1891). LAG-3 is a membrane protein encoded by a gene located on chromosome 12, and is structurally and genetically related to CD4. Similar to CD4, LAG-3 can interact with MHC class II molecules on the cell surface (Baixeras et al., 1992, J. Exp. Med. 176:327-337; Huard et al., 1996, Eur. J. Immunol. 26:1180-1186). It has been suggested that the direct binding of LAG-3 to MHC class II plays a role in down-regulating antigen-dependent stimulation of CD4+T lymphocytes (Huard et al., 1994, Eur. J. Immunol. 24:3216-3221) and LAG-3 blockade has also been shown to reinvigorate CD8+ lymphocytes in both tumor or self-antigen (Gross et al., 2007, J Clin Invest. 117:3383-3392) and viral models (Blackburn et al., 2009, Nat. Immunol. 10:29-37). Further, the intra-cytoplasmic region of LAG-3 can interact with LAP (LAG-3-associated protein), which is a signal transduction molecule involved in the downregulation of the CD3/TCR activation pathway (Iouzalen et al., 2001, Eur. J. Immunol. 31:2885-2891). Moreover, CD4+CD25+ regulatory T cells (Treg) have been shown to express LAG-3 upon activation, which contributes to the suppressor activity of Treg cells (Huang, C. et al., 2004, Immunity 21:503-513). LAG-3 can also negatively regulate T cell homeostasis by Treg cells in both T cell-dependent and independent mechanisms (Workman, C. J. and Vignali, D. A., 2005, J. Immunol. 174:688-695).

LAG-3 has been shown to interact with MHC class II molecules (Huard et al., CD4/major histocompatibility complex class II interaction analyzed with CD4- and lymphocyte activation gene-3 (LAG-3)-Ig fusion proteins, Eur J Immunol. 1995 September; 25(9):2718-21).

Additionally, several kinases are known to be checkpoint inhibitors. For example, CHEK-1, CHEK-2, and A2aR.

CHEK-1 (also known as CHK 1 kinase, CHK1, and checkpoint kinase 1) is a ~54.4-kDa serine/threonine-protein kinase that is involved with checkpoint-mediated cell cycle arrest, and the activation of DNA repair in response to the DNA damage and/or unreplicated DNA.

CHEK-2 (also known as CHK2 kinase, CDS1, CHK2, HuCds1, LFS2, PP1425, RAD53, hCds1, and checkpoint kinase 2) is a ~60.9-kDa. serine/threonine-protein kinase involved in checkpoint-mediated cell cycle arrest, DNA-repair activation, and double-strand break-mediated apoptosis.

A2aR (also known as adenosine A2A receptor, ADORA2A, adenosine A2a receptor, A2aR, ADORA2, and RDC8) is a ~44.7-kDa multi-pass membrane receptor for adenosine and other ligands.

In various embodiments, the immunotherapeutic agent can comprise an antibody or an antigen binding fragment thereof. Within this definition, immune checkpoint inhibitors include bispecific antibodies and immune cell-engaging multivalent antibody/fusion protein/constructs known in the art. In some embodiments, immunotherapeutic agents which comprise bispecific antibodies may include bispecific antibodies that are bivalent and bind either the same epitope of the immune checkpoint molecule, two different epitopes of the same immune checkpoint molecule or different epitopes of two different immune checkpoints.

Persons of ordinary skill in the art can implement several bispecific antibody formats known in the field to target one or more of CTLA4, PD1, PD-L1 TIM-3, LAG-3, various B-7 ligands, B7H3, B7H4, CHK 1 and CHK2 kinases, BTLA, A2aR, OX40, 41BB, LIGHT, CD40, GITR, TGF-beta, SIRP-alpha, TIGIT, VSIG8, SIGLEC7, SIGLEC9, ICOS, FAS, BTNL2 and other for use in the combination described herein.

In various embodiments, the immunotherapeutic agent can include am immune cell-engaging multivalent antibody/fusion protein/construct.

In an embodiment of the disclosure, the checkpoint inhibitor, in combination with a compound of Formula I', is used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression.

In a further embodiment of the disclosure, there is provided a combination therapy for treating cancer, comprising a compound of Formula I' and blockade of checkpoint inhibitors with the potential to elicit potent and durable immune responses with enhanced therapeutic benefit and more manageable toxicity.

In a further embodiment of the disclosure, there is provided a combination therapy for treating cancer, comprising a compound of Formula I' and an immune checkpoint inhibitor. In an embodiment of the disclosure is provided a method for treating cancer and/or preventing the establishment of metastases by employing a checkpoint inhibitor which act synergistically with a compound of Formula I'.

In further embodiments, methods of the disclosure include, one or more of the following: 1) reducing or inhibiting growth, proliferation, mobility or invasiveness of tumor or cancer cells that potentially or do develop metastases, 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilization.

In an embodiment of the disclosure, administration of the immunotherapeutic agent, in combination therapy with a compound of Formula I', provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i e., a therapeutic benefit or a beneficial effect.

A therapeutic benefit or beneficial effect is any objective or subjective, transient, temporary, or long-term improvement in the condition or pathology, or a reduction in onset, severity, duration or frequency of adverse symptom associated with or caused by cell proliferation or a cellular hyperproliferative disorder such as a neoplasia, tumor or cancer, or metastasis. It may lead to improved survival. A satisfactory clinical endpoint of a treatment method in accordance with the disclosure is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore may be, but is not limited to destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells, inhibiting or preventing an increase in neoplasia, tumor or cancer volume (e.g., stabilizing), slowing or inhibiting neoplasia, tumor or cancer progression, worsening or metastasis, or inhibiting neoplasia, tumor or cancer proliferation, growth or metastasis.

In an embodiment of the disclosure, administration of the immunotherapeutic agent, in combination therapy with a compound of Formula I', provides a detectable or measurable improvement or overall response according to the irRC (as derived from time-point response assessments and based on tumor burden), including one of more of the following: (i) irCR-complete disappearance of all lesions, whether measurable or not, and no new lesions (confirmation by a repeat, consecutive assessment no less than 4 weeks from the date first documented), (ii) irPR-decrease in tumor burden.gtoreq.50% relative to baseline (confirmed by a consecutive assessment at least 4 weeks after first documentation).

Optionally, any method described herein may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In additional embodiment, a method prolongs or extends lifespan (survival) of the subject. In a further embodiment, a method improves the quality of life of the subject.

In one embodiment, administration of the immunotherapeutic agent, in combination therapy with a compound of Formula I', results in a clinically relevant improvement in one or more markers of disease status and progression selected from one or more of the following: (i): overall survival, (ii): progression-free survival, (iii): overall response rate, (iv): reduction in metastatic disease, (v): circulating levels of tumor antigens such as carbohydrate antigen 19.9 (CA19.9) and carcinembryonic antigen (CEA) or others depending on tumor, (vii) nutritional status (weight, appetite, serum albumin), (viii): pain control or analgesic use, (ix): CRP/albumin ratio.

Treatment with a compound of Formula I' in combination with an immunotherapeutic agent gives rise to more complex immunity including not only the development of innate immunity and type-1 immunity, but also immunoregulation which more efficiently restores appropriate immune functions.

In various exemplary methods, a checkpoint inhibitor antibody (monoclonal or polyclonal, bispecific, trispecific, or an immune cell-engaging multivalent antibody/fusion protein/construct) directed to a checkpoint molecule of interest (e.g., PD-1) may be sequenced and the polynucleotide sequence may then be cloned into a vector for expression or propagation. The sequence encoding the antibody or antigen-binding fragment thereof of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, methods for producing the recombinant antibodies can include the steps of culturing a host cell containing isolated nucleic acid(s) encoding the antibodies of the present disclosure. Methods for culturing a host cell containing isolated nucleic acid(s) encoding the antibodies of the present disclosure can be done in a variety of ways, depending on the nature of the antibody. In some embodiments, in the case where the antibodies of the disclosure are full length traditional antibodies, for example, a heavy chain variable region and a light chain variable region under conditions such that an antibody is produced and can be isolated.

In general, nucleic acids are provided that encode the antibodies or antigen-binding fragments thereof of the present disclosure. Such polynucleotides encode for both the variable and constant regions of each of the heavy and light chains, although other combinations are also contemplated by the present disclosure. The present disclosure also contemplates oligonucleotide fragments derived from the disclosed polynucleotides and nucleic acid sequences complementary to these polynucleotides.

The polynucleotides can be in the form of RNA, DNA, cDNA, genomic DNA, nucleic acid analogs, and synthetic DNA. The DNA may be double-stranded or single-stranded, and if single stranded, may be the coding (sense) strand or non-coding (anti-sense) strand. The coding sequence that encodes the polypeptide may be identical to the coding sequence or may be a different coding sequence, which sequence, as a result of the redundancy or degeneracy of the genetic code, encodes the same polypeptides.

In some embodiments, nucleic acid(s) encoding the antibodies of the present disclosure are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, and the like) or other components (selection genes, and the like), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, and the like.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, and the like), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. USA. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

Exemplary and illustrative recombinant methods for antibody molecular biology, expression, purification, and screening are described, for example, in Antibody Engineering, edited by Kontermann & Dub el, Springer, Heidelberg, 2001 and 2010 Hayhurst & Georgiou, 2001, Curr. Opin. Chem. Biol. 5:683-689; Maynard & Georgiou, 2000, Annu. Rev. Biomed. Eng. 2:339-76; and Morrison, S. (1985) Science 229:1202, the disclosures of which are incorporated herein by reference in their entireties.

In various embodiments, the polynucleotide sequence encoding the selected variable heavy and light chains may be used for genetic manipulation to humanize the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Immune checkpoint modulator antibodies of the present disclosure can be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or in yeast cells (e.g. Pichia pastoris or Saccharomyces cerevisiae. Methods for expressing antibodies recombinantly in plants or yeast have been disclosed. See, for example, Peeters, et al. Vaccine 19:2756, 2001; Lonberg, N. and D. Huszar Int. Rev. Immunol 13:65, 1995; and Horwitz, A. H. et al., Proc. Natl. Acad. Sci. 85:8678-8682; the disclosures of which are hereby incorporated by reference in their entireties. Methods for making derivatives of antibodies, e.g., domain, single chain, and the like are known in the art.

Immunoassays and flow cytometry sorting techniques such as fluorescence activated cell sorting (FACS) can also be employed to isolate antibodies that are specific for checkpoint molecules.

In some embodiments, a polynucleotide comprises a sequence encoding the heavy chain and/or the light chain variable regions of the checkpoint inhibitor antibody or antigen-binding fragment thereof of the present disclosure. The sequence encoding the antibody or antigen-binding fragment thereof of interest may be maintained in a vector in a host cell and the host cell can then be expanded and frozen for future use. Vectors (including expression vectors) and host cells are further described herein.

The disclosure includes affinity matured checkpoint modulator antibodies. For example, affinity matured antibodies can be produced by procedures known in the art (Marks et al., 1992, Bio/Technology, 10:779-783; Barbas et al., 1994, Proc Nat. Acad. Sci. USA 91:3809-3813. One way of characterizing a CDR of an antibody and/or altering (such as improving) the binding affinity of a polypeptide, such as an antibody, termed "library scanning mutagenesis". An exemplary method for providing affinity matures antibodies and antigen-binding fragments can include replacing one or more amino acid positions in the CDR with two or more (such as 3, 4, 5, 6, 7, 8, 9, 10, 11, 12, 13, 14, 15, 16, 17, 18, 19, or 20) amino acids using art recognized methods, a library of clones are generated, each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a KD of about 10 nM or lower. The library of clones can then be recombinantly introduced into a selection construct using any method known in the art for selection, including phage display, yeast display, and ribosome display.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the KD of the antibody directed to a checkpoint molecule, to increase or decrease kon or to alter the binding specificity of the antibody. Techniques in site-directed mutagenesis are well-known in the art. See, e.g., Sambrook et al. and Ausubel et al.

Pharmaceutical compositions containing a compound of Formula I' according to the present disclosure will comprise an effective amount of a compound of Formula I', an immunotherapeutic agent, and/or both, typically dispersed in a pharmaceutically acceptable carrier. The phrases "pharmaceutically or pharmacologically acceptable" refers to molecular entities and compositions that do not produce adverse, allergic or other untoward reaction when administered to animal, such as, for example, a human, as appropriate. The preparation of an pharmaceutical composition that contains a compound of Formula I' will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier for a combination compositions, containing a compound of Formula I' in admixture with an immunotherapeutic agent as described herein is borate buffer or sterile saline solution (0.9% NaCl).

Formulations of the an immunotherapeutic agent, for example an immune checkpoint modulator antibody used in accordance with the present disclosure can be prepared for storage by mixing an antibody having the desired degree of purity with optional pharmaceutically acceptable carriers, excipients or stabilizers as amply described and illustrated in Remington's Pharmaceutical Sciences 16th edition, Osol, A. Ed. [1980], in the form of lyophilized formulations or aqueous solutions and/or suspensions. Acceptable carriers, excipients, buffers or stabilizers are nontoxic to recipients at the dosages and concentrations employed, and include suitable aqueous and/or non-aqueous excipients that may be employed in the pharmaceutical compositions of the disclosure, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, buffers such as phosphate, citrate, and other organic acids. Antioxidants may be included, for example, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like; preservatives (such as octade-cyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues). Other exemplary pharmaceutically acceptable excipients may include polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In one illustrative embodiment, the pharmaceutical compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. In some embodiments, the checkpoint inhibitor antibodies or antigen-binding fragments thereof of the present disclosure are formulated for and can be lyophilized for storage and reconstituted in a suitable excipient prior to use according to art-known lyophilization and reconstitution techniques. In one exemplary pharmaceutical composition containing one or more checkpoint inhibitor antibodies or antigen-binding fragment thereof, the composition is formulated as a sterile, preservative-free solution of one or more checkpoint inhibitor antibodies or antigen-binding fragment thereof for intravenous or subcutaneous administration. The formulation can be supplied as either a single-use, prefilled pen, as a single-use, for example containing about 1 mL prefilled glass syringe, or as a single-use institutional use vial. Preferably, the pharmaceutical composition containing the checkpoint inhibitor antibody or antigen-binding fragment thereof is clear and colorless, with a pH of about 6.9-5.0, preferably a pH of 6.5-5.0, and even more preferably a pH ranging from about 6.0 to about 5.0. In various embodiments, the formulations comprising the pharmaceutical compositions can contain from about 500 mg to about 10 mg, or from about 400 mg to about 20 mg, or from about 300 mg to about 30 mg or from about 200 mg to about 50 mg of the checkpoint inhibitor antibody or antigen-binding fragment thereof per mL of solution when reconstituted and administered to the subject. Exemplary injection or infusion excipients can include mannitol, citric acid monohydrate, dibasic sodium phosphate dihydrate, monobasic sodium phosphate dihydrate, polysorbate 80, sodium chloride, sodium citrate and water for parenteral administration, for example, intravenously, intramuscularly, intraperitoneally, or subcutaneous administration.

In another exemplary embodiment, one or more immunotherapeutic agents, or an antigen-binding fragment thereof is formulated for intravenous or subcutaneous administration as a sterile aqueous solution containing 1-75 mg/mL, or more preferably, about 5-60 mg/mL, or yet more preferably, about 10-50 mg/mL, or even more preferably, about 10-40 mg/mL of antibody, with sodium acetate, polysorbate 80, and sodium chloride at a pH ranging from about 5 to 6. Preferably, the intravenous or subcutaneous formulation is a sterile aqueous solution containing 5, 10, 15, 20, 25, 30, 35, 40, 45, or 50 mg/mL of the immunotherapeutic agent, for example, an immune checkpoint inhibitor antibody or an antigen-binding fragment thereof, with 20 mM sodium acetate, 0.2 mg/mL polysorbate 80, and 140 mM sodium chloride at pH 5.5. Further, a solution comprising a checkpoint inhibitor antibody or an antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 5-500 mg of an immunotherapeutic agent or antigen-binding fragment thereof of the present disclosure, 10 mM histidine, 5% sucrose, and 0.01% polysorbate 80 at pH 5.8, with or without a compound of Formula I'. This composition may be provided as a lyophilized powder. When the powder is reconstituted at full volume, the composition retains the same formulation. Alternatively, the powder may be reconstituted at half volume, in which case the composition comprises 10-500 mg of an immunotherapeutic agent or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the immunotherapeutic agent formulation. For example, from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof, may be given as a bolus, and the rest of the antibody dose may be administered by intravenous injection. A predetermined dose of the immunotherapeutic agent, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the immunotherapeutic agent formulation. In some exemplary doses, the immunotherapeutic agent formulation can be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof. In some embodiments the dose may be given as a bolus, and the rest of the immunotherapeutic agent dose may be administered by subcutaneous or intravenous injection. A predetermined dose of the immunotherapeutic agent, or antigen-binding fragment thereof, may be administered, for example, over a period of an hour to two hours to five hours.

The formulation herein may also contain more than one active compound as necessary for the particular indication being treated, preferably those with complementary activities that do not adversely affect each other. For example, it may be desirable to provide one or more immunotherapeutic agents with other specificities. Alternatively, or in addition, the composition may comprise an anti-inflammatory agent, a chemotherapeutic agent, a cytotoxic agent, a cytokine, a growth inhibitory agent and/or a small molecule antagonist. Such molecules are suitably present in combination in amounts that are effective for the purpose intended.

The formulations to be used for in vivo administration should be sterile, or nearly so. This is readily accomplished by filtration through sterile filtration membranes.

In various embodiments, illustrative formulations of the pharmaceutical compositions described herein can be prepared using methods widely known in the field of pharmaceutical formulations. In general, such preparatory methods can include the step of bringing the active ingredient into association with a carrier or one or more other accessory ingredients, and then, if desirable, packaging the product into a desired single- or multi-dose unit.

In some embodiments, the composition comprising a compound of Formula I' can be also delivered in a vesicle, and the immunotherapeutic agent can be delivered in the same liposome formulation, or in a separate formulation that is compatible with the liposomal formulation containing the compound of Formula I', In some illustrative examples, a liposome containing one or more liposomal surface moieties for example, polyethylene glycol, antibodies and antibody fragments thereof that target a desired tumor surface antigen, receptor, growth factor, glycoprotein, glycolipid or neoantigen, which are selectively transported into specific cells or organs, thus enhance targeted drug delivery.

In another embodiment, a compound of Formula I' can be delivered in a vesicle, in particular a liposome (see Langer, Science 249:1527-1533 (1990); Treat et al., in LIPOSOMES IN THE THERAPY OF INFECTIOUS DISEASE AND CANCER, Lopez-Berestein and Fidler (eds.), Liss, N.Y., pp. 353-365 (1989); Lopez-Berestein, ibid., pp. 317-327; see generally ibid.).

In yet another embodiment, a compound of Formula I', or the composition containing the combination, or a composition containing the immunotherapeutic agent, can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574

(1989)). In another embodiment, controlled relaease of the compound of Formula I' can comprise polymeric materials to provide sustained, intermediate, pulsatile, or alternate release (see MEDICAL APPLICATIONS OF CONTROLLED RELEASE, Langer and Wise (eds), CRC Pres., Boca Raton, Fla. (1974); CONTROLLED DRUG BIO AVAILABILITY, DRUG PRODUCT DESIGN AND PERFORMANCE, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). Other controlled-release systems discussed in the review by Langer (Science 249:1527-1533 (1990)) can be used.

The optimum concentration of the active ingredient(s) in the chosen medium can be determined empirically, according to procedures well known to the skilled artisan, and will depend on the ultimate pharmaceutical formulation desired and the use to be employed.

The present disclosure also provides a pharmaceutical pack or kit comprising one or more containers filled with one or more of the ingredients of the pharmaceutical compositions of the disclosure, which at minimum will include a compound of Formula I' and one or more checkpoint inhibitor antibodies or antigen-binding fragment thereof as described herein. In other embodiments, the kit may contain one or more further containers providing a pharmaceutically acceptable excipient, for example a diluent. In one embodiment a kit may comprise at least one container, wherein the container can include a compound of Formula I', a checkpoint inhibitor antibody or an antigen-binding fragment thereof of the present disclosure. The kit may also include a set of instructions for preparing and administering the final pharmaceutical composition to the subject in need thereof, for the treatment of a checkpoint molecule-mediated disease or disorder.

Some embodiments of the present disclosure, the immunotherapeutic agent is a population of immune cells, which can be administered in combination with a compound of Formula I' to treat a subject with cancer. In some embodiments, the immunotherapeutic agent is a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T-cell is a CD4+ Th (T helper) cell, a CD8+ cytotoxic T cell, a γδT cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. Transcription Factor Protocols: Methods in Molecular Biology™ 2000; 130: 117-134), chemical (e.g., calcium phosphate or lipid), transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), microinjection of purified DNA directly into the nucleus of the cell (see, e.g., Capecchi M. R. Cell. 1980 November; 22 (2 Pt 2): 479-88), or retrovirus transduction.

Some aspects of the present disclosure provide an "adoptive cell" approach, which involves isolating immune cells (e.g., T-cells) from a subject with cancer, genetically engineering the immune cells (e.g., to express an antigen-binding receptor, such as a chimeric antigen receptor), expanding the cells ex vivo, and then re-introducing the immune cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A "chimeric antigen receptor" refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., Human Gene Therapy. 2015; 26(8):498-505), the disclosure of which is incorporated herein by reference in its entirety.

In some embodiments, an antigen binding receptor is a chimeric antigen receptor (CAR). A T cell that expressed a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., Human Gene Therapy. 2015; 26(8):498-505) the disclosure of which is incorporated herein by reference in its entirety.

There are four generations of CARs, each of which contains different components. First generation CARs join an antibody-derived scFv to the CD3zeta (zeta. or z) intracellular signaling domain of the T-cell receptor through hinge and transmembrane domains. Second generation CARs incorporate an additional domain, e.g., CD28, 4-1BB (4IBB), or ICOS, to supply a costimulatory signal. Third-generation CARs contain two costimulatory domains fused with the TcR CD3-zeta chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2): 151-155) the disclosure of which is incorporated herein by reference in its entirety.

In some embodiments, the chimeric antigen receptor (CAR) is a T-cell redirected for universal cytokine killing (TRUCK), also known as a fourth generation CAR. TRUCKS are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3zeta signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-IBB CARs, but preclinical in vivo studies suggest that 4-IBB CARs may produce superior proliferation and/or persistence. Clinical trials suggest that both of these second-generation CARs are capable of inducing substantial T-cell proliferation in vivo, but CARs containing the 4-IBB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., Human Gene Therapy. 2015; 26(8):498-505; Chmielewski and Hinrich, Expert Opinion on Biological Therapy. 2015; 15(8): 1145-1154 the disclosures of which are incorporated herein by reference in their entireties.

In some embodiments, an illustrative immunotherapeutic agent is a first generation chimeric antigen receptor CAR. In some embodiments, a chimeric antigen receptor is a third generation CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-speciflc scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2: e105, incorporated herein by reference in its entirety). Thus, methods, in some embodiments, comprise delivering to a tumor a combination comprising a compound of Formula I' and an immunotherapeutic agent, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. Sci. Transl. Med. published online Dec. 11, 2013, incorporated herein by reference in its entirety). iCARs contain an antigen-specific inhibitory receptor, for example, to block nonspecific immunosuppression, which may result from extra tumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., Cytotherapy. 2003; 5(3): 211-226; Maude et al., Blood. 2015; 125(26): 4017-4023, each of which is incorporated herein by reference in their entireties).

According to other aspects of the disclosure, the tumor antigenic component in the vaccine of the invention is any natural or synthetic tumor-associated protein or peptide or combination of tumor-associated proteins and/or peptides or glycoproteins or glycopeptides. In still yet other aspects, the antigenic component can be patient-specific or common to many or most patients with a particular type of cancer. According to one aspect, the antigenic component consists of a cell lysate derived from tumor tissue removed from the patient being treated. In another aspect, the lysate can be engineered or synthesized from exosomes derived from tumor tissue. In yet another aspect, the antigenic component consists of a cell lysate derived from tumor tissue extracted from one or more unrelated individuals or from tumor-cell lines.

In various embodiments, an illustrative immunotherapeutic agent comprises one or more cancer vaccines, for use in combination with a compound of Formula I'. The tumor-associated antigen component of the vaccine may be manufactured by any of a variety of well-known techniques. For individual protein components, the antigenic protein is isolated from tumor tissue or a tumor-cell line by standard chromatographic means such as high-pressure liquid chromatography or affinity chromatography or, alternatively, it is synthesized by standard recombinant DNA technology in a suitable expression system, such as *E. coli*, yeast or plants. The tumor-associated antigenic protein is then purified from the expression system by standard chromatographic means. In the case of peptide antigenic components, these are generally prepared by standard automated synthesis. Proteins and peptides can be modified by addition of amino acids, lipids and other agents to improve their incorporation into the delivery system of the vaccine (such as a multilamellar liposome). For a tumor-associated antigenic component derived from the patient's own tumor, or tumors from other individuals, or cell lines, the tumor tissue, or a single cell suspension derived from the tumor tissue, is typically homogenized in a suitable buffer. The homogenate can also be fractionated, such as by centrifugation, to isolate particular cellular components such as cell membranes or soluble material. The tumor material can be used directly or tumor-associated antigens can be extracted for incorporation in the vaccine using a buffer containing a low concentration of a suitable agent such as a detergent. An example of a suitable detergent for extracting antigenic proteins from tumor tissue, tumor cells, and tumor-cell membranes is diheptanoyl phosphatidylcholine. Exosomes derived from tumor tissue or tumor cells, whether autologous or heterologous to the patient, can be used for the antigenic component for incorporation in the vaccine or as a starting material for extraction of tumor-associated antigens.

In some embodiments of the present disclosure, a cancer vaccine, wherein the cancer vaccine includes at least one tumor-associated antigen, at least one immunostimulant, and optionally, at least one cell-based immunotherapeutic agent, in some embodiments, the immunostimulant component in the cancer vaccine of the disclosure is any Biological Response Modifier (BRM) with the ability to enhance the therapeutic cancer vaccine's effectiveness to induce humoral and cellular immune responses against cancer cells in a patient. According to one aspect, the immunostimulant is a cytokine or combination of cytokines. Examples of such cytokines include the interferons, such as IFN-gamma, the interleukins, such as IL-2, IL-15 and IL-23, the colony stimulating factors, such as M-CSF and GM-CSF, and tumor necrosis factor. According to another aspect, the immunostimulant component of the disclosed cancer vaccine includes one or more adjuvant-type immunostimulatory agents such as APC Toll-like Receptor agonists or costimulatory/cell adhesion membrane proteins, with or without immunostimulatory cytokines. Examples of Toll-like Receptor agonists include lipid A and CpG, and costimulatory/adhesion proteins such as CD80, CD86, and ICAM-1.

In some embodiments, the immunostimulant is selected from the group consisting of IFN-gamma (IFN-γ), IL-2, IL-15, IL-23, M-CSF, GM-CSF, tumor necrosis factor, lipid A, CpG, CD80, CD86, and ICAM-1, or combinations thereof. According to other aspects, the cell-based immunotherapeutic agent is selected from the group consisting of dendritic cells, tumor-infiltrating T lymphocytes, chimeric antigen receptor-modified T effector cells directed to the patient's tumor type, B lymphocytes, natural killer cells, bone marrow cells, and any other cell of a patient's immune system, or combinations thereof. In one aspect, the cancer vaccine immunostimulant includes one or more cytokines, such as interleukin 2 (IL-2), GM-CSF, M-CSF, and interferon-gamma (IFN-γ), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the cancer vaccine includes an immunostimulant that is a cytokine selected from the group consisting of interleukin 2 (IL-2), GM-CSF, M-CSF, and interferon-gamma (IFN-γ). In another aspect, the cancer vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the cancer vaccine includes an immunostimulant that is a costimulatory membrane protein and/or cell adhesion protein selected from the group consisting of CD80, CD86, and ICAM-1.

In various embodiments, an immunotherapeutic agent can include a cancer vaccine, wherein the cancer vaccine incorporates any tumor antigen that can be potentially used to construct a fusion protein according to the invention and particularly the following:

(a) cancer-testis antigens including NY-ESO-1, SSX2, SCP1 as well as RAGE, BAGE, GAGE and MAGE family polypeptides, for example, GAGE-1, GAGE-2, MAGE-1 MAGE-2, MAGE-3, MAGE-4, MAGE-5, MAGE-6, and MAGE-12, which can be used, for example, to address melanoma, lung, head and neck, NSCLC, breast, gastrointestinal, and bladder tumors; (b) mutated antigens, including p53, associated with various solid tumors, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; KIA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; FRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gp100; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C vims antigens, human T-cell lymphotropic vims antigens, TSP-180, p185erbB2, p1 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS or any combinations thereof.

In some embodiments, cancer vaccines of the present disclosure for use in combination with a compound of Formula I' can include a tumor antigen comprising the entire amino acid sequence, a portion of it, or specific immunogenic epitopes of one of the following human proteins: TCTN1 (SEQ ID NO. 1; Gene ID: ENSG00000204852), TCTN2 (SEQ ID NO. 2; Gene ID: ENSG00000168778), TCTN3 (SEQ ID NO. 3; Gene ID: ENSG00000119977), HIGD2A (SEQ ID NO. 4; Gene ID: ENSG00000146066), HIGD2B (SEQ ID NO. 5; Gene ID: ENSG00000175202), C4ORF32 (SEQ ID NO. 6; Gene ID: ENSG00000174749), FAM62A (E-SYT1, SEQ ID NO. 7; Gene ID: ENSG00000139641), COLEC11 (SEQ ID NO. 8; Gene ID: ENSG00000118004), FSTL5 (SEQ ID NO. 9; Gene ID: ENSG00000168843), FAM82A2 (SEQ ID NO. 10; Gene ID: ENSG00000137824), SCARA5 (SEQ ID NO. 11; Gene ID: ENSG00000168079), VSTM1 (SEQ ID NO. 12; Gene ID: ENSG00000189068), RNF5 (SEQ ID NO. 13; Gene ID: ENSG00000183574), UNQ6126 (SEQ ID NO. 14; Gene ID: gi |169216088), DPY19L3 (SEQ ID NO. 15; Gene ID: ENSG00000178904), SLC39A10 (SEQ ID NO. 16; gene ID: ENSG00000196950), GPR107 (SEQ ID NO. 17; Gene ID: ENSG00000148358), COL20A1 (SEQ ID NO. 18; Gene ID: ENSG00000101203), GLT25D2 SEQ ID NO. 19; Gene ID: ENSG00000198756), SYTL3 (SEQ ID NO. 20; Gene ID: ENSG00000164674), DENND1B (SEQ ID NO. 21; Gene ID: ENSG00000162701), C6orf98 SEQ ID NO. 22; Gene ID: EG: 387079), FAM69B (SEQ ID NO. 23; Gene ID: ENSG00000165716), EMID1 (SEQ ID NO. 24; Gene ID: OTTHUMG00000030824), KLRG2 SEQ ID NO. 25; GENE ID: ENSG00000188883), ERMP1 (SEQ ID NO. 26; GENE ID: ENSG00000099219), VMO1 (SEQ ID NO. 27; Gene ID: ENSG00000182853), C9orf46 (SEQ ID NO. 28; Gene ID: ENSG00000107020), $F_{1137107}$ (SEQ ID NO. 29; Gene ID: ENSG00000177990), YIPF2 (SEQ ID NO. 30; Gene ID: ENSG00000130733), TRYX3 (SEQ ID NO. 31; PRSS58, ENSG00000258223.2), C14orf135 (SEQ ID NO. 32; Gene ID: ENSG00000126773), ANGPTL7 (SEQ ID NO. 33; Gene ID: ENSG00000171819), TPCN2 SEQ ID NO. 34; Gene ID: ENSG00000162341), C18orf19 (SEQ ID NO. 35; Gene ID: ENSG00000177150), OLFML1 (SEQ ID NO. 36; Gene ID: ENSG00000183801), LYPD4 SEQ ID NO. 37; Gene ID: ENSG00000101203), MEGF8 (SEQ ID NO. 38; Gene ID: ENSG00000105429), $F_{1142986}$ (SEQ ID NO. 39; Gene ID: ENSG00000196460), SLC46A1 SEQ ID NO. 40; Gene ID: ENSG00000076351), FAM180A (SEQ ID NO. 41; Gene ID: ENSG00000189320), CRISP-3 (SEQ ID NO. 42; GENE ID: ENSG00000096006), or combinations thereof. These tumor antigens are disclosed in WO2010/086162, WO2010/086163, WO2011/051278, WO2011/051276, WO2011/051277, WO2011/051280, WO2011/051271, WO2011/135068, WO2014/198919, the contents of which are herein incorporated by reference in their entireties.

In various embodiments, an illustrative immunotherapeutic agent may include an mRNA operable to encode any one or more of the aforementioned cancer antigens useful for synthesizing a cancer vaccine. In some illustrative embodiments, the mRNA based cancer vaccine may have one or more of the following properties: a) the mRNA encoding each cancer antigen is interspersed by cleavage sensitive sites; b) the mRNA encoding each cancer antigen is linked directly to one another without a linker; c) the mRNA encoding each cancer antigen is linked to one another with a single nucleotide linker; d) each cancer antigen comprises a 20-40 amino acids and includes a centrally located SNP mutation; e) at least 40% of the cancer antigens have a highest affinity for class IMHC molecules from the subject; f) at least 40% of the cancer antigens have a highest affinity for class II MHC molecules from the subject; g) at least 40% of the cancer antigens have a predicted binding affinity of IC>500 nM for HLA-A, HLA-B and/or DRB1; h) the mRNA encodes 1 to 15 cancer antigens; i) 10-60% of the cancer antigens have a binding affinity for class I MHC and 10-60% of the cancer antigens have a binding affinity for class II MHC; and/or j) the mRNA encoding the cancer antigens is arranged such that the cancer antigens are ordered to minimize pseudo-epitopes.

In various embodiments, the combination comprising a compound of Formula I' and a cancer vaccine immunotherapeutic agent as disclosed herein can be used to illicit an immune response in a subject against a cancer antigen. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a compound of Formula I' either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, and the like. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, RNA vaccine immunotherapeutic agents of the present disclosure (e.g., mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, and the like.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of g/ml or are measured in units of IU/L (International Units per liter) or mIU/ml (milli International Units per ml). In exemplary embodiments of the invention, an efficacious vaccine produces >0.5 µg/mL, >0.1 µg/mL, >0.2 µg/mL, >0.35 µg/mL, >0.5 µg/mL, >1 µg/mL, >2 µg/mL, >5 µg/mL or >10 µg/mL. In exemplary embodiments of the invention, an efficacious vaccine produces >10 mIU/mL, >20 mIU/mL, >50 mIU/mL, >100 mIU/mL, >200 mIU/mL, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Immunotherapeutic agents comprising a nucleic acid vaccine comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, an illustrative immunotherapeutic agent can include one or more interfering RNAs that can be administered in combination with a compound of Formula I'.

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi). Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetyl cytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methyl guanine, 1-methylinosine, 2,2-dimethyl guanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

Antigens which can be targeted for synthesizing a corresponding antisense RNA molecule can include any antigen that is specific for one or more tumors, for example, antigens exemplified above with reference to cancer vaccines.

In some embodiments, a combination of an immunotherapeutic agent and a compound of Formula I' can include a bispecific antibody immunotherapeutic agent. The bispecific antibody can include a protein construct having a first antigen binding moiety and a second antigen binding site that binds to a cytotoxic immune cell. The first antigen binding site can bind to a tumor antigen that is specifically being treated with the combination of the present invention. For example, the first antigen binding moiety may bind to a non-limiting example of tumor antigens selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKE, TAP and Tenascin among others. In some embodiments, the first antigen binding moiety has specificity to a protein or a peptide that is overexpressed on a tumor cell as compared to a corresponding non-tumor cell. In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGER), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor.

The second antigen-binding moiety is any molecule that specifically binds to an antigen or protein or polypeptide expressed on the surface of a cytotoxic immune cell (a CIK cell). Exemplary non-limiting antigens expressed on the surface of the cytotoxic immune cells suitable for use with the present disclosure may include CD2, CD3, CD4, CD5, CD8, CD11a, CD11b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell. In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for modulation with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In other embodiments, the bispecific antibody modulator is an activator of a costimulatory molecule (e.g., an OX40 agonist). In one embodiment, the OX40 agonist is a bispecific antibody molecule to OX40 and another tumor antigen or a costimulatory antigen. The OX40 agonist can be administered alone, or in combination with other immunomodulators, e.g., in combination with an inhibitor (for example an antibody construct) of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand. In some embodiments, the second antigen binding moiety binds to the Fc receptor on the cytotoxic immune cell, e.g., CIK cell.

In some embodiments, the bispecific antibody immunotherapeutic agent has specificities for a tumor antigen and a CIK cell, which brings the tumor antigen expressing tumor cell in close proximity of the CIK cell, leading to the elimination of the tumor cell through anti-tumor cytotoxicity of CIK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, a combination of an immunotherapeutic agent and a compound of Formula I' can include an immune cell-engaging multivalent antibody/fusion protein/construct immunotherapeutic agent. In various embodiments, an exemplary immunotherapeutic agent can include immune cell-engaging multivalent antibody/fusion protein/construct which may comprise a recombinant structure, for example, all engineered antibodies that do not imitate the original IgG structure. Here, different strategies to multimerize antibody fragments are utilized. For example, shortening the peptide linker between the V domains forces the scFv to self-associate into a dimer (diabody; 55 kDa). Bispecific diabodies are formed by the noncovalent association of two VHA-VLB and VHB-VLA fragments expressed in the same cell. This leads to the formation of heterodimers with two different binding sites. Single-chain diabodies (sc-diabodies) are bispecific molecules where the VHA-VLB and VHB-VLA fragments are linked together by an additional third linker. Tandem-diabodies (Tandabs) are tetravalent bispecific antibodies generated by two scDiabodies.

Also included are the di-diabodies known in the art. This 130-kDa molecule is formed by the fusion of a diabody to the N-terminus of the CH3 domain of an IgG, resulting in an IgG-like structure. Further diabody derivatives are the triabody and the tetra-body, which fold into trimeric and tetrameric fragments by shortening the linker to <5 or 0-2 residues. Also exemplified are (scFv)$_2$ constructs known as 'bispecific T cell engager' (BITE). BITEs are bispecific single-chain antibodies consisting of two scFv antibody fragments, joined via a flexible linker, that are directed against a surface antigen on target cells and CD3 on T cells. Also exemplified are bivalent (Fab)2 and trivalent (Fab)3 antibody formats. Also exemplified are minibodies and trimerbodies generated from scFvs. Exemplary constructs useful to target tumor antigens as can include one or more of: Diabody, Single-chain (sc)-diabody (scFv)2, Mini antibody, Minibody, Barnase-barstar, scFv-Fc, sc(Fab)2, Trimeric antibody constructs, Triabody antibody constructs, Trimerbody antibody constructs, Tribody antibody constucts, Collabody antibody constructs, (scFv-TNFa)3, F(ab) 3/DNL. In each of these exemplified constructs, at least one binding moiety may bind to an antigen or protein or polypeptide expressed on the surface of a cytotoxic immune cell, and at least one binding moiety will bind specifically to an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, a combination of an immunotherapeutic agent and a compound of Formula I' can include a radioconjugate immunotherapeutic agent.

In various embodiments, a radioconjugate is a small molecule or large molecule (herein referred to as a "cell targeting agent"), for example and polypeptide, an antibody or an antibody fragment thereof, that is coupled to or otherwise affixed to a radionuclide, or a plurality of radionuclides, such that the binding of the radioconjugate to its target (a protein or molecule on or in a cancer cell), will lead to the death or morbidity of said cancer cell. In various embodiments, the radioconjugate can be a cell targeting agent labelled with a radionuclide, or the cell targeting agent may be coupled or otherwise affixed to a particle, or microparticle, or nanoparticle containing a plurality of radionuclides, wherein the radionuclides are the same or different. Methods for synthesizing radioconjugates are known in the art, and may include the class of immunoglobulin or antigen binding parts thereof, that are conjugated to a toxic radionuclide.

In some embodiments, the molecule that binds to the cancer cell can be known as a "cell targeting agent". As used herein, an exemplary cell targeting agent can allow the drug-containing nanoparticles or radionuclide to target the specific types of cells of interest. Examples of cell targeting agents include, but are not limited to, small molecules (e.g., folate, adenosine, purine) and large molecule (e.g., peptide or antibody) that bind to or target a tumor associated antigen. Examples of tumor associated antigens include, but are not limited to, adenosine receptors, alpha v beta 3, aminopeptidase P, alpha fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In some embodiments, the cell targeting agent is folate or a folate derivative that binds specifically to folate receptors (FRs). In some embodiments, the cell targeting agent is an antibody, a bispecific antibody, a trispecific antibody or an antigen binding construct thereof, that specifically binds to a cancer antigen selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin αVβ3, Integrin α5β1, MUC1, ERBB2, ERBB3, MET, IGF1R, EPHA3, TRAILR1, TRAILR2, RANKE, FAP and Tenascin among others.

The use of folate as a targeting agent in the radioconjugate also allow both tumor cells and regulatory T (Treg) cells to be targeted for destruction. It is well accepted that high numbers of Treg cells suppress tumor immunity. Specifically, Treg cells suppress (foreign and self) reactive T cells without killing them through contact-dependent or cytokine (e.g., IE-10, TGF-.beta, and the like.) secretion. FR4 is selectively upregulated on Treg cells. It has been shown that antibody blockade of FR4 depleted Treg cells and provoked tumor immunity in tumor-bearing mice. Thus, folate-coated PBM nanoparticles carrying a cytotoxic agent would take FR-expressing cells for their destruction, which would both directly (i.e., BrCa cell) and indirectly (i.e., breast tumor associated and peripheral Treg cells) inhibit tumor progression.

In another further embodiment, the targeting agent is an antibody or peptide, or immune cell-engaging multivalent antibody/fusion protein/constructs capable of binding tumor associated antigens consisting of but not limited to: adenosine receptors, alpha v beta 3, aminopeptidase P, alpha fetoprotein, cancer antigen 125, carcinoembryonic antigen, caveolin-1, chemokine receptors, clusterin, oncofetal antigens, CD20, Human Growth Factor Receptor (HGFR), epithelial tumor antigen, melanoma associated antigen, MUC1, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyrosinase, tyrosine kinases, and the like.

In one embodiment, the treatment method includes the co-administration of a compound as disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from antimicrotubule agents, platinum coordination complexes, alkylating agents, antibiotic agents, topoisomerase II inhibitors, antimetabolites, topoisom erase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agents" include chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfdzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omega 1I (Angew Chem. Inti. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porflromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX®; and (ix) pharmaceutically acceptable salts, acids and derivatives of any of the above.

Chemotherapeutic agents also include antibodies, as described above, including alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgG.sub.1.lamda. antibody genetically modified to recognize interleukin-12 p40 protein.

Chemotherapeutic agents also include "tyrosine kinase inhibitors" including the EGFR inhibitors; small molecule HER2 tyrosine kinase inhibitor such as Mubritonib (TAK165, Takeda); CP-724.714, (Axon Medchem BV, an oral selective inhibitor of the ErbB2 receptor tyrosine kinase); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase 1 inhibitor CI-1040 (available from Pharmacia); quinazolines, such as PD 15303 5,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; antisense molecules (e.g. those that bind to HER-encoding nucleic acid); quinoxalines (U.S. Pat. No. 5,804,396); tryphostins (U.S. Pat. No. 5,804,396); Affinitac (ISIS 3521; Isis/Lilly); PKI166 (Novartis); Semaxinib (Pfizer); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca). Tyrosine kinase inhibitors also include Erlotinib (Tarceva®), Gefitinib (Iressa®), Dasatinib (Sprycel®), Nilotinib (Tasigna®), Crizotinib (Xalkori®), Ruxolitinib (Jakafi®), Vemurafenib (Zelboraf®), Vandetanib (Caprelsa®), Pazopanib (Votrient®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, sari degib, tandutinib, tasocitinib, telatinib, tivantinib, tivozanib, tofacitinib, trametinib, veliparib, vismodegib, volasertib, cobimetinib (Cotellic®), and others.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept (Enbrel), infliximab (Remicade), adalimumab (1-Iumira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-Ml prime; Secreted homotrimeric LTa3 and membrane bound heterotrimer LTal/132 blockers such as Anti-lymphotoxin alpha (LTa); miscellaneous investigational agents such as thioplatin, PS-341, phenylbutyrate, ET-18-OCFE, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bel-2 inhibitor such as oblimersen sodium (GENASENSE) pixantrone; farnesyltransferase inhibitors such as lonafamib (SCH 6636, SARA-SAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include Poly ADP ribose polymerase (PARP) inhibitors: olaparib (Lynparza®), rucaprib (Rubraca®) niraparib (Zejula®), talzoparib (Talzenna®).

Effective combinations of compounds of Formula I' or any formulas as described herein with other agents may be identified through preclinical and clinical testing of the combinations, and will depend on many factors, including disease type and stage of development, overall health of the patient, toxicities and side effects of the agents, and the like.

In some embodiments, compounds as disclosed herein may be used in combination therapy with any of the kinase inhibitors disclosed herein for the treatment of diseases such as cancer. Exemplary kinase inhibitors include imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, a CK1 inhbitor, a CK1-α inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, for treatment of cancer, compounds as disclosed herein may be used in combination with inhibitors of PD-1 or inhibitors of PD-L1, e.g., an anti-PD-1 monoclonal antibody or an anti-PD-L1 monoclonal antibody, for example, nivolumab (Opdivo), pembrolizumab (Keytruda, MK-3475), atezolizumab, avelumab, AMP-224, AMP-514, PDR001, durvalumab, pidilizumab (CT-011), CK-301, BMS 936559, and MPDL3280A; CTLA-4 inhibitors, e.g., an anti-CTLA-4 antibody, for example, ipilimumab (Yervoy) and tremelimumab; and phosphatidylserine inhibitors, for example, bavituximab (PGN401); antibodies to cytokines (IL-10, TGF-β, and the like); other anti-cancer agents such as cemiplimab.

In some embodiments, a compound as described herein can be used in combination with a vaccination protocol for the treatment of cancer. In some embodiments, a compound as described herein can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, Staphylococcus aureus, Pseudomonas Aeruginosa.

In some embodiments, compounds as disclosed herein may be used in combination with inhibitors of PARP, for example, olaparib (Lynparza®), rucaprib (Rubraca®), niraparib (Zejula®), talzoparib (Talzenna®).

The amount of both the compound disclosed herein or salt thereof and the additional one or more additional therapeutic agent (in those compositions which comprise an additional therapeutic agent as described above) that may be combined with carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-10, 000 µg/kg body weight/day of the additional therapeutic agent can be administered.

Labeled Compounds and Assay Methods

Another aspect of the present invention relates to labeled compounds of the invention (radio-labeled, fluorescent-labeled, and the like.) that would be useful not only in imaging techniques but also in assays, both in vitro and in vivo, for localizing and quantitating TAM kinases in tissue samples, including human, and for identifying TAM kinase ligands by inhibition binding of a labeled compound. Accordingly, the present invention includes TAM kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br, or $^{77}$Br will generally be most useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S, and $^{82}$Br.

The present invention can further include synthetic methods for incorporating radio-isotopes into compounds of the invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a TAM by monitoring its concentration variation when contacting with the TAM kinases, through tracking of the labeling. For example, a test compound (labeled) can be evaluated for its ability to reduce binding of another compound which is known to bind to a TAM kinase (i.e., standard compound). Accordingly, the ability of a test compound to compete with the standard compound for binding to the TAM kinase directly correlates to its binding affinity. Conversely, in some other screening assays, the standard compound is labeled, and test compounds are unlabeled. Accordingly, the concentration of the labeled standard compound is monitored in order to evaluate the competition between the standard compound and the test compound, and the relative binding affinity of the test compound is thus ascertained.

Synthesis

Compounds of this invention can be made by the synthetic procedures described below. The starting materials and reagents used in preparing these compounds are either available from commercial suppliers such as Sigma Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991); March's Advanced Organic Chemistry, (John Wiley and Sons, 4$^{th}$ Edition); and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C., and most preferably at about room (or ambient) temperature, e.g., about 20° C. Unless otherwise stated (as in the case of a hydrogenation), all reactions are performed under an atmosphere of nitrogen.

The compounds disclosed and claimed herein have asymmetric carbon atoms or quaternized nitrogen atoms in their structure and may be prepared through the syntheses described herein as single stereoisomers, racemates, or mixtures of enantiomers and diastereomers. The compounds may also exist as geometric isomers. All such single stereoisomers, racemates, and geometric isomers, and mixtures thereof are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereomeric salts or complexes which may be separated, for example, by crystallization; via formation of diastereomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomers may be synthesized by asymmetric synthesis using optically active reagents, substrates, catalysts, or solvents, or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The methods of the present invention may be carried out as semi-continuous or continuous processes, more preferably as continuous processes.

The present invention as described above unless indicated otherwise may be carried out in the presence of a solvent or a mixture of two or more solvents. In particular the solvent is an aqueous or an organic solvent such as the ether-like solvent (e.g. tetrahydrofuran, methyltetrahydrofuran, diisopropyl ether, t-butylmethyl ether, or dibutyl ether), aliphatic hydrocarbon solvent (e.g. hexane, heptane, or pentane), saturated alicyclic hydrocarbon solvent (e.g. cyclohexane or cyclopentane), or aromatic solvent (e.g. toluene, o-, m-, or p-xylene, or t-butyl-benzene) or mixture thereof.

The starting materials and reagents, which do not have their synthetic route explicitly disclosed herein, are generally available from commercial sources or are readily prepared using methods well known to the person skilled in the art.

Processes

In one aspect, the invention provides a process for making a compound of Formula I':

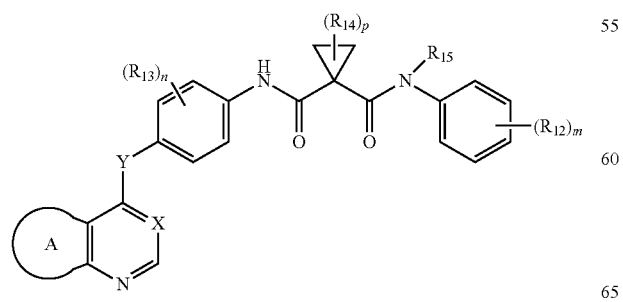

or a pharmaceutically acceptable salt thereof, comprising:
reacting a compound of Formula X:

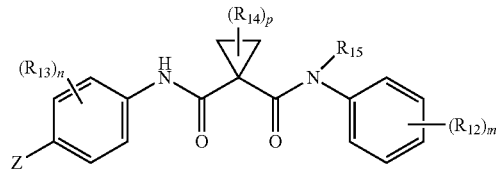

with a compound of Formula XI:

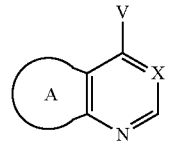

wherein
Ring A, Y, X, $R_{12}$, $R_{13}$, $R_{14}$, and $R_{15}$ are defined herein;
Z is selected from the group consisting of $NH_2$, SH, and OH; and
V is a leaving group.

In another aspect, the invention provides a process for making a compound of Formula I':

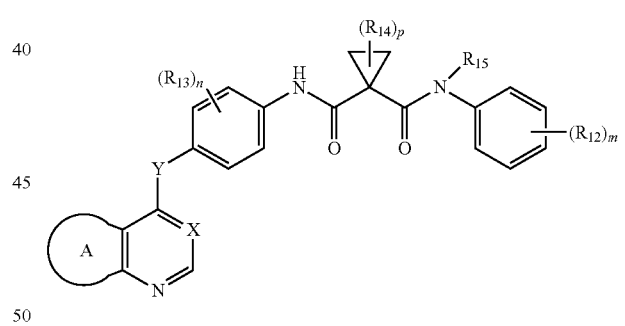

or a pharmaceutically acceptable salt thereof, comprising:
reacting a compound of formula XII:

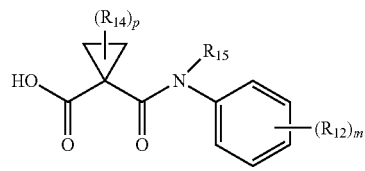

with a compound of formula XIII:

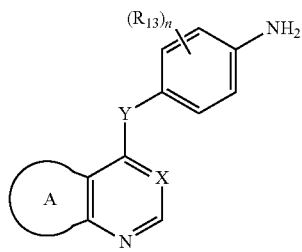

wherein
Ring A, Y, X, $R_{12}$, $R_{13}$, $R_{14}$, and $R_{15}$ are defined herein.

In one embodiment of this aspect, the invention provides making a compound of Formula XIII'

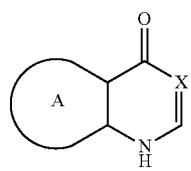

comprising reacting a compound of Formula XIV:

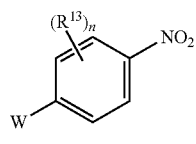

with a compound of Formula XV:

to form a compound of Formula XVI:

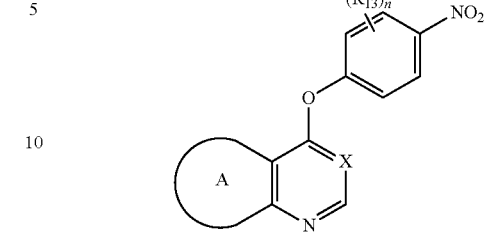

and reducing the compound of Formula XVI to form a compound of Formula XIII.

The following examples are provided for the purpose of further illustration and are not intended to limit the scope of the claimed invention.

EXAMPLES

General Experimental Procedures

The following general procedures are examples of synthesizing compounds of the present invention. One of ordinary skill in the art understands that the general procedures may be adapted to make other compounds of Formula I.

General Procedure A

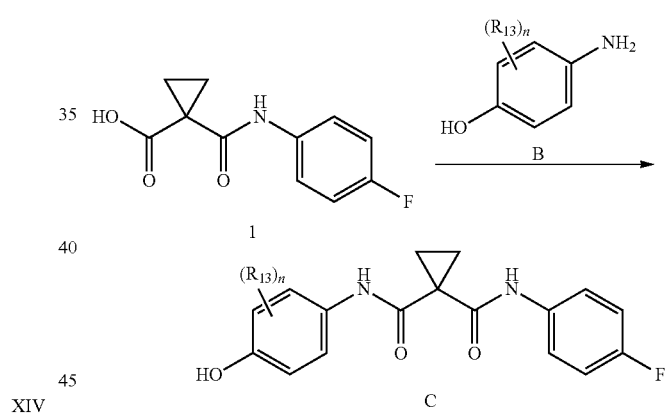

Carboxylic acid compound 1 can be converted to a compound of Formula C by coupling to an intermediate of Formula B using known coupling reagents, such as EDCI, DCC, HATU, BOP, and the like. The reaction can take place in the presence of a base such as, triethylamine, DIEA, pyridine, and the like. The coupling reaction can also take place in the presence of a solvent such as DMF, DMA, DCM, THF, and the like.

General Procedure B

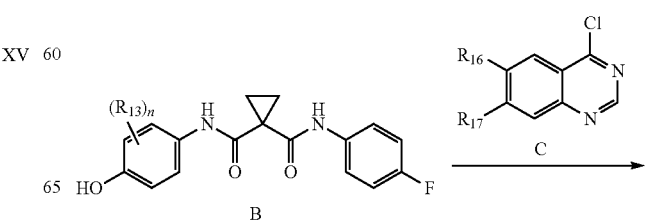

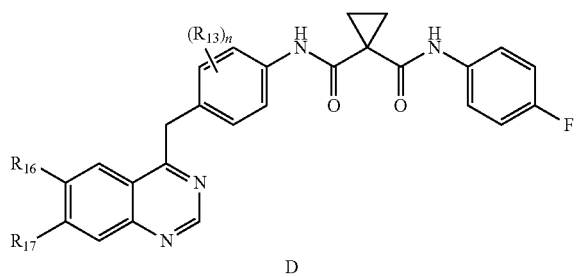

D

A compound of Formula B can be converted to a compound of Formula D by reacting with a compound of Formula C in the presence of a strong base, such as potassium t-butoxide or potassium carbonate, in a polar organic solvent, such as DMSO or DMF. A compound of Formula B can also be converted to a compound of Formula D by reaction with a compound of Formula C under transition metal coupling conditions. Exemplary conditions include a palladium coupling agent, such as Pd(OAc)$_2$ in the presence of 1) TrixiePhos and anisole, or 2) Xphos, K$_3$PO$_4$, toluene, and N-methyl-2-pyrrolidine (NMP).

General Procedure C

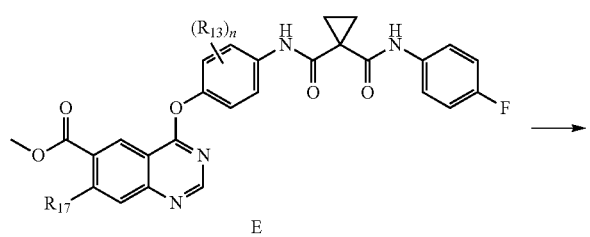

E

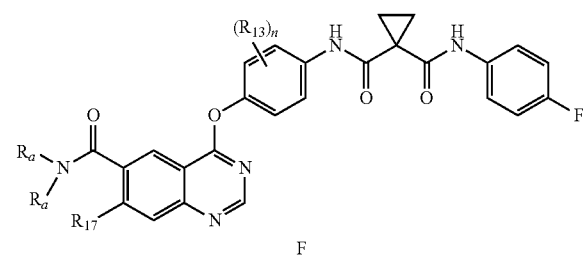

F

Esters of Formula E can be converted to the corresponding amide compounds of Formula I' by first hydrolyzing to the corresponding carboxylic acid and then coupling with an amine of the Formula NH(R$_a$)$_2$, wherein each R$_a$ can be the same or different, or wherein both R$_a$ substituents, together with the nitrogen to which they are attached, form a cyclic structure. The hydrolysis step can be performed with a hydroxide base, such as sodium or lithium hydroxide in a polar solvent such as water, methanol, THF, DMF, DMSO, or any combination thereof. The coupling step can be performed using known coupling reagents, such as EDCI, DCC, HATET, BOP, and the like, in the presence of a base such as, triethylamine, DIEA, pyridine, and the like, and in the presence of a solvent such as DMF, DMA, DCM, THF, and the like.

General Procedure D

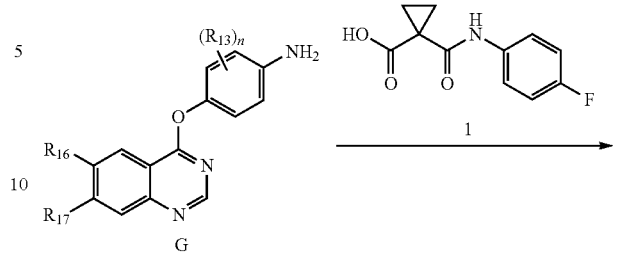

G

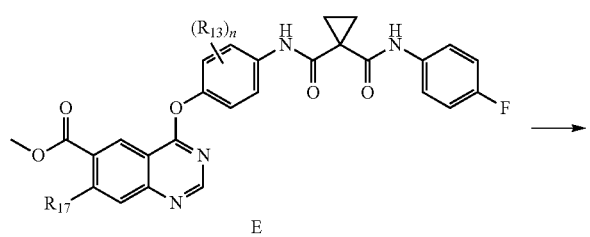

D

A compound of Formula G can be converted to a compound of Formula D by 1) direct coupling with Compound 1 or 2) activation of the carboxylic acid moiety of Compound 1, followed by nucleophilic substitution with a compound of Formula G. The coupling route can be performed using known coupling reagents, such as EDCI, DCC, HATU, BOP, and the like, in the presence of a base such as, triethylamine, DIE A, pyridine, and the like, and in the presence of a solvent such as DMF, DMA, DCM, THF, and the like. Activation of the carboxylic acid moiety of Compound 1 can be accomplished by first esterification of the carboxylic acid of Compound 1 with a phenolic compound such as pentafluorophenol or para-nitrophenol using means known to one having skill in the art, to form the corresponding phenolate. Second, nucleophilic substitution of the activated Compound 1 with a compound of Formula G will provide the compound of Formula D.

General Procedure E

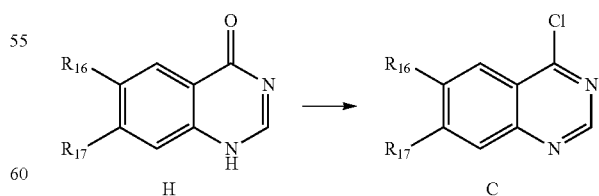

A compound of Formula H can be converted to a compound of Formula C by exposure to chloridating reagent such as oxalyl chloride, SOCl$_2$, and POCl$_3$. The transformation can be performed in the presence of a solvent or under neat conditions.

General Procedure F

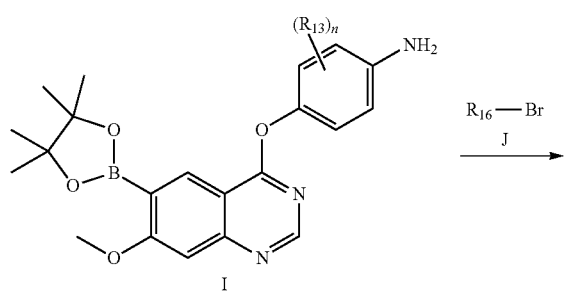

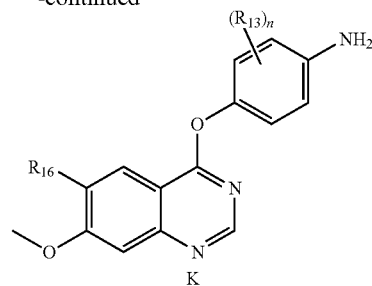

A compound of Formula L can be converted to a compound of Formula K using coupling chemistry, for example a compound of Formula I can be reacted with a compound of Formula M or N in the presence of a transition metal catalyst, such as bis(di-t-butyl(4-dimethylaminophenyl) phosphine)dichloropalladium(II) in a solvent, such as 1,4-doxane, in the presence of a base, such as sodium carbonate, optionally under microwave irradiation.

General Procedure H

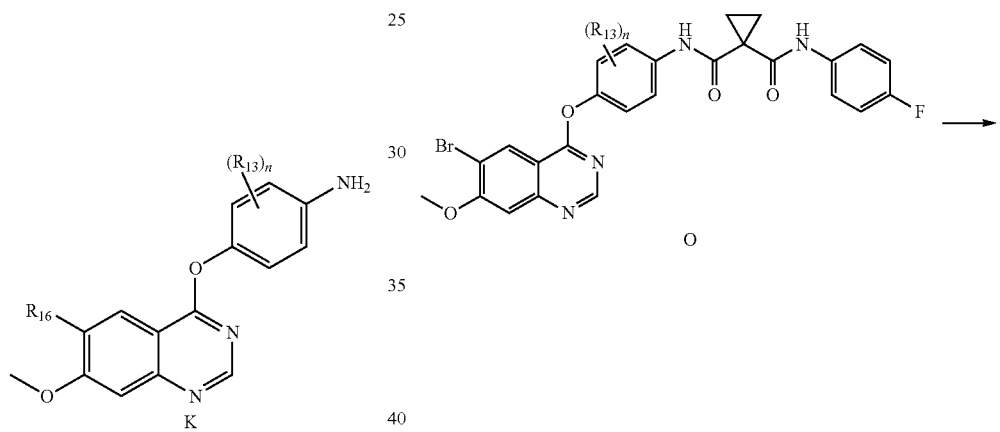

A compound of Formula I can be converted to a compound of Formula K using coupling chemistry. For example a compound of Formula I can be reacted with a compound of Formula J in the presence of a transition metal catalyst, such as bis(di-t-butyl(4-dimethylaminophenyl)phosphine) dichloropalladium(II) in a solvent, such as 1,4-doxane, in the presence of a base, such as sodium carbonate, optionally under microwave irradiation.

General Procedure G

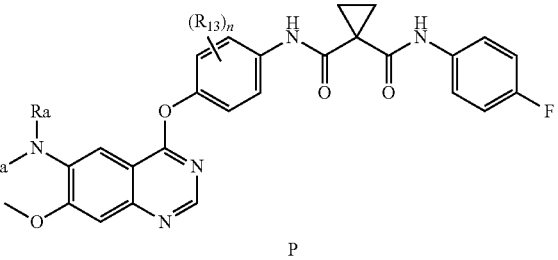

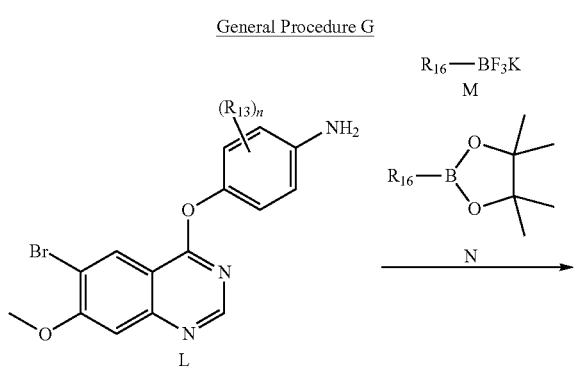

A compound of Formula O can be converted to the corresponding amine compounds of Formula P by coupling with an amine of the Formula $NH(R^a)_2$, wherein each $R^a$ can be the same or different, or wherein both $R^a$ substituents, together with the nitrogen to which they are attached, form a cyclic structure. The coupling step can be performed using a transition metal catalyst, such as bis(tri-t-butylphosphine) palladium(0), in the presence of a base, such as $K_3PO_4$, in a polar solvent, such as DMF, DMSO, or DMA.

General Procedure I

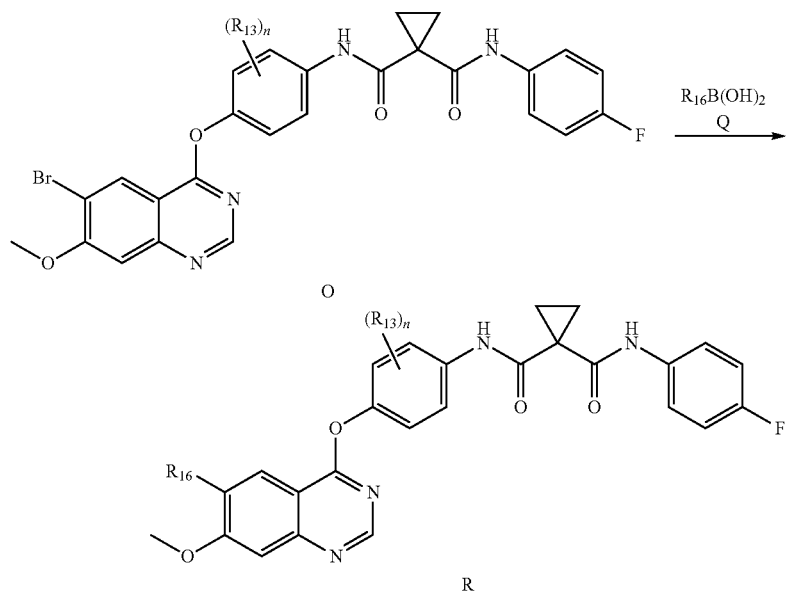

A compound of Formula O can also be converted to a compound of Formula R by coupling with a boronic acid compound of Formula Q in the presence of transition metal catalyst, such as bi s(di-t-butyl (4-dimethylaminophenyl) phosphine)dichloropalladium(II), a base, such as sodium carbonate, and a solvent, such as 1,4-dioxane, optionally under microwave irradiation.

General Procedure J

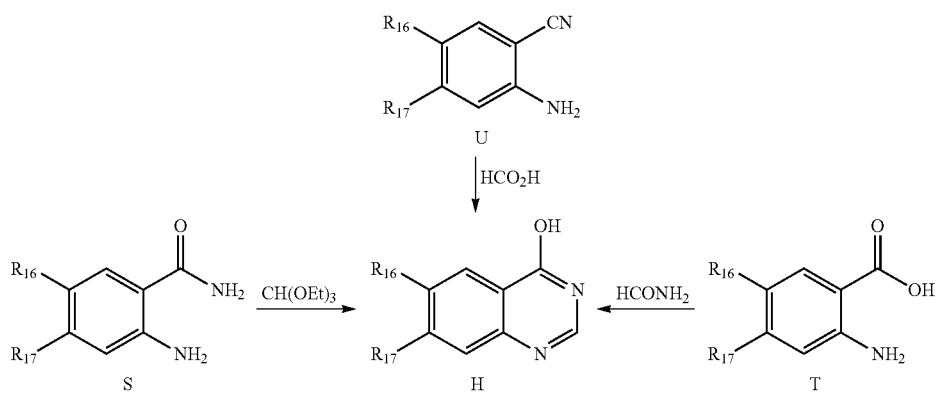

A compound of Formula H (shown here as the enol tautomer) can also be synthesized from a cyano compound of Formula U, an amide compound of Formula S, or a carboxylic acid compound of Formula T. A compound of Formula S is converted to Formula H in the presence of triethyl orthoformate under neat conditions at elevated temperatures, optionally under microwave irradiation. A compound of Formula T is converted to Formula H in the presence of formamide under neat conditions at elevated temperatures, optionally under microwave irradiation. A compound of Formula U is converted to Formula H in the presence of formic acid under neat conditions at elevated temperatures.

General Procedure K

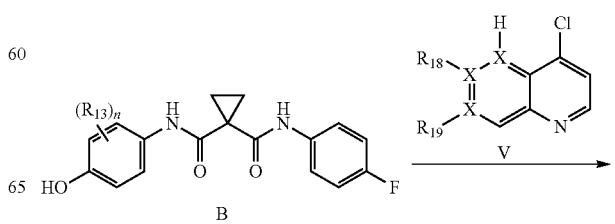

183

-continued

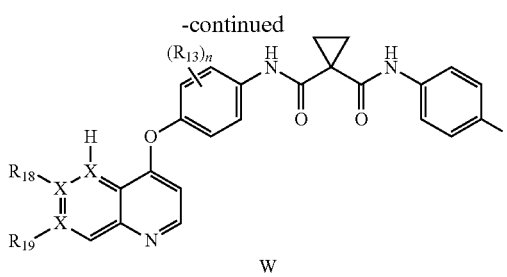

W

A compound of Formula B can be converted to a compound of Formula W by reacting with a compound of Formula V, wherein X is carbon or nitrogen and wherein Rix and/or $R_{19}$ is absent when the X variable they are attached to is a nitrogen, in the presence of a strong base, such as potassium t-butoxide or potassium carbonate, in a polar organic solvent, such as DMSO or DMF. A compound of Formula B can also be converted to a compound of Formula W by reaction with a compound of Formula V under transition metal coupling conditions. Exemplary conditions include a palladium coupling agent, such as Pd(OAc)$_2$ in the presence of 1) TrixiePhos and anisole, or 2) Xphos, K$_3$PO$_4$, toluene, and N-methyl-2-pyrrolidine (NMP).

General Procedure L

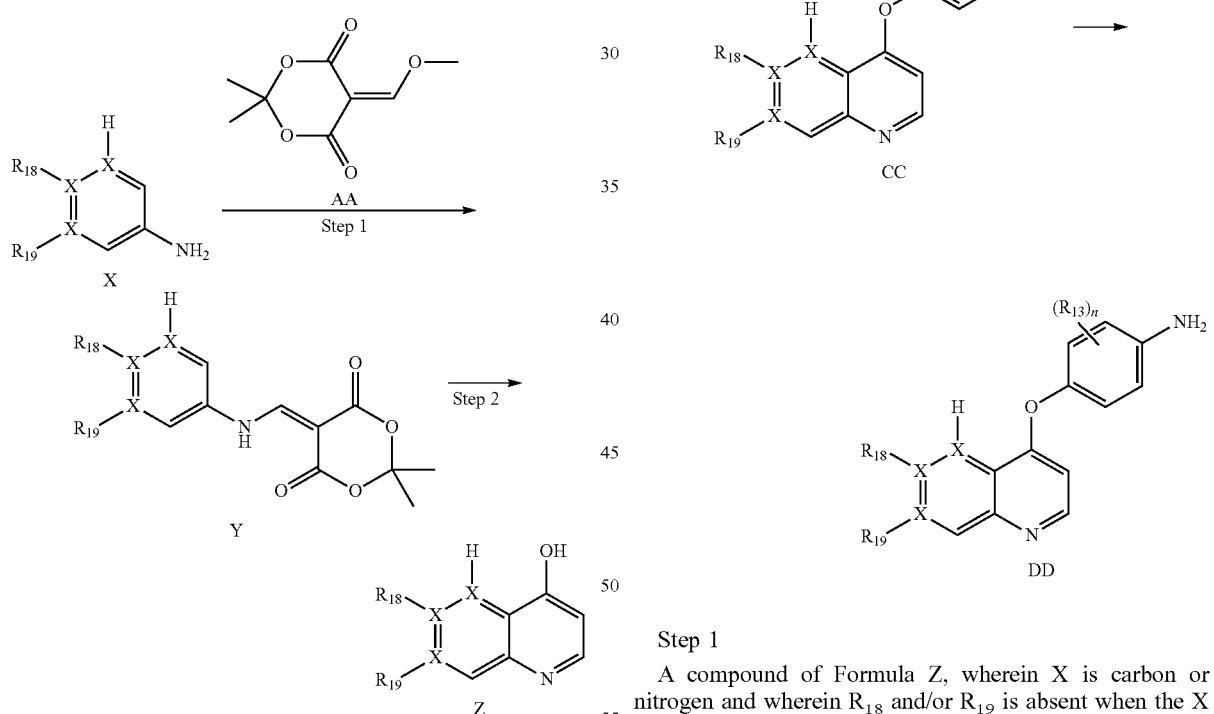

Step 1

A compound of Formula Y can be obtained by reacting a compound of Formula X, wherein the variable X is carbon or nitrogen and wherein $R_{18}$ and/or $R_{19}$ is absent when the X variable they are attached to is a nitrogen, with an acetal compound of Formula AA at elevated temperatures in a solvent such as trimethoxymethane or isopropanol. A compound of Formula AA can also be obtained in situ by first reacting 2,2-Dimethyl-1,3-dioxane-4,6-dione in trimethoxymethane prior to adding a compound of Formula X.

184

Step 2

A compound of Formula Z can be obtained via the intra-cyclization of a compound of Formula Y at elevated temperatures in a high-temperature solvent, such as diphenyl ether or dowtherm.

General Procedure M

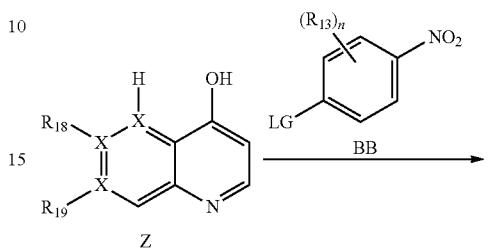

Step 1

A compound of Formula Z, wherein X is carbon or nitrogen and wherein $R_{18}$ and/or $R_{19}$ is absent when the X variable they are attached to is a nitrogen, can be converted to a compound of Formula CC by reacting with a compound of Formula BB, wherein "LG" is a leaving group, in the presence of 1) cesium carbonate, or 2) silver oxide, in a solvent such as acetonitrile, DMF, DMSO, or DMA.

Step 2

The nitro moiety of a compound of Formula CC can be reduced to provide a compound of Formula DD using methods known to those skilled in the art, such as hydrogen gas in the presence of Pd/C or nickel metal, or by reduction with iron metal in the presence of NH$_4$Cl in a solvent such as water, methanol, ethanol, or a combination thereof.

General Procedure N

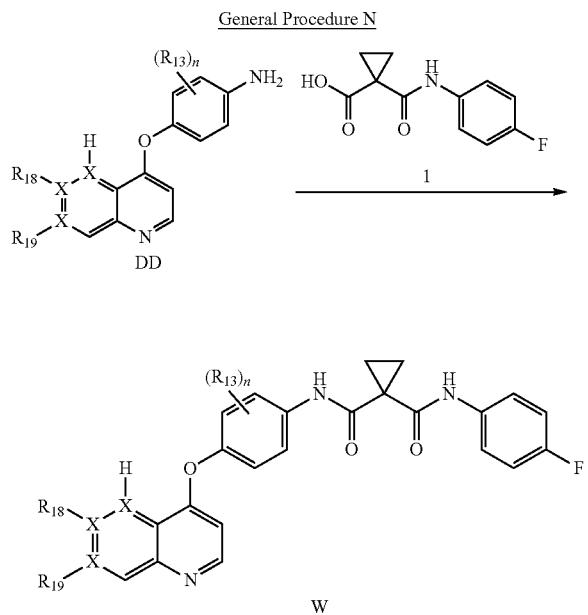

A compound of Formula DD, wherein X is carbon or nitrogen and wherein $R_{18}$ and/or $R_{19}$ is absent when the X variable they are attached to is a nitrogen, can be converted to a compound of Formula W by 1) direct coupling with Compound 1 or 2) activation of the carboxylic acid moiety of Compound 1, followed by nucleophilic substitution with a compound of Formula DD. The coupling route can be performed using known coupling reagents, such as EDCI, DCC, HATU, BOP, and the like, in the presence of a base such as, triethylamine, DIEA, pyridine, and the like, and in the presence of a solvent such as DMF, DMA, DCM, THF, and the like. Activation of the carboxylic acid moiety of Compound 1 can be accomplished by first esterification of the carboxylic acid of Compound 1 with a phenolic compound such as pentafluorophenol or para-nitrophenol using means known to one having skill in the art, to form the corresponding phenolate. Second, nucleophilic substitution of the activated Compound 1 with a compound of Formula DD will provide the compound of Formula W.

General Procedure O

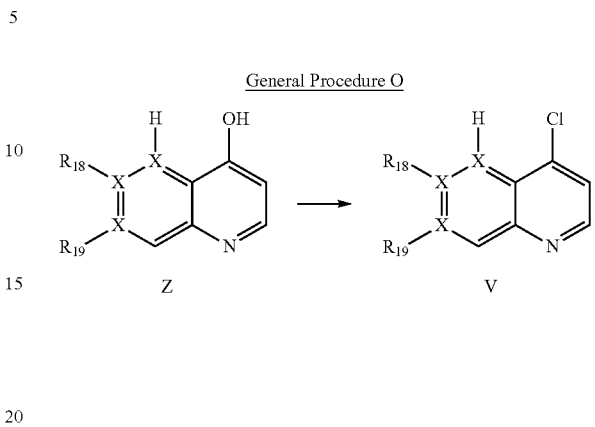

A compound of Formula Z, wherein X is carbon or nitrogen and wherein $R_{18}$ and/or $R_{19}$ is absent when the X variable they are attached to is a nitrogen, can be converted to a compound of Formula V by exposure to chloridating reagent such as oxalyl chloride, $SOCl_2$, and $POCl_3$. The transformation can be performed in the presence of a solvent or under neat conditions.

General Procedure P

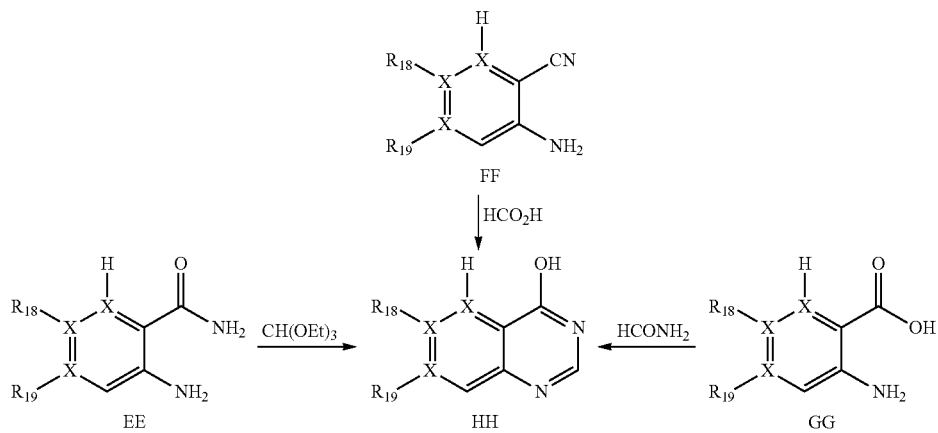

A compound of Formula HH, wherein X is carbon or nitrogen and wherein $R_{18}$ and/or $R_{19}$ is absent when the X variable they are attached to is a nitrogen, can be synthesized from a cyano compound of Formula FF, an amide compound of Formula EE, or a carboxylic acid compound of Formula GG. A compound of Formula EE is converted to Formula HH in the presence of triethyl orthoformate under neat conditions at elevated temperatures, optionally under microwave irradiation. A compound of Formula GG is converted to Formula HH in the presence of formamide under neat conditions at elevated temperatures, optionally under microwave irradiation. A compound of Formula FF is converted to Formula HH in the presence of formic acid under neat conditions at elevated temperatures.

187

General Procedure Q

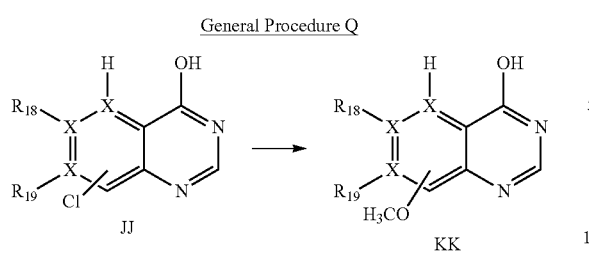

A compound of Formula JJ, wherein X is carbon or nitrogen and wherein $R_{18}$ and/or $R_{19}$ is absent when the X variable they are attached to is a nitrogen, can be converted to a compound of Formula KK by reacting with $NaOCH_3$ in a solvent, preferably anhydrous methanol, at elevated temperature, optionally under microwave irradiation.

The following specific examples are provided so that the invention can be further understood, and are not meant to limit the scope of the invention in any way.

SPECIFIC EXPERIMENTAL PROCEDURES

Example 1: N-(4-Fluorophenyl)-N-(4-hydroxyphenyl)cyclopropane-1,1-dicarboxamide (3)

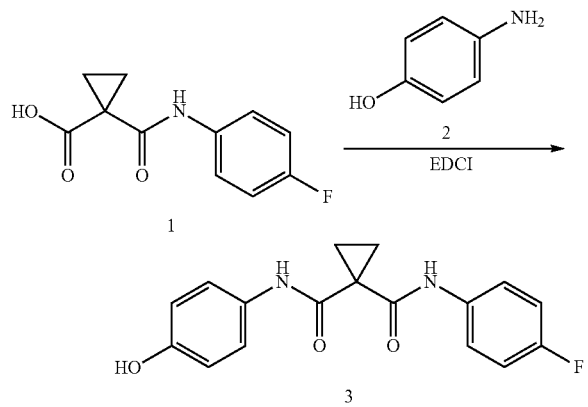

N-(4-Fluorophenyl)-N-(4-hydroxyphenyl)cyclopropane-1,1-dicarboxamide (3)

To a solution of Compound 1 (10 g, 44.80 mmol, 1 eq.) and Compound 2 (5.87 g, 53.8 mmol, 1.2 eq.) in dimethyl acetamide (DMA) (60 mL) was added 3-(ethyliminomethyleneamino)-N,N-dimethyl-propan-1-amine hydrochloride (EDCI) (10.31 g, 53.8 mmol, 1.2 eq.). The mixture was stirred vigorously at 20° C. until the reaction was complete. The mixture was poured into aqueous (aq) saturated $NaHCO_3$ (400 mL) and extracted with EtOAc (4×100 mL). The combined organic phases were washed with aqueous saturated NaCl (100 mL), dried over anhydrous (anhyd) $Na_2SO_4$, and concentrated. Compound 3 (21 g, crude) (50% purity) was obtained. $^1H$ NMR (400 MHz, DMSO-$d_6$) δ 10.16 (br s, 1H), 9.72 (br s, 1H), 7.61 (dd, 2H), 7.34 (d, 2H), 7.13 (t, 2H) 6.68 (d, 2H), 1.42 (s, 4H); MS (EI) for $C_{17}H_{15}FN_2O_3$, found 314.9 (MH+).

188

Example 2: 1-N'-(4-Fluorophenyl)-1-N-(4-pyrido[3,2-d]pyrimidin-4-yloxyphenyl)cyclopropane-1,1-dicarboxamide (7)

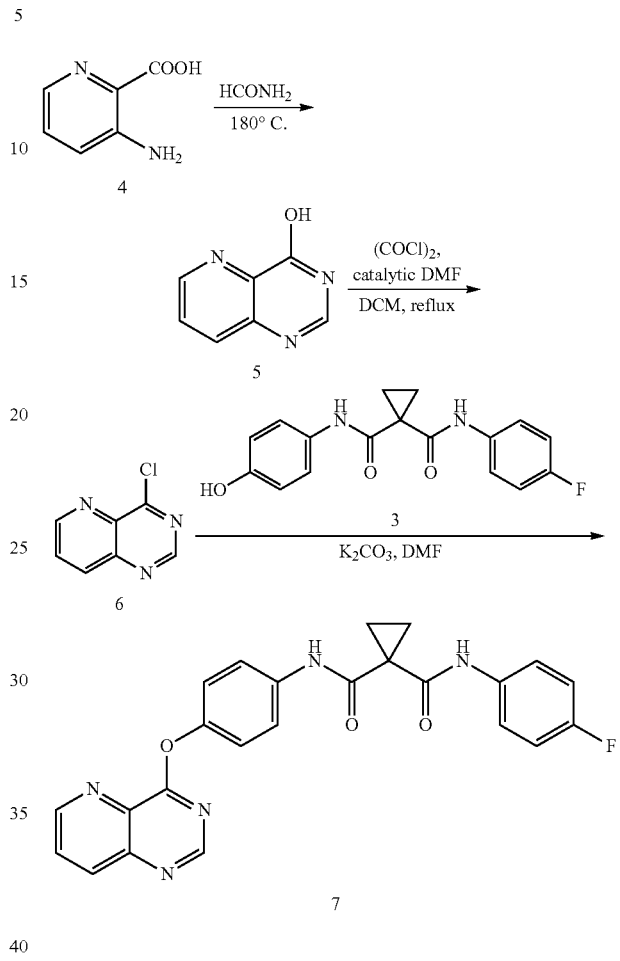

Pyrido[3,2-d]pyrimidin-4-ol (5)

A mixture of Compound 4 (1.0 g, 7.2 mmol) in formamide (2.5 mL) was stirred at 140° C. for 1 hour, then at 170° C. for 1 hour and, finally at 180° C. for 1 hour. The reaction mixture was cooled to room temperature and water was added. The resulting suspension was filtered, and the solid was washed with water and suspended in MeOH. The suspension was filtered, and the solid was washed with DCM followed by hexanes and dried under vacuum to give Compound 5 as brown solid (280 mg, 26% yield). MS for $C_7H_5N_3O$, found 148 (MH+).

4-Chloropyrido[3,2-d]pyrimidine (6)

To a mixture of Compound 5 (160 mg, 1.1 mmol) and DMF (1 drop) in dry DCM (2.0 mL) was added drop wise oxalyl chloride (0.24 mL, 2.5 eq) and the resulting mixture refluxed overnight. The reaction mixture was evaporated, and the residue was treated with cold aq saturated $NaHCO_3$ (<10° C.) and then extracted with EtOAc (3×). The combined extracts were dried over anhydrous $Na_2SO_4$ and evaporated to give Compound 6 as brown solid (83 mg, ~90% purity, ~40% yield). This material was used without further purification in subsequent steps. MS for $C_7H_4ClN_3$, found 166 (MH+).

1-N'-(4-Fluorophenyl)-1-N-(4-pyrido[3,2-d]pyrimidin-4-yloxyphenyl)cyclopropane-1,1-dicarboxamide (7)

A mixture of Compound 6 (39 mg, 0.24 mmol), Compound 3 (63 mg, 0.2 mmol) and K$_2$CO$_3$ (76 mg, 0.55 mmol) in DMF (1.0 mL) was stirred at 80° C. for 20 min. The reaction mixture was cooled to room temperature, and water was added. The resulting suspension was filtered and solid washed with water and dried under vacuum to give crude Compound 7 as a brown solid (89 mg, ~90% purity). Crude Compound 7 (80 mg) was subjected to chromatography on silica gel, eluted with 0-100% EtOAc in hexanes, to give pure Compound 7 as a white solid (70 mg, 79% yield). MS for C$_{24}$H$_{18}$FN$_5$O$_3$, found 444 (MH+).

Example 3: 1-N-[4-(7-Chloropyrido[3,2-d]pyrimidin-4-yl)oxyphenyl]-1-N'-(4-fluorophenyl)cyclopropane-1,1-dicarboxamide (12)

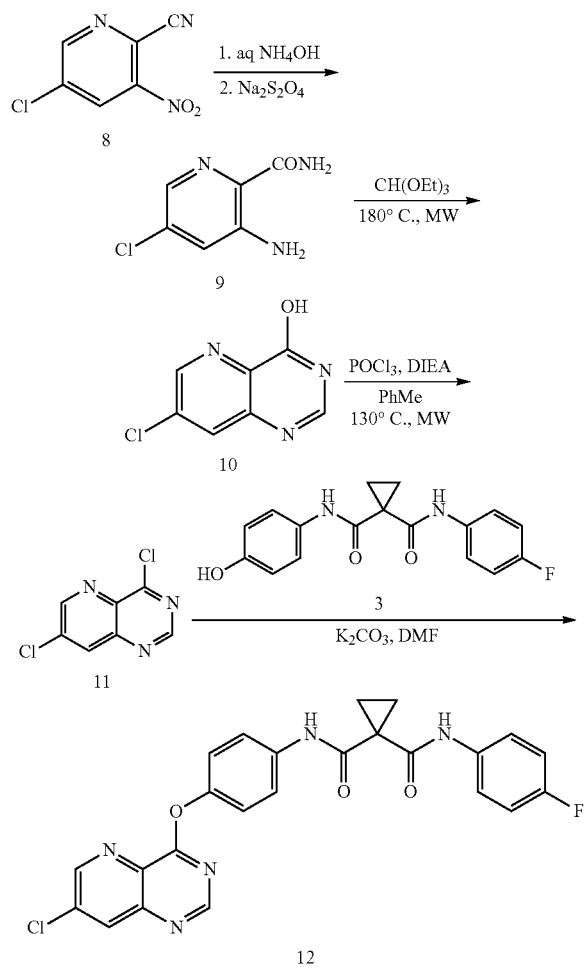

3-Amino-5-chloropicolinamide (9)

To Compound 8 (1.83 g, 10.0 mmol) in water (20 mL) was added 28% aq NH$_4$OH (4.0 mL, 28.5 mmol), and the reaction was stirred at room temperature for 20 min. Sodium hydrosulfite (10.0 g, 85%, 57.3 mmol) was added, and the reaction mixture was stirred at room temperature for 90 min. The yellow precipitate was collected by vacuum filtration to give Compound 9 as yellow solid (0.77 g, 45% yield). MS for C$_6$H$_6$ClN$_3$O, found 172 (MH+).

7-Chloropyrido[3,2-d]pyrimidin-4-ol (10)

A suspension of Compound 9 (220 mg, 1.27 mmol) in triethyl orthoformate (2.5 mL) was irradiated by microwave at 180° C. for 30 min. After cooling to room temperature, the brown precipitate was collected by vacuum filtration and washed with hexanes to give Compound 10 (220 mg, 95% yield). MS for C$_7$H$_4$ClN$_3$O, found 182 (MH+).

4,7-Dichloropyrido[3,2-d]pyrimidine (11)

To a mixture of Compound 10 (90 mg, 0.5 mmol) in toluene (4 mL) was added DIEA (0.25 mL, 1.44 mmol) and phosphorus oxychloride (0.15 mL, 1.64 mmol), and the reaction was stirred at 130° C. under microwave irradiation for 1 hour. After cooling to room temperature, the reaction mixture was concentrated, and the resulting residue was subjected to chromatography on silica gel, eluted with 0-80% EtOAc in hexanes, to give Compound 11 as white crystals (71 mg, 71% yield). MS for C$_7$H$_3$Cl$_2$N$_3$, found 200 (MH+).

1-N-[4-(7-Chloropyrido[3,2-d]pyrimidin-4-yl)oxyphenyl]-1-N'-(4-fluorophenyl)cyclopropane-1,1-dicarboxamide (12)

Compound 12 was made from Compound 11 in a manner analogous to the preparation of Compound 7 from Compound 6 in Step 3 of Example 2. MS for C$_{24}$H$_{17}$ClFN$_5$O$_3$, found 478 (MH+).

1-N-[4-(7-Bromopyrido[3,2-d]pyrimidin-4-yl)oxyphenyl]-1-N'-(4-fluorophenyl)cyclopropane-1,1-dicarboxamide (13)

Compound 13 was prepared in a method analogous to Compound 12 in Example 3, starting the reaction sequence with 5-bromo-3-nitropicolinonitrile in place of Compound 8. MS for C$_{24}$H$_{17}$BrFN$_5$O$_3$, found 522 (MH+).

Example 4: 1-N'-(4-Fluorophenyl)-1-N-[4-(7-methoxypyrido[3,2-d]pyrimidin-4-yl)oxyphenyl]cyclopropane-1,1-dicarboxamide (16)

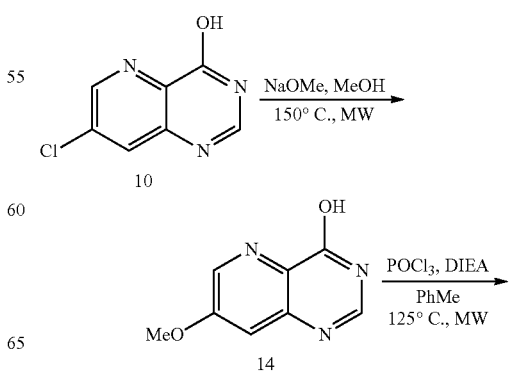

-continued

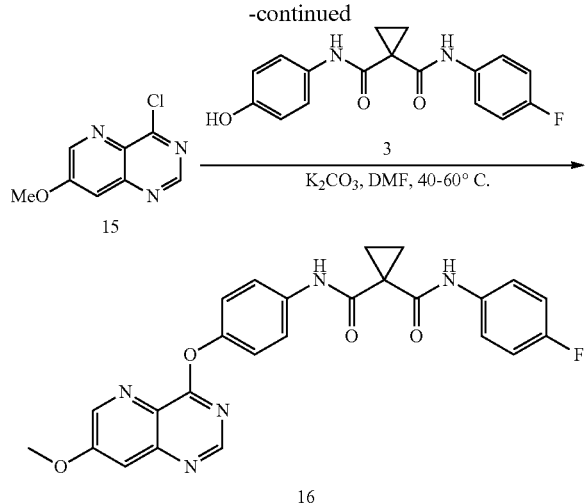

7-Methoxypyrido[3,2-d]pyrimidin-4-ol (14)

A microwave vial was charged with Compound 10 (220 mg, 1.22 mmol) and a 1.0 M solution of sodium methoxide in methanol (6.5 mL, 6.5 mmol). The vial was capped and irradiated in a microwave reactor at 150° C. for 90 min. The reaction was neutralized with aq saturated NH₄Cl (5 mL), concentrated, and diluted with cold water. The resulting precipitate was collected by vacuum filtration and dried in vacuo to provide Compound 14 as an off-white solid (183 mg, 85% yield). MS for $C_8H_7N_3O_2$, found 178 (MH+).

4-Chloro-7-methoxypyrido[3,2-d]pyrimidine (15)

Compound 15 was made from Compound 14 in a manner analogous to the preparation of Compound 11 from Compound 10 in Step 3 of Example 3. MS for $C_8H_6ClN_3O$, found 196 (MH+).

—N'-(4-Fluorophenyl)-1-N-[4-(7-methoxypyrido[3,2-d]pyrimidin-4-yl)oxyphenyl]cyclopropane-1,1-dicarboxamide (16)

Compound 16 was made from Compound 15 in a manner analogous to the preparation of Compound 7 from Compound 6 in Step 3 of Example 2. MS for $C_{25}H_{20}FN_5O_4$, found 474 (MH+).

Example 5: N-(2,5-Difluoro-4-hydroxyphenyl)-N-(4-fluorophenyl)cyclopropane-1,1-dicarboxamide (18)

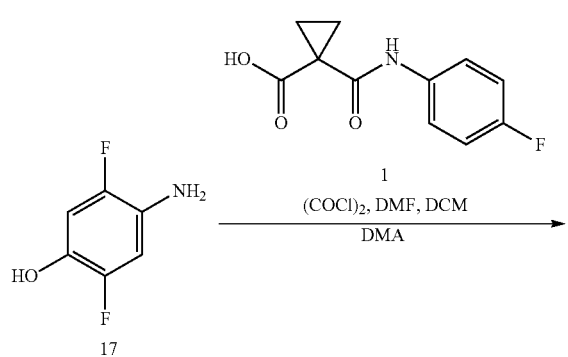

-continued

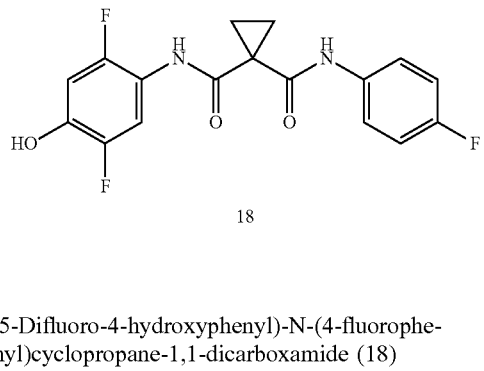

N-(2,5-Difluoro-4-hydroxyphenyl)-N-(4-fluorophenyl)cyclopropane-1,1-dicarboxamide (18)

To a solution of Compound 1 (242.87 mg, 1.03 mmol, 1.5 eq) in DCM (10 mL) was added (COCl)₂ (157.45 mg, 1.24 mmol, 1.8 eq) and then DMF (68.91 umol, 5.30 uL, 0.1 eq). The mixture was stirred for 1 hour at 15° C. To the mixture was added a solution of Compound 17 (100 mg, 689.15 umol, 1.0 eq) in DMA (6 mL), and the resulting mixture was stirred for 1 hour at 15° C. The reaction was quenched with aq NaHCO₃ (50 mL), extracted with EtOAc (3×30 mL). The combined extracts were washed with aq saturated NaCl (2×100 mL), dried over anhydrous Na₂SO₄, and concentrated. The residue was purified by flash column chromatography on silica gel (0-10% MeOH in DCM) to give Compound 18 as a brown solid (180 mg, 67.1% yield). ¹H NMR (400 MHz, DMSO-d₆) δ 10.32 (s, 1H), 10.22 (s, 1H), 9.97 (s, 1H), 7.66-7.54 (m, 3H), 7.16 (t, 2H), 6.83 (dd, 1H), 1.61-1.48 (m, 4H); MS for $C_{17}H_{13}F_3N_2O_3$, found 350.9 (MH+).

Example 6: 1-N'-[2,5-Difluoro-4-(7-methoxypyrido[3,2-d]pyrimidin-4-yl)oxyphenyl]-1-N-(4-fluorophenyl)cyclopropane-1,1-dicarboxamide (19)

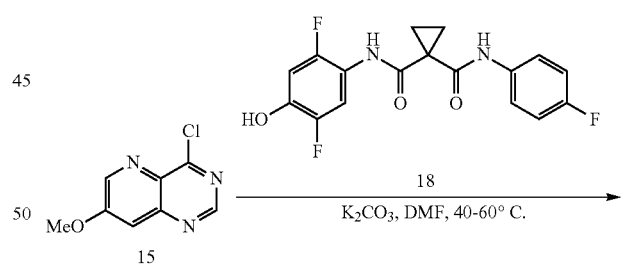

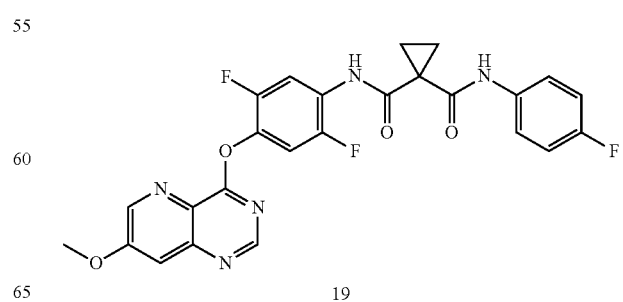

1-N'-[2,5-Difluoro-4-(7-methoxypyrido[3,2-d]pyrimidin-4-yl)oxyphenyl]-1-N-(4-fluorophenyl)cyclopropane-1,1-dicarboxamide (19)

Compound 19 was made from Compound 15 in a manner analogous to the preparation of Compound 7 from Compound 6 in Step 3 of Example 2. MS for $C_{25}H_{18}F_3N_5O_4$, found 510 (MH+).

Example 7: 4-Chloro-6,7-dimethoxypyrido[3,2-d]pyrimidine (27)

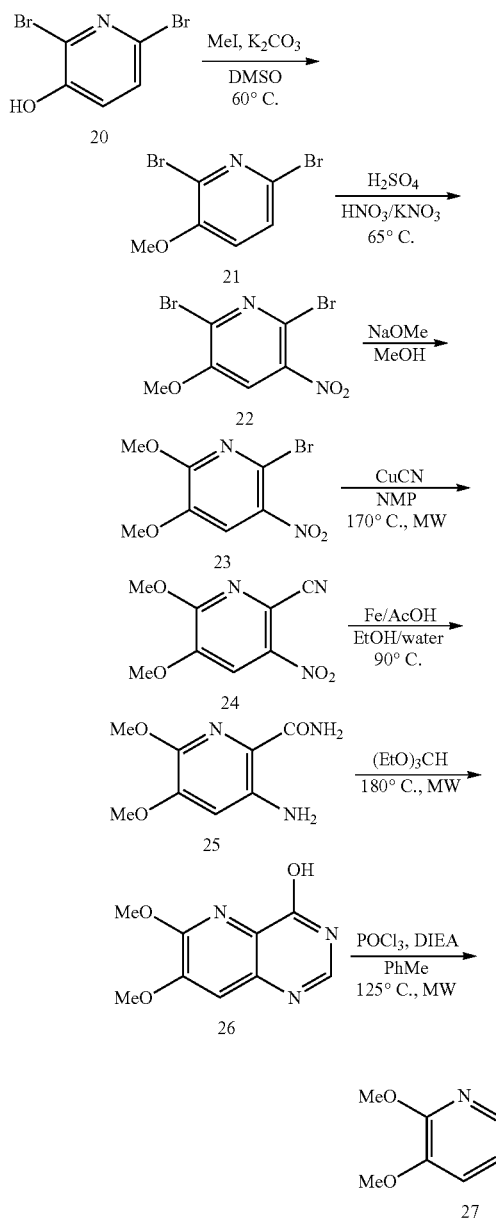

2,6-Dibromo-3-methoxypyridine (21)

To a solution of Compound 20 (2.62 g, 10.4 mmol) in DMSO (4.5 mL) were added $K_2CO_3$ (1.35 g, 9.8 mmol) and methyl iodide (2.2 mL, 35.3 mmol), and the reaction mixture was stirred at 60° C. for 1 hour. The mixture was cooled to room temperature and poured into water (50 mL), and filtered. The resulting solids were washed with ice cold water and dried under vacuum to give Compound 21 (2.5 g, 90% yield). MS for $C_6H_5Br_2NO$, found 268 (MH+).

2,6-Dibromo-3-methoxy-5-nitropyridine (22)

To conc $H_2SO_4$ (15 ml) at 0° C. were added nitric acid (67%, 4.0 mL) and $KNO_3$ (2.0 g) followed by Compound 21 (2.0 g, 7.5 mmol). The reaction mixture was stirred at 65° C. overnight, after which it was poured into crushed ice and neutralized carefully with solid $Na_2CO_3$, then extracted with EtOAc (2 times). The combined organic extracts were concentrated, and the resulting residue was purified by flash silica gel chromatography (0-80% of EtOAc in hexanes) to give Compound 22 (732 mg, 31% yield).

2-Bromo-5,6-dimethoxy-3-nitropyridine (23)

To a solution of Compound 22 (200 mg, 0.64 mmol) in anhydrous MeOH (6 mL) was added NaOMe (46 mg, 0.85 mmol). The reaction mixture was stirred at room temperature for 1 hour and then concentrated under vacuum. The resulting residue was washed with water and filtered. The collected solids were washed with ice cold water and dried under vacuum to give Compound 23 (150 mg, 89% yield).

5,6-Dimethoxy-3-nitropicolinonitrile (24)

A mixture of Compound 23 (150 mg, 0.57 mmol) and CuCN (170 mg, 1.90 mmol) in NMP (5 mL) was heated at 170° C. under microwave irradiation for 10 min and then cooled to room temperature. The reaction mixture was poured into ice water, and the resulting suspension was filtered, washed with water, and resuspended in hot EtOAc for 30 min. The resulting mixture was filtered through Celite®, and the filtrate was concentrated under vacuum to give Compound 24 which was used without further purification.

3-Amino-5,6-dimethoxypicolinamide (25)

Compound 24 was mixed with Fe (130 mg, 2.0 mmol), AcOH (0.4 mL, 6.7 mmol), water (6 mL), and EtOH (14 mL). The mixture was stirred at 90° C. for 20 min and then cooled to room temperature. The pH was adjusted with aq 28% $NH_4OH$ until basic. The resulting mixture was filtered through Celite®. Volatile organics were removed from the filtrate under vacuum, and the resulting mixture was extracted with EtOAc (2 times). The combined EtOAc extracts were concentrated, and the resulting residue was purified by flash silica gel chromatography (0-100% EtOAc in hexanes) to give Compound 25 as an off-white solid (49 mg, 44% yield over 2 steps). MS for $C_8H_{11}N_3O_3$, found 198 (MH+).

6,7-Dimethoxypyrido[3,2-d]pyrimidin-4-ol (26)

Compound 26 was made from Compound 25 in a manner analogous to the preparation of Compound 10 from Compound 9 in Step 2 of Example 3. MS for $C_9H_9N_3O_3$, found 208 (MH+).

6,7-Dimethoxypyrido [3,2-d]pyrimidin-4-ol (27)

Compound 27 was made from Compound 26 in a manner analogous to the preparation of Compound 11 from Compound 10 in Step 3 of Example 3. MS for $C_9H_8ClN_3O_2$, found 226 (MH+).

Example 8: 1-N-[4-(6,7-dimethoxypyrido[3,2-d]pyrimidin-4-yl)oxyphenyl]-1-N'-(4-fluorophenyl)cyclopropane-1,1-dicarboxamide (28)

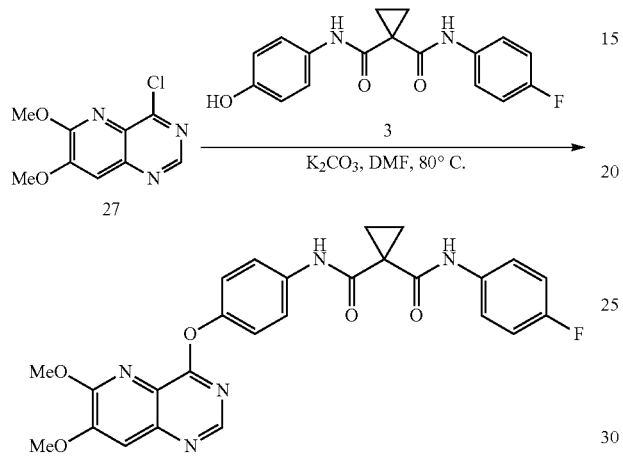

1-N-[4-(6,7-dimethoxypyrido[3,2-d]pyrimidin-4-yl)oxy phenyl]-1-N'-(4-fluorophenyl)cyclopropane-1,1-dicarboxamide (28)

Compound 28 was made from Compound 27 in a manner analogous to the preparation of Compound 7 from Compound 6 in Step 3 of Example 2. MS for $C_{26}H_{22}FN_5O_5$, found 504 (MH+).

The following compounds were prepared from Compound 27 in a method analogous to Compound 28 in Example 8 using the appropriately substituted N-(4-fluorophenyl)-N-(4-hydroxyphenyl)cyclopropane-1,1-dicarboxamides which were synthesized using methods analogous to those used in Example 1 or Example 5.

1-N'-[3-Chloro-4-(6,7-dimethoxypyrido[3,2-d]pyrimidin-4-yl)oxyphenyl]-1-N-(4-fluorophenyl)cyclopropane-1,1-dicarboxamide (29)

MS (EI) for $C_{26}H_{21}ClFN_5O_5$, found 538 (MH+).

1-N'-[4-(6,7-Dimethoxypyrido[3,2-d]pyrimidin-4-yl)oxy-3-fluorophenyl]-1-N-(4-fluorophenyl)cyclopropane-1,1-dicarboxamide (30)

MS (EI) for $C_{26}H_{21}ClFN_5O_5$, found 522 (MH+).

1-N'-[4-(6,7-Dimethoxypyrido[3,2-d]pyrimidin-4-yl)oxy-2-fluorophenyl]-1-N-(4-fluorophenyl)cyclopropane-1,1-dicarboxamide (31)

MS (EI) for $C_{26}H_{21}ClFN_5O_5$, found 522 (MH+).

1-N'-[2-Chloro-4-(6,7-dimethoxypyrido[3,2-d]pyrimidin-4-yl)oxyphenyl]-1-N-(4-fluorophenyl)cyclopropane-1,1-dicarboxamide (32)

MS (EI) for $C_{26}H_{21}ClFN_5O_5$, found 538 (MH+).

1-N'-[4-(6,7-Dimethoxypyrido[3,2-d]pyrimidin-4-yl)oxy-2-methylphenyl]-1-N-(4-fluorophenyl)cyclopropane-1,1-dicarboxamide (33)

MS (EI) for $C_{27}H_{24}FN_5O_5$, found 518 (MH+).

1-N'-[4-(6,7-Dimethoxypyrido[3,2-d]pyrimidin-4-yl)oxy-2,3-difluorophenyl]-1-N-(4-fluorophenyl)cyclopropane-1,1-dicarboxamide (34)

MS (EI) for $C_{26}H_{20}F_3N_5O_5$, found 540 (MH+).

1-N'-[4-(6,7-Dimethoxypyrido[3,2-d]pyrimidin-4-yl)oxy-2,5-difluorophenyl]-1-N-(4-fluorophenyl)cyclopropane-1,1-dicarboxamide (35)

MS (EI) for $C_{26}H_{20}F_3N_5O_5$, found 540 (MH+).

Example 9: 1-N-[4-(6,7-Dimethylpyrido[3,2-d]pyrimidin-4-yl)oxyphenyl]-1-N'-(4-fluorophenyl)cyclopropane-1,1-dicarboxamide (43)

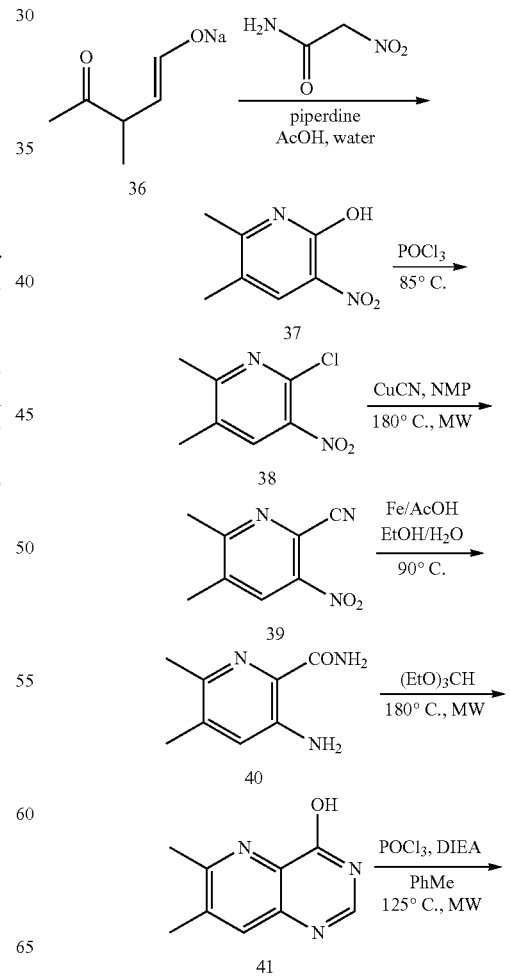

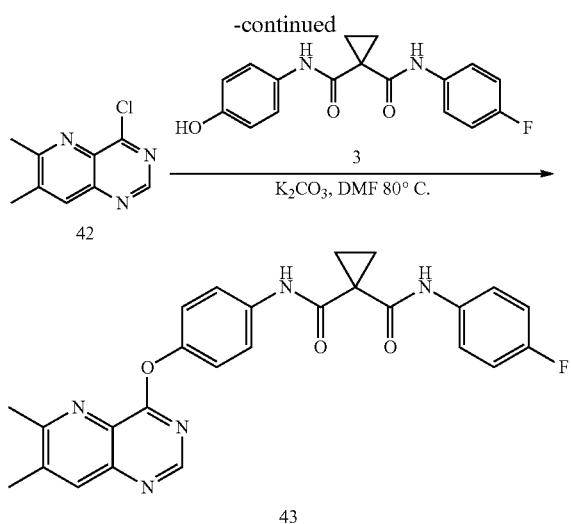

5,6-Dimethyl-3-nitropyridin-2-ol (37)

Compound 37 was obtained from a modification of known procedures for producing 3-cyanopyridinones from the reaction of compounds like 36 with 2-cyanoacetamide (J. Med Chem. 2005, 48(6), 1948-1964). The 2-cyanoacetamide was replaced with 2-nitroacetamide (1.7 g, 16.3 mmol) and reacted with Compound 36 (2.0 g, 14.7 mmol) to produce Compound 37 (780 mg, 32% yield). MS for $C_7H_8N_2O_3$, found 169 (MH+).

2-Chloro-5,6-dimethyl-3-nitropyridine (38)

A mixture of Compound 37 (330 mg, 1.96 mmol) and $POCl_3$ (1.5 mL) was stirred at 85° C. for 4 hours. The mixture was concentrated under vacuum, treated with ice water, neutralized with aq saturated $NaHCO_3$, and extracted with EtOAc (3 times). The combined EtOAc extracts were concentrated, and the residue was subjected to plug filtration through silica gel, eluting with DCM to give Compound 38 (310 mg, 85% yield). MS for $C_7H_7ClN_2O_2$, found 187 (MH+).

5,6-dimethyl-3-nitropicolinonitrile (39)

A mixture of Compound 38 (230 mg, 1.23 mmol) and CuCN (440 mg, 4.91 mmol) in NMP (8 mL) was heated at 180° C. under microwave irradiation for 60 min. EtOAc (40 mL) was added, and the resulting mixture was filtered. The filtrate was washed with water and concentrated under vacuum to give Compound 39, contaminated with NMP, which was used without further purification. MS for $C_8H_7N_3O_2$, found 178 (MH+).

3-Amino-5,6-dimethylpicolinamide (40)

Crude Compound 39 was mixed with Fe (240 mg, 4.28 mmol), AcOH (1.0 mL, 16.7 mmol), water (5 mL), and EtOH (16 mL). The resulting mixture was stirred at 90° C. for 30 min and then cooled to room temperature. The pH was adjusted to basic with 28% aq $NH_4OH$, and the mixture was concentrated under vacuum to remove volatile organics. The resulting mixture was filtered through Celite®, and the filtrate was extracted with EtOAc (3 times). The combined EtOAc extracts were dried over anhydrous $Na_2SO_4$ and concentrated to give Compound 40, still contaminated with NMP from the previous reaction. MS for $C_8H_{11}N_3O$, found 166 (MH+).

6,7-Dimethylpyrido[3,2-d]pyrimidin-4-ol (41)

Compound 41 was made from Compound 40 in a manner analogous to the preparation of Compound 10 from Compound 9 in Step 2 of Example 3. MS for $C_9H_9N_3O$, found 176 (MH+).

4 4-Chloro-6,7-dimethylpyrido[3,2-d]pyrimidine (42)

Compound 42 was made from Compound 41 in a manner analogous to the preparation of Compound 11 from Compound 10 in Step 3 of Example 3. MS for $C_9H_8ClN_3$, found 194 (MH+).

1-N-[4-(6,7-Dimethylpyrido[3,2-d]pyrimidin-4-yl)oxyphenyl]-1-N'-(4-fluorophenyl)cyclopropane-1,1-dicarboxamide (43)

Compound 43 was made from Compound 42 in a manner analogous to the preparation of Compound 7 from Compound 6 in Step 3 of Example 2. MS for $C_{26}H_{22}FN_5O_3$, found 472 (MH+).

Example 10: 1-N'-(4-Fluorophenyl)-1-N-[4-(6,7,8,9-tetrahydropyrimido[5,4-b]quinolin-4-yloxy)phenyl]cyclopropane-1,1-dicarboxamide (52)

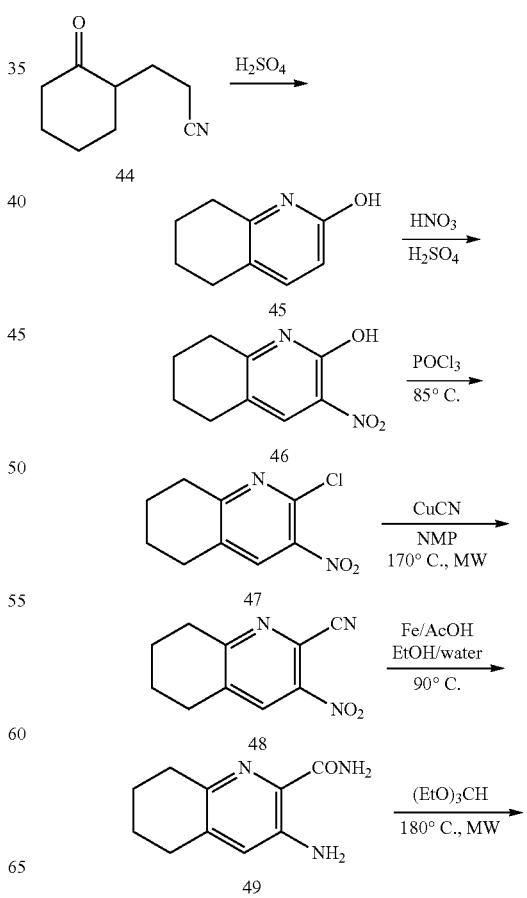

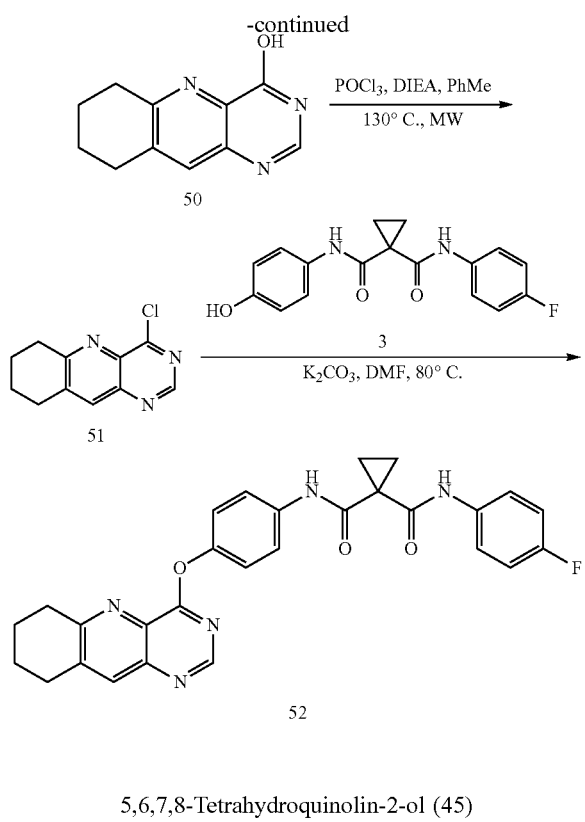

5,6,7,8-Tetrahydroquinolin-2-ol (45)

Compound 44 (2.0 g, 13 mmol) was added dropwise to ice cold $H_2SO_4$ (12 mL), and the resulting mixture was stirred for 3 hours while warming to room temperature. The reaction was then poured over ice, neutralized with concentrated $NH_4OH$, and extracted with DCM (2 times). The combined organic layers were dried over anhydrous $Na_2SO_4$, filtered through Celite®, and concentrated to give Compound 45 as a white solid (1.04 g, 54% yield) which was used in subsequent steps without further purification. MS for $C_9H_{11}NO$, found 150 (MH+).

3-Nitro-5,6,7,8-tetrahydroquinolin-2-ol (46)

Nitric acid (0.5 mL, 67%) was added slowly at 5° C. to a solution of Compound 45 (900 mg, 6.04 mmol) in $H_2SO_4$ (8 ml, 98%) while the temperature was kept below 15° C. The mixture was stirred at 5° C. for an additional 1 hour and then poured onto ice. The resulting precipitate was filtered off, washed with water, and dried to give Compound 46 (766 mg). The filtrate was extracted with DCM. The combined organic extracts were dried over anhydrous $MgSO_4$ and concentrated to give an additional 280 mg of Compound 46 (89% yield total). MS for $C_9H_{10}N_2O_3$, found 195 (MH+).

2-Chloro-3-nitro-5,6,7,8-tetrahydroquinoline (47)

$POCl_3$ (4 mL) was added to Compound 46 (766 mg, 3.95 mmol) and the mixture stirred at 85° C. overnight. After concentrating the reaction mixture, the resulting residue was partitioned between aq saturated $NaHCO_3$ and DCM. The organic layer was washed once with aq saturated NaCl, dried over anhydrous $Na_2SO_4$, and concentrated to give Compound 47, which was used directly in the next step without further purification. MS for $C_9H_9ClN_2O_2$, found 213 (MH+).

3-Nitro-5,6,7,8-tetrahydroquinoline-2-carbonitrile (48)

A mixture of Compound 47 (106 mg, 0.5 mmol) and CuCN (90 mg, 1.0 mmol) in NMP (2.0 mL) was heated at 170° C. under microwave irradiation for 20 min. Another portion of CuCN (40 mg) was added, and irradiation continued for another 40 min. The resulting mixture was poured into ice water (20 mL) and extracted with EtOAc (2 times). The combined EtOAc extracts were dried over anhydrous $Na_2SO_4$ and concentrated to give Compound 48, which was used without further purification. MS for $C_{10}H_9N_3O_2$, found 204 (MH+).

3-Amino-5,6,7,8-tetrahydroquinoline-2-carboxamide (49)

Crude Compound 48 was mixed with Fe (140 mg, 2.5 mmol), AcOH (0.4 mL, 6.7 mmol), water (6 mL), and EtOH (14 mL). The mixture was stirred at 90° C. for 20 min then cooled to room temperature. The pH of the resulting mixture was adjusted to basic with aq 28% $NH_4OH$. Volatile organic solvents were removed under vacuum. The resulting mixture was filtered through Celite®, and the filtrate was concentrated and then extracted with EtOAc (2 times). The combined EtOAc extracts were dried over anhydrous $Na_2SO_4$ and concentrated to give Compound 49 as a brown solid (83 mg, 87% yield over 2 steps). MS for $C_{10}H_{13}N_3O$, found 192 (MH+).

6,7,8,9-Tetrahydropyrimido[5,4-b]quinolin-4-ol (50)

Compound 50 was made from Compound 49 in a manner analogous to the preparation of Compound 10 from Compound 9 in Step 2 of Example 3. MS for $C_{11}H_{11}N_3O$, found 202 (MH+).

4-Chloro-6,7,8,9-tetrahydropyrimido[5,4-b]quinoline (51)

Compound 51 was made from Compound 50 in a manner analogous to the preparation of Compound 11 from Compound 10 in Step 3 of Example 3. MS for $C_{11}H_{10}ClN_3$, found 220 (MH+).

1-N'-(4-Fluorophenyl)-1-N-[4-(6,7,8,9-tetrahydropyrimido[5,4-b]quinolin-4-yloxy)phenyl]cyclopropane-1,1-dicarboxamide (52)

Compound 52 was made from Compound 51 in a manner analogous to the preparation of Compound 7 from Compound 6 in Step 3 of Example 2. MS for $C_{28}H_{24}FN_5O_3$, found 498 (MH+).

Example 11: 1-N-[4-(6-Cyano-7-methoxypyrido[3,2-d]pyrimidin-4-yl)oxyphenyl]-1-N'-(4-fluorophenyl)cyclopropane-1,1-dicarboxamide (57)

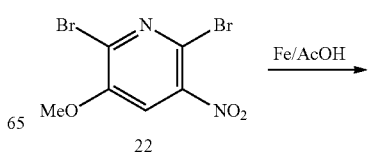

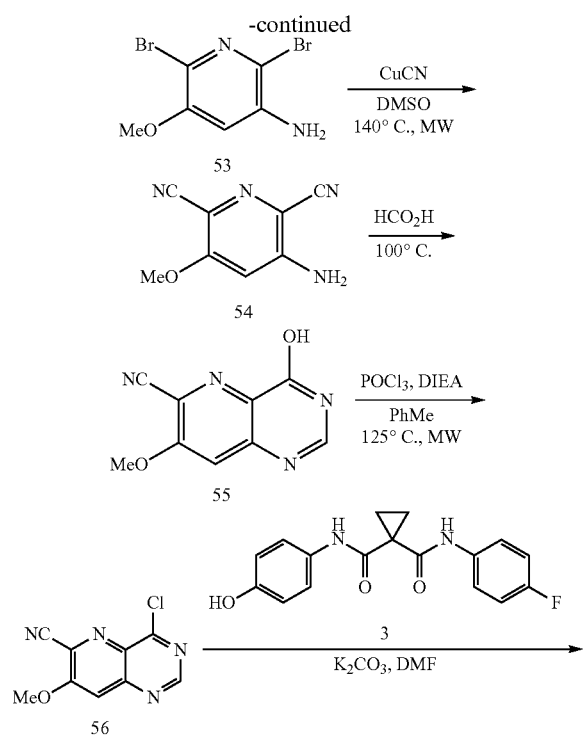

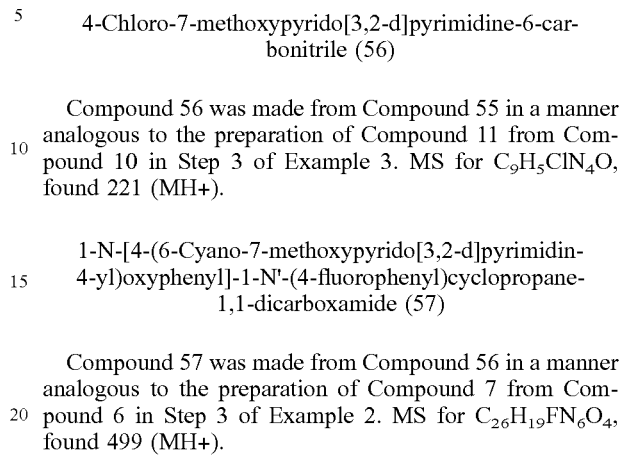

concentrated to a solid. The solid was washed with EtOAc and dried to give Compound 55 (52 mg, 64% yield). MS for $C_9H_6N_4O_2$, found 203 (MH+).

4-Chloro-7-methoxypyrido[3,2-d]pyrimidine-6-carbonitrile (56)

Compound 56 was made from Compound 55 in a manner analogous to the preparation of Compound 11 from Compound 10 in Step 3 of Example 3. MS for $C_9H_5ClN_4O$, found 221 (MH+).

1-N-[4-(6-Cyano-7-methoxypyrido[3,2-d]pyrimidin-4-yl)oxyphenyl]-1-N'-(4-fluorophenyl)cyclopropane-1,1-dicarboxamide (57)

Compound 57 was made from Compound 56 in a manner analogous to the preparation of Compound 7 from Compound 6 in Step 3 of Example 2. MS for $C_{26}H_{19}FN_6O_4$, found 499 (MH+).

Example 12: 4-(3-((4-Chloro-6-methoxypyrido[3,2-d]pyrimidin-7-yl)oxy)propyl)-morpholine (64)

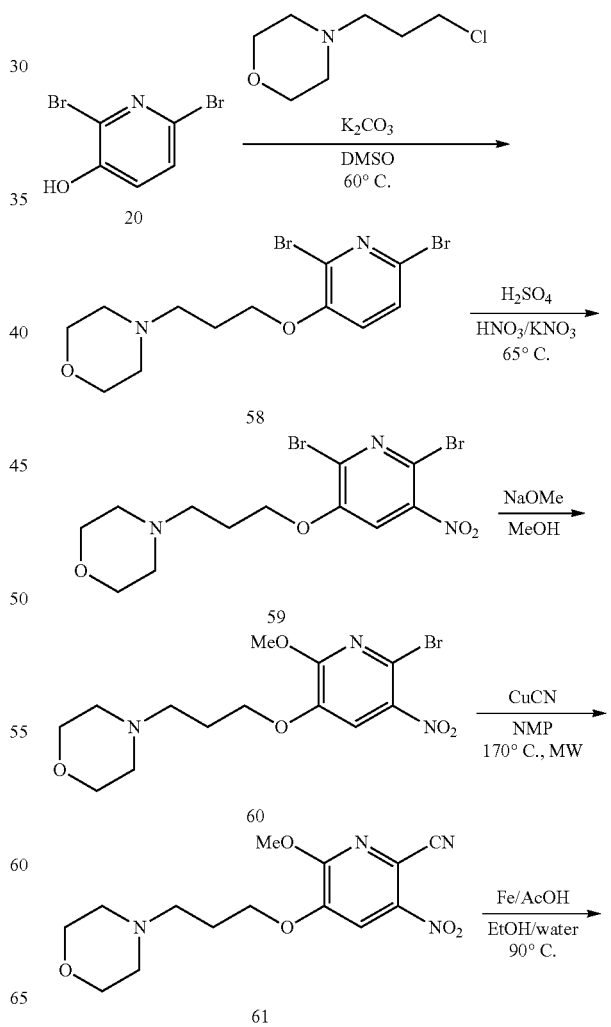

2,6-Dibromo-5-methoxypyridin-3-amine (53)

To Compound 22 (360 mg, 1.15 mmol) was added AcOH (4 mL), followed by Fe powder (260 mg, 4.64 mmol). The reaction mixture was stirred at room temperature for 2 hours and then poured into ice water. The pH of the resulting mixture was adjusted to 7 with $Na_2CO_3$. The resulting solids were filtered and then washed with DCM. The filtrate was dried over anhyd $Na_2SO_4$ and concentrated to give crude Compound 53 (340 mg, ~100% yield). MS for $C_6H_6Br_2N_5O$, found 283 (MH+).

3-Amino-5-methoxypyridine-2,6-dicarbonitrile (54)

A mixture of Compound 53 (270 mg, 0.96 mmol) and CuCN (260 mg, 2.89 mmol) in DMSO (4.5 mL) was heated at 140° C. under microwave irradiation for 60 min. EtOAc (40 mL) was added, and the resulting suspension was filtered. The EtOAc filtrate was washed with water and concentrated under vacuum. The resulting residue was purified by silica gel chromatography (0-100% EtOAc in DCM) to give Compound 54 (78 mg, 47% yield). MS for $C_8H_6N_4O$, found 173 (M-H).

4-Hydroxy-7-methoxypyrido[3,2-d]pyrimidine-6-carbonitrile (55)

Compound 54 (70 mg, 0.40 mmol) in formic acid (1.2 mL, >95%) was stirred at 100-110° C. for 3 days and

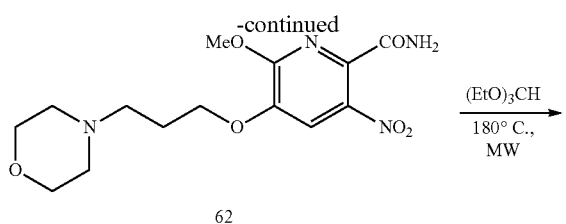
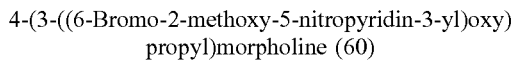
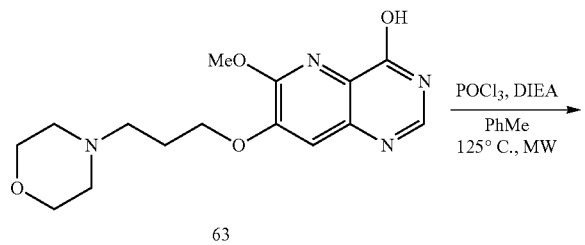
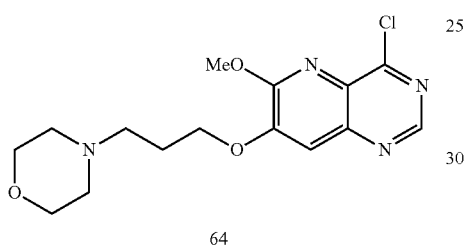

4-(3-((2,6-Dibromopyridin-3-yl)oxy)propyl)morpholine (58)

Compound 58 was synthesized from Compound 20 in a manner analogous to that used to convert Compound 20 to Compound 21 in Step 1 of Example 7, replacing the MeI with 4-(3-chloropropyl)morpholine. MS (EI) for $C_{12}H_{16}Br_2N_2O_2$, found 379 (MH+).

4-(3-((2,6-Dibromo-5-nitropyridin-3-yl)oxy)propyl) morpholine (59)

Compound 59 was synthesized from Compound 58 in a manner analogous to that used to convert Compound 21 to Compound 22 in Example 7.

4-(3-((6-Bromo-2-methoxy-5-nitropyridin-3-yl)oxy) propyl)morpholine (60)

Compound 60 was synthesized from Compound 59 in a manner analogous to that used to convert Compound 22 to Compound 23 in Example 7.

6-Methoxy-5-(3-morpholinopropoxy)-3-nitropicolinonitrile (61)

Compound 61 was synthesized from Compound 60 in a manner analogous to that used to convert Compound 23 to Compound 24 in Example 7.

6-Methoxy-5-(3-morpholinopropoxy)-3-nitropicolinamide (62)

Compound 62 was synthesized from Compound 61 in a manner analogous to that used to convert Compound 24 to Compound 25 in Example 7. MS (EI) for $C_{14}H_{22}N_4O_4$, found 311 (MH+)

6-Methoxy-7-(3-morpholinopropoxy)pyrido[3,2-d] pyrimidin-4-ol (63)

Compound 63 was made from Compound 62 in a manner analogous to the preparation of Compound 10 from Compound 9 in Step 2 of Example 3. MS (EI) for $C_{15}H_{20}N_4O_4$, found 321 (MH+).

4-(3-((4-Chloro-6-methoxypyrido [3,2-d]pyrimidin-7-yl)oxy)propyl)morpholine (64)

Compound 64 was made from Compound 63 in a manner analogous to the preparation of Compound 11 from Compound 10 in Step 3 of Example 3. MS (EI) for $C_{15}H_{19}ClN_4O_3$, found 339 (MH+).

Example 13: 1-N'-(4-Fluorophenyl)-1-N-[4-[6-methoxy-7-(3-morpholin-4-ylpropoxy)pyrido[3,2-d] pyrimidin-4-yl]oxyphenyl]cyclopropane-1,1-dicarboxamide (65)

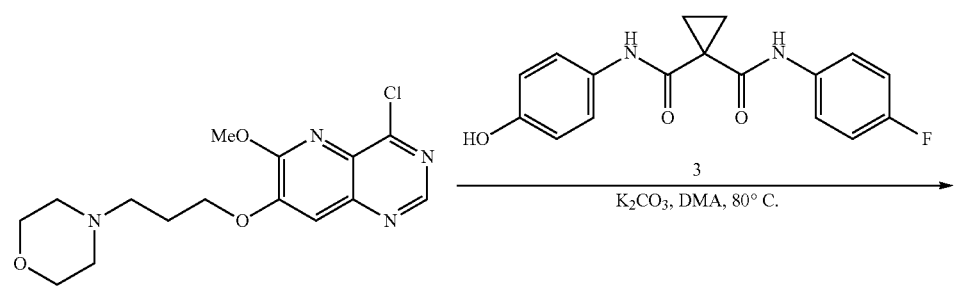

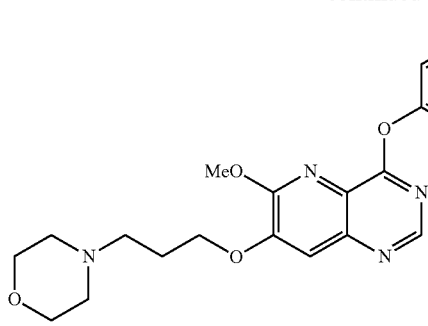

1-N'-(4-Fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide (65)

Compound 65 was made from Compound 64 in a manner analogous to the preparation of Compound 7 from Compound 6 in Step 3 of Example 2. MS for $C_{32}H_{33}FN_6O_6$, found 617 (MH+).

The following compounds were prepared from Compound 64 in a method analogous to Compound 65 in Example 13 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[3-Chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (66)

MS (EI) for $C_{32}H_{32}ClFN_6O_6$, found 651 (MH+).

1-N'-[3-Fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (67)

MS (EI) for $C_{32}H_{32}F_2N_6O_6$, found 635 (MH+).

1-N-(4-Fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide (68)

$^1$H NMR (400 MHz, CDCl$_3$) δ 9.07 (s, 1H), 8.83 (s, 1H), 8.58 (s, 1H), 7.53 (d, 1H), 7.52-7.43 (m, 3H), 7.43 (s, 1H), 7.20 (d, 1H), 7.05 (t, 2H), 4.28 (t, 2H), 4.22 (s, 3H), 3.74 (t, 4H), 2.58 (t, 2H), 2.55-2.43 (m, 4H), 2.19 (s, 3H), 2.17-2.08 (m, 2H), 1.72-1.67 (m, 2H), 1.67-1.62 (m, 2H); MS (EI) for $C_{33}H_{35}FN_6O_6$, found 631.2 (MH+).

1-N'-[2-Fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (69)

$^1$H NMR (400 MHz, CDCl$_3$) δ 9.16 (s, 1H), 8.97 (br s, 1H), 8.61 (s, 1H), 8.32 (t, 1H), 7.51 (dd, 2H), 7.43 (s, 1H), 7.18-7.09 (m, 2H), 7.05 (t, 2H), 4.28 (t, 2H), 4.21 (s, 3H), 3.74 (t, 4H), 2.58 (t, 2H), 2.54-2.45 (m, 4H), 2.18-2.09 (m, 2H), 1.79-1.73 (m, 2H), 1.72-1.66 (m, 2H); MS (EI) for $C_{32}H_{32}F_2N_6O_6$, found 635.1 (MH+).

1-N'-[2-Chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (70)

$^1$H NMR (400 MHz, CDCl$_3$) δ 9.52 (s, 1H), 8.88 (s, 1H), 8.61 (s, 1H), 8.42 (d, 1H), 7.52 (dd, 2H), 7.43 (s, 1H), 7.40 (d, 1H), 7.25 (d, 1H), 7.05 (t, 2H), 4.29 (t, 2H), 4.21 (s, 3H), 3.77-3.69 (m, 4H), 2.58 (t, 2H), 2.55-2.42 (m, 4H), 2.20-2.06 (m, 2H), 1.86-1.78 (m, 2H), 1.71-1.63 (m, 2H); MS (EI) for $C_{32}H_{32}ClFN_6O_6$, found 651.1 (MH+).

1-N-(4-Fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide (71)

$^1$H NMR (400 MHz, CDCl$_3$) δ 9.13 (s, 1H), 8.76 (s, 1H), 8.61 (s, 1H), 7.93 (d, 1H), 7.50 (dd, 2H), 7.42 (s, 1H), 7.18-7.12 (m, 2H), 7.05 (t, 2H), 4.28 (t, 2H), 4.22 (s, 3H), 3.74 (t, 4H), 2.58 (t, 2H), 2.55-2.42 (m, 4H), 2.35 (s, 3H), 2.18-2.09 (m, 2H), 1.76-1.71 (m, 2H), 1.71-1.67 (m, 2H); MS (EI) for $C_{33}H_{35}FN_6O_6$, found 631.2 (MH+).

1-N'-[2,5-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (72)

MS (EI) for $C_{32}H_{31}F_3N_6O_6$, found 653 (MH+).

1-N'-[2,3-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (73)

MS (EI) for $C_{32}H_{31}F_3N_6O_6$, found 653 (MH+).

1-N-(4-Fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide (74)

$^1$H NMR (400 MHz, CDCl$_3$) δ 9.20 (s, 1H), 8.74 (s, 1H), 8.57 (s, 1H), 7.53 (d, 1H), 7.48 (dd, 2H), 7.42 (s, 1H), 7.21 (d, 1H), 7.10-7.02 (m, 3H), 4.28 (t, 2H), 4.23 (s, 3H), 3.77 (s, 3H), 3.74 (t, 4H), 2.57 (t, 2H), 2.54-2.44 (m, 4H), 2.17-2.08 (m, 2H), 1.74-1.68 (m, 2H), 1.66-1.62 (m, 2H); MS (EI) for $C_{33}H_{35}FN_6O_7$, found 647.2 (MH+).

1-N'-[3-Cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (75)

MS (EI) for $C_{33}H_{32}FN_7O_6$, found 642.2 (MH+).

1-N'-[3,5-Difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide (76)

$^1$H NMR (400 MHz, DMSO-$d_6$) δ 10.49 (s, 1H), 10.02 (s, 1H), 8.61 (s, 1H), 7.69 (s, 1H), 7.67-7.58 (m, 4H), 7.16 (t, 2H), 4.30 (t, 2H), 4.10 (s, 3H), 3.58 (t, 4H), 2.45 (t, 2H), 2.38 (s, 4H), 1.98 (quin, 2H), 1.46 (d, 4H); MS (EI) for $C_{32}H_{31}F_3N_6O_6$, found 653.1 (MH+).

Example 14: 1-N'-(4-Fluorophenyl)-1-N-[4-[6-methoxy-7-(2-methoxyethoxy)pyrido[3,2-d]pyrimidin-4-yl]oxyphenyl]cyclopropane-1,1-dicarboxamide (78)

Example 14 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[3-Fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (79)

MS for $C_{28}H_{25}F_2N_5O_6$, found 566 (MH+).

1-N'-[3-Chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (80)

MS for $C_{28}H_{25}F_2N_5O_6$, found 582 (MH+).

1-N'-[2-Fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (81)

MS for $C_{28}H_{25}F_2N_5O_6$, found 566 (MH+).

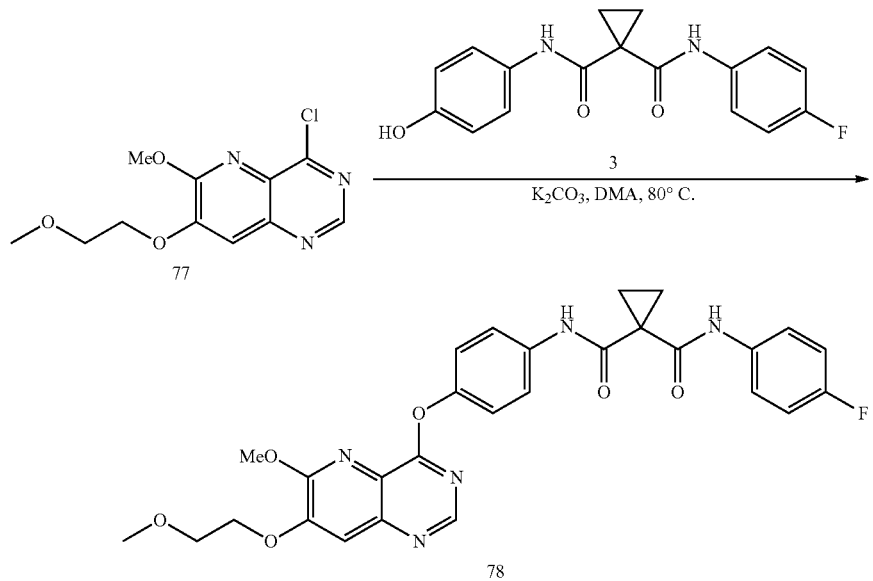

4-Chloro-6-methoxy-7-(2-methoxyethoxy)pyrido[3,2-d]pyrimidine (77)

Compound 77 can be made following a similar sequence of steps to those used to make Compound 64 in Example 12, substituting 1-bromo-2-methoxy ethane or 1-chloro-2-methoxyethane for the 4-(3-chloropropyl)morpholine used in the first step.

1-N'-(4-Fluorophenyl)-1-N-[4-[6-methoxy-7-(2-methoxyethoxy)pyrido[3,2-d]pyrimidin-4-yl]oxyphenyl]cyclopropane-1,1-dicarboxamide (78)

Compound 78 was made from Compound 77 in a manner analogous to the preparation of Compound 7 from Compound 6 in Step 3 of Example 2. MS for $C_{28}H_{26}FN_5O_6$, found 548 (MH+).

The following compounds were prepared from Compound 77 in a method analogous to Compound 78 in 1-N'-[2,3-Difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (82)

MS for $C_{28}H_{24}F_3N_5O_6$, found 584 (MH+).

1-N'-[2,5-Difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide (83)

MS for $C_{28}H_{24}F_3N_5O_6$, found 584 (MH+).

Example 15: 1-N'-(4-Fluorophenyl)-1-N-(4-pyrido[3,4-d]pyrimidin-4-yloxyphenyl)cyclopropane-1,1-dicarboxamide (85)

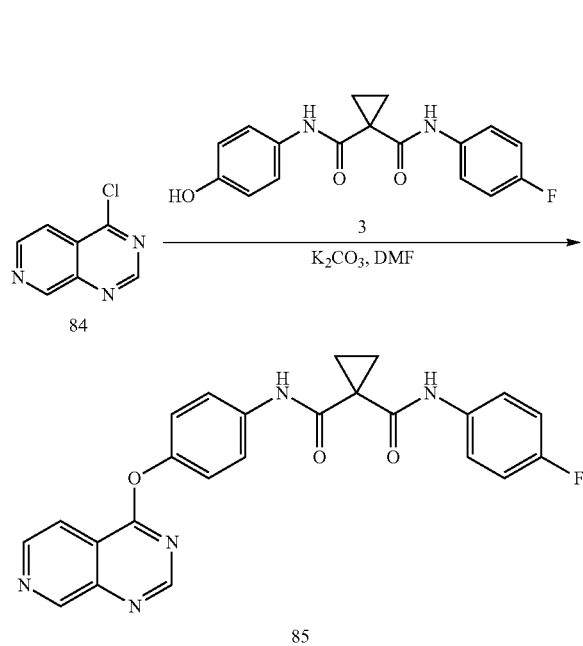

N-(4-Fluorophenyl)-N-(4-(pyrido[3,4-d]pyrimidin-4-yloxy)phenyl)cyclopropane-1,1-dicarboxamide (228)

Compound 85 was made from Compound 84 in a manner analogous to the preparation of Compound 7 from Compound 6 in Step 3 of Example 2. $^1$H NMR (400 MHz, DMSO-$d_6$) δ 10.19 (br s, 1H), 10.08 (br s, 1H), 9.43 (s, 1H), 8.88 (s, 1H), 8.86 (d, 1H), 8.22 (d, 1H), 7.74 (d, 2H), 7.63-7.65 (m, 2H), 7.32 (d, 2H), 7.15 (d, 2H), 1.48 (s, 4H); MS for $C_{24}H_{18}FN_5O_3$, found 444.0 (MH+).

Example 16: 1-N-[4-(6-Chloropyrido[3,4-d]pyrimidin-4-yl)oxyphenyl]-1-N'-(4-fluorophenyl)cyclopropane-1,1-dicarboxamide (88)

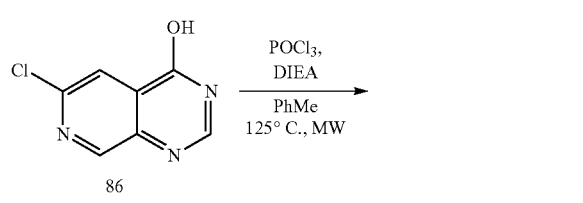

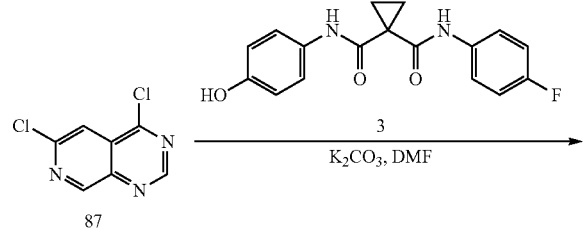

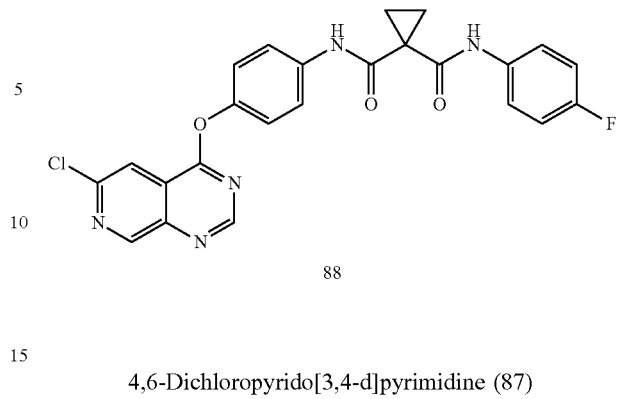

4,6-Dichloropyrido[3,4-d]pyrimidine (87)

Compound 87 was made from Compound 86 in a manner analogous to the preparation of Compound 11 from Compound 10 in Step 3 of Example 3.

1-N-[4-(6-Chloropyrido[3,4-d]pyrimidin-4-yl)oxyphenyl]-1-N'-(4-fluorophenyl)cyclopropane-1,1-dicarboxamide (88)

Compound 88 was made from Compound 87 in a manner analogous to the preparation of Compound 7 from Compound 6 in Step 3 of Example 2. MS for $C_{24}H_{17}ClFN_5O_3$, found 478 (MH+).

Example 17: 1-N'-(4-Fluorophenyl)-1-N-[4-(6-methoxypyrido[3,4-d]pyrimidin-4-yl)oxyphenyl]cyclopropane-1,1-dicarboxamide (91)

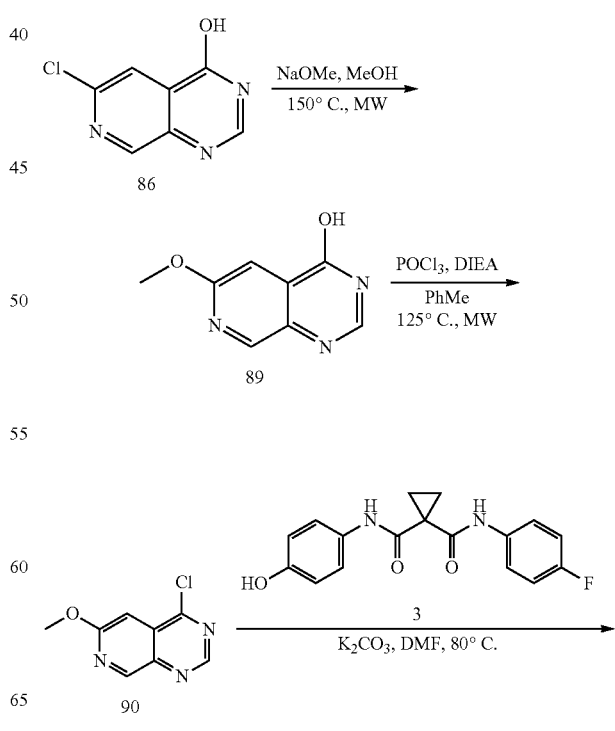

211

-continued

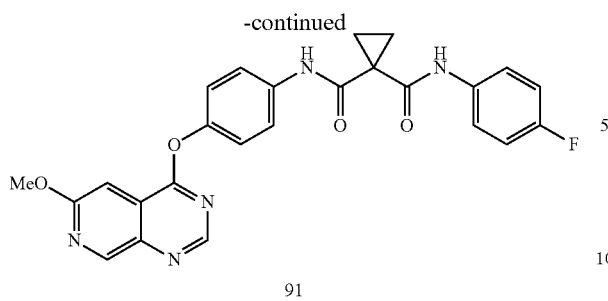

91

6-Methoxypyrido[3,4-d]pyrimidin-4-ol (89)

Compound 89 was made from Compound 86 in a manner analogous to the preparation of Compound 14 from Compound 10 in Step 1 of Example 4.

4-Chloro-6-methoxypyrido[3,4-d]pyrimidine (90)

Compound 90 was made from Compound 89 in a manner analogous to the preparation of Compound 11 from Compound 10 in Step 3 of Example 3.

1-N'-(4-Fluorophenyl)-1-N-[4-(6-methoxypyrido[3,4-d]pyrimidin-4-yl)oxyphenyl]cyclopropane-1,1-dicarboxamide (91)

Compound 91 was made from Compound 90 in a manner analogous to the preparation of Compound 7 from Compound 6 in Step 3 of Example 2. MS for $C_{25}H_{20}FN_5O_4$, found 474 (MH+).

Example 18: 1-N'-(4-Fluorophenyl)-1-N-(4-pyrido[4,3-d]pyrimidin-4-yloxyphenyl)cyclopropane-1,1-dicarboxamide (95)

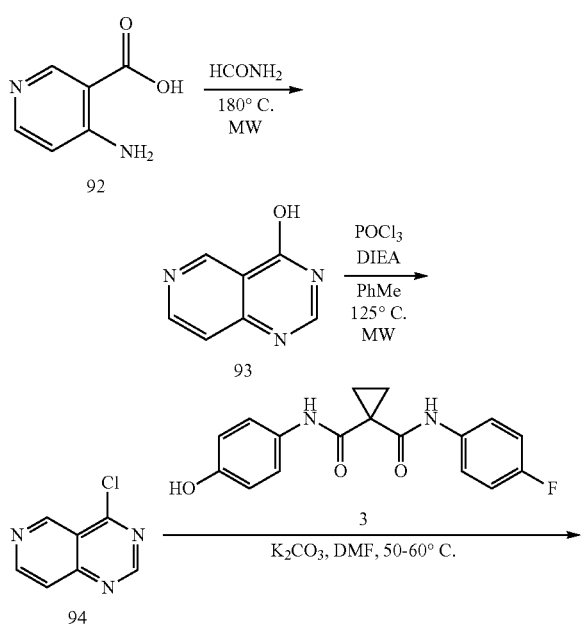

212

-continued

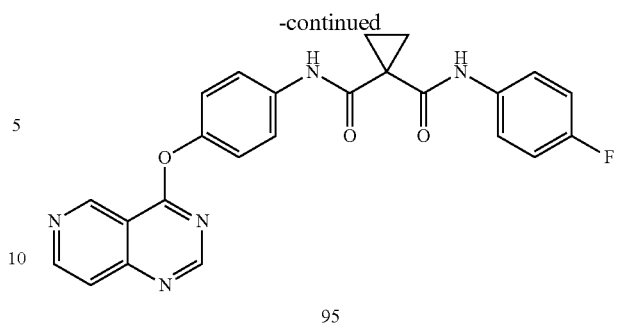

95

Pyrido[4,3-d]pyrimidin-4-ol (93)

Compound 93 was made from Compound 92 in a manner analogous to the preparation of Compound 5 from Compound 4 in Step 1 of Example 2. MS for $C_7H_5N_3O$, found 148 (MH+).

4-Chloropyrido[4,3-d]pyrimidine (94)

Compound 94 was made from Compound 93 in a manner analogous to the preparation of Compound 11 from Compound 10 in Step 3 of Example 3. MS for $C_7H_4ClN_3$, found 166 (MH+).

1-N'-(4-Fluorophenyl)-1-N-(4-pyrido[4,3-d]pyrimidin-4-yloxyphenyl)-cyclopropane-1,1-dicarboxamide (95)

Compound 95 was made from Compound 94 in a manner analogous to the preparation of Compound 7 from Compound 6 in Step 3 of Example 2. MS for $C_{24}H_{18}FN_5O_3$, found 444 (MH+).

Example 19: 1-N-[4-(7-Chloropyrido[4,3-d]pyrimidin-4-yl)oxyphenyl]-1-N'-(4-fluorophenyl)cyclopropane-1,1-dicarboxamide (101)

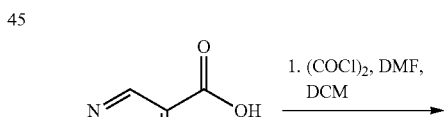

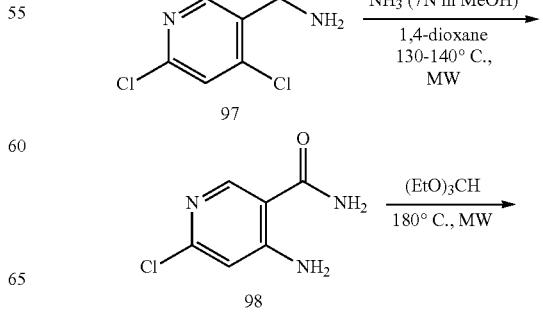

213

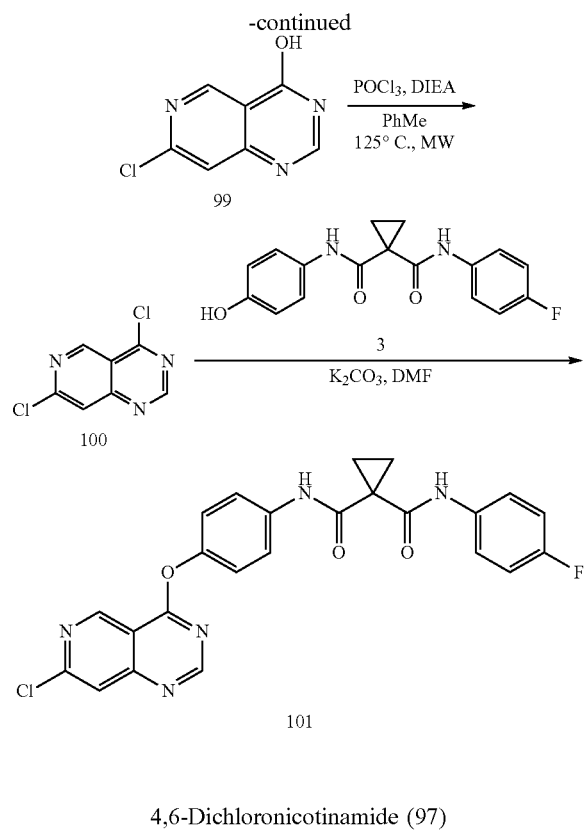

4,6-Dichloronicotinamide (97)

To a suspension of Compound 96 (2.0 g, 10.4 mmol) in DCM (40 mL) cooled to 5° C. was added oxalyl chloride (3 mL, 33.8 mmol) followed by DMF (0.3 mL). The reaction was stirred at 0-5° C. for 2 hours and then allowed to warm to room temperature over 1.5 hours. The volatiles were removed in vacuo, and the crude residue was suspended in THF (40 mL) and then cooled to 0-5° C. To this stirred suspension was added concentrated $NH_4OH$ (15 mL, 28%) dropwise, and the resulting reaction mixture was stirred at room temperature for 1 hour. The volatiles were removed under vacuum, and the crude residue was partitioned between EtOAc and water. The aqueous phase was further extracted with EtOAc (2 times). The combined EtOAc phases were dried over anhydrous $Na_2SO_4$ and concentrated to give Compound 97 as a white solid (1.8 g, 91% yield).

4-Amino-6-chloronicotinamide (98): A mixture of Compound 97 (191 mg, 1.0 mmol) and $NH_3$ (7M in MeOH, 0.15 mL, 1.05 mmol) in 1,4-dioxane (3.5 mL) was heated at 130° C. under microwave irradiation for 1 hour. Additional $NH_3$ (7M in MeOH, 0.55 mL, 3.85 mmol) was added and microwave irradiation continued at 130° C. for an additional 1 hour. One more aliquot of $NH_3$ (7M in MeOH, 0.50 mL, 3.75 mmol) was added, and microwave irradiation continued at 140° C. for 2 hours. The resulting reaction mixture was concentrated, and the residue was suspended in DCM. The resulting solids were filtered, washed with DCM, and dried to give Compound 98 (158 mg, 92% yield). MS for $C_6H_6ClN_3O$, found 172 (MH+).

7-Chloropyrido[4,3-d]pyrimidin-4-ol (99)

Compound 99 was made from Compound 98 in a manner analogous to the preparation of Compound 10 from Compound 9 in Step 2 of Example 3. MS for $C_7H_4ClN_3O$, found 182 (MH+).

214

4,7-Dichloropyrido[4,3-d]pyrimidine (100)

Compound 100 was made from Compound 99 in a manner analogous to the preparation of Compound 11 from Compound 10 in Step 3 of Example 3. MS for $C_7H_3Cl_2N_3$, found 200 (MH+).

1-N-[4-(7-Chloropyrido[4,3-d]pyrimidin-4-yl)oxyphenyl]-1-N'-(4-fluorophenyl)cyclopropane-1,1-dicarboxamide (101)

Compound 101 was made from Compound 100 in a manner analogous to the preparation of Compound 7 from Compound 6 in Step 3 of Example 2. MS for $C_{24}H_{17}ClFN_5O_3$, found 478 (MH+).

Example 20: 1-N'-(4-Fluorophenyl)-1-N-[4-(7-methoxypyrido[4,3-d]pyrimidin-4-yl)oxyphenyl]cyclopropane-1,1-dicarboxamide (104)

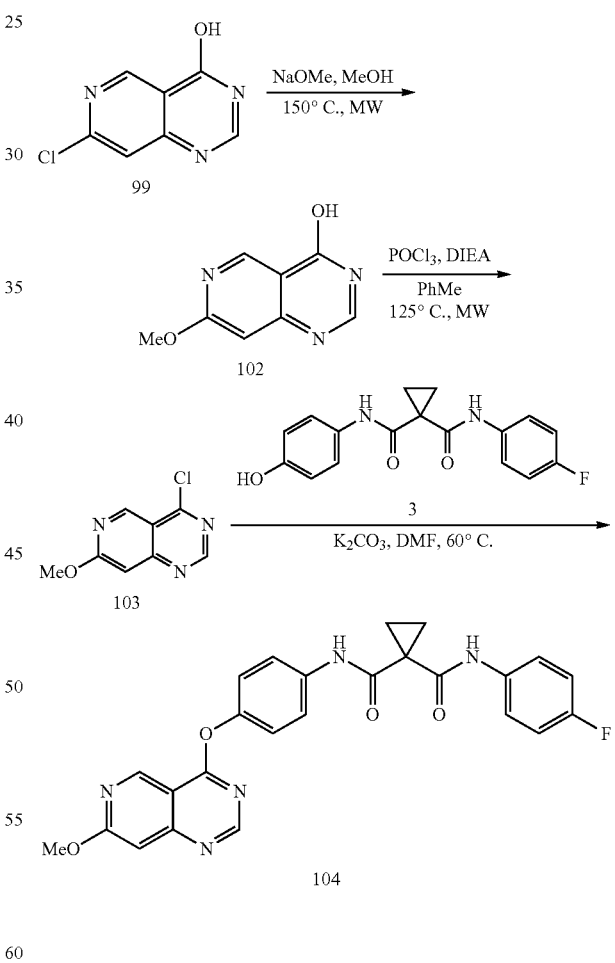

7-Methoxypyrido[4,3-d]pyrimidin-4-ol (102)

Compound 102 was made from Compound 99 in a manner analogous to the preparation of Compound 14 from Compound 10 in Step 1 of Example 4. MS for $C_8H_7N_3O_2$, found 178 (MH+).

4-Chloro-7-methoxypyrido[4,3-d]pyrimidine (103)

Compound 103 was made from Compound 102 in a manner analogous to the preparation of Compound 11 from Compound 10 in Step 3 of Example 3.

1-N'-(4-Fluorophenyl)-1-N-[4-(7-methoxypyrido[4,3-d]pyrimidin-4-yl)oxyphenyl]cyclopropane-1,1-dicarboxamide (104)

Compound 104 was made from Compound 103 in a manner analogous to the preparation of Compound 7 from Compound 6 in Step 3 of Example 2. MS for $C_{25}H_{20}FN_5O_4$, found 474 (MH+).

Example 21: 1-N-[4-(6-Cyanoquinazolin-4-yl)oxyphenyl]-1-N'-(4-fluorophenyl)cyclopropane-1,1-dicarboxamide (106)

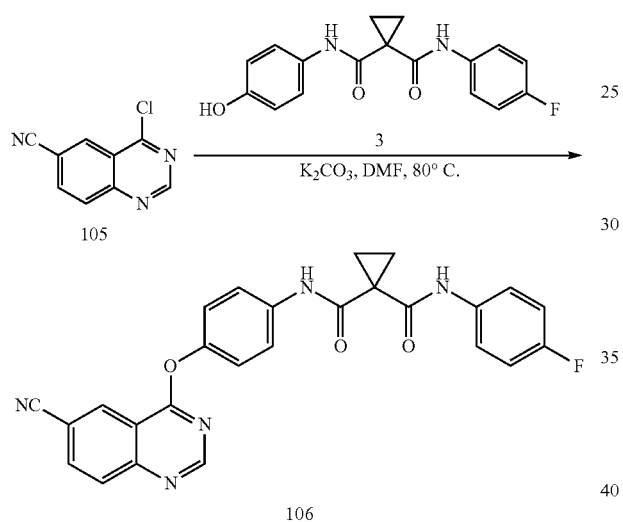

1-N-[4-(6-Cyanoquinazolin-4-yl)oxyphenyl]-1-N'-(4-fluorophenyl)cyclopropane-1,1-dicarboxamide (106)

Compound 106 was made from Compound 105 in a manner analogous to the preparation of Compound 7 from Compound 6 in Step 3 of Example 2. MS for $C_{26}H_{18}FN_5O_3$, found 468 (MH+).

Example 22: 4-Chloro-7-methoxyquinazoline-6-carbonyl chloride (112)

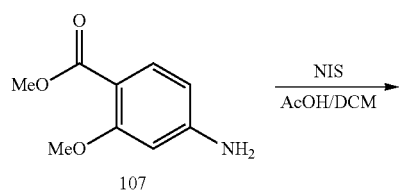

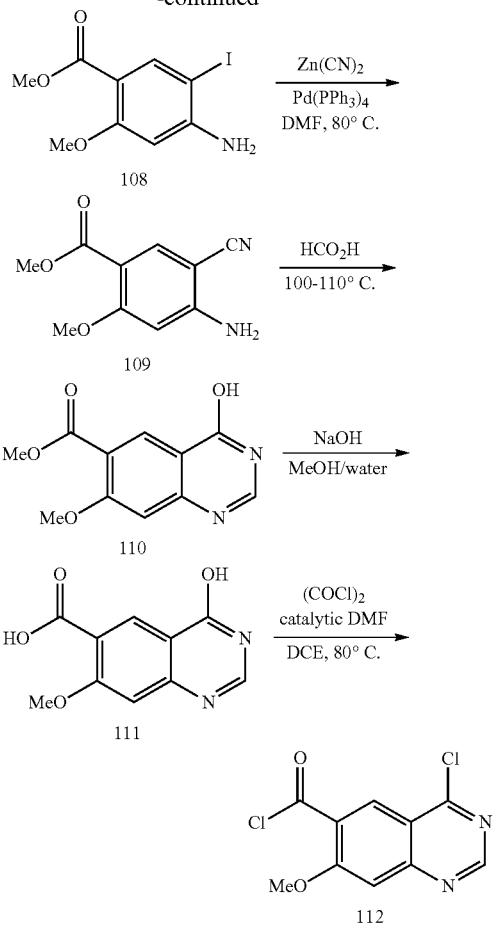

Methyl 4-amino-5-iodo-2-methoxybenzoate (108)

At 0-5° C., N-iodosuccinimide (2.30 g, 10.2 mmol) was added to a suspension of Compound 107 (1.81 g, 10 mmol) in ACOH (25 mL) and DCM (12 mL). The mixture was stirred at 5° C. for 10 min, followed by stirring at room temperature for 3 hours. The mixture was concentrated, and the resulting residue was treated with aq saturated NaHCO₃ until pH 8 was achieved. The resulting suspension was filtered, and the resulting solids were washed with water followed by i-PrOH and hexanes and dried to give Compound 108 (2.72 g, 88% yield) which was used in the next step without further purification. MS for $C_9H_{10}INO_3$, found 308 (MH+).

Methyl 4-amino-5-cyano-2-methoxybenzoate (109)

To a solution of Compound 108 (2.5 g, 8.1 mmol) and dicyanozinc (1.5 g, 12.8 mmol) in DMF (25 mL) under argon, was added Pd(PPh₃)₄ (1.0 g, 0.87 mmol) and the reaction mixture was stirred at 80° C. overnight. Water was added and the resulting suspension was filtered, washed with water, dried and then resuspended in EtOAc. The EtOAc suspension was stirred for 15 min, then filtered and dried to give Compound 109 as an off-white powder (1.5 g, 90% yield). MS for $C_{10}H_{10}N_2O_3$, found 207 (MH+).

Methyl 4-hydroxy-7-methoxyquinazoline-6-carboxylate (110)

Compound 109 (1.5 g, crude from previous step) in formic acid (22 mL, >95%) was stirred at 100-110° C. for 1 day and filtered to remove the white solid. The filtrate was diluted with ether (100 mL), and the resulting suspension was filtered to give Compound 110 (1.01 g, 88% yield). MS for $C_{11}H_{10}N_2O_4$, found 235 (MH+).

4-Hydroxy-7-methoxyquinazoline-6-carboxylic acid (111)

A mixture of Compound 110 (508 mg, 2.17 mmol) and NaOH (1.0 g, 25 mmol) in water (5 mL) and MeOH (5 mL) was stirred at room temperature for 1 hour, concentrated, and the pH adjusted to 3 with coned HCl. The resulting suspension was filtered, and the resulting solids were washed with water and dried to give Compound 111 (390 mg, 82% yield). MS for $C_{10}H_8N_2O_4$, found 221 (MH+).

4-Chloro-7-methoxyquinazoline-6-carbonyl chloride (112)

To a mixture of Compound 111 (110 mg, 0.5 mmol) in 1,2-dichloroethane (5 mL) was added oxalyl chloride (0.6 mL, 7 mmol) followed by a catalytic amount of DMF. The reaction was stirred in a sealed tube at 80° C. for 3 hours and concentrated to give crude Compound 112 which was used directly in subsequent steps without further purification.

Example 23: 1-N'-(4-Fluorophenyl)-1-N-[4-[7-methoxy-6-(oxetan-3-ylcarbamoyl)quinazolin-4-yl]oxyphenyl]cyclopropane-1,1-dicarboxamide (115)

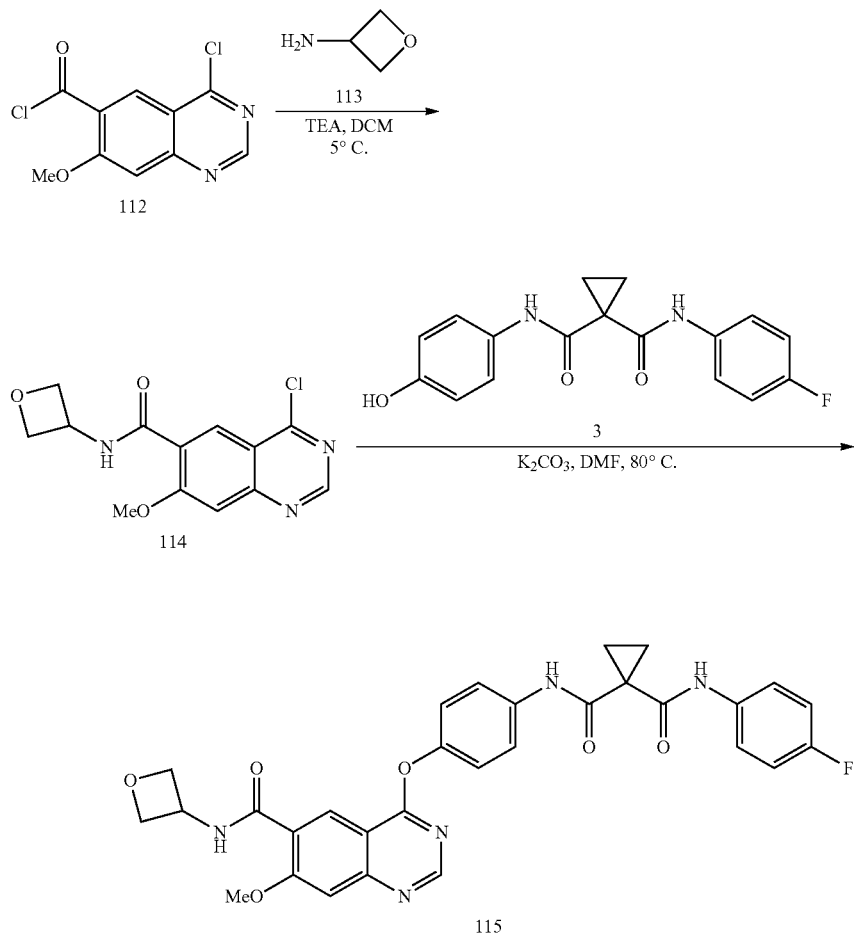 [SMILES: COc1cc2ncnc(Cl)c2cc1C(=O)Cl ; NC1COC1 ; COc1cc2ncnc(Cl)c2cc1C(=O)NC1COC1 ; O=C(Nc1ccc(O)cc1)C1(C(=O)Nc2ccc(F)cc2)CC1 ; COc1cc2ncnc(Oc3ccc(NC(=O)C4(C(=O)Nc5ccc(F)cc5)CC4)cc3)c2cc1C(=O)NC1COC1]

4-Chloro-7-methoxy-N-(oxetan-3-yl)quinazoline-6-carboxamide (114)

Crude Compound 112 was dissolved in DCM (5 mL) and the solution was cooled to 5° C. To the solution was added TEA (0.2 mL, 1.44 mmol) followed by Compound 113 (40 mg, 0.55 mmol) dropwise. The resulting mixture was stirred at 5° C. for 30 min and then concentrated to give crude Compound 114 which was used in the next step without further purification. MS for $C_{13}H_{12}ClN_3O_3$, found 294 (MH+).

1-N'-(4-Fluorophenyl)-1-N-[4-[7-methoxy-6-(oxetan-3-ylcarbamoyl)quinazolin-4-yl]oxyphenyl]cyclopropane-1,1-dicarboxamide (115)

Compound 115 was made from Compound 114 in a manner analogous to the preparation of Compound 7 from Compound 6 in Step 3 of Example 2. MS for $C_{30}H_{26}FN_5O_6$, found 572 (MH+).

The following compounds were prepared using a method analogous to that for Compound 115 in Example 23 by initially reacting Compound 112 with the appropriate amine followed by the coupling of that product to Compound 3 using an analogous method to the way Compound 6 was coupled to Compound 3 in Step 3 of Example 2:

1-N-[4-[6-(Cyclopropylcarbamoyl)-7-methoxyquinazolin-4-yl]oxyphenyl]-1-N'-(4-fluorophenyl)cyclopropane-1,1-dicarboxamide (116)

Cyclopropylamine was used in place of Compound 113. MS for $C_{30}H_{26}FN_5O_5$, found 556 (MH+).

1-N-[4-(6-Carbamoyl-7-methoxyquinazolin-4-yl)oxyphenyl]-1-N'-(4-fluorophenyl)cyclopropane-1,1-dicarboxamide (117)

Ammonia was used in place of Compound 113. MS for $C_{27}H_{22}FN_5O_5$, found 516 (MH+).

1-N'-(4-Fluorophenyl)-1-N-[4-[7-methoxy-6-(2-pyrrolidin-1-ylethylcarbamoyl)quinazolin-4-yl]oxyphenyl]cyclopropane-1,1-dicarboxamide (118)

2-(Pyrrolidin-1-yl)ethan-1-amine was used in place of Compound 113. MS for $C_{33}H_{33}FN_6O_5$, found 613 (MH+).

tert-Butyl (2R)-2-[[[4-[4-[[1-[(4-fluorophenyl)carbamoyl]cyclopropanecarbonyl]-amino]phenoxy]-7-methoxyquinazoline-6-carbonyl]amino]methyl]pyrrolidine-1-carboxylate (119)

t-Butyl (R)-2-(aminomethyl)pyrrolidine-1-carboxylate was used in place of Compound 113. MS for $C_{37}H_{39}FN_6O_7$, found 699 (MH+).

tert-Butyl (2S)-2-[[[4-[4-[[1-[(4-fluorophenyl)carbamoyl]cyclopropanecarbonyl]-amino]phenoxy]-7-methoxyquinazoline-6-carbonyl]amino]methyl]pyrrolidine-1-carboxylate (120)

t-Butyl (S)-2-(aminomethyl)pyrrolidine-1-carboxylate was used in place of Compound 113. MS for $C_{37}H_{39}FN_6O_7$, found 699 (MH+).

Example 24: 1-N'-(4-Fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide (121)

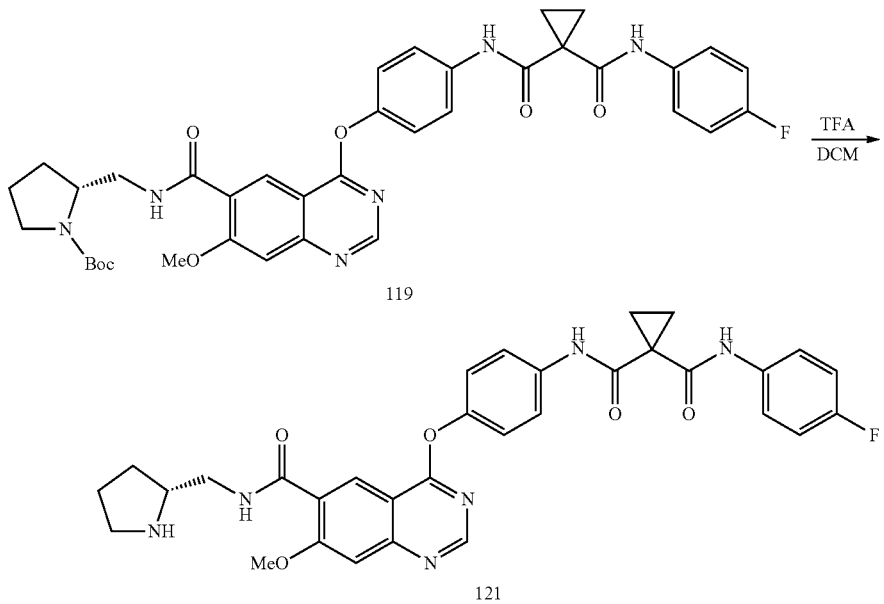

1-N'-(4-Fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide (121)

Compound 121 was synthesized from Compound 119 using standard procedures for N-Boc deprotection using TFA in DCM at room temperature or slightly elevated temperatures. MS for $C_{32}H_{31}FN_6O_5$, found 599 (MH+).

The following compound was prepared from Compound 120 in a manner analogous to the method used to convert Compound 119 to Compound 121 in Example 24:

1-N'-(4-Fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide (122)

MS for $C_{32}H_{31}FN_6O_5$, found 599 (MH+).

Example 25: 1-N'-(4-Fluorophenyl)-1-N-[4-[6-(1-methylpyrazol-4-yl)quinazolin-4-yl]oxyphenyl]cyclopropane-1,1-dicarboxamide (126)

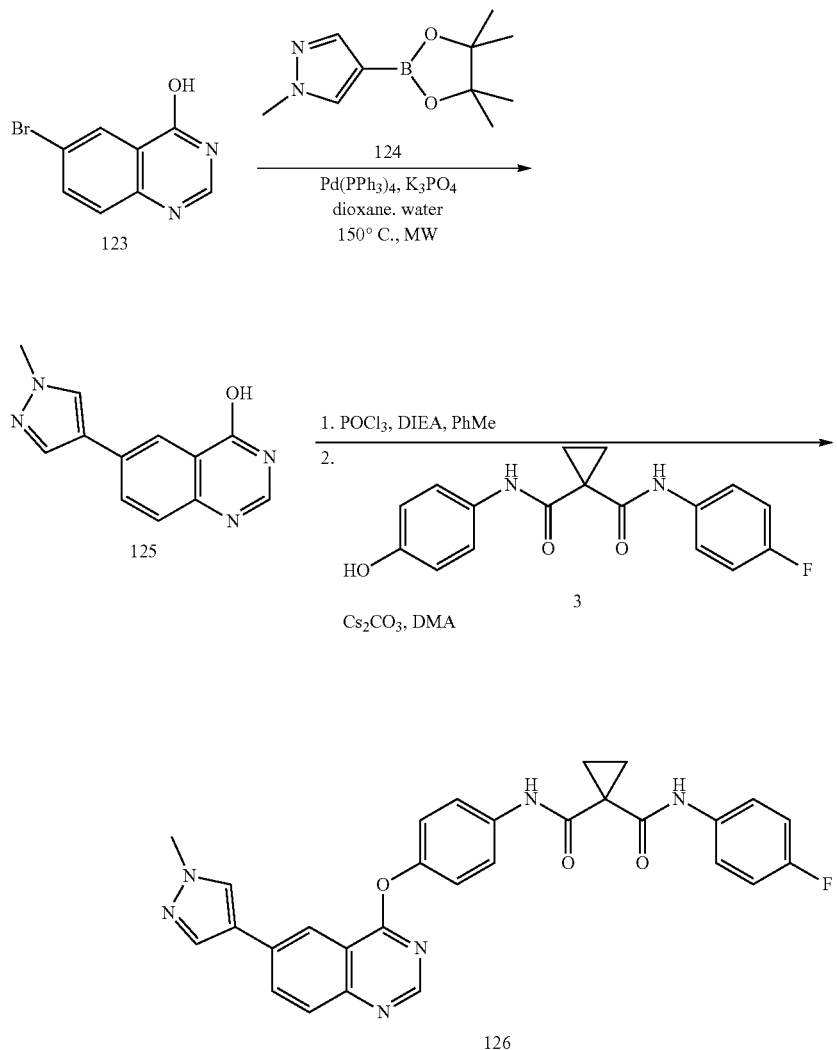

6-(1-Methyl-1H-pyrazol-4-yl)quinazolin-4-ol (125)

In a microwave reaction tube were mixed commercially available Compound 123 (225 mg, 1.0 mmol), Compound 124 (270 mg, 1.3 mmol), $K_3PO_4$ (636 mg, 3.0 mmol), Pd(PPh$_3$)$_4$ (115 mg, 0.1 mmol), 1,4-dioxane (6 mL) and water (3 mL). The reaction mixture was irritated for 20 minutes at 150° C. After cooling, the mixture was diluted with EtOAc, The phases were separated, and the aqueous phase was extracted with 15% MeOH in EtOAc. Removal of the solvents gave crude Compound 125 (crude yield 225 mg) which was used in the next step without further purification.

1-N'-(4-Fluorophenyl)-1-N-[4-[6-(1-methylpyrazol-4-yl)quinazolin-4-yl]oxyphenyl]cyclopropane-1,1-dicarboxamide (126)

To a mixture of crude Compound 125 (225 mg, 1.0 mmol) and DIEA (650 mg, 5 mmol) in PhMe (3 mL) was added POCl$_3$ (766 mg, 5.0 mmol). The mixture was stirred at 105° C. for 2 hour, then cooled to room temperature. The resulting mixture was concentrated, neutralized with cold saturated NaHCO$_3$, and extracted with EtOAc. The extracts were concentrated in vacuo. A mixture of the resulting residue (100 mg, 0.41 mmol), Compound 3 (128 mg, 0.41 mmol) and Cs$_2$CO$_3$ (267 mg, 0.82 mmol) in DMA (1.5 mL) was stirred at 60° C. for 10 hours and then cooled to room temperature. The mixture was diluted with water and extracted with EtOAc. The organic phase was concentrated, and the resulting residue was purified by flash column chromatography and prep HPLC to give Compound 126 (80 mg, 0.15% overall yield in three steps). MS (EI) for $C_{29}H_{23}FN_6O_3$, found: 523 (MH+).

Example 26: 1-N'-(4-Fluorophenyl)-1-N-[4-[7-(1-methylpyrazol-4-yl)pyrido[3,2-d]pyrimidin-4-yl]oxyphenyl]cyclopropane-1,1-dicarboxamide (129)

1-N'-(4-Fluorophenyl)-1-N-[4-[7-(1-methylpyrazol-4-yl)pyrido[3,2-d]pyrimidin-4-yl]oxyphenyl]cyclopropane-1,1-dicarboxamide (129)

A mixture of Compound 128 (115 mg, 220.17 umol, 1 eq), Compound 124 (69 mg, 331.63 umol, 1.51 eq), $K_3PO_4$ (127 mg, 598.31 umol, 2.72 eq) and Pd(dppf)Cl$_2$ (10 mg, 13.67 umol, 6.21e-2 eq) in DMF (1 mL) was degassed and purged

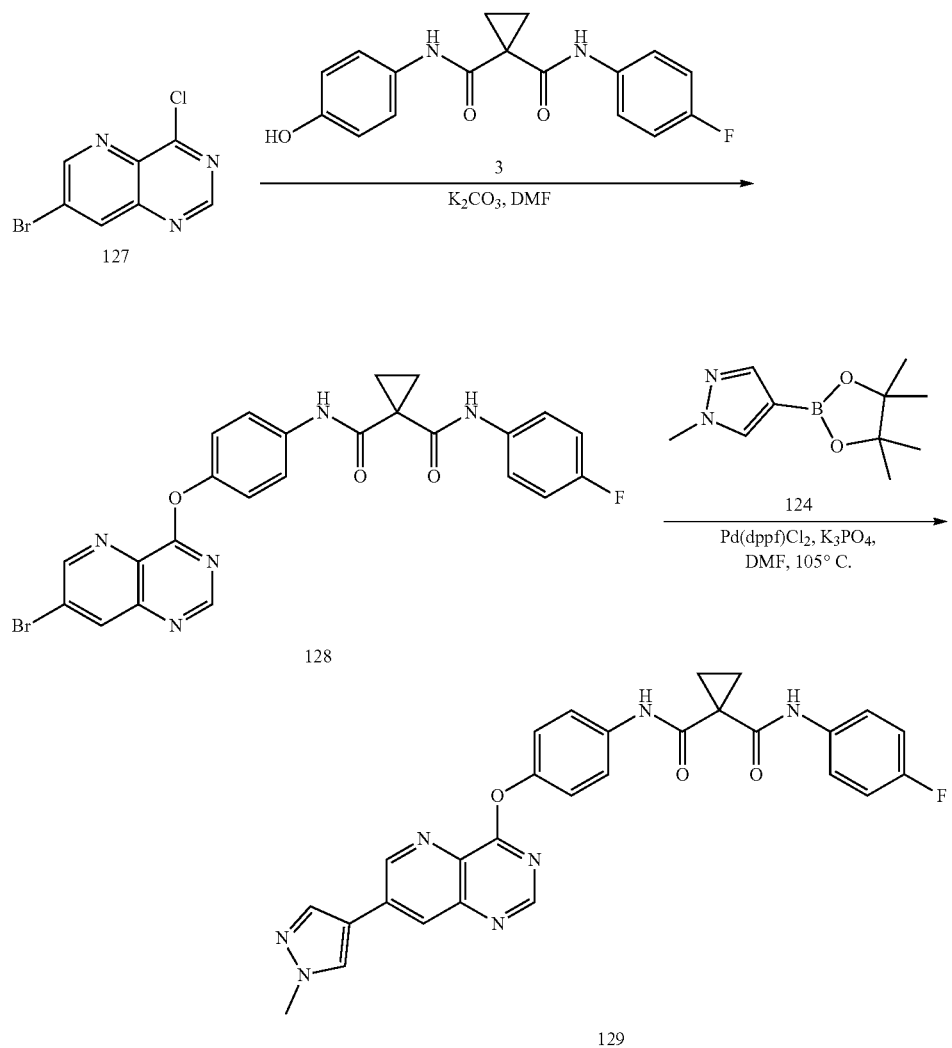

N-(4-((7-Bromopyrido[3,2-d]pyrimidin-4-yl)oxy)phenyl)-N-(4-fluorophenyl)cyclopropane-1,1-dicarboxamide (128)

Compound 128 was made from Compound 127 in a manner analogous to the preparation of Compound 7 from Compound 6 in Step 3 of Example 2. $^1$H NMR (400 MHz, DMSO-d$_6$) δ 10.17 (br s, 1H), 10.07 (br s, 1H), 9.19 (d, 1H), 8.82-8.77 (m, 2H), 7.73 (d, 2H), 7.68-7.60 (m, 2H), 7.28 (d, 2H), 7.15 (t, 2H), 1.47 (s, 4H); MS for $C_{24}H_{17}BrFN_5O_3$, found 524.2 (MH+).

with nitrogen gas 3 times, after which the mixture was stirred at 105° C. for 16 hours under an atmosphere of nitrogen until complete. The mixture was cooled to room temperature and purified by combi-flash (Silica Flash Column, eluent of 50-100% ethyl acetate/petroleum ether gradient) to give Compound 129 as an off-white solid (64.0 mg, 55.5% yield). $^1$H NMR (400 MHz, CDCl$_3$) δ 9.20 (d, 1H), 9.08 (s, 1H), 8.93 (br s, 1H), 8.76 (s, 1H), 8.29 (d, 1H), 8.00 (s, 1H), 7.91 (s, 1H), 7.66 (d, 2H), 7.51-7.45 (m, 2H), 7.30 (d, 2H), 7.04 (t, 2H), 4.04 (s, 3H), 1.67 (s, 4H); MS for $C_{28}H_{22}FN_7O_3$, found 524.2 (MH+).

Example 27: 1-N'-(4-Fluorophenyl)-1-N-[4-[7-(1-methylpyrazol-4-yl)pyrido[4,3-d]pyrimidin-4-yl]oxyphenyl]cyclopropane-1,1-dicarboxamide (130)

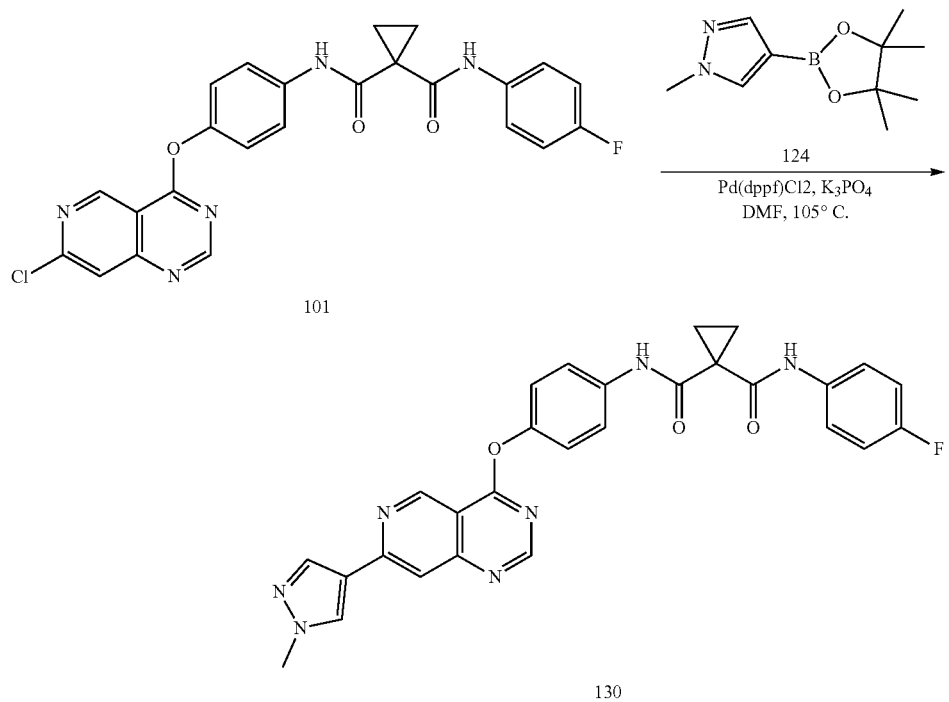

1-N'-(4-Fluorophenyl)-1-N-[4-[7-(1-methylpyrazol-4-yl)pyrido[4,3-d]pyrimidin-4-yl]oxyphenyl]cyclopropane-1,1-dicarboxamide (130)

Compound 130 was made from Compound 101 in a manner analogous to the preparation of Compound 129 from Compound 128 in Step 2 of Example 26. MS for $C_{28}H_{22}FN_7O_3$, found 524.1 (MH+).

Example 28: 6,7-Dimethoxy-1,5-naphthyridin-4-ol (136)

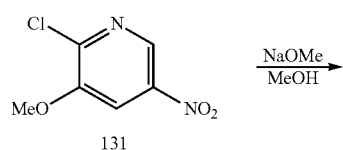

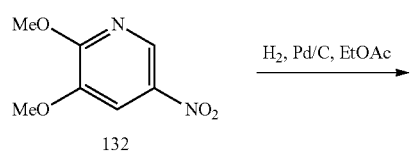

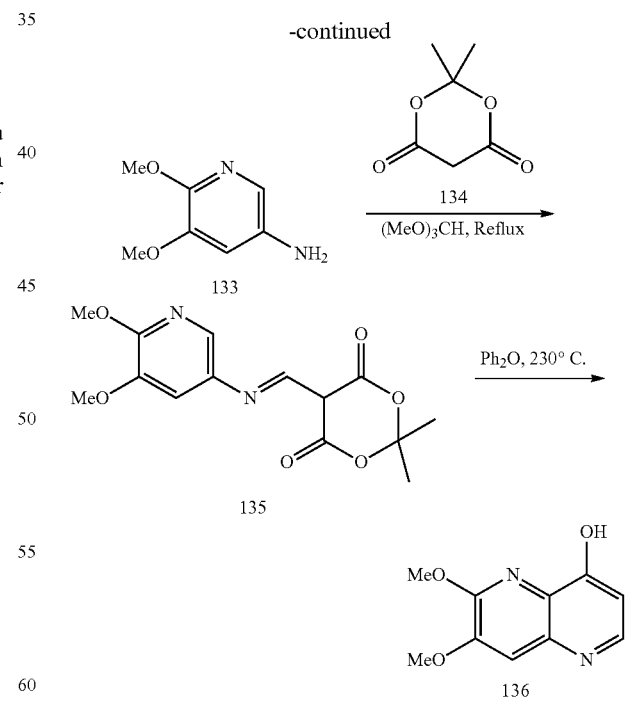

2,3-Dimethoxy-5-nitropyridine (132)

Freshly cut sodium (0.6 g, 26 mmol) was added portionwise to MeOH (50 mL) and the mixture was stirred at room temperature until the sodium dissolved. Compound 131 (3.0 g, 15.9 mmol) was added, and the reaction mixture was stirred at room temperature for 1 hour. Water (100 mL) was added, and the mixture was filtered. The solids were washed with water and dried to give Compound 132 (2.78 g, 95% yield). MS for $C_7H_8N_2O_4$, found 185 (MH+).

2,3-Dimethoxy-5-nitropyridine (133)

To a solution of Compound 132 (2.78 g, 15.1 mmol) in EtOAc (40 mL) under argon was added 10% Pd/C (53% water, 880 mg). The reaction mixture was stirred under one atmosphere of $H_2$ at room temperature overnight and then filtered through Celite®. The filtrate was concentrated under vacuum to provide crude Compound 133 as brown solid (2.31 g, 100% yield). MS for $C_7H_{10}N_2O_2$, found 155 (MH+).

5-(((5,6-Dimethoxypyridin-3-yl)imino)methyl)-2,2-dimethyl-1,3-dioxane-4,6-dione (135)

A solution of triethyl orthoformate (12 mL) and Compound 134 (1.44 g, 10.0 mmol) was stirred at 106° C. for 2.5 hour, followed by the addition of Compound 133 (1.54 g, 10.0 mmol) while maintaining the same temperature. A precipitate appeared within several minutes. The heterogeneous mixture was heated at 105° C. for an additional 10 min, cooled to room temperature and filtered. The solids were washed with hexanes and dried to give crude Compound 135 (3.6 g). MS for $C_{14}H_{16}N_2O_6$, found 309 (MH+).

6,7-Dimethoxy-1,5-naphthyridin-4-ol (136)

A solution of Compound 135 (1.55 g, 5.03 mmol) in diphenyl ether (12 mL) was heated at 250° C. for 30 min, and then cooled to room temperature. Diethyl ether was added, and the mixture was filtered to give crude Compound 136 as a brown solid (0.92 g, 89% yield). MS for $C_{10}H_{10}N_2O_3$, found 207 (MH+).

Example 29: 1-N-[4-[(6,7-Dimethoxy-1,5-naphthyridin-4-yl)oxy]phenyl]-1-N'-(4-fluorophenyl)cyclopropane-1,1-dicarboxamide (139)

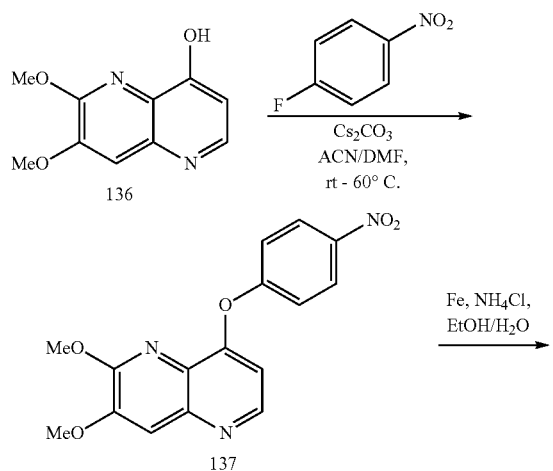

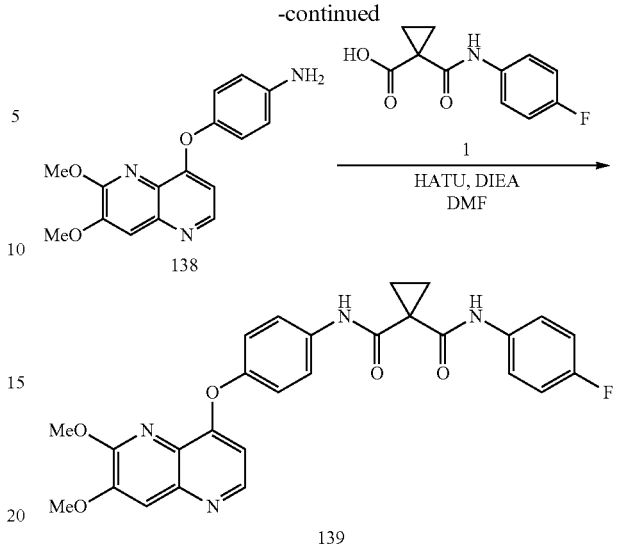

2,3-Dimethoxy-8-(4-nitrophenoxy)-1,5-naphthyridine (137)

A mixture of Compound 136 (61 mg, 0.30 mmol), 1-fluoro-4-nitrobenzene (63 mg, 0.45 mmol), and $Cs_2CO_3$ (198 mg, 0.60 mmol) in acetonitrile (2 mL) was stirred at 60° C. until the reaction was complete. The reaction mixture was diluted with EtOAc (8 mL) and filtered. The filtrated was purified by silica gel column and eluted with 0-100% of EtOAc in hexanes to give Compound 137 (36 mg, 37% yield). MS for $C_{16}H_{13}N_3O_5$, found 328 (MH+).

4-((6,7-Dimethoxy-1,5-naphthyridin-4-yl)oxy)aniline (138)

Compound 137 (36 mg, 0.11 mmol) was mixed with Fe (56 mg, 1.0 mmol), $NH_4Cl$ (108 mg, 2.0 mmol), water (1 mL), and EtOH (3 mL). The mixture was stirred at 85° C. for 60 min, cooled to room temperature, and filtered through Celite. The filtrate was concentrated, and the resulting residue was partitioned between saturated aq $NaHCO_3$ (2 mL) and EtOAc. The aqueous phase was further extracted with EtOAc (2×). The combined extract were dried over $Na_2SO_4$ and evaporated to give crude Compound 138 (30 mg, 91% yield). MS for $C_{16}H_{15}N_3O_3$, found 298 (MH+).

1-N-[4-[(6,7-Dimethoxy-1,5-naphthyridin-4-yl)oxy]phenyl]-1-N'-(4-fluorophenyl)cyclopropane-1,1-dicarboxamide (139)

To a mixture of Compound 138 (30 mg, 0.1 mmol), Compound 1 (36 mg, 0.15 mmol), and DIEA (60 mg, 0.46 mmol) in DMF (1 mL) was added HATU (114 mg, 0.30 mmol), and the reaction was stirred at room temperature overnight. Saturated aq $NaHCO_3$ was added to precipitate the product, which was then filtered, washed with water, and subjected to HPLC purification to give Compound 139 (12 mg, 24% yield). MS for $C_{27}H23FN_4O_5$, found 503 (MH+).

The following compounds were prepared using an analogous three step process to that used in the synthesis of Compound 139 in Example 29 by initially reacting Compound 136 with the appropriately substituted 1-fluoro-4-nitrobenzene. Lower temperatures (40° C.) were used for the first steps:

1-N'-[4-[(6,7-Dimethoxy-1,5-naphthyridin-4-yl)oxy]-3-fluorophenyl]-1-N-(4-fluorophenyl)cyclopropane-1,1-dicarboxamide (140)

1,2-Difluoro-4-nitrobenzene was used in place of 1-fluoro-4-nitrobenzene in step 1. MS (EI) for $C_{27}H_{22}F_2N_4O_5$, found 521 (MH+).

1-N'-[3-Chloro-4-[(6,7-dimethoxy-1,5-naphthyridin-4-yl)oxy]phenyl]-1-N-(4-fluorophenyl)cyclopropane-1,1-dicarboxamide (141)

2-Chloro-1-fluoro-4-nitrobenzene was used in place of 1-fluoro-4-nitrobenzene in step 1. MS (EI) for $C_{27}H_{22}ClFN_4O_5$, found 537 (MH+).

1-N'-[4-[(6,7-Dimethoxy-1,5-naphthyridin-4-yl)oxy]-2,5-difluorophenyl]-1-N-(4-fluorophenyl)cyclopropane-1,1-dicarboxamide (142)

1,2,5-Trifluoro-4-nitrobenzene was used in place of 1-fluoro-4-nitrobenzene in step 1. MS (EI) for $C_{27}H_{21}F_3N_4O_5$, found 539 (MH+).

Example 30: 1-N'-(4-Fluorophenyl)-1-N-[4-[[6-methoxy-7-(2-methoxyethoxy)-1,5-naphthyridin-4-yl]oxy]phenyl]cyclopropane-1,1-dicarboxamide (149)

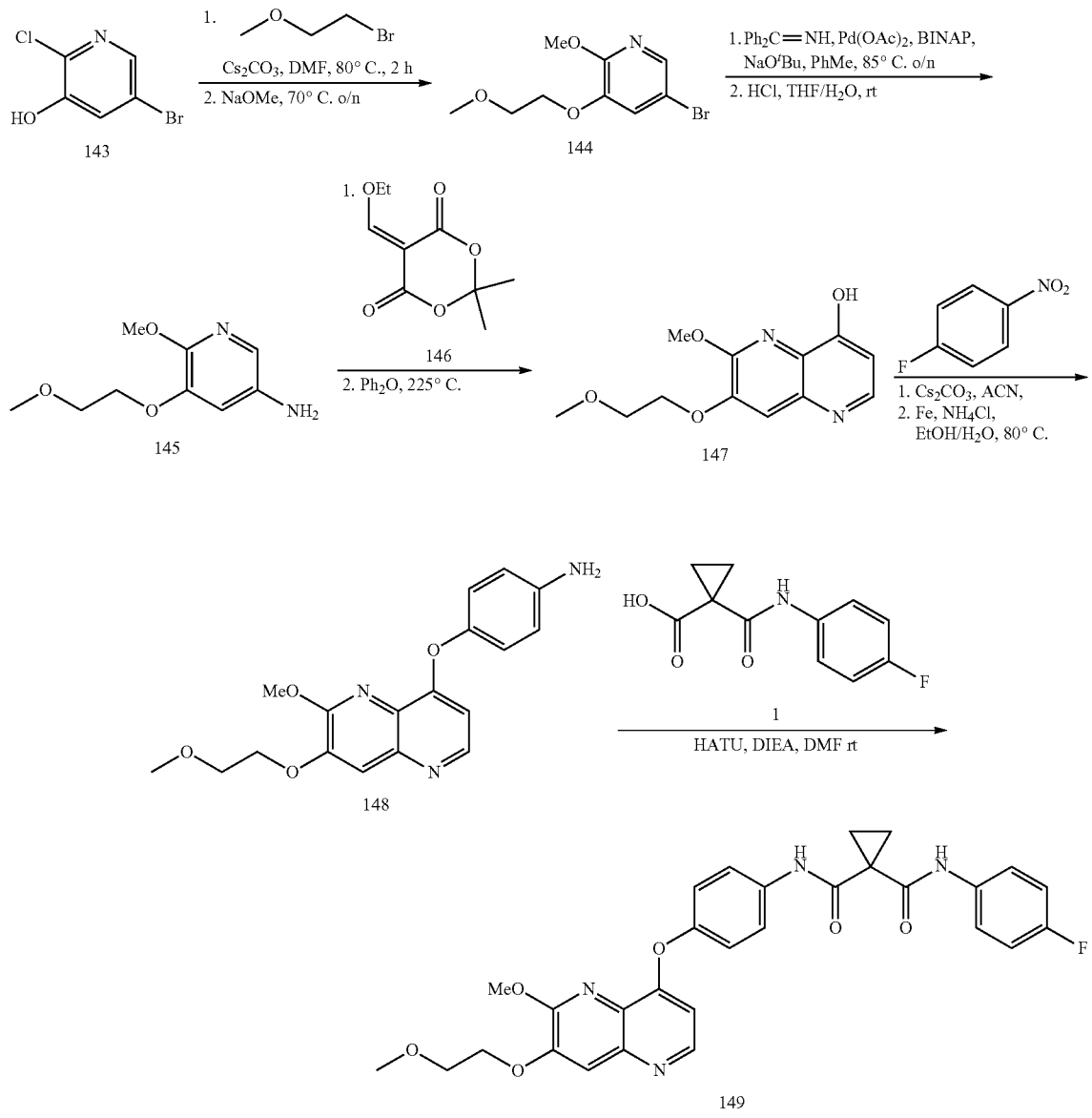

2,3-Dimethoxy-8-(4-nitrophenoxy)-1,5-naphthyridine (144)

A mixture of Compound 143 (2.10 g, 10.0 mmol), 1-bromo-2-methoxy ethane (1.50 g, 10.8 mmol), and $Cs_2CO_3$, (6.6 g, 20.2 mmol) in DMF was stirred at 80° C. for 2 hours, quenched with water, and extracted with EtOAc (2×), The combined extracts were washed with aq saturated NaCl, dried over $Na_2SO_4$, and evaporated to give the crude intermediate product as an off-white solid (2.68 g, MS for $C_8H_9BrClNCO_2$, found 268 (MH+)). This intermediate product (2.68 g, 10.0 mmol) was mixed with NaOMe (3.0 g, 55.5 mmol) in MeOH (40 mL) and heated at 70° C. overnight. The reaction mixture was concentrated to remove MeOH, and the resulting residue was partitioned between water and EtOAc. The EtOAc phase was washed with aq saturated NaCl, dried over $Na_2SO_4$, and evaporated to give crude Compound 144 as an oil containing some residual solvent (3.0 g). MS for $C_9H_{12}BrNO_3$, found 262/264 (MH+).

6-Methoxy-5-(2-methoxyethoxy)pyridin-3-amine (145)

Compound 144 (3.0 g, crude) was mixed with diphenylmethanimine (3.6 g, 20 mmol), Pd(OAc)2 (360 mg, 1.61 mmol), BINAP (1.3 g, 2.08 mmol) and NaO$^t$Bu (1.6 g, 16.7 mmol) in toluene (60 mL). The resulting mixture was degassed with argon and stirred at 85° C. overnight. The reaction mixture was partitioned between water and EtOAc. The organic phase was separated and evaporated to dryness. To the residue was added THF (40 mL) and HCl (aq, 2M, 40 mL), and the resulting mixture was stirred at room temperature overnight. The pH of the reaction mixture was adjusted to pH10 with $NaHCO_3$ and extracted with EtOAc. The extract was concentrated, and the resulting residue was subjected to chromatography on silica gel, eluted with 0-90% EtOAc in hexanes to afford Compound 145 as a brown oil (1.4 g, 71% yield from Compound 143). MS for $C_9H_{14}N_2O_3$, found 199 (MH+).

6,7-Dimethoxy-1,5-naphthyridin-4-yl)oxy)aniline (147)

Compound 147 was made from Compound 145 and Compound 146 in a manner analogous to the preparation of Compound 136 from Compound 133 and Compound 134 in Steps 3 and 4 of Example 28. MS for $C_{12}H_{14}N_2O_4$, found 251 (MH+).

6,7-Dimethoxy-1,5-naphthyridin-4-yl)oxy)aniline (148)

Compound 148 was made from Compound 147 in a manner analogous to the preparation of Compound 138 from Compound 136 in Steps 1 and 2 of Example 29.

1-N'-(4-Fluorophenyl)-1-N-[4-[[6-methoxy-7-(2-methoxyethoxy)-1,5-naphthyridin-4-yl]oxy]phenyl]cyclopropane-1,1-dicarboxamide (149)

Compound 149 was made from Compound 148 in a manner analogous to the preparation of Compound 139 from Compound 138 in Step 3 of Example 29. MS for $C_{29}H_{27}FN_4O_6$, found 547 (MH+).

The following compounds were prepared using an analogous multi-step process to that used in the synthesis of Compound 149 in Example 30. For Compounds 150-152, Compound 147 was reacted with the appropriately substituted 1-fluoro-4-nitrobenzene. For Compound 153, 4-(2-bromoethyl)morpholine replaced the 1-bromo-2-methoxyethane in the first step:

1-N'-[3-Fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide (150)

1,2-Difluoro-4-nitrobenzene was used in place of 1-fluoro-4-nitrobenzene. MS (EI) for $C_{29}H_{26}F_2N_4O_6$, found 565 (MH+).

1-N'-[3-Chloro-4-[[6-methoxy-7-(2-methoxyethoxy)-1,5-naphthyridin-4-yl]oxy]phenyl]-1-N-(4-fluorophenyl)cyclopropane-1,1-dicarboxamide (151)

2-Chloro-1-fluoro-4-nitrobenzene was used in place of 1-fluoro-4-nitrobenzene. MS (EI) for $C_{29}H_{26}ClFN_4O_6$, found 581 (MH+).

1-N'-[2,5-Difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide (152)

1,2,5-Trifluoro-4-nitrobenzene was used in place of 1-fluoro-4-nitrobenzene. MS (EI) for $C_{29}H_{25}F_3N_4O_6$, found 583 (MH+).

1-N'-[2,5-Difluoro-4-[[6-methoxy-7-(2-morpholin-4-ylethoxy)-1,5-naphthyridin-4-yl]oxy]phenyl]-1-N-(4-fluorophenyl)cyclopropane-1,1-dicarboxamide (153)

1,2,5-Trifluoro-4-nitrobenzene was used in place of 1-fluoro-4-nitrobenzene. MS (EI) for $C_{32}H_{30}F_3N_5O_6$, found 638 (MH+).

Example 31: 1-N-[4-(2,3-Dihydro-[1,4]dioxino[2,3-b][1,5]naphthyridin-6-yloxy)phenyl]-1-N'-(4-fluorophenyl)cyclopropane-1,1-dicarboxamide (157)

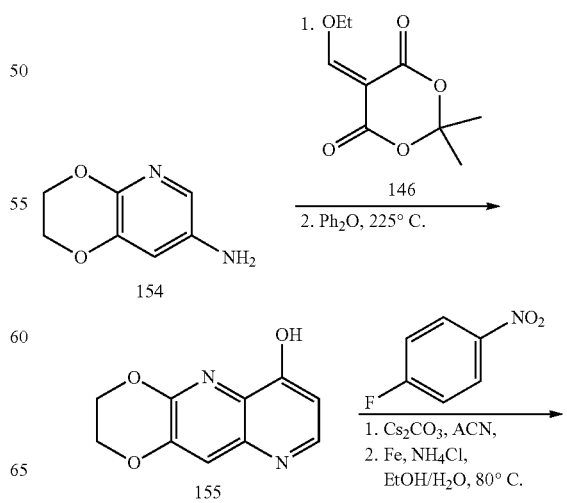

233

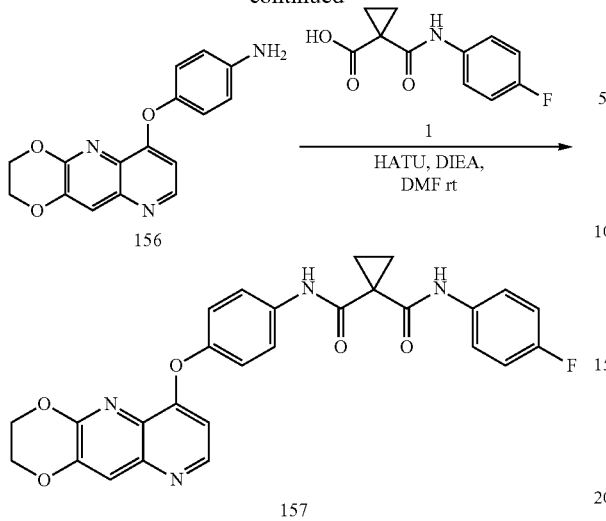

2,3-Dihydro-[1,4]dioxino[2,3-b][1,5]naphthyridin-6-ol (155)

Compound 155 was made from Compound 154 and Compound 146 in a manner analogous to the preparation of Compound 136 from Compound 133 and Compound 134 in Steps 3 and 4 of Example 28. MS for $C_{10}H_8N_2O_3$, found 205 (MH+).

4-((2,3-Dihydro-[1,4]dioxino[2,3-b][1,5]naphthyridin-6-yl)oxy)aniline (156)

Compound 156 was made from Compound 155 in a manner analogous to the preparation of Compound 138 from Compound 136 in Steps 1 and 2 of Example 29.

1-N-[4-(2,3-Dihydro-[1,4]dioxino[2,3-b][1,5]naphthyridin-6-yloxy)phenyl]-1-N'-(4-fluorophenyl)cyclopropane-1,1-dicarboxamide (157)

Compound 157 was made from Compound 156 in a manner analogous to the preparation of Compound 139 from Compound 138 in Step 3 of Example 29. MS for $C_{27}H_{21}FN_4O_5$, found 501 (MH+).

The following compounds were prepared from Compound 155 using an analogous three step process to that used in the synthesis of Compound 139 from Compound 136 in Example 29 by initially reacting Compound 155 with the appropriately substituted 1-fluoro-4-nitrobenzene:

1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide (158)

1,2-Difluoro-4-nitrobenzene was used in place of 1-fluoro-4-nitrobenzene. MS (EI) for $C_{27}H_{20}F_2N_4O_5$, found 519 (MH+).

1-N'-[3-Chloro-4-(2,3-dihydro-[1,4]dioxino[2,3-b][1,5]naphthyridin-6-yloxy)phenyl]-1-N-(4-fluorophenyl)cyclopropane-1,1-dicarboxamide (159)

2-Chloro-1-fluoro-4-nitrobenzene was used in place of 1-fluoro-4-nitrobenzene. MS (EI) for $C_{27}H_{20}ClFN_4O_5$, found 535 (MH+).

234

Example 32: 1-N-[4-[(6-Cyano-7-methoxy-1,5-naphthyridin-4-yl)oxy]phenyl]-1-N'-(4-fluorophenyl)cyclopropane-1,1-dicarboxamide (164)

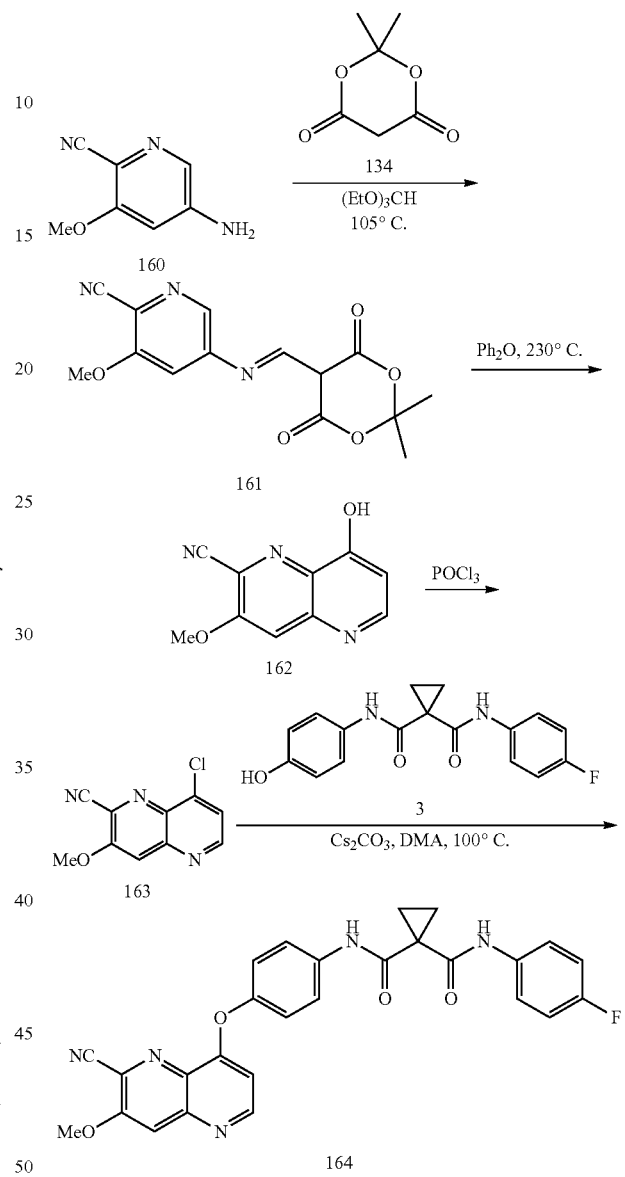

5-(((2,2-Dimethyl-4,6-dioxo-1,3-dioxan-5-yl)methylene)amino)-3-methoxypicolinonitrile (161)

Compound 161 was made from Compound 160 and Compound 134 in a manner analogous to the preparation of Compound 135 from Compound 133 and Compound 134 in Step 3 of Example 28. MS (EI) for $C_{14}H_{13}N_3O_5$, found 304 (MH+).

8-Hydroxy-3-methoxy-1,5-naphthyridine-2-carbonitrile (162)

Compound 162 was made from Compound 161 in a manner analogous to the preparation of Compound 136 from Compound 135 in Step 4 of Example 28. MS (EI) for $C_{10}H_7N_3O_2$, found 202 (MH+).

8-Chloro-3-methoxy-1,5-naphthyridine-2-carbonitrile (163)

Compound 163 was made from Compound 162 in a manner analogous to the preparation of Compound 38 from Compound 37 in Step 2 of Example 9.

1-N-[4-[(6-Cyano-7-methoxy-1,5-naphthyridin-4-yl)oxy]phenyl]-1-N'-(4-fluorophenyl)cyclopropane-1,1-dicarboxamide (164)

Compound 164 was made from Compound 163 and Compound 3 using a variation of the method used to prepare Compound 7 from Compound 6 in Step 3 of Example 2. $Cs_2CO_2$ in DMA was used in place of $K_2CO_3$ in DMF. MS (EI) for $C_{27}H_{20}FN_5O_4$, found 498 (MH+).

The following compounds were prepared from Compound 163 in a method analogous to the method used to make Compound 28 from Compound 27 in Example 8 using the appropriately substituted N-(4-fluorophenyl)-N-(4-hydroxyphenyl)cyclopropane-1,1-dicarboxamides which were synthesized using methods analogous to those used in Example 1 or Example 5:

1-N'-[4-[(6-Cyano-7-methoxy-1,5-naphthyridin-4-yl)oxy]-3-fluorophenyl]-1-N-(4-fluorophenyl)cyclopropane-1,1-dicarboxamide (165)

MS (EI) for $C_{27}H_{19}F_2N_5O_4$, found 516 (MH+).

1-N'-[3-Chloro-4-[(6-cyano-7-methoxy-1,5-naphthyridin-4-yl)oxy]phenyl]-1-N-(4-fluorophenyl)cyclopropane-1,1-dicarboxamide (166)

MS (EI) for $C_{27}H_{19}ClFN_5O_4$, found 532 (MH+).

Example 33: 1-N-[4-[(6-Carbamoyl-7-methoxy-1,5-naphthyridin-4-yl)oxy]phenyl]-1-N'-(4-fluorophenyl)cyclopropane-1,1-dicarboxamide (167)

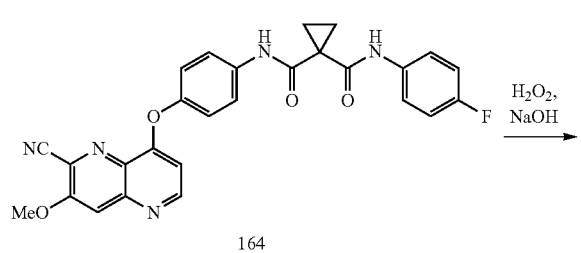

164

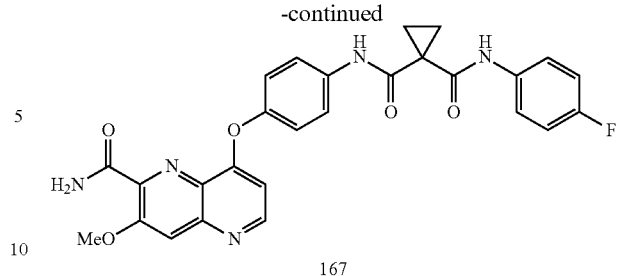

167

1-N-[4-[(6-Carbamoyl-7-methoxy-1,5-naphthyridin-4-yl)oxy]phenyl]-1-N'-(4-fluorophenyl)cyclopropane-1,1-dicarboxamide (167)

To a mixture of compound 164 (17 mg, 0.034 mmol) and NaOH (aq, 50%, 0.2 mL) was added $H_2O_2$ (aq 30%, 1.0 mL). The mixture was stirred at room temperature for 5 min, quenched with saturated $NaHCO_3$, and extracted with EtOAc. The EtOAc extracts were concentrated in vacuo, and the resulting residue was purified by Flash silica gel chromatography (0-10% MeOH in DCM) to give Compound 167 (3 mg, 17% yield). MS (EI) for $C_{27}H_{22}FN_5O_5$, found 516 (MH+).

The following compounds were made using a method analogous to that used to make Compound 167 in Example 33:

1-N'-[4-[(6-Carbamoyl-7-methoxy-1,5-naphthyridin-4-yl)oxy]-3-fluorophenyl]-1-N-(4-fluorophenyl)cyclopropane-1,1-dicarboxamide (168)

Using Compound 165 in place of Compound 164. MS (EI) for $C_{27}H_{21}F_2N_5O_5$, found 534 (MH+).

1-N'-[4-[(6-Carbamoyl-7-methoxy-1,5-naphthyridin-4-yl)oxy]-3-chlorophenyl]-1-N-(4-fluorophenyl)cyclopropane-1,1-dicarboxamide (169)

Using Compound 166 in place of Compound 164. MS (EI) for $C_{27}H_{21}ClFN_5O_5$, found 550 (MH+).

Example 34: 1-N'-(4-Fluorophenyl)-1-N-[4-[[7-methoxy-6-(methylcarbamoyl)-1,5-naphthyridin-4-yl]oxy]phenyl]cyclopropane-1,1-dicarboxamide (172)

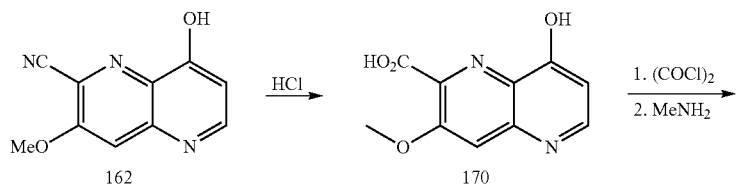

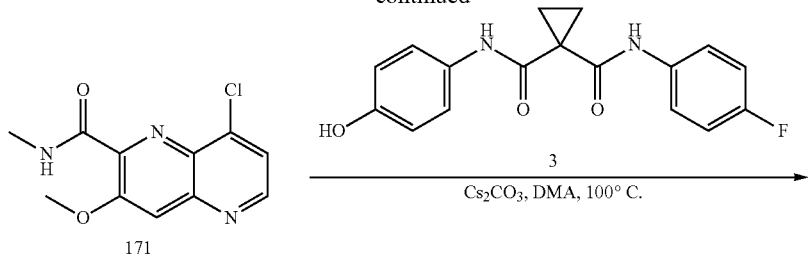

8-Hydroxy-3-methoxy-1,5-naphthyridine-2-carboxylic acid (170)

Compound 162 (100 mg, 0.5 mmol) in concentrated HCl (36%) (2 mL) was stirred at 85° C. overnight. The resulting reaction mixture was concentrated to dryness to give crude Compound 170 which was used in subsequent reactions without further purification. MS (EI) for $C_{10}H_8N_2O_4$, found 221 (MH+).

8-Chloro-3-methoxy-N-methyl-1,5-naphthyridine-2-carboxamide (171)

To crude Compound 170 was added DCE (3 mL) and $(COCl)_2$ (0.3 mL). The reaction mixture was refluxed for 2 hours and concentrated in vacuo, and the resulting residue was dissolved in DCM (5 mL). With efficient stirring at 0° C., TEA (0.8 mL) was added, followed by $MeNH_2 \cdot HCl$ (120 mg). The mixture was stirred at room temperature for 30 min and concentrated to afford crude Compound 171. MS (EI) for $C_{11}H_{10}ClN_3O_2$, found 252 (MH+).

1-N'-(4-Fluorophenyl)-1-N-[4-[[7-methoxy-6-(methylcarbamoyl)-1,5-naphthyridin-4-yl]oxy]phenyl] cyclopropane-1,1-dicarboxamide (172)

Compound 172 was made from Compound 171 and Compound 3 using a variation of the method used to prepare Compound 7 from Compound 6 in Step 3 of Example 2. $Cs_2CO_2$ in DMA was used in place of $K_2CO_3$ in DMF. MS (EI) for $C_{28}H_{24}FN_5O_5$, found 530 (MH+).

The following compound was prepared from Compound 171 in a method analogous to that used to produce Compound 28 from Compound 27 in Example 8 using the appropriately substituted N-(4-fluorophenyl)-N-(4-hydroxyphenyl)cyclopropane-1,1-dicarboxamide which were synthesized using a method analogous to that used in Example 1 or Example 5:

1-N'-[3-Fluoro-4-[[7-methoxy-6-(methylcarbamoyl)-1,5-naphthyridin-4-yl]oxy]phenyl]-1-N-(4-fluorophenyl)cyclopropane-1,1-dicarboxamide (173)

MS (EI) for $C_{28}H_{23}F_2N_5O_5$, found 548 (MH+).

The following compound can be prepared from Compound 170 in a sequence of reactions similar to that followed in Example 34 to form Compound 172 from Compound 170, substituting dimethylamine for the $MeNH_2 \cdot HCl$ in part 2 of step 2:

1-N-[4-[[6-(Dimethylcarbamoyl)-7-methoxy-1,5-naphthyridin-4-yl]oxy]phenyl]-1-N'-(4-fluorophenyl)cyclopropane-1,1-dicarboxamide (174)

MS (EI) for $C_{29}H_{26}FN_5O_5$, found 544 (MH+).

Example 35: 1-N'-[2,5-Difluoro-4-[(7-methoxy-1,5-naphthyridin-4-yl)oxy]phenyl]-1-N-(4-fluorophenyl) cyclopropane-1,1-dicarboxamide (176)

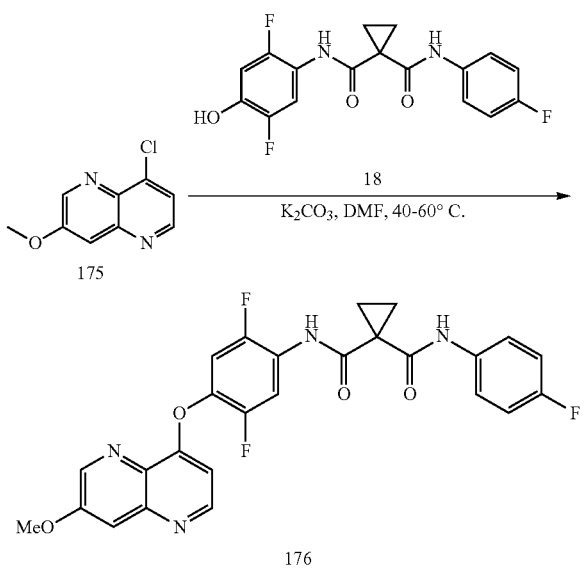

1-N'-[2,5-Difluoro-4-[(7-methoxy-1,5-naphthyridin-4-yl)oxy]phenyl]-1-N-(4-fluorophenyl)cyclopropane-1,1-dicarboxamide (176)
Compound 176 was made from Compound 175 in a manner analogous to the preparation of Compound 7 from Compound 6 in Step 3 of Example 2. MS for $C_{26}H_{19}F_3N_4O_4$, found 509 (MH+).
Example 36: 1-N-[4-[(6-Amino-7-methoxy-1,5-naphthyridin-4-yl)oxy]phenyl]-1-N'-(4-fluorophenyl)cyclopropane-1,1-dicarboxamide (181)
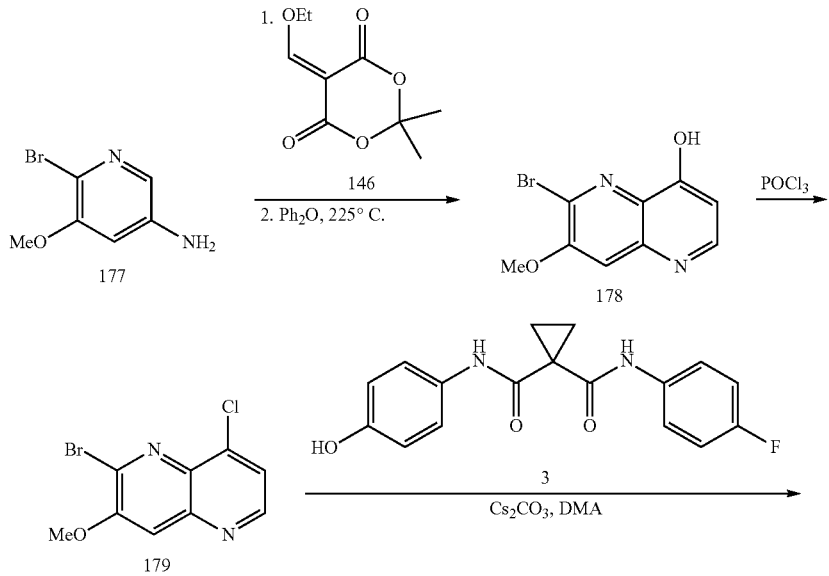
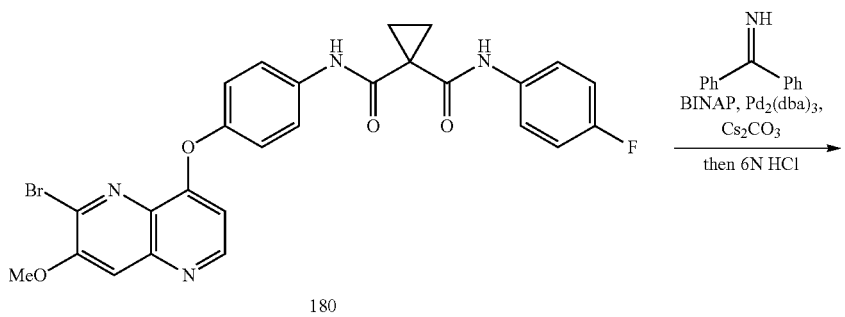

6-Bromo-7-methoxy-1,5-naphthyridin-4-ol (178)

Compound 178 can be made from Compound 177 and Compound 146 in a manner analogous to the preparation of Compound 136 from Compound 133 and Compound 134 in Steps 3 and 4 of Example 28. MS for $C_9H_7BrN_2O_2$, found 255/257 (MH+).

2-Bromo-8-chloro-3-methoxy-1,5-naphthyridine (179)

Compound 179 was made from Compound 178 in a manner analogous to the preparation of Compound 38 from Compound 37 in Step 2 of Example 9.

N-(4-((6-Bromo-7-methoxy-1,5-naphthyridin-4-yl) oxy)phenyl)-N-(4-fluorophenyl)cyclopropane-1,1-dicarboxamide (180)

Compound 180 was made from Compound 179 and Compound 3 using a variation of the method used to prepare Compound 7 from Compound 6 in Step 3 of Example 2. $Cs_2CO_2$ in DMA was used in place of $K_2CO_3$ in DMF. MS (EI) for $C_{26}H_{20}BrFN_4O_4$, found 550 (MH+).

1-N-[4-[(6-Amino-7-methoxy-1,5-naphthyridin-4-yl) oxy]phenyl]-1-N'-(4-fluorophenyl)cyclopropane-1,1-dicarboxamide (181)

A mixture of Compound 180 (50 mg, 0.091 mmol), diphenylmethanimine (181 mg, 1 mmol), $Pd_2(dba)_3$ (18 mg, 0.02 mmol), BINAP (12 mg, 0.02 mmol), and $Cs_2CO_3$ (49 mg, 0.16 mmol) in 1,4-dioxane (1.5 mL) was stirred at 120° C. for 6 hours. The mixture was cooled down to 20° C., diluted with EtOAc, and filtered. The filtrate was concentrated and purified by flash column chromatography and prep HPLC to give the Compound 181 as a solid (0.8 mg, 1.8% yield). MS (EI) for $C_{26}H_{22}FN_5O_4$, found 488 (MH+).

Example 37: 1-N'-(4-Fluorophenyl)-1-N-[4-[[7-methoxy-6-(1-methylpyrazol-4-yl)-1,5-naphthyridin-4-yl]oxy]phenyl]cyclopropane-1,1-dicarboxamide (182)

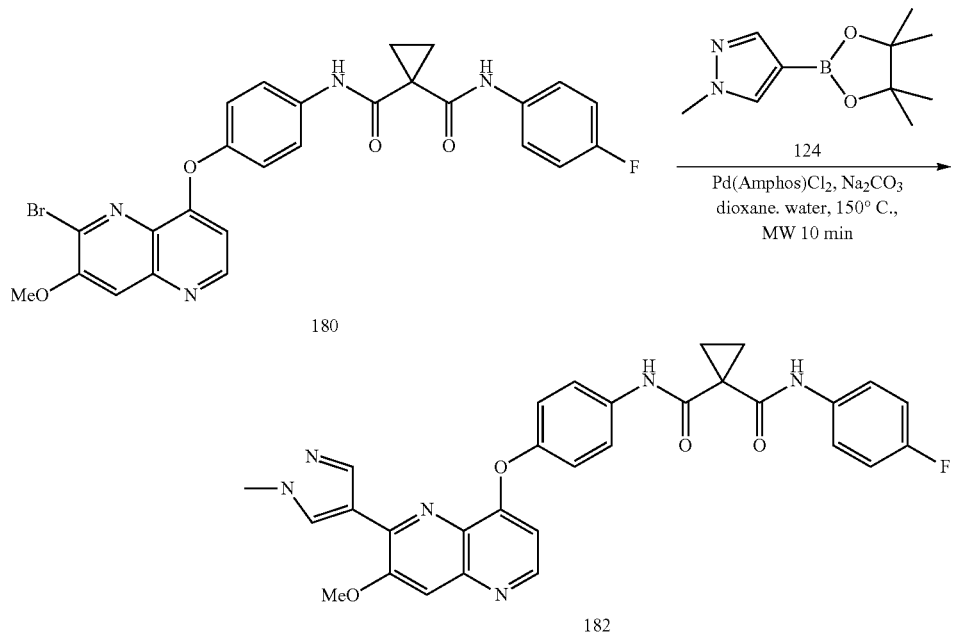

1-N'-(4-Fluorophenyl)-1-N-[4-[[7-methoxy-6-(1-methylpyrazol-4-yl)-1,5-naphthyridin-4-yl]oxy]phenyl]cyclopropane-1,1-dicarboxamide (182)

To a microwave reaction tube were added Compound 180 (50 mg, 0.09 mmol), Compound 124 (31 mg, 0.15 mmol), $Na_2CO_3$ (32 mg, 0.3 mmol), $Pd(Amphos)Cl_2$ (10 mg, 0.014 mmol), 1,4-dioxane (3 mL), and water (0.6 mL). The reaction mixture was irritated for 10 minutes at 150° C. After cooling, the mixture was extracted with EtOAc, washed with aq saturated NaCl, and concentrated. The crude product was purified by prep HPLC to give Compound 182 (2 mg, 3.6%). MS (EI) for $C_{30}H_{25}FN_6O_4$, found 553 (MH+).

The following compounds were prepared from Compound 180 in a method analogous to Compound 182 in Example 37.

243

1-N'-(4-Fluorophenyl)-1-N-[4-[[7-methoxy-6-(1H-pyrazol-4-yl)-1,5-naphthyridin-4-yl]oxy]phenyl]cyclopropane-1,1-dicarboxamide (183)

MS for $C_{29}H_{23}FN_6O_4$, found 539 (MH+).

1-N'-(4-Fluorophenyl)-1-N-[4-[[7-methoxy-6-(2-methylpyrazol-3-yl)-1,5-naphthyridin-4-yl]oxy]phenyl]cyclopropane-1,1-dicarboxamide (184)

MS for $C_{30}H_{25}FN_6O_4$, found 553 (MH+).

Example 38: 1-N'-(4-Fluorophenyl)-1-N-[4-[[6-(1-methylpyrazol-4-yl)-1,5-naphthyridin-4-yl]oxy]phenyl]cyclopropane-1,1-dicarboxamide (189)

244

6-(1-Methyl-1H-pyrazol-4-yl)-1,5-naphthyridin-4-ol (187)

In a microwave reaction tube were mixed Compound 186 (225 mg, 1.0 mmol), Compound 124 (270 mg, 1.3 mmol), $K_3PO_4$ (636 mg, 3.0 mmol), Pd(PPh$_3$)$_4$ (115 mg, 0.1 mmol), 1,4-dioxane (7 mL), and water (3 mL). The reaction mixture was irritated for 20 minutes at 150° C. After cooling, the mixture was diluted with EtOAc. The phases were separated and the aqueous phase was further extracted with 15% MeOH in EtOAc. The solvents were removed from the combined organic phases to give crude Compound 187 (227 mg), which was used in the next step without further purification.

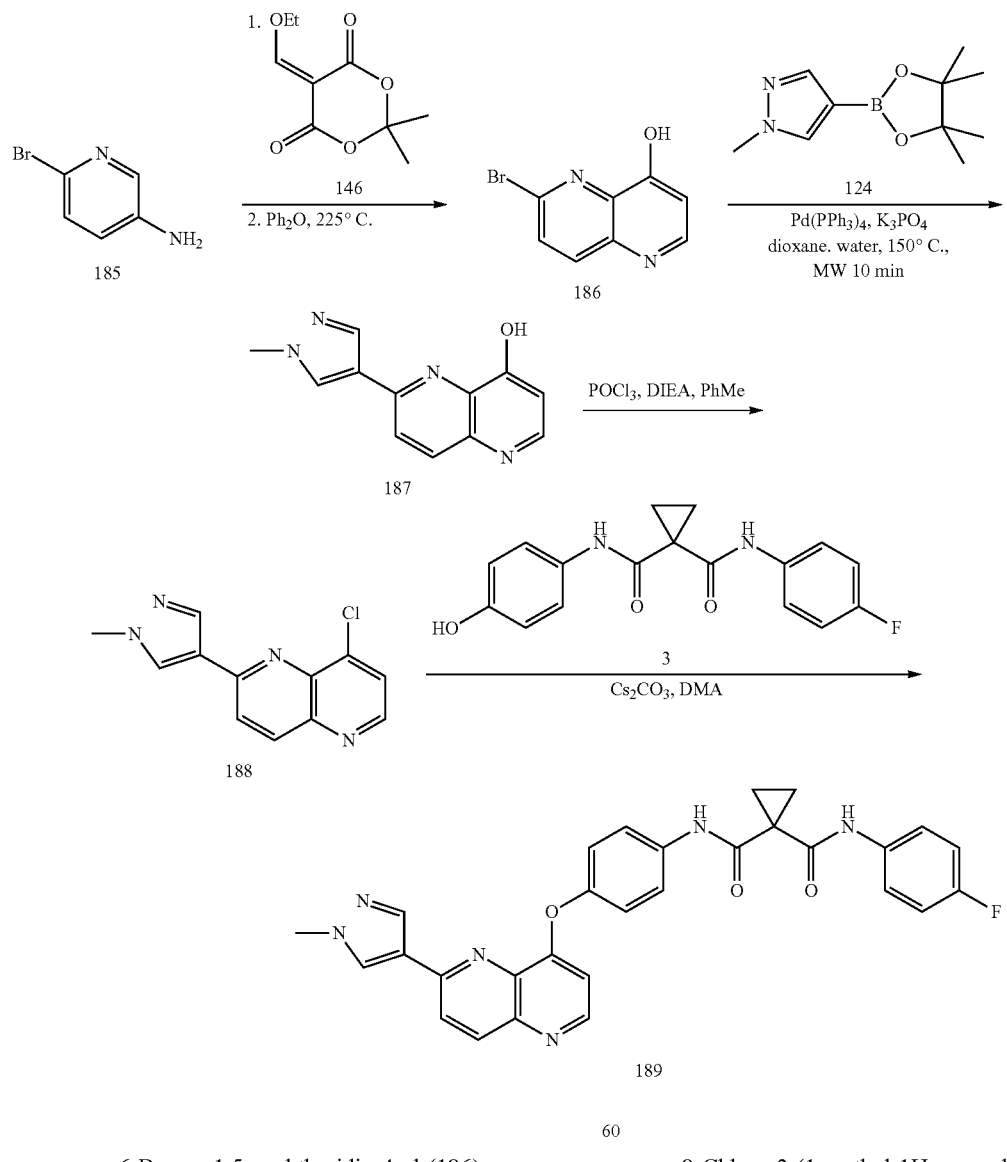

6-Bromo-1,5-naphthyridin-4-ol (186)

Compound 186 can be made from Compound 185 and Compound 146 in a manner analogous to the preparation of Compound 136 from Compound 133 and Compound 134 in Steps 3 and 4 of Example 28.

8-Chloro-2-(1-methyl-1H-pyrazol-4-yl)-1,5-naphthyridine (188)

Compound 188 was made from Compound 187 in a manner analogous to the preparation of Compound 11 from Compound 10 in Step 3 of Example 3. The crude product (36 mg) was used in the next step without further purification.

1-N'-(4-Fluorophenyl)-1-N-[4-[[6-(1-methylpyrazol-4-yl)-1,5-naphthyridin-4-yl]oxy]phenyl]cyclopropane-1,1-dicarboxamide (189)

Compound 189 (2 mg, 0.4% overall yield in 3 steps from Compound 186) was made from Compound 188 and Compound 3 using a variation of the method used to prepare Compound 7 from Compound 6 in Step 3 of Example 2. $Cs_2CO_2$ in DMA was used in place of $K_2CO_3$ in DMF. (EI) for $C_{29}H_{23}FN_6O_3$, found 523 (MH+).

BIOLOGICAL EXAMPLES

Kinase Assays

Kinase activity and compound inhibition were investigated using the $^{33}$P-Phosphoryl transfer radiometric kinase assay, performed using the KinaseProfiler™ service of Eurofins Pharma Discovery Services UK Limited. Dose-response experiments were performed using nine compound concentrations in a 96-well microtiter plate. For each assay, all compounds were prepared to a 50× final assay concentration (50 µM) in 100% DMSO, then diluted in a half-log series, with the final top concentration at 1 µM. This working stock of the compound was added to the assay well as the first component in the reaction, followed by the remaining components as detailed in the following assay protocols below. The positive control wells (100% kinase activity) contain all components of the reaction including 2% DMSO (control for solvent effects), except the compound of interest. Blank wells contain all components of the reaction, with the reference inhibitor, staurosporine. This reference compound was used to abolish kinase activity and generated the 0% kinase activity base-line. $IC_{50}$ values were calculated by nonlinear regression analysis using the sigmoidal dose-response (variable slope) curve fit on XLFit version 5.3 (ID Business Solutions).

Example A: Human AXL Kinase Assay

Human Axl (residues H473-A894 with Q764R, 161 nM) was incubated with 8 mM MOPS pH 7.0, 0.2 mM EDTA, 250 µM KKSRGDYMTMQIG (SEQ ID NO. 43), 10 mM magnesium acetate and 10 µM [γ-33P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example B: Human KDR Kinase Assay

Human KDR (residues K790-V1356, 55 nM) was incubated with 8 mM MOPS pH 7.0, 0.2 mM EDTA, 0.33 mg/mL myelin basic protein, 10 mM magnesium acetate, and 10 µM [γ-$^{33}$P-ATP], The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example C: Human Mer Kinase Assay

Human Mer (residues R557-E882 with H628Q and R794A, 0.7 nM) was incubated with 8 mM MOPS pH 7.0, 0.2 mM EDTA, 30 mM NaCl, 250 µM GGMEDIYFEFMGGKKK (SEQ ID NO. 44), 10 mM magnesium acetate, and 10 µM [γ-33P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated 33P was measured using the Wallac Microbeta scintillation counter (Perkin Elmer).

Example D: Human Met Kinase Assay

Human Met (residues R974-S1390 with A1209G and V1290L, 3.4 nM) was incubated with 8 mM MOPS pH 7.0, 0.2 mM EDTA, 250 UM KKKGQEEEYVFIE (SEQ ID NO. 45), 1 mM sodium orthovanadate, 5 mM sodium-6-glycerophosphate, 10 mM magnesium acetate, and 10 µM [γ-33P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated 33P was measured using the Wallac Microbeta scintillation counter (Perkin Elmer).

Activity data obtained for the Example compounds using the kinase assays in Examples A, C, and D is provided in Table 4 (A: $IC_{50}$≤10 nM; B: 10 nM<IC50≤100 nM; C: 100 nM<$IC_{50}$≤1000 nM; D: $IC_{50}$>1000 nM).

TABLE 4

Biological Activities of Selected Compounds

| Compound No. | IUPAC Name | Axl $IC_{50}$ (nM) | Mer $IC_{50}$ (nM) | c-Met $IC_{50}$ (nM) |
|---|---|---|---|---|
| 7 | 1-N'-(4-fluorophenyl)-1-N-(4-pyrido[3,2-d]pyrimidin-4-yloxyphenyl)cyclopropane-1,1-dicarboxamide | D | D | C |
| 12 | 1-N-[4-(7-chloropyrido[3,2-d]pyrimidin-4-yl)oxyphenyl]-1-N'-(4-fluorophenyl)cyclopropane-1,1-dicarboxamide | D | C | C |
| 13 | 1-N-[4-(7-bromopyrido[3,2-d]pyrimidin-4-yl)oxyphenyl]-1-N'-(4-fluorophenyl)cyclopropane-1,1-dicarboxamide | C | C | C |
| 16 | 1-N'-(4-fluorophenyl)-1-N-[4-(7-methoxypyrido[3,2-d]pyrimidin-4-yl)oxyphenyl]cyclopropane-1,1-dicarboxamide | C | C | B |
| 28 | 1-N-[4-(6,7-dimethoxypyrido[3,2-d]pyrimidin-4-yl)oxyphenyl]-1-N'-(4-fluorophenyl)cyclopropane-1,1-dicarboxamide | A | A | B |
| 29 | 1-N'-[3-chloro-4-(6,7-dimethoxypyrido[3,2-d]pyrimidin-4-yl)oxyphenyl]-1-N-(4- | B | A | A |

TABLE 4-continued

Biological Activities of Selected Compounds

| Compound No. | IUPAC Name | Axl IC$_{50}$ (nM) | Mer IC$_{50}$ (nM) | c-Met IC$_{50}$ (nM) |
|---|---|---|---|---|
| | fluorophenyl)cyclopropane-1,1-dicarboxamide | | | |
| 30 | 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide | A | A | A |
| 43 | 1-N-[4-(6,7-dimethylpyrido[3,2-d]pyrimidin-4-yl)oxyphenyl]-1-N'-(4-fluorophenyl)cyclopropane-1,1-dicarboxamide | C | C | C |
| 52 | 1-N'-(4-fluorophenyl)-1-N-[4-(6,7,8,9-tetrahydropyrimido[5,4-b]quinolin-4-yloxy)phenyl]cyclopropane-1,1-dicarboxamide | C | C | C |
| 57 | 1-N-[4-(6-cyano-7-methoxypyrido[3,2-d]pyrimidin-4-yl)oxyphenyl]-1-N'-(4-fluorophenyl)cyclopropane-1,1-dicarboxamide | C | B | C |
| 65 | 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide | B | A | B |
| 66 | 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide | A | A | A |
| 67 | 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide | A | A | A |
| 85 | 1-N'-(4-fluorophenyl)-1-N-(4-pyrido[3,4-d]pyrimidin-4-yloxyphenyl)cyclopropane-1,1-dicarboxamide | C | C | C |
| 88 | 1-N-[4-(6-chloropyrido[3,4-d]pyrimidin-4-yl)oxyphenyl]-1-N'-(4-fluorophenyl)cyclopropane-1,1-dicarboxamide | C | C | D |
| 91 | 1-N'-(4-fluorophenyl)-1-N-[4-(6-methoxypyrido[3,4-d]pyrimidin-4-yl)oxyphenyl]cyclopropane-1,1-dicarboxamide | C | B | C |
| 95 | 1-N'-(4-fluorophenyl)-1-N-(4-pyrido[4,3-d]pyrimidin-4-yloxyphenyl)cyclopropane-1,1-dicarboxamide | C | C | C |
| 101 | 1-N-[4-(7-chloropyrido[4,3-d]pyrimidin-4-yl)oxyphenyl]-1-N'-(4-fluorophenyl)cyclopropane-1,1-dicarboxamide | C | C | C |
| 104 | 1-N'-(4-fluorophenyl)-1-N-[4-(7-methoxypyrido[4,3-d]pyrimidin-4-yl)oxyphenyl]cyclopropane-1,1-dicarboxamide | B | B | B |
| 106 | 1-N-[4-(6-cyanoquinolin-4-yl)oxyphenyl]-1-N'-(4-fluorophenyl)cyclopropane-1,1-dicarboxamide | D | C | D |
| 115 | 1-N'-(4-fluorophenyl)-1-N-[4-[7-methoxy-6-(oxetan-3-ylcarbamoyl)quinazolin-4-yl]oxyphenyl]cyclopropane-1,1-dicarboxamide | B | B | B |
| 116 | 1-N-[4-[6-(cyclopropylcarbamoyl)-7-methoxyquinazolin-4-yl]oxyphenyl]-1-N'-(4-fluorophenyl)cyclopropane-1,1-dicarboxamide | B | B | B |
| 117 | 1-N-[4-(6-carbamoyl-7-methoxy-quinazolin-4-yl)oxyphenyl]-1-N'-(4-fluorophenyl)cyclopropane-1,1-dicarboxamide | B | A | B |
| 118 | 1-N'-(4-fluorophenyl)-1-N-[4-[7-methoxy-6-(2-pyrrolidin-1-ylethylcarbamoyl)quinazolin-4-yl]oxyphenyl]cyclopropane-1,1-dicarboxamide | B | A | B |
| 119 | tert-butyl (2R)-2-[[[4-[4-[[1-[(4-fluorophenyl)carbamoyl]cyclopropane-carbonyl]amino]phenoxy]-7-methoxyquinazoline-6-carbonyl]amino]methyl]pyrrolidine-1-carboxylate | B | B | C |
| 120 | tert-butyl (2S)-2-[[[4-[4-[[1-[(4-fluorophenyl)carbamoyl]cyclopropane-carbonyl]amino]phenoxy]-7-methoxyquinazoline-6-carbonyl]amino]methyl]pyrrolidine-1-carboxylate | B | B | C |
| 121 | 1-N'-(4-fluorophenyl)-1-N-[4-[7-methoxy-6-[[(2R)-pyrrolidin-2-yl]methylcarbamoyl]quinazolin-4-yl]oxyphenyl]cyclopropane-1,1-dicarboxamide | A | A | A |
| 122 | 1-N'-(4-fluorophenyl)-1-N-[4-[7-methoxy-6-[[(2S)-pyrrolidin-2-yl]methylcarbamoyl]quinazolin-4-yl]oxyphenyl]cyclopropane-1,1-dicarboxamide | A | A | B |
| 139 | 1-N-[4-[(6,7-dimethoxy-1,5-naphthyridin-4-yl)oxy]phenyl]-1-N'-(4-fluorophenyl)cyclopropane-1,1-dicarboxamide | A | A | A |
| 140 | 1-N'-[4-[(6,7-dimethoxy-1,5-naphthyridin-4-yl)oxy]-3-fluorophenyl]-1-N-(4-fluorophenyl)cyclopropane-1,1-dicarboxamide | A | A | A |
| 141 | 1-N'-[3-chloro-4-[(6,7-dimethoxy-1,5-naphthyridin-4-yl)oxy]phenyl]-1-N-(4-fluorophenyl)cyclopropane-1,1-dicarboxamide | B | A | A |

Example E: AXE Autophosphorylation ELISA in A-172 Cells

A-172 glioblastoma cells (ATCC #CRL-1620) were seeded at 2.5×10$^5$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). A-172 cells were incubated at 37° C., 5% CO$_2$ for 24 h and then starved for 24 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 1 µg/mL recombinant human Gas6 (R&D Systems #885-GSB-500) for 15 min, washed with cold PBS, and immediately lysed with 150 µL of cold IX lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 µL/well added into the human phospho-AXL Duo Set IC ELISA (R&D Systems #DYC2228-2). Assay was performed according to manufacturer's instructions and sample phospho-AXL concentrations were extrapolated using human phospho-AXL control (R&D Systems #841645) as a standard. Positive control wells (100% activity) contained Gas6-stimulated, DMSO-treated cell lysates. Negative control wells (0% activity) contained Gas6-stimulated, reference inhibitor-treated cell lysates. IC$_{50}$ values were calculated by nonlinear regression analysis using a 4-parameter logistic curve fit in ActivityBase XL (IDBS).

Example F: Met Autophosphorylation ELISA in PC-3 Cells

PC-3 prostate cancer cells (ATCC #CRL-1435) were seeded at 4×10$^4$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). PC-3 cells were incubated at 37° C., 5% CO$_2$ for 24 h and then starved for 3 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human HGF (R&D Systems #294-HG-250) for 10 min, washed with cold PBS, and immediately lysed with 130 µL of cold IX lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 100 µL/well added into the PathScan phospho-Met (panTyr) Sandwich ELISA (Cell Signaling Technology #7333). Assay was performed according to manufacturer's instructions. Positive control wells (100% activity) contained HGF-stimulated, DMSO-treated cell lysates. Negative control wells (0% activity) contained HGF-stimulated, reference inhibitor-treated cell lysates. IC$_{50}$ values were calculated by nonlinear regression analysis using a 4-parameter logistic curve fit in ActivityBase XL (IDBS).

Example G: KDR Autophosphorylation ELISA in HUVEC Cells

Human umbilical vein endothelial cells or HUVEC (Lonza #C2519A) were seeded at 2×10$^4$ cells/well onto 96-well plates (Corning #3904), in EGM-2 growth medium (Lonza #CC-3162) containing 1% Penicillin Streptomycin (Thermo Fisher #15140-122). HUVEC cells were incubated at 37° C., 5% CO$_2$ for 24 h and then starved for 24 h in serum-free EBM-2 basal medium (Lonza #CC-3156) containing 1% Penicillin Streptomycin. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human VEGF165 (R&D Systems #293-VE-500) for 5 min, washed with cold PBS, and immediately lysed with 130 µL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 µL/well added into the human phospho-KDR Duo Set IC ELISA (R&D Systems #DYC 1766-2). Assay was performed according to manufacturer's instructions and sample phospho-KDR concentrations were extrapolated using human phospho-KDR control (R&D Systems #841421) as a standard. Positive control wells (100% activity) contained VEGF165-stimulated, DMSO-treated cell lysates. Negative control wells (0% activity) contained non-stimulated cell lysates. IC$_{50}$ values were calculated by nonlinear regression analysis using a 4-parameter logistic curve fit in ActivityBase XE (IDBS).

Example H: Mer Autophosphorylation ELISA in Transient Transfected 293A Cells 293A cells (Thermo Fisher #R70507) were seeded at 1.5×10$^6$ cells/well onto 100 mm dish (Greiner #664169), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). 293A cells were incubated at 37° C., 5% CO$_2$ for 24 h and then transfected with 6 µg MERTK DNA (Genecopoeia #EX-Z8208-M02) using TransIT LT1 transfection reagent (Mirus-Bio #MIR2305). After 24 h incubation, the transfected 293A cells were seeded at 1×10$^5$ cells/well onto 96-well plates (Corning #3904) in DMEM growth medium overnight. Test compounds were serially diluted to produce an 8-point dose curve in fresh serum-free medium to a final concentration of 0.3% DMSO (vehicle) and added to the cells and incubated for 1 h. Cells were then immediately lysed with 150 µL of cold IX lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 50 µL/well added into the human phospho-Mer DuoSet IC ELISA (R&D Systems #DYC2579-2). Assay was performed according to manufacturer's instructions and sample phospho-Mer concentrations were extrapolated using human phospho-Mer control (R&D Systems #841793) as a standard. Positive control wells (100% activity) contained DMSO-treated cell lysates. Negative control wells (0% activity) contained reference inhibitor-treated cell lysates. IC$_{50}$ values were calculated by nonlinear regression analysis using a 4-parameter logistic curve fit in ActivityBase XE (IDBS).

Compounds of the present disclosure, as exemplified herein, showed IC$_{50}$ values in the following ranges: A: IC$_{50}$≤10 nM; B: 10 nM<IC$_{50}$≤100 nM; C: 100 nM<IC$_{50}$≤300 nM; D: IC$_{50}$>300 nM. "NT" means not tested.

Activity data obtained for the Example compounds using cell based kinase assays in Examples F, G, H and I is provided in Table 5.

TABLE 5

| Cellular Activities of Selected Compounds | | | | |
|---|---|---|---|---|
| Compound No. | Axl IC$_{50}$ (nM) | Mer IC$_{50}$ (nM) | c-Met IC$_{50}$ (nM) | KDR IC$_{50}$ (nM) |
| 7 | NT | NT | NT | NT |
| 12 | NT | NT | NT | NT |
| 13 | NT | NT | NT | NT |
| 16 | NT | NT | NT | NT |
| 19 | B | B | B | C |
| 28 | B | B | C | B |
| 29 | B | NT | B | A |
| 30 | A | A | B | A |
| 31 | A | B | B | B |
| 32 | B | NT | C | C |
| 33 | C | NT | D | C |

TABLE 5-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 34 | A | A | B | B |
| 35 | A | A | A | B |
| 43 | NT | NT | NT | NT |
| 52 | NT | NT | NT | NT |
| 57 | NT | NT | NT | NT |
| 65 | A | B | B | A |
| 66 | A | NT | B | A |
| 67 | A | A | B | A |
| 68 | B | B | C | B |
| 69 | A | A | B | B |
| 70 | B | B | C | C |
| 71 | B | D | C | B |
| 72 | A | B | B | B |
| 73 | A | A | B | A |
| 74 | C | NT | D | B |
| 75 | B | B | B | B |
| 76 | A | A | B | B |
| 78 | B | NT | C | A |
| 79 | A | A | B | A |
| 80 | B | A | B | A |
| 81 | A | A | B | B |
| 82 | A | B | B | A |
| 83 | A | A | B | A |
| 85 | NT | NT | NT | NT |
| 88 | NT | NT | NT | NT |
| 91 | D | NT | D | D |
| 95 | NT | NT | NT | NT |
| 101 | NT | NT | NT | NT |
| 104 | D | NT | D | D |
| 106 | NT | NT | NT | NT |
| 115 | D | NT | C | B |
| 116 | C | NT | C | B |
| 117 | A | NT | C | B |
| 118 | B | B | C | C |
| 119 | C | NT | D | B |
| 120 | D | NT | D | C |
| 121 | B | NT | C | C |
| 122 | B | NT | C | D |
| 126 | C | NT | D | D |
| 129 | B | C | C | C |
| 130 | B | B | B | A |
| 139 | A | A | B | A |
| 140 | A | A | A | A |
| 141 | B | NT | A | A |
| 142 | A | NT | B | A |
| 149 | A | A | B | A |
| 150 | A | A | A | A |
| 151 | B | B | B | A |
| 152 | A | NT | B | A |
| 153 | A | NT | B | A |
| 157 | D | NT | D | D |
| 158 | D | NT | D | D |
| 159 | D | NT | C | D |
| 164 | C | NT | D | C |
| 165 | B | NT | C | C |
| 166 | C | NT | C | B |
| 167 | C | NT | D | D |
| 168 | D | NT | C | D |
| 169 | B | NT | B | B |
| 172 | C | NT | D | D |
| 173 | C | NT | C | C |
| 174 | D | NT | C | D |
| 176 | A | NT | B | C |
| 181 | NT | NT | NT | NT |
| 182 | NT | NT | NT | NT |
| 183 | D | NT | D | D |
| 184 | D | NT | D | D |
| 189 | NT | NT | NT | NT |

Example I: Pharmacokinetic Studies

Pharmacokinetic properties of select compounds as described herein were assessed in male Sprague-Dawley rats. The non-GLP study was designed to investigate the pharmacokinetics of chosen compounds in plasma following an intravenous or oral dose administration to male Sprague Dawley rats. Two groups of male Sprague-Dawley rats (three animals per group) received either an intravenous or oral (gavage) dose of compound at target dose levels of 3 mg/kg. Animals were observed for any clinically relevant abnormalities during dosing and at each sample collection period.

Animals in the PO group were fasted overnight prior to dose administration. Food was returned following the collection of the 4-hour blood sample. Water was not withheld.

Immediately prior to dosing, the body weight of each animal was recorded. Doses (rounded to the nearest 0.001 mL) were calculated based on the pretreatment body weight (kg) and a dose volume of 2.5 mL/kg for intravenous administration and 5 mL/kg for oral administration. Intravenous formulations were administered via a jugular vein cannula. Immediately after dosing, the cannula was flushed with saline and the line was tied off. The oral dose was administered via a ball-tipped feeding needle. Dosing syringe volumes for administration were second-person verified prior to dosing and that volume along with the results for the concentration verification analysis were used to calculate the actual dose administered. Dosing syringes were weighed immediately prior to and immediately after dosing each animal as a gravimetric check.

Serial blood samples (approximately 200 µL per sample) were collected from each animal at 0.083 (IV dosing only), 0.25, 0.5, 1, 2, 4, 6 (PO dosing only), 8, 24, 32, 48, and 72 hours after dosing. Blood samples were collected into tubes containing K$_2$EDTA via the non-dosing jugular-vein cannula (JVC), which was flushed with an approximately equal volume of saline following each collection.

Blood samples were stored on wet ice until processed to plasma by centrifugation (3500 rpm at 5° C. for 10 minutes) within 1 hour of collection. Plasma samples were transferred into matrix tubes and then stored in a −80° C. freezer.

Plasma samples and dose formulation samples were analyzed for the compounds of interest using liquid chromatography-tandem mass spectrometry (LC-MS/MS) methods. Pharmacokinetic parameter estimates were calculated from the individual animal plasma concentration-time data using the actual dose based on the analysis of the dosing formulations, nominal sampling times (all collections were within an acceptable range of target), and non-compartmental methods. The concentration-time data were analyzed to fit either an intravenous—bolus (IV) plasma analysis model (201) or extra-vascular (PO) dosing plasma analysis model (200) using the software WinNonlin Phoenix version 6.3 (Pharsight). The single-dose pharmacokinetic parameters assessed include, as appropriate: C$_{max}$ (observed peak or maximum concentration); T$_{max}$ (observed time of peak concentration); T$_{1/2}$ (terminal half-life); V$_z$ (volume of distribution based on the terminal phase); V$_{ss}$ (volume of distribution at steady state); AUC$_{INF}$ (area under the concentration-time curve computed from time zero to infinity); AUC$_{last}$ (area under the concentration-time curve computed from time zero to the time of the last quantifiable concentration); C$_0$ (back-extrapolated concentration at time zero); CL (total body clearance); Vz/F (volume of distribution for extravascular administration based on the terminal phase); CLZF (total body clearance for extravascular administration); F % (bioavailability); and MRT$_{last}$ (mean residence time).

Areas-under-the-plasma concentration-time curves (AUC) were estimated using the linear-log trapezoidal rule. The area through the time (T$_{last}$) of the last observable concentration ($C_{last}$) is reported as $AUC_{last}$. AUC extrapolated to infinity, ($AUC_{INF}$) was estimated by adding $AUC_{last}$ and the ratio of $C_{last}/\lambda_z$, where $\lambda_z$ is the terminal rate constant. Apparent terminal half-life ($T_{1/2}$) was calculated as $\ln(2)/\lambda_z$ and determined using the slope of the log-linear terminal phase of the concentration-time curve, defined by a minimum of three plasma concentration-time points. Half-lives are reported if the correlation for the regression line, as measured by r squared, is ≥0.9 when rounded. After IV administration, volume of distribution (Vz) was calculated as $Dose/\lambda_z * AUC_{INF-obs}$, clearance (CL) was calculated as $Dose/AUC_{INF-obs}$ and volume of distribution at steady state ($V_{ss}$) was estimated as $MRT_{INF}*CL$. Mean residence time (MRT) from the time of dosing to the time of the last measurable concentration was calculated as $AUMC_{last}/AUC_{last}$. For model 200 the bioavailability (i.e. fraction of total dose that reaches the systemic circulation) cannot be calculated. Consequently, volume and clearance for this model is Vz/F or CL/F, respectively; where F is defined as bioavailability (i.e. fraction of total dose that reaches the systemic circulation; (Average $AUC_{last-po}$/Average $AUC_{last-iv}$)*[$Dose_{IV}/Dose_{PO}$]*100).

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A compound of Formula I':

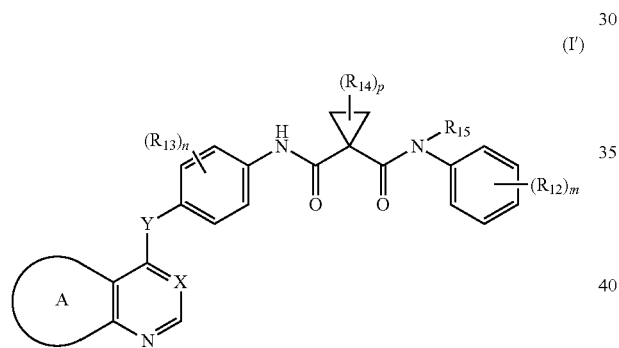

or a pharmaceutically acceptable salt thereof, wherein:

Y is selected from the group consisting of O, S, SO, $SO_2$, NH, and —N($C_{1-6}$ alkyl)-;

ring A is

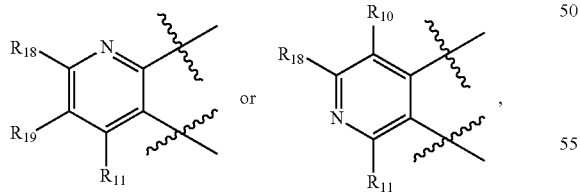

wherein $R_{18}$ and $R_{19}$ are each independently selected from the group consisting of H, halo, ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, 5-14 membered heteroaryl, —CN, —$NO_2$, —$OR^a$, —$SR^a$, —$C(O)R^a$, —$C(O)NR^aR^a$, —$C(O)OR^a$, —$NHR^a$, —$NR^aR^a$, and —$NR^aC(O)R^a$, wherein the ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, and 5-14 membered heteroaryl are each optionally substituted with 1, 2, 3, 4, or 5 substituents independently selected from the group consisting of halo, ($C_1$-$C_6$) alkyl, —CN, and —OH; or $R_{18}$ and $R_{19}$ taken together with the atoms to which they are attached form a fused $C_{3-7}$ cycloalkyl ring or a fused 4- to 10-membered heterocycloalkyl ring;

$R_{10}$ and $R_{11}$ are H;

each $R_{13}$ is independently selected from the group consisting of —H; halo; —OH; —CN; optionally substituted ($C_1$-$C_6$) alkyl; ($C_1$-$C_6$) alkoxy; ($C_1$-$C_6$) haloalkoxy; —$NH_2$; —NH($C_1$-$C_6$)alkyl; —N($C_1$-$C_6$ alkyl)$_2$; and ($C_3$-$C_6$) cycloalkyl;

each $R_{14}$ is independently selected from the group consisting of H, halo, and ($C_1$-$C_6$) alkyl;

$R_{15}$ is H;

each $R_{12}$ is independently selected from the group consisting of —H and halo;

each $R^a$ is independently selected from the group consisting of —H, ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene-, wherein the ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene- of $R^a$ are each optionally substituted with 1, 2, 3, 4, or 5 substituents independently selected from the group consisting of ($C_1$-$C_6$) alkyl, ($C_1$-$C_6$) alkoxy, and —C(O)O($C_1$-$C_4$) alkyl;

the subscript n is an integer of 1, 2, 3, or 4;

the subscript m is an integer of 1, 2, 3, 4, or 5; and the subscript p is an integer of 0, 1, 2, 3, or 4; and X is N or CH.

2. The Compound of claim 1, having Formula I'b or I'd:

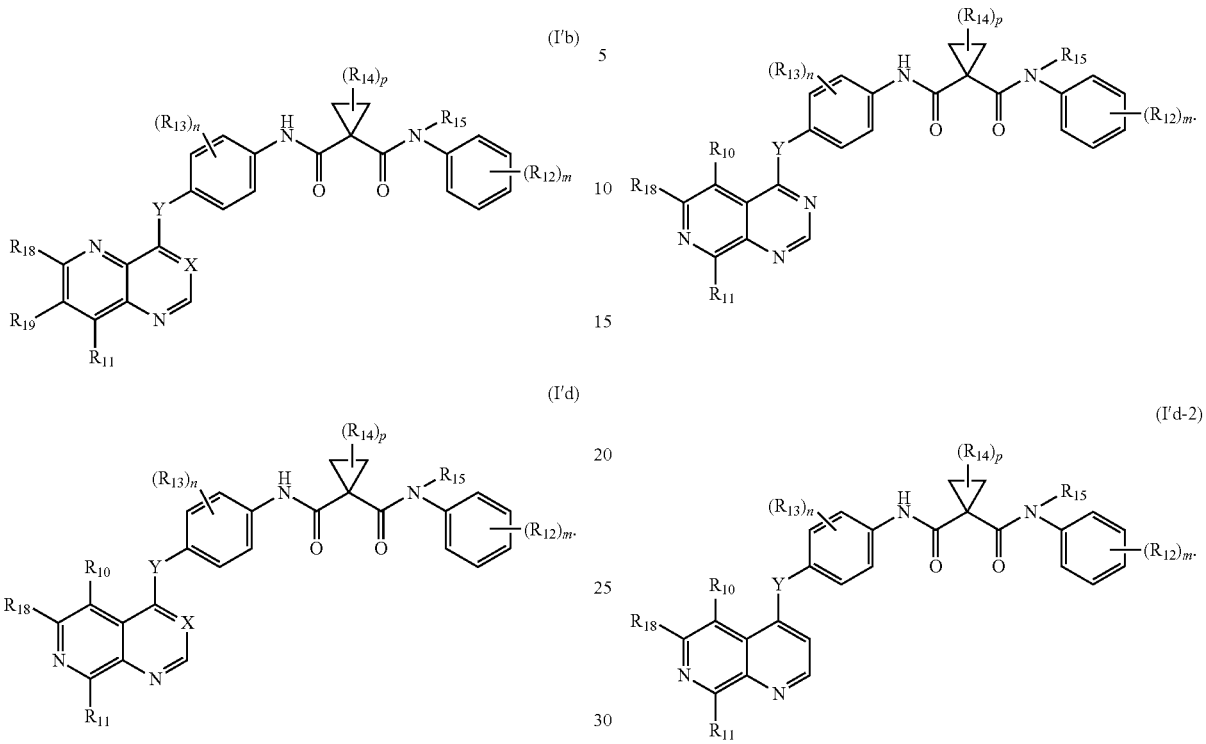

3. The compound of claim 2, having Formula I'b-1, I'b-2, Id'-1, or I'd-2:

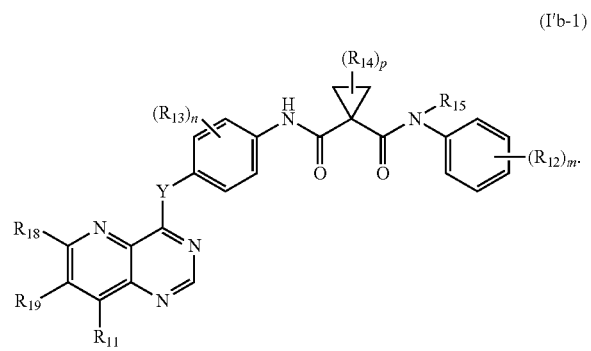

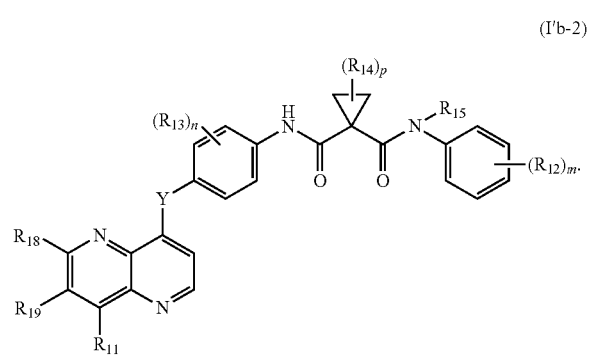

4. The compound of claim 3, wherein $R_{18}$ and $R_{19}$ are each independently selected from the group consisting of —H, halo, $(C_1-C_6)$ alkyl, phenyl, $(C_3-C_{10})$ cycloalkyl, 4-14 membered heterocycloalkyl, 5-14 membered heteroaryl, —CN, —O$(C_1-C_6)$ alkyl, —C(O)$(C_1-C_6)$ alkyl, —C(O)NH$_2$, —C(O)NH$(C_1-C_6)$ alkyl, —C(O)N$((C_1-C_6)$ alkyl$)_2$, —C(O)O$(C_1-C_6)$ alkyl, —NH$(C_1-C_6)$ alkyl, —N$((C_1-C_6)$ alkyl$)_2$, —NHC(O)$(C_1-C_6)$ alkyl, —O$(C_1-C_4$ alkylene-(4-14 membered heterocycloalkyl)), O$(C_1-C_6$ alkoxy-$C_1-C_6$ alkyl)), and —NH$_2$.

5. The compound of claim 3, wherein $R_{18}$ and $R_{19}$ are each independently H, halo, CN, $R^a$NHC(O)—, —OR$^a$ or 5- or 6-membered heteroaryl optionally substituted with $(C_1-C_6)$ alkyl.

6. The compound of claim 5, wherein the subscript m is 1; the subscript n is 1; and the subscript p is 1.

7. The compound of claim 1, wherein the compound is selected from the group consisting of:
  1-N'-(4-fluorophenyl)-1-N-(4-pyrido[3,2-d]pyrimidin-4-yloxyphenyl)cyclopropane-1,1-dicarboxamide
  1-N-[4-(7-chloropyrido[3,2-d]pyrimidin-4-yl)oxyphenyl]-1-N'-(4-fluorophenyl)cyclopropane-1,1-dicarboxamide
  1-N-[4-(7-bromopyrido[3,2-d]pyrimidin-4-yl)oxyphenyl]-1-N'-(4-fluorophenyl)cyclopropane-1,1-dicarboxamide
  1-N'- (4-fluorophenyl)-1-N-[4-(7-methoxypyrido[3,2-d]pyrimidin-4-yl)oxyphenyl]cyclopropane-1,1-dicarboxamide
  1-N'-[2,5-difluoro-4-(7-methoxypyrido[3,2-d]pyrimidin-4-yl)oxyphenyl]-1-N-(4-fluorophenyl)cyclopropane-1,1-dicarboxamide
  1-N-[4-(6,7-dimethoxypyrido[3,2-d]pyrimidin-4-yl)oxyphenyl]-1-N'-(4-fluorophenyl)cyclopropane-1,1-dicarboxamide 1-N'-[3-chloro-4-(6,7-dimethoxypyrido[3,2-d]pyrimidin-4-yl)oxyphenyl]-1-N-(4-fluorophenyl)cyclopropane-1,1-dicarboxamide 1-N'-[4-(6,7-dimethoxypyrido[3,2-d]pyrimidin-4-yl)oxy-3-fluorophenyl]-1-N-(4-fluorophenyl)cyclopropane-1,1-dicarboxamide 1-N'-[4-(6,7-dimethoxypyrido[3,2-d]pyrimidin-4-yl)oxy-2-fluorophenyl]-1-N-(4-fluorophenyl)cyclopropane-1,1-dicarboxamide 1-N'-[2-chloro-4-(6,7-dimethoxypyrido[3,2-d]pyrimidin-4-yl)oxyphenyl]-1-N-(4-fluorophenyl)cyclopropane-1,1-dicarboxamide 1-N'-[4-(6,7-dimethoxypyrido[3,2-d]pyrimidin-4-yl)oxy-2-methylphenyl]-1-N-(4-fluorophenyl)cyclopropane-1,1-dicarboxamide 1-N'-[4-(6,7-dimethoxypyrido[3,2-d]pyrimidin-4-yl)oxy-2,3-difluorophenyl]-1-N-(4-fluorophenyl)cyclopropane-1,1-dicarboxamide 1-N'-[4-(6,7-dimethoxypyrido[3,2-d]pyrimidin-4-yl)oxy-2,5-difluorophenyl]-1-N-(4-fluorophenyl)cyclopropane-1,1-dicarboxamide 1-N-[4-(6,7-dimethylpyrido[3,2-d]pyrimidin-4-yl)oxyphenyl]-1-N'-(4-fluorophenyl)cyclopropane-1,1-dicarboxamide 1-N'-(4-fluorophenyl)-1-N-[4-(6,7,8,9-tetrahydropyrimido[5,4-b]quinolin-4-yloxy)phenyl]cyclopropane-1,1-dicarboxamide 1-N-[4-(6-cyano-7-methoxypyrido[3,2-d]pyrimidin-4-yl)oxyphenyl]-1-N'-(4-fluorophenyl)cyclopropane-1,1-dicarboxamide 1-N'-(4-fluorophenyl)-1-N-[4-[6-methoxy-7-(3-morpholin-4-ylpropoxy)pyrido[3,2-d]pyrimidin-4-yl]oxyphenyl]cyclopropane-1,1-dicarboxamide 1-N'-[3-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N'-[3-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N-(4-fluorophenyl)-1-N'-[4-[6-methoxy-7-(3-morpholin-4-ylpropoxy)pyrido[3,2-d]pyrimidin-4-yl]oxy-3-methylphenyl]cyclopropane-1,1-dicarboxamide 1-N'-[2-fluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N'-[2-chloro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N-(4-fluorophenyl)-1-N'-[4-[6-methoxy-7-(3-morpholin-4-ylpropoxy)pyrido[3,2-d]pyrimidin-4-yl]oxy-2-methylphenyl]cyclopropane-1,1-dicarboxamide 1-N'-[2,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N'-[2,3-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N-(4-fluorophenyl)-1-N'-[3-methoxy-4-[6-methoxy-7-(3-morpholin-4-ylpropoxy)pyrido[3,2-d]pyrimidin-4-yl]oxyphenyl]cyclopropane-1,1-dicarboxamide 1-N'-[3-cyano-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N'-[3,5-difluoro-4-[6-methoxy-7-(3-morpholin-4-ylpropoxy)pyrido[3,2-d]pyrimidin-4-yl]oxyphenyl]-1-N-(4-fluorophenyl)cyclopropane-1,1-dicarboxamide 1-N'-(4-fluorophenyl)-1-N-[4-[6-methoxy-7-(2-methoxyethoxy)pyrido[3,2-d]pyrimidin-4-yl]oxyphenyl]cyclopropane-1,1-dicarboxamide 1-N'-[3-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide 1-N'-[3-chloro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide 1-N'-[2-fluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide 1-N'-[2,3-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide 1-N'-[2,5-difluoro-4-[6-methoxy-7-(2-methoxyethoxy)pyrido[3,2-d]pyrimidin-4-yl]oxyphenyl]-1-N-(4-fluorophenyl)cyclopropane-1,1-dicarboxamide 1-N'-(4-fluorophenyl)-1-N-(4-pyrido[3,4-d]pyrimidin-4-yloxyphenyl)cyclopropane-1,1-dicarboxamide 1-N-[4-(6-chloropyrido[3,4-d]pyrimidin-4-yl)oxyphenyl]-1-N'-(4-fluorophenyl)cyclopropane-1,1-dicarboxamide 1-N'-(4-fluorophenyl)-1-N-[4-(6-methoxypyrido[3,4-d]pyrimidin-4-yl)oxyphenyl]cyclopropane-1,1-dicarboxamide 1-N'-(4-fluorophenyl)-1-N-[4-[7-(1-methylpyrazol-4-yl)pyrido[3,2-d]pyrimidin-4-yl]oxyphenyl]cyclopropane-1,1-dicarboxamide 1-N-[4-[(6,7-dimethoxy-1,5-naphthyridin-4-yl)oxy]phenyl]-1-N'-(4-fluorophenyl)cyclopropane-1,1-dicarboxamide 1-N'-[4-[(6,7-dimethoxy-1,5-naphthyridin-4-yl)oxy]-3-fluorophenyl]-1-N-(4-fluorophenyl)cyclopropane-1,1-dicarboxamide 1-N'-[3-chloro-4-[(6,7-dimethoxy-1,5-naphthyridin-4-yl)oxy]phenyl]-1-N-(4-fluorophenyl)cyclopropane-1,1-dicarboxamide 1-N'-[4-[(6,7-dimethoxy-1,5-naphthyridin-4-yl)oxy]-2,5-difluorophenyl]-1-N-(4-fluorophenyl)cyclopropane-1,1-dicarboxamide 1-N'-(4-fluorophenyl)-1-N-[4-[[6-methoxy-7-(2-methoxyethoxy)-1,5-naphthyridin-4-yl]oxy]phenyl]cyclopropane-1,1-dicarboxamide 1-N'-[3-fluoro-4-[[6-methoxy-7-(2-methoxyethoxy)-1,5-naphthyridin-4-yl]oxy]phenyl]-1-N-(4-fluorophenyl)cyclopropane-1,1-dicarboxamide 1-N'-[3-chloro-4-[[6-methoxy-7-(2-methoxyethoxy)-1,5-naphthyridin-4-yl]oxy]phenyl]-1-N-(4-fluorophenyl)cyclopropane-1,1-dicarboxamide 1-N'-[2,5-difluoro-4-[[6-methoxy-7-(2-methoxyethoxy)-1,5-naphthyridin-4-yl]oxy]phenyl]-1-N-(4-fluorophenyl)cyclopropane-1,1-dicarboxamide 1-N'-[2,5-difluoro-4-[[6-methoxy-7-(2-morpholin-4-ylethoxy)-1,5-naphthyridin-4-yl]oxy]phenyl]-1-N-(4-fluorophenyl)cyclopropane-1,1-dicarboxamide 1-N-[4-(2,3-dihydro-[1,4]dioxino[2,3-b][1,5]naphthyridin-6-yloxy)phenyl]-1-N'-(4-fluorophenyl)cyclopropane-1,1-dicarboxamide 1-N'-[4-(2,3-dihydro-[1,4]dioxino[2,3-b][1,5]naphthyridin-6-yloxy)-3-fluorophenyl]-1-N-(4-fluorophenyl)cyclopropane-1,1-dicarboxamide 1-N'-[3-chloro-4-(2,3-dihydro-[1,4]dioxino[2,3-b][1,5]naphthyridin-6-yloxy)phenyl]-1-N-(4-fluorophenyl)cyclopropane-1,1-dicarboxamide 1-N-[4-[(6-cyano-7-methoxy-1,5-naphthyridin-4-yl)oxy]phenyl]-1-N'-(4-fluorophenyl)cyclopropane-1,1-dicarboxamide
1-N'-[4-[(6-cyano-7-methoxy-1,5-naphthyridin-4-yl)oxy]-3-fluorophenyl]-1-N-(4-fluorophenyl)cyclopropane-1,1-dicarboxamide
1-N'-[3-chloro-4-[(6-cyano-7-methoxy-1,5-naphthyridin-4-yl)oxy]phenyl]-1-N-(4-fluorophenyl)cyclopropane-1,1-dicarboxamide
1-N-[4-[(6-carbamoyl-7-methoxy-1,5-naphthyridin-4-yl)oxy]phenyl]-1-N'-(4-fluorophenyl)cyclopropane-1,1-dicarboxamide
1-N'-[4-[(6-carbamoyl-7-methoxy-1,5-naphthyridin-4-yl)oxy]-3-fluorophenyl]-1-N-(4-fluorophenyl)cyclopropane-1,1-dicarboxamide
1-N'-[4-[(6-carbamoyl-7-methoxy-1,5-naphthyridin-4-yl)oxy]-3-chlorophenyl]-1-N-(4-fluorophenyl)cyclopropane-1,1-dicarboxamide
1-N'-(4-fluorophenyl)-1-N-[4-[[7-methoxy-6-(methylcarbamoyl)-1,5-naphthyridin-4-yl]oxy]phenyl]cyclopropane-1,1-dicarboxamide
1-N'-[3-fluoro-4-[[7-methoxy-6-(methylcarbamoyl)-1,5-naphthyridin-4-yl]oxy]phenyl]-1-N-(4-fluorophenyl)cyclopropane-1,1-dicarboxamide
1-N-[4-[[6-(dimethylcarbamoyl)-7-methoxy-1,5-naphthyridin-4-yl]oxy]phenyl]-1-N'-(4-fluorophenyl)cyclopropane-1,1-dicarboxamide
1-N'-[2,5-difluoro-4-[(7-methoxy-1,5-naphthyridin-4-yl)oxy]phenyl]-1-N-(4-fluorophenyl)cyclopropane-1,1-dicarboxamide
1-N-[4-[(6-amino-7-methoxy-1,5-naphthyridin-4-yl)oxy]phenyl]-1-N'-(4-fluorophenyl)cyclopropane-1,1-dicarboxamide
1-N'-(4-fluorophenyl)-1-N-[4-[[7-methoxy-6-(1-methylpyrazol-4-yl)-1,5-naphthyridin-4-yl]oxy]phenyl]cyclopropane-1,1-dicarboxamide
1-N'-(4-fluorophenyl)-1-N-[4-[[7-methoxy-6-(1H-pyrazol-4-yl)-1,5-naphthyridin-4-yl]oxy]phenyl]cyclopropane-1,1-dicarboxamide
1-N'-(4-fluorophenyl)-1-N-[4-[[7-methoxy-6-(2-methylpyrazol-3-yl)-1,5-naphthyridin-4-yl]oxy]phenyl]cyclopropane-1,1-dicarboxamide, and
1-N'-(4-fluorophenyl)-1-N-[4-[[6-(1-methylpyrazol-4-yl)-1,5-naphthyridin-4-yl]oxy]phenyl]cyclopropane-1,1-dicarboxamide
or a pharmaceutically acceptable salt thereof.

8. The compound of claim 1, having Formula I:

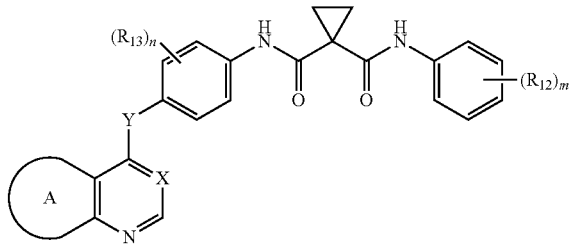

I wherein:
X is N or CH;
Y is O, S, SO, $SO_2$, NH, or N—($C_1$-$C_6$ alkyl);
$R_{13}$ is selected from the group consisting of —H, halo, —CN, and optionally substituted $C_{1-6}$ alkyl;
$R_{12}$ is —H or halo;

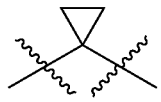 [SMILES: *C1(*)CC1]

is optionally substituted with one, two, three, or four groups independently selected from the group consisting of halo, and $C_1$-$C_6$ alkyl, wherein "〰" indicate points of attachment;

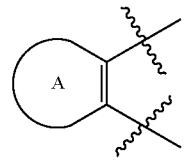

is selected from the group consisting of

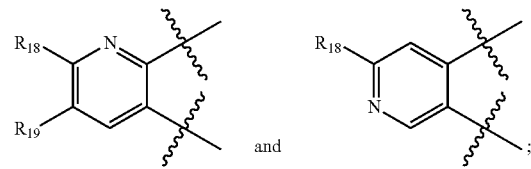

wherein $R_{18}$ and $R_{19}$ are selected from the group consisting of H, halo, —CN, optionally substituted $C_1$-$C_6$ alkyl, C(O)$NR_5R_6$, optionally substituted 5 or 6-membered heteroaryl, and optionally substituted $C_1$-$C_6$ alkoxy; or
when

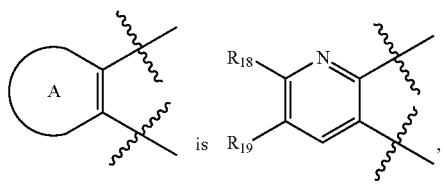

$R_{18}$ and $R_{19}$ can be joined together to form a 5 or 6-membered optionally substituted cycloalkyl or heterocycloalkyl;
$R_5$ and $R_6$ are selected from the group consisting of H, optionally substituted $C_{1-6}$ alkyl; and
m and n are each independently 1 or 2.

9. The compound of claim 8, wherein $R_{19}$ is selected from the group consisting of optionally substituted $C_1$-$C_6$ alkoxy and —CN.

10. The compound of claim 1, wherein

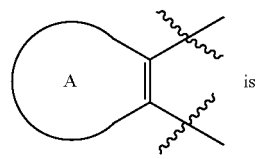 is

425
-continued

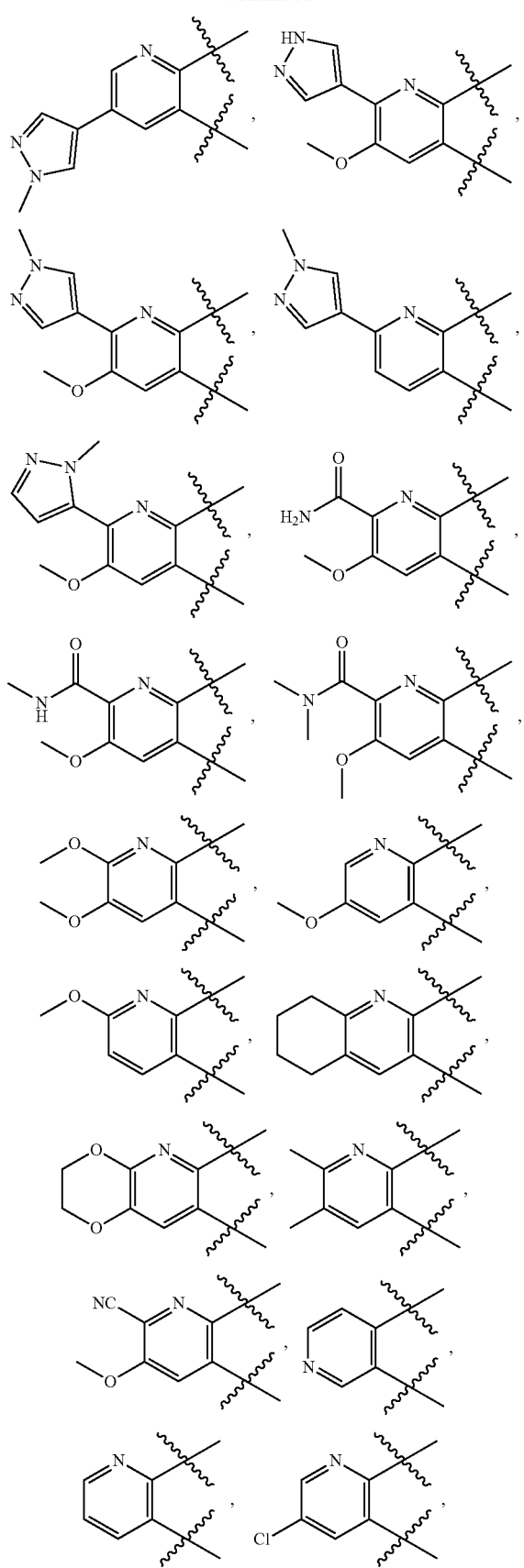

426
-continued

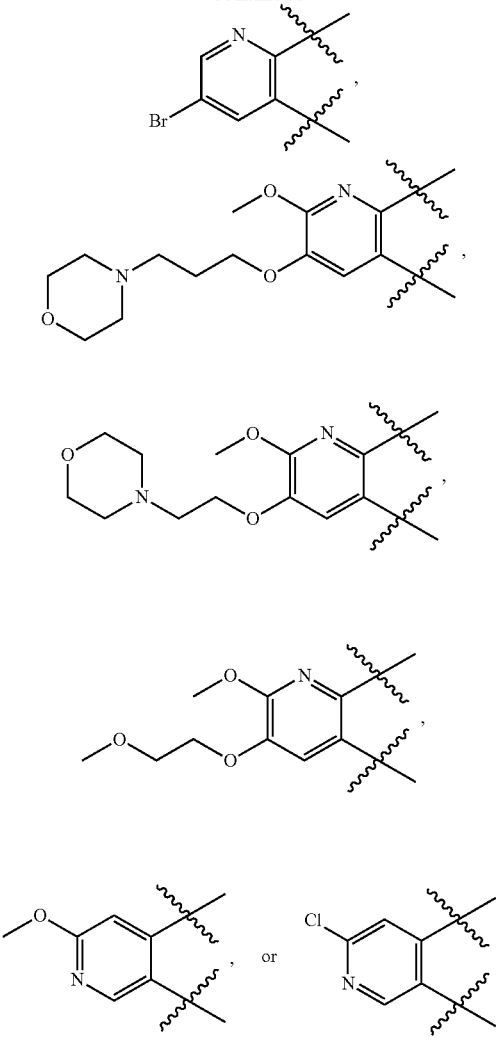

11. The compound of claim 8, wherein X is N.
12. The compound of claim 11, wherein $R_{13}$ is H.
13. The compound of claim 8, wherein

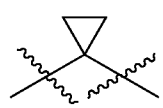 [SMILES: *C1(*)CC1]

is not substituted.

14. The compound of claim 13, wherein $R_{12}$ is halo.
15. The compound of claim 14, wherein $R_{12}$ is para fluoro.
16. The compound of claim 8, wherein $R_{18}$ and $R_{19}$ are joined together, with the atoms to which they are attached, to form a 5- or 6-membered optionally substituted heterocycloalkyl.
17. The compound of claim 16, wherein Y is O.
18. A pharmaceutical composition comprising a compound of claim 1 or a pharmaceutically acceptable salt thereof and a pharmaceutically acceptable carrier or excipient.

19. A process for making a compound of Formula I':

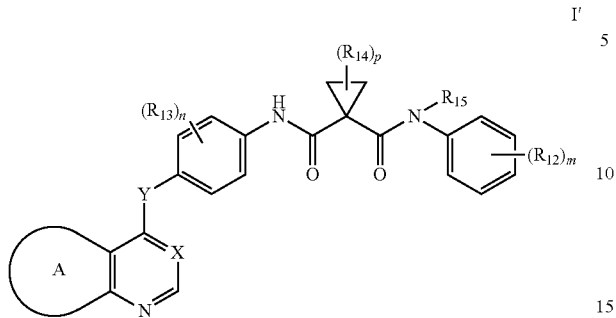

or a pharmaceutically acceptable salt thereof, comprising:
reacting a compound of Formula X:

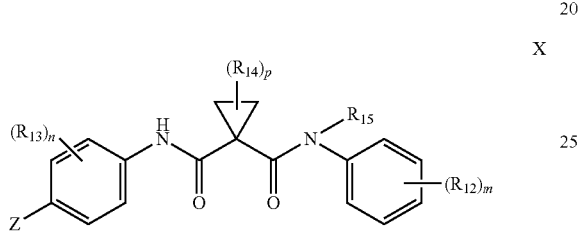

with a compound of Formula XI:

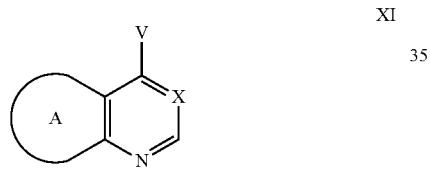

wherein
Y is selected from the group consisting of O, S, SO, $SO_2$, NH, and —N($C_{1-6}$ alkyl)-;
Z is selected from the group consisting of $NH_2$, SH, and OH;
V is a leaving group;
ring A is

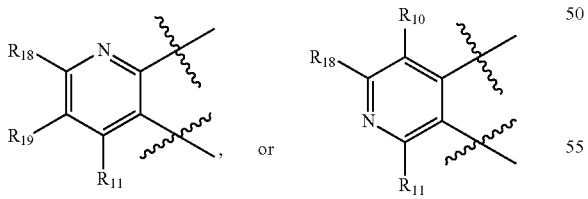

and X is N or CH, wherein
$R_{18}$ and $R_{19}$ are each independently selected from the group consisting of H, halo, ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, 5-14 membered heteroaryl, —CN, —$NO_2$, —$OR^a$, —$SR^a$, —C(O)$R^a$, —C(O)$NR^aR^a$, —C(O)$OR^a$, —$NHR^a$, —$NR^aR^a$, and —$NR^aC(O)R^a$, wherein the ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, and 5-14 membered heteroaryl are each optionally substituted with 1, 2, 3, 4, or 5 substituents independently selected from the group consisting of halo, ($C_1$-$C_6$) alkyl, —CN, and —OH; or $R_{18}$ and $R_{19}$ taken together with the atoms to which they are attached form a fused $C_{3-7}$ cycloalkyl ring or a fused 4- to 10-membered heterocycloalkyl ring;

$R_{10}$ and $R_{11}$ are H;

each $R_{13}$ is independently selected from the group consisting of —H; halo; —OH; —CN; optionally substituted ($C_1$-$C_6$) alkyl; ($C_1$-$C_6$) alkoxy; ($C_1$-$C_6$) haloalkoxy; —$NH_2$; —NH(C-$C_6$)alkyl; —N($C_1$-$C_6$ alkyl)$_2$; and ($C_3$-$C_6$) cycloalkyl;

each $R_{14}$ is independently selected from the group consisting of H, halo, and ($C_1$-$C_6$) alkyl;

$R_{15}$ is H;

each $R_{12}$ is independently selected from the group consisting of —H and halo;

each $R^a$ is independently selected from the group consisting of —H, ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene-, wherein the ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene- of $R^a$ are each optionally substituted with 1, 2, 3, 4, or 5 substituents independently selected from the group consisting of ($C_1$-$C_6$) alkyl, ($C_1$-$C_6$) alkoxy, and —C(O)O($C_1$-$C_4$) alkyl;

the subscript n is an integer of 1, 2, 3, or 4;

the subscript m is an integer of 1, 2, 3, 4, or 5; and the subscript p is an integer of 0, 1, 2, 3, or 4.

20. A process for making a compound of Formula I':

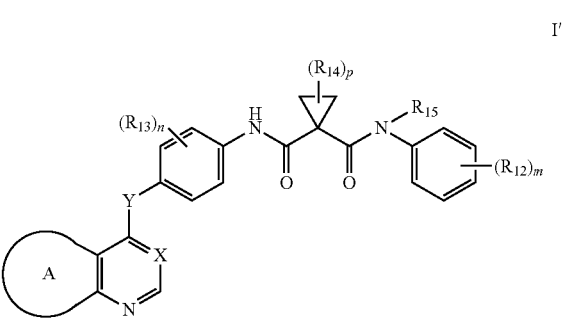

or a pharmaceutically acceptable salt thereof, comprising:
reacting a compound of formula XII:

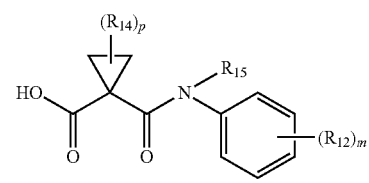

with a compound of formula XIII:

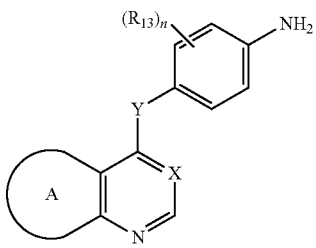

wherein
Y is selected from the group consisting of O, S, SO, $SO_2$, NH, and —N($C_{1-6}$ alkyl)-;
ring A is

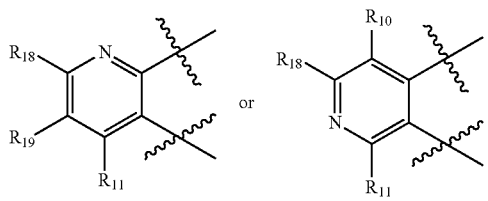

and X is N or CH, wherein
$R_{18}$ and $R_{19}$ are each independently selected from the group consisting of H, halo, ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, 5-14 membered heteroaryl, —CN, —$NO_2$, —$OR^a$, —$SR^a$, —C(O)$R^a$, —C(O)N$R^a R^a$, —C(O)O$R^a$, —NH$R^a$, —N$R^a R^a$, and —N$R^a$C(O)$R^a$, wherein the ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 4-14 membered heterocycloalkyl, phenyl, and 5-14 membered heteroaryl are each optionally substituted with 1, 2, 3, 4, or 5 substituents independently selected from the group consisting of halo, ($C_1$-$C_6$) alkyl, —CN, and —OH, or $R_{18}$ and $R_{19}$ taken together with the atoms to which they are attached form a fused $C_{3-7}$ cycloalkyl ring or a fused 4- to 10-membered heterocycloalkyl ring;

$R_{10}$ and $R_{11}$ are H;

each $R_{13}$ is independently selected from the group consisting of —H; halo; —OH; —CN; optionally substituted ($C_1$-$C_6$) alkyl; ($C_1$-$C_6$) alkoxy; ($C_1$-$C_6$) haloalkoxy; —$NH_2$; —NH($C_1$-$C_6$)alkyl; —N($C_1$-$C_6$ alkyl)$_2$; and ($C_3$-$C_6$) cycloalkyl;

each $R_{14}$ is independently selected from the group consisting of H, halo, and ($C_1$-$C_6$) alkyl;

$R_{15}$ is H;

each $R_{12}$ is independently selected from the group consisting of —H and halo;

each $R^a$ is independently selected from the group consisting of —H, ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene-, wherein the ($C_1$-$C_6$) alkyl, ($C_3$-$C_{10}$) cycloalkyl, 4-14 membered heterocycloalkyl, and (4-14 membered heterocycloalkyl)-($C_1$-$C_4$) alkylene- of $R^a$ are each optionally substituted with 1, 2, 3, 4, or 5 substituents independently selected from the group consisting of ($C_1$-$C_6$) alkyl, ($C_1$-$C_6$) alkoxy, and —C(O)O($C_1$-$C_4$) alkyl;

the subscript n is an integer of 1, 2, 3, or 4;
the subscript m is an integer of 1, 2, 3, 4, or 5; and
the subscript p is an integer of 0, 1, 2, 3, or 4.

* * * * *

SEQUENCE LISTING

<160> NUMBER OF SEQ ID NOS: 45

<210> SEQ ID NO 1
<211> LENGTH: 587
<212> TYPE: PRT
<213> ORGANISM: Homo sapiens

<400> SEQUENCE: 1

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
            20                  25                  30

Glu Gly Leu Asn Ser Thr Glu Ala Ala Leu Ala Thr Phe Gly Thr Phe
        35                  40                  45

Pro Ser Thr Arg Pro Pro Gly Thr Pro Arg Ala Pro Gly Pro Ser Ser
    50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
            100                 105                 110

Val Thr Gly Asp Ser Gln Phe Cys Ser Gln Lys Ala Val Ile Tyr Ser
        115                 120                 125

Leu Asn Phe Thr Ala Asn Pro Pro Gln Arg Val Phe Glu Leu Val Asp
    130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
        195                 200                 205

Tyr Gly Val Pro Leu Gln Thr Ser Asp Ser Phe Leu Arg Phe Pro Ser

```
            210                 215                 220
Ser Leu Thr Ser Ser Leu Cys Thr Asp Asn Asn Pro Ala Ala Phe Leu
225                 230                 235                 240

Val Asn Gln Ala Val Lys Cys Thr Arg Lys Ile Asn Leu Glu Gln Cys
                245                 250                 255

Glu Glu Ile Glu Ala Leu Ser Met Ala Phe Tyr Ser Ser Pro Glu Ile
            260                 265                 270

Leu Arg Val Pro Asp Ser Arg Lys Lys Val Pro Ile Thr Val Gln Ser
                275                 280                 285

Ile Val Ile Gln Ser Leu Asn Lys Thr Leu Thr Arg Arg Glu Asp Thr
            290                 295                 300

Asp Val Leu Gln Pro Thr Leu Val Asn Ala Gly His Phe Ser Leu Cys
305                 310                 315                 320

Val Asn Val Val Leu Glu Val Lys Tyr Ser Leu Thr Tyr Thr Asp Ala
                325                 330                 335

Gly Glu Val Thr Lys Ala Asp Leu Ser Phe Val Leu Gly Thr Val Ser
            340                 345                 350

Ser Val Val Val Pro Leu Gln Gln Lys Phe Glu Ile His Phe Leu Gln
                355                 360                 365

Glu Asn Thr Gln Pro Val Pro Leu Ser Gly Asn Pro Gly Tyr Val Val
370                 375                 380

Gly Leu Pro Leu Ala Ala Gly Phe Gln Pro His Lys Gly Ser Gly Ile
385                 390                 395                 400

Ile Gln Thr Thr Asn Arg Tyr Gly Gln Leu Thr Ile Leu His Ser Thr
                405                 410                 415

Thr Glu Gln Asp Cys Leu Ala Leu Glu Gly Val Arg Thr Pro Val Leu
                420                 425                 430

Phe Gly Tyr Thr Met Gln Ser Gly Cys Lys Leu Arg Leu Thr Gly Ala
                435                 440                 445

Leu Pro Cys Gln Leu Val Ala Gln Lys Val Lys Ser Leu Leu Trp Gly
450                 455                 460

Gln Gly Phe Pro Asp Tyr Val Ala Pro Phe Gly Asn Ser Gln Ala Gln
465                 470                 475                 480

Asp Met Leu Asp Trp Val Pro Ile His Phe Ile Thr Gln Ser Phe Asn
                485                 490                 495

Arg Lys Asp Ser Cys Gln Leu Pro Gly Ala Leu Val Ile Glu Val Lys
                500                 505                 510

Trp Thr Lys Tyr Gly Ser Leu Leu Asn Pro Gln Ala Lys Ile Val Asn
                515                 520                 525

Val Thr Ala Asn Leu Ile Ser Ser Ser Phe Pro Glu Ala Asn Ser Gly
530                 535                 540

Asn Glu Arg Thr Ile Leu Ile Ser Thr Ala Val Thr Phe Val Asp Val
545                 550                 555                 560

Ser Ala Pro Ala Glu Ala Gly Phe Arg Ala Pro Pro Ala Ile Asn Ala
                565                 570                 575

Arg Leu Pro Phe Asn Phe Phe Phe Pro Phe Val
                580                 585
```

<210> SEQ ID NO 2
<211> LENGTH: 697
<212> TYPE: PRT
<213> ORGANISM: Homo sapiens

<400> SEQUENCE: 2

```
Met Gly Phe Gln Pro Pro Ala Ala Leu Leu Leu Arg Leu Phe Leu Leu
  1               5                  10                  15

Gln Gly Ile Leu Arg Leu Leu Trp Gly Asp Leu Ala Phe Ile Pro Pro
             20                  25                  30

Phe Ile Arg Met Ser Gly Pro Ala Val Ser Ala Ser Leu Val Gly Asp
             35                  40                  45

Thr Glu Gly Val Thr Val Ser Leu Ala Val Leu Gln Asp Glu Ala Gly
 50                  55                  60

Ile Leu Pro Ile Pro Thr Cys Gly Val Leu Asn Asn Glu Thr Glu Asp
 65                  70                  75                  80

Trp Ser Val Thr Val Ile Pro Gly Ala Lys Val Leu Glu Val Thr Val
             85                  90                  95

Arg Trp Lys Arg Gly Leu Asp Trp Cys Ser Ser Asn Glu Thr Asp Ser
            100                 105                 110

Phe Ser Glu Ser Pro Cys Ile Leu Gln Thr Leu Leu Val Ser Ala Ser
            115                 120                 125

His Asn Ser Ser Cys Ser Ala His Leu Leu Ile Gln Val Glu Ile Tyr
            130                 135                 140

Ala Asn Ser Ser Leu Thr His Asn Ala Ser Glu Asn Val Thr Val Ile
145                 150                 155                 160

Pro Asn Gln Val Tyr Gln Pro Leu Gly Pro Cys Pro Cys Asn Leu Thr
            165                 170                 175

Ala Gly Ala Cys Asp Val Arg Cys Cys Asp Gln Glu Cys Ser Ser
            180                 185                 190

Asn Leu Thr Thr Leu Phe Arg Arg Ser Cys Phe Thr Gly Val Phe Gly
            195                 200                 205

Gly Asp Val Asn Pro Pro Phe Asp Gln Leu Cys Ser Ala Gly Thr Thr
            210                 215                 220

Thr Arg Gly Val Pro Asp Trp Phe Pro Phe Leu Cys Val Gln Ser Pro
225                 230                 235                 240

Leu Ala Asn Thr Pro Phe Leu Gly Tyr Phe Tyr His Gly Ala Val Ser
            245                 250                 255

Pro Lys Gln Asp Ser Ser Phe Glu Val Tyr Val Asp Thr Asp Ala Lys
            260                 265                 270

Asp Phe Ala Asp Phe Gly Tyr Lys Gln Gly Asp Pro Ile Met Thr Val
            275                 280                 285

Lys Lys Ala Tyr Phe Thr Ile Pro Gln Val Ser Leu Ala Gly Gln Cys
            290                 295                 300

Met Gln Asn Ala Pro Val Ala Phe Leu His Asn Phe Asp Val Lys Cys
305                 310                 315                 320

Val Thr Asn Leu Glu Leu Tyr Gln Glu Arg Asp Gly Ile Ile Asn Ala
            325                 330                 335

Lys Ile Lys Asn Val Ala Leu Gly Gly Ile Val Thr Pro Lys Val Ile
            340                 345                 350

Tyr Glu Glu Ala Thr Asp Leu Asp Lys Phe Ile Thr Asn Thr Glu Thr
            355                 360                 365

Pro Leu Asn Asn Gly Ser Thr Pro Arg Ile Val Asn Val Glu Glu His
            370                 375                 380

Tyr Ile Phe Lys Trp Asn Asn Thr Ile Ser Glu Ile Asn Val Lys
385                 390                 395                 400

Ile Phe Arg Ala Glu Ile Asn Ala His Gln Lys Gly Ile Met Thr Gln
            405                 410                 415

Arg Phe Val Val Lys Phe Leu Ser Tyr Asn Ser Gly Asn Glu Glu Glu
```

```
                    420                 425                 430
Leu Ser Gly Asn Pro Gly Tyr Gln Leu Gly Lys Pro Val Arg Ala Leu
            435                 440                 445

Asn Ile Asn Arg Met Asn Asn Val Thr Thr Leu His Leu Trp Gln Ser
        450                 455                 460

Ala Gly Arg Gly Leu Cys Thr Ser Ala Thr Phe Lys Pro Ile Leu Phe
465                 470                 475                 480

Gly Glu Asn Val Leu Ser Gly Cys Leu Leu Glu Val Gly Ile Asn Glu
                485                 490                 495

Asn Cys Thr Gln Leu Arg Glu Asn Ala Val Glu Arg Leu Asp Ser Leu
            500                 505                 510

Ile Gln Ala Thr His Val Ala Met Arg Gly Asn Ser Asp Tyr Ala Asp
        515                 520                 525

Leu Ser Asp Gly Trp Leu Glu Ile Ile Arg Val Asp Ala Pro Asp Pro
530                 535                 540

Gly Ala Asp Pro Leu Ala Ser Ser Val Asn Gly Met Cys Leu Asp Ile
545                 550                 555                 560

Pro Ala His Leu Ser Ile Arg Ile Leu Ile Ser Asp Ala Gly Ala Val
                565                 570                 575

Glu Gly Ile Thr Gln Gln Glu Ile Leu Gly Val Glu Thr Arg Phe Ser
            580                 585                 590

Ser Val Asn Trp Gln Tyr Gln Cys Gly Leu Thr Cys Glu His Lys Ala
        595                 600                 605

Asp Leu Leu Pro Ile Ser Ala Ser Val Gln Phe Ile Lys Ile Pro Ala
610                 615                 620

Gln Leu Pro His Pro Leu Thr Arg Phe Gln Ile Asn Tyr Thr Glu Tyr
625                 630                 635                 640

Asp Cys Asn Arg Asn Glu Val Cys Trp Pro Gln Leu Leu Tyr Pro Trp
                645                 650                 655

Thr Gln Tyr Tyr Gln Gly Glu Leu His Ser Gln Cys Val Ala Lys Gly
            660                 665                 670

Leu Leu Leu Leu Leu Phe Leu Thr Leu Ala Leu Phe Leu Ser Asn Pro
        675                 680                 685

Trp Thr Arg Ile Cys Lys Ala Tyr Ser
690                 695

<210> SEQ ID NO 3
<211> LENGTH: 607
<212> TYPE: PRT
<213> ORGANISM: Homo sapiens

<400> SEQUENCE: 3

Met Arg Thr Pro Gln Leu Ala Leu Leu Gln Val Phe Phe Leu Val Phe
1               5                   10                  15

Pro Asp Gly Val Arg Pro Gln Pro Ser Ser Pro Ser Gly Ala Val
                20                  25                  30

Pro Thr Ser Leu Glu Leu Gln Arg Gly Thr Asp Gly Thr Leu Gln
            35                  40                  45

Ser Pro Ser Glu Ala Thr Ala Thr Arg Pro Ala Val Pro Gly Leu Pro
        50                  55                  60

Thr Val Val Pro Thr Leu Val Thr Pro Ser Ala Pro Gly Asn Arg Thr
65                  70                  75                  80

Val Asp Leu Phe Pro Val Leu Pro Ile Cys Val Cys Asp Leu Thr Pro
                85                  90                  95
```

```
Gly Ala Cys Asp Ile Asn Cys Cys Asp Arg Asp Cys Tyr Leu Leu
            100                 105                 110

His Pro Arg Thr Val Phe Ser Phe Cys Leu Pro Gly Ser Val Arg Ser
        115                 120                 125

Ser Ser Trp Val Cys Val Asp Asn Ser Val Ile Phe Arg Ser Asn Ser
    130                 135                 140

Pro Phe Pro Ser Arg Val Phe Met Asp Ser Asn Gly Ile Arg Gln Phe
145                 150                 155                 160

Cys Val His Val Asn Asn Ser Asn Leu Asn Tyr Phe Gln Lys Leu Gln
                165                 170                 175

Lys Val Asn Ala Thr Asn Phe Gln Ala Leu Ala Ala Glu Phe Gly Gly
            180                 185                 190

Glu Ser Phe Thr Ser Thr Phe Gln Thr Gln Ser Pro Ser Phe Tyr
        195                 200                 205

Arg Ala Gly Asp Pro Ile Leu Thr Tyr Phe Pro Lys Trp Ser Val Ile
210                 215                 220

Ser Leu Leu Arg Gln Pro Ala Gly Val Gly Ala Gly Gly Leu Cys Ala
225                 230                 235                 240

Glu Ser Asn Pro Ala Gly Phe Leu Glu Ser Lys Ser Thr Thr Cys Thr
                245                 250                 255

Arg Phe Phe Lys Asn Leu Ala Ser Ser Cys Thr Leu Asp Ser Ala Leu
            260                 265                 270

Asn Ala Ala Ser Tyr Tyr Asn Phe Thr Val Leu Lys Val Pro Arg Ser
        275                 280                 285

Met Thr Asp Pro Gln Asn Met Glu Phe Gln Val Pro Val Ile Leu Thr
    290                 295                 300

Ser Gln Ala Asn Ala Pro Leu Leu Ala Gly Asn Thr Cys Gln Asn Val
305                 310                 315                 320

Val Ser Gln Val Thr Tyr Glu Ile Glu Thr Asn Gly Thr Phe Gly Ile
                325                 330                 335

Gln Lys Val Ser Val Ser Leu Gly Gln Thr Asn Leu Thr Val Glu Pro
            340                 345                 350

Gly Ala Ser Leu Gln Gln His Phe Ile Leu Arg Phe Arg Ala Phe Gln
        355                 360                 365

Gln Ser Thr Ala Ala Ser Leu Thr Ser Pro Arg Ser Gly Asn Pro Gly
    370                 375                 380

Tyr Ile Val Gly Lys Pro Leu Leu Ala Leu Thr Asp Asp Ile Ser Tyr
385                 390                 395                 400

Ser Met Thr Leu Leu Gln Ser Gln Gly Asn Gly Ser Cys Ser Val Lys
                405                 410                 415

Arg His Glu Val Gln Phe Gly Val Asn Ala Ile Ser Gly Cys Lys Leu
            420                 425                 430

Arg Leu Lys Lys Ala Asp Cys Ser His Leu Gln Gln Glu Ile Tyr Gln
        435                 440                 445

Thr Leu His Gly Arg Pro Arg Pro Glu Tyr Val Ala Ile Phe Gly Asn
    450                 455                 460

Ala Asp Pro Ala Gln Lys Gly Gly Trp Thr Arg Ile Leu Asn Arg His
465                 470                 475                 480

Cys Ser Ile Ser Ala Ile Asn Cys Thr Ser Cys Cys Leu Ile Pro Val
                485                 490                 495

Ser Leu Glu Ile Gln Val Leu Trp Ala Tyr Val Gly Leu Leu Ser Asn
            500                 505                 510

Pro Gln Ala His Val Ser Gly Val Arg Phe Leu Tyr Gln Cys Gln Ser
```

```
                515                 520                 525
Ile Gln Asp Ser Gln Val Thr Glu Val Ser Leu Thr Thr Leu Val
            530                 535                 540

Asn Phe Val Asp Ile Thr Gln Lys Pro Gln Pro Arg Gly Gln Pro
545                 550                 555                 560

Lys Met Asp Trp Lys Trp Pro Phe Asp Phe Pro Phe Lys Val Ala
                565                 570                 575

Phe Ser Arg Gly Val Phe Ser Gln Lys Cys Ser Val Ser Pro Ile Leu
            580                 585                 590

Ile Leu Cys Leu Leu Leu Leu Gly Val Leu Asn Leu Glu Thr Met
                595                 600                 605

<210> SEQ ID NO 4
<211> LENGTH: 106
<212> TYPE: PRT
<213> ORGANISM: Homo sapiens

<400> SEQUENCE: 4

Met Ala Thr Pro Gly Pro Val Ile Pro Glu Val Pro Phe Glu Pro Ser
1               5                   10                  15

Lys Pro Pro Val Ile Glu Gly Leu Ser Pro Thr Val Tyr Arg Asn Pro
                20                  25                  30

Glu Ser Phe Lys Glu Lys Phe Val Arg Lys Thr Arg Glu Asn Pro Val
            35                  40                  45

Val Pro Ile Gly Cys Leu Ala Thr Ala Ala Leu Thr Tyr Gly Leu
        50                  55                  60

Tyr Ser Phe His Arg Gly Asn Ser Gln Arg Ser Gln Leu Met Met Arg
65              70                  75                  80

Thr Arg Ile Ala Ala Gln Gly Phe Thr Val Ala Ala Ile Leu Leu Gly
                85                  90                  95

Leu Ala Val Thr Ala Met Lys Ser Arg Pro
            100                 105

<210> SEQ ID NO 5
<211> LENGTH: 106
<212> TYPE: PRT
<213> ORGANISM: Homo sapiens

<400> SEQUENCE: 5

Met Ala Thr Leu Gly Phe Val Thr Pro Glu Ala Pro Phe Glu Ser Ser
1               5                   10                  15

Lys Pro Pro Ile Phe Glu Gly Leu Ser Pro Thr Val Tyr Ser Asn Pro
                20                  25                  30

Glu Gly Phe Lys Glu Lys Phe Leu Arg Lys Thr Arg Glu Asn Pro Val
            35                  40                  45

Val Pro Ile Gly Phe Leu Cys Thr Ala Ala Val Leu Thr Asn Gly Leu
        50                  55                  60

Tyr Cys Phe His Gln Gly Asn Ser Gln Cys Ser Arg Leu Met Met His
65              70                  75                  80

Thr Gln Ile Ala Ala Gln Gly Phe Thr Ile Ala Ala Ile Leu Leu Gly
                85                  90                  95

Leu Ala Ala Thr Ala Met Lys Ser Pro Pro
            100                 105

<210> SEQ ID NO 6
<211> LENGTH: 132
<212> TYPE: PRT
```

<213> ORGANISM: Homo sapiens

<400> SEQUENCE: 6

Met Cys Ser Ala Gly Glu Leu Leu Arg Gly Gly Asp Gly Gly Glu Arg
1               5                   10                  15

Asp Glu Asp Gly Asp Ala Leu Ala Glu Arg Glu Ala Ala Gly Thr Gly
            20                  25                  30

Trp Asp Pro Gly Ala Ser Pro Arg Arg Gly Gln Arg Pro Lys Glu
        35                  40                  45

Ser Glu Gln Asp Val Glu Asp Ser Gln Asn His Thr Gly Glu Pro Val
    50                  55                  60

Gly Asp Asp Tyr Lys Lys Met Gly Thr Leu Phe Gly Glu Leu Asn Lys
65                  70                  75                  80

Asn Leu Ile Asn Met Gly Phe Thr Arg Met Tyr Phe Gly Glu Arg Ile
                85                  90                  95

Val Glu Pro Val Ile Val Ile Phe Phe Trp Val Met Leu Trp Phe Leu
            100                 105                 110

Gly Leu Gln Ala Leu Gly Leu Val Ala Val Leu Cys Leu Val Ile Ile
        115                 120                 125

Tyr Val Gln Gln
    130

<210> SEQ ID NO 7
<211> LENGTH: 1104
<212> TYPE: PRT
<213> ORGANISM: Homo sapiens

<400> SEQUENCE: 7

Met Glu Arg Ser Pro Gly Glu Gly Pro Ser Pro Ser Pro Met Asp Gln
1               5                   10                  15

Pro Ser Ala Pro Ser Asp Pro Thr Asp Gln Pro Pro Ala Ala His Ala
            20                  25                  30

Lys Pro Asp Pro Gly Ser Gly Gly Gln Pro Ala Gly Pro Gly Ala Ala
        35                  40                  45

Gly Glu Ala Leu Ala Val Leu Thr Ser Phe Gly Arg Arg Leu Leu Val
    50                  55                  60

Leu Ile Pro Val Tyr Leu Ala Gly Ala Val Gly Leu Ser Val Gly Phe
65                  70                  75                  80

Val Leu Phe Gly Leu Ala Leu Tyr Leu Gly Trp Arg Arg Val Arg Asp
                85                  90                  95

Glu Lys Glu Arg Ser Leu Arg Ala Ala Arg Gln Leu Leu Asp Asp Glu
            100                 105                 110

Glu Gln Leu Thr Ala Lys Thr Leu Tyr Met Ser His Arg Glu Leu Pro
        115                 120                 125

Ala Trp Val Ser Phe Pro Asp Val Glu Lys Ala Glu Trp Leu Asn Lys
    130                 135                 140

Ile Val Ala Gln Val Trp Pro Phe Leu Gly Gln Tyr Met Glu Lys Leu
145                 150                 155                 160

Leu Ala Glu Thr Val Ala Pro Ala Val Arg Gly Ser Asn Pro His Leu
                165                 170                 175

Gln Thr Phe Thr Phe Thr Arg Val Glu Leu Gly Glu Lys Pro Leu Arg
            180                 185                 190

Ile Ile Gly Val Lys Val His Pro Gly Gln Arg Lys Glu Gln Ile Leu
        195                 200                 205

Leu Asp Leu Asn Ile Ser Tyr Val Gly Asp Val Gln Ile Asp Val Glu

```
                    210                 215                 220
Val Lys Lys Tyr Phe Cys Lys Ala Gly Val Lys Gly Met Gln Leu His
225                 230                 235                 240

Gly Val Leu Arg Val Ile Leu Glu Pro Leu Ile Gly Asp Leu Pro Phe
                245                 250                 255

Val Gly Ala Val Ser Met Phe Phe Ile Arg Arg Pro Thr Leu Asp Ile
                260                 265                 270

Asn Trp Thr Gly Met Thr Asn Leu Leu Asp Ile Pro Gly Leu Ser Ser
            275                 280                 285

Leu Ser Asp Thr Met Ile Met Asp Ser Ile Ala Ala Phe Leu Val Leu
            290                 295                 300

Pro Asn Arg Leu Leu Val Pro Leu Val Pro Asp Leu Gln Asp Val Ala
305                 310                 315                 320

Gln Leu Arg Ser Pro Leu Pro Arg Gly Ile Ile Arg Ile His Leu Leu
                325                 330                 335

Ala Ala Arg Gly Leu Ser Ser Lys Asp Lys Tyr Val Lys Gly Leu Ile
                340                 345                 350

Glu Gly Lys Ser Asp Pro Tyr Ala Leu Val Arg Leu Gly Thr Gln Thr
            355                 360                 365

Phe Cys Ser Arg Val Ile Asp Glu Glu Leu Asn Pro Gln Trp Gly Glu
370                 375                 380

Thr Tyr Glu Val Met Val His Glu Val Pro Gly Gln Glu Ile Glu Val
385                 390                 395                 400

Glu Val Phe Asp Lys Asp Pro Asp Lys Asp Asp Phe Leu Gly Arg Met
                405                 410                 415

Lys Leu Asp Val Gly Lys Val Leu Gln Ala Ser Val Leu Asp Asp Trp
                420                 425                 430

Phe Pro Leu Gln Gly Gly Gln Gly Gln Val His Leu Arg Leu Glu Trp
            435                 440                 445

Leu Ser Leu Leu Ser Asp Ala Glu Lys Leu Glu Gln Val Leu Gln Trp
            450                 455                 460

Asn Trp Gly Val Ser Ser Arg Pro Asp Pro Ser Ala Ala Ile Leu
465                 470                 475                 480

Val Val Tyr Leu Asp Arg Ala Gln Asp Leu Pro Leu Lys Lys Gly Asn
                485                 490                 495

Lys Glu Pro Asn Pro Met Val Gln Leu Ser Ile Gln Asp Val Thr Gln
            500                 505                 510

Glu Ser Lys Ala Val Tyr Ser Thr Asn Cys Pro Val Trp Glu Glu Ala
            515                 520                 525

Phe Arg Phe Phe Leu Gln Asp Pro Gln Ser Gln Glu Leu Asp Val Gln
            530                 535                 540

Val Lys Asp Asp Ser Arg Ala Leu Thr Leu Gly Ala Leu Thr Leu Pro
545                 550                 555                 560

Leu Ala Arg Leu Leu Thr Ala Pro Glu Leu Ile Leu Asp Gln Trp Phe
                565                 570                 575

Gln Leu Ser Ser Ser Gly Pro Asn Ser Arg Leu Tyr Met Lys Leu Val
            580                 585                 590

Met Arg Ile Leu Tyr Leu Asp Ser Ser Glu Ile Cys Phe Pro Thr Val
            595                 600                 605

Pro Gly Cys Pro Gly Ala Trp Asp Val Asp Ser Glu Asn Pro Gln Arg
            610                 615                 620

Gly Ser Ser Val Asp Ala Pro Pro Arg Pro Cys His Thr Thr Pro Asp
625                 630                 635                 640
```

Ser Gln Phe Gly Thr Glu His Val Leu Arg Ile His Val Leu Glu Ala
             645                 650                 655

Gln Asp Leu Ile Ala Lys Asp Arg Phe Leu Gly Gly Leu Val Lys Gly
            660                 665                 670

Lys Ser Asp Pro Tyr Val Lys Leu Lys Leu Ala Gly Arg Ser Phe Arg
            675                 680                 685

Ser His Val Val Arg Glu Asp Leu Asn Pro Arg Trp Asn Glu Val Phe
        690                 695                 700

Glu Val Ile Val Thr Ser Val Pro Gly Gln Glu Leu Glu Val Glu Val
705                 710                 715                 720

Phe Asp Lys Asp Leu Asp Lys Asp Phe Leu Gly Arg Cys Lys Val
                725                 730                 735

Arg Leu Thr Thr Val Leu Asn Ser Gly Phe Leu Asp Glu Trp Leu Thr
            740                 745                 750

Leu Glu Asp Val Pro Ser Gly Arg Leu His Leu Arg Leu Glu Arg Leu
        755                 760                 765

Thr Pro Arg Pro Thr Ala Ala Glu Leu Glu Glu Val Leu Gln Val Asn
770                 775                 780

Ser Leu Ile Gln Thr Gln Lys Ser Ala Glu Leu Ala Ala Ala Leu Leu
785                 790                 795                 800

Ser Ile Tyr Met Glu Arg Ala Glu Asp Leu Pro Leu Arg Lys Gly Thr
                805                 810                 815

Lys His Leu Ser Pro Tyr Ala Thr Leu Thr Val Gly Asp Ser Ser His
            820                 825                 830

Lys Thr Lys Thr Ile Ser Gln Thr Ser Ala Pro Val Trp Asp Glu Ser
            835                 840                 845

Ala Ser Phe Leu Ile Arg Lys Pro His Thr Glu Ser Leu Glu Leu Gln
        850                 855                 860

Val Arg Gly Glu Gly Thr Gly Val Leu Gly Ser Leu Ser Leu Pro Leu
865                 870                 875                 880

Ser Glu Leu Leu Val Ala Asp Gln Leu Cys Leu Asp Arg Trp Phe Thr
                885                 890                 895

Leu Ser Ser Gly Gln Gly Gln Val Leu Leu Arg Ala Gln Leu Gly Ile
            900                 905                 910

Leu Val Ser Gln His Ser Gly Val Glu Ala His Ser His Ser Tyr Ser
        915                 920                 925

His Ser Ser Ser Leu Ser Glu Glu Pro Glu Leu Ser Gly Gly Pro
        930                 935                 940

Pro His Ile Thr Ser Ser Ala Pro Glu Leu Arg Gln Arg Leu Thr His
945                 950                 955                 960

Val Asp Ser Pro Leu Glu Ala Pro Ala Gly Pro Leu Gly Gln Val Lys
                965                 970                 975

Leu Thr Leu Trp Tyr Tyr Ser Glu Glu Arg Lys Leu Val Ser Ile Val
            980                 985                 990

His Gly Cys Arg Ser Leu Arg Gln Asn Gly Arg Asp Pro Pro Asp Pro
        995                 1000                1005

Tyr Val Ser Leu Leu Leu Leu Pro Asp Lys Asn Arg Gly Thr Lys
    1010                1015                1020

Arg Arg Thr Ser Gln Lys Lys Arg Thr Leu Ser Pro Glu Phe Asn
    1025                1030                1035

Glu Arg Phe Glu Trp Glu Leu Pro Leu Asp Glu Ala Gln Arg Arg
    1040                1045                1050

```
Lys Leu Asp Val Ser Val Lys Ser Asn Ser Ser Phe Met Ser Arg
    1055                1060                1065

Glu Arg Glu Leu Leu Gly Lys Val Gln Leu Asp Leu Ala Glu Thr
    1070                1075                1080

Asp Leu Ser Gln Gly Val Ala Arg Trp Tyr Asp Leu Met Asp Asn
    1085                1090                1095

Lys Asp Lys Gly Ser Ser
    1100

<210> SEQ ID NO 8
<211> LENGTH: 271
<212> TYPE: PRT
<213> ORGANISM: Homo sapiens

<400> SEQUENCE: 8

Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Asp Ala Gly Glu
        35                  40                  45

Lys Gly Asp Lys Gly Ala Pro Gly Arg Pro Gly Arg Val Gly Pro Thr
    50                  55                  60

Gly Glu Lys Gly Asp Met Gly Asp Lys Gly Gln Lys Gly Ser Val Gly
65                  70                  75                  80

Arg His Gly Lys Ile Gly Pro Ile Gly Ser Lys Gly Glu Lys Gly Asp
                85                  90                  95

Ser Gly Asp Ile Gly Pro Pro Gly Pro Asn Gly Glu Pro Gly Leu Pro
            100                 105                 110

Cys Glu Cys Ser Gln Leu Arg Lys Ala Ile Gly Glu Met Asp Asn Gln
        115                 120                 125

Val Ser Gln Leu Thr Ser Glu Leu Lys Phe Ile Lys Asn Ala Val Ala
    130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Gly Arg Gly Gly Thr
                165                 170                 175

Leu Ser Met Pro Lys Asp Glu Ala Ala Asn Gly Leu Met Ala Ala Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp His Ser Pro Met Arg Thr
    210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Thr Thr Met Tyr Phe Met Cys Glu Phe Asp Lys Glu Asn Met
            260                 265                 270

<210> SEQ ID NO 9
<211> LENGTH: 847
<212> TYPE: PRT
<213> ORGANISM: Homo sapiens

<400> SEQUENCE: 9
```

```
Met Phe Lys Cys Trp Ser Val Val Leu Val Leu Gly Phe Ile Phe Leu
1               5                   10                  15

Glu Ser Glu Gly Arg Pro Thr Lys Glu Gly Gly Tyr Gly Leu Lys Ser
            20                  25                  30

Tyr Gln Pro Leu Met Arg Leu Arg His Lys Gln Glu Lys Asn Gln Glu
            35                  40                  45

Ser Ser Arg Val Lys Gly Phe Met Ile Gln Asp Gly Pro Phe Gly Ser
50                  55                  60

Cys Glu Asn Lys Tyr Cys Gly Leu Gly Arg His Cys Val Thr Ser Arg
65                  70                  75                  80

Glu Thr Gly Gln Ala Glu Cys Ala Cys Met Asp Leu Cys Lys Arg His
                85                  90                  95

Tyr Lys Pro Val Cys Gly Ser Asp Gly Glu Phe Tyr Glu Asn His Cys
            100                 105                 110

Glu Val His Arg Ala Ala Cys Leu Lys Lys Gln Lys Ile Thr Ile Val
            115                 120                 125

His Asn Glu Asp Cys Phe Phe Lys Gly Asp Lys Cys Lys Thr Thr Glu
            130                 135                 140

Tyr Ser Lys Met Lys Asn Met Leu Leu Asp Leu Gln Asn Gln Lys Tyr
145                 150                 155                 160

Ile Met Gln Glu Asn Glu Asn Pro Asn Gly Asp Asp Ile Ser Arg Lys
                165                 170                 175

Lys Leu Leu Val Asp Gln Met Phe Lys Tyr Phe Asp Ala Asp Ser Asn
            180                 185                 190

Gly Leu Val Asp Ile Asn Glu Leu Thr Gln Val Ile Lys Gln Glu Glu
            195                 200                 205

Leu Gly Lys Asp Leu Phe Asp Cys Thr Leu Tyr Val Leu Leu Lys Tyr
            210                 215                 220

Asp Asp Phe Asn Ala Asp Lys His Leu Ala Leu Glu Glu Phe Tyr Arg
225                 230                 235                 240

Ala Phe Gln Val Ile Gln Leu Ser Leu Pro Glu Asp Gln Lys Leu Ser
                245                 250                 255

Ile Thr Ala Ala Thr Val Gly Gln Ser Ala Val Leu Ser Cys Ala Ile
            260                 265                 270

Gln Gly Thr Leu Arg Pro Pro Ile Ile Trp Lys Arg Asn Asn Ile Ile
            275                 280                 285

Leu Asn Asn Leu Asp Leu Glu Asp Ile Asn Asp Phe Gly Asp Asp Gly
            290                 295                 300

Ser Leu Tyr Ile Thr Lys Val Thr Thr His Val Gly Asn Tyr Thr
305                 310                 315                 320

Cys Tyr Ala Asp Gly Tyr Glu Gln Val Tyr Gln Thr His Ile Phe Gln
            325                 330                 335

Val Asn Val Pro Pro Val Ile Arg Val Tyr Pro Glu Ser Gln Ala Arg
            340                 345                 350

Glu Pro Gly Val Thr Ala Ser Leu Arg Cys His Ala Glu Gly Ile Pro
            355                 360                 365

Lys Pro Gln Leu Gly Trp Leu Lys Asn Gly Ile Asp Ile Thr Pro Lys
370                 375                 380

Leu Ser Lys Gln Leu Thr Leu Gln Ala Asn Gly Ser Glu Val His Ile
385                 390                 395                 400

Ser Asn Val Arg Tyr Glu Asp Thr Gly Ala Tyr Thr Cys Ile Ala Lys
            405                 410                 415

Asn Glu Ala Gly Val Asp Glu Asp Ile Ser Ser Leu Phe Val Glu Asp
```

```
                420             425             430
Ser Ala Arg Lys Thr Leu Ala Asn Ile Leu Trp Arg Glu Glu Gly Leu
            435                 440                 445

Gly Ile Gly Asn Met Phe Tyr Val Phe Tyr Glu Asp Gly Ile Lys Val
450                 455                 460

Ile Gln Pro Ile Glu Cys Glu Phe Gln Arg His Ile Lys Pro Ser Glu
465                 470                 475                 480

Lys Leu Leu Gly Phe Gln Asp Glu Val Cys Pro Lys Ala Glu Gly Asp
            485                 490                 495

Glu Val Gln Arg Cys Val Trp Ala Ser Ala Val Asn Val Lys Asp Lys
            500                 505                 510

Phe Ile Tyr Val Ala Gln Pro Thr Leu Asp Arg Val Leu Ile Val Asp
            515                 520                 525

Val Gln Ser Gln Lys Val Gln Ala Val Ser Thr Asp Pro Val Pro
            530                 535                 540

Val Lys Leu His Tyr Asp Lys Ser His Asp Gln Val Trp Val Leu Ser
545                 550                 555                 560

Trp Gly Thr Leu Glu Lys Thr Ser Pro Thr Leu Gln Val Ile Thr Leu
            565                 570                 575

Ala Ser Gly Asn Val Pro His His Thr Ile His Thr Gln Pro Val Gly
            580                 585                 590

Lys Gln Phe Asp Arg Val Asp Asp Phe Phe Ile Pro Thr Thr Thr Leu
            595                 600                 605

Ile Ile Thr His Met Arg Phe Gly Phe Ile Leu His Lys Asp Glu Ala
            610                 615                 620

Ala Leu Gln Lys Ile Asp Leu Glu Thr Met Ser Tyr Ile Lys Thr Ile
625                 630                 635                 640

Asn Leu Lys Asp Tyr Lys Cys Val Pro Gln Ser Leu Ala Tyr Thr His
            645                 650                 655

Leu Gly Gly Tyr Tyr Phe Ile Gly Cys Lys Pro Asp Ser Thr Gly Ala
            660                 665                 670

Val Ser Pro Gln Val Met Val Asp Gly Val Thr Asp Ser Val Ile Gly
            675                 680                 685

Phe Asn Ser Asp Val Thr Gly Thr Pro Tyr Val Ser Pro Asp Gly His
            690                 695                 700

Tyr Leu Val Ser Ile Asn Asp Val Lys Gly Leu Val Arg Val Gln Tyr
705                 710                 715                 720

Ile Thr Ile Arg Gly Glu Ile Gln Glu Ala Phe Asp Ile Tyr Thr Asn
            725                 730                 735

Leu His Ile Ser Asp Leu Ala Phe Gln Pro Ser Phe Thr Glu Ala His
            740                 745                 750

Gln Tyr Asn Ile Tyr Gly Ser Ser Thr Gln Thr Asp Val Leu Phe
            755                 760                 765

Val Glu Leu Ser Ser Gly Lys Val Lys Met Ile Lys Ser Leu Lys Glu
            770                 775                 780

Pro Leu Lys Ala Glu Glu Trp Pro Trp Asn Arg Lys Asn Arg Gln Ile
785                 790                 795                 800

Gln Asp Ser Gly Leu Phe Gly Gln Tyr Leu Met Thr Pro Ser Lys Asp
            805                 810                 815

Ser Leu Phe Ile Leu Asp Gly Arg Leu Asn Lys Leu Asn Cys Glu Ile
            820                 825                 830

Thr Glu Val Glu Lys Gly Asn Thr Val Ile Trp Val Gly Asp Ala
            835                 840                 845
```

```
<210> SEQ ID NO 10
<211> LENGTH: 470
<212> TYPE: PRT
<213> ORGANISM: Homo sapiens

<400> SEQUENCE: 10

Met Ser Arg Leu Gly Ala Leu Gly Gly Ala Arg Ala Gly Leu Gly Leu
1               5                   10                  15

Leu Leu Gly Thr Ala Ala Gly Leu Gly Phe Leu Cys Leu Leu Tyr Ser
            20                  25                  30

Gln Arg Trp Lys Arg Thr Gln Arg His Gly Arg Ser Gln Ser Leu Pro
        35                  40                  45

Asn Ser Leu Asp Tyr Thr Gln Thr Ser Asp Pro Gly Arg His Val Met
50                  55                  60

Leu Leu Arg Ala Val Pro Gly Ala Gly Asp Ala Ser Val Leu Pro
65                  70                  75                  80

Ser Leu Pro Arg Glu Gly Gln Glu Lys Val Leu Asp Arg Leu Asp Phe
                85                  90                  95

Val Leu Thr Ser Leu Val Ala Leu Arg Arg Glu Val Glu Glu Leu Arg
            100                 105                 110

Ser Ser Leu Arg Gly Leu Ala Gly Glu Ile Val Gly Glu Val Arg Cys
        115                 120                 125

His Met Glu Glu Asn Gln Arg Val Ala Arg Arg Arg Phe Pro Phe
130                 135                 140

Val Arg Glu Arg Ser Asp Ser Thr Gly Ser Ser Ser Val Tyr Phe Thr
145                 150                 155                 160

Ala Ser Ser Gly Ala Thr Phe Thr Asp Ala Glu Ser Glu Gly Gly Tyr
                165                 170                 175

Thr Thr Ala Asn Ala Glu Ser Asp Asn Glu Arg Asp Ser Asp Lys Glu
            180                 185                 190

Ser Glu Asp Gly Glu Asp Glu Val Ser Cys Glu Thr Val Lys Met Gly
        195                 200                 205

Arg Lys Asp Ser Leu Asp Leu Glu Glu Glu Ala Ala Ser Gly Ala Ser
210                 215                 220

Ser Ala Leu Glu Ala Gly Gly Ser Ser Gly Leu Glu Asp Val Leu Pro
225                 230                 235                 240

Leu Leu Gln Gln Ala Asp Glu Leu His Arg Gly Asp Glu Gln Gly Lys
                245                 250                 255

Arg Glu Gly Phe Gln Leu Leu Leu Asn Asn Lys Leu Val Tyr Gly Ser
            260                 265                 270

Arg Gln Asp Phe Leu Trp Arg Leu Ala Arg Ala Tyr Ser Asp Met Cys
        275                 280                 285

Glu Leu Thr Glu Glu Val Ser Glu Lys Lys Ser Tyr Ala Leu Asp Gly
290                 295                 300

Lys Glu Glu Ala Glu Ala Leu Glu Lys Gly Asp Glu Ser Ala Asp
305                 310                 315                 320

Cys His Leu Trp Tyr Ala Val Leu Cys Gly Gln Leu Ala Glu His Glu
                325                 330                 335

Ser Ile Gln Arg Ile Gln Ser Gly Phe Ser Phe Lys Glu His Val
            340                 345                 350

Asp Lys Ala Ile Ala Leu Gln Pro Glu Asn Pro Met Ala His Phe Leu
        355                 360                 365

Leu Gly Arg Trp Cys Tyr Gln Val Ser His Leu Ser Trp Leu Glu Lys
```

```
              370                 375                 380
Lys Thr Ala Thr Ala Leu Leu Glu Ser Pro Leu Ser Ala Thr Val Glu
385                 390                 395                 400

Asp Ala Leu Gln Ser Phe Leu Lys Ala Glu Glu Leu Gln Pro Gly Phe
                405                 410                 415

Ser Lys Ala Gly Arg Val Tyr Ile Ser Lys Cys Tyr Arg Glu Leu Gly
                420                 425                 430

Lys Asn Ser Glu Ala Arg Trp Trp Met Lys Leu Ala Leu Glu Leu Pro
                435                 440                 445

Asp Val Thr Lys Glu Asp Leu Ala Ile Gln Lys Asp Leu Glu Glu Leu
                450                 455                 460

Glu Val Ile Leu Arg Asp
465                 470

<210> SEQ ID NO 11
<211> LENGTH: 495
<212> TYPE: PRT
<213> ORGANISM: Homo sapiens

<400> SEQUENCE: 11

Met Glu Asn Lys Ala Met Tyr Leu His Thr Val Ser Asp Cys Asp Thr
1               5                   10                  15

Ser Ser Ile Cys Glu Asp Ser Phe Asp Gly Arg Ser Leu Ser Lys Leu
                20                  25                  30

Asn Leu Cys Glu Asp Gly Pro Cys His Lys Arg Arg Ala Ser Ile Cys
            35                  40                  45

Cys Thr Gln Leu Gly Ser Leu Ser Ala Leu Lys His Ala Val Leu Gly
        50                  55                  60

Leu Tyr Leu Leu Val Phe Leu Ile Leu Val Gly Ile Phe Ile Leu Ala
65                  70                  75                  80

Val Ser Arg Pro Arg Ser Ser Pro Asp Leu Lys Ala Leu Thr Arg
                85                  90                  95

Asn Val Asn Arg Leu Asn Glu Ser Phe Arg Asp Leu Gln Leu Arg Leu
                100                 105                 110

Leu Gln Ala Pro Leu Gln Ala Asp Leu Thr Glu Gln Val Trp Lys Val
            115                 120                 125

Gln Asp Ala Leu Gln Asn Gln Ser Asp Ser Leu Leu Ala Leu Ala Gly
        130                 135                 140

Ala Val Gln Arg Leu Glu Gly Ala Leu Trp Gly Leu Gln Ala Gln Ala
145                 150                 155                 160

Val Gln Thr Glu Gln Ala Val Ala Leu Leu Arg Asp Arg Thr Gly Gln
                165                 170                 175

Gln Ser Asp Thr Ala Gln Leu Glu Leu Tyr Gln Leu Gln Val Glu Ser
            180                 185                 190

Asn Ser Ser Gln Leu Leu Leu Arg Arg His Ala Gly Leu Leu Asp Gly
        195                 200                 205

Leu Ala Arg Arg Val Gly Ile Leu Gly Glu Glu Leu Ala Asp Val Gly
    210                 215                 220

Gly Val Leu Arg Gly Leu Asn His Ser Leu Ser Tyr Asp Val Ala Leu
225                 230                 235                 240

His Arg Thr Arg Leu Gln Asp Leu Arg Val Leu Val Ser Asn Ala Ser
                245                 250                 255

Glu Asp Thr Arg Arg Leu Arg Leu Ala His Val Gly Met Glu Leu Gln
            260                 265                 270
```

Leu Lys Gln Glu Leu Ala Met Leu Asn Ala Val Thr Glu Asp Leu Arg
            275                 280                 285

Leu Lys Asp Trp Glu His Ser Ile Ala Leu Arg Asn Ile Ser Leu Ala
            290                 295                 300

Lys Gly Pro Pro Gly Pro Lys Gly Asp Gln Gly Asp Glu Gly Lys Glu
305                 310                 315                 320

Gly Arg Pro Gly Ile Pro Gly Leu Pro Gly Leu Arg Gly Leu Pro Gly
            325                 330                 335

Glu Arg Gly Thr Pro Gly Leu Pro Gly Pro Lys Gly Asp Asp Gly Lys
            340                 345                 350

Leu Gly Ala Thr Gly Pro Met Gly Met Arg Gly Phe Lys Gly Asp Arg
            355                 360                 365

Gly Pro Lys Gly Glu Lys Gly Glu Lys Gly Asp Arg Ala Gly Asp Ala
370                 375                 380

Ser Gly Val Glu Ala Pro Met Met Ile Arg Leu Val Asn Gly Ser Gly
385                 390                 395                 400

Pro His Glu Gly Arg Val Glu Val Tyr His Asp Arg Arg Trp Gly Thr
            405                 410                 415

Val Cys Asp Asp Gly Trp Asp Lys Lys Asp Gly Asp Val Val Cys Arg
            420                 425                 430

Met Leu Gly Phe Arg Gly Val Glu Glu Val Tyr Arg Thr Ala Arg Phe
            435                 440                 445

Gly Gln Gly Thr Gly Arg Ile Trp Met Asp Asp Val Ala Cys Lys Gly
            450                 455                 460

Thr Glu Glu Thr Ile Phe Arg Cys Ser Phe Ser Lys Trp Gly Val Thr
465                 470                 475                 480

Asn Cys Gly His Ala Glu Asp Ala Ser Val Thr Cys Asn Arg His
            485                 490                 495

<210> SEQ ID NO 12
<211> LENGTH: 236
<212> TYPE: PRT
<213> ORGANISM: Homo sapiens

<400> SEQUENCE: 12

Met Thr Ala Glu Phe Leu Ser Leu Leu Cys Leu Gly Leu Cys Leu Gly
1               5                   10                  15

Tyr Glu Asp Glu Lys Lys Asn Glu Lys Pro Pro Lys Pro Ser Leu His
            20                  25                  30

Ala Trp Pro Ser Ser Val Val Glu Ala Glu Ser Asn Val Thr Leu Lys
            35                  40                  45

Cys Gln Ala His Ser Gln Asn Val Thr Phe Val Leu Arg Lys Val Asn
        50                  55                  60

Asp Ser Gly Tyr Lys Gln Glu Gln Ser Ser Ala Glu Asn Glu Ala Glu
65                  70                  75                  80

Phe Pro Phe Thr Asp Leu Lys Pro Lys Asp Ala Gly Arg Tyr Phe Cys
                85                  90                  95

Ala Tyr Lys Thr Thr Ala Ser His Glu Trp Ser Glu Ser Ser Glu His
            100                 105                 110

Leu Gln Leu Val Val Thr Asp Lys His Asp Glu Leu Glu Ala Pro Ser
            115                 120                 125

Met Lys Thr Asp Thr Arg Thr Ile Phe Val Ala Ile Phe Ser Cys Ile
        130                 135                 140

Ser Ile Leu Leu Leu Phe Leu Ser Val Phe Ile Ile Tyr Arg Cys Ser
145                 150                 155                 160

-continued

```
Gln His Ser Ser Ser Glu Ser Thr Lys Arg Thr Ser His Ser
            165                 170                 175

Lys Leu Pro Glu Gln Glu Ala Ala Glu Ala Asp Leu Ser Asn Met Glu
            180                 185                 190

Arg Val Ser Leu Ser Thr Ala Asp Pro Gln Gly Val Thr Tyr Ala Glu
            195                 200                 205

Leu Ser Thr Ser Ala Leu Ser Glu Ala Ala Ser Asp Thr Thr Gln Glu
            210                 215                 220

Pro Pro Gly Ser His Glu Tyr Ala Ala Leu Lys Val
225                 230                 235

<210> SEQ ID NO 13
<211> LENGTH: 180
<212> TYPE: PRT
<213> ORGANISM: Homo sapiens

<400> SEQUENCE: 13

Met Ala Ala Ala Glu Glu Asp Gly Gly Pro Glu Gly Pro Asn Arg
1               5                   10                  15

Glu Arg Gly Gly Ala Gly Ala Thr Phe Glu Cys Asn Ile Cys Leu Glu
            20                  25                  30

Thr Ala Arg Glu Ala Val Val Ser Val Cys Gly His Leu Tyr Cys Trp
            35                  40                  45

Pro Cys Leu His Gln Trp Leu Glu Thr Arg Pro Glu Arg Gln Glu Cys
            50                  55                  60

Pro Val Cys Lys Ala Gly Ile Ser Arg Glu Lys Val Val Pro Leu Tyr
65                  70                  75                  80

Gly Arg Gly Ser Gln Lys Pro Gln Asp Pro Arg Leu Lys Thr Pro Pro
                    85                  90                  95

Arg Pro Gln Gly Gln Arg Pro Ala Pro Glu Ser Arg Gly Gly Phe Gln
            100                 105                 110

Pro Phe Gly Asp Thr Gly Gly Phe His Phe Ser Phe Gly Val Gly Ala
            115                 120                 125

Phe Pro Phe Gly Phe Phe Thr Thr Val Phe Asn Ala His Glu Pro Phe
130                 135                 140

Arg Arg Gly Thr Gly Val Asp Leu Gly Gln Gly His Pro Ala Ser Ser
145                 150                 155                 160

Trp Gln Asp Ser Leu Phe Leu Phe Leu Ala Ile Phe Phe Phe Phe Trp
                    165                 170                 175

Leu Leu Ser Ile
            180

<210> SEQ ID NO 14
<211> LENGTH: 157
<212> TYPE: PRT
<213> ORGANISM: Homo sapiens

<400> SEQUENCE: 14

Met Leu Pro Glu Gln Gly Pro Gln Pro Ser Thr Met Pro Leu Trp Cys
1               5                   10                  15

Leu Leu Ala Ala Cys Thr Ser Leu Pro Arg Gln Ala Thr Met Leu
            20                  25                  30

Glu Glu Ala Ala Ser Pro Asn Glu Ala Val His Ala Ser Thr Ser Gly
            35                  40                  45

Ser Gly Ala Leu Thr Asp Gln Thr Phe Thr Asp Leu Ser Ala Ala Glu
            50                  55                  60
```

```
Ala Ser Ser Glu Glu Val Pro Asp Phe Met Glu Val Pro His Ser Val
 65                  70                  75                  80

His His Lys Ile Asn Cys Phe Phe Tyr Leu Glu Lys Gln Leu Cys Gln
                 85                  90                  95

Leu Pro Ser Pro Leu Cys Leu Ser Ser Leu Leu Thr Leu Lys Leu Lys
            100                 105                 110

Thr Thr Val Pro Ala Pro Gly Arg Trp Trp Ser Phe Gln Pro His Lys
        115                 120                 125

Ala Phe Pro Leu Leu Val Gly Thr Pro Gly Ser Trp Gln Ser Thr Ile
    130                 135                 140

Asp Pro Ala Trp Ala Ala Pro Ser Gln Pro Ser Pro Gly
145                 150                 155

<210> SEQ ID NO 15
<211> LENGTH: 716
<212> TYPE: PRT
<213> ORGANISM: Homo sapiens

<400> SEQUENCE: 15

Met Met Ser Ile Arg Gln Arg Arg Glu Ile Arg Ala Thr Glu Val Ser
 1               5                  10                  15

Glu Asp Phe Pro Ala Gln Glu Glu Asn Val Lys Leu Glu Asn Lys Leu
                 20                  25                  30

Pro Ser Gly Cys Thr Ser Arg Arg Leu Trp Lys Ile Leu Ser Leu Thr
             35                  40                  45

Ile Gly Gly Thr Ile Ala Leu Cys Ile Gly Leu Leu Thr Ser Val Tyr
 50                  55                  60

Leu Ala Thr Leu His Glu Asn Asp Leu Trp Phe Ser Asn Ile Lys Glu
 65                  70                  75                  80

Val Glu Arg Glu Ile Ser Phe Arg Thr Glu Cys Gly Leu Tyr Tyr Ser
                 85                  90                  95

Tyr Tyr Lys Gln Met Leu Gln Ala Pro Thr Leu Val Gln Gly Phe His
            100                 105                 110

Gly Leu Ile Tyr Asp Asn Lys Thr Glu Ser Met Lys Thr Ile Asn Leu
        115                 120                 125

Leu Gln Arg Met Asn Ile Tyr Gln Glu Val Phe Leu Ser Ile Leu Tyr
    130                 135                 140

Arg Val Leu Pro Ile Gln Lys Tyr Leu Glu Pro Val Tyr Phe Tyr Ile
145                 150                 155                 160

Tyr Thr Leu Phe Gly Leu Gln Ala Ile Tyr Val Thr Ala Leu Tyr Ile
                165                 170                 175

Thr Ser Trp Leu Leu Ser Gly Thr Trp Leu Ser Gly Leu Leu Ala Ala
            180                 185                 190

Phe Trp Tyr Val Thr Asn Arg Ile Asp Thr Thr Arg Val Glu Phe Thr
        195                 200                 205

Ile Pro Leu Arg Glu Asn Trp Ala Leu Pro Phe Ala Ile Gln Ile
    210                 215                 220

Ala Ala Ile Thr Tyr Phe Leu Arg Pro Asn Leu Gln Pro Leu Ser Glu
225                 230                 235                 240

Arg Leu Thr Leu Leu Ala Ile Phe Ile Ser Thr Phe Leu Phe Ser Leu
                245                 250                 255

Thr Trp Gln Phe Asn Gln Phe Met Met Leu Met Gln Ala Leu Val Leu
            260                 265                 270

Phe Thr Leu Asp Ser Leu Asp Met Leu Pro Ala Val Lys Ala Thr Trp
```

```
            275                 280                 285
Leu Tyr Gly Ile Gln Ile Thr Ser Leu Leu Val Cys Ile Leu Gln
290                 295                 300
Phe Phe Asn Ser Met Ile Leu Gly Ser Leu Leu Ile Ser Phe Asn Leu
305                 310                 315                 320
Ser Val Phe Ile Ala Arg Lys Leu Gln Lys Asn Leu Lys Thr Gly Ser
                325                 330                 335
Phe Leu Asn Arg Leu Gly Lys Leu Leu Leu His Leu Phe Met Val Leu
            340                 345                 350
Cys Leu Thr Leu Phe Leu Asn Asn Ile Ile Lys Lys Ile Leu Asn Leu
        355                 360                 365
Lys Ser Asp Glu His Ile Phe Lys Phe Leu Lys Ala Lys Phe Gly Leu
370                 375                 380
Gly Ala Thr Arg Asp Phe Asp Ala Asn Leu Tyr Leu Cys Glu Glu Ala
385                 390                 395                 400
Phe Gly Leu Leu Pro Phe Asn Thr Phe Gly Arg Leu Ser Asp Thr Leu
                405                 410                 415
Leu Phe Tyr Ala Tyr Ile Phe Val Leu Ser Ile Thr Val Ile Val Ala
            420                 425                 430
Phe Val Val Ala Phe His Asn Leu Ser Asp Ser Thr Asn Gln Gln Ser
        435                 440                 445
Val Gly Lys Met Glu Lys Gly Thr Val Asp Leu Lys Pro Glu Thr Ala
450                 455                 460
Tyr Asn Leu Ile His Thr Ile Leu Phe Gly Phe Leu Ala Leu Ser Thr
465                 470                 475                 480
Met Arg Met Lys Tyr Leu Trp Thr Ser His Met Cys Val Phe Ala Ser
                485                 490                 495
Phe Gly Leu Cys Ser Pro Glu Ile Trp Glu Leu Leu Lys Ser Val
            500                 505                 510
His Leu Tyr Asn Pro Lys Arg Ile Cys Ile Met Arg Tyr Ser Val Pro
        515                 520                 525
Ile Leu Ile Leu Leu Tyr Leu Cys Tyr Lys Phe Trp Pro Gly Met Met
530                 535                 540
Asp Glu Leu Ser Glu Leu Arg Glu Phe Tyr Asp Pro Asp Thr Val Glu
545                 550                 555                 560
Leu Met Asn Trp Ile Asn Ser Asn Thr Pro Arg Lys Ala Val Phe Ala
                565                 570                 575
Gly Ser Met Gln Leu Leu Ala Gly Val Lys Leu Cys Thr Gly Arg Thr
            580                 585                 590
Leu Thr Asn His Pro His Tyr Glu Asp Ser Ser Leu Arg Glu Arg Thr
        595                 600                 605
Arg Ala Val Tyr Gln Ile Tyr Ala Lys Arg Ala Pro Glu Glu Val His
610                 615                 620
Ala Leu Leu Arg Ser Phe Gly Thr Asp Tyr Val Ile Leu Glu Asp Ser
625                 630                 635                 640
Ile Cys Tyr Glu Arg Arg His Arg Arg Gly Cys Arg Leu Arg Asp Leu
                645                 650                 655
Leu Asp Ile Ala Asn Gly His Met Met Asp Gly Pro Gly Glu Asn Asp
            660                 665                 670
Pro Asp Leu Lys Pro Ala Asp His Pro Arg Phe Cys Glu Glu Ile Lys
        675                 680                 685
Arg Asn Leu Pro Pro Tyr Val Ala Tyr Phe Thr Arg Val Phe Gln Asn
690                 695                 700
```

```
Lys Thr Phe His Val Tyr Lys Leu Ser Arg Asn Lys
705                 710             715

<210> SEQ ID NO 16
<211> LENGTH: 831
<212> TYPE: PRT
<213> ORGANISM: Homo sapiens

<400> SEQUENCE: 16

Met Lys Val His Met His Thr Lys Phe Cys Leu Ile Cys Leu Leu Thr
1               5                   10                  15

Phe Ile Phe His His Cys Asn His Cys His Glu Glu His Asp His Gly
                20                  25                  30

Pro Glu Ala Leu His Arg Gln His Arg Gly Met Thr Glu Leu Glu Pro
            35                  40                  45

Ser Lys Phe Ser Lys Gln Ala Ala Glu Asn Glu Lys Lys Tyr Tyr Ile
50                  55                  60

Glu Lys Leu Phe Glu Arg Tyr Gly Glu Asn Gly Arg Leu Ser Phe Phe
65                  70                  75                  80

Gly Leu Glu Lys Leu Leu Thr Asn Leu Gly Leu Gly Glu Arg Lys Val
                85                  90                  95

Val Glu Ile Asn His Glu Asp Leu Gly His Asp His Val Ser His Leu
            100                 105                 110

Asp Ile Leu Ala Val Gln Glu Gly Lys His Phe His Ser His Asn His
            115                 120                 125

Gln His Ser His Asn His Leu Asn Ser Glu Asn Gln Thr Val Thr Ser
130                 135                 140

Val Ser Thr Lys Arg Asn His Lys Cys Asp Pro Glu Lys Glu Thr Val
145                 150                 155                 160

Glu Val Ser Val Lys Ser Asp Asp Lys His Met His Asp His Asn His
                165                 170                 175

Arg Leu Arg His His His Arg Leu His His His Leu Asp His Asn Asn
            180                 185                 190

Thr His His Phe His Asn Asp Ser Ile Thr Pro Ser Glu Arg Gly Glu
            195                 200                 205

Pro Ser Asn Glu Pro Ser Thr Glu Thr Asn Lys Thr Gln Glu Gln Ser
210                 215                 220

Asp Val Lys Leu Pro Lys Gly Lys Arg Lys Lys Lys Gly Arg Lys Ser
225                 230                 235                 240

Asn Glu Asn Ser Glu Val Ile Thr Pro Gly Phe Pro Pro Asn His Asp
                245                 250                 255

Gln Gly Glu Gln Tyr Glu His Asn Arg Val His Lys Pro Asp Arg Val
            260                 265                 270

His Asn Pro Gly His Ser His Val His Leu Pro Glu Arg Asn Gly His
            275                 280                 285

Asp Pro Gly Arg Gly His Gln Asp Leu Asp Pro Asp Asn Glu Gly Glu
290                 295                 300

Leu Arg His Thr Arg Lys Arg Glu Ala Pro His Val Lys Asn Asn Ala
305                 310                 315                 320

Ile Ile Ser Leu Arg Lys Asp Leu Asn Glu Asp His His His Glu
                325                 330                 335

Cys Leu Asn Val Thr Gln Leu Leu Lys Tyr Tyr Gly His Gly Ala Asn
            340                 345                 350

Ser Pro Ile Ser Thr Asp Leu Phe Thr Tyr Leu Cys Pro Ala Leu Leu
```

```
            355                 360                 365
Tyr Gln Ile Asp Ser Arg Leu Cys Ile Glu His Phe Asp Lys Leu Leu
    370                 375                 380

Val Glu Asp Ile Asn Lys Asp Lys Asn Leu Val Pro Glu Asp Glu Ala
385                 390                 395                 400

Asn Ile Gly Ala Ser Ala Trp Ile Cys Gly Ile Ser Ile Thr Val
                405                 410                 415

Ile Ser Leu Leu Ser Leu Leu Gly Val Ile Leu Val Pro Ile Ile Asn
            420                 425                 430

Gln Gly Cys Phe Lys Phe Leu Leu Thr Phe Leu Val Ala Leu Ala Val
            435                 440                 445

Gly Thr Met Ser Gly Asp Ala Leu Leu His Leu Leu Pro His Ser Gln
            450                 455                 460

Gly Gly His Asp His Ser His Gln His Ala His Gly His Gly His Ser
465                 470                 475                 480

His Gly His Glu Ser Asn Lys Phe Leu Glu Glu Tyr Asp Ala Val Leu
                485                 490                 495

Lys Gly Leu Val Ala Leu Gly Gly Ile Tyr Leu Leu Phe Ile Ile Glu
            500                 505                 510

His Cys Ile Arg Met Phe Lys His Tyr Lys Gln Gln Arg Gly Lys Gln
            515                 520                 525

Lys Trp Phe Met Lys Gln Asn Thr Glu Glu Ser Thr Ile Gly Arg Lys
            530                 535                 540

Leu Ser Asp His Lys Leu Asn Asn Thr Pro Asp Ser Asp Trp Leu Gln
545                 550                 555                 560

Leu Lys Pro Leu Ala Gly Thr Asp Asp Ser Val Val Ser Glu Asp Arg
                565                 570                 575

Leu Asn Glu Thr Glu Leu Thr Asp Leu Glu Gly Gln Gln Glu Ser Pro
            580                 585                 590

Pro Lys Asn Tyr Leu Cys Ile Glu Glu Lys Ile Ile Asp His Ser
            595                 600                 605

His Ser Asp Gly Leu His Thr Ile His Glu His Asp Leu His Ala Ala
610                 615                 620

Ala His Asn His His Gly Glu Asn Lys Thr Val Leu Arg Lys His Asn
625                 630                 635                 640

His Gln Trp His His Lys His Ser His His Ser His Gly Pro Cys His
                645                 650                 655

Ser Gly Ser Asp Leu Lys Glu Thr Gly Ile Ala Asn Ile Ala Trp Met
                660                 665                 670

Val Ile Met Gly Asp Gly Ile His Asn Phe Ser Asp Gly Leu Ala Ile
            675                 680                 685

Gly Ala Ala Phe Ser Ala Gly Leu Thr Gly Gly Ile Ser Thr Ser Ile
            690                 695                 700

Ala Val Phe Cys His Glu Leu Pro His Glu Leu Gly Asp Phe Ala Val
            705                 710                 715                 720

Leu Leu Lys Ala Gly Met Thr Val Lys Gln Ala Ile Val Tyr Asn Leu
                725                 730                 735

Leu Ser Ala Met Met Ala Tyr Ile Gly Met Leu Ile Gly Thr Ala Val
            740                 745                 750

Gly Gln Tyr Ala Asn Asn Ile Thr Leu Trp Ile Phe Ala Val Thr Ala
            755                 760                 765

Gly Met Phe Leu Tyr Val Ala Leu Val Asp Met Leu Pro Glu Met Leu
770                 775                 780
```

```
His Gly Asp Gly Asp Asn Glu Glu His Gly Phe Cys Pro Val Gly Gln
785                 790                 795                 800

Phe Ile Leu Gln Asn Leu Gly Leu Leu Phe Gly Phe Ala Ile Met Leu
            805                 810                 815

Val Ile Ala Leu Tyr Glu Asp Lys Ile Val Phe Asp Ile Gln Phe
        820                 825                 830

<210> SEQ ID NO 17
<211> LENGTH: 600
<212> TYPE: PRT
<213> ORGANISM: Homo sapiens

<400> SEQUENCE: 17

Met Ala Ala Leu Ala Pro Val Gly Ser Pro Ala Ser Arg Gly Pro Arg
1               5                   10                  15

Leu Ala Ala Gly Leu Arg Leu Leu Pro Met Leu Gly Leu Leu Gln Leu
                20                  25                  30

Leu Ala Glu Pro Gly Leu Gly Arg Val His His Leu Ala Leu Lys Asp
            35                  40                  45

Asp Val Arg His Lys Val His Leu Asn Thr Phe Gly Phe Phe Lys Asp
        50                  55                  60

Gly Tyr Met Val Val Asn Val Ser Ser Leu Ser Leu Asn Glu Pro Glu
65                  70                  75                  80

Asp Lys Asp Val Thr Ile Gly Phe Ser Leu Asp Arg Thr Lys Asn Asp
                85                  90                  95

Gly Phe Ser Ser Tyr Leu Asp Glu Asp Val Asn Tyr Cys Ile Leu Lys
            100                 105                 110

Lys Gln Ser Val Ser Val Thr Leu Leu Ile Leu Asp Ile Ser Arg Ser
        115                 120                 125

Glu Val Arg Val Lys Ser Pro Pro Glu Ala Gly Thr Gln Leu Pro Lys
130                 135                 140

Ile Ile Phe Ser Arg Asp Glu Lys Val Leu Gly Gln Ser Gln Glu Pro
145                 150                 155                 160

Asn Val Asn Pro Ala Ser Ala Gly Asn Gln Thr Gln Lys Thr Gln Asp
                165                 170                 175

Gly Gly Lys Ser Lys Arg Ser Thr Val Asp Ser Lys Ala Met Gly Glu
            180                 185                 190

Lys Ser Phe Ser Val His Asn Asn Gly Gly Ala Val Ser Phe Gln Phe
        195                 200                 205

Phe Phe Asn Ile Ser Thr Asp Asp Gln Glu Gly Leu Tyr Ser Leu Tyr
210                 215                 220

Phe His Lys Cys Leu Gly Lys Glu Leu Pro Ser Asp Lys Phe Thr Phe
225                 230                 235                 240

Ser Leu Asp Ile Glu Ile Thr Glu Lys Asn Pro Asp Ser Tyr Leu Ser
                245                 250                 255

Ala Gly Glu Ile Pro Leu Pro Lys Leu Tyr Ile Ser Met Ala Phe Phe
            260                 265                 270

Phe Phe Leu Ser Gly Thr Ile Trp Ile His Ile Leu Arg Lys Arg Arg
        275                 280                 285

Asn Asp Val Phe Lys Ile His Trp Leu Met Ala Ala Leu Pro Phe Thr
290                 295                 300

Lys Ser Leu Ser Leu Val Phe His Ala Ile Asp Tyr His Tyr Ile Ser
305                 310                 315                 320

Ser Gln Gly Phe Pro Ile Glu Gly Trp Ala Val Val Tyr Tyr Ile Thr
```

```
            325                 330                 335
His Leu Lys Gly Ala Leu Leu Phe Ile Thr Ile Ala Leu Ile Gly
        340                 345                 350

Thr Gly Trp Ala Phe Ile Lys His Ile Leu Ser Asp Lys Asp Lys
        355                 360                 365

Ile Phe Met Ile Val Ile Pro Leu Gln Val Leu Ala Asn Val Ala Tyr
370                 375                 380

Ile Ile Ile Glu Ser Thr Glu Glu Gly Thr Thr Glu Tyr Gly Leu Trp
385                 390                 395                 400

Lys Asp Ser Leu Phe Leu Val Asp Leu Leu Cys Cys Gly Ala Ile Leu
                405                 410                 415

Phe Pro Val Val Trp Ser Ile Arg His Leu Gln Glu Ala Ser Ala Thr
                420                 425                 430

Asp Gly Lys Gly Asp Ser Met Gly Pro Leu Gln Gln Arg Ala Asn Leu
                435                 440                 445

Arg Ala Gly Ser Arg Ile Glu Ser His His Phe Ala Gln Ala Asp Leu
450                 455                 460

Glu Leu Leu Ala Ser Ser Cys Pro Pro Ala Ser Val Ser Gln Arg Ala
465                 470                 475                 480

Gly Ile Thr Ala Ala Ile Asn Leu Ala Lys Leu Lys Leu Phe Arg His
                485                 490                 495

Tyr Tyr Val Leu Ile Val Cys Tyr Ile Tyr Phe Thr Arg Ile Ile Ala
                500                 505                 510

Phe Leu Leu Lys Leu Ala Val Pro Phe Gln Trp Lys Trp Leu Tyr Gln
                515                 520                 525

Leu Leu Asp Glu Thr Ala Thr Leu Val Phe Phe Val Leu Thr Gly Tyr
530                 535                 540

Lys Phe Arg Pro Ala Ser Asp Asn Pro Tyr Leu Gln Leu Ser Gln Glu
545                 550                 555                 560

Glu Glu Asp Leu Glu Met Glu Ser Val Val Thr Thr Ser Gly Val Met
                565                 570                 575

Glu Ser Met Lys Lys Val Lys Lys Val Thr Asn Gly Ser Val Glu Pro
                580                 585                 590

Gln Gly Glu Trp Glu Gly Ala Val
                595                 600

<210> SEQ ID NO 18
<211> LENGTH: 1284
<212> TYPE: PRT
<213> ORGANISM: Homo sapiens

<400> SEQUENCE: 18

Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
                20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95
```

```
Glu Leu Thr Gly Ser Gly Arg Phe Leu Leu Ala Arg Arg Glu Phe Val
            100                 105                 110

Ile Glu Asp Leu Lys Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Ala Gly Pro Gln Phe Arg Cys Leu Pro Pro Val
                165                 170                 175

Pro Ala Asp Met Val Phe Leu Val Asp Gly Ser Trp Ser Ile Gly His
            180                 185                 190

Ser His Phe Gln Gln Val Lys Asp Phe Leu Ala Ser Val Ile Ala Pro
    195                 200                 205

Phe Glu Ile Gly Pro Asp Lys Val Gln Val Gly Leu Thr Gln Tyr Ser
210                 215                 220

Gly Asp Ala Gln Thr Glu Trp Asp Leu Asn Ser Leu Ser Thr Lys Glu
225                 230                 235                 240

Gln Val Leu Ala Ala Val Arg Arg Leu Arg Tyr Lys Gly Gly Asn Thr
                245                 250                 255

Phe Thr Gly Leu Ala Leu Thr His Val Leu Gly Gln Asn Leu Gln Pro
            260                 265                 270

Ala Ala Gly Leu Arg Pro Glu Ala Lys Val Val Ile Leu Val Thr
    275                 280                 285

Asp Gly Lys Ser Gln Asp Val His Thr Ala Ala Arg Val Leu Lys
290                 295                 300

Asp Leu Gly Val Asn Val Phe Ala Val Gly Val Lys Asn Ala Asp Glu
305                 310                 315                 320

Ala Glu Leu Arg Leu Leu Ala Ser Pro Pro Arg Asp Ile Thr Val His
                325                 330                 335

Ser Val Leu Asp Phe Leu Gln Leu Gly Ala Leu Ala Gly Leu Leu Ser
            340                 345                 350

Arg Leu Ile Cys Gln Arg Leu Gln Gly Gly Ser Pro Arg Gln Gly Pro
        355                 360                 365

Ala Ala Ala Pro Ala Leu Asp Thr Leu Pro Ala Pro Thr Ser Leu Val
    370                 375                 380

Leu Ser Gln Val Thr Ser Ser Ile Arg Leu Ser Trp Thr Pro Ala
385                 390                 395                 400

Pro Arg His Pro Leu Lys Tyr Leu Ile Val Trp Arg Ala Ser Arg Gly
                405                 410                 415

Gly Thr Pro Arg Glu Val Val Val Glu Gly Pro Ala Ala Ser Thr Glu
            420                 425                 430

Leu His Asn Leu Ala Ser Arg Thr Glu Tyr Leu Val Ser Val Phe Pro
        435                 440                 445

Ile Tyr Glu Gly Gly Val Gly Glu Gly Leu Arg Gly Leu Val Thr Thr
    450                 455                 460

Ala Pro Leu Pro Pro Arg Ala Leu Thr Leu Ala Ala Val Thr Pro
465                 470                 475                 480

Arg Thr Val His Leu Thr Trp Gln Pro Ser Ala Gly Ala Thr His Tyr
                485                 490                 495

Leu Val Arg Cys Ser Pro Ala Ser Pro Lys Gly Glu Glu Glu Arg
            500                 505                 510

Glu Val Gln Val Gly Arg Pro Glu Val Leu Leu Asp Gly Leu Glu Pro
```

```
            515                 520                 525
Gly Arg Asp Tyr Glu Val Ser Val Gln Ser Leu Arg Gly Pro Glu Gly
            530                 535                 540
Ser Glu Ala Arg Gly Ile Arg Ala Arg Thr Pro Thr Leu Ala Pro Pro
545                 550                 555                 560
Arg His Leu Gly Phe Ser Asp Val Ser His Asp Ala Ala Arg Val Phe
                565                 570                 575
Trp Glu Gly Ala Pro Arg Pro Val Arg Leu Val Arg Val Thr Tyr Val
            580                 585                 590
Ser Ser Glu Gly Gly His Ser Gly Gln Thr Glu Ala Pro Gly Asn Ala
            595                 600                 605
Thr Ser Ala Thr Leu Gly Pro Leu Ser Ser Ser Thr Thr Tyr Thr Val
            610                 615                 620
Arg Val Thr Cys Leu Tyr Pro Gly Gly Gly Ser Ser Thr Leu Thr Gly
625                 630                 635                 640
Arg Val Thr Thr Lys Lys Ala Pro Ser Pro Ser Gln Leu Ser Met Thr
                645                 650                 655
Glu Leu Pro Gly Asp Ala Val Gln Leu Ala Trp Val Ala Ala Ala Pro
            660                 665                 670
Ser Gly Val Leu Val Tyr Gln Ile Thr Trp Thr Pro Leu Gly Glu Gly
            675                 680                 685
Lys Ala His Glu Ile Ser Val Pro Gly Asn Leu Gly Thr Ala Val Leu
690                 695                 700
Pro Gly Leu Gly Arg His Thr Glu Tyr Asp Val Thr Ile Leu Ala Tyr
705                 710                 715                 720
Tyr Arg Asp Gly Ala Arg Ser Asp Pro Val Ser Leu Arg Tyr Thr Pro
                725                 730                 735
Ser Thr Val Ser Arg Ser Pro Pro Ser Asn Leu Ala Leu Ala Ser Glu
            740                 745                 750
Thr Pro Asp Ser Leu Gln Val Ser Trp Thr Pro Pro Leu Gly Arg Val
            755                 760                 765
Leu His Tyr Trp Leu Thr Tyr Ala Pro Ala Ser Gly Leu Gly Pro Glu
            770                 775                 780
Lys Ser Val Ser Val Pro Gly Ala Arg Ser His Val Thr Leu Pro Asp
785                 790                 795                 800
Leu Gln Ala Ala Thr Lys Tyr Arg Val Leu Val Ser Ala Ile Tyr Ala
                805                 810                 815
Ala Gly Arg Ser Glu Ala Val Ser Ala Thr Gly Gln Thr Ala Cys Pro
            820                 825                 830
Ala Leu Arg Pro Asp Gly Ser Leu Pro Gly Phe Asp Leu Met Val Ala
            835                 840                 845
Phe Ser Leu Val Glu Lys Ala Tyr Ala Ser Ile Arg Gly Val Ala Met
            850                 855                 860
Glu Pro Ser Ala Phe Gly Gly Thr Pro Thr Phe Thr Leu Phe Lys Asp
865                 870                 875                 880
Ala Gln Leu Thr Arg Arg Val Ser Asp Val Tyr Pro Ala Pro Leu Pro
                885                 890                 895
Pro Glu His Thr Ile Val Phe Leu Val Arg Leu Leu Pro Glu Thr Pro
            900                 905                 910
Arg Glu Ala Phe Ala Leu Trp Gln Met Thr Ala Glu Asp Phe Gln Pro
            915                 920                 925
Leu Leu Gly Val Leu Leu Asp Ala Gly Lys Lys Ser Leu Thr Tyr Phe
            930                 935                 940
```

His Arg Asp Pro Arg Ala Ala Leu Gln Glu Ala Thr Phe Asp Pro Gln
945                 950                 955                 960

Glu Val Arg Lys Ile Phe Phe Gly Ser Phe His Lys Val His Val Ala
            965                 970                 975

Val Gly Arg Ser Lys Val Arg Leu Tyr Val Asp Cys Arg Lys Val Ala
            980                 985                 990

Glu Arg Pro Leu Gly Glu Met Gly Ser Pro Pro Ala Ala Gly Phe Val
        995                 1000                1005

Thr Leu Gly Arg Leu Ala Lys Ala Arg Gly Pro Arg Ser Ser Ser
    1010                1015                1020

Ala Ala Phe Gln Leu Gln Met Leu Gln Ile Val Cys Ser Asp Thr
    1025                1030                1035

Trp Ala Asp Glu Asp Arg Cys Cys Glu Leu Pro Ala Ser Arg Asp
    1040                1045                1050

Gly Glu Thr Cys Pro Ala Phe Val Ser Ala Cys Ser Cys Ser Ser
    1055                1060                1065

Glu Thr Pro Gly Pro Pro Gly Pro Gln Gly Pro Pro Gly Leu Pro
    1070                1075                1080

Gly Arg Asn Gly Thr Pro Gly Glu Gln Gly Phe Pro Gly Pro Arg
    1085                1090                1095

Gly Pro Pro Gly Val Lys Gly Glu Lys Gly Asp His Gly Leu Pro
    1100                1105                1110

Gly Leu Gln Gly His Pro Gly His Gln Gly Ile Pro Gly Arg Val
    1115                1120                1125

Gly Leu Gln Gly Pro Lys Gly Met Arg Gly Leu Glu Gly Thr Ala
    1130                1135                1140

Gly Leu Pro Gly Pro Pro Gly Pro Arg Gly Phe Gln Gly Met Ala
    1145                1150                1155

Gly Ala Arg Gly Thr Ser Gly Glu Arg Gly Pro Pro Gly Thr Val
    1160                1165                1170

Gly Pro Thr Gly Leu Pro Gly Pro Lys Gly Glu Arg Gly Glu Lys
    1175                1180                1185

Gly Glu Pro Gln Ser Leu Ala Thr Leu Tyr Gln Leu Val Ser Gln
    1190                1195                1200

Ala Ser His Val Ser Lys Phe Asp Ser Phe His Glu Asn Thr Arg
    1205                1210                1215

Pro Pro Met Pro Ile Leu Glu Gln Lys Leu Glu Pro Gly Thr Glu
    1220                1225                1230

Pro Leu Gly Ser Pro Gly Thr Arg Ser Lys Ala Leu Val Pro Gly
    1235                1240                1245

Glu Trp Gly Arg Gly Gly Arg His Leu Glu Gly Arg Gly Glu Pro
    1250                1255                1260

Gly Ala Val Gly Gln Met Gly Ser Pro Gly Gln Gln Gly Ala Ser
    1265                1270                1275

Thr Gln Gly Leu Trp Glu
    1280

<210> SEQ ID NO 19
<211> LENGTH: 626
<212> TYPE: PRT
<213> ORGANISM: Homo sapiens

<400> SEQUENCE: 19

Met Ala Ala Arg Pro Ala Ala Thr Leu Ala Trp Ser Leu Leu Leu Leu

-continued

```
1               5                   10                  15
Ser Ser Ala Leu Leu Arg Glu Gly Cys Arg Ala Arg Phe Val Ala Glu
            20                  25                  30

Arg Asp Ser Glu Asp Gly Glu Glu Pro Val Val Phe Pro Glu Ser
            35                  40                  45

Pro Leu Gln Ser Pro Thr Val Leu Val Ala Val Leu Ala Arg Asn Ala
            50                  55                  60

Ala His Thr Leu Pro His Phe Leu Gly Cys Leu Glu Arg Leu Asp Tyr
65                  70                  75                  80

Pro Lys Ser Arg Met Ala Ile Trp Ala Ala Thr Asp His Asn Val Asp
                85                  90                  95

Asn Thr Thr Glu Ile Phe Arg Glu Trp Leu Lys Asn Val Gln Arg Leu
                100                 105                 110

Tyr His Tyr Val Glu Trp Arg Pro Met Asp Glu Pro Glu Ser Tyr Pro
            115                 120                 125

Asp Glu Ile Gly Pro Lys His Trp Pro Thr Ser Arg Phe Ala His Val
            130                 135                 140

Met Lys Leu Arg Gln Ala Ala Leu Arg Thr Ala Arg Glu Lys Trp Ser
145                 150                 155                 160

Asp Tyr Ile Leu Phe Ile Asp Val Asp Asn Phe Leu Thr Asn Pro Gln
                165                 170                 175

Thr Leu Asn Leu Leu Ile Ala Glu Asn Lys Thr Ile Val Ala Pro Met
            180                 185                 190

Leu Glu Ser Arg Gly Leu Tyr Ser Asn Phe Trp Cys Gly Ile Thr Pro
            195                 200                 205

Lys Gly Phe Tyr Lys Arg Thr Pro Asp Tyr Val Gln Ile Arg Glu Trp
210                 215                 220

Lys Arg Thr Gly Cys Phe Pro Val Pro Met Val His Ser Thr Phe Leu
225                 230                 235                 240

Ile Asp Leu Arg Lys Glu Ala Ser Asp Lys Leu Thr Phe Tyr Pro Pro
                245                 250                 255

His Gln Asp Tyr Thr Trp Thr Phe Asp Asp Ile Ile Val Phe Ala Phe
            260                 265                 270

Ser Ser Arg Gln Ala Gly Ile Gln Met Tyr Leu Cys Asn Arg Glu His
            275                 280                 285

Tyr Gly Tyr Leu Pro Ile Pro Leu Lys Pro His Gln Thr Leu Gln Glu
            290                 295                 300

Asp Ile Glu Asn Leu Ile His Val Gln Ile Glu Ala Met Ile Asp Arg
305                 310                 315                 320

Pro Pro Met Glu Pro Ser Gln Tyr Val Ser Val Pro Lys Tyr Pro
                325                 330                 335

Asp Lys Met Gly Phe Asp Glu Ile Phe Met Ile Asn Leu Lys Arg Arg
            340                 345                 350

Lys Asp Arg Arg Asp Arg Met Leu Arg Thr Leu Tyr Glu Gln Glu Ile
            355                 360                 365

Glu Val Lys Ile Val Glu Ala Val Asp Gly Lys Ala Leu Asn Thr Ser
            370                 375                 380

Gln Leu Lys Ala Leu Asn Ile Glu Met Leu Pro Gly Tyr Arg Asp Pro
385                 390                 395                 400

Tyr Ser Ser Arg Pro Leu Thr Arg Gly Glu Ile Gly Cys Phe Leu Ser
                405                 410                 415

His Tyr Ser Val Trp Lys Glu Val Ile Asp Arg Glu Leu Glu Lys Thr
            420                 425                 430
```

-continued

```
Leu Val Ile Glu Asp Asp Val Arg Phe Glu His Gln Phe Lys Lys Lys
            435                 440                 445

Leu Met Lys Leu Met Asp Asn Ile Asp Gln Ala Gln Leu Asp Trp Glu
    450                 455                 460

Leu Ile Tyr Ile Gly Arg Lys Arg Met Gln Val Lys Glu Pro Glu Lys
465                 470                 475                 480

Ala Val Pro Asn Val Ala Asn Leu Val Glu Ala Asp Tyr Ser Tyr Trp
                485                 490                 495

Thr Leu Gly Tyr Val Ile Ser Leu Glu Gly Ala Gln Lys Leu Val Gly
            500                 505                 510

Ala Asn Pro Phe Gly Lys Met Leu Pro Val Asp Glu Phe Leu Pro Val
    515                 520                 525

Met Tyr Asn Lys His Pro Val Ala Glu Tyr Lys Glu Tyr Tyr Glu Ser
    530                 535                 540

Arg Asp Leu Lys Ala Phe Ser Ala Glu Pro Leu Leu Ile Tyr Pro Thr
545                 550                 555                 560

His Tyr Thr Gly Gln Pro Gly Tyr Leu Ser Asp Thr Glu Thr Ser Thr
                565                 570                 575

Ile Trp Asp Asn Glu Thr Val Ala Thr Asp Trp Asp Arg Thr His Ala
            580                 585                 590

Trp Lys Ser Arg Lys Gln Ser Arg Ile Tyr Ser Asn Ala Lys Asn Thr
    595                 600                 605

Glu Ala Leu Pro Pro Pro Thr Ser Leu Asp Thr Val Pro Ser Arg Asp
    610                 615                 620

Glu Leu
625

<210> SEQ ID NO 20
<211> LENGTH: 610
<212> TYPE: PRT
<213> ORGANISM: Homo sapiens

<400> SEQUENCE: 20

Met Ala Gln Glu Ile Asp Leu Ser Ala Leu Lys Glu Leu Glu Arg Glu
1               5                   10                  15

Ala Ile Leu Gln Val Leu Tyr Arg Asp Gln Ala Val Gln Asn Thr Glu
                20                  25                  30

Glu Glu Arg Thr Arg Lys Leu Lys Thr His Leu Gln His Leu Arg Trp
            35                  40                  45

Lys Gly Ala Lys Asn Thr Asp Trp Glu His Lys Glu Lys Cys Cys Ala
    50                  55                  60

Arg Cys Gln Gln Val Leu Gly Phe Leu Leu His Arg Gly Ala Val Cys
65                  70                  75                  80

Arg Gly Cys Ser His Arg Val Cys Ala Gln Cys Arg Val Phe Leu Arg
                85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
    115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Leu Gln Glu Phe
```

-continued

```
                165                 170                 175
Gly Gln Phe Arg Gly Phe Asn Lys Ser Val Glu Asn Leu Phe Leu Ser
            180                 185                 190
Leu Ala Thr His Val Lys Lys Leu Ser Lys Ser Gln Asn Asp Met Thr
            195                 200                 205
Ser Glu Lys His Leu Leu Ala Thr Gly Pro Arg Gln Cys Val Gly Gln
210                 215                 220
Thr Glu Arg Arg Ser Gln Ser Asp Thr Ala Val Asn Val Thr Thr Arg
225                 230                 235                 240
Lys Val Ser Ala Pro Asp Ile Leu Lys Pro Leu Asn Gln Glu Asp Pro
                245                 250                 255
Lys Cys Ser Thr Asn Pro Ile Leu Lys Gln Gln Asn Leu Pro Ser Ser
                260                 265                 270
Pro Ala Pro Ser Thr Ile Phe Ser Gly Gly Phe Arg His Gly Ser Leu
                275                 280                 285
Ile Ser Ile Asp Ser Thr Cys Thr Glu Met Gly Asn Phe Asp Asn Ala
            290                 295                 300
Asn Val Thr Gly Glu Ile Glu Phe Ala Ile His Tyr Cys Phe Lys Thr
305                 310                 315                 320
His Ser Leu Glu Ile Cys Ile Lys Ala Cys Lys Asn Leu Ala Tyr Gly
                325                 330                 335
Glu Glu Lys Lys Lys Lys Cys Asn Pro Tyr Val Lys Thr Tyr Leu Leu
            340                 345                 350
Pro Asp Arg Ser Ser Gln Gly Lys Arg Lys Thr Gly Val Gln Arg Asn
            355                 360                 365
Thr Val Asp Pro Thr Phe Gln Glu Thr Leu Lys Tyr Gln Val Ala Pro
            370                 375                 380
Ala Gln Leu Val Thr Arg Gln Leu Gln Val Ser Val Trp His Leu Gly
385                 390                 395                 400
Thr Leu Ala Arg Arg Val Phe Leu Gly Glu Val Ile Ile Pro Leu Ala
                405                 410                 415
Thr Trp Asp Phe Glu Asp Ser Thr Thr Gln Ser Phe Arg Trp His Pro
            420                 425                 430
Leu Arg Ala Lys Ala Glu Lys Tyr Glu Asp Ser Val Pro Gln Ser Asn
            435                 440                 445
Gly Glu Leu Thr Val Arg Ala Lys Leu Val Leu Pro Ser Arg Pro Arg
            450                 455                 460
Lys Leu Gln Glu Ala Gln Glu Gly Thr Asp Gln Pro Ser Leu His Gly
465                 470                 475                 480
Gln Leu Cys Leu Val Val Leu Gly Ala Lys Asn Leu Pro Val Arg Pro
                485                 490                 495
Asp Gly Thr Leu Asn Ser Phe Val Lys Gly Cys Leu Thr Leu Pro Asp
            500                 505                 510
Gln Gln Lys Leu Arg Leu Lys Ser Pro Val Leu Arg Lys Gln Ala Cys
            515                 520                 525
Pro Gln Trp Lys His Ser Phe Val Phe Ser Gly Val Thr Pro Ala Gln
            530                 535                 540
Leu Arg Gln Ser Ser Leu Glu Leu Thr Val Trp Asp Gln Ala Leu Phe
545                 550                 555                 560
Gly Met Asn Asp Arg Leu Leu Gly Gly Thr Arg Leu Gly Ser Lys Gly
                565                 570                 575
Asp Thr Ala Val Gly Gly Asp Ala Cys Ser Leu Ser Lys Leu Gln Trp
            580                 585                 590
```

```
Gln Lys Val Leu Ser Ser Pro Asn Leu Trp Thr Asp Met Thr Leu Val
            595                 600                 605

Leu His
    610

<210> SEQ ID NO 21
<211> LENGTH: 775
<212> TYPE: PRT
<213> ORGANISM: Homo sapiens

<400> SEQUENCE: 21

Met Asp Cys Arg Thr Lys Ala Asn Pro Asp Arg Thr Phe Asp Leu Val
1               5                   10                  15

Leu Lys Val Lys Cys His Ala Ser Glu Asn Glu Asp Pro Val Val Leu
            20                  25                  30

Trp Lys Phe Pro Glu Asp Phe Gly Asp Gln Glu Ile Leu Gln Ser Val
        35                  40                  45

Pro Lys Phe Cys Phe Pro Phe Asp Val Glu Arg Val Ser Gln Asn Gln
    50                  55                  60

Val Gly Gln His Phe Thr Phe Val Leu Thr Asp Ile Glu Ser Lys Gln
65                  70                  75                  80

Arg Phe Gly Phe Cys Arg Leu Thr Ser Gly Thr Ile Cys Leu Cys
                85                  90                  95

Ile Leu Ser Tyr Leu Pro Trp Phe Glu Val Tyr Lys Leu Leu Asn
                100                 105                 110

Thr Leu Ala Asp Tyr Leu Ala Lys Glu Leu Glu Asn Asp Leu Asn Glu
            115                 120                 125

Thr Leu Arg Ser Leu Tyr Asn His Pro Val Pro Lys Ala Asn Thr Pro
        130                 135                 140

Val Asn Leu Ser Val Asn Gln Glu Ile Phe Ile Ala Cys Glu Gln Val
145                 150                 155                 160

Leu Lys Asp Gln Pro Ala Leu Val Pro His Ser Tyr Phe Ile Ala Pro
                165                 170                 175

Asp Val Thr Gly Leu Pro Thr Ile Pro Glu Ser Arg Asn Leu Thr Glu
                180                 185                 190

Tyr Phe Val Ala Val Asp Val Asn Asn Met Leu Gln Leu Tyr Ala Ser
            195                 200                 205

Met Leu His Glu Arg Arg Ile Val Ile Ser Ser Lys Leu Ser Thr
        210                 215                 220

Leu Thr Ala Cys Ile His Gly Ser Ala Ala Leu Leu Tyr Pro Met Tyr
225                 230                 235                 240

Trp Gln His Ile Tyr Ile Pro Val Leu Pro Pro His Leu Leu Asp Tyr
                245                 250                 255

Cys Cys Ala Pro Met Pro Tyr Leu Ile Gly Ile His Ser Ser Leu Ile
                260                 265                 270

Glu Arg Val Lys Asn Lys Ser Leu Glu Asp Val Val Met Leu Asn Val
            275                 280                 285

Asp Thr Asn Thr Leu Glu Ser Pro Phe Ser Asp Leu Asn Asn Leu Pro
        290                 295                 300

Ser Asp Val Val Ser Ala Leu Lys Asn Lys Leu Lys Lys Gln Ser Thr
305                 310                 315                 320

Ala Thr Gly Asp Gly Val Ala Arg Ala Phe Leu Arg Ala Gln Ala Ala
                325                 330                 335

Leu Phe Gly Ser Tyr Arg Asp Ala Leu Arg Tyr Lys Pro Gly Glu Pro
```

-continued

```
                340             345             350
Ile Thr Phe Cys Glu Glu Ser Phe Val Lys His Arg Ser Ser Val Met
            355             360             365

Lys Gln Phe Leu Glu Thr Ala Ile Asn Leu Gln Leu Phe Lys Gln Phe
370             375             380

Ile Asp Gly Arg Leu Ala Lys Leu Asn Ala Gly Arg Gly Phe Ser Asp
385             390             395             400

Val Phe Glu Glu Ile Thr Ser Gly Gly Phe Cys Gly Gly Asn Pro
            405             410             415

Arg Ser Tyr Gln Gln Trp Val His Thr Val Lys Gly Gly Ala Leu
            420             425             430

Phe Asn Thr Ala Met Thr Lys Ala Thr Pro Ala Val Arg Thr Ala Tyr
            435             440             445

Lys Phe Ala Lys Asn His Ala Lys Leu Gly Leu Lys Glu Val Lys Ser
            450             455             460

Lys Leu Lys His Lys Glu Asn Glu Glu Asp Tyr Gly Thr Cys Ser Ser
465             470             475             480

Ser Val Gln Tyr Thr Pro Val Tyr Lys Leu His Asn Glu Lys Gly Gly
            485             490             495

Asn Ser Glu Lys Arg Lys Leu Ala Gln Ala Arg Leu Lys Arg Pro Leu
            500             505             510

Lys Ser Leu Asp Gly Ala Leu Tyr Asp Asp Glu Asp Asp Asp Ile
            515             520             525

Glu Arg Ala Ser Lys Leu Ser Ser Gly Asp Gly Glu Glu Ala Ser Ala
            530             535             540

Tyr Leu Tyr Glu Ser Asp Asp Ser Val Glu Thr Arg Val Lys Thr Pro
545             550             555             560

Tyr Ser Gly Glu Met Asp Leu Leu Gly Glu Ile Leu Asp Thr Leu Ser
            565             570             575

Thr His Ser Ser Asp Gln Gly Lys Leu Ala Ala Ala Lys Ser Leu Asp
            580             585             590

Phe Phe Arg Ser Met Asp Asp Ile Asp Tyr Lys Pro Thr Asn Lys Ser
            595             600             605

Asn Ala Pro Ser Glu Asn Asn Leu Ala Phe Leu Cys Gly Gly Ser Gly
            610             615             620

Asp Gln Ala Glu Trp Asn Leu Gly Gln Asp Asp Ser Ala Leu His Gly
625             630             635             640

Lys His Leu Pro Pro Ser Pro Arg Lys Arg Val Ser Ser Ser Gly Leu
            645             650             655

Thr Asp Ser Leu Phe Ile Leu Lys Glu Glu Asn Ser Asn Lys His Leu
            660             665             670

Gly Ala Asp Asn Val Ser Asp Pro Thr Ser Gly Leu Asp Phe Gln Leu
            675             680             685

Thr Ser Pro Glu Val Ser Gln Thr Asp Lys Gly Lys Thr Glu Lys Arg
            690             695             700

Glu Thr Leu Ser Gln Ile Ser Asp Asp Leu Leu Ile Pro Gly Leu Gly
705             710             715             720

Arg His Ser Ser Thr Phe Val Pro Trp Glu Lys Glu Gly Lys Glu Ala
            725             730             735

Lys Glu Thr Ser Glu Asp Ile Gly Leu Leu His Glu Val Val Ser Leu
            740             745             750

Cys His Met Thr Ser Asp Phe Gln Gln Ser Leu Asn Ile Ser Asp Lys
            755             760             765
```

```
Asn Thr Asn Gly Asn Gln Thr
        770             775

<210> SEQ ID NO 22
<211> LENGTH: 8797
<212> TYPE: PRT
<213> ORGANISM: Homo sapiens

<400> SEQUENCE: 22

Met Ala Thr Ser Arg Gly Ala Ser Arg Cys Pro Arg Asp Ile Ala Asn
1               5                   10                  15

Val Met Gln Arg Leu Gln Asp Glu Gln Glu Ile Val Gln Lys Arg Thr
            20                  25                  30

Phe Thr Lys Trp Ile Asn Ser His Leu Ala Lys Arg Lys Pro Pro Met
        35                  40                  45

Val Val Asp Asp Leu Phe Glu Asp Met Lys Asp Gly Val Lys Leu Leu
    50                  55                  60

Ala Leu Leu Glu Val Leu Ser Gly Gln Lys Leu Pro Cys Glu Gln Gly
65                  70                  75                  80

Arg Arg Met Lys Arg Ile His Ala Val Ala Asn Ile Gly Thr Ala Leu
                85                  90                  95

Lys Phe Leu Glu Gly Arg Lys Ile Lys Leu Val Asn Ile Asn Ser Thr
            100                 105                 110

Asp Ile Ala Asp Gly Arg Pro Ser Ile Val Leu Gly Leu Met Trp Thr
        115                 120                 125

Ile Ile Leu Tyr Phe Gln Ile Glu Glu Leu Thr Ser Asn Leu Pro Gln
    130                 135                 140

Leu Gln Ser Leu Ser Ser Ala Ser Ser Val Asp Ser Ile Val Ser
145                 150                 155                 160

Ser Glu Thr Pro Ser Pro Ser Lys Arg Lys Val Thr Thr Lys Ile
                165                 170                 175

Gln Gly Asn Ala Lys Lys Ala Leu Leu Lys Trp Val Gln Tyr Thr Ala
            180                 185                 190

Gly Lys Gln Thr Gly Ile Glu Val Lys Asp Phe Gly Lys Ser Trp Arg
        195                 200                 205

Ser Gly Val Ala Phe His Ser Val Ile His Ala Ile Arg Pro Glu Leu
    210                 215                 220

Val Asp Leu Glu Thr Val Lys Gly Arg Ser Asn Arg Glu Asn Leu Glu
225                 230                 235                 240

Asp Ala Phe Thr Ile Ala Glu Thr Glu Leu Gly Ile Pro Arg Leu Leu
                245                 250                 255

Asp Pro Glu Asp Val Asp Val Asp Lys Pro Asp Glu Lys Ser Ile Met
            260                 265                 270

Thr Tyr Val Ala Gln Phe Leu Lys His Tyr Pro Asp Ile His Asn Ala
        275                 280                 285

Ser Thr Asp Gly Gln Glu Asp Glu Ile Leu Pro Gly Phe Pro Ser
    290                 295                 300

Phe Ala Asn Ser Val Gln Asn Phe Lys Arg Glu Asp Arg Val Ile Phe
305                 310                 315                 320

Lys Glu Met Lys Val Trp Ile Glu Gln Phe Glu Arg Asp Leu Thr Arg
                325                 330                 335

Ala Gln Met Val Glu Ser Asn Leu Gln Asp Lys Tyr Gln Ser Phe Lys
            340                 345                 350

His Phe Arg Val Gln Tyr Glu Met Lys Arg Lys Gln Ile Glu His Leu
```

```
            355                 360                 365
Ile Gln Pro Leu His Arg Asp Gly Lys Leu Ser Leu Asp Gln Ala Leu
            370                 375                 380

Val Lys Gln Ser Trp Asp Arg Val Thr Ser Arg Leu Phe Asp Trp His
385                 390                 395                 400

Ile Gln Leu Asp Lys Ser Leu Pro Ala Pro Leu Gly Thr Ile Gly Ala
                405                 410                 415

Trp Leu Tyr Arg Ala Glu Val Ala Leu Arg Glu Glu Ile Thr Val Gln
            420                 425                 430

Gln Val His Glu Glu Thr Ala Asn Thr Ile Gln Arg Lys Leu Glu Gln
                435                 440                 445

His Lys Asp Leu Leu Gln Asn Thr Asp Ala His Lys Arg Ala Phe His
            450                 455                 460

Glu Ile Tyr Arg Thr Arg Ser Val Asn Gly Ile Pro Val Pro Pro Asp
465                 470                 475                 480

Gln Leu Glu Asp Met Ala Glu Arg Phe His Phe Val Ser Ser Thr Ser
                485                 490                 495

Glu Leu His Leu Met Lys Met Glu Phe Leu Glu Leu Lys Tyr Arg Leu
            500                 505                 510

Leu Ser Leu Leu Val Leu Ala Glu Ser Lys Leu Lys Ser Trp Ile Ile
            515                 520                 525

Lys Tyr Gly Arg Arg Glu Ser Val Glu Gln Leu Leu Gln Asn Tyr Val
530                 535                 540

Ser Phe Ile Glu Asn Ser Lys Phe Phe Glu Gln Tyr Glu Val Thr Tyr
545                 550                 555                 560

Gln Ile Leu Lys Gln Thr Ala Glu Met Tyr Val Lys Ala Asp Gly Ser
                565                 570                 575

Val Glu Glu Ala Glu Asn Val Met Lys Phe Met Asn Glu Thr Thr Ala
                580                 585                 590

Gln Trp Arg Asn Leu Ser Val Glu Val Arg Ser Val Arg Ser Met Leu
            595                 600                 605

Glu Glu Val Ile Ser Asn Trp Asp Arg Tyr Gly Asn Thr Val Ala Ser
610                 615                 620

Leu Gln Ala Trp Leu Glu Asp Ala Glu Lys Met Leu Asn Gln Ser Glu
625                 630                 635                 640

Asn Ala Lys Lys Asp Phe Phe Arg Asn Leu Pro His Trp Ile Gln Gln
                645                 650                 655

His Thr Ala Met Asn Asp Ala Gly Asn Phe Leu Ile Glu Thr Cys Asp
            660                 665                 670

Glu Met Val Ser Arg Asp Leu Lys Gln Gln Leu Leu Leu Leu Asn Gly
            675                 680                 685

Arg Trp Arg Glu Leu Phe Met Glu Val Lys Gln Tyr Ala Gln Ala Asp
            690                 695                 700

Glu Met Asp Arg Met Lys Lys Glu Tyr Thr Asp Cys Val Val Thr Leu
705                 710                 715                 720

Ser Ala Phe Ala Thr Glu Ala His Lys Lys Leu Ser Glu Pro Leu Glu
                725                 730                 735

Val Ser Phe Met Asn Val Lys Leu Leu Ile Gln Asp Leu Glu Asp Ile
            740                 745                 750

Glu Gln Arg Val Pro Val Met Asp Ala Gln Tyr Lys Ile Ile Thr Lys
            755                 760                 765

Thr Ala His Leu Ile Thr Lys Glu Ser Pro Gln Glu Glu Gly Lys Glu
            770                 775                 780
```

```
Met Phe Ala Thr Met Ser Lys Leu Lys Glu Gln Leu Thr Lys Val Lys
785                 790                 795                 800

Glu Cys Tyr Ser Pro Leu Leu Tyr Glu Ser Gln Gln Leu Leu Ile Pro
                805                 810                 815

Leu Glu Glu Leu Glu Lys Gln Met Thr Ser Phe Tyr Asp Ser Leu Gly
                820                 825                 830

Lys Ile Asn Glu Ile Ile Thr Val Leu Glu Arg Glu Ala Gln Ser Ser
                835                 840                 845

Ala Leu Phe Lys Gln Lys His Gln Glu Leu Leu Ala Cys Gln Glu Asn
                850                 855                 860

Cys Lys Lys Thr Leu Thr Leu Ile Glu Lys Gly Ser Gln Ser Val Gln
865                 870                 875                 880

Lys Phe Val Thr Leu Ser Asn Val Leu Lys His Phe Asp Gln Thr Arg
                885                 890                 895

Leu Gln Arg Gln Ile Ala Asp Ile His Val Ala Phe Gln Ser Met Val
                900                 905                 910

Lys Lys Thr Gly Asp Trp Lys Lys His Val Glu Thr Asn Ser Arg Leu
                915                 920                 925

Met Lys Lys Phe Glu Glu Ser Arg Ala Glu Leu Glu Lys Val Leu Arg
930                 935                 940

Ile Ala Gln Glu Gly Leu Glu Glu Lys Gly Asp Pro Glu Glu Leu Leu
945                 950                 955                 960

Arg Arg His Thr Glu Phe Phe Ser Gln Leu Asp Gln Arg Val Leu Asn
                965                 970                 975

Ala Phe Leu Lys Ala Cys Asp Glu Leu Thr Asp Ile Leu Pro Glu Gln
                980                 985                 990

Glu Gln Gln Gly Leu Gln Glu Ala  Val Arg Lys Leu His  Lys Gln Trp
                995                 1000                1005

Lys Asp  Leu Gln Gly Glu Ala  Pro Tyr His Leu Leu  His Leu Lys
     1010                1015                1020

Ile Asp  Val Glu Lys Asn Arg  Phe Leu Ala Ser Val  Glu Glu Cys
     1025                1030                1035

Arg Thr  Glu Leu Asp Arg Glu  Thr Lys Leu Met Pro  Gln Glu Gly
     1040                1045                1050

Ser Glu  Lys Ile Ile Lys Glu  His Arg Val Phe Phe  Ser Asp Lys
     1055                1060                1065

Gly Pro  His His Leu Cys Glu  Lys Arg Leu Gln Leu  Ile Glu Glu
     1070                1075                1080

Leu Cys  Val Lys Leu Pro Val  Arg Asp Pro Val Arg  Asp Thr Pro
     1085                1090                1095

Gly Thr  Cys His Val Thr Leu  Lys Glu Leu Arg Ala  Ala Ile Asp
     1100                1105                1110

Ser Thr  Tyr Arg Lys Leu Met  Glu Asp Pro Asp Lys  Trp Lys Asp
     1115                1120                1125

Tyr Thr  Ser Arg Phe Ser Glu  Phe Ser Ser Trp Ile  Ser Thr Asn
     1130                1135                1140

Glu Thr  Gln Leu Lys Gly Ile  Lys Gly Glu Ala Ile  Asp Thr Ala
     1145                1150                1155

Asn His  Gly Glu Val Lys Arg  Ala Val Glu Glu Ile  Arg Asn Gly
     1160                1165                1170

Val Thr  Lys Arg Gly Glu Thr  Leu Ser Trp Leu Lys  Ser Arg Leu
     1175                1180                1185
```

```
Lys Val Leu Thr Glu Val Ser Ser Glu Asn Glu Ala Gln Lys Gln
    1190            1195                1200

Gly Asp Glu Leu Ala Lys Leu Ser Ser Ser Phe Lys Ala Leu Val
    1205            1210                1215

Thr Leu Leu Ser Glu Val Glu Lys Met Leu Ser Asn Phe Gly Asp
    1220            1225                1230

Cys Val Gln Tyr Lys Glu Ile Val Lys Asn Ser Leu Glu Glu Leu
    1235            1240                1245

Ile Ser Gly Ser Lys Glu Val Gln Glu Gln Ala Glu Lys Ile Leu
    1250            1255                1260

Asp Thr Glu Asn Leu Phe Glu Ala Gln Gln Leu Leu His His
    1265            1270                1275

Gln Gln Lys Thr Lys Arg Ile Ser Ala Lys Lys Arg Asp Val Gln
    1280            1285                1290

Gln Gln Ile Ala Gln Ala Gln Gln Gly Glu Gly Gly Leu Pro Asp
    1295            1300                1305

Arg Gly His Glu Glu Leu Arg Lys Leu Glu Ser Thr Leu Asp Gly
    1310            1315                1320

Leu Glu Arg Ser Arg Glu Arg Gln Glu Arg Arg Ile Gln Val Thr
    1325            1330                1335

Leu Arg Lys Trp Glu Arg Phe Glu Thr Asn Lys Glu Thr Val Val
    1340            1345                1350

Arg Tyr Leu Phe Gln Thr Gly Ser Ser His Glu Arg Phe Leu Ser
    1355            1360                1365

Phe Ser Ser Leu Glu Ser Leu Ser Ser Glu Leu Glu Gln Thr Lys
    1370            1375                1380

Glu Phe Ser Lys Arg Thr Glu Ser Ile Ala Val Gln Ala Glu Asn
    1385            1390                1395

Leu Val Lys Glu Ala Ser Glu Ile Pro Leu Gly Pro Gln Asn Lys
    1400            1405                1410

Gln Leu Leu Gln Gln Gln Ala Lys Ser Ile Lys Glu Gln Val Lys
    1415            1420                1425

Lys Leu Glu Asp Thr Leu Glu Asp Ile Lys Thr Met Glu Met
    1430            1435                1440

Val Lys Thr Lys Trp Asp His Phe Gly Ser Asn Phe Glu Thr Leu
    1445            1450                1455

Ser Val Trp Ile Thr Glu Lys Glu Lys Glu Leu Asn Ala Leu Glu
    1460            1465                1470

Thr Ser Ser Ser Ala Met Asp Met Gln Ile Ser Gln Ile Lys Val
    1475            1480                1485

Thr Ile Gln Glu Ile Glu Ser Lys Leu Ser Ser Ile Val Gly Leu
    1490            1495                1500

Glu Glu Glu Ala Gln Ser Phe Ala Gln Phe Val Thr Thr Gly Glu
    1505            1510                1515

Ser Ala Arg Ile Lys Ala Lys Leu Thr Gln Ile Arg Arg Tyr Gly
    1520            1525                1530

Glu Glu Leu Arg Glu His Ala Gln Cys Leu Glu Gly Thr Ile Leu
    1535            1540                1545

Gly His Leu Ser Gln Gln Gln Lys Phe Glu Glu Asn Leu Arg Lys
    1550            1555                1560

Ile Gln Gln Ser Val Ser Glu Phe Glu Asp Lys Leu Ala Val Pro
    1565            1570                1575

Ile Lys Ile Cys Ser Ser Ala Thr Glu Thr Tyr Lys Val Leu Gln
```

-continued

```
            1580                1585               1590
Glu His Met Asp Leu Cys Gln Ala Leu Glu Ser Leu Ser Ser Ala
            1595                1600               1605
Ile Thr Ala Phe Ser Ala Ser Ala Arg Lys Val Val Asn Arg Asp
            1610                1615               1620
Ser Cys Val Gln Glu Ala Ala Ala Leu Gln Gln Gln Tyr Glu Asp
            1625                1630               1635
Ile Leu Arg Arg Ala Lys Glu Arg Gln Thr Ala Leu Glu Asn Leu
            1640                1645               1650
Leu Ala His Trp Gln Arg Leu Glu Lys Glu Leu Ser Ser Phe Leu
            1655                1660               1665
Thr Trp Leu Glu Arg Gly Glu Ala Lys Ala Ser Ser Pro Glu Met
            1670                1675               1680
Asp Ile Ser Ala Asp Arg Val Lys Val Glu Gly Glu Leu Gln Leu
            1685                1690               1695
Ile Gln Ala Leu Gln Asn Glu Val Val Ser Gln Ala Ser Phe Tyr
            1700                1705               1710
Ser Lys Leu Leu Gln Leu Lys Glu Ser Leu Phe Ser Val Ala Ser
            1715                1720               1725
Lys Asp Asp Val Lys Met Met Lys Leu His Leu Glu Gln Leu Asp
            1730                1735               1740
Glu Arg Trp Arg Asp Leu Pro Gln Ile Ile Asn Lys Arg Ile Asn
            1745                1750               1755
Phe Leu Gln Ser Val Val Ala Glu His Gln Gln Phe Asp Glu Leu
            1760                1765               1770
Leu Leu Ser Phe Ser Val Trp Ile Lys Leu Phe Leu Ser Glu Leu
            1775                1780               1785
Gln Thr Thr Ser Glu Ile Ser Ile Met Asp His Gln Val Ala Leu
            1790                1795               1800
Thr Arg His Lys Asp His Ala Ala Glu Val Glu Ser Lys Lys Gly
            1805                1810               1815
Glu Leu Gln Ser Leu Gln Gly His Leu Ala Lys Leu Gly Ser Leu
            1820                1825               1830
Gly Arg Ala Glu Asp Leu His Leu Leu Gln Gly Lys Ala Glu Asp
            1835                1840               1845
Cys Phe Gln Leu Phe Glu Glu Ala Ser Gln Val Val Glu Arg Arg
            1850                1855               1860
Gln Leu Ala Leu Ser His Leu Ala Glu Phe Leu Gln Ser His Ala
            1865                1870               1875
Ser Leu Ser Gly Ile Leu Arg Gln Leu Arg Gln Thr Val Glu Ala
            1880                1885               1890
Thr Asn Ser Met Asn Lys Asn Glu Ser Asp Leu Ile Glu Lys Asp
            1895                1900               1905
Leu Asn Asp Ala Leu Gln Asn Ala Lys Ala Leu Glu Ser Ala Ala
            1910                1915               1920
Val Ser Leu Asp Gly Ile Leu Ser Lys Ala Gln Tyr His Leu Lys
            1925                1930               1935
Ile Gly Ser Ser Glu Gln Arg Thr Ser Cys Arg Ala Thr Ala Asp
            1940                1945               1950
Gln Leu Cys Gly Glu Val Glu Arg Ile Gln Asn Leu Leu Gly Thr
            1955                1960               1965
Lys Gln Ser Glu Ala Asp Ala Leu Ala Val Leu Lys Lys Ala Phe
            1970                1975               1980
```

```
Gln Asp Gln Lys Glu Glu Leu Leu Lys Ser Ile Glu Asp Ile Glu
    1985              1990              1995

Glu Arg Thr Asp Lys Glu Arg Leu Lys Glu Pro Thr Arg Gln Ala
    2000              2005              2010

Leu Gln Gln Arg Leu Arg Val Phe Asn Gln Leu Glu Asp Glu Leu
    2015              2020              2025

Asn Ser His Glu His Glu Leu Cys Trp Leu Lys Asp Lys Ala Lys
    2030              2035              2040

Gln Ile Ala Gln Lys Asp Val Ala Phe Ala Pro Glu Val Asp Arg
    2045              2050              2055

Glu Ile Asn Arg Leu Glu Val Thr Trp Asp Asp Thr Lys Arg Leu
    2060              2065              2070

Ile His Glu Asn Gln Gly Gln Cys Cys Gly Leu Ile Asp Leu Met
    2075              2080              2085

Arg Glu Tyr Gln Asn Leu Lys Ser Ala Val Ser Lys Val Leu Glu
    2090              2095              2100

Asn Ala Ser Ser Val Ile Val Thr Arg Thr Thr Ile Lys Asp Gln
    2105              2110              2115

Glu Asp Leu Lys Trp Ala Phe Ser Lys His Glu Thr Ala Lys Asn
    2120              2125              2130

Lys Met Asn Tyr Lys Gln Lys Asp Leu Asp Asn Phe Thr Ser Lys
    2135              2140              2145

Gly Lys His Leu Leu Ser Glu Leu Lys Lys Ile His Ser Ser Asp
    2150              2155              2160

Phe Ser Leu Val Lys Thr Asp Met Glu Ser Thr Val Asp Lys Trp
    2165              2170              2175

Leu Asp Val Ser Glu Lys Leu Glu Glu Asn Met Asp Arg Leu Arg
    2180              2185              2190

Val Ser Leu Ser Ile Trp Asp Asp Val Leu Ser Thr Arg Asp Glu
    2195              2200              2205

Ile Glu Gly Trp Ser Asn Asn Cys Val Pro Gln Met Ala Glu Asn
    2210              2215              2220

Ile Ser Asn Leu Asp Asn His Leu Arg Ala Glu Glu Leu Leu Lys
    2225              2230              2235

Glu Phe Glu Ser Glu Val Lys Asn Lys Ala Leu Arg Leu Glu Glu
    2240              2245              2250

Leu His Ser Lys Val Asn Asp Leu Lys Glu Leu Thr Lys Asn Leu
    2255              2260              2265

Glu Thr Pro Pro Asp Leu Gln Phe Ile Glu Ala Asp Leu Met Gln
    2270              2275              2280

Lys Leu Glu His Ala Lys Glu Ile Thr Glu Val Ala Lys Gly Thr
    2285              2290              2295

Leu Lys Asp Phe Thr Ala Gln Ser Thr Gln Val Glu Lys Phe Ile
    2300              2305              2310

Asn Asp Ile Thr Thr Trp Phe Thr Lys Val Glu Glu Ser Leu Met
    2315              2320              2325

Asn Cys Ala Gln Asn Glu Thr Cys Glu Ala Leu Lys Lys Val Lys
    2330              2335              2340

Asp Ile Gln Lys Glu Leu Gln Ser Gln Ser Asn Ile Ser Ser
    2345              2350              2355

Thr Gln Glu Asn Leu Asn Ser Leu Cys Arg Lys Tyr His Ser Ala
    2360              2365              2370
```

| | | | | | | | | | | | |
|---|---|---|---|---|---|---|---|---|---|---|---|
|Glu|Leu 2375|Glu|Ser|Leu|Gly 2380|Arg|Ala|Met|Thr Gly 2385|Leu|Ile|Lys|Lys|

Glu Leu Glu Ser Leu Gly Arg Ala Met Thr Gly Leu Ile Lys Lys
    2375            2380            2385

His Glu Ala Val Ser Gln Leu Cys Ser Lys Thr Gln Ala Ser Leu
    2390            2395            2400

Gln Glu Ser Leu Glu Lys His Phe Ser Glu Ser Met Gln Glu Phe
    2405            2410            2415

Gln Glu Trp Phe Leu Gly Ala Lys Ala Ala Lys Glu Ser Ser
    2420            2425            2430

Asp Arg Thr Gly Asp Ser Lys Val Leu Glu Ala Lys Leu His Asp
    2435            2440            2445

Leu Gln Asn Ile Leu Asp Ser Val Ser Asp Gly Gln Ser Lys Leu
    2450            2455            2460

Asp Ala Val Thr Gln Glu Gly Gln Thr Leu Tyr Ala His Leu Ser
    2465            2470            2475

Lys Gln Ile Val Ser Ser Ile Gln Glu Gln Ile Thr Lys Ala Asn
    2480            2485            2490

Glu Glu Phe Gln Ala Phe Leu Lys Gln Cys Leu Lys Asp Lys Gln
    2495            2500            2505

Ala Leu Gln Asp Cys Ala Ser Glu Leu Gly Ser Phe Glu Asp Gln
    2510            2515            2520

His Arg Lys Leu Asn Leu Trp Ile His Glu Met Glu Glu Arg Phe
    2525            2530            2535

Asn Thr Glu Asn Leu Gly Glu Ser Lys Gln His Ile Pro Glu Lys
    2540            2545            2550

Lys Asn Glu Val His Lys Val Glu Met Phe Leu Gly Glu Leu Leu
    2555            2560            2565

Ala Ala Arg Glu Ser Leu Asp Lys Leu Ser Gln Arg Gly Gln Leu
    2570            2575            2580

Leu Ser Glu Glu Gly His Gly Ala Gly Gln Glu Gly Arg Leu Cys
    2585            2590            2595

Ser Gln Leu Leu Thr Ser His Gln Asn Leu Leu Arg Met Thr Lys
    2600            2605            2610

Glu Lys Leu Arg Ser Cys Gln Val Ala Leu Gln Glu His Glu Ala
    2615            2620            2625

Leu Glu Glu Ala Leu Gln Ser Met Trp Phe Trp Val Lys Ala Ile
    2630            2635            2640

Gln Asp Arg Leu Ala Cys Ala Glu Ser Thr Leu Gly Ser Lys Asp
    2645            2650            2655

Thr Leu Glu Lys Arg Leu Ser Gln Ile Gln Asp Ile Leu Leu Met
    2660            2665            2670

Lys Gly Glu Gly Glu Val Lys Leu Asn Met Ala Ile Gly Lys Gly
    2675            2680            2685

Glu Gln Ala Leu Arg Ser Ser Asn Lys Glu Gly Gln Arg Val Ile
    2690            2695            2700

Gln Thr Gln Leu Glu Thr Leu Lys Glu Val Trp Ala Asp Ile Met
    2705            2710            2715

Ser Ser Ser Val His Ala Gln Ser Thr Leu Glu Ser Val Ile Ser
    2720            2725            2730

Gln Trp Asn Asp Tyr Val Glu Arg Lys Asn Gln Leu Glu Gln Trp
    2735            2740            2745

Met Glu Ser Val Asp Gln Lys Ile Glu His Pro Leu Gln Pro Gln
    2750            2755            2760

Pro Gly Leu Lys Glu Lys Phe Val Leu Leu Asp His Leu Gln Ser

```
              2765                2770                2775

Ile Leu Ser Glu Ala Glu Asp His Thr Arg Ala Leu His Arg Leu
    2780                2785                2790

Ile Ala Lys Ser Arg Glu Leu Tyr Glu Lys Thr Glu Asp Glu Ser
    2795                2800                2805

Phe Lys Asp Thr Ala Gln Glu Glu Leu Lys Thr Gln Phe Asn Asp
    2810                2815                2820

Ile Met Thr Val Ala Lys Glu Lys Met Arg Lys Val Glu Glu Ile
    2825                2830                2835

Val Lys Asp His Leu Met Tyr Leu Asp Ala Val His Glu Phe Thr
    2840                2845                2850

Asp Trp Leu His Ser Ala Lys Glu Glu Leu His Arg Trp Ser Asp
    2855                2860                2865

Met Ser Gly Asp Ser Ser Ala Thr Gln Lys Lys Leu Ser Lys Ile
    2870                2875                2880

Lys Glu Leu Ile Asp Ser Arg Glu Ile Gly Ala Ser Arg Leu Ser
    2885                2890                2895

Arg Val Glu Ser Leu Ala Pro Glu Val Lys Gln Asn Thr Thr Ala
    2900                2905                2910

Ser Gly Cys Glu Leu Met His Thr Glu Met Gln Ala Leu Arg Ala
    2915                2920                2925

Asp Trp Lys Gln Trp Glu Asp Ser Val Phe Gln Thr Gln Ser Cys
    2930                2935                2940

Leu Glu Asn Leu Val Ser Gln Met Ala Leu Ser Glu Gln Glu Phe
    2945                2950                2955

Ser Gly Gln Val Ala Gln Leu Glu Gln Ala Leu Glu Gln Phe Ser
    2960                2965                2970

Ala Leu Leu Lys Thr Trp Ala Gln Gln Leu Thr Leu Leu Glu Gly
    2975                2980                2985

Lys Asn Thr Asp Glu Glu Ile Val Glu Cys Trp His Lys Gly Gln
    2990                2995                3000

Glu Ile Leu Asp Ala Leu Gln Lys Ala Glu Pro Arg Thr Glu Asp
    3005                3010                3015

Leu Lys Ser Gln Leu Asn Glu Leu Cys Arg Phe Ser Arg Asp Leu
    3020                3025                3030

Ser Thr Tyr Ser Gly Lys Val Ser Gly Leu Ile Lys Glu Tyr Asn
    3035                3040                3045

Cys Leu Cys Leu Gln Ala Ser Lys Gly Cys Gln Asn Lys Glu Gln
    3050                3055                3060

Ile Leu Gln Gln Arg Phe Arg Lys Ala Phe Arg Asp Phe Gln Gln
    3065                3070                3075

Trp Leu Val Asn Ala Lys Ile Thr Thr Ala Lys Cys Phe Asp Ile
    3080                3085                3090

Pro Gln Asn Ile Ser Glu Val Ser Thr Ser Leu Gln Lys Ile Gln
    3095                3100                3105

Glu Phe Leu Ser Glu Ser Glu Asn Gly Gln His Lys Leu Asn Met
    3110                3115                3120

Met Leu Ser Lys Gly Glu Leu Leu Ser Thr Leu Leu Thr Lys Glu
    3125                3130                3135

Lys Ala Lys Gly Ile Gln Ala Lys Val Thr Ala Ala Lys Glu Asp
    3140                3145                3150

Trp Lys Asn Phe His Ser Asn Leu His Gln Lys Glu Ser Ala Leu
    3155                3160                3165
```

-continued

```
Glu Asn Leu Lys Ile Gln Met Lys Asp Phe Glu Val Ser Ala Glu
    3170                3175                3180

Pro Ile Gln Asp Trp Leu Ser Lys Thr Glu Lys Met Val His Glu
    3185                3190                3195

Ser Ser Asn Arg Leu Tyr Asp Leu Pro Ala Lys Arg Arg Glu Gln
    3200                3205                3210

Gln Lys Leu Gln Ser Val Leu Glu Glu Ile His Cys Tyr Glu Pro
    3215                3220                3225

Gln Leu Asn Arg Leu Lys Glu Lys Ala Gln Gln Leu Trp Glu Gly
    3230                3235                3240

Gln Ala Ala Ser Lys Ser Phe Arg His Arg Val Ser Gln Leu Ser
    3245                3250                3255

Ser Gln Tyr Leu Ala Leu Ser Asn Leu Thr Lys Glu Lys Val Ser
    3260                3265                3270

Arg Leu Asp Arg Ile Val Ala Glu His Asn Gln Phe Ser Leu Gly
    3275                3280                3285

Ile Lys Glu Leu Gln Asp Trp Met Thr Asp Ala Ile His Met Leu
    3290                3295                3300

Asp Ser Tyr Cys His Pro Thr Ser Asp Lys Ser Val Leu Asp Ser
    3305                3310                3315

Arg Thr Leu Lys Leu Glu Ala Leu Leu Ser Val Lys Gln Glu Lys
    3320                3325                3330

Glu Ile Gln Met Lys Met Ile Val Thr Arg Gly Glu Ser Val Leu
    3335                3340                3345

Gln Asn Thr Ser Pro Glu Gly Ile Pro Thr Ile Gln Gln Gln Leu
    3350                3355                3360

Gln Ser Val Lys Asp Met Trp Ala Ser Leu Leu Ser Ala Gly Ile
    3365                3370                3375

Arg Cys Lys Ser Gln Leu Glu Gly Ala Leu Ser Lys Trp Thr Ser
    3380                3385                3390

Tyr Gln Asp Gly Val Arg Gln Phe Ser Gly Trp Met Asp Ser Met
    3395                3400                3405

Glu Ala Asn Leu Asn Glu Ser Glu Arg Gln His Ala Glu Leu Arg
    3410                3415                3420

Asp Lys Thr Thr Met Leu Gly Lys Ala Lys Leu Leu Asn Glu Glu
    3425                3430                3435

Val Leu Ser Tyr Ser Ser Leu Leu Glu Thr Ile Glu Val Lys Gly
    3440                3445                3450

Ala Gly Met Thr Glu His Tyr Val Thr Gln Leu Glu Leu Gln Asp
    3455                3460                3465

Leu Gln Glu Arg Tyr Arg Ala Ile Gln Glu Arg Ala Lys Glu Ala
    3470                3475                3480

Val Thr Lys Ser Glu Lys Leu Val Arg Leu His Gln Glu Tyr Gln
    3485                3490                3495

Arg Asp Leu Lys Ala Phe Glu Val Trp Leu Gly Gln Glu Gln Glu
    3500                3505                3510

Lys Leu Asp Gln Tyr Ser Val Leu Glu Gly Asp Ala His Thr His
    3515                3520                3525

Glu Thr Thr Leu Arg Asp Leu Gln Glu Leu Gln Val His Cys Ala
    3530                3535                3540

Glu Gly Gln Ala Leu Leu Asn Ser Val Leu His Thr Arg Glu Asp
    3545                3550                3555
```

```
Val Ile Pro Ser Gly Ile Pro Gln Ala Glu Asp Arg Ala Leu Glu
3560            3565            3570

Ser Leu Arg Gln Asp Trp Gln Ala Tyr Gln His Arg Leu Ser Glu
3575            3580            3585

Thr Arg Thr Gln Phe Asn Asn Val Val Asn Lys Leu Arg Leu Met
3590            3595            3600

Glu Gln Lys Phe Gln Gln Val Asp Glu Trp Leu Lys Thr Ala Glu
3605            3610            3615

Glu Lys Val Ser Pro Arg Thr Arg Arg Gln Ser Asn Arg Ala Thr
3620            3625            3630

Lys Glu Ile Gln Leu His Gln Met Lys Lys Trp His Glu Glu Val
3635            3640            3645

Thr Ala Tyr Arg Asp Glu Val Glu Glu Val Gly Ala Arg Ala Gln
3650            3655            3660

Glu Ile Leu Asp Glu Ser His Val Asn Ser Arg Met Gly Cys Gln
3665            3670            3675

Ala Thr Gln Leu Thr Ser Arg Tyr Gln Ala Leu Leu Leu Gln Val
3680            3685            3690

Leu Glu Gln Ile Lys Phe Leu Glu Glu Glu Ile Gln Ser Leu Glu
3695            3700            3705

Glu Ser Glu Ser Ser Leu Ser Ser Tyr Ser Asp Trp Tyr Gly Ser
3710            3715            3720

Thr His Lys Asn Phe Lys Asn Val Ala Thr Lys Ile Asp Lys Val
3725            3730            3735

Asp Thr Val Met Met Gly Lys Lys Leu Lys Thr Leu Glu Val Leu
3740            3745            3750

Leu Lys Asp Met Glu Lys Gly His Ser Leu Leu Lys Ser Ala Arg
3755            3760            3765

Glu Lys Gly Glu Arg Ala Val Lys Tyr Leu Glu Glu Gly Glu Ala
3770            3775            3780

Glu Arg Leu Arg Lys Glu Ile His Asp His Met Glu Gln Leu Lys
3785            3790            3795

Glu Leu Thr Ser Thr Val Arg Lys Glu His Met Thr Leu Glu Lys
3800            3805            3810

Gly Leu His Leu Ala Lys Glu Phe Ser Asp Lys Cys Lys Ala Leu
3815            3820            3825

Thr Gln Trp Ile Ala Glu Tyr Gln Glu Ile Leu His Val Pro Glu
3830            3835            3840

Glu Pro Lys Met Glu Leu Tyr Glu Lys Lys Ala Gln Leu Ser Lys
3845            3850            3855

Tyr Lys Ser Leu Gln Gln Thr Val Leu Ser His Glu Pro Ser Val
3860            3865            3870

Lys Ser Val Arg Glu Lys Gly Glu Ala Leu Leu Glu Leu Val Gln
3875            3880            3885

Asp Val Thr Leu Lys Asp Lys Ile Asp Gln Leu Gln Ser Asp Tyr
3890            3895            3900

Gln Asp Leu Cys Ser Ile Gly Lys Glu His Val Phe Ser Leu Glu
3905            3910            3915

Ala Lys Val Lys Asp His Glu Asp Tyr Asn Ser Glu Leu Gln Glu
3920            3925            3930

Val Glu Lys Trp Leu Leu Gln Met Ser Gly Arg Leu Val Ala Pro
3935            3940            3945

Asp Leu Leu Glu Thr Ser Ser Leu Glu Thr Ile Thr Gln Gln Leu
```

-continued

```
         3950                3955                3960
Ala His  His Lys Ala Met Met  Glu Glu Ile Ala Gly  Phe Glu Asp
         3965                3970                3975

Arg Leu  Asn Asn Leu Gln Met  Lys Gly Asp Thr Leu  Ile Gly Gln
         3980                3985                3990

Cys Ala  Asp His Leu Gln Ala  Lys Leu Lys Gln Asn  Val His Ala
         3995                4000                4005

His Leu  Gln Gly Thr Lys Asp  Ser Tyr Ser Ala Ile  Cys Ser Thr
         4010                4015                4020

Ala Gln  Arg Met Tyr Gln Ser  Leu Glu His Glu Leu  Gln Lys His
         4025                4030                4035

Val Ser  Arg Gln Asp Thr Leu  Gln Gln Cys Gln Ala  Trp Leu Ser
         4040                4045                4050

Ala Val  Gln Pro Asp Leu Glu  Pro Ser Pro Gln Pro  Pro Leu Ser
         4055                4060                4065

Arg Ala  Glu Ala Ile Lys Gln  Val Lys His Phe Arg  Ala Leu Gln
         4070                4075                4080

Glu Gln  Ala Arg Thr Tyr Leu  Asp Leu Leu Cys Ser  Met Cys Asp
         4085                4090                4095

Leu Ser  Asn Ala Ser Val Lys  Thr Thr Ala Lys Asp  Ile Gln Gln
         4100                4105                4110

Thr Glu  Gln Thr Ile Glu Gln  Lys Leu Val Gln Ala  Gln Asn Leu
         4115                4120                4125

Thr Gln  Gly Trp Glu Glu Ile  Lys His Leu Lys Ser  Glu Leu Trp
         4130                4135                4140

Ile Tyr  Leu Gln Asp Ala Asp  Gln Gln Leu Gln Asn  Met Lys Arg
         4145                4150                4155

Arg His  Ser Glu Leu Glu Leu  Asn Ile Ala Gln Asn  Met Val Ser
         4160                4165                4170

Gln Val  Lys Asp Phe Val Lys  Lys Leu Gln Ser Lys  Gln Ala Ser
         4175                4180                4185

Val Asn  Thr Ile Ile Glu Lys  Val Asn Lys Leu Thr  Lys Lys Glu
         4190                4195                4200

Glu Ser  Pro Glu His Lys Glu  Ile Asn His Leu Asn  Asp Gln Trp
         4205                4210                4215

Leu Asp  Leu Cys Arg Gln Ser  Asn Asn Leu Cys Leu  Gln Arg Glu
         4220                4225                4230

Glu Asp  Leu Gln Arg Thr Arg  Asp Tyr His Asp Cys  Met Asn Val
         4235                4240                4245

Val Glu  Val Phe Leu Glu Lys  Phe Thr Thr Glu Trp  Asp Asn Leu
         4250                4255                4260

Ala Arg  Ser Asp Ala Glu Ser  Thr Ala Val His Leu  Glu Ala Leu
         4265                4270                4275

Lys Lys  Leu Ala Leu Ala Leu  Gln Glu Arg Lys Tyr  Ala Ile Glu
         4280                4285                4290

Asp Leu  Lys Asp Gln Lys Gln  Lys Met Ile Glu His  Leu Asn Leu
         4295                4300                4305

Asp Asp  Lys Glu Leu Val Lys  Glu Gln Thr Ser His  Leu Glu Gln
         4310                4315                4320

Arg Trp  Phe Gln Leu Glu Asp  Leu Ile Lys Arg Lys  Ile Gln Val
         4325                4330                4335

Ser Val  Thr Asn Leu Glu Glu  Leu Asn Val Val Gln  Ser Arg Phe
         4340                4345                4350
```

```
Gln Glu Leu Met Glu Trp Ala Glu Gln Gln Pro Asn Ile Ala
    4355              4360            4365

Glu Ala Leu Lys Gln Ser Pro Pro Asp Met Ala Gln Asn Leu
    4370              4375            4380

Leu Met Asp His Leu Ala Ile Cys Ser Glu Leu Glu Ala Lys Gln
    4385              4390            4395

Met Leu Leu Lys Ser Leu Ile Lys Asp Ala Asp Arg Val Met Ala
    4400              4405            4410

Asp Leu Gly Leu Asn Glu Arg Gln Val Ile Gln Lys Ala Leu Ser
    4415              4420            4425

Asp Ala Gln Ser His Val Asn Cys Leu Ser Asp Leu Val Gly Gln
    4430              4435            4440

Arg Arg Lys Tyr Leu Asn Lys Ala Leu Ser Glu Lys Thr Gln Phe
    4445              4450            4455

Leu Met Ala Val Phe Gln Ala Thr Ser Gln Ile Gln Gln His Glu
    4460              4465            4470

Arg Lys Ile Met Phe Arg Glu His Ile Cys Leu Leu Pro Asp Asp
    4475              4480            4485

Val Ser Lys Gln Val Lys Thr Cys Lys Ser Ala Gln Ala Ser Leu
    4490              4495            4500

Lys Thr Tyr Gln Asn Glu Val Thr Gly Leu Trp Ala Gln Gly Arg
    4505              4510            4515

Glu Leu Met Lys Glu Val Thr Glu Gln Glu Lys Ser Glu Val Leu
    4520              4525            4530

Gly Lys Leu Gln Glu Leu Gln Ser Val Tyr Asp Ser Val Leu Gln
    4535              4540            4545

Lys Cys Ser His Arg Leu Gln Glu Leu Glu Lys Asn Leu Val Ser
    4550              4555            4560

Arg Lys His Phe Lys Glu Asp Phe Asp Lys Ala Cys His Trp Leu
    4565              4570            4575

Lys Gln Ala Asp Ile Val Thr Phe Pro Glu Ile Asn Leu Met Asn
    4580              4585            4590

Glu Ser Ser Glu Leu His Thr Gln Leu Ala Lys Tyr Gln Asn Ile
    4595              4600            4605

Leu Glu Gln Ser Pro Glu Tyr Glu Asn Leu Leu Leu Thr Leu Gln
    4610              4615            4620

Arg Thr Gly Gln Thr Ile Leu Pro Ser Leu Asn Glu Val Asp His
    4625              4630            4635

Ser Tyr Leu Ser Glu Lys Leu Asn Ala Leu Pro Arg Gln Phe Asn
    4640              4645            4650

Val Ile Val Ala Leu Ala Lys Asp Lys Phe Tyr Lys Val Gln Glu
    4655              4660            4665

Ala Ile Leu Ala Arg Lys Glu Tyr Ala Ser Leu Ile Glu Leu Thr
    4670              4675            4680

Thr Gln Ser Leu Ser Glu Leu Glu Ala Gln Phe Leu Arg Met Ser
    4685              4690            4695

Lys Val Pro Thr Asp Leu Ala Val Glu Glu Ala Leu Ser Leu Gln
    4700              4705            4710

Asp Gly Cys Arg Ala Ile Leu Asp Glu Val Ala Gly Leu Gly Glu
    4715              4720            4725

Ala Val Asp Glu Leu Asn Gln Lys Lys Glu Gly Phe Arg Ser Thr
    4730              4735            4740
```

-continued

```
Gly Gln Pro Trp Gln Pro Asp Lys Met Leu His Leu Val Thr Leu
4745                4750                4755

Tyr His Arg Leu Lys Arg Gln Thr Glu Gln Arg Val Ser Leu Leu
4760                4765                4770

Glu Asp Thr Thr Ser Ala Tyr Gln Glu His Glu Lys Met Cys Gln
4775                4780                4785

Gln Leu Glu Arg Gln Leu Lys Ser Val Lys Glu Gln Ser Lys
4790                4795                4800

Val Asn Glu Glu Thr Leu Pro Ala Glu Glu Lys Leu Lys Met Tyr
4805                4810                4815

His Ser Leu Ala Gly Ser Leu Gln Asp Ser Gly Ile Val Leu Lys
4820                4825                4830

Arg Val Thr Ile His Leu Glu Asp Leu Ala Pro His Leu Asp Pro
4835                4840                4845

Leu Ala Tyr Glu Lys Ala Arg His Gln Ile Gln Ser Trp Gln Gly
4850                4855                4860

Glu Leu Lys Leu Leu Thr Ser Ala Ile Gly Glu Thr Val Thr Glu
4865                4870                4875

Cys Glu Ser Arg Met Val Gln Ser Ile Asp Phe Gln Thr Glu Met
4880                4885                4890

Ser Arg Ser Leu Asp Trp Leu Arg Arg Val Lys Ala Glu Leu Ser
4895                4900                4905

Gly Pro Val Tyr Leu Asp Leu Asn Leu Gln Asp Ile Gln Glu Glu
4910                4915                4920

Ile Arg Lys Ile Gln Ile His Gln Glu Glu Val Gln Ser Ser Leu
4925                4930                4935

Arg Ile Met Asn Ala Leu Ser His Lys Glu Lys Glu Lys Phe Thr
4940                4945                4950

Lys Ala Lys Glu Leu Ile Ser Ala Asp Leu Glu His Ser Leu Ala
4955                4960                4965

Glu Leu Ser Glu Leu Asp Gly Asp Ile Gln Glu Ala Leu Arg Thr
4970                4975                4980

Arg Gln Ala Thr Leu Thr Glu Ile Tyr Ser Gln Cys Gln Arg Tyr
4985                4990                4995

Tyr Gln Val Phe Gln Ala Ala Asn Asp Trp Leu Glu Asp Ala Gln
5000                5005                5010

Glu Leu Leu Gln Leu Ala Gly Asn Gly Leu Asp Val Glu Ser Ala
5015                5020                5025

Glu Glu Asn Leu Lys Ser His Met Glu Phe Phe Ser Thr Glu Asp
5030                5035                5040

Gln Phe His Ser Asn Leu Glu Glu Leu His Ser Leu Val Ala Thr
5045                5050                5055

Leu Asp Pro Leu Ile Lys Pro Thr Gly Lys Glu Asp Leu Glu Gln
5060                5065                5070

Lys Val Ala Ser Leu Glu Leu Arg Ser Gln Arg Met Ser Arg Asp
5075                5080                5085

Ser Gly Ala Gln Val Asp Leu Leu Gln Arg Cys Thr Ala Gln Trp
5090                5095                5100

His Asp Tyr Gln Lys Ala Arg Glu Glu Val Ile Glu Leu Met Asn
5105                5110                5115

Asp Thr Glu Lys Lys Leu Ser Glu Phe Ser Leu Leu Lys Thr Ser
5120                5125                5130

Ser Ser His Glu Ala Glu Glu Lys Leu Ser Glu His Lys Ala Leu
```

-continued

```
            5135                5140                5145
Val Ser Val Val Asn Ser Phe His Glu Lys Ile Val Ala Leu Glu
    5150                5155                5160
Glu Lys Ala Ser Gln Leu Glu Lys Thr Gly Asn Asp Ala Ser Lys
    5165                5170                5175
Ala Thr Leu Ser Arg Ser Met Thr Thr Val Trp Gln Arg Trp Thr
    5180                5185                5190
Arg Leu Arg Ala Val Ala Gln Asp Gln Glu Lys Ile Leu Glu Asp
    5195                5200                5205
Ala Val Asp Glu Trp Thr Gly Phe Asn Asn Lys Val Lys Lys Ala
    5210                5215                5220
Thr Glu Met Ile Asp Gln Leu Gln Asp Lys Leu Pro Gly Ser Ser
    5225                5230                5235
Ala Glu Lys Ala Ser Lys Ala Glu Leu Leu Thr Leu Leu Glu Tyr
    5240                5245                5250
His Asp Thr Phe Val Leu Glu Leu Glu Gln Gln Gln Ser Ala Leu
    5255                5260                5265
Gly Met Leu Arg Gln Gln Thr Leu Ser Met Leu Gln Asp Gly Ala
    5270                5275                5280
Ala Pro Thr Pro Gly Glu Glu Pro Pro Leu Met Gln Glu Ile Thr
    5285                5290                5295
Ala Met Gln Asp Arg Cys Leu Asn Met Gln Glu Lys Val Lys Thr
    5300                5305                5310
Asn Gly Lys Leu Val Lys Gln Glu Leu Lys Asp Arg Glu Met Val
    5315                5320                5325
Glu Thr Gln Ile Asn Ser Val Lys Cys Trp Val Gln Glu Thr Lys
    5330                5335                5340
Glu Tyr Leu Gly Asn Pro Thr Ile Glu Ile Asp Ala Gln Leu Glu
    5345                5350                5355
Glu Leu Gln Ile Leu Leu Thr Glu Ala Thr Asn His Arg Gln Asn
    5360                5365                5370
Ile Glu Lys Met Ala Glu Glu Gln Lys Glu Lys Tyr Leu Gly Leu
    5375                5380                5385
Tyr Thr Ile Leu Pro Ser Glu Leu Ser Leu Gln Leu Ala Glu Val
    5390                5395                5400
Ala Leu Asp Leu Lys Ile Arg Asp Gln Ile Gln Asp Lys Ile Lys
    5405                5410                5415
Glu Val Glu Gln Ser Lys Ala Thr Ser Gln Glu Leu Ser Arg Gln
    5420                5425                5430
Ile Gln Lys Leu Ala Lys Asp Leu Thr Thr Ile Leu Thr Lys Leu
    5435                5440                5445
Lys Ala Lys Thr Asp Asn Val Val Gln Ala Lys Thr Asp Gln Lys
    5450                5455                5460
Val Leu Gly Glu Glu Leu Asp Gly Cys Asn Ser Lys Leu Met Glu
    5465                5470                5475
Leu Asp Ala Ala Val Gln Lys Phe Leu Glu Gln Asn Gly Gln Leu
    5480                5485                5490
Gly Lys Pro Leu Ala Lys Lys Ile Gly Lys Leu Thr Glu Leu His
    5495                5500                5505
Gln Gln Thr Ile Arg Gln Ala Glu Asn Arg Leu Ser Lys Leu Asn
    5510                5515                5520
Gln Ala Ala Ser His Leu Glu Glu Tyr Asn Glu Met Leu Glu Leu
    5525                5530                5535
```

```
Ile Leu Lys Trp Ile Glu Lys Ala Lys Val Leu Ala His Gly Thr
    5540            5545            5550

Ile Ala Trp Asn Ser Ala Ser Gln Leu Arg Glu Gln Tyr Ile Leu
    5555            5560            5565

His Gln Thr Leu Leu Glu Glu Ser Lys Glu Ile Asp Ser Glu Leu
    5570            5575            5580

Glu Ala Met Thr Glu Lys Leu Gln Tyr Leu Thr Ser Val Tyr Cys
    5585            5590            5595

Thr Glu Lys Met Ser Gln Gln Val Ala Glu Leu Gly Arg Glu Thr
    5600            5605            5610

Glu Glu Leu Arg Gln Met Ile Lys Ile Arg Leu Gln Asn Leu Gln
    5615            5620            5625

Asp Ala Ala Lys Asp Met Lys Lys Phe Glu Ala Glu Leu Lys Lys
    5630            5635            5640

Leu Gln Ala Ala Leu Glu Gln Ala Gln Ala Thr Leu Thr Ser Pro
    5645            5650            5655

Glu Val Gly Arg Leu Ser Leu Lys Glu Gln Leu Ser His Arg Gln
    5660            5665            5670

His Leu Leu Ser Glu Met Glu Ser Leu Lys Pro Lys Val Gln Ala
    5675            5680            5685

Val Gln Leu Cys Gln Ser Ala Leu Arg Ile Pro Glu Asp Val Val
    5690            5695            5700

Ala Ser Leu Pro Leu Cys His Ala Ala Leu Arg Leu Gln Glu Glu
    5705            5710            5715

Ala Ser Arg Leu Gln His Thr Ala Ile Gln Gln Cys Asn Ile Met
    5720            5725            5730

Gln Glu Ala Val Val Gln Tyr Glu Gln Tyr Glu Gln Glu Met Lys
    5735            5740            5745

His Leu Gln Gln Leu Ile Glu Gly Ala His Arg Glu Ile Glu Asp
    5750            5755            5760

Lys Pro Val Ala Thr Ser Asn Ile Gln Glu Leu Gln Ala Gln Ile
    5765            5770            5775

Ser Arg His Glu Glu Leu Ala Gln Lys Ile Lys Gly Tyr Gln Glu
    5780            5785            5790

Gln Ile Ala Ser Leu Asn Ser Lys Cys Lys Met Leu Thr Met Lys
    5795            5800            5805

Ala Lys His Ala Thr Met Leu Leu Thr Val Thr Glu Val Glu Gly
    5810            5815            5820

Leu Ala Glu Gly Thr Glu Asp Leu Asp Gly Glu Leu Leu Pro Thr
    5825            5830            5835

Pro Ser Ala His Pro Ser Val Val Met Met Thr Ala Gly Arg Cys
    5840            5845            5850

His Thr Leu Leu Ser Pro Val Thr Glu Glu Ser Gly Glu Glu Gly
    5855            5860            5865

Thr Asn Ser Glu Ile Ser Ser Pro Pro Ala Cys Arg Ser Pro Ser
    5870            5875            5880

Pro Val Ala Asn Thr Asp Ala Ser Val Asn Gln Asp Ile Ala Tyr
    5885            5890            5895

Tyr Gln Ala Leu Ser Ala Glu Arg Leu Gln Thr Asp Ala Ala Lys
    5900            5905            5910

Ile His Pro Ser Thr Ser Ala Ser Gln Glu Phe Tyr Glu Pro Gly
    5915            5920            5925
```

```
Leu Glu Pro Ser Ala Thr Ala Lys Leu Gly Asp Leu Gln Arg Ser
5930                5935                5940

Trp Glu Thr Leu Lys Asn Val Ile Ser Glu Lys Gln Arg Thr Leu
5945                5950                5955

Tyr Glu Ala Leu Glu Arg Gln Gln Lys Tyr Gln Asp Ser Leu Gln
5960                5965                5970

Ser Ile Ser Thr Lys Met Glu Ala Ile Glu Leu Lys Leu Ser Glu
5975                5980                5985

Ser Pro Glu Pro Gly Arg Ser Pro Glu Ser Gln Met Ala Glu His
5990                5995                6000

Gln Ala Leu Met Asp Glu Ile Leu Met Leu Gln Asp Glu Ile Asn
6005                6010                6015

Glu Leu Gln Ser Ser Leu Ala Glu Glu Leu Val Ser Glu Ser Cys
6020                6025                6030

Glu Ala Asp Pro Ala Glu Gln Leu Ala Leu Gln Ser Thr Leu Thr
6035                6040                6045

Val Leu Ala Glu Arg Met Ser Thr Ile Arg Met Lys Ala Ser Gly
6050                6055                6060

Lys Arg Gln Leu Leu Glu Glu Lys Leu Asn Asp Gln Leu Glu Glu
6065                6070                6075

Gln Arg Gln Glu Gln Ala Leu Gln Arg Tyr Arg Cys Glu Ala Asp
6080                6085                6090

Glu Leu Asp Ser Trp Leu Leu Ser Thr Lys Ala Thr Leu Asp Thr
6095                6100                6105

Ala Leu Ser Pro Pro Lys Glu Pro Met Asp Met Glu Ala Gln Leu
6110                6115                6120

Met Asp Cys Gln Asn Met Leu Val Glu Ile Glu Gln Lys Val Val
6125                6130                6135

Ala Leu Ser Glu Leu Ser Val His Asn Glu Asn Leu Leu Leu Glu
6140                6145                6150

Gly Lys Ala His Thr Lys Asp Glu Ala Glu Gln Leu Ala Gly Lys
6155                6160                6165

Leu Arg Arg Leu Lys Gly Ser Leu Leu Glu Leu Gln Arg Ala Leu
6170                6175                6180

His Asp Lys Gln Leu Asn Met Gln Gly Thr Ala Gln Glu Lys Glu
6185                6190                6195

Glu Ser Asp Val Asp Leu Thr Ala Thr Gln Ser Pro Gly Val Gln
6200                6205                6210

Glu Trp Leu Ala Gln Ala Arg Thr Thr Trp Thr Gln Gln Arg Gln
6215                6220                6225

Ser Ser Leu Gln Gln Gln Lys Glu Leu Glu Gln Glu Leu Ala Glu
6230                6235                6240

Gln Lys Ser Leu Leu Arg Ser Val Ala Ser Arg Gly Glu Glu Ile
6245                6250                6255

Leu Ile Gln His Ser Ala Ala Glu Thr Ser Gly Asp Ala Gly Glu
6260                6265                6270

Lys Pro Asp Val Leu Ser Gln Glu Leu Gly Met Glu Gly Glu Lys
6275                6280                6285

Ser Ser Ala Glu Asp Gln Met Arg Met Lys Trp Glu Ser Leu His
6290                6295                6300

Gln Glu Phe Ser Thr Lys Lys Leu Leu Gln Asn Val Leu Glu
6305                6310                6315

Gln Glu Gln Glu Gln Val Leu Tyr Ser Arg Pro Asn Arg Leu Leu
```

```
              6320              6325              6330

Ser Gly Val Pro Leu Tyr Lys Gly Asp Val Pro Thr Gln Asp Lys
            6335              6340              6345

Ser Ala Val Thr Ser Leu Leu Asp Gly Leu Asn Gln Ala Phe Glu
            6350              6355              6360

Glu Val Ser Ser Gln Ser Gly Gly Ala Lys Arg Gln Ser Ile His
            6365              6370              6375

Leu Glu Gln Lys Leu Tyr Asp Gly Val Ser Ala Thr Ser Thr Trp
            6380              6385              6390

Leu Asp Asp Val Glu Glu Arg Leu Phe Val Ala Thr Ala Leu Leu
            6395              6400              6405

Pro Glu Glu Thr Glu Thr Cys Leu Phe Asn Gln Glu Ile Leu Ala
            6410              6415              6420

Lys Asp Ile Lys Glu Met Ser Glu Glu Met Asp Lys Asn Lys Asn
            6425              6430              6435

Leu Phe Ser Gln Ala Phe Pro Glu Asn Gly Asp Asn Arg Asp Val
            6440              6445              6450

Ile Glu Asp Thr Leu Gly Cys Leu Leu Gly Arg Leu Ser Leu Leu
            6455              6460              6465

Asp Ser Val Val Asn Gln Arg Cys His Gln Met Lys Glu Arg Leu
            6470              6475              6480

Gln Gln Ile Leu Asn Phe Gln Asn Asp Leu Lys Val Leu Phe Thr
            6485              6490              6495

Ser Leu Ala Asp Asn Lys Tyr Ile Ile Leu Gln Lys Leu Ala Asn
            6500              6505              6510

Val Phe Glu Gln Pro Val Ala Glu Gln Ile Glu Ala Ile Gln Gln
            6515              6520              6525

Ala Glu Asp Gly Leu Lys Glu Phe Asp Ala Gly Ile Ile Glu Leu
            6530              6535              6540

Lys Arg Arg Gly Asp Lys Leu Gln Val Glu Gln Pro Ser Met Gln
            6545              6550              6555

Glu Leu Ser Lys Leu Gln Asp Met Tyr Asp Glu Leu Met Met Ile
            6560              6565              6570

Ile Gly Ser Arg Arg Ser Gly Leu Asn Gln Asn Leu Thr Leu Lys
            6575              6580              6585

Ser Gln Tyr Glu Arg Ala Leu Gln Asp Leu Ala Asp Leu Leu Glu
            6590              6595              6600

Thr Gly Gln Glu Lys Met Ala Gly Asp Gln Lys Ile Ile Val Ser
            6605              6610              6615

Ser Lys Glu Glu Ile Gln Gln Leu Leu Asp Lys His Lys Glu Tyr
            6620              6625              6630

Phe Gln Gly Leu Glu Ser His Met Ile Leu Thr Glu Thr Leu Phe
            6635              6640              6645

Arg Lys Ile Ile Ser Phe Ala Val Gln Lys Glu Thr Gln Phe His
            6650              6655              6660

Thr Glu Leu Met Ala Gln Ala Ser Ala Val Leu Lys Arg Ala His
            6665              6670              6675

Lys Arg Gly Val Glu Leu Glu Tyr Ile Leu Glu Thr Trp Ser His
            6680              6685              6690

Leu Asp Glu Asp Gln Gln Glu Leu Ser Arg Gln Leu Glu Val Val
            6695              6700              6705

Glu Ser Ser Ile Pro Ser Val Gly Leu Val Glu Glu Asn Glu Asp
            6710              6715              6720
```

-continued

```
Arg Leu Ile Asp Arg Ile Thr Leu Tyr Gln His Leu Lys Ser Ser
    6725                6730                6735

Leu Asn Glu Tyr Gln Pro Lys Leu Tyr Gln Val Leu Asp Asp Gly
    6740                6745                6750

Lys Arg Leu Leu Ile Ser Ile Ser Cys Ser Asp Leu Glu Ser Gln
    6755                6760                6765

Leu Asn Gln Leu Gly Glu Cys Trp Leu Ser Asn Thr Asn Lys Met
    6770                6775                6780

Ser Lys Glu Leu His Arg Leu Glu Thr Ile Leu Lys His Trp Thr
    6785                6790                6795

Arg Tyr Gln Ser Glu Ser Ala Asp Leu Ile His Trp Leu Gln Ser
    6800                6805                6810

Ala Lys Asp Arg Leu Glu Phe Trp Thr Gln Gln Ser Val Thr Val
    6815                6820                6825

Pro Gln Glu Leu Glu Met Val Arg Asp His Leu Asn Ala Phe Leu
    6830                6835                6840

Glu Phe Ser Lys Glu Val Asp Ala Gln Ser Ser Leu Lys Ser Ser
    6845                6850                6855

Val Leu Ser Thr Gly Asn Gln Leu Leu Arg Leu Lys Lys Val Asp
    6860                6865                6870

Thr Ala Thr Leu Arg Ser Glu Leu Ser Arg Ile Asp Ser Gln Trp
    6875                6880                6885

Thr Asp Leu Leu Thr Asn Ile Pro Ala Val Gln Glu Lys Leu His
    6890                6895                6900

Gln Leu Gln Met Asp Lys Leu Pro Ser Arg His Ala Ile Ser Glu
    6905                6910                6915

Val Met Ser Trp Ile Ser Leu Met Glu Asn Val Ile Gln Lys Asp
    6920                6925                6930

Glu Asp Asn Ile Lys Asn Ser Ile Gly Tyr Lys Ala Ile His Glu
    6935                6940                6945

Tyr Leu Gln Lys Tyr Lys Gly Phe Lys Ile Asp Ile Asn Cys Lys
    6950                6955                6960

Gln Leu Thr Val Asp Phe Val Asn Gln Ser Val Leu Gln Ile Ser
    6965                6970                6975

Ser Gln Asp Val Glu Ser Lys Arg Ser Asp Lys Thr Asp Phe Ala
    6980                6985                6990

Glu Gln Leu Gly Ala Met Asn Lys Ser Trp Gln Ile Leu Gln Gly
    6995                7000                7005

Leu Val Thr Glu Lys Ile Gln Leu Leu Glu Gly Leu Leu Glu Ser
    7010                7015                7020

Trp Ser Glu Tyr Glu Asn Asn Val Gln Cys Leu Lys Thr Trp Phe
    7025                7030                7035

Glu Thr Gln Glu Lys Arg Leu Lys Gln Gln His Arg Ile Gly Asp
    7040                7045                7050

Gln Ala Ser Val Gln Asn Ala Leu Lys Asp Cys Gln Asp Leu Glu
    7055                7060                7065

Asp Leu Ile Lys Ala Lys Glu Lys Glu Val Glu Lys Ile Glu Gln
    7070                7075                7080

Asn Gly Leu Ala Leu Ile Gln Asn Lys Lys Glu Asp Val Ser Ser
    7085                7090                7095

Ile Val Met Ser Thr Leu Arg Glu Leu Gly Gln Thr Trp Ala Asn
    7100                7105                7110
```

```
Leu Asp His Met Val Gly Gln Leu Lys Ile Leu Leu Lys Ser Val
7115                     7120                    7125

Leu Asp Gln Trp Ser Ser His Lys Val Ala Phe Asp Lys Ile Asn
7130                     7135                    7140

Ser Tyr Leu Met Glu Ala Arg Tyr Ser Leu Ser Arg Phe Arg Leu
7145                     7150                    7155

Leu Thr Gly Ser Leu Glu Ala Val Gln Val Gln Val Asp Asn Leu
7160                     7165                    7170

Gln Asn Leu Gln Asp Asp Leu Glu Lys Gln Glu Arg Ser Leu Gln
7175                     7180                    7185

Lys Phe Gly Ser Ile Thr Asn Gln Leu Leu Lys Glu Cys His Pro
7190                     7195                    7200

Pro Val Thr Glu Thr Leu Thr Asn Thr Leu Lys Glu Val Asn Met
7205                     7210                    7215

Arg Trp Asn Asn Leu Leu Glu Glu Ile Ala Glu Gln Leu Gln Ser
7220                     7225                    7230

Ser Lys Ala Leu Leu Gln Leu Trp Gln Arg Tyr Lys Asp Tyr Ser
7235                     7240                    7245

Lys Gln Cys Ala Ser Thr Val Gln Gln Gln Glu Asp Arg Thr Asn
7250                     7255                    7260

Glu Leu Leu Lys Ala Ala Thr Asn Lys Asp Ile Ala Asp Asp Glu
7265                     7270                    7275

Val Ala Thr Trp Ile Gln Asp Cys Asn Asp Leu Leu Lys Gly Leu
7280                     7285                    7290

Gly Thr Val Lys Asp Ser Leu Phe Phe Leu His Glu Leu Gly Glu
7295                     7300                    7305

Gln Leu Lys Gln Gln Val Asp Ala Ser Ala Ala Ser Ala Ile Gln
7310                     7315                    7320

Ser Asp Gln Leu Ser Leu Ser Gln His Leu Cys Ala Leu Glu Gln
7325                     7330                    7335

Ala Leu Cys Lys Gln Gln Thr Ser Leu Gln Ala Gly Val Leu Asp
7340                     7345                    7350

Tyr Glu Thr Phe Ala Lys Ser Leu Glu Ala Leu Glu Ala Trp Ile
7355                     7360                    7365

Val Glu Ala Glu Glu Ile Leu Gln Gly Gln Asp Pro Ser His Ser
7370                     7375                    7380

Ser Asp Leu Ser Thr Ile Gln Glu Arg Met Glu Glu Leu Lys Gly
7385                     7390                    7395

Gln Met Leu Lys Phe Ser Ser Met Ala Pro Asp Leu Asp Arg Leu
7400                     7405                    7410

Asn Glu Leu Gly Tyr Arg Leu Pro Leu Asn Asp Lys Glu Ile Lys
7415                     7420                    7425

Arg Met Gln Asn Leu Asn Arg His Trp Ser Leu Ile Ser Ser Gln
7430                     7435                    7440

Thr Thr Glu Arg Phe Ser Lys Leu Gln Ser Phe Leu Leu Gln His
7445                     7450                    7455

Gln Thr Phe Leu Glu Lys Cys Glu Thr Trp Met Glu Phe Leu Val
7460                     7465                    7470

Gln Thr Glu Gln Lys Leu Ala Val Glu Ile Ser Gly Asn Tyr Gln
7475                     7480                    7485

His Leu Leu Glu Gln Gln Arg Ala His Glu Leu Phe Gln Ala Glu
7490                     7495                    7500

Met Phe Ser Arg Gln Gln Ile Leu His Ser Ile Ile Ile Asp Gly
```

```
                7505                7510                7515
Gln Arg Leu Leu Glu Gln Gly Gln Val Asp Asp Arg Asp Glu Phe
            7520                7525                7530
Asn Leu Lys Leu Thr Leu Leu Ser Asn Gln Trp Gln Gly Val Ile
            7535                7540                7545
Arg Arg Ala Gln Gln Arg Arg Gly Ile Ile Asp Ser Gln Ile Arg
            7550                7555                7560
Gln Trp Gln Arg Tyr Arg Glu Met Ala Glu Lys Leu Arg Lys Trp
            7565                7570                7575
Leu Val Glu Val Ser Tyr Leu Pro Met Ser Gly Leu Gly Ser Val
            7580                7585                7590
Pro Ile Pro Leu Gln Gln Ala Arg Thr Leu Phe Asp Glu Val Gln
            7595                7600                7605
Phe Lys Glu Lys Val Phe Leu Arg Gln Gln Gly Ser Tyr Ile Leu
            7610                7615                7620
Thr Val Glu Ala Gly Lys Gln Leu Leu Leu Ser Ala Asp Ser Gly
            7625                7630                7635
Ala Glu Ala Ala Leu Gln Ala Glu Leu Ala Glu Ile Gln Glu Lys
            7640                7645                7650
Trp Lys Ser Ala Ser Met Arg Leu Glu Glu Gln Lys Lys Lys Leu
            7655                7660                7665
Ala Phe Leu Leu Lys Asp Trp Glu Lys Cys Glu Lys Gly Ile Ala
            7670                7675                7680
Asp Ser Leu Glu Lys Leu Arg Thr Phe Lys Lys Lys Leu Ser Gln
            7685                7690                7695
Ser Leu Pro Asp His His Glu Glu Leu His Ala Glu Gln Met Arg
            7700                7705                7710
Cys Lys Glu Leu Glu Asn Ala Val Gly Ser Trp Thr Asp Asp Leu
            7715                7720                7725
Thr Gln Leu Ser Leu Leu Lys Asp Thr Leu Ser Ala Tyr Ile Ser
            7730                7735                7740
Ala Asp Asp Ile Ser Ile Leu Asn Glu Arg Val Glu Leu Leu Gln
            7745                7750                7755
Arg Gln Trp Glu Glu Leu Cys His Gln Leu Ser Leu Arg Arg Gln
            7760                7765                7770
Gln Ile Gly Glu Arg Leu Asn Glu Trp Ala Val Phe Ser Glu Lys
            7775                7780                7785
Asn Lys Glu Leu Cys Glu Trp Leu Thr Gln Met Glu Ser Lys Val
            7790                7795                7800
Ser Gln Asn Gly Asp Ile Leu Ile Glu Glu Met Ile Glu Lys Leu
            7805                7810                7815
Lys Lys Asp Tyr Gln Glu Glu Ile Ala Ile Ala Gln Glu Asn Lys
            7820                7825                7830
Ile Gln Leu Gln Gln Met Gly Glu Arg Leu Ala Lys Ala Ser His
            7835                7840                7845
Glu Ser Lys Ala Ser Glu Ile Glu Tyr Lys Leu Gly Lys Val Asn
            7850                7855                7860
Asp Arg Trp Gln His Leu Leu Asp Leu Ile Ala Ala Arg Val Lys
            7865                7870                7875
Lys Leu Lys Glu Thr Leu Val Ala Val Gln Gln Leu Asp Lys Asn
            7880                7885                7890
Met Ser Ser Leu Arg Thr Trp Leu Ala His Ile Glu Ser Glu Leu
            7895                7900                7905
```

```
Ala Lys Pro Ile Val Tyr Asp Ser Cys Asn Ser Glu Glu Ile Gln
    7910            7915                7920

Arg Lys Leu Asn Glu Gln Gln Glu Leu Gln Arg Asp Ile Glu Lys
    7925            7930                7935

His Ser Thr Gly Val Ala Ser Val Leu Asn Leu Cys Glu Val Leu
    7940            7945                7950

Leu His Asp Cys Asp Ala Cys Ala Thr Asp Ala Glu Cys Asp Ser
    7955            7960                7965

Ile Gln Gln Ala Thr Arg Asn Leu Asp Arg Arg Trp Arg Asn Ile
    7970            7975                7980

Cys Ala Met Ser Met Glu Arg Arg Leu Lys Ile Glu Glu Thr Trp
    7985            7990                7995

Arg Leu Trp Gln Lys Phe Leu Asp Asp Tyr Ser Arg Phe Glu Asp
    8000            8005                8010

Trp Leu Lys Ser Ser Glu Arg Thr Ala Ala Phe Pro Ser Ser Ser
    8015            8020                8025

Gly Val Ile Tyr Thr Val Ala Lys Glu Glu Leu Lys Lys Phe Glu
    8030            8035                8040

Ala Phe Gln Arg Gln Val His Glu Cys Leu Thr Gln Leu Glu Leu
    8045            8050                8055

Ile Asn Lys Gln Tyr Arg Arg Leu Ala Arg Glu Asn Arg Thr Asp
    8060            8065                8070

Ser Ala Cys Ser Leu Lys Gln Met Val His Glu Gly Asn Gln Arg
    8075            8080                8085

Trp Asp Asn Leu Gln Lys Arg Val Thr Ser Ile Leu Arg Arg Leu
    8090            8095                8100

Lys His Phe Ile Gly Gln Arg Glu Glu Phe Glu Thr Ala Arg Asp
    8105            8110                8115

Ser Ile Leu Val Trp Leu Thr Glu Met Asp Leu Gln Leu Thr Asn
    8120            8125                8130

Ile Glu His Phe Ser Glu Cys Asp Val Gln Ala Lys Ile Lys Gln
    8135            8140                8145

Leu Lys Ala Phe Gln Gln Glu Ile Ser Leu Asn His Asn Lys Ile
    8150            8155                8160

Glu Gln Ile Ile Ala Gln Gly Glu Gln Leu Ile Glu Lys Ser Glu
    8165            8170                8175

Pro Leu Asp Ala Ala Ile Ile Glu Glu Glu Leu Asp Glu Leu Arg
    8180            8185                8190

Arg Tyr Cys Gln Glu Val Phe Gly Arg Val Glu Arg Tyr His Lys
    8195            8200                8205

Lys Leu Ile Arg Leu Pro Leu Pro Asp Asp Glu His Asp Leu Ser
    8210            8215                8220

Asp Arg Glu Leu Glu Leu Glu Asp Ser Ala Ala Leu Ser Asp Leu
    8225            8230                8235

His Trp His Asp Arg Ser Ala Asp Ser Leu Leu Ser Pro Gln Pro
    8240            8245                8250

Ser Ser Asn Leu Ser Leu Ser Leu Ala Gln Pro Leu Arg Ser Glu
    8255            8260                8265

Arg Ser Gly Arg Asp Thr Pro Ala Ser Val Asp Ser Ile Pro Leu
    8270            8275                8280

Glu Trp Asp His Asp Tyr Asp Leu Ser Arg Asp Leu Glu Ser Ala
    8285            8290                8295
```

```
Met Ser Arg Ala Leu Pro Ser Glu Asp Glu Glu Gly Gln Asp Asp
    8300                8305                8310

Lys Asp Phe Tyr Leu Arg Gly Ala Val Gly Leu Ser Gly Asp His
    8315                8320                8325

Ser Ala Leu Glu Ser Gln Ile Arg Gln Leu Gly Lys Ala Leu Asp
    8330                8335                8340

Asp Ser Arg Phe Gln Ile Gln Gln Thr Glu Asn Ile Ile Arg Ser
    8345                8350                8355

Lys Thr Pro Thr Gly Pro Glu Leu Asp Thr Ser Tyr Lys Gly Tyr
    8360                8365                8370

Met Lys Leu Leu Gly Glu Cys Ser Ser Ser Ile Asp Ser Val Lys
    8375                8380                8385

Arg Leu Glu His Lys Leu Lys Glu Glu Glu Glu Ser Leu Pro Gly
    8390                8395                8400

Phe Val Asn Leu His Ser Thr Glu Thr Gln Thr Ala Gly Val Ile
    8405                8410                8415

Asp Arg Trp Glu Leu Leu Gln Ala Gln Ala Leu Ser Lys Glu Leu
    8420                8425                8430

Arg Met Lys Gln Asn Leu Gln Lys Trp Gln Gln Phe Asn Ser Asp
    8435                8440                8445

Leu Asn Ser Ile Trp Ala Trp Leu Gly Asp Thr Glu Glu Glu Leu
    8450                8455                8460

Glu Gln Leu Gln Arg Leu Glu Leu Ser Thr Asp Ile Gln Thr Ile
    8465                8470                8475

Glu Leu Gln Ile Lys Lys Leu Lys Glu Leu Gln Lys Ala Val Asp
    8480                8485                8490

His Arg Lys Ala Ile Ile Leu Ser Ile Asn Leu Cys Ser Pro Glu
    8495                8500                8505

Phe Thr Gln Ala Asp Ser Lys Glu Ser Arg Asp Leu Gln Asp Arg
    8510                8515                8520

Leu Ser Gln Met Asn Gly Arg Trp Asp Arg Val Cys Ser Leu Leu
    8525                8530                8535

Glu Glu Trp Arg Gly Leu Leu Gln Asp Ala Leu Met Gln Cys Gln
    8540                8545                8550

Gly Phe His Glu Met Ser His Gly Leu Leu Leu Met Leu Glu Asn
    8555                8560                8565

Ile Asp Arg Arg Lys Asn Glu Ile Val Pro Ile Asp Ser Asn Leu
    8570                8575                8580

Asp Ala Glu Ile Leu Gln Asp His His Lys Gln Leu Met Gln Ile
    8585                8590                8595

Lys His Glu Leu Leu Glu Ser Gln Leu Arg Val Ala Ser Leu Gln
    8600                8605                8610

Asp Met Ser Cys Gln Leu Leu Val Asn Ala Glu Gly Thr Asp Cys
    8615                8620                8625

Leu Glu Ala Lys Glu Lys Val His Val Ile Gly Asn Arg Leu Lys
    8630                8635                8640

Leu Leu Leu Lys Glu Val Ser Arg His Ile Lys Glu Leu Glu Lys
    8645                8650                8655

Leu Leu Asp Val Ser Ser Ser Gln Gln Asp Leu Ser Ser Trp Ser
    8660                8665                8670

Ser Ala Asp Glu Leu Asp Thr Ser Gly Ser Val Ser Pro Thr Ser
    8675                8680                8685

Gly Arg Ser Thr Pro Asn Arg Gln Lys Thr Pro Arg Gly Lys Cys
```

```
                    8690                8695                8700

Ser Leu Ser Gln Pro Gly Pro Ser Val Ser Ser Pro His Ser Arg
        8705                8710                8715

Ser Thr Lys Gly Gly Ser Asp Ser Ser Leu Ser Glu Pro Gly Pro
        8720                8725                8730

Gly Arg Ser Gly Arg Gly Phe Leu Phe Arg Val Leu Arg Ala Ala
        8735                8740                8745

Leu Pro Leu Gln Leu Leu Leu Leu Leu Ile Gly Leu Ala Cys
        8750                8755                8760

Leu Val Pro Met Ser Glu Glu Asp Tyr Ser Cys Ala Leu Ser Asn
        8765                8770                8775

Asn Phe Ala Arg Ser Phe His Pro Met Leu Arg Tyr Thr Asn Gly
        8780                8785                8790

Pro Pro Pro Leu
    8795

<210> SEQ ID NO 23
<211> LENGTH: 431
<212> TYPE: PRT
<213> ORGANISM: Homo sapiens

<400> SEQUENCE: 23

Met Arg Arg Leu Arg Arg Leu Ala His Leu Val Leu Phe Cys Pro Phe
1               5                   10                  15

Ser Lys Arg Leu Gln Gly Arg Leu Pro Gly Leu Arg Val Arg Cys Ile
            20                  25                  30

Phe Leu Ala Trp Leu Gly Val Phe Ala Gly Ser Trp Leu Val Tyr Val
        35                  40                  45

His Tyr Ser Ser Tyr Ser Glu Arg Cys Arg Gly His Val Cys Gln Val
    50                  55                  60

Val Ile Cys Asp Gln Tyr Arg Lys Gly Ile Ile Ser Gly Ser Val Cys
65                  70                  75                  80

Gln Asp Leu Cys Glu Leu His Met Val Glu Trp Arg Thr Cys Leu Ser
                85                  90                  95

Val Ala Pro Gly Gln Gln Val Tyr Ser Gly Leu Trp Arg Asp Lys Asp
            100                 105                 110

Val Thr Ile Lys Cys Gly Ile Glu Glu Thr Leu Asp Ser Lys Ala Arg
        115                 120                 125

Ser Asp Ala Ala Pro Arg Arg Glu Leu Val Leu Phe Asp Lys Pro Thr
    130                 135                 140

Arg Gly Thr Ser Ile Lys Glu Phe Arg Glu Met Thr Leu Ser Phe Leu
145                 150                 155                 160

Lys Ala Asn Leu Gly Asp Leu Pro Ser Leu Pro Ala Leu Val Gly Gln
                165                 170                 175

Val Leu Leu Met Ala Asp Phe Asn Lys Asp Asn Arg Val Ser Leu Ala
            180                 185                 190

Glu Ala Lys Ser Val Trp Ala Leu Leu Gln Arg Asn Glu Phe Leu Leu
        195                 200                 205

Leu Leu Ser Leu Gln Glu Lys Glu His Ala Ser Arg Leu Leu Gly Tyr
    210                 215                 220

Cys Gly Asp Leu Tyr Leu Thr Glu Gly Val Pro His Gly Ala Trp His
225                 230                 235                 240

Ala Ala Ala Leu Pro Pro Leu Arg Pro Leu Leu Pro Pro Ala Leu
                245                 250                 255
```

Gln Gly Ala Leu Gln Gln Trp Leu Gly Pro Ala Trp Pro Trp Arg Ala
                260                 265                 270

Lys Ile Ala Ile Gly Leu Leu Glu Phe Val Glu Leu Phe His Gly
            275                 280                 285

Ser Tyr Gly Thr Phe Tyr Met Cys Glu Thr Thr Leu Ala Asn Val Gly
        290                 295                 300

Tyr Thr Ala Thr Tyr Asp Phe Lys Met Ala Asp Leu Gln Gln Val Ala
305                 310                 315                 320

Pro Glu Ala Thr Val Arg Arg Phe Leu Gln Gly Arg Arg Cys Glu His
                325                 330                 335

Ser Thr Asp Cys Thr Tyr Gly Arg Asp Cys Arg Ala Pro Cys Asp Arg
                340                 345                 350

Leu Met Arg Gln Cys Lys Gly Asp Leu Ile Gln Pro Asn Leu Ala Lys
                355                 360                 365

Val Cys Ala Leu Leu Arg Gly Tyr Leu Leu Pro Gly Ala Pro Ala Asp
                370                 375                 380

Leu Arg Glu Glu Leu Gly Thr Gln Leu Arg Thr Cys Thr Thr Leu Ser
385                 390                 395                 400

Gly Leu Ala Ser Gln Val Glu Ala His His Ser Leu Val Leu Ser His
                405                 410                 415

Leu Lys Thr Leu Leu Trp Lys Lys Ile Ser Asn Thr Lys Tyr Ser
                420                 425                 430

<210> SEQ ID NO 24
<211> LENGTH: 441
<212> TYPE: PRT
<213> ORGANISM: Homo sapiens

<400> SEQUENCE: 24

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
                20                  25                  30

Arg Arg Asn Trp Cys Ser Tyr Val Val Thr Arg Thr Ile Ser Cys His
            35                  40                  45

Val Gln Asn Gly Thr Tyr Leu Gln Arg Val Leu Gln Asn Cys Pro Trp
        50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Ala Ser Ser Ala Ser Leu
                100                 105                 110

Glu Pro Met Trp Ser Gly Ser Thr Met Arg Arg Met Ala Leu Arg Pro
            115                 120                 125

Thr Ala Phe Ser Gly Cys Leu Asn Cys Ser Lys Val Ser Glu Leu Thr
        130                 135                 140

Glu Arg Leu Lys Val Leu Glu Ala Lys Met Thr Met Leu Thr Val Ile
145                 150                 155                 160

Glu Gln Pro Val Pro Pro Thr Pro Ala Thr Pro Glu Asp Pro Ala Pro
                165                 170                 175

Leu Trp Gly Pro Pro Ala Gln Gly Ser Pro Gly Asp Gly Gly Leu
            180                 185                 190

Gln Asp Gln Val Gly Ala Trp Gly Leu Pro Gly Pro Thr Gly Pro Lys
        195                 200                 205

```
Gly Asp Ala Gly Ser Arg Gly Pro Met Gly Met Arg Gly Pro Pro Gly
    210                 215                 220

Pro Gln Gly Pro Pro Gly Ser Pro Gly Arg Ala Gly Ala Val Gly Thr
225                 230                 235                 240

Pro Gly Glu Arg Gly Pro Pro Gly Pro Gly Pro Pro Gly Pro Pro
                245                 250                 255

Gly Pro Pro Ala Pro Val Gly Pro Pro His Ala Arg Ile Ser Gln His
            260                 265                 270

Gly Asp Pro Leu Leu Ser Asn Thr Phe Thr Glu Thr Asn Asn His Trp
            275                 280                 285

Pro Gln Gly Pro Thr Gly Pro Pro Gly Pro Pro Gly Pro Met Gly Pro
        290                 295                 300

Pro Gly Pro Pro Gly Pro Thr Gly Val Pro Gly Ser Pro Gly His Ile
305                 310                 315                 320

Gly Pro Pro Gly Pro Thr Gly Pro Lys Gly Ile Ser Gly His Pro Gly
                325                 330                 335

Glu Lys Gly Glu Arg Gly Leu Arg Gly Glu Pro Gly Pro Gln Gly Ser
            340                 345                 350

Ala Gly Gln Arg Gly Glu Pro Gly Pro Lys Gly Asp Pro Gly Glu Lys
        355                 360                 365

Ser His Trp Gly Glu Gly Leu His Gln Leu Arg Glu Ala Leu Lys Ile
    370                 375                 380

Leu Ala Glu Arg Val Leu Ile Leu Glu Thr Met Ile Gly Leu Tyr Glu
385                 390                 395                 400

Pro Glu Leu Gly Ser Gly Ala Gly Pro Ala Gly Thr Gly Thr Pro Ser
                405                 410                 415

Leu Leu Arg Gly Lys Arg Gly Gly His Ala Thr Asn Tyr Arg Ile Val
            420                 425                 430

Ala Pro Arg Ser Arg Asp Glu Arg Gly
        435                 440

<210> SEQ ID NO 25
<211> LENGTH: 409
<212> TYPE: PRT
<213> ORGANISM: Homo sapiens

<400> SEQUENCE: 25

Met Glu Glu Ser Trp Glu Ala Ala Pro Gly Gln Ala Gly Ala Glu
1               5                   10                  15

Leu Pro Met Glu Pro Val Gly Ser Leu Val Pro Thr Leu Glu Gln Pro
            20                  25                  30

Gln Val Pro Ala Lys Val Arg Gln Pro Glu Gly Pro Glu Ser Ser Pro
        35                  40                  45

Ser Pro Ala Gly Ala Val Glu Lys Ala Ala Gly Ala Gly Leu Glu Pro
    50                  55                  60

Ser Ser Lys Lys Lys Pro Pro Ser Pro Arg Pro Gly Ser Pro Arg Val
65                  70                  75                  80

Pro Pro Leu Ser Leu Gly Tyr Gly Val Cys Pro Glu Pro Pro Ser Pro
                85                  90                  95

Gly Pro Ala Leu Val Lys Leu Pro Arg Asn Gly Glu Ala Pro Gly Ala
            100                 105                 110

Glu Pro Ala Pro Ser Ala Trp Ala Pro Met Glu Leu Gln Val Asp Val
        115                 120                 125

Arg Val Lys Pro Val Gly Ala Ala Gly Gly Ser Ser Thr Pro Ser Pro
```

```
                130                 135                 140
Arg Pro Ser Thr Arg Phe Leu Lys Val Pro Val Pro Glu Ser Pro Ala
145                 150                 155                 160

Phe Ser Arg His Ala Asp Pro Ala His Gln Leu Leu Arg Ala Pro
                165                 170                 175

Ser Gln Gly Gly Thr Trp Gly Arg Arg Ser Pro Leu Ala Ala Ala Arg
            180                 185                 190

Thr Glu Ser Gly Cys Asp Ala Glu Gly Arg Ala Ser Pro Ala Glu Gly
            195                 200                 205

Ser Ala Gly Ser Pro Gly Ser Pro Thr Cys Cys Arg Cys Lys Glu Leu
210                 215                 220

Gly Leu Glu Lys Glu Asp Ala Ala Leu Leu Pro Arg Ala Gly Leu Asp
225                 230                 235                 240

Gly Asp Glu Lys Leu Pro Arg Ala Val Thr Leu Thr Gly Leu Pro Met
            245                 250                 255

Tyr Val Lys Ser Leu Tyr Trp Ala Leu Ala Phe Met Ala Val Leu Leu
            260                 265                 270

Ala Val Ser Gly Val Val Ile Val Leu Ala Ser Arg Ala Gly Ala
            275                 280                 285

Arg Cys Gln Gln Cys Pro Pro Gly Trp Val Leu Ser Glu Glu His Cys
290                 295                 300

Tyr Tyr Phe Ser Ala Glu Ala Gln Ala Trp Glu Ala Ser Gln Ala Phe
305                 310                 315                 320

Cys Ser Ala Tyr His Ala Thr Leu Pro Leu Leu Ser His Thr Gln Asp
            325                 330                 335

Phe Leu Gly Arg Tyr Pro Val Ser Arg His Ser Trp Val Gly Ala Trp
            340                 345                 350

Arg Gly Pro Gln Gly Trp His Trp Ile Asp Glu Ala Pro Leu Pro Pro
            355                 360                 365

Gln Leu Leu Pro Glu Asp Gly Glu Asp Asn Leu Asp Ile Asn Cys Gly
            370                 375                 380

Ala Leu Glu Glu Gly Thr Leu Val Ala Ala Asn Cys Ser Thr Pro Arg
385                 390                 395                 400

Pro Trp Val Cys Ala Lys Gly Thr Gln
            405
```

```
<210> SEQ ID NO 26
<211> LENGTH: 904
<212> TYPE: PRT
<213> ORGANISM: Homo sapiens

<400> SEQUENCE: 26

Met Glu Trp Gly Ser Glu Ser Ala Ala Val Arg Arg His Arg Val Gly
1               5                   10                  15

Val Glu Arg Arg Glu Gly Ala Ala Ala Pro Pro Pro Glu Arg Glu
            20                  25                  30

Ala Arg Ala Gln Glu Pro Leu Val Asp Gly Cys Ser Gly Gly Gly Arg
            35                  40                  45

Thr Arg Lys Arg Ser Pro Gly Gly Ser Gly Gly Ala Ser Arg Gly Ala
50                  55                  60

Gly Thr Gly Leu Ser Glu Val Arg Ala Ala Leu Gly Leu Ala Leu Tyr
65                  70                  75                  80

Leu Ile Ala Leu Arg Thr Leu Val Gln Leu Ser Leu Gln Gln Leu Val
            85                  90                  95
```

```
Leu Arg Gly Ala Ala Gly His Arg Gly Phe Asp Ala Leu Gln Ala
            100                 105                 110

Arg Asp Tyr Leu Glu His Ile Thr Ser Ile Gly Pro Arg Thr Thr Gly
            115                 120                 125

Ser Pro Glu Asn Glu Ile Leu Thr Val His Tyr Leu Leu Glu Gln Ile
130                 135                 140

Lys Leu Ile Glu Val Gln Ser Asn Ser Leu His Lys Ile Ser Val Asp
145                 150                 155                 160

Val Gln Arg Pro Thr Gly Ser Phe Ser Ile Asp Phe Leu Gly Gly Phe
                165                 170                 175

Thr Ser Tyr Tyr Asp Asn Ile Thr Asn Val Val Lys Leu Glu Pro
            180                 185                 190

Arg Asp Gly Ala Gln His Ala Val Leu Ala Asn Cys His Phe Asp Ser
            195                 200                 205

Val Ala Asn Ser Pro Gly Ala Ser Asp Asp Ala Val Ser Cys Ser Val
            210                 215                 220

Met Leu Glu Val Leu Arg Val Leu Ser Thr Ser Ser Glu Ala Leu His
225                 230                 235                 240

His Ala Val Ile Phe Leu Phe Asn Gly Ala Glu Glu Asn Val Leu Gln
                245                 250                 255

Ala Ser His Gly Phe Ile Thr Gln His Pro Trp Ala Ser Leu Ile Arg
            260                 265                 270

Ala Phe Ile Asn Leu Glu Ala Ala Gly Val Gly Gly Lys Glu Leu Val
            275                 280                 285

Phe Gln Thr Gly Pro Glu Asn Pro Trp Leu Val Gln Ala Tyr Val Ser
290                 295                 300

Ala Ala Lys His Pro Phe Ala Ser Val Val Ala Gln Glu Val Phe Gln
305                 310                 315                 320

Ser Gly Ile Ile Pro Ser Asp Thr Asp Phe Arg Ile Tyr Arg Asp Phe
                325                 330                 335

Gly Asn Ile Pro Gly Ile Asp Leu Ala Phe Ile Glu Asn Gly Tyr Ile
            340                 345                 350

Tyr His Thr Lys Tyr Asp Thr Ala Asp Arg Ile Leu Thr Asp Ser Ile
            355                 360                 365

Gln Arg Ala Gly Asp Asn Ile Leu Ala Val Leu Lys His Leu Ala Thr
370                 375                 380

Ser Asp Met Leu Ala Ala Ser Lys Tyr Arg His Gly Asn Met Val
385                 390                 395                 400

Phe Phe Asp Val Leu Gly Leu Phe Val Ile Ala Tyr Pro Ser Arg Ile
                405                 410                 415

Gly Ser Ile Ile Asn Tyr Met Val Val Met Gly Val Val Leu Tyr Leu
            420                 425                 430

Gly Lys Lys Phe Leu Gln Pro Lys His Lys Thr Gly Asn Tyr Lys Lys
            435                 440                 445

Asp Phe Leu Cys Gly Leu Gly Ile Thr Leu Ile Ser Trp Phe Thr Ser
450                 455                 460

Leu Val Thr Val Leu Ile Ile Ala Val Phe Ile Ser Leu Ile Gly Gln
465                 470                 475                 480

Ser Leu Ser Trp Tyr Asn His Phe Tyr Val Ser Val Cys Leu Tyr Gly
                485                 490                 495

Thr Ala Thr Val Ala Lys Ile Ile Leu Ile His Thr Leu Ala Lys Arg
            500                 505                 510

Phe Tyr Tyr Met Asn Ala Ser Ala Gln Tyr Leu Gly Glu Val Phe Phe
```

```
                515                 520                 525
Asp Ile Ser Leu Phe Val His Cys Cys Phe Leu Val Thr Leu Thr Tyr
        530                 535                 540
Gln Gly Leu Cys Ser Ala Phe Ile Ser Ala Val Trp Val Ala Phe Pro
545                 550                 555                 560
Leu Leu Thr Lys Leu Cys Val His Lys Asp Phe Lys Gln His Gly Ala
                565                 570                 575
Gln Gly Lys Phe Ile Ala Phe Tyr Leu Leu Gly Met Phe Ile Pro Tyr
            580                 585                 590
Leu Tyr Ala Leu Tyr Leu Ile Trp Ala Val Phe Glu Met Phe Thr Pro
            595                 600                 605
Ile Leu Gly Arg Ser Gly Ser Glu Ile Pro Pro Asp Val Val Leu Ala
        610                 615                 620
Ser Ile Leu Ala Gly Cys Thr Met Ile Leu Ser Ser Tyr Phe Ile Asn
625                 630                 635                 640
Phe Ile Tyr Leu Ala Lys Ser Thr Lys Lys Thr Met Leu Thr Leu Thr
                645                 650                 655
Leu Val Cys Ala Ile Thr Phe Leu Leu Val Cys Ser Gly Thr Phe Phe
            660                 665                 670
Pro Tyr Ser Ser Asn Pro Ala Asn Pro Lys Pro Lys Arg Val Phe Leu
            675                 680                 685
Gln His Met Thr Arg Thr Phe His Asp Leu Glu Gly Asn Ala Val Lys
        690                 695                 700
Arg Asp Ser Gly Ile Trp Ile Asn Gly Phe Asp Tyr Thr Gly Ile Ser
705                 710                 715                 720
His Ile Thr Pro His Ile Pro Glu Ile Asn Asp Ser Ile Arg Ala His
                725                 730                 735
Cys Glu Glu Asn Ala Pro Leu Cys Gly Phe Pro Trp Tyr Leu Pro Val
            740                 745                 750
His Phe Leu Ile Arg Lys Asn Trp Tyr Leu Pro Ala Pro Glu Val Ser
            755                 760                 765
Pro Arg Asn Pro Pro His Phe Arg Leu Ile Ser Lys Glu Gln Thr Pro
770                 775                 780
Trp Asp Ser Ile Lys Leu Thr Phe Glu Ala Thr Gly Pro Ser His Met
785                 790                 795                 800
Ser Phe Tyr Val Arg Ala His Lys Gly Ser Thr Leu Ser Gln Trp Ser
                805                 810                 815
Leu Gly Asn Gly Thr Pro Val Thr Ser Lys Gly Gly Asp Tyr Phe Val
            820                 825                 830
Phe Tyr Ser His Gly Leu Gln Ala Ser Ala Trp Gln Phe Trp Ile Glu
            835                 840                 845
Val Gln Val Ser Glu Glu His Pro Glu Gly Met Val Thr Val Ala Ile
        850                 855                 860
Ala Ala His Tyr Leu Ser Gly Glu Asp Lys Arg Ser Pro Gln Leu Asp
865                 870                 875                 880
Ala Leu Lys Glu Lys Phe Pro Asp Trp Thr Phe Pro Ser Ala Trp Val
                885                 890                 895
Cys Thr Tyr Asp Leu Phe Val Phe
            900

<210> SEQ ID NO 27
<211> LENGTH: 202
<212> TYPE: PRT
<213> ORGANISM: Homo sapiens
```

```
<400> SEQUENCE: 27

Met Glu Arg Gly Ala Gly Ala Lys Leu Leu Pro Leu Leu Leu Leu Leu
1               5                   10                  15

Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Val Glu Pro Pro Gln Gly Ile Pro Gly Asp Asp Thr Ala Leu Asn
65                  70                  75                  80

Gly Ile Arg Leu His Cys Ala Arg Gly Asn Val Leu Gly Asn Thr His
                85                  90                  95

Val Val Glu Ser Gln Ser Gly Ser Trp Gly Glu Trp Ser Glu Pro Leu
            100                 105                 110

Trp Cys Arg Gly Gly Ala Tyr Leu Val Ala Phe Ser Leu Arg Val Glu
        115                 120                 125

Ala Pro Thr Thr Leu Gly Asp Asn Thr Ala Ala Asn Asn Val Arg Phe
    130                 135                 140

Arg Cys Ser Asp Gly Glu Glu Leu Gln Gly Pro Gly Leu Ser Trp Gly
145                 150                 155                 160

Asp Phe Gly Asp Trp Ser Asp His Cys Pro Lys Gly Ala Cys Gly Leu
                165                 170                 175

Gln Thr Lys Ile Gln Gly Pro Arg Gly Leu Gly Asp Asp Thr Ala Leu
            180                 185                 190

Asn Asp Ala Arg Leu Phe Cys Cys Arg Ser
            195                 200

<210> SEQ ID NO 28
<211> LENGTH: 147
<212> TYPE: PRT
<213> ORGANISM: Homo sapiens

<400> SEQUENCE: 28

Met Gly Phe Ile Phe Ser Lys Ser Met Asn Glu Ser Met Lys Asn Gln
1               5                   10                  15

Lys Glu Phe Met Leu Met Asn Ala Arg Leu Gln Leu Glu Arg Gln Leu
            20                  25                  30

Ile Met Gln Ser Glu Met Arg Glu Arg Gln Met Ala Met Gln Ile Ala
            35                  40                  45

Trp Ser Arg Glu Phe Leu Lys Tyr Phe Gly Thr Phe Phe Gly Leu Ala
    50                  55                  60

Ala Ile Ser Leu Thr Ala Gly Ala Ile Lys Lys Lys Pro Ala Phe
65                  70                  75                  80

Leu Val Pro Ile Val Pro Leu Ser Phe Ile Leu Thr Tyr Gln Tyr Asp
                85                  90                  95

Leu Gly Tyr Gly Thr Leu Leu Glu Arg Met Lys Gly Glu Ala Glu Asp
            100                 105                 110

Ile Leu Glu Thr Glu Lys Ser Lys Leu Gln Leu Pro Arg Gly Met Ile
            115                 120                 125

Thr Phe Glu Ser Ile Glu Lys Ala Arg Lys Glu Gln Ser Arg Phe Phe
    130                 135                 140

Ile Asp Lys
145
```

-continued

```
<210> SEQ ID NO 29
<211> LENGTH: 758
<212> TYPE: PRT
<213> ORGANISM: Homo sapiens

<400> SEQUENCE: 29

Met Arg Lys Gln Gly Val Ser Ser Lys Arg Leu Gln Ser Ser Gly Arg
1               5                   10                  15

Ser Gln Ser Lys Gly Arg Arg Gly Ala Ser Leu Ala Arg Glu Pro Glu
            20                  25                  30

Val Glu Glu Met Glu Lys Ser Ala Leu Gly Gly Lys Leu Pro
        35                  40                  45

Arg Gly Ser Trp Arg Ser Ser Pro Gly Arg Ile Gln Ser Leu Lys Glu
    50                  55                  60

Arg Lys Gly Leu Glu Leu Glu Val Val Ala Lys Thr Phe Leu Leu Gly
65                  70                  75                  80

Pro Phe Gln Phe Val Arg Asn Ser Leu Ala Gln Leu Arg Glu Lys Val
                85                  90                  95

Gln Glu Leu Gln Ala Arg Arg Phe Ser Ser Arg Thr Thr Leu Gly Ile
            100                 105                 110

Ala Val Phe Val Ala Ile Leu His Trp Leu His Leu Val Thr Leu Phe
        115                 120                 125

Glu Asn Asp Arg His Phe Ser His Leu Ser Ser Leu Glu Arg Glu Met
    130                 135                 140

Thr Phe Arg Thr Glu Met Gly Leu Tyr Tyr Ser Tyr Phe Lys Thr Ile
145                 150                 155                 160

Ile Glu Ala Pro Ser Phe Leu Glu Gly Leu Trp Met Ile Met Asn Asp
                165                 170                 175

Arg Leu Thr Glu Tyr Pro Leu Ile Ile Asn Ala Ile Lys Arg Phe His
            180                 185                 190

Leu Tyr Pro Glu Val Ile Ile Ala Ser Trp Tyr Cys Thr Phe Met Gly
        195                 200                 205

Ile Met Asn Leu Phe Gly Leu Glu Thr Lys Thr Cys Trp Asn Val Thr
    210                 215                 220

Arg Ile Glu Pro Leu Asn Glu Val Gln Ser Cys Glu Gly Leu Gly Asp
225                 230                 235                 240

Pro Ala Cys Phe Tyr Val Gly Val Ile Phe Ile Leu Asn Gly Leu Met
                245                 250                 255

Met Gly Leu Phe Phe Met Tyr Gly Ala Tyr Leu Ser Gly Thr Gln Leu
            260                 265                 270

Gly Gly Leu Ile Thr Val Leu Cys Phe Phe Asn His Gly Glu Ala
        275                 280                 285

Thr Arg Val Met Trp Thr Pro Pro Leu Arg Glu Ser Phe Ser Tyr Pro
    290                 295                 300

Phe Leu Val Leu Gln Met Cys Ile Leu Thr Leu Ile Leu Arg Thr Ser
305                 310                 315                 320

Ser Asn Asp Arg Arg Pro Phe Ile Ala Leu Cys Leu Ser Asn Val Ala
                325                 330                 335

Phe Met Leu Pro Trp Gln Phe Ala Gln Phe Ile Leu Phe Thr Gln Ile
            340                 345                 350

Ala Ser Leu Phe Pro Met Tyr Val Val Gly Tyr Ile Glu Pro Ser Lys
        355                 360                 365

Phe Gln Lys Ile Ile Tyr Met Asn Met Ile Ser Val Thr Leu Ser Phe
```

```
                370                 375                 380
Ile Leu Met Phe Gly Asn Ser Met Tyr Leu Ser Ser Tyr Tyr Ser Ser
385                 390                 395                 400

Ser Leu Leu Met Thr Trp Ala Ile Ile Leu Lys Arg Asn Glu Ile Gln
                405                 410                 415

Lys Leu Gly Val Ser Lys Leu Asn Phe Trp Leu Ile Gln Gly Ser Ala
                420                 425                 430

Trp Trp Cys Gly Thr Ile Ile Leu Lys Phe Leu Thr Ser Lys Ile Leu
                435                 440                 445

Gly Val Ser Asp His Ile Arg Leu Ser Asp Leu Ile Ala Ala Arg Ile
                450                 455                 460

Leu Arg Tyr Thr Asp Phe Asp Thr Leu Ile Tyr Thr Cys Ala Pro Glu
465                 470                 475                 480

Phe Asp Phe Met Glu Lys Ala Thr Pro Leu Arg Tyr Thr Lys Thr Leu
                485                 490                 495

Leu Leu Pro Val Val Met Val Ile Thr Cys Phe Ile Phe Lys Lys Thr
                500                 505                 510

Val Arg Asp Ile Ser Tyr Val Leu Ala Thr Asn Ile Tyr Leu Arg Lys
                515                 520                 525

Gln Leu Leu Glu His Ser Glu Leu Ala Phe His Thr Leu Gln Leu Leu
                530                 535                 540

Val Phe Thr Ala Leu Ala Ile Leu Ile Met Arg Leu Lys Met Phe Leu
545                 550                 555                 560

Thr Pro His Met Cys Val Met Ala Ser Leu Ile Cys Ser Arg Gln Leu
                565                 570                 575

Phe Gly Trp Leu Phe Arg Arg Val Arg Phe Glu Lys Val Ile Phe Gly
                580                 585                 590

Ile Leu Thr Val Met Ser Ile Gln Gly Tyr Ala Asn Leu Arg Asn Gln
                595                 600                 605

Trp Ser Ile Ile Gly Glu Phe Asn Asn Leu Pro Gln Glu Glu Leu Leu
                610                 615                 620

Gln Trp Ile Lys Tyr Ser Thr Thr Ser Asp Ala Val Phe Ala Gly Ala
625                 630                 635                 640

Met Pro Thr Met Ala Ser Ile Lys Leu Ser Thr Leu His Pro Ile Val
                645                 650                 655

Asn His Pro His Tyr Glu Asp Ala Asp Leu Arg Ala Arg Thr Lys Ile
                660                 665                 670

Val Tyr Ser Thr Tyr Ser Arg Lys Ser Ala Lys Glu Val Arg Asp Lys
                675                 680                 685

Leu Leu Glu Leu His Val Asn Tyr Tyr Val Leu Glu Glu Ala Trp Cys
                690                 695                 700

Val Val Arg Thr Lys Pro Gly Cys Ser Met Leu Glu Ile Trp Asp Val
705                 710                 715                 720

Glu Asp Pro Ser Asn Ala Ala Asn Pro Pro Leu Cys Ser Val Leu Leu
                725                 730                 735

Glu Asp Ala Arg Pro Tyr Phe Thr Thr Val Phe Gln Asn Ser Val Tyr
                740                 745                 750

Arg Val Leu Lys Val Asn
                755

<210> SEQ ID NO 30
<211> LENGTH: 316
<212> TYPE: PRT
<213> ORGANISM: Homo sapiens
```

<400> SEQUENCE: 30

| Met | Ala | Ser | Ala | Asp | Glu | Leu | Thr | Phe | His | Glu | Phe | Glu | Glu | Ala | Thr |
|---|---|---|---|---|---|---|---|---|---|---|---|---|---|---|---|
| 1 | | | | 5 | | | | | 10 | | | | | 15 | |

| Asn | Leu | Leu | Ala | Asp | Thr | Pro | Asp | Ala | Ala | Thr | Thr | Ser | Arg | Ser | Asp |
|---|---|---|---|---|---|---|---|---|---|---|---|---|---|---|---|
| | | | 20 | | | | | 25 | | | | | 30 | | |

| Gln | Leu | Thr | Pro | Gln | Gly | His | Val | Ala | Val | Ala | Val | Gly | Ser | Gly | Gly |
|---|---|---|---|---|---|---|---|---|---|---|---|---|---|---|---|
| | | 35 | | | | | 40 | | | | | 45 | | | |

| Ser | Tyr | Gly | Ala | Glu | Asp | Glu | Val | Glu | Glu | Glu | Ser | Asp | Lys | Ala | Ala |
|---|---|---|---|---|---|---|---|---|---|---|---|---|---|---|---|
| | 50 | | | | | 55 | | | | | 60 | | | | |

| Leu | Leu | Gln | Glu | Gln | Gln | Gln | Gln | Gln | Pro | Gly | Phe | Trp | Thr | Phe |
|---|---|---|---|---|---|---|---|---|---|---|---|---|---|---|
| 65 | | | | 70 | | | | | 75 | | | | | 80 |

| Ser | Tyr | Tyr | Gln | Ser | Phe | Phe | Asp | Val | Asp | Thr | Ser | Gln | Val | Leu | Asp |
|---|---|---|---|---|---|---|---|---|---|---|---|---|---|---|---|
| | | | | 85 | | | | | 90 | | | | | 95 | |

| Arg | Ile | Lys | Gly | Ser | Leu | Leu | Pro | Arg | Pro | Gly | His | Asn | Phe | Val | Arg |
|---|---|---|---|---|---|---|---|---|---|---|---|---|---|---|---|
| | | | 100 | | | | | 105 | | | | | 110 | | |

| His | His | Leu | Arg | Asn | Arg | Pro | Asp | Leu | Tyr | Gly | Pro | Phe | Trp | Ile | Cys |
|---|---|---|---|---|---|---|---|---|---|---|---|---|---|---|---|
| | | 115 | | | | | 120 | | | | | 125 | | | |

| Ala | Thr | Leu | Ala | Phe | Val | Leu | Ala | Val | Thr | Gly | Asn | Leu | Thr | Leu | Val |
|---|---|---|---|---|---|---|---|---|---|---|---|---|---|---|---|
| | 130 | | | | | 135 | | | | | 140 | | | | |

| Leu | Ala | Gln | Arg | Arg | Asp | Pro | Ser | Ile | His | Tyr | Ser | Pro | Gln | Phe | His |
|---|---|---|---|---|---|---|---|---|---|---|---|---|---|---|---|
| 145 | | | | | 150 | | | | | 155 | | | | | 160 |

| Lys | Val | Thr | Val | Ala | Gly | Ile | Ser | Ile | Tyr | Cys | Tyr | Ala | Trp | Leu | Val |
|---|---|---|---|---|---|---|---|---|---|---|---|---|---|---|---|
| | | | | 165 | | | | | 170 | | | | | 175 | |

| Pro | Leu | Ala | Leu | Trp | Gly | Phe | Leu | Arg | Trp | Arg | Lys | Gly | Val | Gln | Glu |
|---|---|---|---|---|---|---|---|---|---|---|---|---|---|---|---|
| | | | 180 | | | | | 185 | | | | | 190 | | |

| Arg | Met | Gly | Pro | Tyr | Thr | Phe | Leu | Glu | Thr | Val | Cys | Ile | Tyr | Gly | Tyr |
|---|---|---|---|---|---|---|---|---|---|---|---|---|---|---|---|
| | | 195 | | | | | 200 | | | | | 205 | | | |

| Ser | Leu | Phe | Val | Phe | Ile | Pro | Met | Val | Val | Leu | Trp | Leu | Ile | Pro | Val |
|---|---|---|---|---|---|---|---|---|---|---|---|---|---|---|---|
| | 210 | | | | | 215 | | | | | 220 | | | | |

| Pro | Trp | Leu | Gln | Trp | Leu | Phe | Gly | Ala | Leu | Ala | Leu | Gly | Leu | Ser | Ala |
|---|---|---|---|---|---|---|---|---|---|---|---|---|---|---|---|
| 225 | | | | | 230 | | | | | 235 | | | | | 240 |

| Ala | Gly | Leu | Val | Phe | Thr | Leu | Trp | Pro | Val | Val | Arg | Glu | Asp | Thr | Arg |
|---|---|---|---|---|---|---|---|---|---|---|---|---|---|---|---|
| | | | | 245 | | | | | 250 | | | | | 255 | |

| Leu | Val | Ala | Thr | Val | Leu | Leu | Ser | Val | Val | Val | Leu | His | Ala | Leu |
|---|---|---|---|---|---|---|---|---|---|---|---|---|---|---|
| | | | 260 | | | | | 265 | | | | | 270 | |

| Leu | Ala | Met | Gly | Cys | Lys | Leu | Tyr | Phe | Phe | Gln | Ser | Leu | Pro | Pro | Glu |
|---|---|---|---|---|---|---|---|---|---|---|---|---|---|---|---|
| | | | 275 | | | | | 280 | | | | | 285 | | |

| Asn | Val | Ala | Pro | Pro | Pro | Gln | Ile | Thr | Ser | Leu | Pro | Ser | Asn | Ile | Ala |
|---|---|---|---|---|---|---|---|---|---|---|---|---|---|---|---|
| | 290 | | | | | 295 | | | | | 300 | | | | |

| Leu | Ser | Pro | Thr | Leu | Pro | Gln | Ser | Leu | Ala | Pro | Ser |
|---|---|---|---|---|---|---|---|---|---|---|---|
| 305 | | | | 310 | | | | | 315 | | |

<210> SEQ ID NO 31
<211> LENGTH: 241
<212> TYPE: PRT
<213> ORGANISM: Homo sapiens

<400> SEQUENCE: 31

| Met | Lys | Phe | Ile | Leu | Leu | Trp | Ala | Leu | Leu | Asn | Leu | Thr | Val | Ala | Leu |
|---|---|---|---|---|---|---|---|---|---|---|---|---|---|---|---|
| 1 | | | | 5 | | | | | 10 | | | | | 15 | |

| Ala | Phe | Asn | Pro | Asp | Tyr | Thr | Val | Ser | Ser | Thr | Pro | Pro | Tyr | Leu | Val |
|---|---|---|---|---|---|---|---|---|---|---|---|---|---|---|---|
| | | | 20 | | | | | 25 | | | | | 30 | | |

| Tyr | Leu | Lys | Ser | Asp | Tyr | Leu | Pro | Cys | Ala | Gly | Val | Leu | Ile | His | Pro |
|---|---|---|---|---|---|---|---|---|---|---|---|---|---|---|---|
| | | | 35 | | | | | 40 | | | | | 45 | | |

```
Leu Trp Val Ile Thr Ala Ala His Cys Asn Leu Pro Lys Leu Arg Val
             50                  55                  60

Ile Leu Gly Val Thr Ile Pro Ala Asp Ser Asn Glu Lys His Leu Gln
 65                  70                  75                  80

Val Ile Gly Tyr Glu Lys Met Ile His His Pro His Phe Ser Val Thr
                 85                  90                  95

Ser Ile Asp His Asp Ile Met Leu Ile Lys Leu Lys Thr Glu Ala Glu
                100                 105                 110

Leu Asn Asp Tyr Val Lys Leu Ala Asn Leu Pro Tyr Gln Thr Ile Ser
                115                 120                 125

Glu Asn Thr Met Cys Ser Val Ser Thr Trp Ser Tyr Asn Val Cys Asp
130                 135                 140

Ile Tyr Lys Glu Pro Asp Ser Leu Gln Thr Val Asn Ile Ser Val Ile
145                 150                 155                 160

Ser Lys Pro Gln Cys Arg Asp Ala Tyr Lys Thr Tyr Asn Ile Thr Glu
                165                 170                 175

Asn Met Leu Cys Val Gly Ile Val Pro Gly Arg Arg Gln Pro Cys Lys
                180                 185                 190

Glu Val Ser Ala Ala Pro Ala Ile Cys Asn Gly Met Leu Gln Gly Ile
                195                 200                 205

Leu Ser Phe Ala Asp Gly Cys Val Leu Arg Ala Asp Val Gly Ile Tyr
210                 215                 220

Ala Lys Ile Phe Tyr Tyr Ile Pro Trp Ile Glu Asn Val Ile Gln Asn
225                 230                 235                 240

Asn

<210> SEQ ID NO 32
<211> LENGTH: 1172
<212> TYPE: PRT
<213> ORGANISM: Homo sapiens

<400> SEQUENCE: 32

Met Ser Pro Asp Val Pro Leu Leu Asn Asp Tyr Lys Gln Asp Phe Phe
 1               5                  10                  15

Leu Lys Arg Phe Pro Gln Thr Val Leu Gly Gly Pro Arg Phe Lys Leu
                 20                  25                  30

Gly Tyr Cys Ala Pro Pro Tyr Ile Tyr Val Asn Gln Ile Ile Leu Phe
             35                  40                  45

Leu Met Pro Trp Val Trp Gly Gly Val Gly Thr Leu Leu Tyr Gln Leu
 50                  55                  60

Gly Ile Leu Lys Asp Tyr Tyr Thr Ala Ala Leu Ser Gly Gly Leu Met
 65                  70                  75                  80

Leu Phe Thr Ala Phe Val Ile Gln Phe Thr Ser Leu Tyr Ala Lys Asn
                 85                  90                  95

Lys Ser Thr Thr Val Glu Arg Ile Leu Thr Thr Asp Ile Leu Ala Glu
                100                 105                 110

Glu Asp Glu His Glu Phe Thr Ser Cys Thr Gly Ala Glu Thr Val Lys
                115                 120                 125

Phe Leu Ile Pro Gly Lys Lys Tyr Val Ala Asn Thr Val Phe His Ser
130                 135                 140

Ile Leu Ala Gly Leu Ala Cys Gly Leu Gly Thr Trp Tyr Leu Leu Pro
145                 150                 155                 160

Asn Arg Ile Thr Leu Leu Tyr Gly Ser Thr Gly Gly Thr Ala Leu Leu
                165                 170                 175
```

Phe Phe Phe Gly Trp Met Thr Leu Cys Ile Ala Glu Tyr Ser Leu Ile
            180                 185                 190

Val Asn Thr Ala Thr Glu Thr Ala Thr Phe Gln Thr Gln Asp Thr Tyr
            195                 200                 205

Glu Ile Ile Pro Leu Met Arg Pro Leu Tyr Ile Phe Phe Phe Val Ser
210                 215                 220

Val Asp Leu Ala His Arg Phe Val Asn Met Pro Ala Leu Glu His
225                 230                 235                 240

Met Asn Gln Ile Leu His Ile Leu Phe Val Phe Leu Pro Phe Leu Trp
            245                 250                 255

Ala Leu Gly Thr Leu Pro Pro Asp Ala Leu Leu Leu Trp Ala Met
            260                 265                 270

Glu Gln Val Leu Glu Phe Gly Leu Gly Gly Ser Ser Met Ser Thr His
            275                 280                 285

Leu Arg Leu Leu Val Met Phe Ile Met Ser Ala Gly Thr Ala Ile Ala
            290                 295                 300

Ser Tyr Phe Ile Pro Ser Thr Val Gly Val Val Leu Phe Met Thr Gly
305                 310                 315                 320

Phe Gly Phe Leu Leu Ser Leu Asn Leu Ser Asp Met Gly His Lys Ile
            325                 330                 335

Gly Thr Lys Ser Lys Asp Leu Pro Ser Gly Pro Glu Lys His Phe Ser
            340                 345                 350

Trp Lys Glu Cys Leu Phe Tyr Ile Ile Ile Leu Val Leu Ala Leu Leu
            355                 360                 365

Glu Thr Ser Leu Leu His His Phe Ala Gly Phe Ser Gln Ile Ser Lys
            370                 375                 380

Ser Asn Ser Gln Ala Ile Val Gly Tyr Gly Leu Met Ile Leu Leu Ile
385                 390                 395                 400

Ile Leu Trp Ile Leu Arg Glu Ile Gln Ser Val Tyr Ile Ile Gly Ile
            405                 410                 415

Phe Arg Asn Pro Phe Tyr Pro Lys Asp Val Gln Thr Val Thr Val Phe
            420                 425                 430

Phe Glu Lys Gln Thr Arg Leu Met Lys Ile Gly Ile Val Arg Arg Ile
            435                 440                 445

Leu Leu Thr Leu Val Ser Pro Phe Ala Met Ile Ala Phe Leu Ser Leu
            450                 455                 460

Asp Ser Ser Leu Gln Gly Leu His Ser Val Ser Val Cys Ile Gly Phe
465                 470                 475                 480

Thr Arg Ala Phe Arg Met Val Trp Gln Asn Thr Glu Asn Ala Leu Leu
            485                 490                 495

Glu Thr Val Ile Val Ser Thr Val His Leu Ile Ser Ser Thr Asp Ile
            500                 505                 510

Trp Trp Asn Arg Ser Leu Asp Thr Gly Leu Arg Leu Leu Val Gly
            515                 520                 525

Ile Ile Arg Asp Arg Leu Ile Gln Phe Ile Ser Lys Leu Gln Phe Ala
            530                 535                 540

Val Thr Val Leu Leu Thr Ser Trp Thr Glu Lys Lys Gln Arg Arg Lys
545                 550                 555                 560

Thr Thr Ala Thr Leu Cys Ile Leu Asn Ile Val Phe Ser Pro Phe Val
            565                 570                 575

Leu Val Ile Ile Val Phe Ser Thr Leu Leu Ser Ser Pro Leu Leu Pro
            580                 585                 590

-continued

```
Leu Phe Thr Leu Pro Val Phe Leu Val Gly Phe Pro Arg Pro Ile Gln
        595                 600                 605

Ser Trp Pro Gly Ala Ala Gly Thr Thr Ala Cys Val Cys Ala Asp Thr
    610                 615                 620

Val Tyr Tyr Tyr Gln Met Val Pro Arg Leu Thr Ala Val Leu Gln Thr
625                 630                 635                 640

Ala Met Ala Ala Gly Ser Leu Gly Leu Leu Pro Gly Ser His Tyr
                645                 650                 655

Leu Gly Arg Phe Gln Asp Arg Leu Met Trp Ile Met Ile Leu Glu Cys
                660                 665                 670

Gly Tyr Thr Tyr Cys Ser Ile Asn Ile Lys Gly Leu Glu Leu Gln Glu
                675                 680                 685

Thr Ser Cys His Thr Ala Glu Ala Arg Arg Val Asp Glu Val Phe Glu
                690                 695                 700

Asp Ala Phe Glu Gln Glu Tyr Thr Arg Val Cys Ser Leu Asn Glu His
705                 710                 715                 720

Phe Gly Asn Val Leu Thr Pro Cys Thr Val Leu Pro Val Lys Leu Tyr
                725                 730                 735

Ser Asp Ala Arg Asn Val Leu Ser Gly Ile Ile Asp Ser His Glu Asn
                740                 745                 750

Leu Lys Glu Phe Lys Gly Asp Leu Ile Lys Val Leu Val Trp Ile Leu
                755                 760                 765

Val Gln Tyr Cys Ser Lys Arg Pro Gly Met Lys Glu Asn Val His Asn
                770                 775                 780

Thr Glu Asn Lys Gly Lys Ala Pro Leu Met Leu Pro Ala Leu Asn Thr
785                 790                 795                 800

Leu Pro Pro Lys Ser Pro Glu Asp Ile Asp Ser Leu Asn Ser Glu
                805                 810                 815

Thr Phe Asn Asp Trp Ser Asp Asn Ile Phe Asp Glu Pro Thr
                820                 825                 830

Ile Lys Lys Val Ile Glu Glu Lys His Gln Leu Lys Asp Leu Pro Gly
                835                 840                 845

Thr Asn Leu Phe Ile Pro Gly Ser Val Glu Ser Gln Arg Val Gly Asp
850                 855                 860

His Ser Thr Gly Thr Val Pro Glu Asn Asp Leu Tyr Lys Ala Val Leu
865                 870                 875                 880

Leu Gly Tyr Pro Ala Val Asp Lys Gly Lys Gln Glu Asp Met Pro Tyr
                885                 890                 895

Ile Pro Leu Met Glu Phe Ser Cys Ser His Ser His Leu Val Cys Leu
                900                 905                 910

Pro Ala Glu Trp Arg Thr Ser Cys Met Pro Ser Ser Lys Met Lys Glu
                915                 920                 925

Met Ser Ser Leu Phe Pro Glu Asp Trp Tyr Gln Phe Val Leu Arg Gln
                930                 935                 940

Leu Glu Cys Tyr His Ser Glu Glu Lys Ala Ser Asn Val Leu Glu Glu
945                 950                 955                 960

Ile Ala Lys Asp Lys Val Leu Lys Asp Phe Tyr Val His Thr Val Met
                965                 970                 975

Thr Cys Tyr Phe Ser Leu Phe Gly Ile Asp Asn Met Ala Pro Ser Pro
                980                 985                 990

Gly His Ile Leu Arg Val Tyr Gly  Gly Val Leu Pro Trp  Ser Val Ala
                995                 1000                1005

Leu Asp  Trp Leu Thr Glu Lys  Pro Glu Leu Phe Gln  Leu Ala Leu
```

```
             1010                1015                1020

Lys Ala Phe Arg Tyr Thr Leu Lys Leu Met Ile Asp Lys Ala Ser
        1025                1030                1035

Leu Gly Pro Ile Glu Asp Phe Arg Glu Leu Ile Lys Tyr Leu Glu
        1040                1045                1050

Glu Tyr Glu Arg Asp Trp Tyr Ile Gly Leu Val Ser Asp Glu Lys
        1055                1060                1065

Trp Lys Glu Ala Ile Leu Gln Glu Lys Pro Tyr Leu Phe Ser Leu
        1070                1075                1080

Gly Tyr Asp Ser Asn Met Gly Ile Tyr Thr Gly Arg Val Leu Ser
        1085                1090                1095

Leu Gln Glu Leu Leu Ile Gln Val Gly Lys Leu Asn Pro Glu Ala
        1100                1105                1110

Val Arg Gly Gln Trp Ala Asn Leu Ser Trp Glu Leu Leu Tyr Ala
        1115                1120                1125

Thr Asn Asp Asp Glu Glu Arg Tyr Ser Ile Gln Ala His Pro Leu
        1130                1135                1140

Leu Leu Arg Asn Leu Thr Val Gln Ala Ala Glu Pro Pro Leu Gly
        1145                1150                1155

Tyr Pro Ile Tyr Ser Ser Lys Pro Leu His Ile His Leu Tyr
        1160                1165                1170
```

<210> SEQ ID NO 33
<211> LENGTH: 346
<212> TYPE: PRT
<213> ORGANISM: Homo sapiens

<400> SEQUENCE: 33

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
                20                  25                  30

Lys Thr Pro Ala Gln Pro Gln Leu Lys Ala Ala Asn Cys Cys Glu Glu
        35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205
```

```
Ile His Arg Leu Ser Arg Gln Pro Thr Arg Leu Arg Val Glu Met Glu
210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345

<210> SEQ ID NO 34
<211> LENGTH: 752
<212> TYPE: PRT
<213> ORGANISM: Homo sapiens

<400> SEQUENCE: 34

Met Ala Glu Pro Gln Ala Glu Ser Pro Leu Leu Gly Gly Ala Arg
1               5                   10                  15

Gly Gly Gly Gly Asp Trp Pro Ala Gly Leu Thr Thr Tyr Arg Ser Ile
                20                  25                  30

Gln Val Gly Pro Gly Ala Ala Arg Trp Asp Leu Cys Ile Asp Gln
            35                  40                  45

Ala Val Val Phe Ile Glu Asp Ala Ile Gln Tyr Arg Ser Ile Asn His
        50                  55                  60

Arg Val Asp Ala Ser Ser Met Trp Leu Tyr Arg Tyr Tyr Ser Asn
65                  70                  75                  80

Val Cys Gln Arg Thr Leu Ser Phe Thr Ile Phe Leu Ile Leu Phe Leu
                85                  90                  95

Ala Phe Ile Glu Thr Pro Ser Ser Leu Thr Ser Thr Ala Asp Val Arg
            100                 105                 110

Tyr Arg Ala Ala Pro Trp Glu Pro Pro Cys Gly Leu Thr Glu Ser Val
        115                 120                 125

Glu Val Leu Cys Leu Leu Val Phe Ala Ala Asp Leu Ser Val Lys Gly
    130                 135                 140

Tyr Leu Phe Gly Trp Ala His Phe Gln Lys Asn Leu Trp Leu Leu Gly
145                 150                 155                 160

Tyr Leu Val Val Leu Val Val Ser Leu Val Asp Trp Thr Val Ser Leu
                165                 170                 175

Ser Leu Val Cys His Glu Pro Leu Arg Ile Arg Arg Leu Leu Arg Pro
            180                 185                 190

Phe Phe Leu Leu Gln Asn Ser Ser Met Met Lys Lys Thr Leu Lys Cys
        195                 200                 205

Ile Arg Trp Ser Leu Pro Glu Met Ala Ser Val Gly Leu Leu Leu Ala
    210                 215                 220

Ile His Leu Cys Leu Phe Thr Met Phe Gly Met Leu Leu Phe Ala Gly
225                 230                 235                 240
```

```
Gly Lys Gln Asp Asp Gly Gln Asp Arg Glu Arg Leu Thr Tyr Phe Gln
            245                 250                 255

Asn Leu Pro Glu Ser Leu Thr Ser Leu Leu Val Leu Leu Thr Thr Ala
            260                 265                 270

Asn Asn Pro Asp Val Met Ile Pro Ala Tyr Ser Lys Asn Arg Ala Tyr
            275                 280                 285

Ala Ile Phe Phe Ile Val Phe Thr Val Ile Gly Ser Leu Phe Leu Met
            290                 295                 300

Asn Leu Leu Thr Ala Ile Ile Tyr Ser Gln Phe Arg Gly Tyr Leu Met
305                     310                 315                 320

Lys Ser Leu Gln Thr Ser Leu Phe Arg Arg Arg Leu Gly Thr Arg Ala
                325                 330                 335

Ala Phe Glu Val Leu Ser Ser Met Val Gly Glu Gly Gly Ala Phe Pro
            340                 345                 350

Gln Ala Val Gly Val Lys Pro Gln Asn Leu Leu Gln Val Leu Gln Lys
            355                 360                 365

Val Gln Leu Asp Ser Ser His Lys Gln Ala Met Met Glu Lys Val Arg
            370                 375                 380

Ser Tyr Gly Ser Val Leu Leu Ser Ala Glu Glu Phe Gln Lys Leu Phe
385                     390                 395                 400

Asn Glu Leu Asp Arg Ser Val Val Lys Glu His Pro Arg Pro Glu
                405                 410                 415

Tyr Gln Ser Pro Phe Leu Gln Ser Ala Gln Phe Leu Phe Gly His Tyr
                420                 425                 430

Tyr Phe Asp Tyr Leu Gly Asn Leu Ile Ala Leu Ala Asn Leu Val Ser
            435                 440                 445

Ile Cys Val Phe Leu Val Leu Asp Ala Asp Val Leu Pro Ala Glu Arg
            450                 455                 460

Asp Asp Phe Ile Leu Gly Ile Leu Asn Cys Val Phe Ile Val Tyr Tyr
465                 470                 475                 480

Leu Leu Glu Met Leu Leu Lys Val Phe Ala Leu Gly Leu Arg Gly Tyr
                485                 490                 495

Leu Ser Tyr Pro Ser Asn Val Phe Asp Gly Leu Leu Thr Val Val Leu
            500                 505                 510

Leu Val Leu Glu Ile Ser Thr Leu Ala Val Tyr Arg Leu Pro His Pro
            515                 520                 525

Gly Trp Arg Pro Glu Met Val Gly Leu Leu Ser Leu Trp Asp Met Thr
            530                 535                 540

Arg Met Leu Asn Met Leu Ile Val Phe Arg Phe Leu Arg Ile Ile Pro
545                 550                 555                 560

Ser Met Lys Leu Met Ala Val Val Ala Ser Thr Val Leu Gly Leu Val
                565                 570                 575

Gln Asn Met Arg Ala Phe Gly Gly Ile Leu Val Val Tyr Tyr Val
            580                 585                 590

Phe Ala Ile Ile Gly Ile Asn Leu Phe Arg Gly Val Ile Val Ala Leu
            595                 600                 605

Pro Gly Asn Ser Ser Leu Ala Pro Ala Asn Gly Ser Ala Pro Cys Gly
            610                 615                 620

Ser Phe Glu Gln Leu Glu Tyr Trp Ala Asn Asn Phe Asp Asp Phe Ala
625                 630                 635                 640

Ala Ala Leu Val Thr Leu Trp Asn Leu Met Val Val Asn Asn Trp Gln
                645                 650                 655
```

```
Val Phe Leu Asp Ala Tyr Arg Arg Tyr Ser Gly Pro Trp Ser Lys Ile
            660                 665                 670

Tyr Phe Val Leu Trp Trp Leu Val Ser Ser Val Ile Trp Val Asn Leu
        675                 680                 685

Phe Leu Ala Leu Ile Leu Glu Asn Phe Leu His Lys Trp Asp Pro Arg
        690                 695                 700

Ser His Leu Gln Pro Leu Ala Gly Thr Pro Glu Ala Thr Tyr Gln Met
705                 710                 715                 720

Thr Val Glu Leu Leu Phe Arg Asp Ile Leu Glu Pro Gly Glu Asp
                725                 730                 735

Glu Leu Thr Glu Arg Leu Ser Gln His Pro His Leu Trp Leu Cys Arg
        740                 745                 750

<210> SEQ ID NO 35
<211> LENGTH: 272
<212> TYPE: PRT
<213> ORGANISM: Homo sapiens

<400> SEQUENCE: 35

Met Gln Trp Asn Val Pro Arg Thr Val Ser Arg Leu Ala Arg Arg Thr
1               5                   10                  15

Cys Leu Glu Pro His Asn Ala Gly Leu Phe Gly His Cys Gln Asn Val
            20                  25                  30

Lys Gly Pro Leu Leu Leu Tyr Asn Ala Glu Ser Lys Val Val Leu Val
        35                  40                  45

Gln Gly Pro Gln Lys Gln Trp Leu His Leu Ser Ala Ala Gln Cys Val
    50                  55                  60

Ala Lys Glu Arg Arg Pro Leu Asp Ala His Pro Pro Gln Pro Gly Val
65                  70                  75                  80

Leu Arg His Lys Gln Gly Lys Gln His Val Ser Phe Arg Arg Val Phe
            85                  90                  95

Ser Ser Ser Ala Thr Ala Gln Gly Thr Pro Glu Lys Lys Glu Glu Pro
            100                 105                 110

Asp Pro Leu Gln Asp Lys Ser Ile Ser Leu Tyr Gln Arg Phe Lys Lys
        115                 120                 125

Thr Phe Arg Gln Tyr Gly Lys Val Leu Ile Pro Val His Leu Ile Thr
    130                 135                 140

Ser Gly Val Trp Phe Gly Thr Phe Tyr Ala Ala Leu Lys Gly Val
145                 150                 155                 160

Asn Val Val Pro Phe Leu Glu Leu Ile Gly Leu Pro Asp Ser Val Val
            165                 170                 175

Ser Ile Leu Lys Asn Ser Gln Ser Gly Asn Ala Leu Thr Ala Tyr Ala
            180                 185                 190

Leu Phe Lys Ile Ala Thr Pro Ala Arg Tyr Thr Val Thr Leu Gly Gly
        195                 200                 205

Thr Ser Val Thr Val Lys Tyr Leu Arg Ser His Gly Tyr Met Ser Thr
    210                 215                 220

Pro Pro Pro Val Lys Glu Tyr Leu Gln Asp Arg Met Glu Glu Thr Lys
225                 230                 235                 240

Glu Leu Ile Thr Glu Lys Met Glu Glu Thr Lys Asp Arg Leu Thr Glu
            245                 250                 255

Lys Leu Gln Glu Thr Lys Glu Lys Val Ser Phe Lys Lys Val Glu
        260                 265                 270

<210> SEQ ID NO 36
```

<211> LENGTH: 402
<212> TYPE: PRT
<213> ORGANISM: Homo sapiens

<400> SEQUENCE: 36

```
Met Met Val Ala Leu Arg Gly Ala Ser Ala Leu Leu Val Leu Phe Leu
1               5                   10                  15

Ala Ala Phe Leu Pro Pro Gln Cys Thr Gln Asp Pro Ala Met Val
            20                  25                  30

His Tyr Ile Tyr Gln Arg Phe Arg Val Leu Glu Gln Gly Leu Glu Lys
        35                  40                  45

Cys Thr Gln Ala Thr Arg Ala Tyr Ile Gln Gly Phe Gln Glu Phe Ser
    50                  55                  60

Lys Asn Ile Ser Val Met Leu Gly Arg Cys Gln Thr Tyr Thr Ser Glu
65                  70                  75                  80

Tyr Lys Ser Ala Val Gly Asn Leu Ala Leu Arg Val Glu Arg Ala Gln
                85                  90                  95

Arg Glu Ile Asp Tyr Ile Gln Tyr Leu Arg Glu Ala Asp Glu Cys Ile
            100                 105                 110

Glu Ser Glu Asp Lys Thr Leu Ala Glu Met Leu Leu Gln Glu Ala Glu
        115                 120                 125

Glu Glu Lys Lys Ile Arg Thr Leu Leu Asn Ala Ser Cys Asp Asn Met
130                 135                 140

Leu Met Gly Ile Lys Ser Leu Lys Ile Val Lys Met Met Asp Thr
145                 150                 155                 160

His Gly Ser Trp Met Lys Asp Ala Val Tyr Asn Ser Pro Lys Val Tyr
                165                 170                 175

Leu Leu Ile Gly Ser Arg Asn Asn Thr Val Trp Glu Phe Ala Asn Ile
            180                 185                 190

Arg Ala Phe Met Glu Asp Asn Thr Lys Pro Ala Pro Arg Lys Gln Ile
        195                 200                 205

Leu Thr Leu Ser Trp Gln Gly Thr Gly Gln Val Ile Tyr Lys Gly Phe
    210                 215                 220

Leu Phe His Asn Gln Ala Thr Ser Asn Glu Ile Ile Lys Tyr Asn
225                 230                 235                 240

Leu Gln Lys Arg Thr Val Glu Asp Arg Met Leu Leu Pro Gly Gly Val
                245                 250                 255

Gly Arg Ala Leu Val Tyr Gln His Ser Pro Ser Thr Tyr Ile Asp Leu
            260                 265                 270

Ala Val Asp Glu His Gly Leu Trp Ala Ile His Ser Gly Pro Gly Thr
        275                 280                 285

His Ser His Leu Val Leu Thr Lys Ile Glu Pro Gly Thr Leu Gly Val
    290                 295                 300

Glu His Ser Trp Asp Thr Pro Cys Arg Ser Gln Asp Ala Glu Ala Ser
305                 310                 315                 320

Phe Leu Leu Cys Gly Val Leu Tyr Val Val Tyr Ser Thr Gly Gly Gln
                325                 330                 335

Gly Pro His Arg Ile Thr Cys Ile Tyr Asp Pro Leu Gly Thr Ile Ser
            340                 345                 350

Glu Glu Asp Leu Pro Asn Leu Phe Phe Pro Lys Arg Pro Arg Ser His
        355                 360                 365

Ser Met Ile His Tyr Asn Pro Arg Asp Lys Gln Leu Tyr Ala Trp Asn
    370                 375                 380

Glu Gly Asn Gln Ile Ile Tyr Lys Leu Gln Thr Lys Arg Lys Leu Pro
```

385             390             395             400

Leu Lys

<210> SEQ ID NO 37
<211> LENGTH: 246
<212> TYPE: PRT
<213> ORGANISM: Homo sapiens

<400> SEQUENCE: 37

Met Gly Pro Gln His Leu Arg Leu Val Gln Leu Phe Cys Leu Leu Gly
1               5                   10                  15

Ala Ile Ser Thr Leu Pro Arg Ala Gly Ala Leu Leu Cys Tyr Glu Ala
            20                  25                  30

Thr Ala Ser Arg Phe Arg Ala Val Ala Phe His Asn Trp Lys Trp Leu
        35                  40                  45

Leu Met Arg Asn Met Val Cys Lys Leu Gln Glu Gly Cys Glu Glu Thr
    50                  55                  60

Leu Val Phe Ile Glu Thr Gly Thr Ala Arg Gly Val Val Gly Phe Lys
65                  70                  75                  80

Gly Cys Ser Ser Ser Ser Tyr Pro Ala Gln Ile Ser Tyr Leu Val
                85                  90                  95

Ser Pro Pro Gly Val Ser Ile Ala Ser Tyr Ser Arg Val Cys Arg Ser
            100                 105                 110

Tyr Leu Cys Asn Asn Leu Thr Asn Leu Glu Pro Phe Val Lys Leu Lys
            115                 120                 125

Ala Ser Thr Pro Lys Ser Ile Thr Ser Ala Ser Cys Ser Cys Pro Thr
        130                 135                 140

Cys Val Gly Glu His Met Lys Asp Cys Leu Pro Asn Phe Val Thr Thr
145                 150                 155                 160

Asn Ser Cys Pro Leu Ala Ala Ser Thr Cys Tyr Ser Ser Thr Leu Lys
                165                 170                 175

Phe Gln Ala Gly Phe Leu Asn Thr Thr Phe Leu Leu Met Gly Cys Ala
            180                 185                 190

Arg Glu His Asn Gln Leu Leu Ala Asp Phe His His Ile Gly Ser Ile
        195                 200                 205

Lys Val Thr Glu Val Leu Asn Ile Leu Glu Lys Ser Gln Ile Val Gly
    210                 215                 220

Ala Ala Ser Ser Arg Gln Asp Pro Ala Trp Gly Val Val Leu Gly Leu
225                 230                 235                 240

Leu Phe Ala Phe Arg Asp
                245

<210> SEQ ID NO 38
<211> LENGTH: 2845
<212> TYPE: PRT
<213> ORGANISM: Homo sapiens

<400> SEQUENCE: 38

Met Ala Leu Gly Lys Val Leu Ala Met Ala Leu Val Leu Ala Leu Ala
1               5                   10                  15

Val Leu Gly Ser Leu Ser Pro Gly Ala Arg Ala Gly Asp Cys Lys Gly
            20                  25                  30

Gln Arg Gln Val Leu Arg Glu Ala Pro Gly Phe Val Thr Asp Gly Ala
        35                  40                  45

Gly Asn Tyr Ser Val Asn Gly Asn Cys Glu Trp Leu Ile Glu Ala Pro
    50                  55                  60

```
Ser Pro Gln His Arg Ile Leu Leu Asp Phe Leu Phe Leu Asp Thr Glu
 65                  70                  75                  80

Cys Thr Tyr Asp Tyr Leu Phe Val Tyr Asp Gly Asp Ser Pro Arg Gly
                 85                  90                  95

Pro Leu Leu Ala Ser Leu Ser Gly Ser Thr Arg Pro Pro Ile Glu
                100                 105                 110

Ala Ser Ser Gly Lys Met Leu Leu His Leu Phe Ser Asp Ala Asn Tyr
             115                 120                 125

Asn Leu Leu Gly Phe Asn Ala Ser Phe Arg Phe Ser Leu Cys Pro Gly
            130                 135                 140

Gly Cys Gln Ser His Gly Gln Cys Gln Pro Pro Gly Val Cys Ala Cys
145                 150                 155                 160

Glu Pro Gly Trp Gly Gly Pro Asp Cys Gly Leu Gln Glu Cys Ser Ala
                165                 170                 175

Tyr Cys Gly Ser His Gly Thr Cys Ala Ser Pro Leu Gly Pro Cys Arg
                180                 185                 190

Cys Glu Pro Gly Phe Leu Gly Arg Ala Cys Asp Leu His Leu Trp Glu
                195                 200                 205

Asn Gln Gly Ala Gly Trp Trp His Asn Val Ser Ala Arg Asp Pro Ala
210                 215                 220

Phe Ser Ala Arg Ile Gly Ala Ala Gly Ala Phe Leu Ser Pro Pro Gly
225                 230                 235                 240

Leu Leu Ala Val Phe Gly Gly Gln Asp Leu Asn Asn Ala Leu Gly Asp
                245                 250                 255

Leu Val Leu Tyr Asn Phe Ser Ala Asn Thr Trp Glu Ser Trp Asp Leu
                260                 265                 270

Ser Pro Ala Pro Ala Arg His Ser His Val Ala Val Ala Trp Ala
                275                 280                 285

Gly Ser Leu Val Leu Met Gly Gly Glu Leu Ala Asp Gly Ser Leu Thr
290                 295                 300

Asn Asp Val Trp Ala Phe Ser Pro Leu Gly Arg Gly His Trp Glu Leu
305                 310                 315                 320

Leu Ala Pro Pro Ala Ser Ser Ser Gly Pro Pro Gly Leu Ala Gly
                325                 330                 335

His Ala Ala Leu Val Asp Asp Val Trp Leu Tyr Val Ser Gly Gly
                340                 345                 350

Arg Thr Pro His Asp Leu Phe Ser Ser Gly Leu Phe Arg Phe Arg Leu
                355                 360                 365

Asp Ser Thr Ser Gly Gly Tyr Trp Glu Gln Val Ile Pro Ala Gly Gly
                370                 375                 380

Arg Pro Pro Ala Ala Thr Gly His Ser Met Val Phe His Ala Pro Ser
385                 390                 395                 400

Arg Ala Leu Leu Val His Gly Gly His Arg Pro Ser Thr Ala Arg Phe
                405                 410                 415

Ser Val Arg Val Asn Ser Thr Glu Leu Phe His Val Asp Arg His Val
                420                 425                 430

Trp Thr Thr Leu Lys Gly Arg Asp Gly Leu Gln Gly Pro Arg Glu Arg
                435                 440                 445

Ala Phe His Thr Ala Ser Val Leu Gly Asn Tyr Met Val Val Tyr Gly
                450                 455                 460

Gly Asn Val His Thr His Tyr Gln Glu Glu Lys Cys Tyr Glu Asp Gly
465                 470                 475                 480
```

```
Ile Phe Phe Tyr His Leu Gly Cys His Gln Trp Val Ser Gly Ala Glu
                485                 490                 495

Leu Ala Pro Pro Gly Thr Pro Glu Gly Arg Ala Ala Pro Pro Ser Gly
            500                 505                 510

Arg Tyr Ser His Val Ala Ala Val Leu Gly Gly Ser Val Leu Leu Val
        515                 520                 525

Ala Gly Gly Tyr Ser Gly Arg Pro Arg Gly Asp Leu Met Ala Tyr Lys
    530                 535                 540

Val Pro Pro Phe Val Phe Gln Ala Pro Ala Pro Asp Tyr His Leu Asp
545                 550                 555                 560

Tyr Cys Ser Met Tyr Thr Asp His Ser Val Cys Ser Arg Asp Pro Glu
                565                 570                 575

Cys Ser Trp Cys Gln Gly Ala Cys Gln Ala Ala Pro Pro Gly Thr
            580                 585                 590

Pro Leu Gly Ala Cys Pro Ala Ala Ser Cys Leu Gly Leu Gly Arg Leu
        595                 600                 605

Leu Gly Asp Cys Gln Ala Cys Leu Ala Phe Ser Ser Pro Thr Ala Pro
    610                 615                 620

Pro Arg Gly Pro Gly Thr Leu Gly Trp Cys Val His Asn Glu Ser Cys
625                 630                 635                 640

Leu Pro Arg Pro Glu Gln Ala Arg Cys Arg Gly Glu Gln Ile Ser Gly
                645                 650                 655

Thr Val Gly Trp Trp Gly Pro Ala Pro Val Phe Val Thr Ser Leu Glu
            660                 665                 670

Ala Cys Val Thr Gln Ser Phe Leu Pro Gly Leu His Leu Leu Thr Phe
        675                 680                 685

Gln Gln Pro Pro Asn Thr Ser Gln Pro Asp Lys Val Ser Ile Val Arg
    690                 695                 700

Ser Thr Thr Ile Thr Leu Thr Pro Ser Ala Glu Thr Asp Val Ser Leu
705                 710                 715                 720

Val Tyr Arg Gly Phe Ile Tyr Pro Met Leu Pro Gly Gly Pro Gly Gly
                725                 730                 735

Pro Gly Ala Glu Asp Val Ala Val Trp Thr Arg Ala Gln Arg Leu His
            740                 745                 750

Val Leu Ala Arg Met Ala Arg Gly Pro Asp Thr Glu Asn Met Glu Glu
        755                 760                 765

Val Gly Arg Trp Val Ala His Gln Glu Lys Glu Thr Arg Leu Gln
    770                 775                 780

Arg Pro Gly Ser Ala Arg Leu Phe Pro Leu Pro Gly Arg Asp His Lys
785                 790                 795                 800

Tyr Ala Val Glu Ile Gln Gly Gln Leu Asn Gly Ser Ala Gly Pro Gly
                805                 810                 815

His Ser Glu Leu Thr Leu Leu Trp Asp Arg Thr Gly Val Pro Gly Gly
            820                 825                 830

Ser Glu Ile Ser Phe Phe Leu Glu Pro Tyr Arg Ser Ser Cys
        835                 840                 845

Thr Ser Tyr Ser Ser Cys Leu Gly Cys Leu Ala Asp Gln Gly Cys Gly
    850                 855                 860

Trp Cys Leu Thr Ser Ala Thr Cys His Leu Arg Gln Gly Gly Ala His
865                 870                 875                 880

Cys Gly Asp Asp Gly Ala Gly Gly Ser Leu Leu Val Leu Val Pro Thr
                885                 890                 895

Leu Cys Pro Leu Cys Glu Glu His Arg Asp Cys His Ala Cys Thr Gln
```

```
                900                 905                 910
Asp Pro Phe Cys Glu Trp His Gln Ser Thr Ser Arg Lys Gly Asp Ala
            915                 920                 925

Ala Cys Ser Arg Arg Gly Arg Gly Arg Gly Ala Leu Lys Ser Pro Glu
930                 935                 940

Glu Cys Pro Pro Leu Cys Ser Gln Arg Leu Thr Cys Glu Asp Cys Leu
945                 950                 955                 960

Ala Asn Ser Ser Gln Cys Ala Trp Cys Gln Ser Thr His Thr Cys Phe
                965                 970                 975

Leu Phe Ala Ala Tyr Leu Ala Arg Tyr Pro His Gly Gly Cys Arg Gly
            980                 985                 990

Trp Asp Asp Ser Val His Ser Glu Pro Arg Cys Arg Ser Cys Asp Gly
        995                 1000                1005

Phe Leu Thr Cys His Glu Cys Leu Gln Ser His Glu Cys Gly Trp
    1010                1015                1020

Cys Gly Asn Glu Asp Asn Pro Thr Leu Gly Arg Cys Leu Gln Gly
    1025                1030                1035

Asp Phe Ser Gly Pro Leu Gly Gly Asn Cys Ser Leu Trp Val
    1040                1045                1050

Gly Glu Gly Leu Gly Leu Pro Val Ala Leu Pro Ala Arg Trp Ala
    1055                1060                1065

Tyr Ala Arg Cys Pro Asp Val Asp Glu Cys Arg Leu Gly Leu Ala
    1070                1075                1080

Arg Cys His Pro Arg Ala Thr Cys Leu Asn Thr Pro Leu Ser Tyr
    1085                1090                1095

Glu Cys His Cys Gln Arg Gly Tyr Gln Gly Asp Gly Ile Ser His
    1100                1105                1110

Cys Asn Arg Thr Cys Leu Glu Asp Cys Gly His Gly Val Cys Ser
    1115                1120                1125

Gly Pro Pro Asp Phe Thr Cys Val Cys Asp Leu Gly Trp Thr Ser
    1130                1135                1140

Asp Leu Pro Pro Pro Thr Pro Ala Pro Gly Pro Ala Pro Arg
    1145                1150                1155

Cys Ser Arg Asp Cys Gly Cys Ser Phe His Ser His Cys Arg Lys
    1160                1165                1170

Arg Gly Pro Gly Phe Cys Asp Glu Cys Gln Asp Trp Thr Trp Gly
    1175                1180                1185

Glu His Cys Glu Arg Cys Arg Pro Gly Ser Phe Gly Asn Ala Thr
    1190                1195                1200

Gly Ser Arg Gly Cys Arg Pro Cys Gln Cys Asn Gly His Gly Asp
    1205                1210                1215

Pro Arg Arg Gly His Cys Asp Asn Leu Ser Gly Leu Cys Phe Cys
    1220                1225                1230

Gln Asp His Thr Glu Gly Ala His Cys Gln Leu Cys Ser Pro Gly
    1235                1240                1245

Tyr Tyr Gly Asp Pro Arg Ala Gly Gly Ser Cys Phe Arg Glu Cys
    1250                1255                1260

Gly Gly Arg Ala Leu Leu Thr Asn Val Ser Ser Val Ala Leu Gly
    1265                1270                1275

Ser Arg Arg Val Gly Gly Leu Leu Pro Pro Gly Gly Ala Ala
    1280                1285                1290

Arg Ala Gly Pro Gly Leu Ser Tyr Cys Val Trp Val Val Ser Ala
    1295                1300                1305
```

```
Thr Glu Glu Leu Gln Pro Cys Ala Pro Gly Thr Leu Cys Pro Pro
    1310            1315                1320

Leu Thr Leu Thr Phe Ser Pro Asp Ser Ser Thr Pro Cys Thr Leu
    1325            1330                1335

Ser Tyr Val Leu Ala Phe Asp Gly Phe Pro Arg Phe Leu Asp Thr
    1340            1345                1350

Gly Val Val Gln Ser Asp Arg Ser Leu Ile Ala Ala Phe Cys Gly
    1355            1360                1365

Gln Arg Arg Asp Arg Pro Leu Thr Val Gln Ala Leu Ser Gly Leu
    1370            1375                1380

Leu Val Leu His Trp Glu Ala Asn Gly Ser Ser Trp Gly Phe
    1385            1390                1395

Asn Ala Ser Val Gly Ser Ala Arg Cys Gly Ser Gly Gly Pro Gly
    1400            1405                1410

Ser Cys Pro Val Pro Gln Glu Cys Val Pro Gln Asp Gly Ala Ala
    1415            1420                1425

Gly Ala Gly Leu Cys Arg Cys Pro Gln Gly Trp Ala Gly Pro His
    1430            1435                1440

Cys Arg Met Ala Leu Cys Pro Glu Asn Cys Asn Ala His Thr Gly
    1445            1450                1455

Ala Gly Thr Cys Asn Gln Ser Leu Gly Val Cys Ile Cys Ala Glu
    1460            1465                1470

Gly Phe Gly Gly Pro Asp Cys Ala Thr Lys Leu Asp Gly Gly Gln
    1475            1480                1485

Leu Val Trp Glu Thr Leu Met Asp Ser Arg Leu Ser Ala Asp Thr
    1490            1495                1500

Ala Ser Arg Phe Leu His Arg Leu Gly His Thr Met Val Asp Gly
    1505            1510                1515

Pro Asp Ala Thr Leu Trp Met Phe Gly Gly Leu Gly Leu Pro Gln
    1520            1525                1530

Gly Leu Leu Gly Asn Leu Tyr Arg Tyr Ser Val Ser Glu Arg Arg
    1535            1540                1545

Trp Thr Gln Met Leu Ala Gly Ala Glu Asp Gly Gly Pro Gly Pro
    1550            1555                1560

Ser Pro Arg Ser Phe His Ala Ala Ala Tyr Val Pro Ala Gly Arg
    1565            1570                1575

Gly Ala Met Tyr Leu Leu Gly Gly Leu Thr Ala Gly Gly Val Thr
    1580            1585                1590

Arg Asp Phe Trp Val Leu Asn Leu Thr Thr Leu Gln Trp Arg Gln
    1595            1600                1605

Glu Lys Ala Pro Gln Thr Val Glu Leu Pro Ala Val Ala Gly His
    1610            1615                1620

Thr Leu Thr Ala Arg Arg Gly Leu Ser Leu Leu Leu Val Gly Gly
    1625            1630                1635

Tyr Ser Pro Glu Asn Gly Phe Asn Gln Gln Leu Leu Glu Tyr Gln
    1640            1645                1650

Leu Ala Thr Gly Thr Trp Val Ser Gly Ala Gln Ser Gly Thr Pro
    1655            1660                1665

Pro Thr Gly Leu Tyr Gly His Ser Ala Val Tyr His Glu Ala Thr
    1670            1675                1680

Asp Ser Leu Tyr Val Phe Gly Gly Phe Arg Phe His Val Glu Leu
    1685            1690                1695
```

```
Ala Ala Pro Ser Pro Glu Leu Tyr Ser Leu His Cys Pro Asp Arg
    1700            1705                1710

Thr Trp Ser Leu Leu Ala Pro Ser Gln Gly Ala Lys Arg Asp Arg
    1715            1720                1725

Met Arg Asn Val Arg Gly Ser Ser Arg Gly Leu Gly Gln Val Pro
    1730            1735                1740

Gly Glu Gln Pro Gly Ser Trp Gly Phe Arg Glu Val Arg Lys Lys
    1745            1750                1755

Met Ala Leu Trp Ala Ala Leu Ala Gly Thr Gly Gly Phe Leu Glu
    1760            1765                1770

Glu Ile Ser Pro His Leu Lys Glu Pro Arg Pro Arg Leu Phe His
    1775            1780                1785

Ala Ser Ala Leu Leu Gly Asp Thr Met Val Val Leu Gly Gly Arg
    1790            1795                1800

Ser Asp Pro Asp Glu Phe Ser Ser Asp Val Leu Leu Tyr Gln Val
    1805            1810                1815

Asn Cys Asn Ala Trp Leu Leu Pro Asp Leu Thr Arg Ser Ala Ser
    1820            1825                1830

Val Gly Pro Pro Met Glu Glu Ser Val Ala His Ala Val Ala Ala
    1835            1840                1845

Val Gly Ser Arg Leu Tyr Ile Ser Gly Gly Phe Gly Gly Val Ala
    1850            1855                1860

Leu Gly Arg Leu Leu Ala Leu Thr Leu Pro Pro Asp Pro Cys Arg
    1865            1870                1875

Leu Leu Ser Ser Pro Glu Ala Cys Asn Gln Ser Gly Ala Cys Thr
    1880            1885                1890

Trp Cys His Gly Ala Cys Leu Ser Gly Asp Gln Ala His Arg Leu
    1895            1900                1905

Gly Cys Gly Gly Ser Pro Cys Ser Pro Met Pro Arg Ser Pro Glu
    1910            1915                1920

Glu Cys Arg Arg Leu Arg Thr Cys Ser Glu Cys Leu Ala Arg His
    1925            1930                1935

Pro Arg Thr Leu Gln Pro Gly Asp Gly Glu Ala Ser Thr Pro Arg
    1940            1945                1950

Cys Lys Trp Cys Thr Asn Cys Pro Glu Gly Ala Cys Ile Gly Arg
    1955            1960                1965

Asn Gly Ser Cys Thr Ser Glu Asn Asp Cys Arg Ile Asn Gln Arg
    1970            1975                1980

Glu Val Phe Trp Ala Gly Asn Cys Ser Glu Ala Ala Cys Gly Ala
    1985            1990                1995

Ala Asp Cys Glu Gln Cys Thr Arg Glu Gly Lys Cys Met Trp Thr
    2000            2005                2010

Arg Gln Phe Lys Arg Thr Gly Glu Thr Arg Arg Ile Leu Ser Val
    2015            2020                2025

Gln Pro Thr Tyr Asp Trp Thr Cys Phe Ser His Ser Leu Leu Asn
    2030            2035                2040

Val Ser Pro Met Pro Val Glu Ser Ser Pro Pro Leu Pro Cys Pro
    2045            2050                2055

Thr Pro Cys His Leu Leu Pro Asn Cys Thr Ser Cys Leu Asp Ser
    2060            2065                2070

Lys Gly Ala Asp Gly Gly Trp Gln His Cys Val Trp Ser Ser Ser
    2075            2080                2085

Leu Gln Gln Cys Leu Ser Pro Ser Tyr Leu Pro Leu Arg Cys Met
```

-continued

```
                2090                2095                2100
Ala Gly Gly Cys Gly Arg Leu Leu Arg Gly Pro Glu Ser Cys Ser
    2105                2110                2115
Leu Gly Cys Ala Gln Ala Thr Gln Cys Ala Leu Cys Leu Arg Arg
    2120                2125                2130
Pro His Cys Gly Trp Cys Ala Trp Gly Gly Gln Asp Gly Gly Gly
    2135                2140                2145
Arg Cys Met Glu Gly Gly Leu Ser Gly Pro Arg Asp Gly Leu Thr
    2150                2155                2160
Cys Gly Arg Pro Gly Ala Ser Trp Ala Phe Leu Ser Cys Pro Pro
    2165                2170                2175
Glu Asp Glu Cys Ala Asn Gly His His Asp Cys Asn Glu Thr Gln
    2180                2185                2190
Asn Cys His Asp Gln Pro His Gly Tyr Glu Cys Ser Cys Lys Thr
    2195                2200                2205
Gly Tyr Thr Met Asp Asn Met Thr Gly Leu Cys Arg Pro Val Cys
    2210                2215                2220
Ala Gln Gly Cys Val Asn Gly Ser Cys Val Glu Pro Asp His Cys
    2225                2230                2235
Arg Cys His Phe Gly Phe Val Gly Arg Asn Cys Ser Thr Glu Cys
    2240                2245                2250
Arg Cys Asn Arg His Ser Glu Cys Ala Gly Val Gly Ala Arg Asp
    2255                2260                2265
His Cys Leu Leu Cys Arg Asn His Thr Lys Gly Ser His Cys Glu
    2270                2275                2280
Gln Cys Leu Pro Leu Phe Val Gly Ser Ala Val Gly Gly Gly Thr
    2285                2290                2295
Cys Arg Pro Cys His Ala Phe Cys Arg Gly Asn Ser His Ile Cys
    2300                2305                2310
Ile Ser Arg Lys Glu Leu Gln Met Ser Lys Gly Glu Pro Lys Lys
    2315                2320                2325
Tyr Ser Leu Asp Pro Glu Glu Ile Glu Asn Trp Val Thr Glu Gly
    2330                2335                2340
Pro Ser Glu Asp Glu Ala Val Cys Val Asn Cys Gln Asn Asn Ser
    2345                2350                2355
Tyr Gly Glu Lys Cys Glu Ser Cys Leu Gln Gly Tyr Phe Leu Leu
    2360                2365                2370
Asp Gly Lys Cys Thr Lys Cys Gln Cys Asn Gly His Ala Asp Thr
    2375                2380                2385
Cys Asn Glu Gln Asp Gly Thr Gly Cys Pro Cys Gln Asn Asn Thr
    2390                2395                2400
Glu Thr Gly Thr Cys Gln Gly Ser Ser Pro Ser Asp Arg Arg Asp
    2405                2410                2415
Cys Tyr Lys Tyr Gln Cys Ala Lys Cys Arg Glu Ser Phe His Gly
    2420                2425                2430
Ser Pro Leu Gly Gly Gln Gln Cys Tyr Arg Leu Ile Ser Val Glu
    2435                2440                2445
Gln Glu Cys Cys Leu Asp Pro Thr Ser Gln Thr Asn Cys Phe His
    2450                2455                2460
Glu Pro Lys Arg Arg Ala Leu Gly Pro Gly Arg Thr Val Leu Phe
    2465                2470                2475
Gly Val Gln Pro Lys Phe Thr Asn Val Asp Ile Arg Leu Thr Leu
    2480                2485                2490
```

Asp Val Thr Phe Gly Ala Val Asp Leu Tyr Val Ser Thr Ser Tyr
2495                2500                    2505

Asp Thr Phe Val Val Arg Val Ala Pro Asp Thr Gly Val His Thr
2510                2515                    2520

Val His Ile Gln Pro Pro Pro Ala Pro Pro Pro Pro Pro Pro Pro
2525                2530                    2535

Ala Asp Gly Gly Pro Arg Gly Ala Gly Asp Pro Gly Gly Ala Gly
2540                2545                    2550

Ala Ser Ser Gly Pro Gly Ala Pro Ala Glu Pro Arg Val Arg Glu
2555                2560                    2565

Val Trp Pro Arg Gly Leu Ile Thr Tyr Val Thr Val Thr Glu Pro
2570                2575                    2580

Ser Ala Val Leu Val Val Arg Gly Val Arg Asp Arg Leu Val Ile
2585                2590                    2595

Thr Tyr Pro His Glu His His Ala Leu Lys Ser Ser Arg Phe Tyr
2600                2605                    2610

Leu Leu Leu Leu Gly Val Gly Asp Pro Ser Gly Pro Gly Ala Asn
2615                2620                    2625

Gly Ser Ala Asp Ser Gln Gly Leu Leu Phe Phe Arg Gln Asp Gln
2630                2635                    2640

Ala His Ile Asp Leu Phe Val Phe Phe Ser Val Phe Phe Ser Cys
2645                2650                    2655

Phe Phe Leu Phe Leu Ser Leu Cys Val Leu Leu Trp Lys Ala Lys
2660                2665                    2670

Gln Ala Leu Asp Gln Arg Gln Glu Gln Arg Arg His Leu Gln Glu
2675                2680                    2685

Met Thr Lys Met Ala Ser Arg Pro Phe Ala Lys Val Thr Val Cys
2690                2695                    2700

Phe Pro Pro Asp Pro Thr Ala Pro Ala Ser Ala Trp Lys Pro Ala
2705                2710                    2715

Gly Leu Pro Pro Pro Ala Phe Arg Arg Ser Glu Pro Phe Leu Ala
2720                2725                    2730

Pro Leu Leu Leu Thr Gly Ala Gly Gly Pro Trp Gly Pro Met Gly
2735                2740                    2745

Gly Gly Cys Cys Pro Pro Ala Ile Pro Ala Thr Ala Gly Leu
2750                2755                    2760

Arg Ala Gly Pro Ile Thr Leu Glu Pro Thr Glu Asp Gly Met Ala
2765                2770                    2775

Gly Val Ala Thr Leu Leu Leu Gln Leu Pro Gly Gly Pro His Ala
2780                2785                    2790

Pro Asn Gly Ala Cys Leu Gly Ser Ala Leu Val Thr Leu Arg His
2795                2800                    2805

Arg Leu His Glu Tyr Cys Gly Gly Gly Gly Ala Gly Gly Ser
2810                2815                    2820

Gly His Gly Thr Gly Ala Gly Arg Lys Gly Leu Leu Ser Gln Asp
2825                2830                    2835

Asn Leu Thr Ser Met Ser Leu
2840                2845

<210> SEQ ID NO 39
<211> LENGTH: 586
<212> TYPE: PRT
<213> ORGANISM: Homo sapiens

<400> SEQUENCE: 39

Met Ala Glu Gly Val Pro Ala Ser Pro Ser Ser Gly Glu Gly Ser Arg
1               5                   10                  15

Gly Pro His Ser Gly Val Ile Gln Trp Leu Val Asp Asn Phe Cys Ile
            20                  25                  30

Cys Glu Glu Cys Ser Val Pro Arg Cys Leu Met Tyr Glu Ile Tyr Val
        35                  40                  45

Glu Thr Cys Gly Gln Asn Thr Glu Asn Gln Val Asn Pro Ala Thr Phe
    50                  55                  60

Gly Lys Leu Val Arg Leu Val Phe Pro Asp Leu Gly Thr Arg Arg Leu
65              70                  75                  80

Gly Thr Arg Gly Ser Ala Arg Tyr His Tyr Asp Gly Ile Cys Ile Lys
            85                  90                  95

Lys Ser Ser Phe Phe Tyr Ala Gln Tyr Cys Tyr Leu Ile Gly Glu Lys
            100                 105                 110

Arg Tyr His Ser Gly Asp Ala Ile Ala Phe Glu Lys Ser Thr Asn Tyr
        115                 120                 125

Asn Ser Ile Ile Gln Gln Glu Ala Thr Cys Glu Asp His Ser Pro Met
    130                 135                 140

Lys Thr Asp Pro Val Gly Ser Pro Leu Ser Glu Phe Arg Arg Cys Pro
145             150                 155                 160

Phe Leu Glu Gln Glu Gln Ala Lys Lys Tyr Ser Cys Asn Met Met Ala
            165                 170                 175

Phe Leu Ala Asp Glu Tyr Cys Asn Tyr Cys Arg Asp Ile Leu Arg Asn
            180                 185                 190

Val Glu Asp Leu Leu Thr Ser Phe Trp Lys Ser Leu Gln Gln Asp Thr
        195                 200                 205

Val Met Leu Met Ser Leu Pro Asp Val Cys Gln Leu Phe Lys Cys Tyr
    210                 215                 220

Asp Val Gln Leu Tyr Lys Gly Ile Glu Asp Val Leu His Asp Phe
225             230                 235                 240

Leu Glu Asp Val Ser Ile Gln Tyr Leu Lys Ser Val Gln Leu Phe Ser
            245                 250                 255

Lys Lys Phe Lys Leu Trp Leu Leu Asn Ala Leu Glu Gly Val Pro Ala
            260                 265                 270

Leu Leu Gln Ile Ser Lys Leu Lys Glu Val Thr Leu Phe Val Lys Arg
        275                 280                 285

Leu Arg Arg Lys Thr Tyr Leu Ser Asn Met Ala Lys Thr Met Arg Met
    290                 295                 300

Val Leu Lys Ser Lys Arg Arg Val Ser Val Leu Lys Ser Asp Leu Gln
305             310                 315                 320

Ala Ile Ile Asn Gln Gly Thr Leu Ala Thr Ser Lys Lys Ala Leu Ala
            325                 330                 335

Ser Asp Arg Ser Gly Ala Asp Glu Leu Glu Asn Asn Pro Glu Met Lys
            340                 345                 350

Cys Leu Arg Asn Leu Ile Ser Leu Leu Gly Thr Ser Thr Asp Leu Arg
        355                 360                 365

Val Phe Leu Ser Cys Leu Ser Ser His Leu Gln Ala Phe Val Phe Gln
    370                 375                 380

Thr Ser Arg Ser Lys Glu Glu Phe Thr Lys Leu Ala Ala Ser Phe Gln
385             390                 395                 400

Leu Arg Trp Asn Leu Leu Leu Thr Ala Val Ser Lys Ala Met Thr Leu
            405                 410                 415

-continued

Cys His Arg Asp Ser Phe Gly Ser Trp His Leu Phe His Leu Leu Leu
            420                 425                 430

Leu Glu Tyr Met Ile His Ile Leu Gln Ser Cys Leu Glu Glu Glu Glu
            435                 440                 445

Glu Glu Glu Asp Met Gly Thr Val Lys Glu Met Leu Pro Asp Asp Pro
450                 455                 460

Thr Leu Gly Gln Pro Asp Gln Ala Leu Phe His Ser Leu Asn Ser Ser
465                 470                 475                 480

Leu Ser Gln Ala Cys Ala Ser Pro Ser Met Glu Pro Leu Gly Val Met
                485                 490                 495

Pro Thr His Met Gly Gln Gly Arg Tyr Pro Val Gly Val Ser Asn Met
                500                 505                 510

Val Leu Arg Ile Leu Gly Phe Leu Val Asp Thr Ala Met Gly Asn Lys
            515                 520                 525

Leu Ile Gln Val Leu Leu Glu Asp Glu Thr Thr Glu Ser Ala Val Lys
            530                 535                 540

Leu Ser Leu Pro Met Gly Gln Glu Ala Leu Ile Thr Leu Lys Asp Gly
545                 550                 555                 560

Gln Gln Phe Val Ile Gln Ile Ser Asp Val Pro Gln Ser Ser Glu Asp
                565                 570                 575

Ile Tyr Phe Arg Glu Asn Asn Ala Asn Val
                580                 585

<210> SEQ ID NO 40
<211> LENGTH: 459
<212> TYPE: PRT
<213> ORGANISM: Homo sapiens

<400> SEQUENCE: 40

Met Glu Gly Ser Ala Ser Pro Pro Glu Lys Pro Arg Ala Arg Pro Ala
1                 5                   10                  15

Ala Ala Val Leu Cys Arg Gly Pro Val Glu Pro Leu Val Phe Leu Ala
            20                  25                  30

Asn Phe Ala Leu Val Leu Gln Gly Pro Leu Thr Thr Gln Tyr Leu Trp
        35                  40                  45

His Arg Phe Ser Ala Asp Leu Gly Tyr Asn Gly Thr Arg Gln Arg Gly
    50                  55                  60

Gly Cys Ser Asn Arg Ser Ala Asp Pro Thr Met Gln Glu Val Glu Thr
65                  70                  75                  80

Leu Thr Ser His Trp Thr Leu Tyr Met Asn Val Gly Gly Phe Leu Val
                85                  90                  95

Gly Leu Phe Ser Ser Thr Leu Leu Gly Ala Trp Ser Asp Ser Val Gly
            100                 105                 110

Arg Arg Pro Leu Leu Val Leu Ala Ser Leu Gly Leu Leu Leu Gln Ala
        115                 120                 125

Leu Val Ser Val Phe Val Val Gln Leu Gln Leu His Val Gly Tyr Phe
    130                 135                 140

Val Leu Gly Arg Ile Leu Cys Ala Leu Gly Asp Phe Gly Leu Leu
145                 150                 155                 160

Leu Ala Ala Ser Phe Ala Ser Val Ala Asp Val Ser Ser Ser Arg Ser
                165                 170                 175

Arg Thr Phe Arg Met Ala Leu Leu Glu Ala Ser Ile Gly Val Ala Gly
            180                 185                 190

Met Leu Ala Ser Leu Leu Gly Gly His Trp Leu Arg Ala Gln Gly Tyr

```
                195                 200                 205
Ala Asn Pro Phe Trp Leu Ala Leu Ala Leu Leu Ile Ala Met Thr Leu
    210                 215                 220

Tyr Ala Ala Phe Cys Phe Gly Glu Thr Leu Lys Glu Pro Lys Ser Thr
225                 230                 235                 240

Arg Leu Phe Thr Phe Arg His His Arg Ser Ile Val Gln Leu Tyr Val
                245                 250                 255

Ala Pro Ala Pro Glu Lys Ser Arg Lys His Leu Ala Leu Tyr Ser Leu
            260                 265                 270

Ala Ile Phe Val Val Ile Thr Val His Phe Gly Ala Gln Asp Ile Leu
        275                 280                 285

Thr Leu Tyr Glu Leu Ser Thr Pro Leu Cys Trp Asp Ser Lys Leu Ile
    290                 295                 300

Gly Tyr Gly Ser Ala Ala Gln His Leu Pro Tyr Leu Thr Ser Leu Leu
305                 310                 315                 320

Ala Leu Lys Leu Leu Gln Tyr Cys Leu Ala Asp Ala Trp Val Ala Glu
                325                 330                 335

Ile Gly Leu Ala Phe Asn Ile Leu Gly Met Val Val Phe Ala Phe Ala
            340                 345                 350

Thr Ile Thr Pro Leu Met Phe Thr Gly Tyr Gly Leu Leu Phe Leu Ser
        355                 360                 365

Leu Val Ile Thr Pro Val Ile Arg Ala Lys Leu Ser Lys Leu Val Arg
    370                 375                 380

Glu Thr Glu Gln Gly Ala Leu Phe Ser Ala Val Ala Cys Val Asn Ser
385                 390                 395                 400

Leu Ala Met Leu Thr Ala Ser Gly Ile Phe Asn Ser Leu Tyr Pro Ala
                405                 410                 415

Thr Leu Asn Phe Met Lys Gly Phe Pro Phe Leu Leu Gly Ala Gly Leu
            420                 425                 430

Leu Leu Ile Pro Ala Val Leu Ile Gly Met Leu Glu Lys Ala Asp Pro
        435                 440                 445

His Leu Glu Phe Gln Gln Phe Pro Gln Ser Pro
    450                 455

<210> SEQ ID NO 41
<211> LENGTH: 173
<212> TYPE: PRT
<213> ORGANISM: Homo sapiens

<400> SEQUENCE: 41

Met His Trp Lys Met Leu Leu Leu Leu Leu Tyr Tyr Asn Ala Glu
1               5                   10                  15

Ala Ser Met Cys His Arg Trp Ser Arg Ala Val Leu Phe Pro Ala Ala
                20                  25                  30

His Arg Pro Lys Arg Ser Ser Ser Leu Pro Leu Asn Pro Val Leu Gln
            35                  40                  45

Thr Ser Leu Glu Glu Val Glu Leu Leu Tyr Glu Phe Leu Leu Ala Glu
        50                  55                  60

Leu Glu Ile Ser Pro Asp Leu Gln Ile Ser Ile Lys Asp Glu Glu Leu
65                  70                  75                  80

Ala Ser Leu Arg Lys Ala Ser Asp Phe Arg Thr Val Cys Asn Asn Val
                85                  90                  95

Ile Pro Lys Ser Ile Pro Asp Ile Arg Arg Leu Ser Ala Ser Leu Ser
            100                 105                 110
```

```
Ser His Pro Gly Ile Leu Lys Lys Glu Asp Phe Glu Arg Thr Val Leu
        115                 120                 125

Thr Leu Ala Tyr Thr Ala Tyr Arg Thr Ala Leu Ser His Gly His Gln
130                 135                 140

Lys Asp Ile Trp Ala Gln Ser Leu Val Ser Leu Phe Gln Ala Leu Arg
145                 150                 155                 160

His Asp Leu Met Arg Ser Ser Gln Pro Gly Val Pro Pro
                165                 170
```

<210> SEQ ID NO 42
<211> LENGTH: 245
<212> TYPE: PRT
<213> ORGANISM: Homo sapiens

<400> SEQUENCE: 42

```
Met Thr Leu Phe Pro Val Leu Leu Phe Leu Val Ala Gly Leu Leu Pro
1               5                   10                  15

Ser Phe Pro Ala Asn Glu Asp Lys Asp Pro Ala Phe Thr Ala Leu Leu
                20                  25                  30

Thr Thr Gln Thr Gln Val Gln Arg Glu Ile Val Asn Lys His Asn Glu
            35                  40                  45

Leu Arg Arg Ala Val Ser Pro Pro Ala Arg Asn Met Leu Lys Met Glu
50                  55                  60

Trp Asn Lys Glu Ala Ala Ala Asn Ala Gln Lys Trp Ala Asn Gln Cys
65                  70                  75                  80

Asn Tyr Arg His Ser Asn Pro Lys Asp Arg Met Thr Ser Leu Lys Cys
                85                  90                  95

Gly Glu Asn Leu Tyr Met Ser Ser Ala Ser Ser Ser Trp Ser Gln Ala
            100                 105                 110

Ile Gln Ser Trp Phe Asp Glu Tyr Asn Asp Phe Asp Phe Gly Val Gly
            115                 120                 125

Pro Lys Thr Pro Asn Ala Val Val Gly His Tyr Thr Gln Val Val Trp
130                 135                 140

Tyr Ser Ser Tyr Leu Val Gly Cys Gly Asn Ala Tyr Cys Pro Asn Gln
145                 150                 155                 160

Lys Val Leu Lys Tyr Tyr Val Cys Gln Tyr Cys Pro Ala Gly Asn
                165                 170                 175

Trp Ala Asn Arg Leu Tyr Val Pro Tyr Glu Gln Gly Ala Pro Cys Ala
            180                 185                 190

Ser Cys Pro Asp Asn Cys Asp Asp Gly Leu Cys Thr Asn Gly Cys Lys
            195                 200                 205

Tyr Glu Asp Leu Tyr Ser Asn Cys Lys Ser Leu Lys Leu Thr Leu Thr
210                 215                 220

Cys Lys His Gln Leu Val Arg Asp Ser Cys Lys Ala Ser Cys Asn Cys
225                 230                 235                 240

Ser Asn Ser Ile Tyr
                245
```

<210> SEQ ID NO 43
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 43

Lys Lys Ser Arg Gly Asp Tyr Met Thr Met Gln Ile Gly

```
                            1               5                   10

<210> SEQ ID NO 44
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 44

Gly Gly Met Glu Asp Ile Tyr Phe Glu Phe Met Gly Gly Lys Lys Lys
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 45

Lys Lys Lys Gly Gln Glu Glu Glu Tyr Val Phe Ile Glu
1               5                   10
```